United States Patent
Wu et al.

(10) Patent No.: US 12,358,951 B2
(45) Date of Patent: *Jul. 15, 2025

(54) CYCLIC PEPTIDE ANTIBIOTICS

(71) Applicant: Genentech, Inc., South San Francisco, CA (US)

(72) Inventors: Guosheng Wu, Beijing (CN); Emily J. Hanan, Redwood City, CA (US); Marie-Gabrielle Braun, San Francisco, CA (US); Sharada S. Labadie, Sunnyvale, CA (US); Keira Garland, San Francisco, CA (US); Richard M. Pastor, San Francisco, CA (US); Paul Anthony Gibbons, San Francisco, CA (US); Yuhong Fu, Beijing (CN); Yun-Xing Cheng, Beijing (CN)

(73) Assignee: Genentech, Inc., South San Francisco, CA (US)

( * ) Notice: Subject to any disclaimer, the term of this patent is extended or adjusted under 35 U.S.C. 154(b) by 972 days.

This patent is subject to a terminal disclaimer.

(21) Appl. No.: 17/447,361

(22) Filed: Sep. 10, 2021

(65) Prior Publication Data
US 2023/0025834 A1    Jan. 26, 2023

Related U.S. Application Data

(63) Continuation of application No. PCT/US2020/022272, filed on Mar. 12, 2020.

(30) Foreign Application Priority Data

Mar. 14, 2019   (WO) ................ PCT/CN2019/078189

(51) Int. Cl.
  *C07K 7/00*   (2006.01)
  *C07K 7/56*   (2006.01)
  *A61K 38/00*  (2006.01)
(52) U.S. Cl.
  CPC .............. *C07K 7/56* (2013.01); *A61K 38/00* (2013.01)
(58) Field of Classification Search
  CPC ............ C07K 7/56; C07K 7/06; A61K 38/00
  See application file for complete search history.

(56) References Cited

U.S. PATENT DOCUMENTS

| 5,384,309 A | 1/1995 | Barker et al. |
| 10,787,490 B2 | 9/2020 | Bhandari et al. |

FOREIGN PATENT DOCUMENTS

| JP | S53-141202 A | 12/1978 |
| JP | S55-47644 A | 4/1980 |
| WO | 2017/079820 A1 | 5/2017 |
| WO | 2019/052545 A1 | 3/2019 |

OTHER PUBLICATIONS

Kiho et al. (2004) Structure-activity relationships of globomycin analogues as antibiotics, Bioorganic & Medicinal Chemistry, vol. 12, No. 2. pp. 337-361.*
"International Preliminary Report on Patentability—PCT/CN2018/105821" (Issuance Date: Mar. 17, 2020), :pp. 1-8 (Mar. 26, 2020).
"International Preliminary Report on Patentability—PCT/US2020/022272" (Report Issuance Date: Aug. 25, 2021, Chapter I),: pp. 1-11 (Sep. 23, 2021).
"International Search Report—PCT/CN2018/105821" (w/Written Opinion), :pp. 1-13 (Dec. 12, 2018).
"International Search Report—PCT/US2020/022272" (w/Written Opinion), :pp. 1-18 (Aug. 13, 2020).
Kiho, T., et al., "Structure-activity relationships of globomycin analogues as antibiotics" Bioorg Med Chem 12(2):337-361 (Jan. 15, 2004).
Kiho, T., et al., "Synthesis and Antimicrobial Activity of Novel Globomycin Analogues" Bioorg Med Chem Lett 13(14):2315-2318 (Jul. 21, 2003).
Kiho, T., et al., "Total synthesis and NMR conformational study of signal peptidase II inhibitors, globomycin and SF-1902 A5" Tetrahedron 59(10):1685-1697 (Mar. 3, 2003).
Sarabia, F., et al., "Solid Phase Synthesis of Globomycin and SF-1902 A5" J Org Chem 76(7):2132-2144 (Apr. 1, 2011).
Uchida, H., et al., "Synthesis of tris-bridged cyclic peptides as an active site mimic of lipase" Chem Pharm Bull- Pharm Soc of JP 45(7):1228-1230 (Jul. 15, 1997).

\* cited by examiner

*Primary Examiner* — Jeanette M Lieb
(74) *Attorney, Agent, or Firm* — Brian L. Buckwalter

(57) ABSTRACT

Provided herein are antibacterial compounds, wherein the compounds in some embodiments have broad spectrum bioactivity. In various embodiments, the compounds act by inhibition of lipoprotein signal peptidase II (LspA), a key protein in bacteria. Pharmaceutical compositions and methods for treatment using the compounds described herein are also provided.

22 Claims, No Drawings

CYCLIC PEPTIDE ANTIBIOTICS

CROSS REFERENCE TO RELATED APPLICATIONS

This application is a Continuation of International Application PCT/US2020/022272 filed on Mar. 12, 2020, which is entitled to the benefit of priority application PCT/CN2019/078189 filed on Mar. 14, 2019, the disclosures of which are incorporated herein by reference.

BACKGROUND OF THE INVENTION

Antibiotic resistance is a serious and growing phenomenon in contemporary medicine and has emerged as a major public health concern of the 21st century. Therefore, novel classes of broad-spectrum antibiotics, especially those that target novel mechanisms of action, are needed to treat multidrug-resistant pathogens. The Type II signal peptidase LspA plays a critical role in the biosynthesis of Gram-negative bacterial lipoproteins. Blocking of lipoprotein synthesis via inhibition of LspA function not only depletes essential as well as virulence-associated lipoproteins but can also lead to accumulation of mislocalized unprocessed lipoproteins, all of which leads to bacterial cell death. LspA inhibitors thus offer a novel approach to combatting Gram-negative bacterial infection.

SUMMARY OF THE INVENTION

Described herein are novel macrocyclic compounds for the treatment of microbial infections, such as for the treatment of bacterial infections. In various embodiments, the present disclosure provides cyclic peptide, depsipeptide, and peptide-containing compounds for the treatment of bacterial infections. In various embodiments, the present disclosure provides classes and subclasses of chemical compounds structurally related to globomycin for the treatment of bacterial infections. In various embodiments, the cyclic peptide, depsipeptide and peptide containing compounds act by inhibition of lipoprotein signal peptidase II (LspA), a key enzyme involved in the posttranslational processing of lipoproteins in bacteria.

Disclosed herein is a compound of Formula (I), or a pharmaceutically acceptable salt, solvate, or stereoisomer thereof:

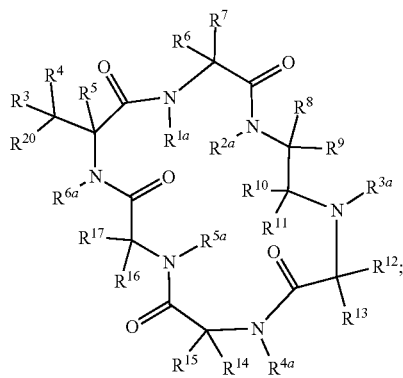

Formula (I)

wherein:

$R^{1a}$, $R^{2a}$, $R^{4a}$, $R^{5a}$, and $R^{6a}$ are each independently hydrogen or optionally substituted $C_1$-$C_6$ alkyl;

$R^{3a}$ is hydrogen, optionally substituted $C_1$-$C_{20}$ alkyl, optionally substituted $C_2$-$C_{20}$ alkenyl, optionally substituted $C_2$-$C_{20}$ alkynyl, optionally substituted cycloalkyl, optionally substituted ($C_1$-$C_6$ alkyl)cycloalkyl, optionally substituted heterocycloalkyl, optionally substituted ($C_1$-$C_6$ alkyl)heterocycloalkyl, optionally substituted aryl, optionally substituted ($C_1$-$C_6$ alkyl)aryl, optionally substituted heteroaryl, or optionally substituted ($C_1$-$C_6$ alkyl)heteroaryl;

$R^{20}$ is hydroxyl or —$NR^1R^2$;

$R^1$ and $R^2$ are each independently hydrogen, optionally substituted $C_1$-$C_6$ alkyl, optionally substituted $C_2$-$C_6$ alkenyl, optionally substituted $C_2$-$C_6$ alkynyl, optionally substituted cycloalkyl, optionally substituted ($C_1$-$C_6$ alkyl)cycloalkyl, optionally substituted heterocycloalkyl, optionally substituted ($C_1$-$C_6$ alkyl)heterocycloalkyl, optionally substituted aryl, optionally substituted ($C_1$-$C_6$ alkyl)aryl, optionally substituted heteroaryl, optionally substituted ($C_1$-$C_6$ alkyl)heteroaryl, —$S(=O)_2R^a$, —$S(=O)_2NR^bR^c$, —$C(=O)R^a$, —$C(=O)OR^b$, —$C(=O)NR^bR^c$, or —$(C=NR^b)NR^bR^c$;

or $R^1$ and $R^2$ are taken together with the nitrogen atom to which they are attached to form an optionally substituted heterocycloalkyl;

$R^3$ and $R^4$ are each independently hydrogen, optionally substituted $C_1$-$C_6$ alkyl, optionally substituted $C_2$-$C_6$ alkenyl, optionally substituted $C_2$-$C_6$ alkynyl, optionally substituted cycloalkyl, optionally substituted heterocycloalkyl, optionally substituted aryl, or optionally substituted heteroaryl;

or $R^3$ and $R^4$ are taken together with the carbon atom to which they are attached to form an oxo;

$R^5$ is hydrogen, halogen, optionally substituted $C_1$-$C_6$ alkyl, optionally substituted $C_2$-$C_6$ alkenyl, or optionally substituted $C_2$-$C_6$ alkynyl;

$R^6$ and $R^7$ are each independently hydrogen, halogen, optionally substituted $C_1$-$C_6$ alkyl, optionally substituted $C_2$-$C_6$ alkenyl, optionally substituted $C_2$-$C_6$ alkynyl, optionally substituted cycloalkyl, optionally substituted ($C_1$-$C_6$ alkyl)cycloalkyl, optionally substituted heterocycloalkyl, optionally substituted ($C_1$-$C_6$ alkyl)heterocycloalkyl, optionally substituted aryl, optionally substituted ($C_1$-$C_6$ alkyl)aryl, optionally substituted heteroaryl, or optionally substituted ($C_1$-$C_6$ alkyl)heteroaryl;

$R^8$ and $R^9$ are each independently hydrogen, halogen, optionally substituted $C_1$-$C_6$ alkyl, optionally substituted $C_2$-$C_6$ alkenyl, optionally substituted $C_2$-$C_6$ alkynyl, optionally substituted cycloalkyl, optionally substituted ($C_1$-$C_6$ alkyl)cycloalkyl, optionally substituted heterocycloalkyl, optionally substituted ($C_1$-$C_6$ alkyl)heterocycloalkyl, optionally substituted aryl, optionally substituted ($C_1$-$C_6$ alkyl)aryl, optionally substituted heteroaryl, or optionally substituted ($C_1$-$C_6$ alkyl)heteroaryl;

or $R^{3a}$ and $R^8$ are taken together with the atoms to which they are attached to form an optionally substituted heterocycloalkyl;

$R^{10}$ and $R^{11}$ are each independently hydrogen, halogen, optionally substituted $C_1$-$C_6$ alkyl, optionally substituted $C_2$-$C_{20}$ alkenyl, optionally substituted $C_2$-$C_6$ alkynyl, optionally substituted cycloalkyl, optionally substituted ($C_1$-$C_6$ alkyl)cycloalkyl, optionally substituted heterocycloalkyl, optionally substituted ($C_1$-$C_6$ alkyl)heterocycloalkyl, optionally substituted aryl, optionally substituted ($C_1$-$C_6$ alkyl)aryl, optionally substituted heteroaryl, or optionally substituted ($C_1$-$C_6$ alkyl)heteroaryl;

$R^{12}$ and $R^{13}$ are each independently hydrogen, halogen, optionally substituted $C_1$-$C_{20}$ alkyl, optionally substituted $C_2$-$C_6$ alkenyl, optionally substituted $C_2$-$C_6$ alkynyl, optionally substituted cycloalkyl, optionally substituted ($C_1$-$C_6$ alkyl)cycloalkyl, optionally substituted heterocycloalkyl, optionally substituted ($C_1$-$C_6$ alkyl)heterocycloalkyl, optionally substituted aryl, optionally substituted ($C_1$-$C_6$ alkyl)aryl, optionally substituted heteroaryl, or optionally substituted ($C_1$-$C_6$ alkyl)heteroaryl;

$R^{14}$ and $R^{15}$ are each independently hydrogen, halogen, optionally substituted $C_1$-$C_6$ alkyl, optionally substituted $C_2$-$C_6$ alkenyl, optionally substituted $C_2$-$C_6$ alkynyl, optionally substituted cycloalkyl, optionally substituted ($C_1$-$C_6$ alkyl)cycloalkyl, optionally substituted heterocycloalkyl, optionally substituted ($C_1$-$C_6$ alkyl)heterocycloalkyl, optionally substituted aryl, optionally substituted ($C_1$-$C_6$ alkyl)aryl, optionally substituted heteroaryl, or optionally substituted ($C_1$-$C_6$ alkyl)heteroaryl;

$R^{16}$ and $R^{17}$ are each independently hydrogen, halogen, optionally substituted $C_1$-$C_6$ alkyl, optionally substituted $C_2$-$C_6$ alkenyl, optionally substituted $C_2$-$C_6$ alkynyl, optionally substituted cycloalkyl, optionally substituted ($C_1$-$C_6$ alkyl)cycloalkyl, optionally substituted heterocycloalkyl, optionally substituted ($C_1$-$C_6$ alkyl)heterocycloalkyl, optionally substituted aryl, optionally substituted ($C_1$-$C_6$ alkyl)aryl, optionally substituted heteroaryl, or optionally substituted ($C_1$-$C_6$ alkyl)heteroaryl;

each $R^a$ is independently optionally substituted $C_1$-$C_6$ alkyl, optionally substituted $C_2$-$C_6$ alkenyl, optionally substituted $C_2$-$C_6$ alkynyl, optionally substituted cycloalkyl, optionally substituted heterocycloalkyl, optionally substituted aryl, or optionally substituted heteroaryl;

each $R^b$ and $R^c$ is independently hydrogen, optionally substituted $C_1$-$C_6$ alkyl, optionally substituted $C_2$-$C_6$ alkenyl, optionally substituted $C_2$-$C_6$ alkynyl, optionally substituted cycloalkyl, optionally substituted heterocycloalkyl, optionally substituted aryl, or optionally substituted heteroaryl;

or $R^b$ and $R^c$ are taken together with the nitrogen atom to which they are attached to form an optionally substituted heterocycloalkyl.

Also disclosed herein is a compound of Formula (Ia) or a pharmaceutically acceptable salt, solvate, or stereoisomer thereof:

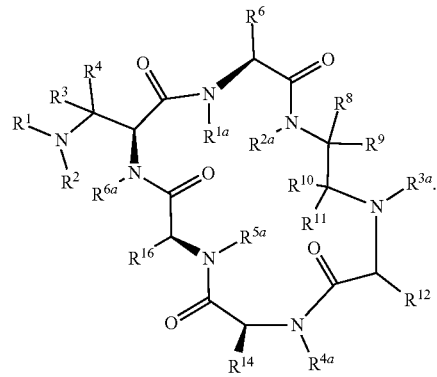

Formula (Ia)

Also disclosed herein is a compound of Formula (Ib) or a pharmaceutically acceptable salt, solvate, or stereoisomer thereof:

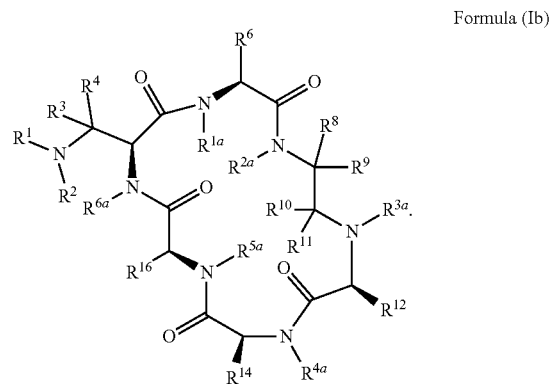

Formula (Ib)

Also disclosed herein is a compound of Formula (II) or a pharmaceutically acceptable salt, solvate, or stereoisomer thereof:

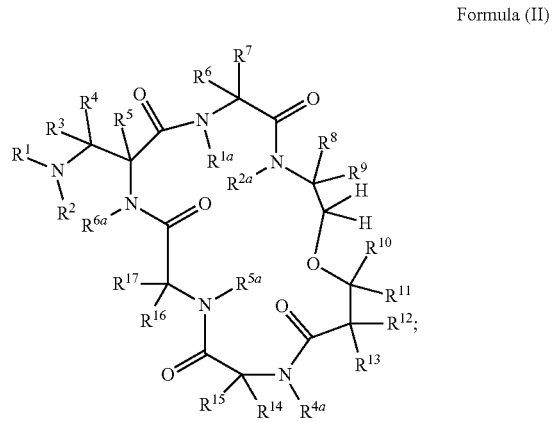

Formula (II)

wherein:
$R^{1a}$, $R^{2a}$, $R^{3a}$, $R^{4a}$, $R^{5a}$, and $R^{6a}$ are each independently hydrogen or optionally substituted $C_1$-$C_6$ alkyl;
$R^1$ and $R^2$ are each independently hydrogen, optionally substituted $C_1$-$C_6$ alkyl, optionally substituted $C_2$-$C_6$ alkenyl, optionally substituted $C_2$-$C_6$ alkynyl, optionally substituted cycloalkyl, optionally substituted ($C_1$-$C_6$ alkyl)cycloalkyl, optionally substituted heterocycloalkyl, optionally substituted ($C_1$-$C_6$ alkyl)heterocycloalkyl, optionally substituted aryl, optionally substituted ($C_1$-$C_6$ alkyl)aryl, optionally substituted heteroaryl, optionally substituted ($C_1$-$C_6$ alkyl)heteroaryl, —S(=O)$_2$R$^a$, —S(=O)$_2$NR$^b$R$^c$, —C(=O)R$^a$, —C(=O)OR$^b$, —C(=O)NR$^b$R$^c$, or —(C=NR$^b$)NR$^b$R$^c$;

or R$^1$ and R$^2$ are taken together with the nitrogen atom to which they are attached to form an optionally substituted heterocycloalkyl;

R$^3$ and R$^4$ are each independently hydrogen, optionally substituted $C_1$-$C_6$ alkyl, optionally substituted $C_2$-$C_6$ alkenyl, optionally substituted $C_2$-$C_6$ alkynyl, optionally substituted cycloalkyl, optionally substituted heterocycloalkyl, optionally substituted aryl, or optionally substituted heteroaryl;

or R$^3$ and R$^4$ are taken together with the carbon atom to which they are attached to form an oxo;

R$^5$ is hydrogen, halogen, optionally substituted $C_1$-$C_6$ alkyl, optionally substituted $C_2$-$C_6$ alkenyl, or optionally substituted $C_2$-$C_6$ alkynyl;

R$^6$ and R$^7$ are each independently hydrogen, halogen, optionally substituted $C_1$-$C_6$ alkyl, optionally substituted $C_2$-$C_6$ alkenyl, optionally substituted $C_2$-$C_6$ alkynyl, optionally substituted cycloalkyl, optionally substituted ($C_1$-$C_6$ alkyl)cycloalkyl, optionally substituted heterocycloalkyl, optionally substituted ($C_1$-$C_6$ alkyl)heterocycloalkyl, optionally substituted aryl, optionally substituted ($C_1$-$C_6$ alkyl)aryl, optionally substituted heteroaryl, or optionally substituted ($C_1$-$C_6$ alkyl)heteroaryl;

R$^8$ and R$^9$ are each independently hydrogen, halogen, optionally substituted $C_1$-$C_6$ alkyl, optionally substituted $C_2$-$C_6$ alkenyl, optionally substituted $C_2$-$C_6$ alkynyl, optionally substituted cycloalkyl, optionally substituted ($C_1$-$C_6$ alkyl)cycloalkyl, optionally substituted heterocycloalkyl, optionally substituted ($C_1$-$C_6$ alkyl)heterocycloalkyl, optionally substituted aryl, optionally substituted ($C_1$-$C_6$ alkyl)aryl, optionally substituted heteroaryl, or optionally substituted ($C_1$-$C_6$ alkyl)heteroaryl;

R$^{10}$ and R$^{11}$ are each independently hydrogen, halogen, optionally substituted $C_1$-$C_{20}$ alkyl, optionally substituted $C_2$-$C_{20}$ alkenyl, optionally substituted $C_2$-$C_{20}$ alkynyl, optionally substituted cycloalkyl, optionally substituted ($C_1$-$C_6$ alkyl)cycloalkyl, optionally substituted heterocycloalkyl, optionally substituted ($C_1$-$C_6$ alkyl)heterocycloalkyl, optionally substituted aryl, optionally substituted ($C_1$-$C_6$ alkyl)aryl, optionally substituted heteroaryl, or optionally substituted ($C_1$-$C_6$ alkyl)heteroaryl;

R$^{12}$ and R$^{13}$ are each independently hydrogen, halogen, optionally substituted $C_1$-$C_6$ alkyl, optionally substituted $C_2$-$C_6$ alkenyl, optionally substituted $C_2$-$C_6$ alkynyl, optionally substituted cycloalkyl, optionally substituted ($C_1$-$C_6$ alkyl)cycloalkyl, optionally substituted heterocycloalkyl, optionally substituted ($C_1$-$C_6$ alkyl)heterocycloalkyl, optionally substituted aryl, optionally substituted ($C_1$-$C_6$ alkyl)aryl, optionally substituted heteroaryl, or optionally substituted ($C_1$-$C_6$ alkyl)heteroaryl;

or R$^{10}$ and R$^{12}$ are taken together to form an optionally substituted cycloalkyl or an optionally substituted cycloalkenyl;

R$^{14}$ and R$^{15}$ are each independently hydrogen, halogen, optionally substituted $C_1$-$C_6$ alkyl, optionally substituted $C_2$-$C_6$ alkenyl, optionally substituted $C_2$-$C_6$ alkynyl, optionally substituted cycloalkyl, optionally substituted ($C_1$-$C_6$ alkyl)cycloalkyl, optionally substituted heterocycloalkyl, optionally substituted ($C_1$-$C_6$ alkyl)heterocycloalkyl, optionally substituted aryl, optionally substituted ($C_1$-$C_6$ alkyl)aryl, optionally substituted heteroaryl, or optionally substituted ($C_1$-$C_6$ alkyl)heteroaryl;

or R$^{14}$ and R$^{4a}$ are taken together with the atoms to which they are attached to form an optionally substituted heterocycloalkyl;

R$^{16}$ and R$^{17}$ are each independently hydrogen, halogen, optionally substituted $C_1$-$C_6$ alkyl, optionally substituted $C_2$-$C_6$ alkenyl, optionally substituted $C_2$-$C_6$ alkynyl, optionally substituted cycloalkyl, optionally substituted ($C_1$-$C_6$ alkyl)cycloalkyl, optionally substituted heterocycloalkyl, optionally substituted ($C_1$-$C_6$ alkyl)heterocycloalkyl, optionally substituted aryl, optionally substituted ($C_1$-$C_6$ alkyl)aryl, optionally substituted heteroaryl, or optionally substituted ($C_1$-$C_6$ alkyl)heteroaryl;

R$^{18}$ and R$^{19}$ are each independently hydrogen, halogen, optionally substituted $C_1$-$C_6$ alkyl, optionally substituted $C_2$-$C_6$ alkenyl, optionally substituted $C_2$-$C_6$ alkynyl, optionally substituted cycloalkyl, optionally substituted ($C_1$-$C_6$ alkyl)cycloalkyl, optionally substituted heterocycloalkyl, optionally substituted ($C_1$-$C_6$ alkyl)heterocycloalkyl, optionally substituted aryl, optionally substituted ($C_1$-$C_6$ alkyl)aryl, optionally substituted heteroaryl, or optionally substituted ($C_1$-$C_6$ alkyl)heteroaryl;

or R$^{18}$ and R$^{19}$ are taken together with the carbon atom to which they are attached to form an oxo;

each R$^a$ is independently optionally substituted $C_1$-$C_6$ alkyl, optionally substituted $C_2$-$C_6$ alkenyl, optionally substituted $C_2$-$C_6$ alkynyl, optionally substituted cycloalkyl, optionally substituted heterocycloalkyl, optionally substituted aryl, or optionally substituted heteroaryl;

each R$^b$ and R$^c$ is independently hydrogen, optionally substituted $C_1$-$C_6$ alkyl, optionally substituted $C_2$-$C_6$ alkenyl, optionally substituted $C_2$-$C_6$ alkynyl, optionally substituted cycloalkyl, optionally substituted heterocycloalkyl, optionally substituted aryl, or optionally substituted heteroaryl;

or R$^b$ and R$^c$ are taken together with the nitrogen atom to which they are attached to form an optionally substituted heterocycloalkyl;

or a pharmaceutically acceptable salt, solvate, or stereoisomer thereof;

wherein the compound is selected from the group consisting of:
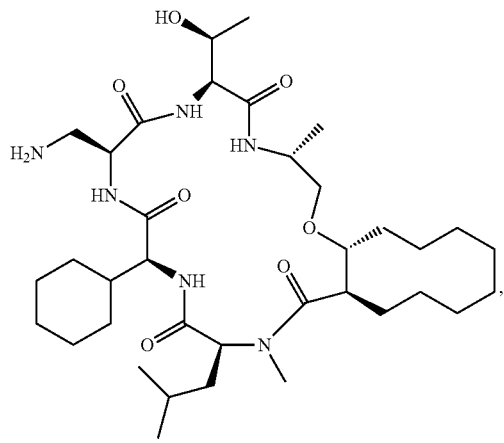
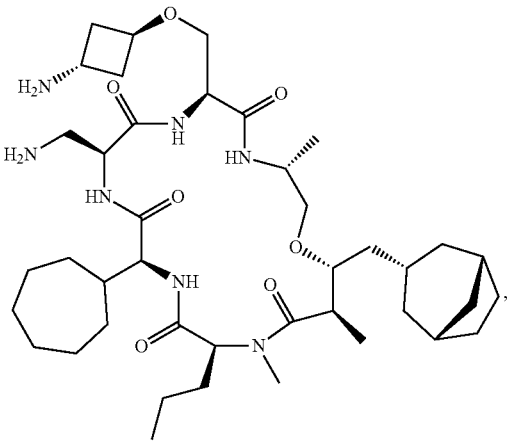
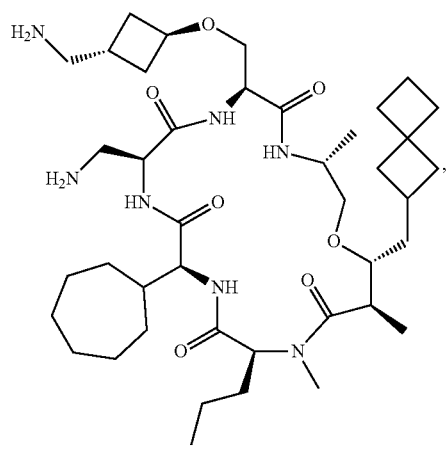
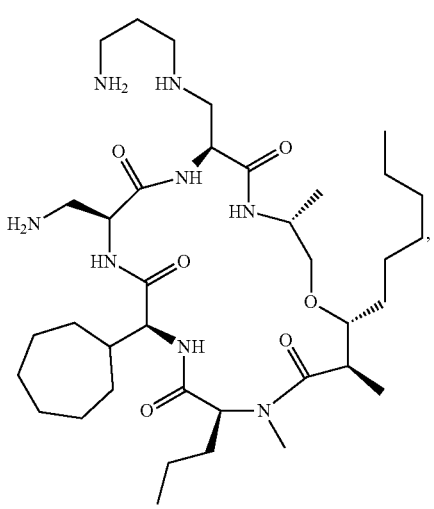
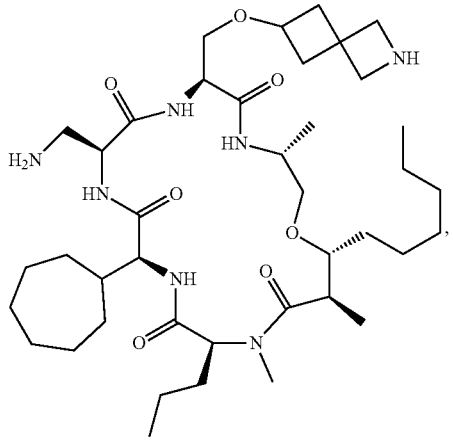
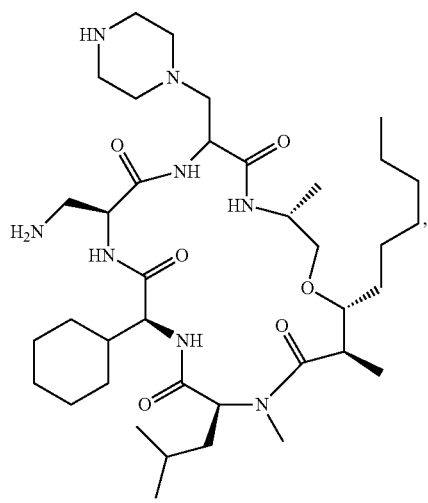

9
-continued
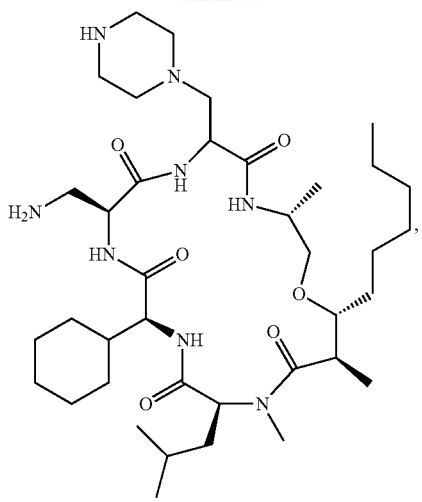
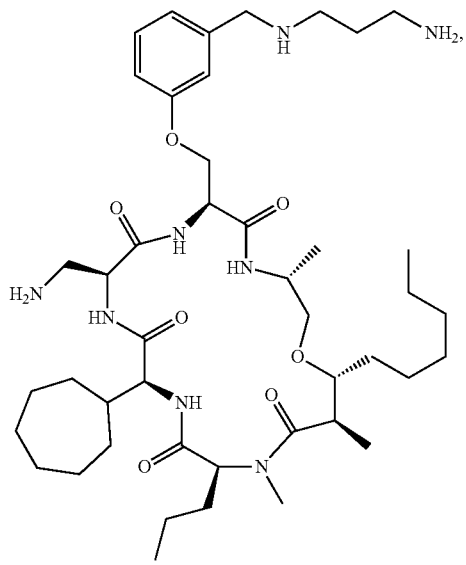
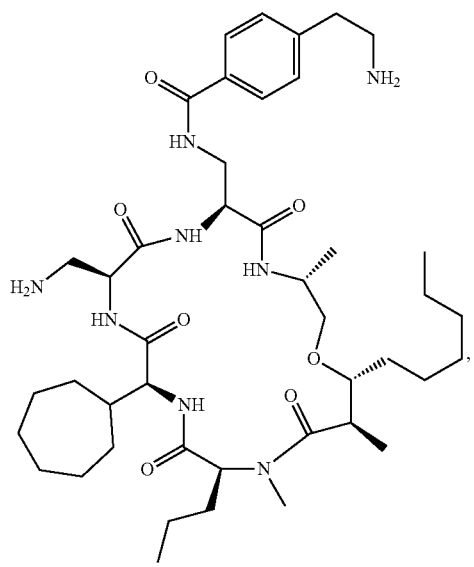
10
-continued
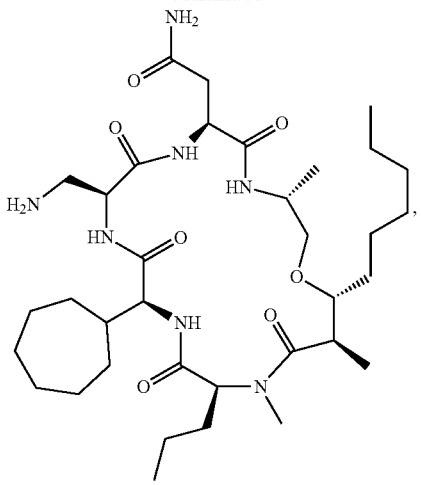
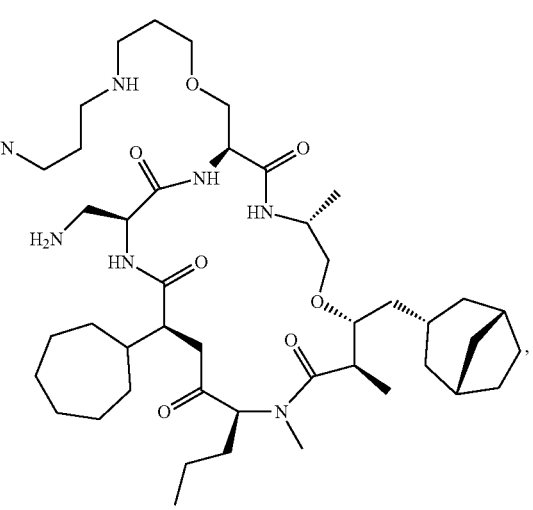
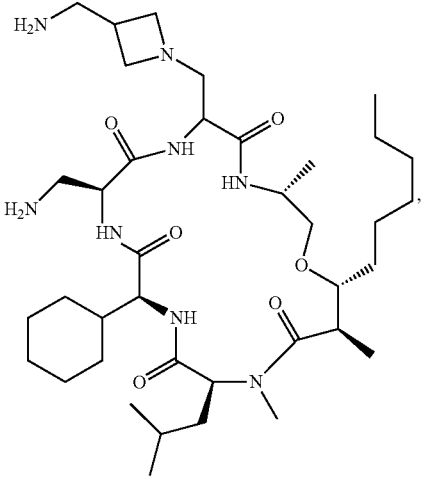

11
-continued
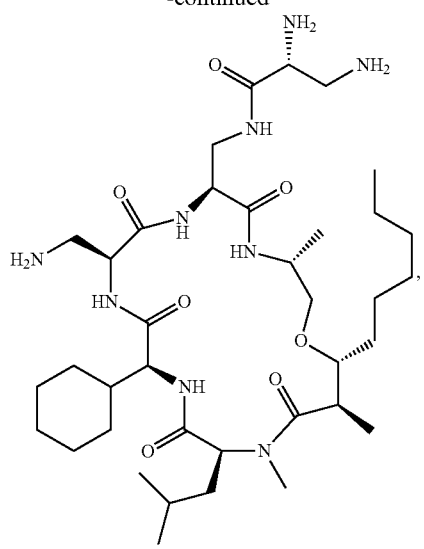
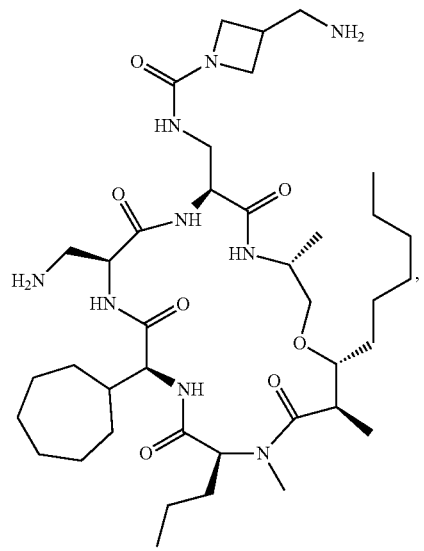
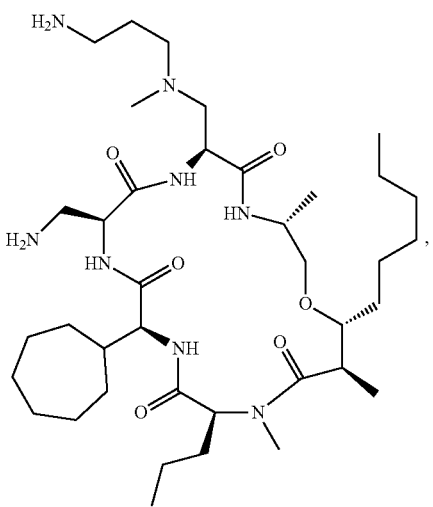
12
-continued
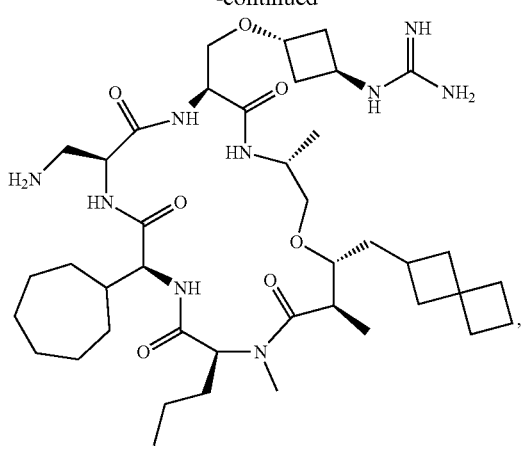
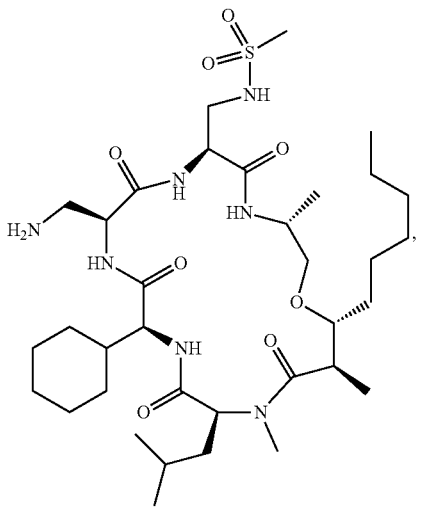
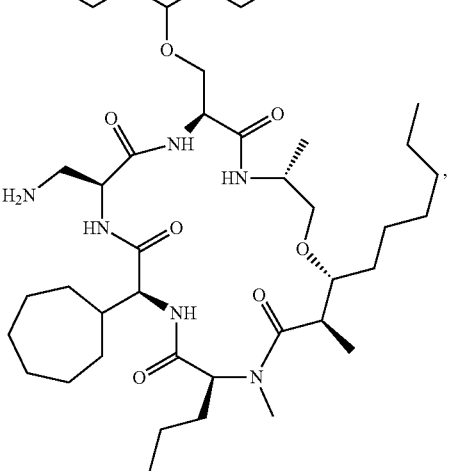

13
-continued
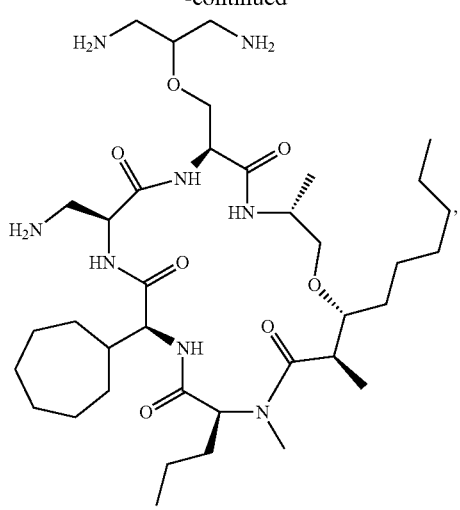
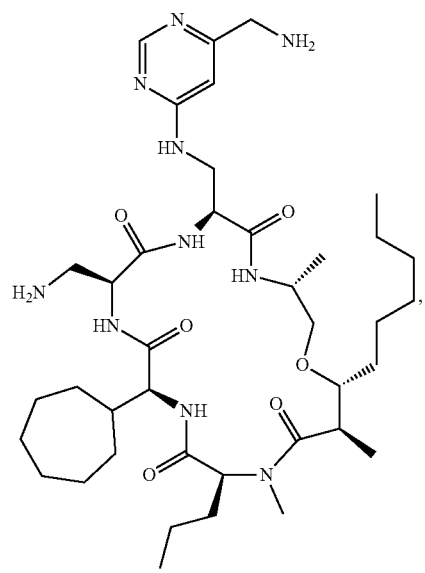
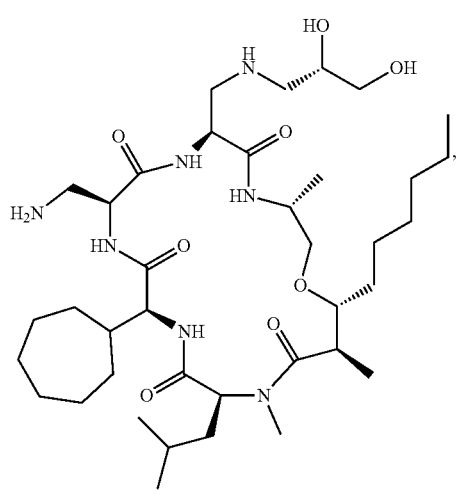
14
-continued
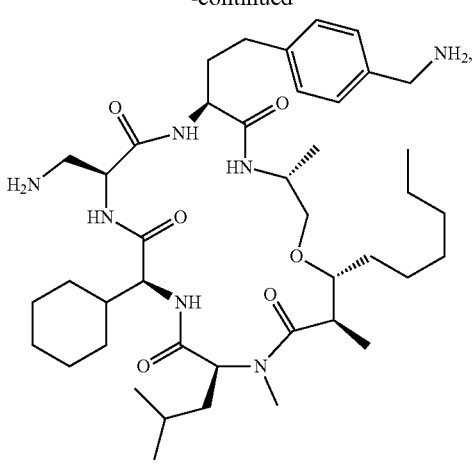
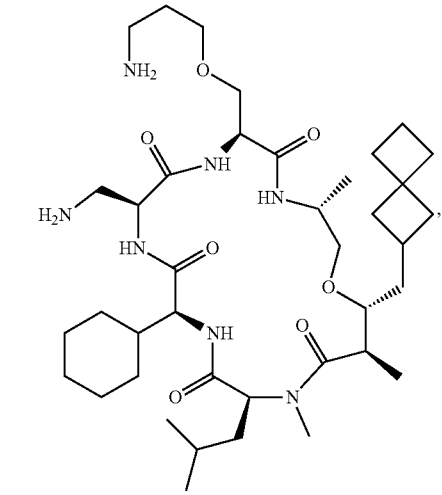
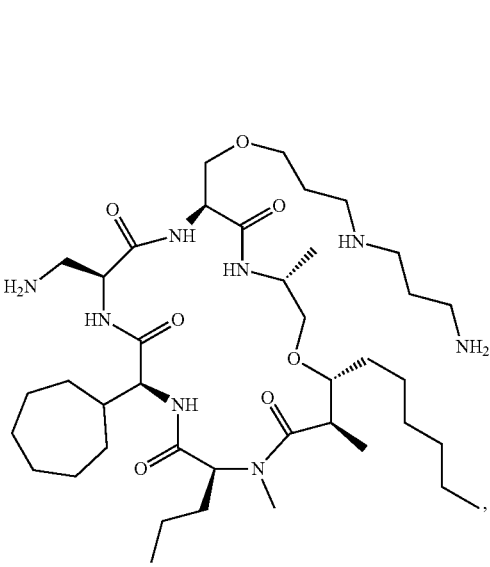

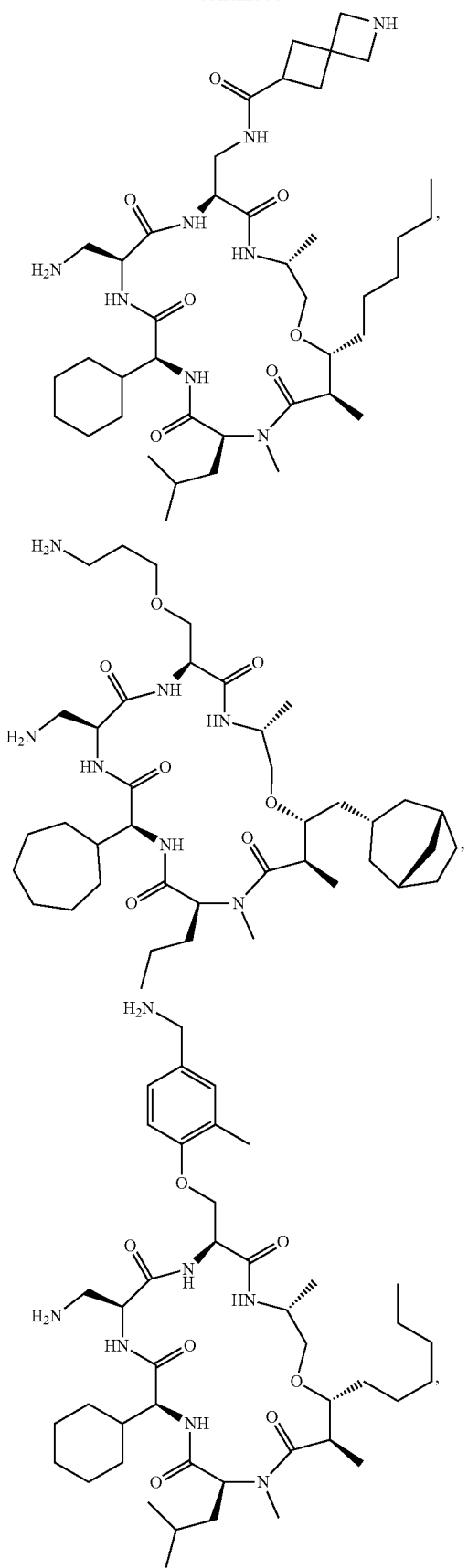
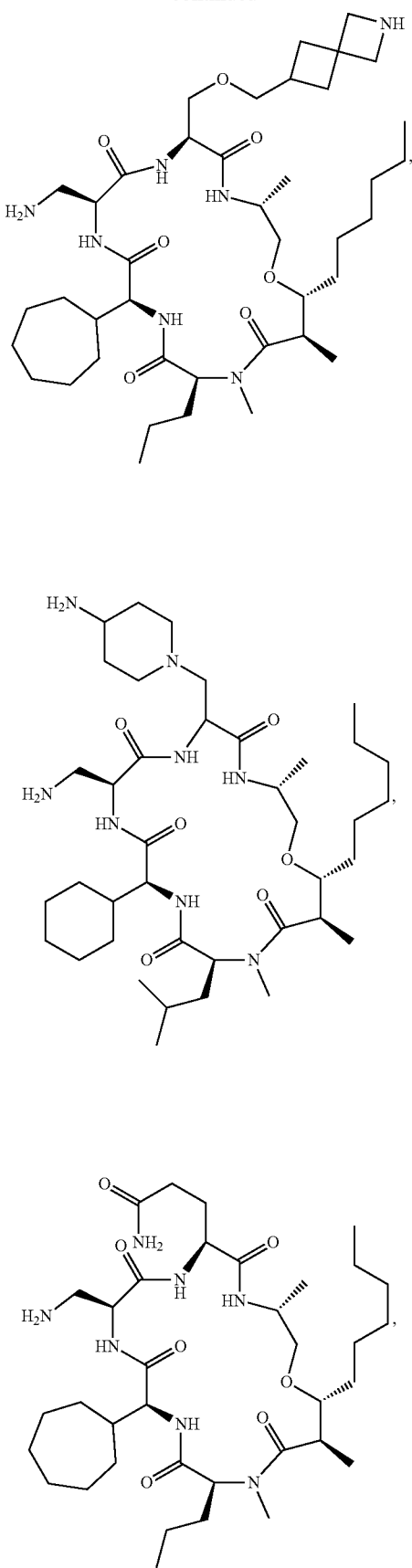

-continued
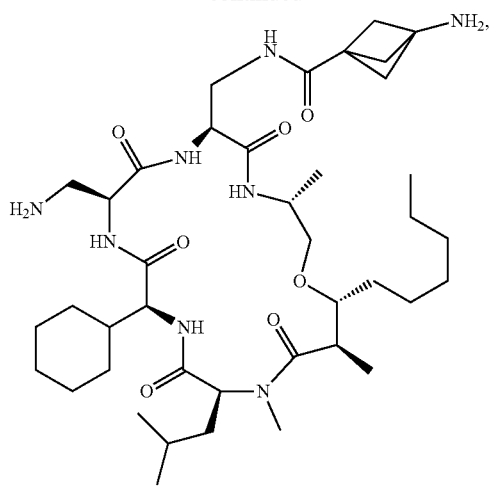
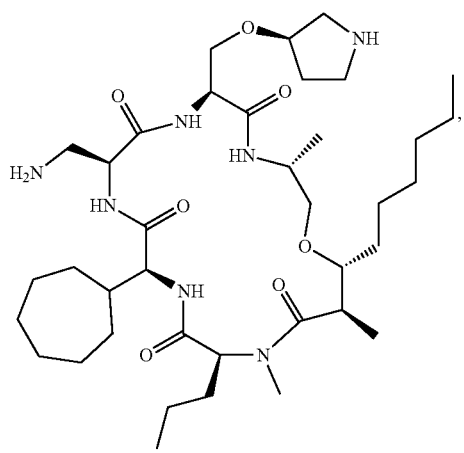
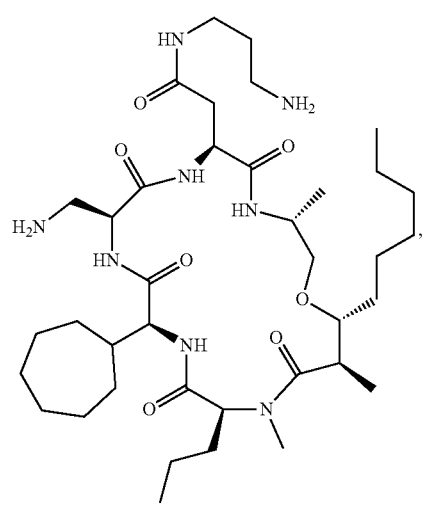
-continued
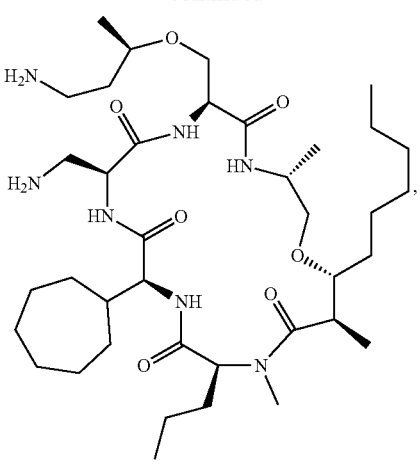
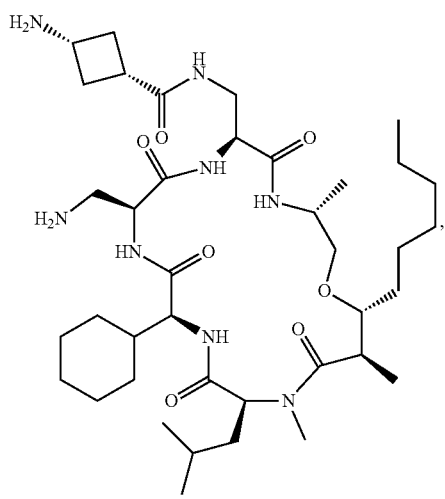
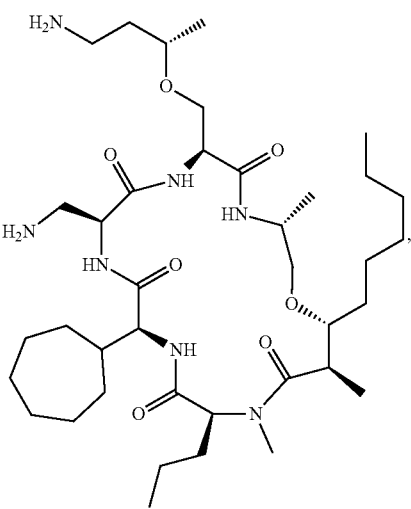

-continued
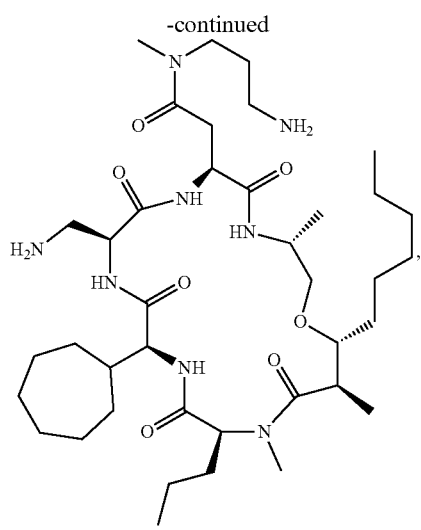
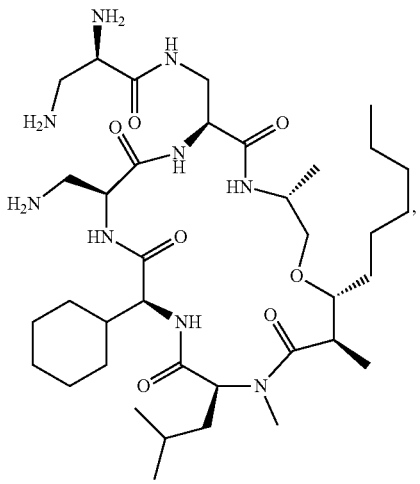
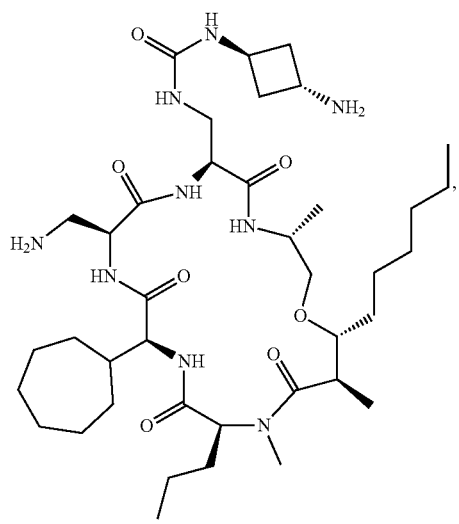
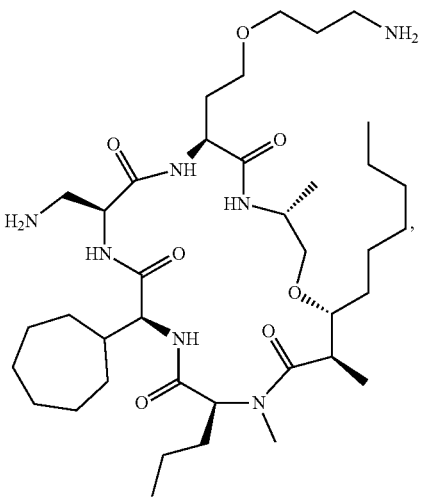
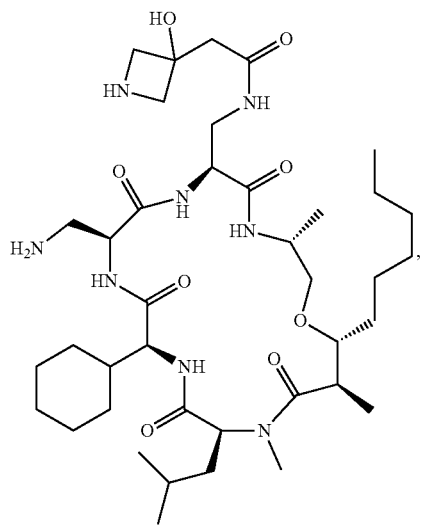
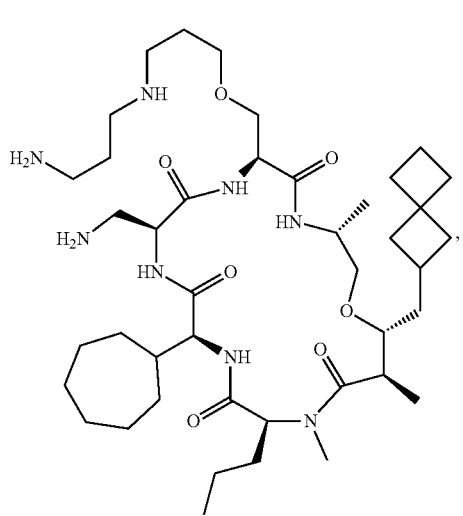

-continued

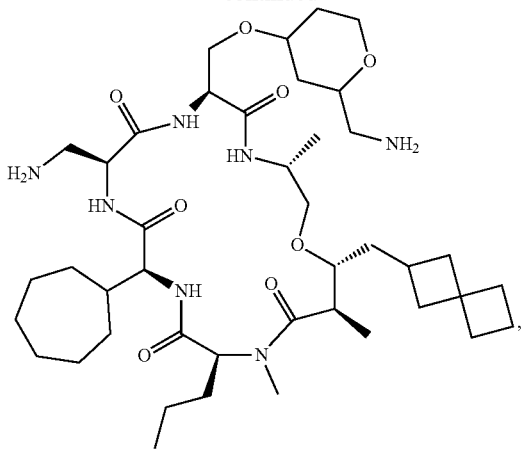

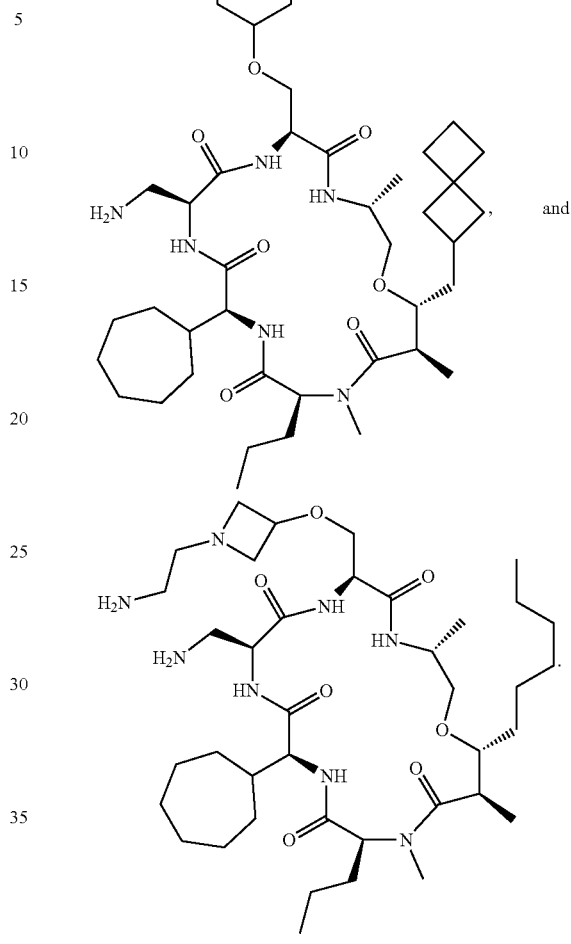

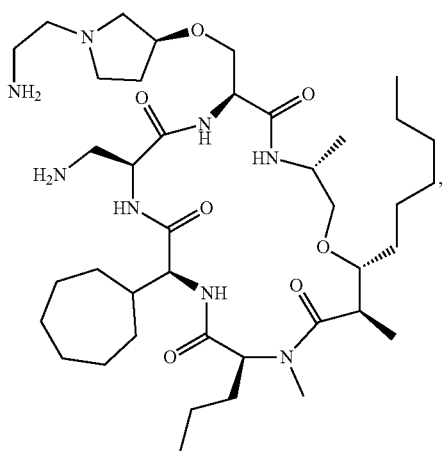

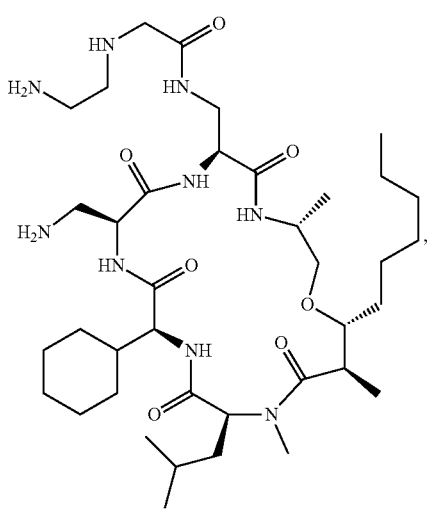

Also disclosed herein is a pharmaceutical composition comprising the compound disclosed herein, or a pharmaceutically acceptable salt, solvate, or stereoisomer thereof, and a pharmaceutically acceptable excipient.

Also disclosed herein is the use of a compound disclosed herein, or a pharmaceutically acceptable salt, solvate, or stereoisomer thereof, for preparation of a medicament for treatment of a bacterial infection in a patient.

Also disclosed herein is a method of treatment of a bacterial infection in a mammal, comprising administering to the mammal an effective amount of a compound disclosed herein, or a pharmaceutically acceptable salt, solvate, or stereoisomer thereof, to the mammal at a frequency and for a duration sufficient to provide a beneficial effect to the mammal.

INCORPORATION BY REFERENCE

All publications, patents, and patent applications mentioned in this specification are herein incorporated by reference to the same extent as if each individual publication, patent, or patent application was specifically and individually indicated to be incorporated by reference.

DETAILED DESCRIPTION OF THE INVENTION

Definitions

As used herein and in the appended claims, the singular forms "a," "and," and "the" include plural referents unless the context clearly dictates otherwise. Thus, for example, reference to "an agent" includes a plurality of such agents, and reference to "the cell" includes reference to one or more cells (or to a plurality of cells) and equivalents thereof known to those skilled in the art, and so forth. When ranges are used herein for physical properties, such as molecular weight, or chemical properties, such as chemical formulae, all combinations and subcombinations of ranges and specific embodiments therein are intended to be included. The term "about" when referring to a number or a numerical range means that the number or numerical range referred to is an approximation within experimental variability (or within statistical experimental error), and thus the number or numerical range, in some instances, will vary between 1% and 15% of the stated number or numerical range. The term "comprising" (and related terms such as "comprise" or "comprises" or "having" or "including") is not intended to exclude that in other certain embodiments, for example, an embodiment of any composition of matter, composition, method, or process, or the like, described herein, "consist of" or "consist essentially of" the described features.

As used in the specification and appended claims, unless specified to the contrary, the following terms have the meaning indicated below.

"Alkyl" refers to an optionally substituted straight-chain, or optionally substituted branched-chain saturated hydrocarbon monoradical having from one to about ten carbon atoms, or from one to six carbon atoms, wherein a sp3-hybridized carbon of the alkyl residue is attached to the rest of the molecule by a single bond. Examples include, but are not limited to, methyl, ethyl, n-propyl, isopropyl, 2-methyl-1-propyl, 2-methyl-2-propyl, 2-methyl-1-butyl, 3-methyl-1-butyl, 2-methyl-3-butyl, 2,2-dimethyl-1-propyl, 2-methyl-1-pentyl, 3-methyl-1-pentyl, 4-methyl-1-pentyl, 2-methyl-2-pentyl, 3-methyl-2-pentyl, 4-methyl-2-pentyl, 2,2-dimethyl-1-butyl, 3,3-dimethyl-1-butyl, 2-ethyl-1-butyl, n-butyl, isobutyl, sec-butyl, t-butyl, n-pentyl, isopentyl, neopentyl, tert-amyl and hexyl, and longer alkyl groups, such as heptyl, octyl, and the like. Whenever it appears herein, a numerical range such as "$C_1$-$C_6$ alkyl" means that the alkyl group consists of 1 carbon atom, 2 carbon atoms, 3 carbon atoms, 4 carbon atoms, 5 carbon atoms or 6 carbon atoms, although the present definition also covers the occurrence of the term "alkyl" where no numerical range is designated. In some embodiments, the alkyl is a $C_1$-$C_{20}$ alkyl, $C_1$-$C_{10}$ alkyl, a $C_1$-$C_9$ alkyl, a $C_1$-$C_8$ alkyl, a $C_1$-$C_7$ alkyl, a $C_1$-$C_6$ alkyl, a $C_1$-$C_5$ alkyl, a $C_1$-$C_4$ alkyl, a $C_1$-$C_3$ alkyl, a $C_1$-$C_2$ alkyl, or a $C_1$ alkyl. Unless stated otherwise specifically in the specification, an alkyl group is optionally substituted as described below, for example, with oxo, halogen, amino, nitrile, nitro, hydroxyl, haloalkyl, alkoxy, aryl, cycloalkyl, heterocycloalkyl, heteroaryl, and the like. In some embodiments, the alkyl is optionally substituted with oxo, halogen, —CN, —CF$_3$, —OH, —OMe, —NH$_2$, or —NO$_2$. In some embodiments, the alkyl is optionally substituted with oxo, halogen, —CN, —CF$_3$, —OH, or —OMe. In some embodiments, the alkyl is optionally substituted with halogen.

"Alkenyl" refers to an optionally substituted straight-chain, or optionally substituted branched-chain hydrocarbon monoradical having one or more carbon-carbon double-bonds and having from two to about ten carbon atoms, more preferably two to about six carbon atoms, wherein a sp2-hybridized carbon of the alkenyl residue is attached to the rest of the molecule by a single bond. The group may be in either the cis or trans conformation about the double bond(s), and should be understood to include both isomers. Examples include, but are not limited to ethenyl (—CH═CH$_2$), 1-propenyl (—CH$_2$CH═CH$_2$), isopropenyl [—C(CH$_3$)═CH$_2$], butenyl, 1,3-butadienyl and the like. Whenever it appears herein, a numerical range such as "$C_2$-$C_6$ alkenyl" means that the alkenyl group may consist of 2 carbon atoms, 3 carbon atoms, 4 carbon atoms, 5 carbon atoms or 6 carbon atoms, although the present definition also covers the occurrence of the term "alkenyl" where no numerical range is designated. In some embodiments, the alkenyl is a $C_2$-$C_{20}$ alkenyl, a $C_2$-$C_{10}$ alkenyl, a $C_2$-$C_9$ alkenyl, a $C_2$-$C_8$ alkenyl, a $C_2$-$C_7$ alkenyl, a $C_2$-$C_6$ alkenyl, a $C_2$-$C_5$ alkenyl, a $C_2$-$C_4$ alkenyl, a $C_2$-$C_3$ alkenyl, or a $C_2$ alkenyl. Unless stated otherwise specifically in the specification, an alkenyl group is optionally substituted as described below, for example, with oxo, halogen, amino, nitrile, nitro, hydroxyl, haloalkyl, alkoxy, aryl, cycloalkyl, heterocycloalkyl, heteroaryl, and the like. In some embodiments, an alkenyl is optionally substituted with oxo, halogen, —CN, —CF$_3$, —OH, —OMe, —NH$_2$, or —NO$_2$. In some embodiments, an alkenyl is optionally substituted with oxo, halogen, —CN, —CF$_3$, —OH, or —OMe. In some embodiments, the alkenyl is optionally substituted with halogen.

"Alkynyl" refers to an optionally substituted straight-chain or optionally substituted branched-chain hydrocarbon monoradical having one or more carbon-carbon triple-bonds and having from two to about ten carbon atoms, more preferably from two to about six carbon atoms. Examples include, but are not limited to ethynyl, 2-propynyl, 2-butynyl, 1,3-butadiynyl and the like. Whenever it appears herein, a numerical range such as "$C_2$-$C_6$ alkynyl" means that the alkynyl group may consist of 2 carbon atoms, 3 carbon atoms, 4 carbon atoms, 5 carbon atoms or 6 carbon atoms, although the present definition also covers the occurrence of the term "alkynyl" where no numerical range is designated. In some embodiments, the alkynyl is a $C_2$-$C_{20}$ alkynyl, a $C_2$-$C_{10}$ alkynyl, a $C_2$-$C_9$ alkynyl, a $C_2$-$C_8$ alkynyl, a $C_2$-$C_7$ alkynyl, a $C_2$-$C_6$ alkynyl, a $C_2$-$C_5$ alkynyl, a $C_2$-$C_4$ alkynyl, a $C_2$-$C_3$ alkynyl, or a $C_2$ alkynyl. Unless stated otherwise specifically in the specification, an alkynyl group is optionally substituted as described below, for example, with oxo, halogen, amino, nitrile, nitro, hydroxyl, haloalkyl, alkoxy, aryl, cycloalkyl, heterocycloalkyl, heteroaryl, and the like. In some embodiments, an alkynyl is optionally substituted with oxo, halogen, —CN, —CF$_3$, —OH, —OMe, —NH$_2$, or —NO$_2$. In some embodiments, an alkynyl is optionally substituted with oxo, halogen, —CN, —CF$_3$, —OH, or —OMe. In some embodiments, the alkynyl is optionally substituted with halogen.

"Alkylene" refers to a straight or branched divalent hydrocarbon chain. Unless stated otherwise specifically in the specification, an alkylene group may be optionally substituted as described below, for example, with oxo, halogen, amino, nitrile, nitro, hydroxyl, haloalkyl, alkoxy, aryl, cycloalkyl, heterocycloalkyl, heteroaryl, and the like. In some embodiments, an alkylene is optionally substituted with oxo, halogen, —CN, —CF$_3$, —OH, —OMe, —NH$_2$, or —NO$_2$. In some embodiments, an alkylene is optionally substituted with oxo, halogen, —CN, —CF$_3$, —OH, or —OMe. In some embodiments, the alkylene is optionally substituted with halogen.

"Alkoxy" refers to a radical of the formula —OR$_a$ where R$_a$ is an alkyl radical as defined. Unless stated otherwise specifically in the specification, an alkoxy group may be optionally substituted as described below, for example, with oxo, halogen, amino, nitrile, nitro, hydroxyl, haloalkyl, alkoxy, aryl, cycloalkyl, heterocycloalkyl, heteroaryl, and the like. In some embodiments, an alkoxy is optionally substituted with oxo, halogen, —CN, —CF$_3$, —OH, —OMe, —NH$_2$, or —NO$_2$. In some embodiments, an alkoxy is optionally substituted with oxo, halogen, —CN, —CF$_3$, —OH, or —OMe. In some embodiments, the alkoxy is optionally substituted with halogen.

"Aryl" refers to a radical derived from a hydrocarbon ring system comprising hydrogen, 6 to 30 carbon atoms and at least one aromatic ring. The aryl radical may be a monocyclic, bicyclic, tricyclic or tetracyclic ring system, which may include fused (when fused with a cycloalkyl or heterocycloalkyl ring, the aryl is bonded through an aromatic ring atom) or bridged ring systems. In some embodiments, the aryl is a 6- to 10-membered aryl. In some embodiments, the aryl is a 6-membered aryl. Aryl radicals include, but are not limited to, aryl radicals derived from the hydrocarbon ring systems of anthrylene, naphthylene, phenanthrylene, anthracene, azulene, benzene, chrysene, fluoranthene, fluorene, as-indacene, s-indacene, indane, indene, naphthalene, phenalene, phenanthrene, pleiadene, pyrene, and triphenylene. In some embodiments, the aryl is phenyl. Unless stated otherwise specifically in the specification, an aryl may be optionally substituted as described below, for example, with halogen, amino, nitrile, nitro, hydroxyl, alkyl, alkenyl, alkynyl, haloalkyl, alkoxy, aryl, cycloalkyl, heterocycloalkyl, heteroaryl, and the like. In some embodiments, an aryl is optionally substituted with halogen, methyl, ethyl, —CN, —CF$_3$, —OH, —OMe, —NH$_2$, or —NO$_2$. In some embodiments, an aryl is optionally substituted with halogen, methyl, ethyl, —CN, —CF$_3$, —OH, or —OMe. In some embodiments, the aryl is optionally substituted with halogen or methyl. In some embodiments, the aryl is optionally substituted with halogen.

"Cycloalkyl" refers to a stable, partially or fully saturated, monocyclic or polycyclic carbocyclic ring, which may include fused (when fused with an aryl or a heteroaryl ring, the cycloalkyl is bonded through a non-aromatic ring atom) or bridged ring systems. Representative cycloalkyls include, but are not limited to, cycloalkyls having from three to fifteen carbon atoms ($C_3$-$C_{15}$ cycloalkyl), from three to ten carbon atoms ($C_3$-$C_{10}$ cycloalkyl), from three to eight carbon atoms ($C_3$-$C_8$ cycloalkyl), from three to six carbon atoms ($C_3$-$C_6$ cycloalkyl), from three to five carbon atoms ($C_3$-$C_5$ cycloalkyl), or three to four carbon atoms ($C_3$-$C_4$ cycloalkyl). In some embodiments, the cycloalkyl is a 3- to 6-membered cycloalkyl. In some embodiments, the cycloalkyl is a 5- to 6-membered cycloalkyl. Monocyclic cycloalkyls include, for example, cyclopropyl, cyclobutyl, cyclopentyl, cyclohexyl, cycloheptyl, and cyclooctyl. Polycyclic cycloalkyls or carbocycles include, for example, adamantyl, norbornyl, decalinyl, bicyclo[3.3.0]octane, bicyclo[4.3.0]nonane, cis-decalin, trans-decalin, bicyclo[2.1.1]hexane, bicyclo[2.2.1]heptane, bicyclo[2.2.2]octane, bicyclo[3.2.2]nonane, and bicyclo[3.3.2]decane, and 7,7-dimethyl-bicyclo[2.2.1]heptanyl. Partially saturated cycloalkyls include, for example cyclopentenyl, cyclohexenyl, cycloheptenyl, and cyclooctenyl. Unless stated otherwise specifically in the specification, a cycloalkyl is optionally substituted as described below, for example, with oxo, halogen, amino, nitrile, nitro, hydroxyl, alkyl, alkenyl, alkynyl, haloalkyl, alkoxy, aryl, cycloalkyl, heterocycloalkyl, heteroaryl, and the like. In some embodiments, a cycloalkyl is optionally substituted with oxo, halogen, methyl, ethyl, —CN, —CF$_3$, —OH, —OMe, —NH$_2$, or —NO$_2$. In some embodiments, a cycloalkyl is optionally substituted with oxo, halogen, methyl, ethyl, —CN, —CF$_3$, —OH, or —OMe. In some embodiments, the cycloalkyl is optionally substituted with halogen or methyl. In some embodiments, the cycloalkyl is optionally substituted with halogen.

"Halo" or "halogen" refers to bromo, chloro, fluoro, or iodo. In some embodiments, halogen is fluoro or chloro. In some embodiments, halogen is fluoro.

"Haloalkyl" refers to an alkyl radical, as defined above, that is substituted by one or more halo radicals, as defined above, e.g., trifluoromethyl, difluoromethyl, fluoromethyl, trichloromethyl, 2,2,2-trifluoroethyl, 1,2-difluoroethyl, 3-bromo-2-fluoropropyl, 1,2-dibromoethyl, and the like.

"Heterocycloalkyl" refers to a stable 3- to 24-membered partially or fully saturated ring radical comprising 2 to 23 carbon atoms and from one to 8 heteroatoms selected from the group consisting of nitrogen, oxygen, phosphorous and sulfur. Unless stated otherwise specifically in the specification, the heterocycloalkyl radical may be a monocyclic, bicyclic, tricyclic or tetracyclic ring system, which may include fused (when fused with an aryl or a heteroaryl ring, the heterocycloalkyl is bonded through a non-aromatic ring atom) or bridged ring systems; and the nitrogen, carbon or sulfur atoms in the heterocycloalkyl radical may be optionally oxidized; the nitrogen atom may be optionally quaternized. In some embodiments, the heterocycloalkyl is a 3- to 6-membered heterocycloalkyl. In some embodiments, the heterocycloalkyl is a 5- to 6-membered heterocycloalkyl. Examples of such heterocycloalkyl radicals include, but are not limited to, aziridinyl, azetidinyl, dioxolanyl, thienyl[1,3]dithianyl, decahydroisoquinolyl, imidazolinyl, imidazolidinyl, isothiazolidinyl, isoxazolidinyl, morpholinyl, octahydroindolyl, octahydroisoindolyl, 2-oxopiperazinyl, 2-oxopiperidinyl, 2-oxopyrrolidinyl, oxazolidinyl, piperidinyl, piperazinyl, 4-piperidonyl, pyrrolidinyl, pyrazolidinyl, quinuclidinyl, thiazolidinyl, tetrahydrofuryl, trithianyl, tetrahydropyranyl, thiomorpholinyl, thiamorpholinyl, 1-oxo-thiomorpholinyl, 1,1-dioxo-thiomorpholinyl, 1,3-dihydroisobenzofuran-1-yl, 3-oxo-1,3-dihydroisobenzofuran-1-yl, methyl-2-oxo-1,3-dioxol-4-yl, and 2-oxo-1,3-dioxol-4-yl. The term heterocycloalkyl also includes all ring forms of the carbohydrates, including but not limited to the monosaccharides, the disaccharides and the oligosaccharides. Unless otherwise noted, heterocycloalkyls have from 2 to 10 carbons in the ring. It is understood that when referring to the number of carbon atoms in a heterocycloalkyl, the number of carbon atoms in the heterocycloalkyl is not the same as the total number of atoms (including the heteroatoms) that make up the heterocycloalkyl (i.e. skeletal atoms of the heterocycloalkyl ring). Unless stated otherwise specifically in the specification, a heterocycloalkyl is optionally substituted as described below, for example, with oxo, halogen, amino, nitrile, nitro, hydroxyl, alkyl, alkenyl, alkynyl, haloalkyl, alkoxy, aryl, cycloalkyl, heterocycloalkyl, heteroaryl, and the like. In some embodiments, a heterocycloalkyl is optionally substituted with oxo, halogen, methyl, ethyl, —CN, —CF$_3$, —OH, —OMe, —NH$_2$, or —NO$_2$. In some embodiments, a heterocycloalkyl is optionally substituted with oxo, halogen, methyl, ethyl, —CN, —CF$_3$, —OH, or —OMe. In some embodiments, the heterocycloalkyl is optionally substituted with halogen or methyl. In some embodiments, the heterocycloalkyl is optionally substituted with halogen.

"Heteroalkyl" refers to an alkyl group in which one or more skeletal atoms of the alkyl are selected from an atom other than carbon, e.g., oxygen, nitrogen (e.g. —NH—, —N(alkyl)-), sulfur, or combinations thereof. A heteroalkyl is attached to the rest of the molecule at a carbon atom of the heteroalkyl. In one aspect, a heteroalkyl is a $C_1$-$C_6$ heteroalkyl. Unless stated otherwise specifically in the specification, a Heteroalkyl is optionally substituted as described below, for example, with oxo, halogen, amino, nitrile, nitro, hydroxyl, alkyl, alkenyl, alkynyl, haloalkyl, alkoxy, aryl, cycloalkyl, heterocycloalkyl, heteroaryl, and the like. In some embodiments, a heteroalkyl is optionally substituted with oxo, halogen, methyl, ethyl, —CN, —$CF_3$, —OH, —OMe, —$NH_2$, or —$NO_2$. In some embodiments, a heteroalkyl is optionally substituted with oxo, halogen, methyl, ethyl, —CN, —$CF_3$, —OH, or —OMe. In some embodiments, the heteroalkyl is optionally substituted with halogen.

"Heteroaryl" refers to a 5- to 14-membered ring system radical comprising hydrogen atoms, one to thirteen carbon atoms, one to six heteroatoms selected from the group consisting of nitrogen, oxygen, phosphorous and sulfur, and at least one aromatic ring. The heteroaryl radical may be a monocyclic, bicyclic, tricyclic or tetracyclic ring system, which may include fused (when fused with a cycloalkyl or heterocycloalkyl ring, the heteroaryl is bonded through an aromatic ring atom) or bridged ring systems; and the nitrogen, carbon or sulfur atoms in the heteroaryl radical may be optionally oxidized; the nitrogen atom may be optionally quaternized. In some embodiments, the heteroaryl is a 5- to 10-membered heteroaryl. In some embodiments, the heteroaryl is a 5- to 6-membered heteroaryl. Examples include, but are not limited to, azepinyl, acridinyl, benzimidazolyl, benzothiazolyl, benzindolyl, benzodioxolyl, benzofuranyl, benzooxazolyl, benzothiazolyl, benzothiadiazolyl, benzo[b][1,4]dioxepinyl, 1,4-benzodioxanyl, benzonaphthofuranyl, benzoxazolyl, benzodioxolyl, benzodioxinyl, benzopyranyl, benzopyranonyl, benzofuranyl, benzofuranonyl, benzothienyl (benzothiophenyl), benzotriazolyl, benzo[4,6]imidazo[1,2-a]pyridinyl, carbazolyl, cinnolinyl, dibenzofuranyl, dibenzothiophenyl, furanyl, furanonyl, isothiazolyl, imidazolyl, indazolyl, indolyl, indazolyl, isoindolyl, indolinyl, isoindolinyl, isoquinolyl, indolizinyl, isoxazolyl, naphthyridinyl, oxadiazolyl, 2-oxoazepinyl, oxazolyl, oxiranyl, 1-oxidopyridinyl, 1-oxidopyrimidinyl, 1-oxidopyrazinyl, 1-oxidopyridazinyl, 1-phenyl-1H-pyrrolyl, phenazinyl, phenothiazinyl, phenoxazinyl, phthalazinyl, pteridinyl, purinyl, pyrrolyl, pyrazolyl, pyridinyl, pyrazinyl, pyrimidinyl, pyridazinyl, quinazolinyl, quinoxalinyl, quinolinyl, quinuclidinyl, isoquinolinyl, tetrahydroquinolinyl, thiazolyl, thiadiazolyl, triazolyl, tetrazolyl, triazinyl, and thiophenyl (i.e., thienyl). Unless stated otherwise specifically in the specification, a heteroaryl is optionally substituted as described below, for example, with halogen, amino, nitrile, nitro, hydroxyl, alkyl, alkenyl, alkynyl, haloalkyl, alkoxy, aryl, cycloalkyl, heterocycloalkyl, heteroaryl, and the like. In some embodiments, a heteroaryl is optionally substituted with halogen, methyl, ethyl, —CN, —$CF_3$, —OH, —OMe, —$NH_2$, or —$NO_2$. In some embodiments, a heteroaryl is optionally substituted with halogen, methyl, ethyl, —CN, —$CF_3$, —OH, or —OMe. In some embodiments, the heteroaryl is optionally substituted with halogen or methyl. In some embodiments, the heteroaryl is optionally substituted with halogen.

The term "oxo" means =O.

The terms "treat," "prevent," "ameliorate," and "inhibit," as well as words stemming therefrom, as used herein, do not necessarily imply 100% or complete treatment, prevention, amelioration, or inhibition. Rather, there are varying degrees of treatment, prevention, amelioration, and inhibition of which one of ordinary skill in the art recognizes as having a potential benefit or therapeutic effect. In this respect, the disclosed methods can provide any amount of any level of treatment, prevention, amelioration, or inhibition of the disorder in a mammal. For example, a disorder, including symptoms or conditions thereof, may be reduced by, for example, about 100%, about 90%, about 80%, about 70%, about 60%, about 50%, about 40%, about 30%, about 20%, or about 10%. Furthermore, the treatment, prevention, amelioration, or inhibition provided by the methods disclosed herein can include treatment, prevention, amelioration, or inhibition of one or more conditions or symptoms of the disorder, e.g., cancer or an inflammatory disease. Also, for purposes herein, "treatment," "prevention," "amelioration," or "inhibition" encompass delaying the onset of the disorder, or a symptom or condition thereof.

The terms "effective amount" or "therapeutically effective amount," as used herein, refer to a sufficient amount of a compound disclosed herein being administered which will relieve to some extent one or more of the symptoms of the disease or condition being treated, e.g., cancer or an inflammatory disease. In some embodiments, the result is a reduction and/or alleviation of the signs, symptoms, or causes of a disease, or any other desired alteration of a biological system. For example, an "effective amount" for therapeutic uses is the amount of the composition comprising a compound disclosed herein required to provide a clinically significant decrease in disease symptoms. In some embodiments, an appropriate "effective" amount in any individual case is determined using techniques, such as a dose escalation study.

As used herein, "individual" (as in the subject of the treatment) means both mammals and non-mammals. Mammals include, for example, humans; non-human primates, e.g. apes and monkeys; and non-primates, e.g. dogs, cats, cattle, horses, sheep, and goats. Non-mammals include, for example, fish and birds.

The terms "disease" or "disorder" are used interchangeably, and are used to refer to diseases or conditions wherein a bacterial signal peptidase plays a role in the biochemical mechanisms involved in the disease or disorder such that a therapeutically beneficial effect can be achieved by acting on the enzyme. "Acting on" signal peptidase can include binding to signal peptidase and/or inhibiting the bioactivity of an signal peptidase.

Compounds

In one aspect described herein are compounds of Formula (I):

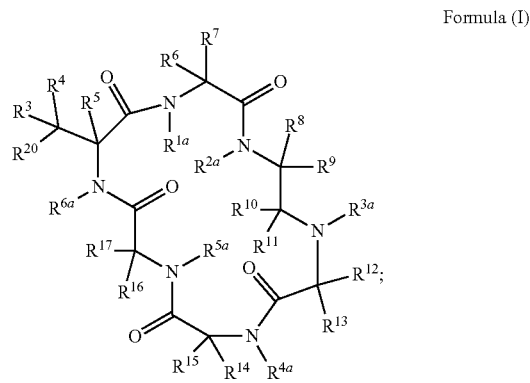

Formula (I)

wherein:
$R^{1a}$, $R^{2a}$, $R^{4a}$, $R^{5a}$, and $R^{6a}$ are each independently hydrogen or optionally substituted $C_1$-$C_6$ alkyl;
$R^{3a}$ is hydrogen, optionally substituted $C_1$-$C_{20}$ alkyl, optionally substituted $C_2$-$C_{20}$ alkenyl, optionally substituted $C_2$-$C_{20}$ alkynyl, optionally substituted cycloalkyl, optionally substituted ($C_1$-$C_6$ alkyl)cycloalkyl, optionally substituted heterocycloalkyl, optionally substituted ($C_1$-$C_6$ alkyl)heterocycloalkyl, optionally substituted aryl, optionally substituted ($C_1$-$C_6$ alkyl)aryl, optionally substituted heteroaryl, or optionally substituted ($C_1$-$C_6$ alkyl)heteroaryl;
$R^{20}$ is hydroxyl or —$NR^1R^2$;
$R^1$ and $R^2$ are each independently hydrogen, optionally substituted $C_1$-$C_6$ alkyl, optionally substituted $C_2$-$C_6$ alkenyl, optionally substituted $C_2$-$C_6$ alkynyl, optionally substituted cycloalkyl, optionally substituted ($C_1$-$C_6$ alkyl)cycloalkyl, optionally substituted heterocycloalkyl, optionally substituted ($C_1$-$C_6$ alkyl)heterocycloalkyl, optionally substituted aryl, optionally substituted ($C_1$-$C_6$ alkyl)aryl, optionally substituted heteroaryl, optionally substituted ($C_1$-$C_6$ alkyl)heteroaryl, —$S(=O)_2R^a$, —$S(=O)_2NR^bR^c$, —$C(=O)R^a$, —$C(=O)OR^b$, —$C(=O)NR^bR^c$, or —$(C=NR^b)NR^bR^c$;
or $R^1$ and $R^2$ are taken together with the nitrogen atom to which they are attached to form an optionally substituted heterocycloalkyl;
$R^3$ and $R^4$ are each independently hydrogen, optionally substituted $C_1$-$C_6$ alkyl, optionally substituted $C_2$-$C_6$ alkenyl, optionally substituted $C_2$-$C_6$ alkynyl, optionally substituted cycloalkyl, optionally substituted heterocycloalkyl, optionally substituted aryl, or optionally substituted heteroaryl;
or $R^3$ and $R^4$ are taken together with the carbon atom to which they are attached to form an oxo;
$R^5$ is hydrogen, halogen, optionally substituted $C_1$-$C_6$ alkyl, optionally substituted $C_2$-$C_6$ alkenyl, or optionally substituted $C_2$-$C_6$ alkynyl;
$R^6$ and $R^7$ are each independently hydrogen, halogen, optionally substituted $C_1$-$C_6$ alkyl, optionally substituted $C_2$-$C_6$ alkenyl, optionally substituted $C_2$-$C_6$ alkynyl, optionally substituted cycloalkyl, optionally substituted ($C_1$-$C_6$ alkyl)cycloalkyl, optionally substituted heterocycloalkyl, optionally substituted ($C_1$-$C_6$ alkyl)heterocycloalkyl, optionally substituted aryl, optionally substituted ($C_1$-$C_6$ alkyl)aryl, optionally substituted heteroaryl, or optionally substituted ($C_1$-$C_6$ alkyl)heteroaryl;
$R^8$ and $R^9$ are each independently hydrogen, halogen, optionally substituted $C_1$-$C_6$ alkyl, optionally substituted $C_2$-$C_6$ alkenyl, optionally substituted $C_2$-$C_6$ alkynyl, optionally substituted cycloalkyl, optionally substituted ($C_1$-$C_6$ alkyl)cycloalkyl, optionally substituted heterocycloalkyl, optionally substituted ($C_1$-$C_6$ alkyl)heterocycloalkyl, optionally substituted aryl, optionally substituted ($C_1$-$C_6$ alkyl)aryl, optionally substituted heteroaryl, or optionally substituted ($C_1$-$C_6$ alkyl)heteroaryl;
or $R^{3a}$ and $R^8$ are taken together with the atoms to which they are attached to form an optionally substituted heterocycloalkyl;
$R^{10}$ and $R^{11}$ are each independently hydrogen, halogen, optionally substituted $C_1$-$C_6$ alkyl, optionally substituted $C_2$-$C_{20}$ alkenyl, optionally substituted $C_2$-$C_6$ alkynyl, optionally substituted cycloalkyl, optionally substituted ($C_1$-$C_6$ alkyl)cycloalkyl, optionally substituted heterocycloalkyl, optionally substituted ($C_1$-$C_6$ alkyl)heterocycloalkyl, optionally substituted aryl, optionally substituted ($C_1$-$C_6$ alkyl)aryl, optionally substituted heteroaryl, or optionally substituted ($C_1$-$C_6$ alkyl)heteroaryl;
$R^{12}$ and $R^{13}$ are each independently hydrogen, halogen, optionally substituted $C_1$-$C_{20}$ alkyl, optionally substituted $C_2$-$C_6$ alkenyl, optionally substituted $C_2$-$C_6$ alkynyl, optionally substituted cycloalkyl, optionally substituted ($C_1$-$C_6$ alkyl)cycloalkyl, optionally substituted heterocycloalkyl, optionally substituted ($C_1$-$C_6$ alkyl)heterocycloalkyl, optionally substituted aryl, optionally substituted ($C_1$-$C_6$ alkyl)aryl, optionally substituted heteroaryl, or optionally substituted ($C_1$-$C_6$ alkyl)heteroaryl;
$R^{14}$ and $R^{15}$ are each independently hydrogen, halogen, optionally substituted $C_1$-$C_6$ alkyl, optionally substituted $C_2$-$C_6$ alkenyl, optionally substituted $C_2$-$C_6$ alkynyl, optionally substituted cycloalkyl, optionally substituted ($C_1$-$C_6$ alkyl)cycloalkyl, optionally substituted heterocycloalkyl, optionally substituted ($C_1$-$C_6$ alkyl)heterocycloalkyl, optionally substituted aryl, optionally substituted ($C_1$-$C_6$ alkyl)aryl, optionally substituted heteroaryl, or optionally substituted ($C_1$-$C_6$ alkyl)heteroaryl;
$R^{16}$ and $R^{17}$ are each independently hydrogen, halogen, optionally substituted $C_1$-$C_6$ alkyl, optionally substituted $C_2$-$C_6$ alkenyl, optionally substituted $C_2$-$C_6$ alkynyl, optionally substituted cycloalkyl, optionally substituted ($C_1$-$C_6$ alkyl)cycloalkyl, optionally substituted heterocycloalkyl, optionally substituted ($C_1$-$C_6$ alkyl)heterocycloalkyl, optionally substituted aryl, optionally substituted ($C_1$-$C_6$ alkyl)aryl, optionally substituted heteroaryl, or optionally substituted ($C_1$-$C_6$ alkyl)heteroaryl;
each $R^a$ is independently optionally substituted $C_1$-$C_6$ alkyl, optionally substituted $C_2$-$C_6$ alkenyl, optionally substituted $C_2$-$C_6$ alkynyl, optionally substituted cycloalkyl, optionally substituted heterocycloalkyl, optionally substituted aryl, or optionally substituted heteroaryl;
each $R^b$ and $R^c$ is independently hydrogen, optionally substituted $C_1$-$C_6$ alkyl, optionally substituted $C_2$-$C_6$ alkenyl, optionally substituted $C_2$-$C_6$ alkynyl, optionally substituted cycloalkyl, optionally substituted heterocycloalkyl, optionally substituted aryl, or optionally substituted heteroaryl;
or $R^b$ and $R^c$ are taken together with the nitrogen atom to which they are attached to form an optionally substituted heterocycloalkyl;
or a pharmaceutically acceptable salt, solvate, or stereoisomer thereof.

In some embodiments of a compound of Formula (I), $R^{20}$ is hydroxyl. In some embodiments of a compound of Formula (I), $R^{20}$ is —$NR^1R^2$.

In some embodiments of a compound of Formula (I), $R^5$ is hydrogen.

In some embodiments of a compound of Formula (I), $R^7$ is hydrogen.

In some embodiments of a compound of Formula (I), $R^{13}$ is hydrogen.

In some embodiments of a compound of Formula (I), $R^{15}$ is hydrogen.

In some embodiments of a compound of Formula (I), $R^{17}$ is hydrogen.

In some embodiments of a compound of Formula (I), the compound has the structure of Formula (Ia):

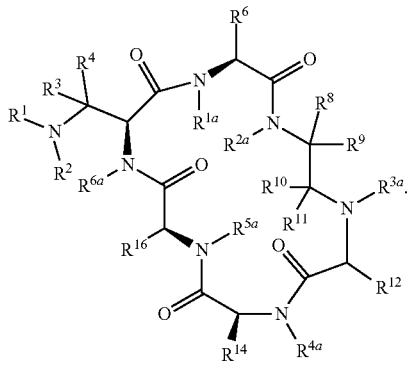

Formula (Ia)

In some embodiments of a compound of Formula (I), the compound has the structure of Formula (Ib):

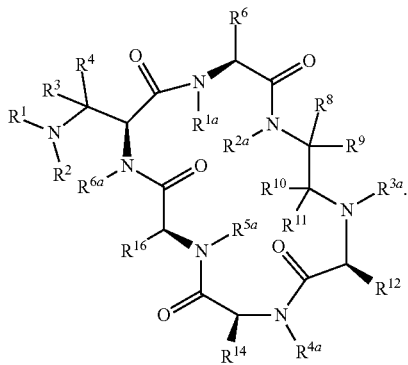

Formula (Ib)

In some embodiments of a compound of Formula (I), $R^1$ is hydrogen.

In some embodiments of a compound of Formula (I), $R^2$ is hydrogen.

In some embodiments of a compound of Formula (I), $R^3$ and $R^4$ are hydrogen.

In some embodiments of a compound of Formula (I), $R^{1a}$ is hydrogen or $C_1$-$C_6$ alkyl. In some embodiments of a compound of Formula (I), $R^{1a}$ is hydrogen.

In some embodiments of a compound of Formula (I), $R^{2a}$ is hydrogen or $C_1$-$C_6$ alkyl. In some embodiments of a compound of Formula (I), $R^{2a}$ is hydrogen.

In some embodiments of a compound of Formula (I), $R^{4a}$ is hydrogen or $C_1$-$C_6$ alkyl. In some embodiments of a compound of Formula (I), $R^{4a}$ is hydrogen.

In some embodiments of a compound of Formula (I), $R^{5a}$ is hydrogen or $C_1$-$C_6$ alkyl. In some embodiments of a compound of Formula (I), $R^{5a}$ is hydrogen.

In some embodiments of a compound of Formula (I), $R^{6a}$ is hydrogen or $C_1$-$C_6$ alkyl. In some embodiments of a compound of Formula (I), $R^{6a}$ is hydrogen.

In some embodiments of a compound of Formula (I), $R^9$ is hydrogen.

In some embodiments of a compound of Formula (I), $R^{10}$ is hydrogen.

In some embodiments of a compound of Formula (I), $R^{11}$ is hydrogen.

In some embodiments of a compound of Formula (I), $R^8$ is hydrogen or $C_1$-$C_6$ alkyl optionally substituted with one, two, or three halogen.

In some embodiments of a compound of Formula (I), $R^8$ is hydrogen or $C_1$-$C_6$ alkyl.

In some embodiments of a compound of Formula (I), $R^{3a}$ and $R^8$ are taken together with the atoms to which they are attached to form an optionally substituted heterocycloalkyl.

In some embodiments of a compound of Formula (I), $R^{3a}$ and $R^8$ are taken together with the atoms to which they are attached to form an azetidinyl, a pyrrolidinyl, or a piperidinyl.

In some embodiments of a compound of Formula (I), $R^6$ is optionally substituted $C_1$-$C_6$ alkyl or optionally substituted heterocycloalkyl.

In some embodiments of a compound of Formula (I), $R^6$ is optionally substituted $C_1$-$C_6$ alkyl.

In some embodiments of a compound of Formula (I), $R^6$ is $C_1$-$C_6$ alkyl optionally substituted with one, two, or three halogen, —$OR^b$, —$NR^bR^c$, —$NC(=NR^b)NR^bR^c$, —$S(=O)_2R^a$, —$NR^bS(=O)_2R^a$, —$S(=O)_2NR^bR^c$, —$C(=O)R^a$, —$OC(=O)R^a$, —$C(=O)OR^a$, —$OC(=O)OR^b$, —$C(=O)NR^bR^c$, —$NR^bC(=O)[C(R^d)_2]_{1-4}NR^bR^c$, —$O[C(R^d)_2]_{2-4}OR^b$, —$O[C(R^d)_2]_{2-4}NR^bR^c$, —$NR^b[C(R^d)_2]_{2-4}NR^bR^c$, —$O[C(R^d)_2]_{2-4}O[C(R^d)_2]_{2-4}NR^bR^c$, —$O[C(R^d)_2]_{2-4}NC(=NR^b)NR^bR^c$, —$OC(=O)NR^bR^c$, —$NR^bC(=O)NR^bR^c$, —$NR^bC(=O)R^a$, —$NR^bC(=O)OR^b$, —O-(cycloalkyl)$NR^bR^c$, —O-(heterocycloalkyl)$NR^bR^c$, —O-(aryl)$NR^bR^c$, —O-(heteroaryl)$NR^bR^c$, —O-(cycloalkyl)($C_1$-$C_6$ alkyl)$NR^bR^c$, —O-(heterocycloalkyl)($C_1$-$C_6$ alkyl)$NR^bR^c$, —O-(aryl)($C_1$-$C_6$ alkyl)$NR^bR^c$, —O-(heteroaryl)($C_1$-$C_6$ alkyl)$NR^bR^c$, aryl, or heteroaryl; and each $R^d$ is independently hydrogen, halogen, —OH, —$OCH_3$, or $C_1$-$C_6$ alkyl.

In some embodiments of a compound of Formula (I), $R^6$ is $C_1$-$C_6$ alkyl optionally substituted with one, two, or three —$OR^b$, —$NR^bR^c$, —$C(=O)NR^bR^c$, —$O[C(R^d)_2]_{2-4}NR^bR^c$, —$NR^b[C(R^d)_2]_{2-4}NR^bR^c$, —O-(cycloalkyl)$NR^bR^c$, —O-(cycloalkyl)($C_1$-$C_6$ alkyl)$NR^bR^c$; and each $R^d$ is independently hydrogen, halogen, —OH, —$OCH_3$, or $C_1$-$C_6$ alkyl.

In some embodiments of a compound of Formula (I), $R^6$ is $C_1$-$C_6$ alkyl optionally substituted with one, two, or three —$OR^b$.

In some embodiments of a compound of Formula (I), $R^6$ is

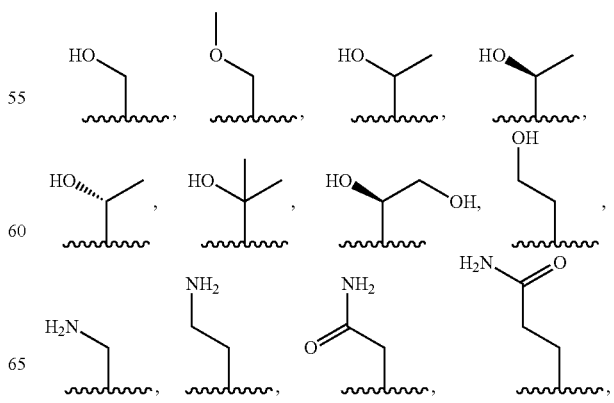

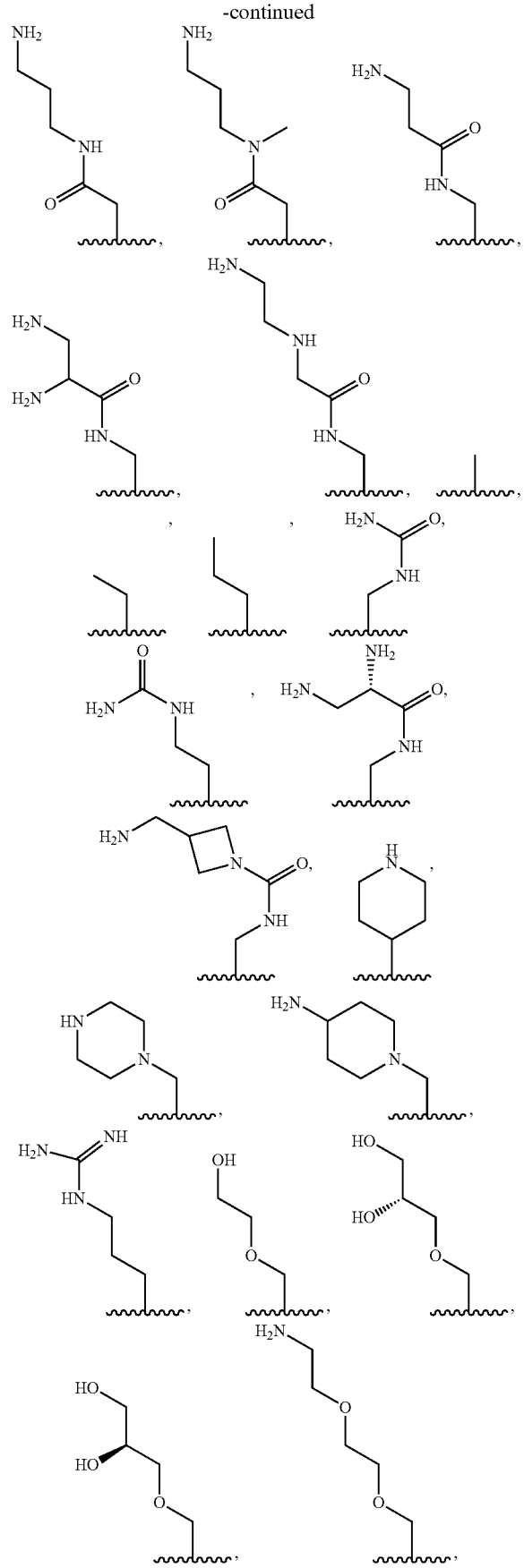
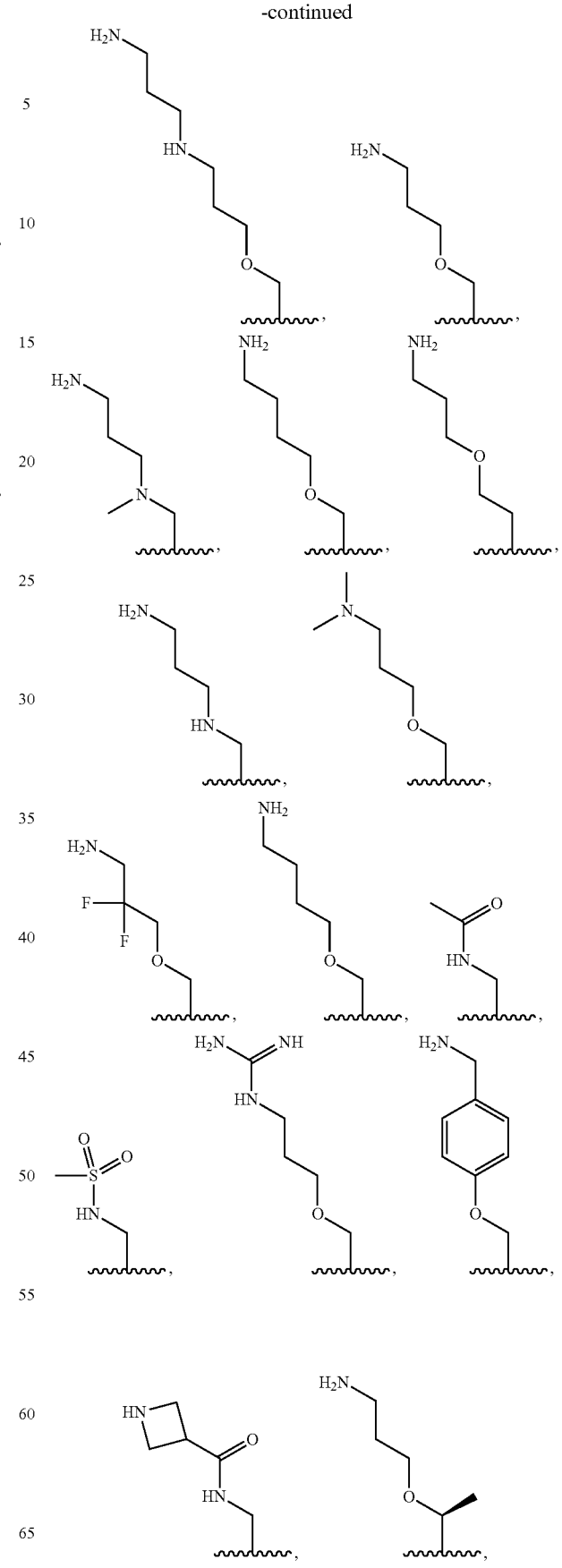

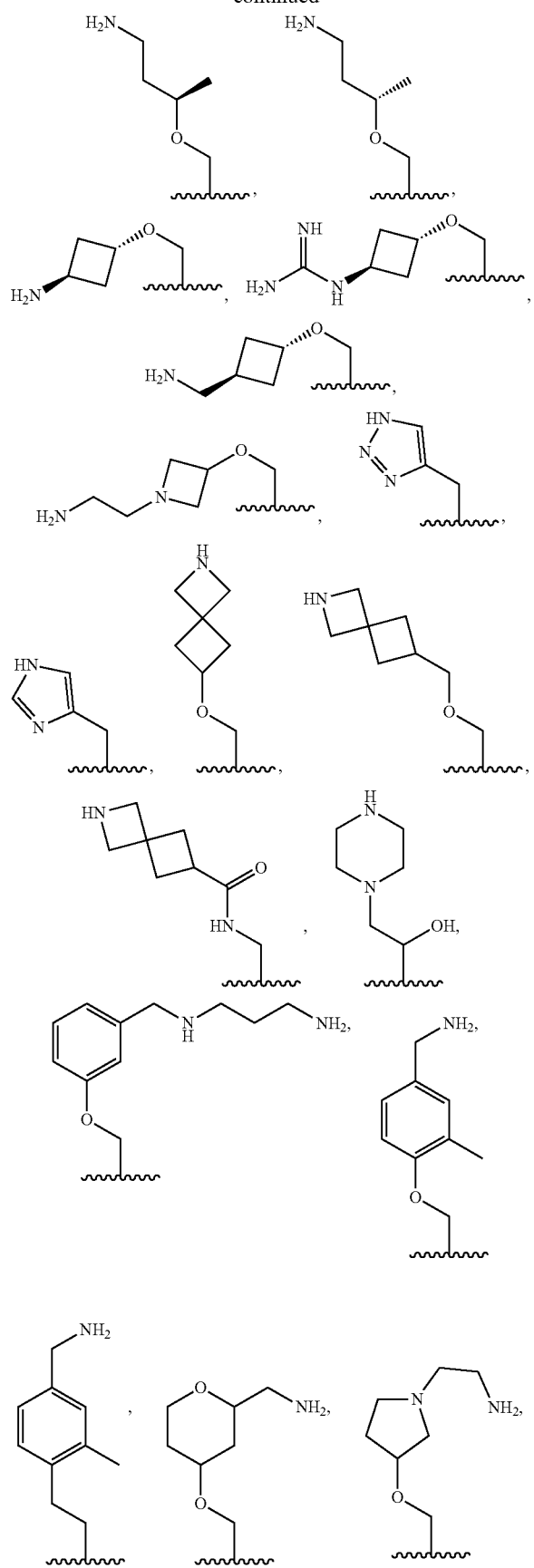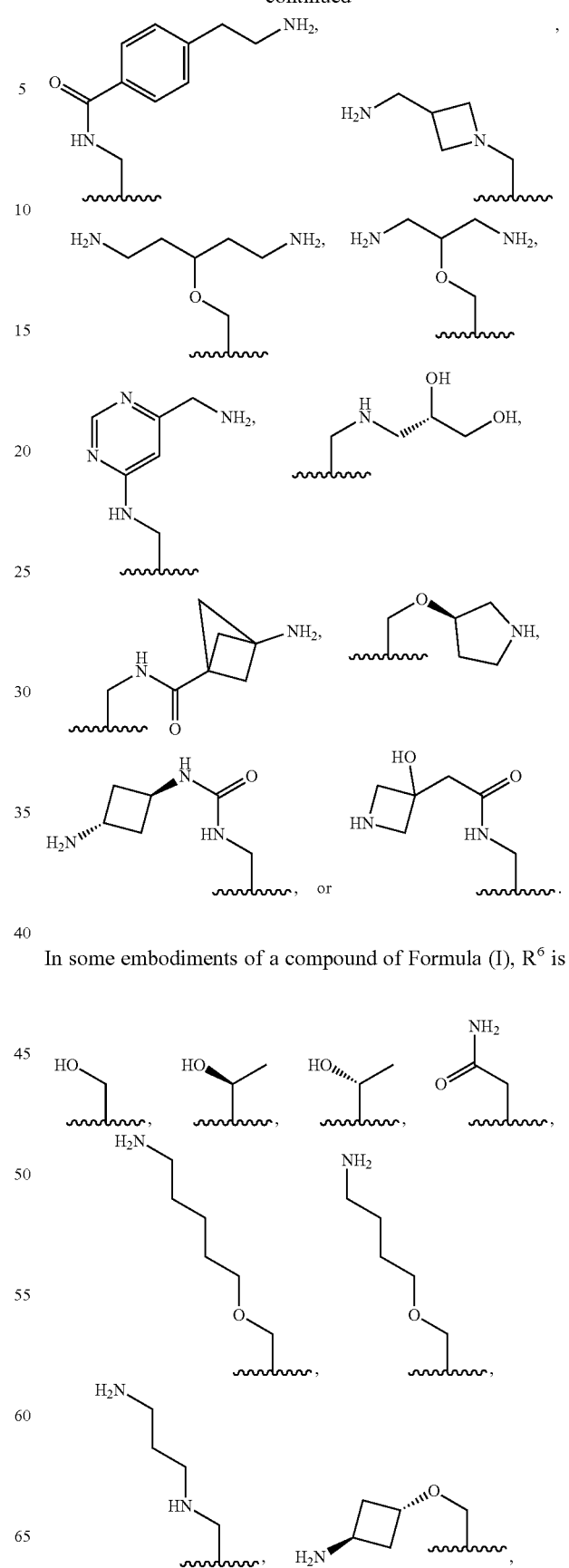
In some embodiments of a compound of Formula (I), $R^6$ is

-continued

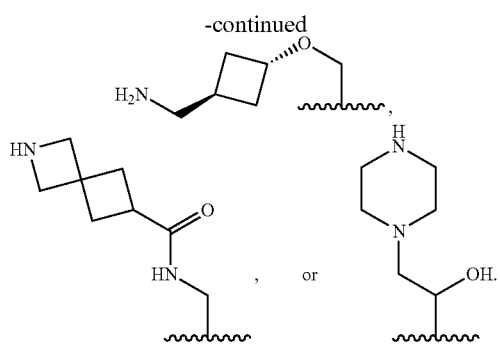

In some embodiments of a compound of Formula (I), $R^6$ is

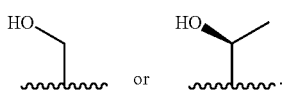

In some embodiments of a compound of Formula (I), $R^{12}$ is hydrogen or optionally substituted $C_1$-$C_6$ alkyl. In some embodiments of a compound of Formula (I), $R^{12}$ is $C_1$-$C_6$ alkyl optionally substituted with one, two, or three halogen or —$OCH_3$. In some embodiments of a compound of Formula (I), $R^{12}$ is $C_1$-$C_6$ alkyl or $C_1$-$C_6$ haloalkyl. In some embodiments of a compound of Formula (I), $R^{12}$ is

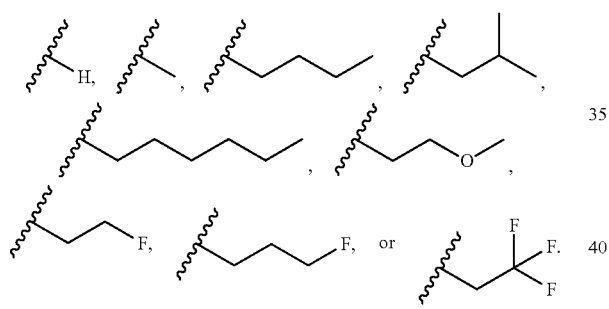

In some embodiments of a compound of Formula (I), $R^{14}$ is optionally substituted $C_1$-$C_6$ alkyl or optionally substituted ($C_1$-$C_6$ alkyl)cycloalkyl. In some embodiments of a compound of Formula (I), $R^{14}$ is $C_1$-$C_6$ alkyl.

In some embodiments of a compound of Formula (I), $R^{14}$ is

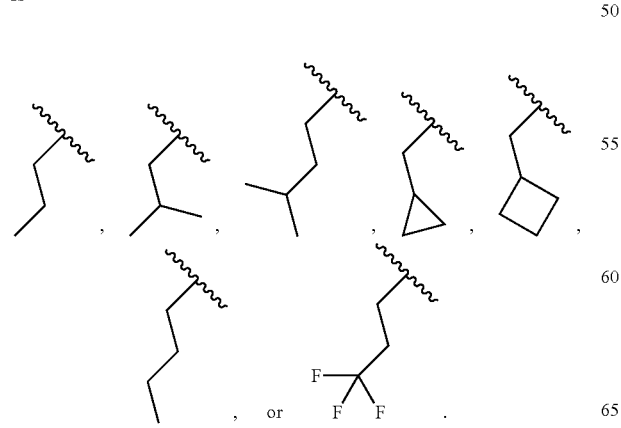

In some embodiments of a compound of Formula (I), $R^{14}$ is

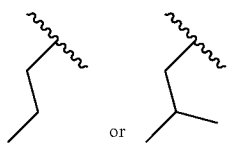

In some embodiments of a compound of Formula (I), $R^{16}$ is optionally substituted $C_1$-$C_6$ alkyl or optionally substituted cycloalkyl. In some embodiments of a compound of Formula (I), $R^{16}$ is $C_3$-$C_7$ cycloalkyl. In some embodiments of a compound of Formula (I), $R^{16}$ is cyclohexyl.

In some embodiments of a compound of Formula (I), $R^{16}$ is

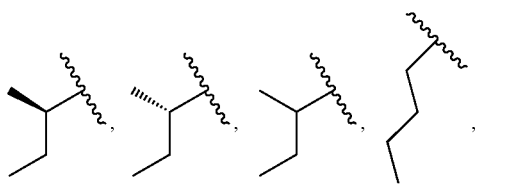
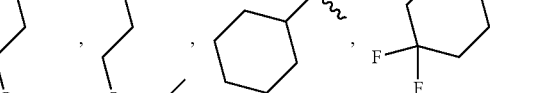

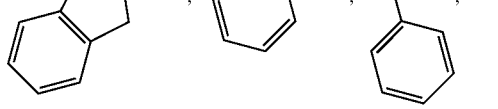
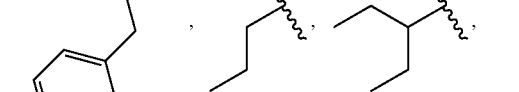
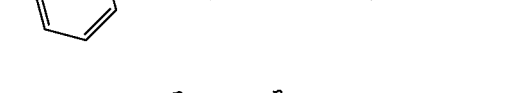

In some embodiments of a compound of Formula (I), $R^{16}$ is

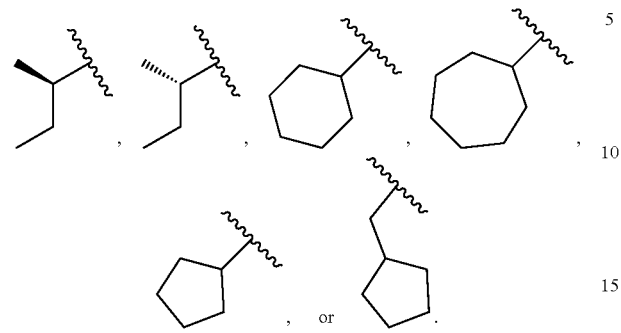

In some embodiments of a compound of Formula (I), $R^{16}$ is

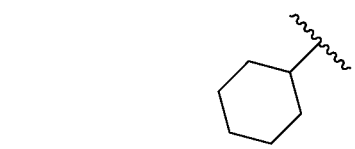

In some embodiments of a compound of Formula (I), $R^{3a}$ is optionally substituted $C_1$-$C_{20}$ alkyl, optionally substituted $C_2$-$C_{20}$ alkynyl, optionally substituted ($C_1$-$C_6$ alkyl)cycloalkyl, or optionally substituted ($C_1$-$C_6$ alkyl)aryl. In some embodiments of a compound of Formula (I), $R^{3a}$ is $C_1$-$C_6$ alkyl optionally substituted with one, two, or three halogen. In some embodiments of a compound of Formula (I), $R^{3a}$ is ($C_1$-$C_6$ alkyl)aryl optionally substituted with one, two, or three $C_1$-$C_6$ alkyl. In some embodiments of a compound of Formula (I), $R^{3a}$ is ($C_1$-$C_6$ alkyl)cycloalkyl. In some embodiments of a compound of Formula (I), $R^{3a}$ is

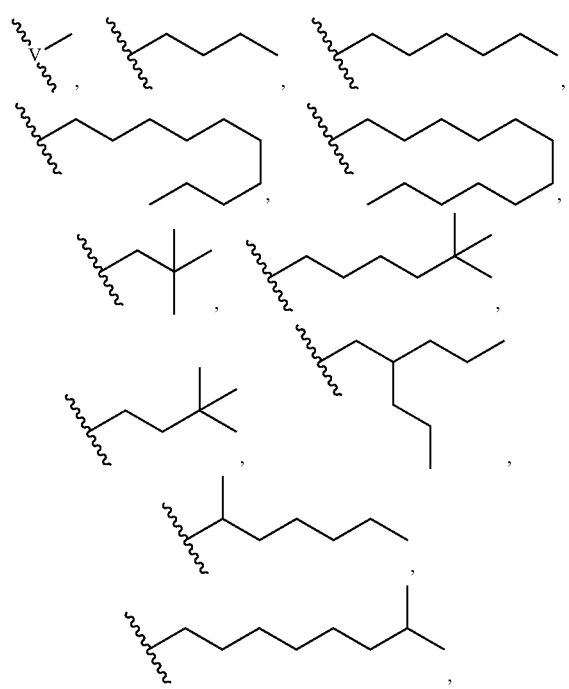

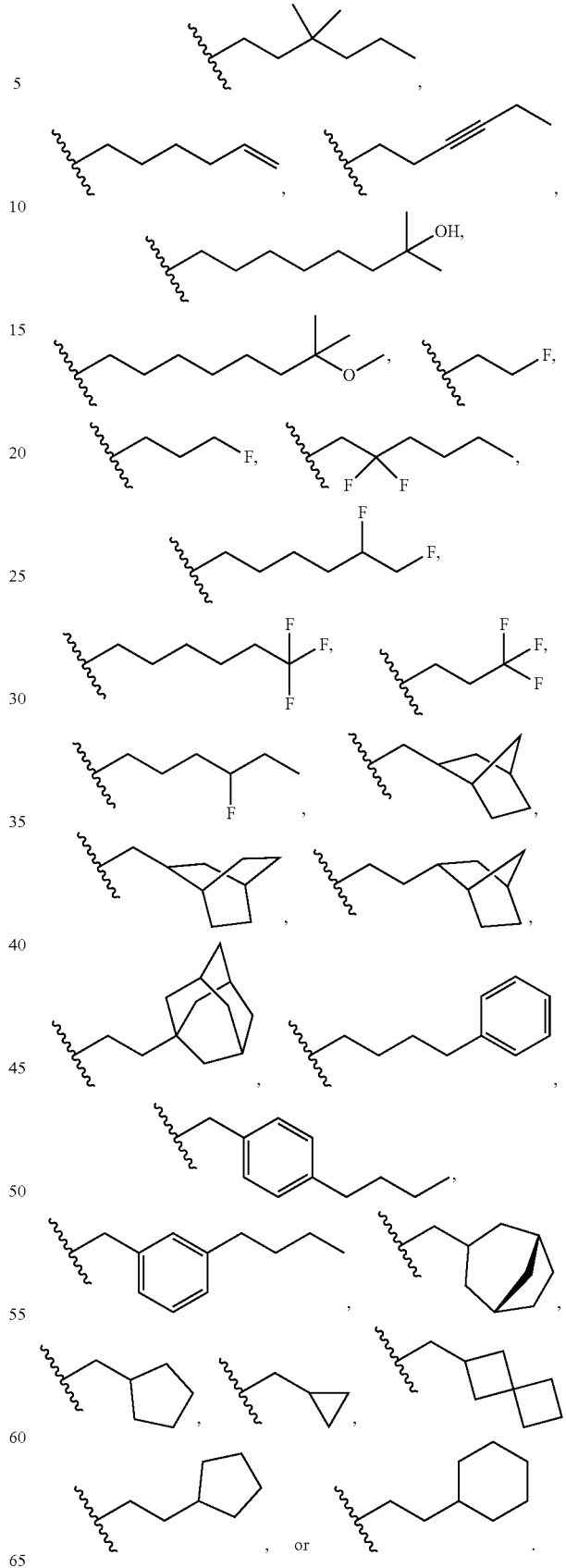

In some embodiments of a compound of Formula (I), $R^{3a}$ is

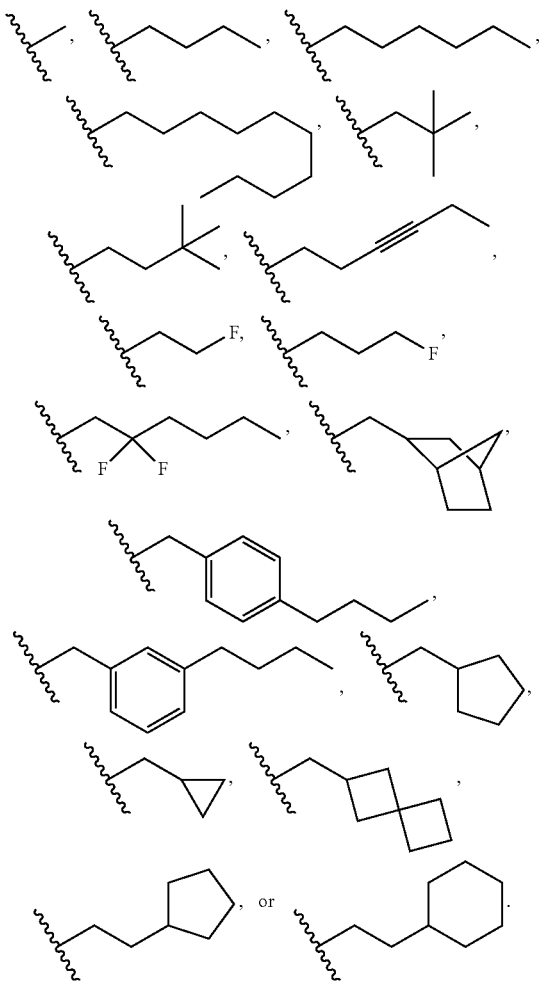

In some embodiments of a compound of Formula (I), each $R^a$ is independently $C_1$-$C_6$ alkyl.

In some embodiments of a compound of Formula (I), each $R^b$ and $R^c$ is independently hydrogen or $C_1$-$C_6$ alkyl.

In one aspect described herein are compounds of Formula (II):

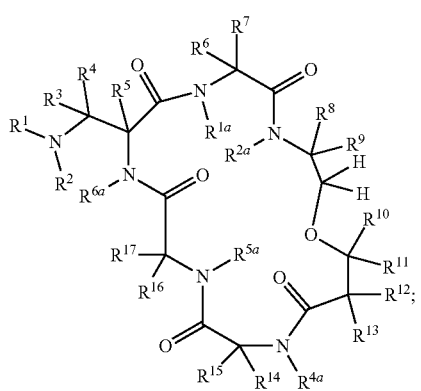

Formula (II)

wherein:

$R^{1a}$, $R^{2a}$, $R^{3a}$, $R^{4a}$, $R^{5a}$, and $R^{6a}$ are each independently hydrogen or optionally substituted $C_1$-$C_6$ alkyl;

$R^1$ and $R^2$ are each independently hydrogen, optionally substituted $C_1$-$C_6$ alkyl, optionally substituted $C_2$-$C_6$ alkenyl, optionally substituted $C_2$-$C_6$ alkynyl, optionally substituted cycloalkyl, optionally substituted ($C_1$-$C_6$ alkyl)cycloalkyl, optionally substituted heterocycloalkyl, optionally substituted ($C_1$-$C_6$ alkyl)heterocycloalkyl, optionally substituted aryl, optionally substituted ($C_1$-$C_6$ alkyl)aryl, optionally substituted heteroaryl, optionally substituted ($C_1$-$C_6$ alkyl)heteroaryl, —S(=O)$_2$R$^a$, —S(=O)$_2$NR$^b$R$^c$, —C(=O)R$^a$, —C(=O)OR$^b$, —C(=O)NR$^b$R$^c$, or —(C=NR$^b$)NR$^b$R$^c$;

or $R^1$ and $R^2$ are taken together with the nitrogen atom to which they are attached to form an optionally substituted heterocycloalkyl;

$R^3$ and $R^4$ are each independently hydrogen, optionally substituted $C_1$-$C_6$ alkyl, optionally substituted $C_2$-$C_6$ alkenyl, optionally substituted $C_2$-$C_6$ alkynyl, optionally substituted cycloalkyl, optionally substituted heterocycloalkyl, optionally substituted aryl, or optionally substituted heteroaryl;

or $R^3$ and $R^4$ are taken together with the carbon atom to which they are attached to form an oxo;

$R^5$ is hydrogen, halogen, optionally substituted $C_1$-$C_6$ alkyl, optionally substituted $C_2$-$C_6$ alkenyl, or optionally substituted $C_2$-$C_6$ alkynyl;

$R^6$ and $R^7$ are each independently hydrogen, halogen, optionally substituted $C_1$-$C_6$ alkyl, optionally substituted $C_2$-$C_6$ alkenyl, optionally substituted $C_2$-$C_6$ alkynyl, optionally substituted cycloalkyl, optionally substituted ($C_1$-$C_6$ alkyl)cycloalkyl, optionally substituted heterocycloalkyl, optionally substituted ($C_1$-$C_6$ alkyl)heterocycloalkyl, optionally substituted aryl, optionally substituted ($C_1$-$C_6$ alkyl)aryl, optionally substituted heteroaryl, or optionally substituted ($C_1$-$C_6$ alkyl)heteroaryl;

$R^8$ and $R^9$ are each independently hydrogen, halogen, optionally substituted $C_1$-$C_6$ alkyl, optionally substituted $C_2$-$C_6$ alkenyl, optionally substituted $C_2$-$C_6$ alkynyl, optionally substituted cycloalkyl, optionally substituted ($C_1$-$C_6$ alkyl)cycloalkyl, optionally substituted heterocycloalkyl, optionally substituted ($C_1$-$C_6$ alkyl)heterocycloalkyl, optionally substituted aryl, optionally substituted ($C_1$-$C_6$ alkyl)aryl, optionally substituted heteroaryl, or optionally substituted ($C_1$-$C_6$ alkyl)heteroaryl;

$R^{10}$ and $R^{11}$ are each independently hydrogen, halogen, optionally substituted $C_1$-$C_{20}$ alkyl, optionally substituted $C_2$-$C_{20}$ alkenyl, optionally substituted $C_2$-$C_{20}$ alkynyl, optionally substituted cycloalkyl, optionally substituted ($C_1$-$C_6$ alkyl)cycloalkyl, optionally substituted heterocycloalkyl, optionally substituted ($C_1$-$C_6$ alkyl)heterocycloalkyl, optionally substituted aryl, optionally substituted ($C_1$-$C_6$ alkyl)aryl, optionally substituted heteroaryl, or optionally substituted ($C_1$-$C_6$ alkyl)heteroaryl;

$R^{12}$ and $R^{13}$ are each independently hydrogen, halogen, optionally substituted $C_1$-$C_6$ alkyl, optionally substituted $C_2$-$C_6$ alkenyl, optionally substituted $C_2$-$C_6$ alkynyl, optionally substituted cycloalkyl, optionally substituted ($C_1$-$C_6$ alkyl)cycloalkyl, optionally substituted heterocycloalkyl, optionally substituted ($C_1$-$C_6$ alkyl) heterocycloalkyl, optionally substituted aryl, optionally substituted (C₁-C₆ alkyl)aryl, optionally substituted heteroaryl, or optionally substituted (C₁-C₆ alkyl)heteroaryl;

or R¹⁰ and R¹² are taken together to form an optionally substituted cycloalkyl or an optionally substituted cycloalkenyl;

R¹⁴ and R¹⁵ are each independently hydrogen, halogen, optionally substituted C₁-C₆ alkyl, optionally substituted C₂-C₆ alkenyl, optionally substituted C₂-C₆ alkynyl, optionally substituted cycloalkyl, optionally substituted (C₁-C₆ alkyl)cycloalkyl, optionally substituted heterocycloalkyl, optionally substituted (C₁-C₆ alkyl) heterocycloalkyl, optionally substituted aryl, optionally substituted (C₁-C₆ alkyl)aryl, optionally substituted heteroaryl, or optionally substituted (C₁-C₆ alkyl)heteroaryl;

or R¹⁴ and R⁴ᵃ are taken together with the atoms to which they are attached to form an optionally substituted heterocycloalkyl;

R¹⁶ and R¹⁷ are each independently hydrogen, halogen, optionally substituted C₁-C₆ alkyl, optionally substituted C₂-C₆ alkenyl, optionally substituted C₂-C₆ alkynyl, optionally substituted cycloalkyl, optionally substituted (C₁-C₆ alkyl)cycloalkyl, optionally substituted heterocycloalkyl, optionally substituted (C₁-C₆ alkyl) heterocycloalkyl, optionally substituted aryl, optionally substituted (C₁-C₆ alkyl)aryl, optionally substituted heteroaryl, or optionally substituted (C₁-C₆ alkyl)heteroaryl;

R¹⁸ and R¹⁹ are each independently hydrogen, halogen, optionally substituted C₁-C₆ alkyl, optionally substituted C₂-C₆ alkenyl, optionally substituted C₂-C₆ alkynyl, optionally substituted cycloalkyl, optionally substituted (C₁-C₆ alkyl)cycloalkyl, optionally substituted heterocycloalkyl, optionally substituted (C₁-C₆ alkyl) heterocycloalkyl, optionally substituted aryl, optionally substituted (C₁-C₆ alkyl)aryl, optionally substituted heteroaryl, or optionally substituted (C₁-C₆ alkyl)heteroaryl;

or R¹⁸ and R¹⁹ are taken together with the carbon atom to which they are attached to form an oxo;

each Rᵃ is independently optionally substituted C₁-C₆ alkyl, optionally substituted C₂-C₆ alkenyl, optionally substituted C₂-C₆ alkynyl, optionally substituted cycloalkyl, optionally substituted heterocycloalkyl, optionally substituted aryl, or optionally substituted heteroaryl;

each Rᵇ and Rᶜ is independently hydrogen, optionally substituted C₁-C₆ alkyl, optionally substituted C₂-C₆ alkenyl, optionally substituted C₂-C₆ alkynyl, optionally substituted cycloalkyl, optionally substituted heterocycloalkyl, optionally substituted aryl, or optionally substituted heteroaryl;

or Rᵇ and Rᶜ are taken together with the nitrogen atom to which they are attached to form an optionally substituted heterocycloalkyl;

or a pharmaceutically acceptable salt, solvate, or stereoisomer thereof;

wherein the compound is selected from the group consisting of:

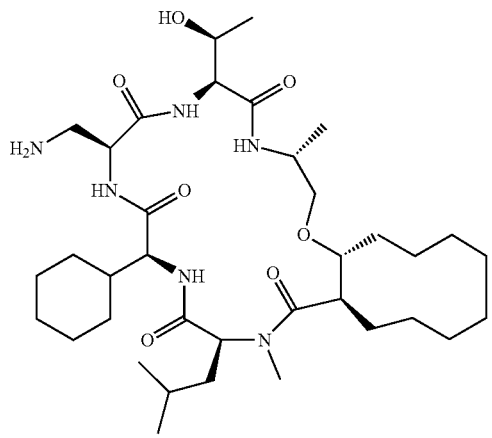

,

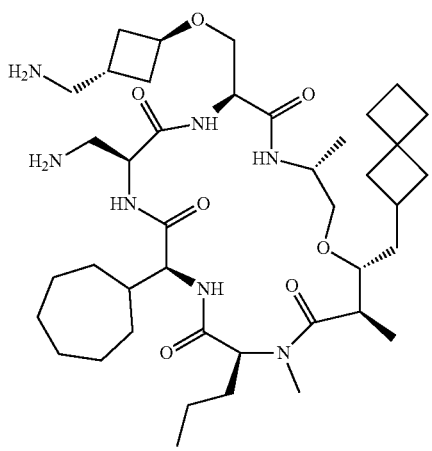

,

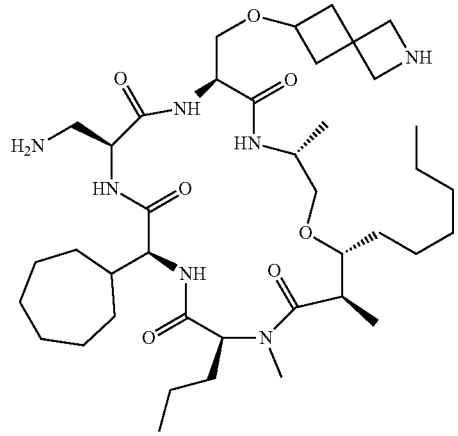

,

45
-continued
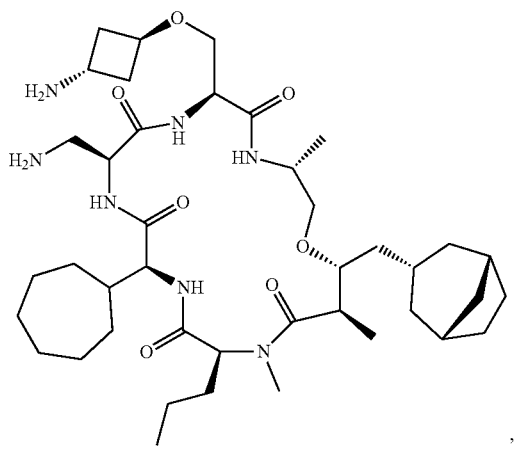
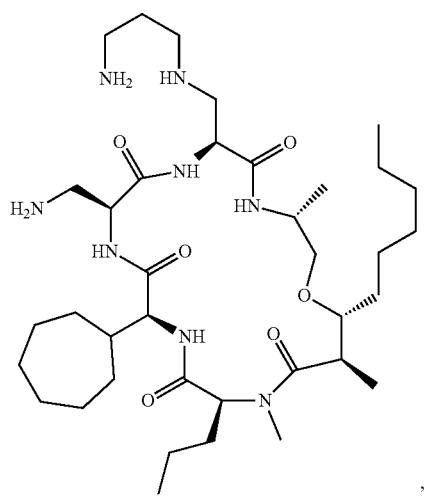
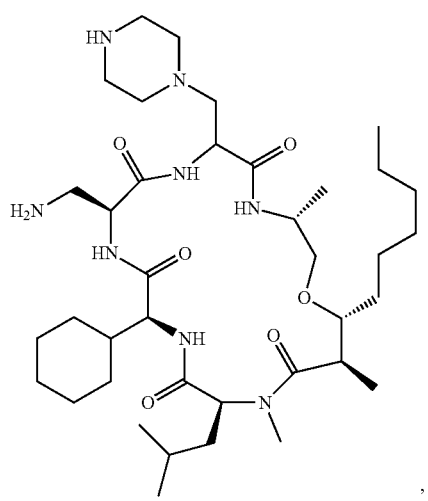
46
-continued
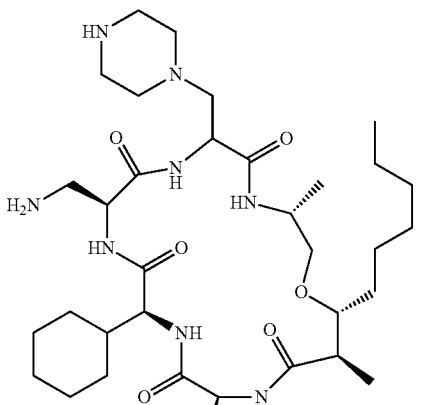
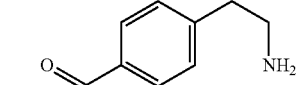
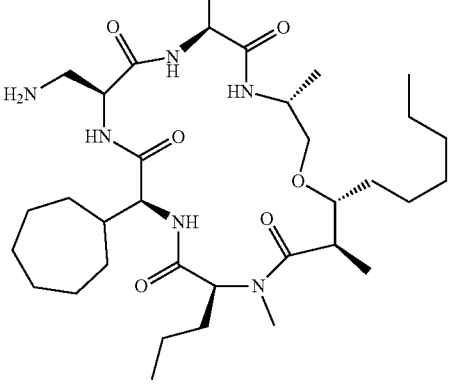
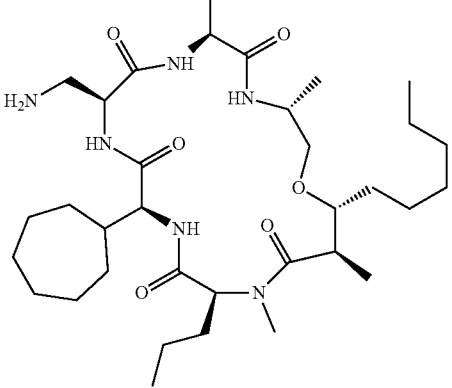

-continued
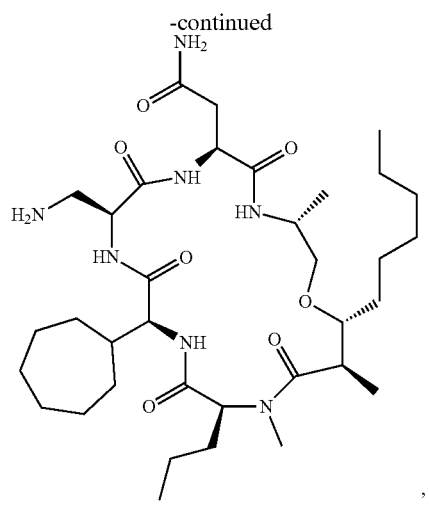
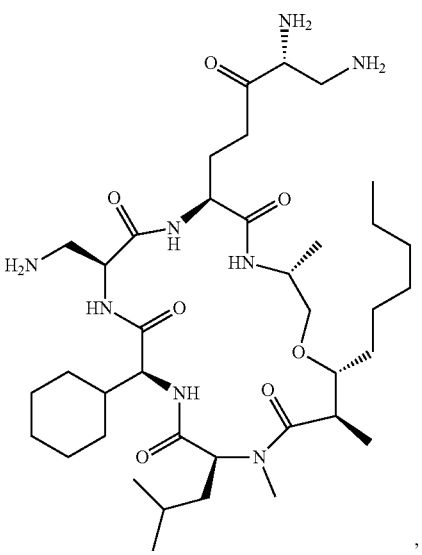
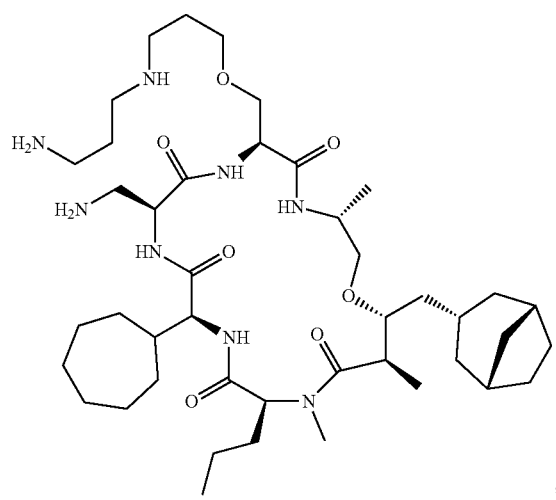
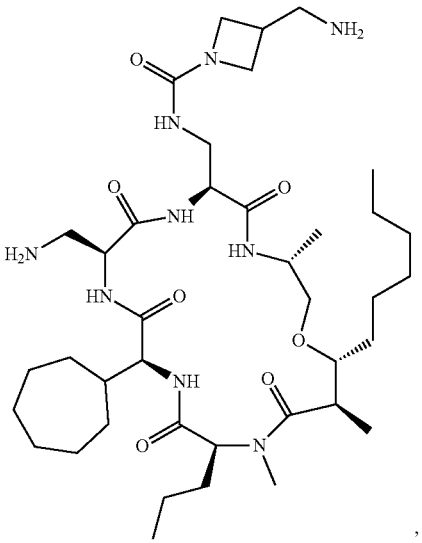
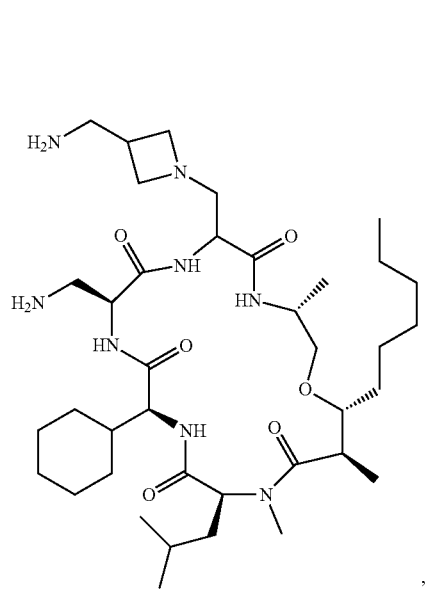
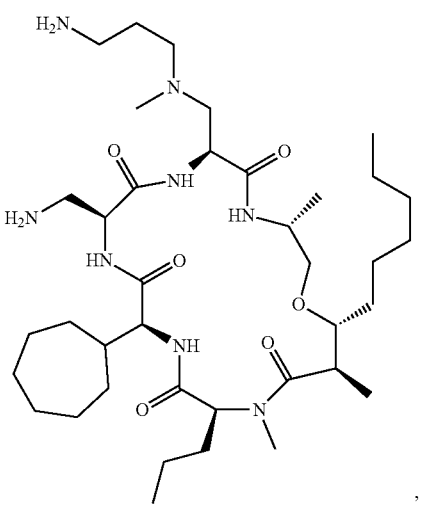

49
-continued
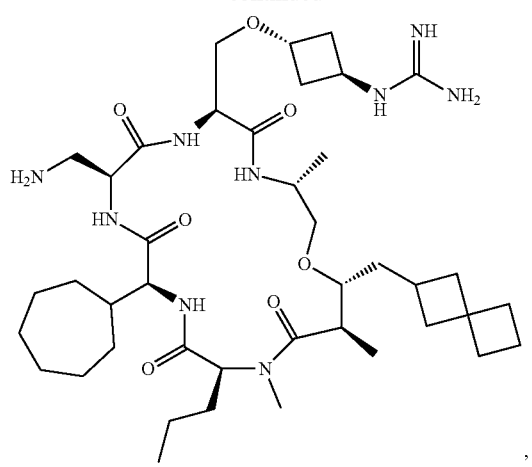
50
-continued
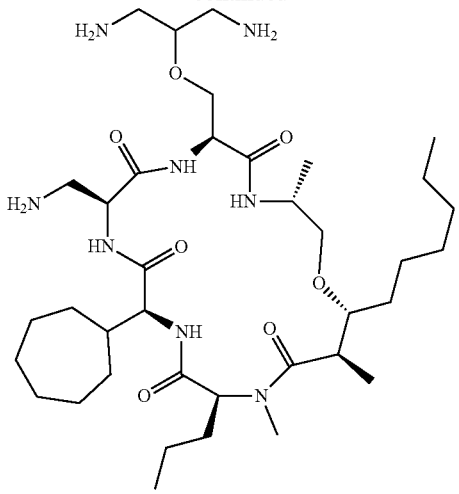
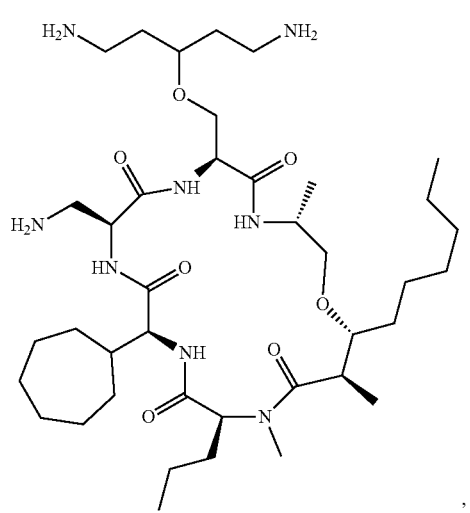
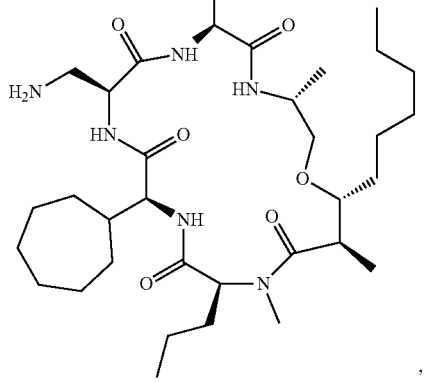
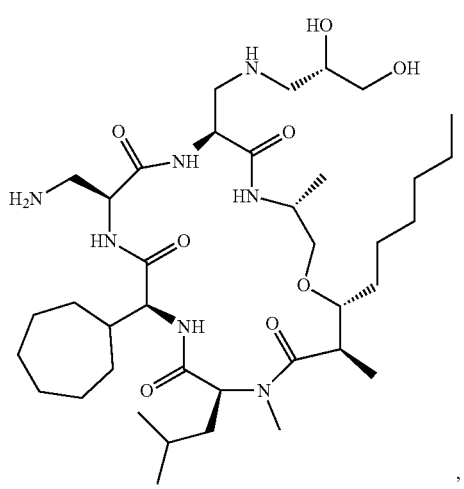

51
-continued
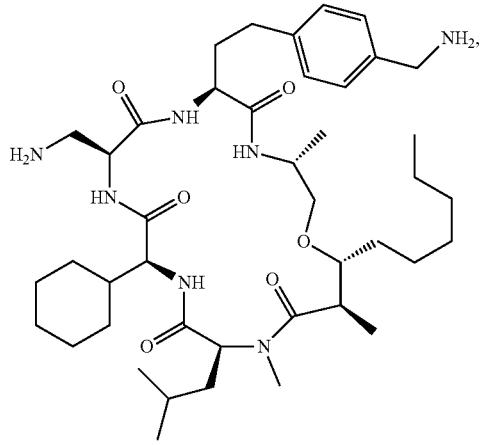
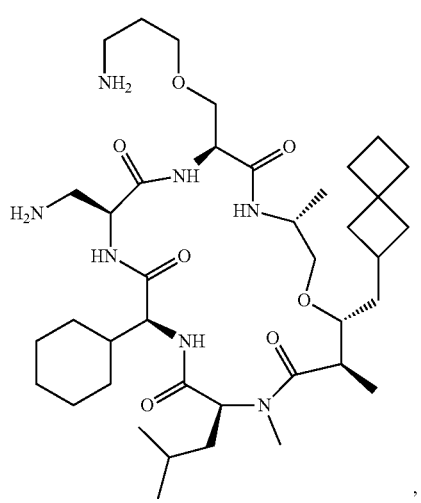
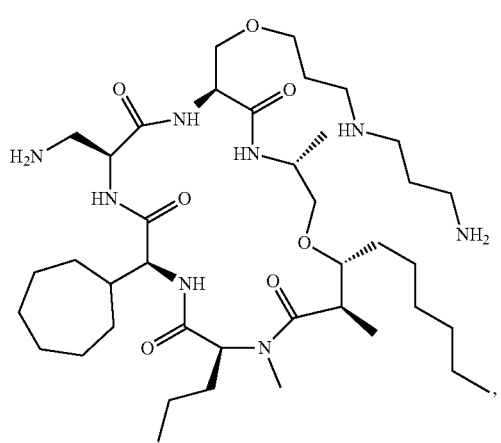
52
-continued
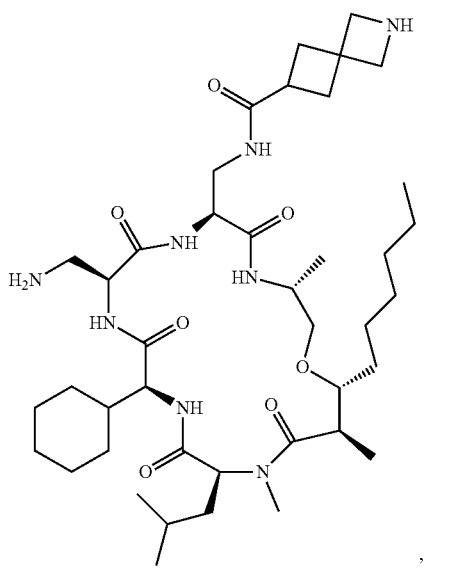
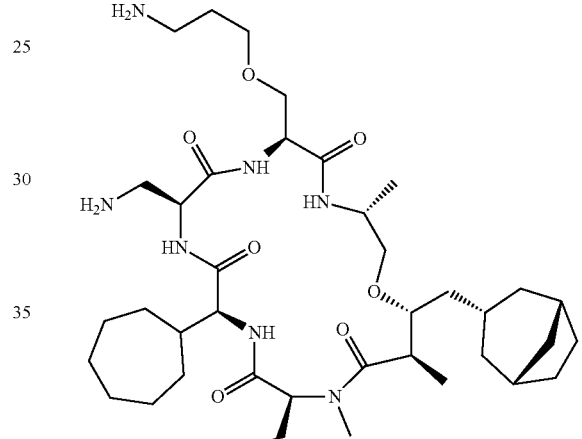
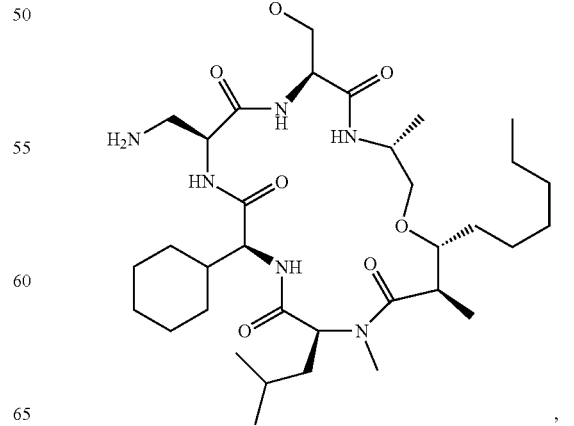

53
-continued
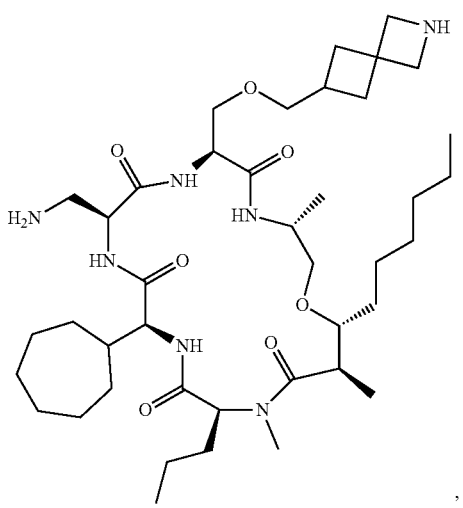
,
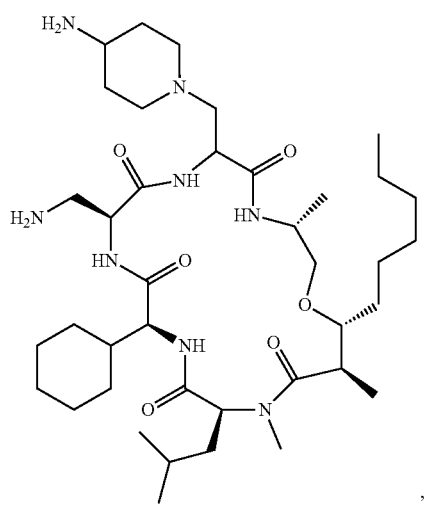
,
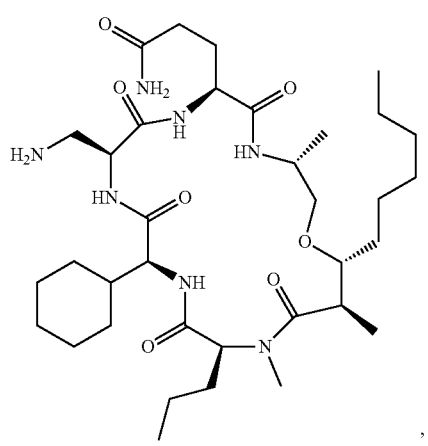
,
54
-continued
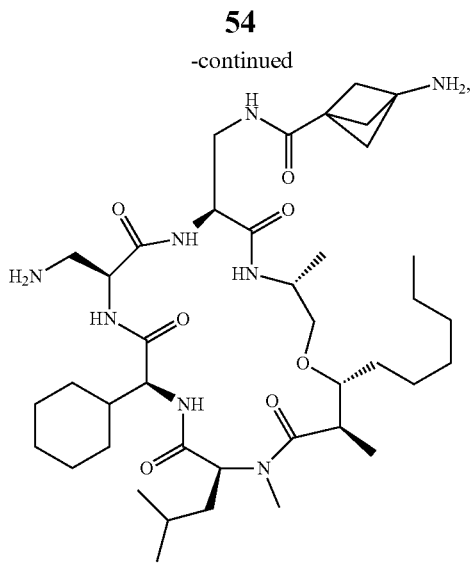
,
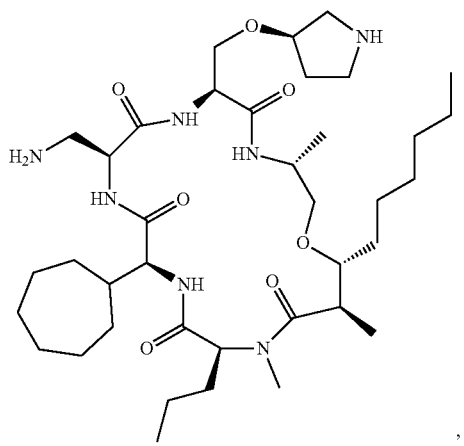
,
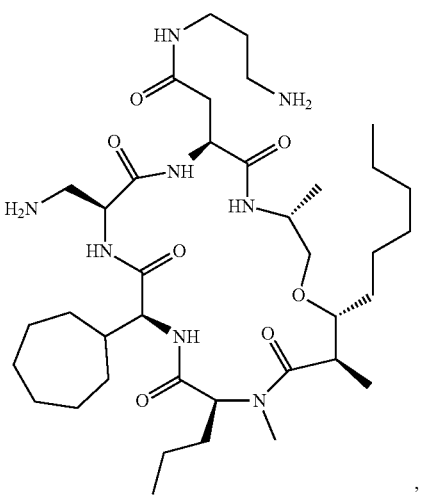
, 55
-continued
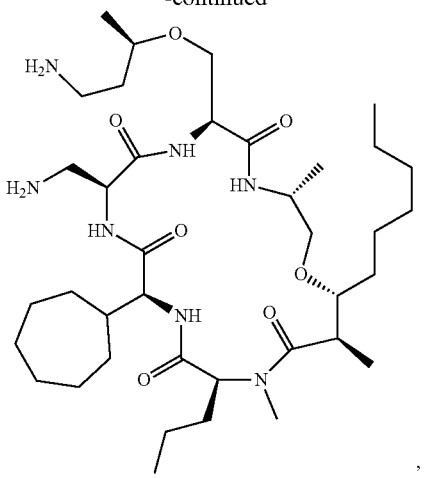
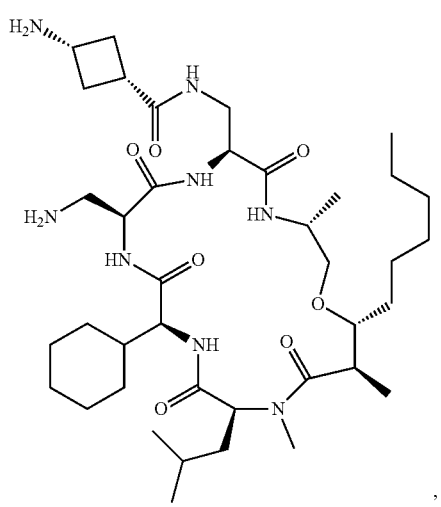
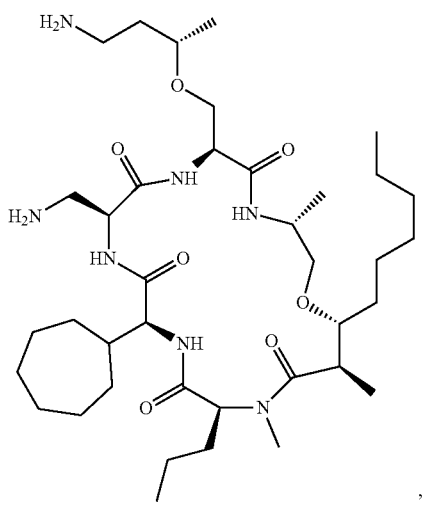
56
-continued
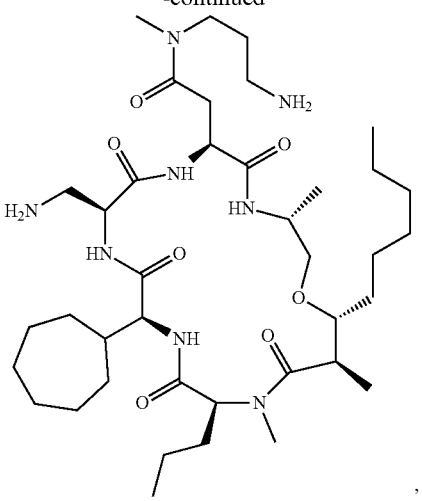
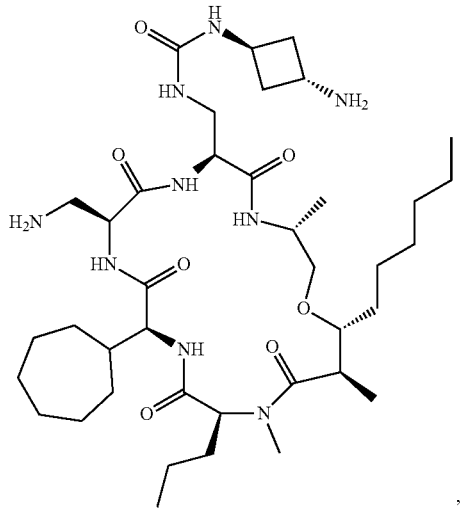
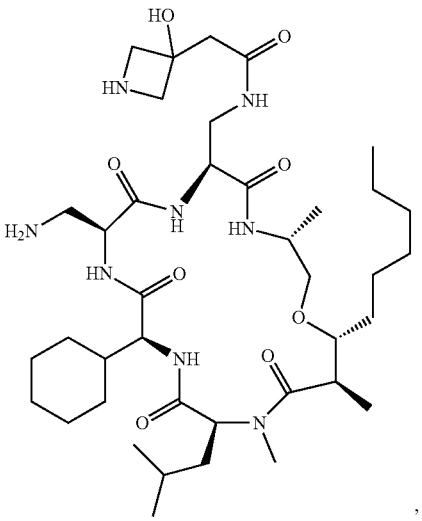

57
-continued
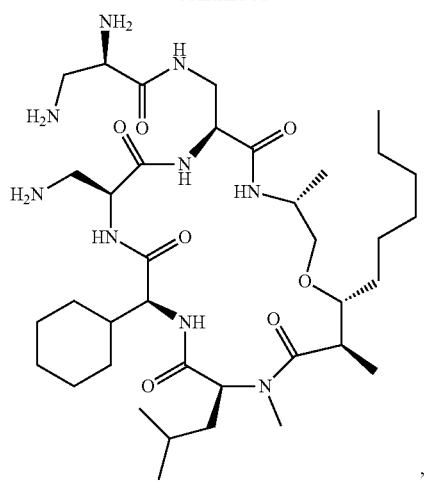
58
-continued
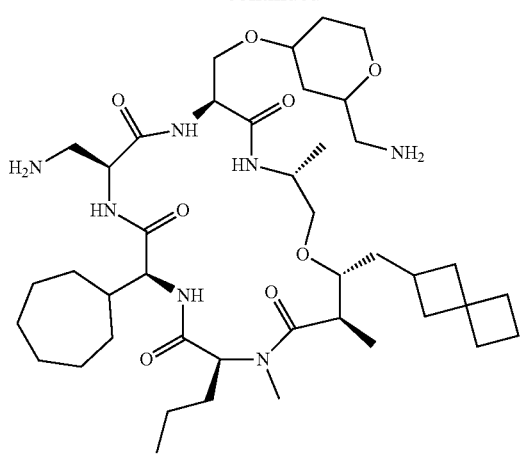
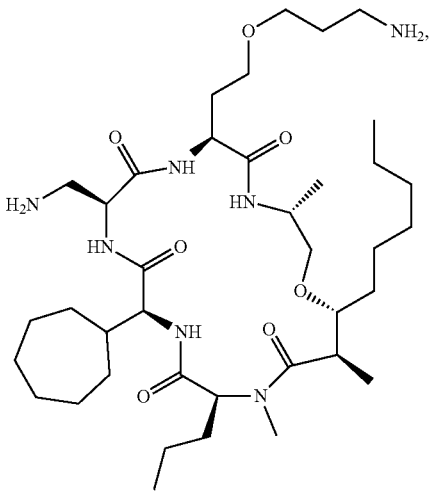
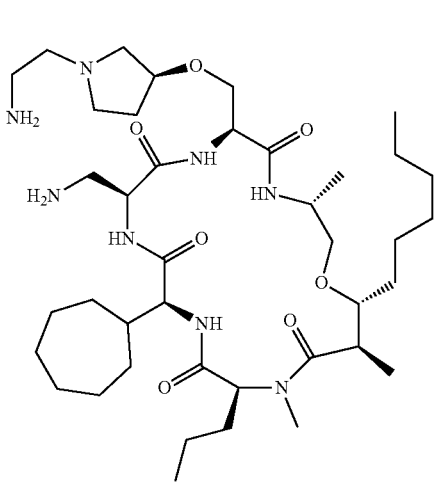
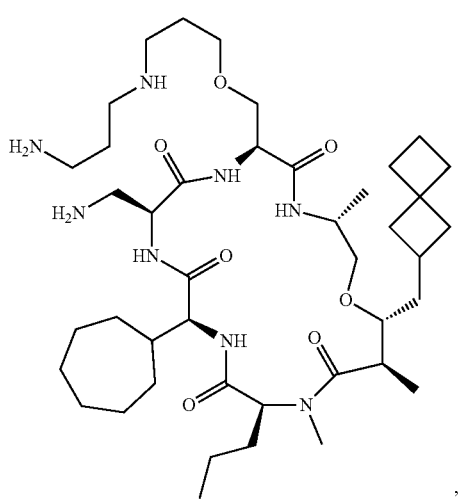

59

-continued

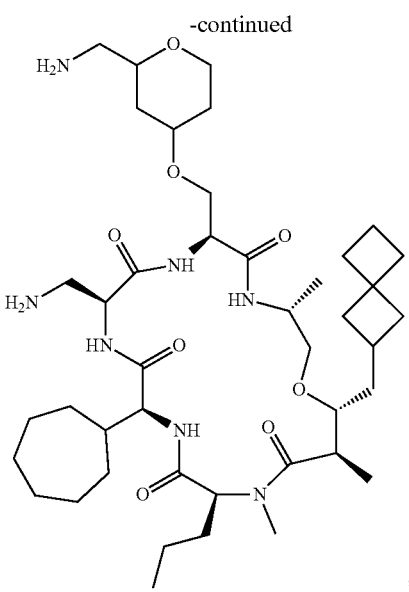

, and

60

-continued

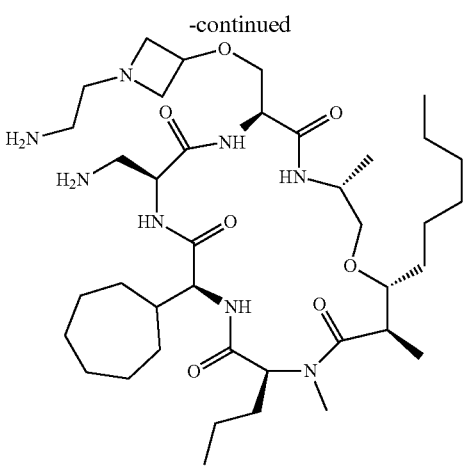

In some embodiments, the compound disclosed herein is selected from a compound in table 1 or a pharmaceutically acceptable salt, solvate, or stereoisomer thereof.

TABLE 1

| Ex. | Structure | Name |
|---|---|---|
| 1 | 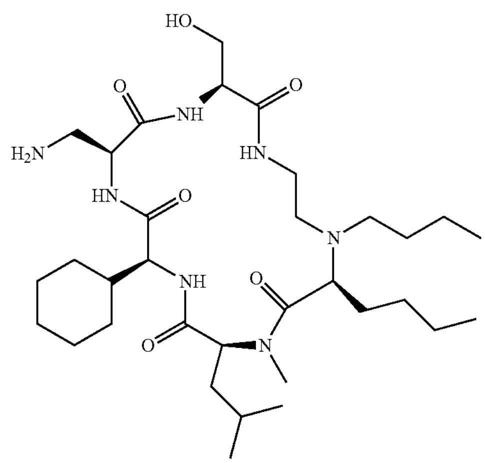 [SMILES: CCCC[C@H]1C(=O)N(C)[C@@H](CC(C)C)C(=O)N[C@@H](C2CCCCC2)C(=O)N[C@@H](CN)C(=O)N[C@@H](CO)C(=O)NCCN1CCCC] | (3S,6S,9S,12S,15S)-6-(Aminomethyl)-15,16-dibutyl-9-cyclohexyl-3-(hydroxymethyl)-12-isobutyl-13-methyl-1,4,7,10,13,16-hexaazacyclooctadecane-2,5,8,11,14-pentaone |
| 2 | 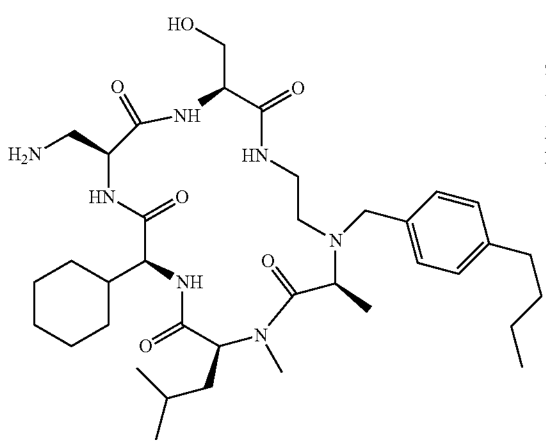 [SMILES: CCCCc1ccc(CN2CCNC(=O)[C@H](CO)NC(=O)[C@H](CN)NC(=O)[C@H](C3CCCCC3)NC(=O)[C@H](CC(C)C)N(C)C(=O)[C@@H]2C)cc1] | (3S,6S,9S,12S,15S)-6-(Aminomethyl)-16-(4-butylbenzyl)-9-cyclohexyl-3-(hydroxymethyl)-12-isobutyl-13,15-dimethyl-1,4,7,10,13,16-hexaazacyclooctadecane-2,5,8,11,14-pentaone |

TABLE 1-continued

| Ex. | Structure | Name |
|---|---|---|
| 3 | 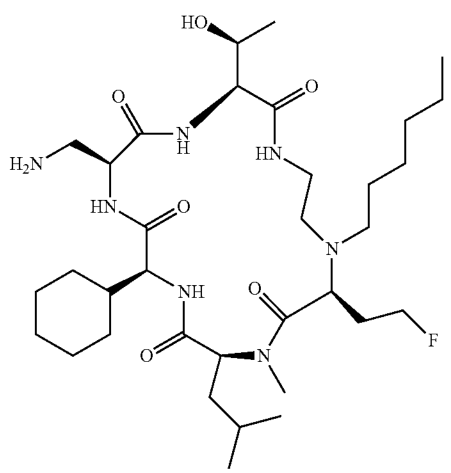 [SMILES: CCCCCCN1CCNC(=O)[C@H]([C@H](C)O)NC(=O)[C@H](CN)NC(=O)[C@H](C2CCCCC2)NC(=O)[C@H](CC(C)C)N(C)C(=O)[C@@H]1CCF] | (3S,6S,9S,12S,15S)-6-(Aminomethyl)-9-cyclohexyl-15-(2-fluoroethyl)-16-hexyl-3-((S)-1-hydroxyethyl)-12-isobutyl-13-methyl-1,4,7,10,13,16-hexaazacyclooctadecane-2,5,8,11,14-pentaone |
| 4 | 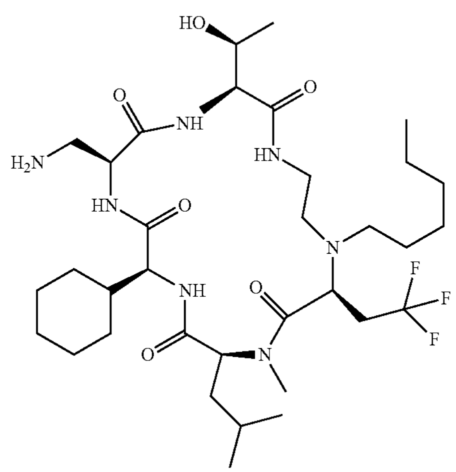 [SMILES: CCCCCCN1CCNC(=O)[C@H]([C@H](C)O)NC(=O)[C@H](CN)NC(=O)[C@H](C2CCCCC2)NC(=O)[C@H](CC(C)C)N(C)C(=O)[C@@H]1CC(F)(F)F] | (3S,6S,9S,12S,15S)-6-(Aminomethyl)-9-cyclohexyl-16-hexyl-3-((S)-1-hydroxyethyl)-12-isobutyl-13-methyl-15-(2,2,2-trifluoroethyl)-1,4,7,10,13,16-hexaazacyclooctadecane-2,5,8,11,14-pentaone |
| 5 | 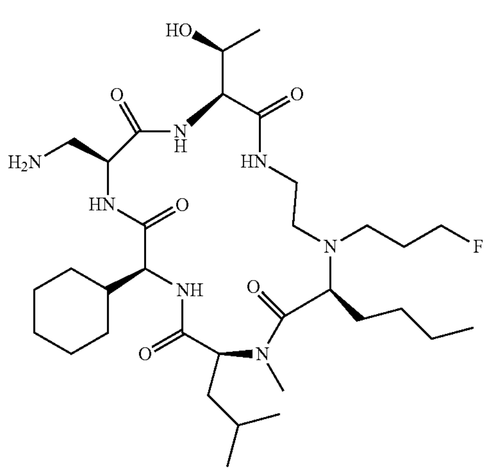 [SMILES: CCCC[C@H]1C(=O)N(C)[C@@H](CC(C)C)C(=O)N[C@@H](C2CCCCC2)C(=O)N[C@@H](CN)C(=O)N[C@@H]([C@H](C)O)C(=O)NCCN1CCCF] | (3S,6S,9S,12S,15S)-6-(Aminomethyl)-15-butyl-9-cyclohexyl-16-(3-fluoropropyl)-3-((S)-1-hydroxyethyl)-12-isobutyl-13-methyl-1,4,7,10,13,16-hexaazacyclooctadecane-2,5,8,11,14-pentaone |

TABLE 1-continued

| Ex. | Structure | Name |
|---|---|---|
| 6 | 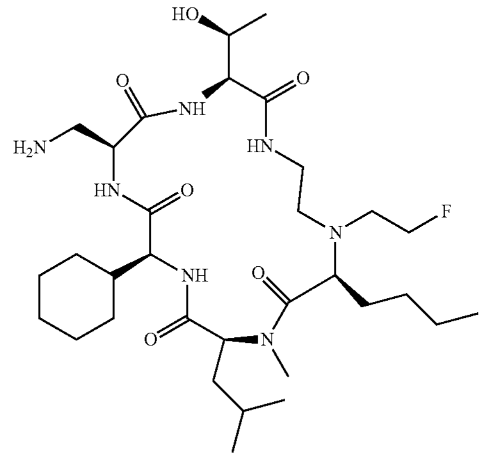 [SMILES: CCCC[C@H]1C(=O)N(C)[C@@H](CC(C)C)C(=O)N[C@@H](C2CCCCC2)C(=O)N[C@@H](CN)C(=O)N[C@@H]([C@H](C)O)C(=O)NCCN1CCF] | (3S,6S,9S,12S,15S)-6-(Aminomethyl)-15-butyl-9-cyclohexyl-16-(2-fluoroethyl)-3-((S)-1-hydroxyethyl)-12-isobutyl-13-methyl-1,4,7,10,13,16-hexaazacyclooctadecane-2,5,8,11,14-pentaone |
| 7 | 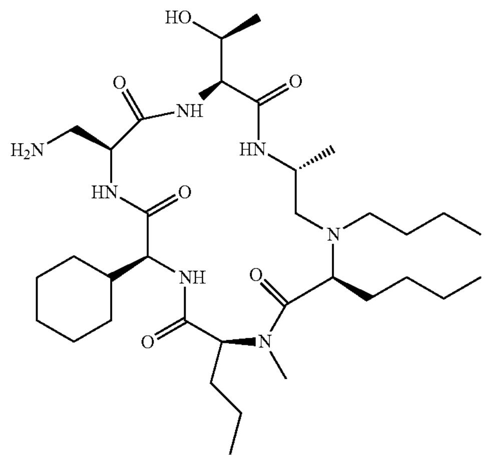 [SMILES: CCCC[C@H]1C(=O)N(C)[C@@H](CCC)C(=O)N[C@@H](C2CCCCC2)C(=O)N[C@@H](CN)C(=O)N[C@@H]([C@H](C)O)C(=O)N[C@H](C)CN1CCCC] | (3S,6S,9S,12S,15S,18R)-6-(Aminomethyl)-15,16-dibutyl-9-cyclohexyl-3-((S)-1-hydroxyethyl)-13,18-dimethyl-12-propyl-1,4,7,10,13,16-hexaazacyclooctadecane-2,5,8,11,14-pentaone |
| 8 | 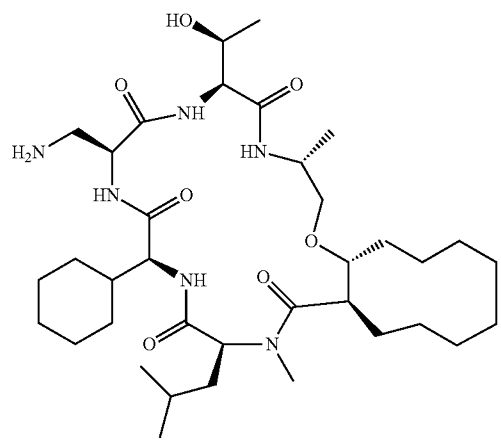 [SMILES: CC(C)C[C@H]1C(=O)N[C@@H](C2CCCCC2)C(=O)N[C@@H](CN)C(=O)N[C@@H]([C@H](C)O)C(=O)N[C@H](C)CO[C@@H]2CCCCCCCC[C@H]2C(=O)N1C] | (1R,4S,7S,10S,13S,16R,19R)-10-(Aminomethyl)-7-cyclohexyl-13-[(1S)-1-hydroxyethyl]-4-isobutyl-3,16-dimethyl-18-oxa-3,6,9,12,15-pentazabicyclo[17.8.0]heptacosane-2,5,8,11,14-pentone |

TABLE 1-continued

| Ex. | Structure | Name |
|---|---|---|
| 9 | 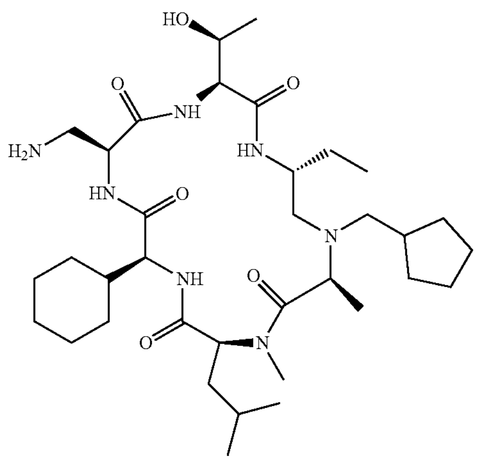 [SMILES: CC[C@@H]1CN(CC2CCCC2)[C@@H](C)C(=O)N(C)[C@@H](CC(C)C)C(=O)N[C@@H](C2CCCCC2)C(=O)N[C@@H](CN)C(=O)N[C@@H]([C@H](C)O)C(=O)N1] | (3S,6S,9S,12S,15S,18R)-6-(Aminomethyl)-9-cyclohexyl-16-(cyclopentylmethyl)-18-ethyl-3-((S)-1-hydroxyethyl)-12-isobutyl-13,15-dimethyl-1,4,7,10,13,16-hexaazacyclooctadecane-2,5,8,11,14-pentaone |
| 10 | 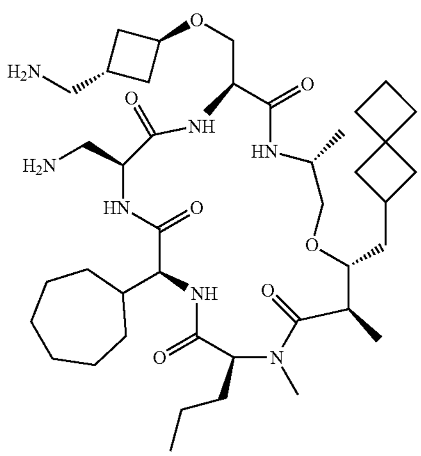 [SMILES: CCC[C@H]1C(=O)N[C@@H](C2CCCCCC2)C(=O)N[C@@H](CN)C(=O)N[C@@H](CO[C@H]2C[C@H](CN)C2)C(=O)N[C@H](C)CO[C@H](CC2CC3(CCC3)C2)[C@@H](C)C(=O)N1C] | (3R,6S,9S,12S,15S,18R,19R)-9-(Aminomethyl)-6-(((1r,3S)-3-(aminomethyl)cyclobutoxy)methyl)-12-cycloheptyl-3,16,18-trimethyl-15-propyl-19-(spiro[3.3]heptan-2-ylmethyl)-1-oxa-4,7,10,13,16-pentaazacyclononadecane-5,8,11,14,17-pentaone |
| 11 | 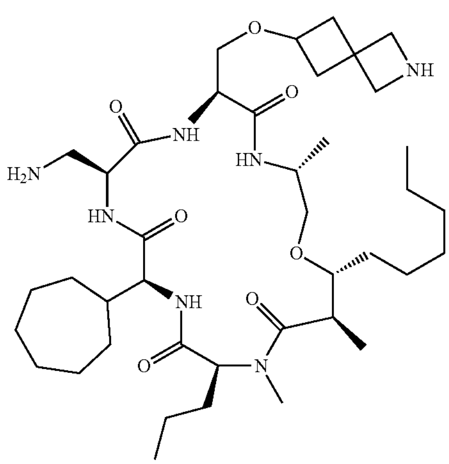 [SMILES: CCCCCC[C@H]1OC[C@@H](C)NC(=O)[C@H](COC2CC3(CNC3)C2)NC(=O)[C@H](CN)NC(=O)[C@H](C2CCCCCC2)NC(=O)[C@H](CCC)N(C)C(=O)[C@@H]1C] | (3R,6S,9S,12S,15S,18R,19R)-6-(((2-Azaspiro[3.3]heptan-6-yl)oxy)methyl)-9-(aminomethyl)-12-cycloheptyl-19-hexyl-3,16,18-trimethyl-15-propyl-1-oxa-4,7,10,13,16-pentaazacyclononadecane-5,8,11,14,17-pentaone |

TABLE 1-continued

| Ex. | Structure | Name |
|---|---|---|
| 12 | 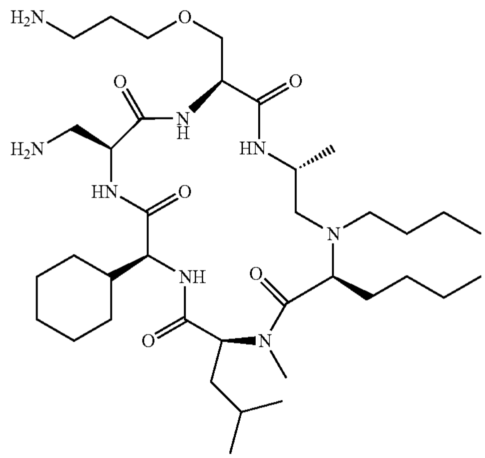 [SMILES: CCCC[C@H]1C(=O)N(C)[C@@H](CC(C)C)C(=O)N[C@@H](C2CCCCC2)C(=O)N[C@@H](CN)C(=O)N[C@@H](COCCCN)C(=O)N[C@H](C)CN1CCCC] | (3S,6S,9S,12S,15S,18R)-6-(Aminomethyl)-3-((3-aminopropoxy)methyl)-15,16-dibutyl-9-cyclohexyl-12-isobutyl-13,18-dimethyl-1,4,7,10,13,16-hexaazacyclooctadecane-2,5,8,11,14-pentaone |
| 13 | 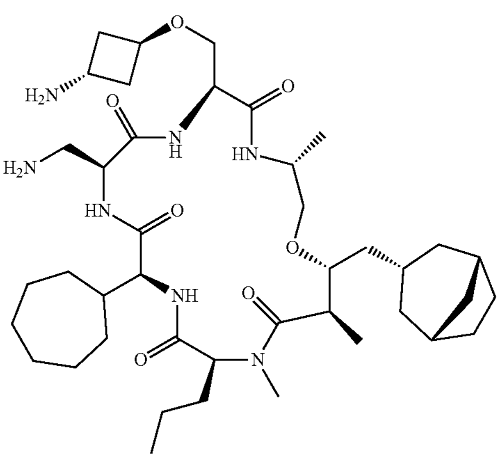 [SMILES: CCC[C@H]1C(=O)N[C@@H](C2CCCCCC2)C(=O)N[C@@H](CN)C(=O)N[C@@H](CO[C@H]2C[C@H](N)C2)C(=O)N[C@H](C)CO[C@H](C[C@@H]2C[C@@H]3CC[C@@H](C3)C2)[C@@H](C)C(=O)N1C] | (3R,6S,9S,12S,15S,18R,19R)-6-(((1r,3S)-3-Aminocyclobutoxy)methyl)-9-(aminomethyl)-19-((1R,3s,5S)-bicyclo[3.2.1]octan-3-ylmethyl)-12-cycloheptyl-3,16,18-trimethyl-15-propyl-1-oxa-4,7,10,13,16-pentaazacyclononadecane-5,8,11,14,17-pentaone |
| 14 | 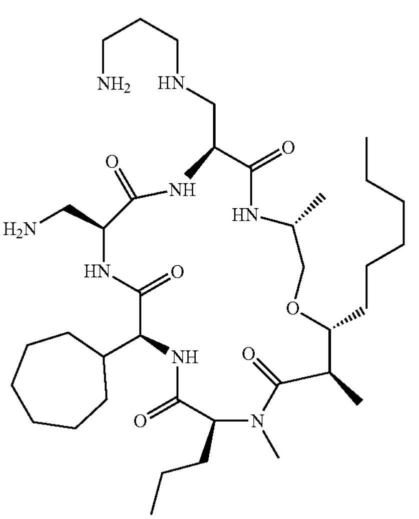 [SMILES: CCCCCC[C@H]1OC[C@@H](C)NC(=O)[C@H](CNCCCN)NC(=O)[C@H](CN)NC(=O)[C@H](C2CCCCCC2)NC(=O)[C@H](CCC)N(C)C(=O)[C@@H]1C] | (3R,6S,9S,12S,15S,18R,19R)-9-(Aminomethyl)-6-[(3-aminopropylamino)methyl]-12-cycloheptyl-19-hexyl-3,16,18-trimethyl-15-propyl-1-oxa-4,7,10,13,16-pentaazacyclononadecane-5,8,11,14,17-pentone |

TABLE 1-continued

| Ex. | Structure | Name |
|---|---|---|
| 15 | 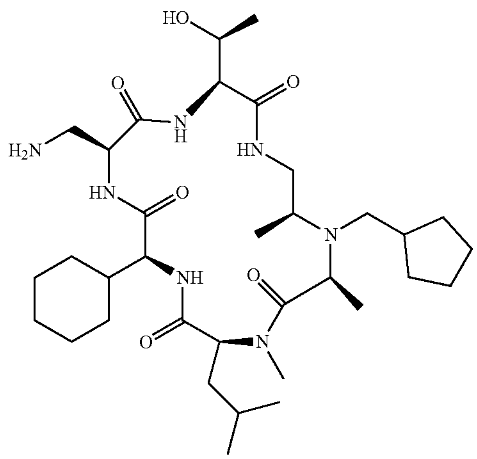 [SMILES: CC(C)C[C@H]1C(=O)N[C@@H](C2CCCCC2)C(=O)N[C@@H](CN)C(=O)N[C@@H]([C@H](C)O)C(=O)NC[C@H](C)N(CC2CCCC2)[C@@H](C)C(=O)N1C] | (3S,6S,9S,12S,15S,17S)-6-(Aminomethyl)-9-cyclohexyl-16-(cyclopentylmethyl)-3-((S)-1-hydroxyethyl)-12-isobutyl-13,15,17-trimethyl-1,4,7,10,13,16-hexaazacyclooctadecane-2,5,8,11,14-pentaone |
| 16 | 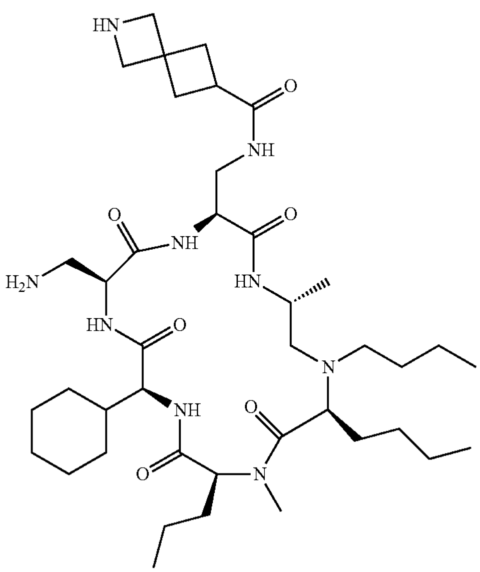 [SMILES: CCCC[C@H]1C(=O)N(C)[C@@H](CCC)C(=O)N[C@@H](C2CCCCC2)C(=O)N[C@@H](CN)C(=O)N[C@@H](CNC(=O)C2CC3(CNC3)C2)C(=O)N[C@H](C)CN1CCCC] | N-[[(2S,5R,8S,11S,14S,17S)-17-(Aminomethyl)-7,8-dibutyl-14-cyclohexyl-5,10-dimethyl-3,9,12,15,18-pentaoxo-11-propyl-1,4,7,10,13,16-hexaazacyclooctadec-2-yl]methyl]-2-azaspiro[3.3]heptane-6-carboxamide |
| 17 | 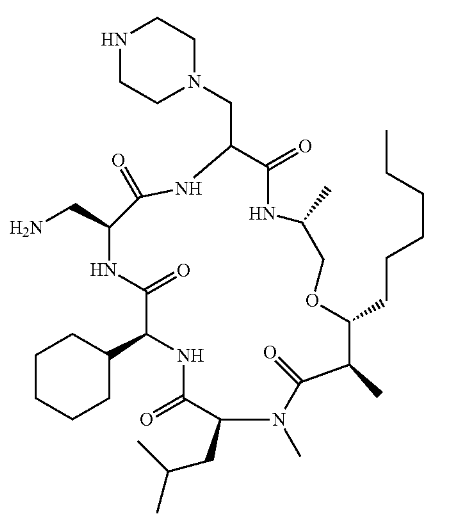 [SMILES: CCCCCC[C@H]1OC[C@@H](C)NC(=O)C(CN2CCNCC2)NC(=O)[C@H](CN)NC(=O)[C@H](C2CCCCC2)NC(=O)[C@H](CC(C)C)N(C)C(=O)[C@@H]1C] | (3R,6S,9S,12S,15S,18R,19R)-9-(aminomethyl)-12-cyclohexyl-19-hexyl-15-isobutyl-3,16,18-trimethyl-6-(piperazin-1-ylmethyl)-1-oxa-4,7,10,13,16-pentaazacyclononadecane-5,8,11,14,17-pentaone (single unknown stereoisomer) |

TABLE 1-continued

| Ex. | Structure | Name |
| --- | --- | --- |
| 18 | 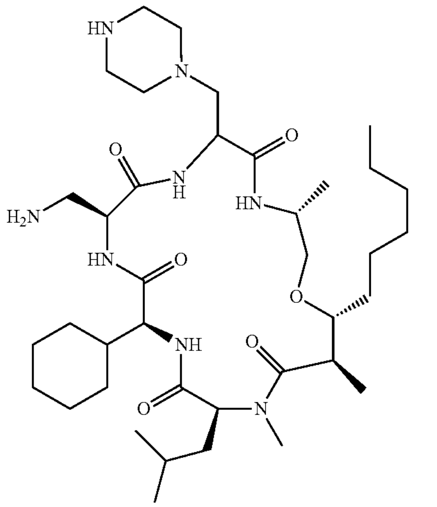 [SMILES: CCCCCC[C@H]1OC[C@@H](C)NC(=O)C(CN2CCNCC2)NC(=O)[C@H](CN)NC(=O)[C@H](C2CCCCC2)NC(=O)[C@H](CC(C)C)N(C)C(=O)[C@@H]1C] | (3R,6S,9S,12S,15S,18R,19R)-9-(aminomethyl)-12-cyclohexyl-19-hexyl-15-isobutyl-3,16,18-trimethyl-6-(piperazin-1-ylmethyl)-1-oxa-4,7,10,13,16-pentaazacyclononadecane-5,8,11,14,17-pentaone (single unknown stereoisomer) |
| 19 | 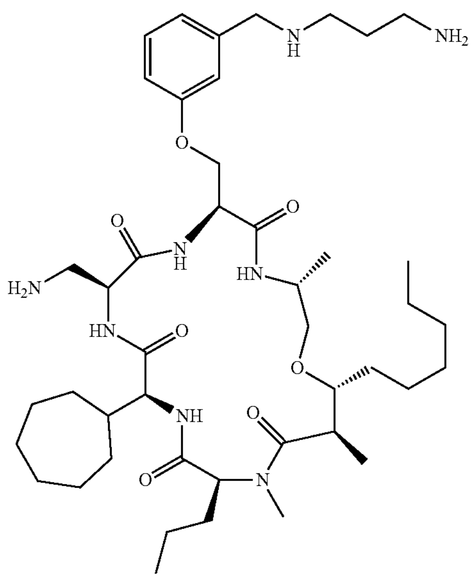 [SMILES: CCCCCC[C@H]1OC[C@@H](C)NC(=O)[C@H](COc2cccc(CNCCCN)c2)NC(=O)[C@H](CN)NC(=O)[C@H](C2CCCCCC2)NC(=O)[C@H](CCC)N(C)C(=O)[C@@H]1C] | (3R,6S,9S,12S,15S,18R,19R)-9-(Aminomethyl)-6-((3-(((3-aminopropyl)amino)methyl)phenoxy)methyl)-12-cycloheptyl-19-hexyl-3,16,18-trimethyl-15-propyl-1-oxa-4,7,10,13,16-pentaazacyclononadecane-5,8,11,14,17-pentaone |
| 20 | 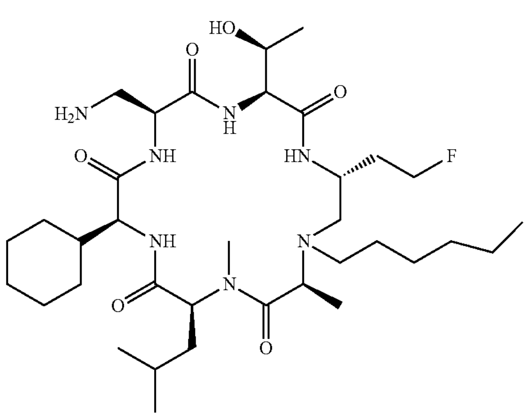 [SMILES: CCCCCCN1C[C@@H](CCF)NC(=O)[C@H]([C@H](C)O)NC(=O)[C@H](CN)NC(=O)[C@H](C2CCCCC2)NC(=O)[C@H](CC(C)C)N(C)C(=O)[C@@H]1C] | (3S,6S,9S,12S,15S,18R)-6-(Aminomethyl)-9-cyclohexyl-18-(2-fluoroethyl)-16-hexyl-3-((S)-1-hydroxyethyl)-12-isobutyl-13,15-dimethyl-1,4,7,10,13,16-hexaazacyclooctadecane-2,5,8,11,14-pentaone |

TABLE 1-continued

| Ex. | Structure | Name |
|---|---|---|
| 21 | 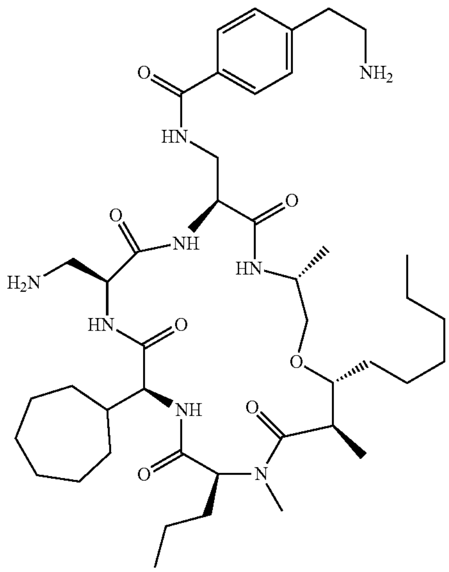 [SMILES: CCCCCC[C@H]1OC[C@@H](C)NC(=O)[C@H](CNC(=O)c2ccc(CCN)cc2)NC(=O)[C@H](CN)NC(=O)[C@H](C2CCCCCC2)NC(=O)[C@H](CCC)N(C)C(=O)[C@@H]1C] | 4-(2-Aminoethyl)-N-[[(3R,6S,9S,12S,15S,18R,19R)-9-(aminomethyl)-12-cycloheptyl-19-hexyl-3,16,18-trimethyl-5,8,11,14,17-pentaoxo-15-propyl-1-oxa-4,7,10,13,16-pentazacyclononadec-6-yl]methyl]benzamide |
| 22 | 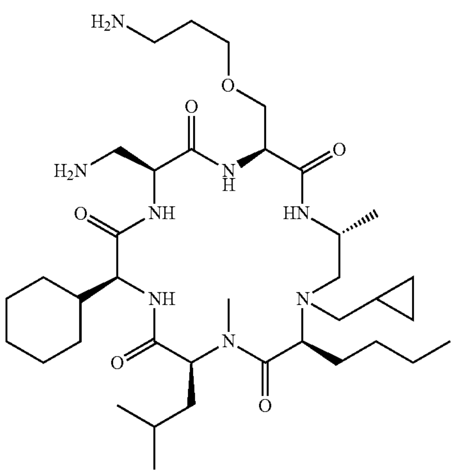 [SMILES: CCCC[C@H]1C(=O)N(C)[C@@H](CC(C)C)C(=O)N[C@@H](C2CCCCC2)C(=O)N[C@@H](CN)C(=O)N[C@@H](COCCCN)C(=O)N[C@H](C)CN1CC1CC1] | (3S,6S,9S,12S,15S,18R)-6-(aminomethyl)-3-((3-aminopropoxy)methyl)-15-butyl-9-cyclohexyl-16-(cyclopropylmethyl)-12-isobutyl-13,18-dimethyl-1,4,7,10,13,16-hexaazacyclooctadecane-2,5,8,11,14-pentaone |
| 23 | 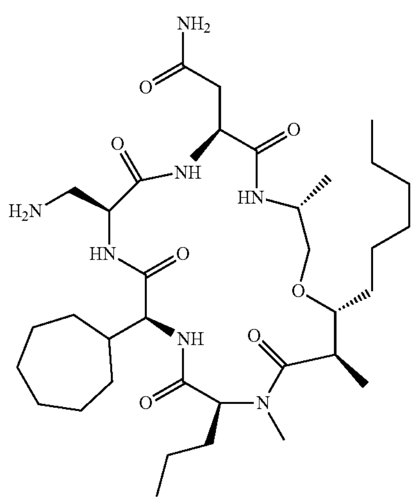 [SMILES: CCCCCC[C@H]1OC[C@@H](C)NC(=O)[C@H](CC(N)=O)NC(=O)[C@H](CN)NC(=O)[C@H](C2CCCCCC2)NC(=O)[C@H](CCC)N(C)C(=O)[C@@H]1C] | 2-((3R,6S,9S,12S,15S,18R,19R)-9-(Aminomethyl)-12-cycloheptyl-19-hexyl-3,16,18-trimethyl-5,8,11,14,17-pentaoxo-15-propyl-1-oxa-4,7,10,13,16-pentaazacyclononadecan-6-yl)acetamide |

TABLE 1-continued

| Ex. | Structure | Name |
|---|---|---|
| 24 | 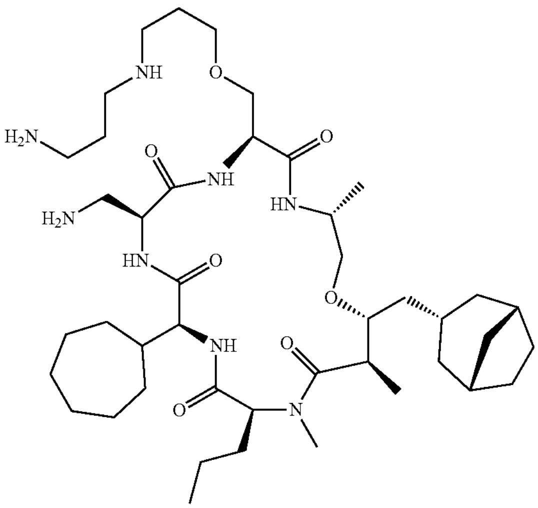 [SMILES: CCC[C@H]1C(=O)N[C@@H](C2CCCCCC2)C(=O)N[C@@H](CN)C(=O)N[C@@H](COCCCNCCCN)C(=O)N[C@H](C)CO[C@H](C[C@@H]2C[C@@H]3CC[C@@H](C3)C2)[C@@H](C)C(=O)N1C] | (3R,6S,9S,12S,15S,18R,19R)-9-(Aminomethyl)-6-((3-((3-aminopropyl)amino)propoxy)methyl)-19-((1R,3s,5S)-bicyclo[3.2.1]octan-3-ylmethyl)-12-cycloheptyl-3,16,18-trimethyl-15-propyl-1-oxa-4,7,10,13,16-pentaazacyclononadecane-5,8,11,14,17-pentaone |
| 25 | 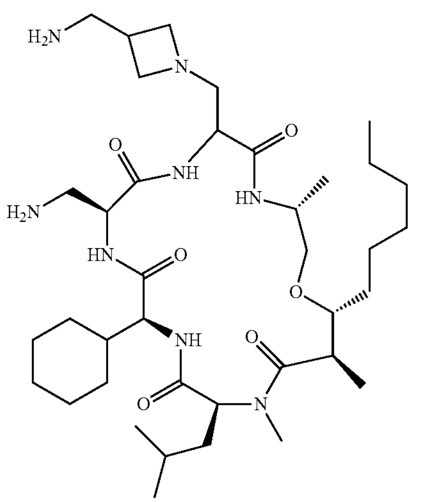 [SMILES: CCCCCC[C@H]1OC[C@@H](C)NC(=O)C(CN2CC(CN)C2)NC(=O)[C@H](CN)NC(=O)[C@H](C2CCCCC2)NC(=O)[C@H](CC(C)C)N(C)C(=O)[C@@H]1C] | (3R,9S,12S,15S,18R,19R)-9-(Aminomethyl)-6-((3-(aminomethyl)azetidin-1-yl)methyl)-12-cyclohexyl-19-hexyl-15-isobutyl-3,16,18-trimethyl-1-oxa-4,7,10,13,16-pentaazacyclononadecane-5,8,11,14,17-pentaone |
| 26 | 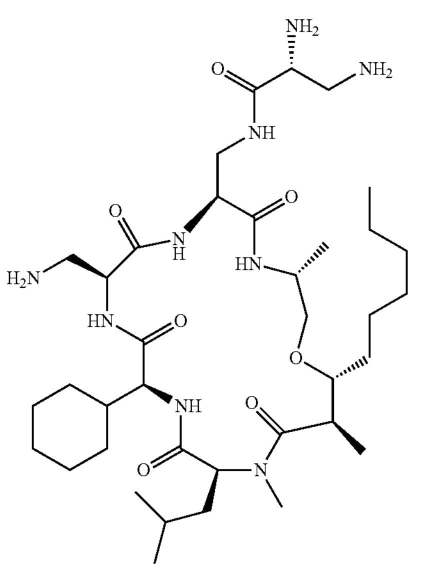 [SMILES: CCCCCC[C@H]1OC[C@@H](C)NC(=O)[C@H](CNC(=O)[C@H](N)CN)NC(=O)[C@H](CN)NC(=O)[C@H](C2CCCCC2)NC(=O)[C@H](CC(C)C)N(C)C(=O)[C@@H]1C] | (2S)-2,3-Diamino-N-[[(3R,6S,9S,12S,15S,18R,19R)-9-(aminomethyl)-12-cyclohexyl-19-hexyl-15-isobutyl-3,16,18-trimethy1-5,8,11,14,17-pentaoxo-1-oxa-4,7,10,13,16-pentazacyclononadec-6-yl]methyl]propanamide |

TABLE 1-continued

| Ex. | Structure | Name |
|---|---|---|
| 27 | 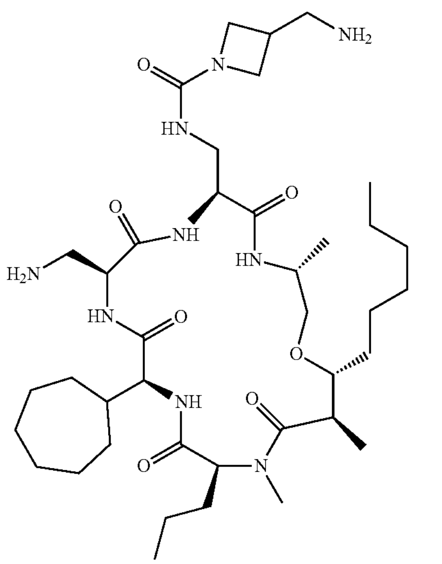 [SMILES: CCCCCC[C@H]1OC[C@@H](C)NC(=O)[C@H](CNC(=O)N2CC(CN)C2)NC(=O)[C@H](CN)NC(=O)[C@H](C2CCCCCC2)NC(=O)[C@H](CCC)N(C)C(=O)[C@@H]1C] | 3-(Aminomethyl)-N-[[(3R,6S,9S,12S,15S,18R,19R)-9-(aminomethyl)-12-cycloheptyl-19-hexyl-3,16,18-trimethyl-5,8,11,14,17-pentaoxo-15-propyl-1-oxa-4,7,10,13,16-pentazacyclononadec-6-yl]methyl]azetidine-1-carboxamide |
| 28 | 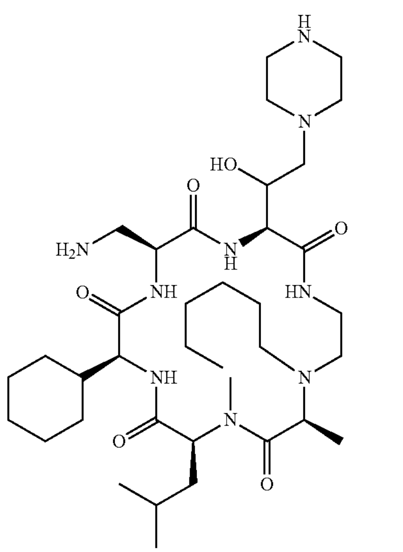 [SMILES: CCCCCCN1CCNC(=O)[C@H](C(O)CN2CCNCC2)NC(=O)[C@H](CN)NC(=O)[C@H](C2CCCCC2)NC(=O)[C@H](CC(C)C)N(C)C(=O)[C@@H]1C] | (3S,6S,9S,12S,15S)-6-(Aminomethyl)-9-cyclohexyl-16-hexyl-3-(1-hydroxy-2-(piperazin-1-yl)ethyl)-12-isobutyl-13,15-dimethyl-1,4,7,10,13,16-hexaazacyclooctadecane-2,5,8,11,14-pentaone |
| 29 | 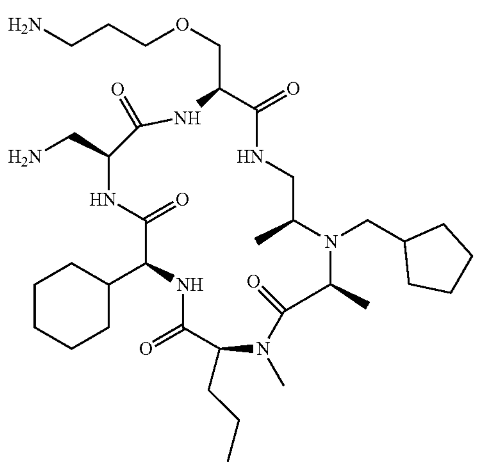 [SMILES: CCC[C@H]1C(=O)N[C@@H](C2CCCCC2)C(=O)N[C@@H](CN)C(=O)N[C@@H](COCCCN)C(=O)NC[C@H](C)N(CC2CCCC2)[C@@H](C)C(=O)N1C] | (3S,6S,9S,12S,15S,17S)-6-(Aminomethyl)-3-((3-aminopropoxy)methyl)-9-cyclohexyl-16-(cyclopentylmethyl)-13,15,17-trimethyl-12-propyl-1,4,7,10,13,16-hexaazacyclooctadecane-2,5,8,11,14-pentaone |

TABLE 1-continued

| Ex. | Structure | Name |
|---|---|---|
| 30 | 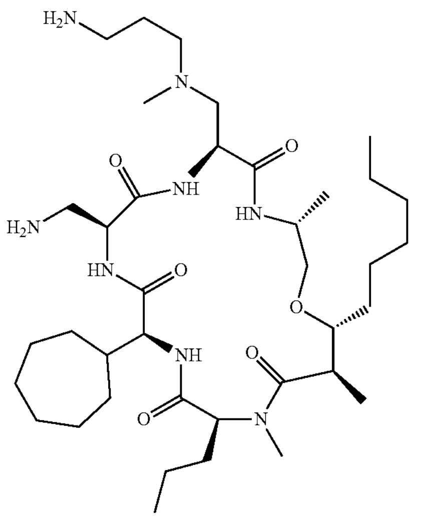 [SMILES: CCCCCC[C@H]1OC[C@@H](C)NC(=O)[C@H](CN(C)CCCN)NC(=O)[C@H](CN)NC(=O)[C@H](C2CCCCCC2)NC(=O)[C@H](CCC)N(C)C(=O)[C@@H]1C] | (3R,6S,9S,12S,15S,18R,19R)-9-(Aminomethyl)-6-[[3-aminopropyl(methyl)amino]methyl]-12-cycloheptyl-19-hexyl-3,16,18-trimethyl-15-propyl-1-oxa-4,7,10,13,16-pentazacyclononadecane-5,8,11,14,17-pentone |
| 31 | 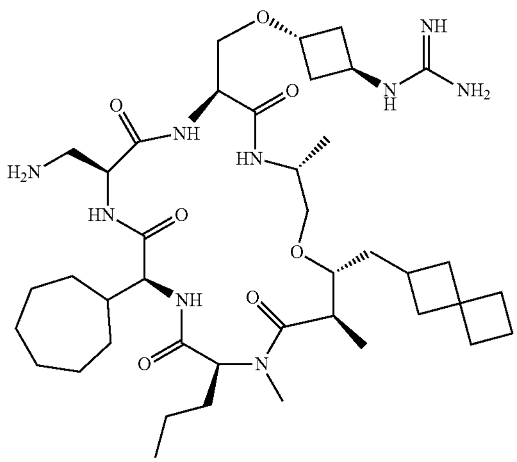 [SMILES: CCC[C@H]1C(=O)N[C@@H](C2CCCCCC2)C(=O)N[C@@H](CN)C(=O)N[C@@H](CO[C@H]2C[C@H](NC(=N)N)C2)C(=O)N[C@H](C)CO[C@H](CC2CC3(CCC3)C2)[C@@H](C)C(=O)N1C] | 1-((1S,3r)-3-(((3R,6S,9S,12S,15S,18R,19R)-9-(Aminomethyl)-12-cycloheptyl-3,16,18-trimethyl-5,8,11,14,17-pentaoxo-15-propyl-19-(spiro[3.3]heptan-2-ylmethyl)-1-oxa-4,7,10,13,16-pentaazacyclononadecan-6-yl)methoxy)cyclobutyl)guanidine |
| 32 | 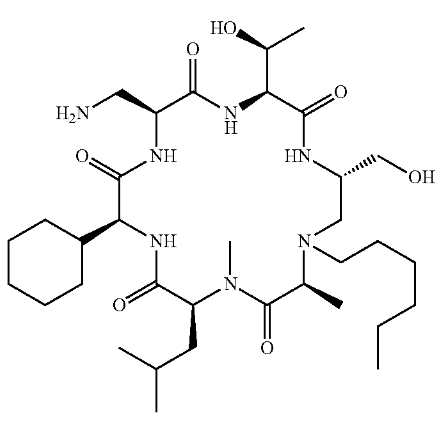 [SMILES: CCCCCCN1C[C@@H](CO)NC(=O)[C@H]([C@H](C)O)NC(=O)[C@H](CN)NC(=O)[C@H](C2CCCCC2)NC(=O)[C@H](CC(C)C)N(C)C(=O)[C@@H]1C] | (3S,6S,9S,12S,15S,18S)-6-(Aminomethyl)-16-butyl-9-cyclohexyl-3-((S)-1-hydroxyethyl)-18-(hydroxymethyl)-12-isobutyl-13,15-dimethyl-1,4,7,10,13,16-hexaazacyclooctadecane-2,5,8,11,14-pentaone |

TABLE 1-continued

| Ex. | Structure | Name |
|---|---|---|
| 33 | 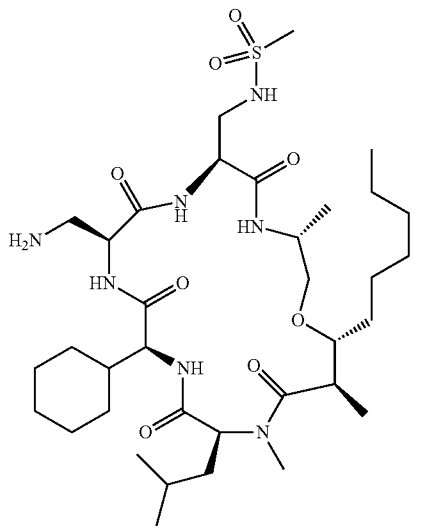 [SMILES: CCCCCC[C@H]1OC[C@@H](C)NC(=O)[C@H](CNS(C)(=O)=O)NC(=O)[C@H](CN)NC(=O)[C@H](C2CCCCC2)NC(=O)[C@H](CC(C)C)N(C)C(=O)[C@@H]1C] | N-[[(3R,6S,9S,12S,15S,18R,19R)-9-(Aminomethyl)-12-cyclohexyl-19-hexyl-15-isobutyl-3,16,18-trimethyl-5,8,11,14,17-pentaoxo-1-oxa-4,7,10,13,16-pentazacyclononadec-6-yl]methyl]methanesulfonamide |
| 34 | 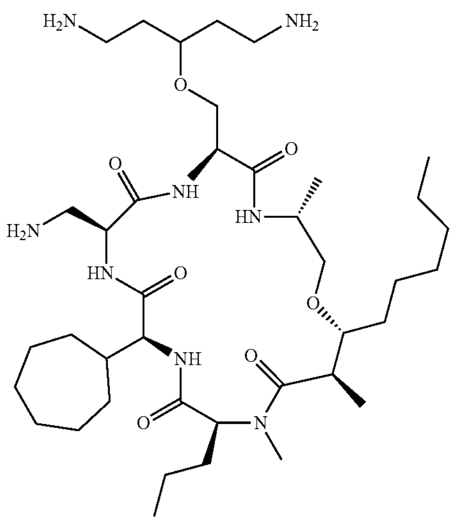 [SMILES: CCCCCC[C@H]1OC[C@@H](C)NC(=O)[C@H](COC(CCN)CCN)NC(=O)[C@H](CN)NC(=O)[C@H](C2CCCCCC2)NC(=O)[C@H](CCC)N(C)C(=O)[C@@H]1C] | (3R,6S,9S,12S,15S,18R,19R)-9-(Aminomethyl)-12-cycloheptyl-6-(((1,5-diaminopentan-3-yl)oxy)methyl)-19-hexyl-3,16,18-trimethyl-15-propyl-1-oxa-4,7,10,13,16-pentaazacyclononadecane-5,8,11,14,17-pentaone |
| 35 | 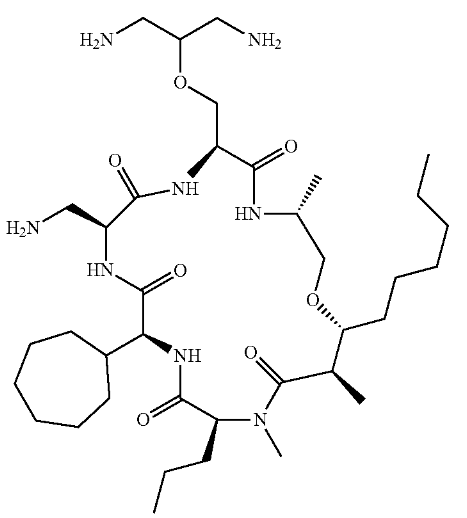 [SMILES: CCCCCC[C@H]1OC[C@@H](C)NC(=O)[C@H](COC(CN)CN)NC(=O)[C@H](CN)NC(=O)[C@H](C2CCCCCC2)NC(=O)[C@H](CCC)N(C)C(=O)[C@@H]1C] | (3R,6S,9S,12S,15S,18R,19R)-9-(Aminomethyl)-12-cycloheptyl-6-(((1,3-diaminopropan-2-yl)oxy)methyl)-19-hexyl-3,16,18-trimethyl-15-propyl-1-oxa-4,7,10,13,16-pentaazacyclononadecane-5,8,11,14,17-pentaone |

TABLE 1-continued

| Ex. | Structure | Name |
|---|---|---|
| 36 | 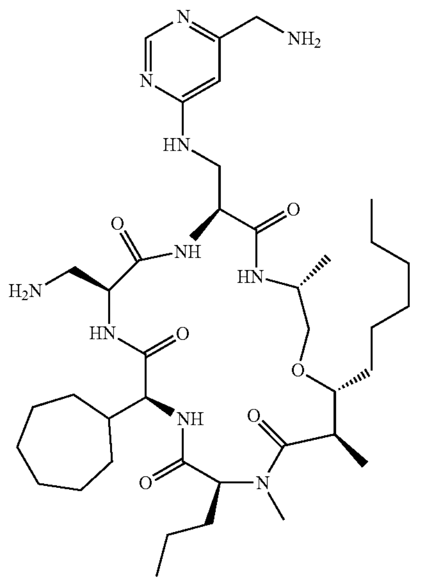 [SMILES: CCCCCC[C@H]1OC[C@@H](C)NC(=O)[C@H](CNc2cc(CN)ncn2)NC(=O)[C@H](CN)NC(=O)[C@H](C2CCCCCC2)NC(=O)[C@H](CCC)N(C)C(=O)[C@@H]1C] | (3R,6S,9S,12S,15S,18R,19R)-9-(Aminomethyl)-6-[[[6-(aminomethyl)pyrimidin-4-yl]amino]methyl]-12-cycloheptyl-19-hexyl-3,16,18-trimethyl-15-propyl-1-oxa-4,7,10,13,16-pentazacyclononadecane-5,8,11,14,17-pentone |
| 37 | 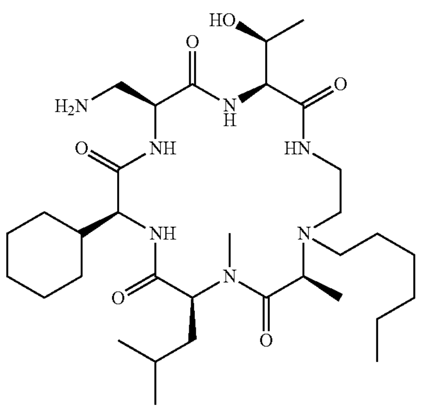 [SMILES: CCCCCCN1CCNC(=O)[C@H]([C@H](C)O)NC(=O)[C@H](CN)NC(=O)[C@H](C2CCCCC2)NC(=O)[C@H](CC(C)C)N(C)C(=O)[C@@H]1C] | (3S,6S,9S,12S,15S)-6-(Aminomethyl)-9-cyclohexyl-16-hexyl-3-((S)-1-hydroxyethyl)-12-isobutyl-13,15-dimethyl-1,4,7,10,13,16-hexaazacyclooctadecane-2,5,8,11,14-pentaone |
| 38 | 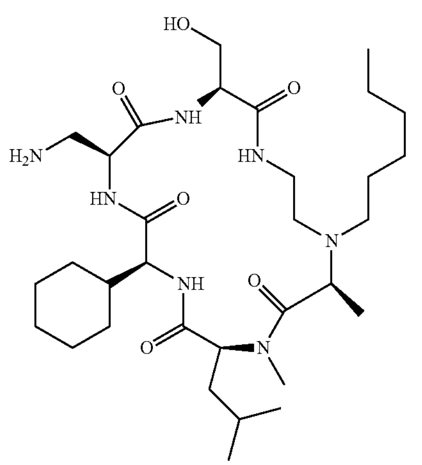 [SMILES: CCCCCCN1CCNC(=O)[C@H](CO)NC(=O)[C@H](CN)NC(=O)[C@H](C2CCCCC2)NC(=O)[C@H](CC(C)C)N(C)C(=O)[C@@H]1C] | (3S,6S,9S,12S,15S)-6-(aminomethyl)-9-cyclohexyl-16-hexyl-3-(hydroxymethyl)-12-isobutyl-13,15-dimethyl-1,4,7,10,13,16-hexaazacyclooctadecane-2,5,8,11,14-pentaone |

TABLE 1-continued

| Ex. | Structure | Name |
|---|---|---|
| 39 | 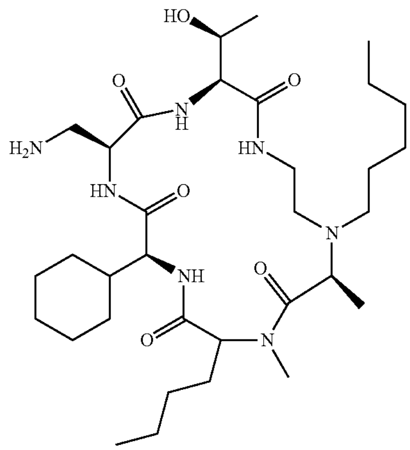 [SMILES: CCCCCCN1CCNC(=O)[C@H]([C@H](C)O)NC(=O)[C@H](CN)NC(=O)[C@H](C2CCCCC2)NC(=O)C(CCCC)N(C)C(=O)[C@@H]1C] | (3S,6S,9S,12S,15S)-6-(aminomethyl)-12-butyl-9-cyclohexyl-16-hexyl-3-((S)-1-hydroxyethyl)-13,15-dimethyl-1,4,7,10,13,16-hexaazacyclooctadecane-2,5,8,11,14-pentaone |
| 40 | 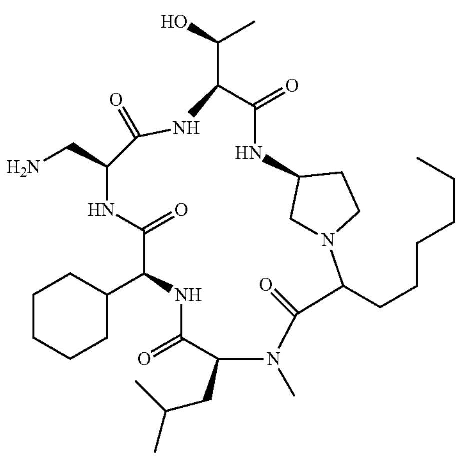 [SMILES: CCCCCCC1C(=O)N(C)[C@@H](CC(C)C)C(=O)N[C@@H](C2CCCCC2)C(=O)N[C@@H](CN)C(=O)N[C@@H]([C@H](C)O)C(=O)N[C@H]2CCN1C2] | (5S,8S,11S,14S,17S)-11-(aminomethyl)-8-cyclohexyl-2-hexyl-14-((S)-1-hydroxyethyl)-5-isobutyl-4-methyl-1,4,7,10,13,16-hexaazabicyclo[15.2.1]icosane-3,6,9,12,15-pentaone (mixture of diastereomers) |
| 41 | 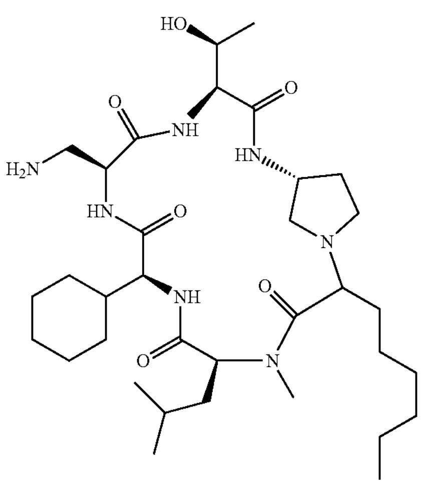 [SMILES: CCCCCCC1C(=O)N(C)[C@@H](CC(C)C)C(=O)N[C@@H](C2CCCCC2)C(=O)N[C@@H](CN)C(=O)N[C@@H]([C@H](C)O)C(=O)N[C@@H]2CCN1C2] | (5S,8S,11S,14S,17S)-11-(aminomethyl)-8-cyclohexyl-2-hexyl-14-((S)-1-hydroxyethyl)-5-isobutyl-4-methyl-1,4,7,10,13,16-hexaazabicyclo[15.2.1]icosane-3,6,9,12,15-pentaone (single unknown stereoisomer) |

TABLE 1-continued

| Ex. | Structure | Name |
|---|---|---|
| 42 | 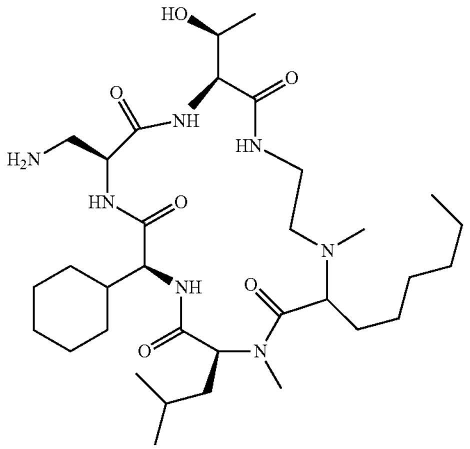 [SMILES: CCCCCCC1C(=O)N(C)[C@@H](CC(C)C)C(=O)N[C@@H](C2CCCCC2)C(=O)N[C@@H](CN)C(=O)N[C@@H]([C@H](C)O)C(=O)NCCN1C] | (3S,6S,9S,12S)-6-(aminomethyl)-9-cyclohexyl-15-hexyl-3-((S)-1-hydroxyethyl)-12-isobutyl-13,16-dimethyl-1,4,7,10,13,16-hexaazacyclooctadecane-2,5,8,11,14-pentaone |
| 43 | 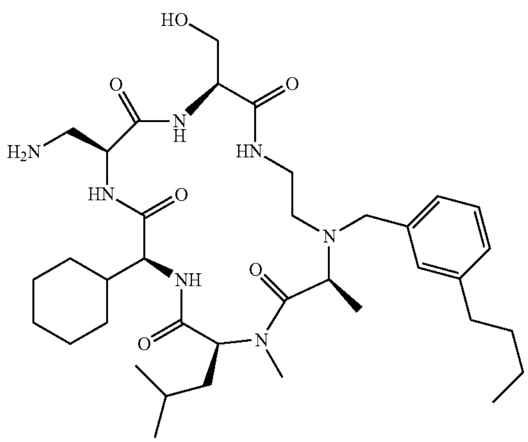 [SMILES: CCCCc1cccc(CN2CCNC(=O)[C@H](CO)NC(=O)[C@H](CN)NC(=O)[C@H](C3CCCCC3)NC(=O)[C@H](CC(C)C)N(C)C(=O)[C@@H]2C)c1] | (3S,6S,9S,12S,15S)-6-(aminomethyl)-16-(3-butylbenzyl)-9-cyclohexyl-3-(hydroxymethyl)-12-isobutyl-13,15-dimethyl-1,4,7,10,13,16-hexaazacyclooctadecane-2,5,8,11,14-pentaone |
| 44 | 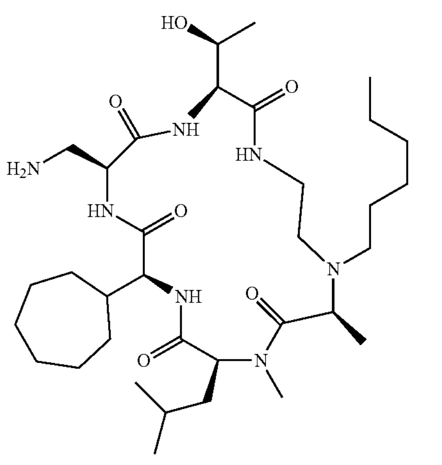 [SMILES: CCCCCCN1CCNC(=O)[C@H]([C@H](C)O)NC(=O)[C@H](CN)NC(=O)[C@H](C2CCCCCC2)NC(=O)[C@H](CC(C)C)N(C)C(=O)[C@@H]1C] | (3S,6S,9S,12S,15S)-6-(aminomethyl)-9-cycloheptyl-16-hexyl-3-((S)-1-hydroxyethyl)-12-isobutyl-13,15-dimethyl-1,4,7,10,13,16-hexaazacyclooctadecane-2,5,8,11,14-pentaone |

TABLE 1-continued

| Ex. | Structure | Name |
|---|---|---|
| 45 | 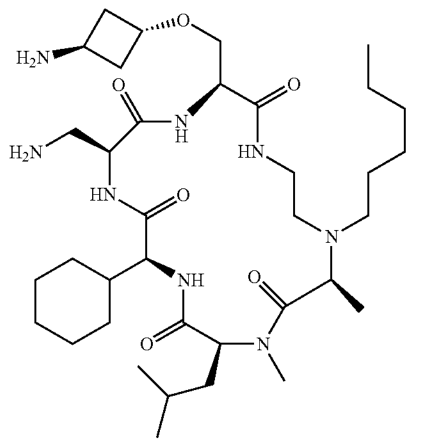 [SMILES: CCCCCCN1CCNC(=O)[C@H](CO[C@H]2C[C@H](N)C2)NC(=O)[C@H](CN)NC(=O)[C@H](C2CCCCC2)NC(=O)[C@H](CC(C)C)N(C)C(=O)[C@@H]1C] | (3S,6S,9S,12S,15S)-3-(((1r,3S)-3-aminocyclobutoxy)methyl)-6-(aminomethyl)-9-cyclohexyl-16-hexyl-12-isobutyl-13,15-dimethyl-1,4,7,10,13,16-hexaazacyclooctadecane-2,5,8,11,14-pentaone |
| 46 | 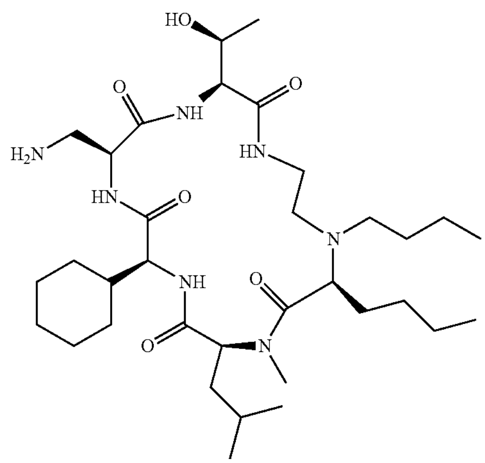 [SMILES: CCCC[C@H]1C(=O)N(C)[C@@H](CC(C)C)C(=O)N[C@@H](C2CCCCC2)C(=O)N[C@@H](CN)C(=O)N[C@@H]([C@H](C)O)C(=O)NCCN1CCCC] | (3S,6S,9S,12S,15S)-6-(aminomethyl)-15,16-dibutyl-9-cyclohexyl-3-((S)-1-hydroxyethyl)-12-isobutyl-13-methyl-1,4,7,10,13,16-hexaazacyclooctadecane-2,5,8,11,14-pentaone |
| 47 | 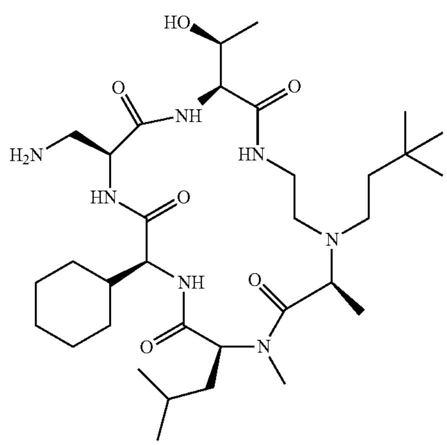 [SMILES: CC(C)C[C@H]1C(=O)N[C@@H](C2CCCCC2)C(=O)N[C@@H](CN)C(=O)N[C@@H]([C@H](C)O)C(=O)NCCN(CCC(C)(C)C)[C@@H](C)C(=O)N1C] | (3S,6S,9S,12S,15S)-6-(aminomethyl)-9-cyclohexyl-16-(3,3-dimethylbutyl)-3-((S)-1-hydroxyethyl)-12-isobutyl-13,15-dimethyl-1,4,7,10,13,16-hexaazacyclooctadecane-2,5,8,11,14-pentaone |

TABLE 1-continued

| Ex. | Structure | Name |
|---|---|---|
| 48 | 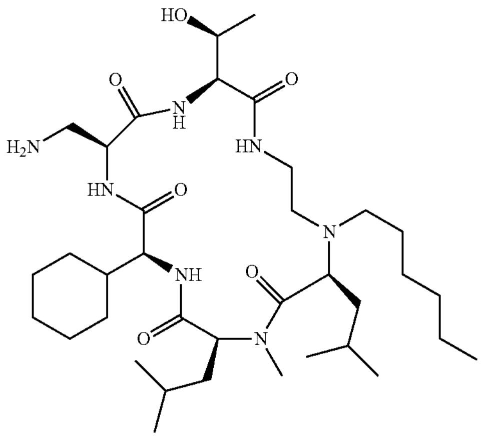 [SMILES: CCCCCCN1CCNC(=O)[C@H]([C@H](C)O)NC(=O)[C@H](CN)NC(=O)[C@H](C2CCCCC2)NC(=O)[C@H](CC(C)C)N(C)C(=O)[C@@H]1CC(C)C] | (3S,6S,9S,12S,15S)-6-(aminomethyl)-9-cyclohexyl-16-hexyl-3-((S)-1-hydroxyethyl)-12,15-diisobutyl-13-methyl-1,4,7,10,13,16-hexaazacyclooctadecane-2,5,8,11,14-pentaone |
| 49 | 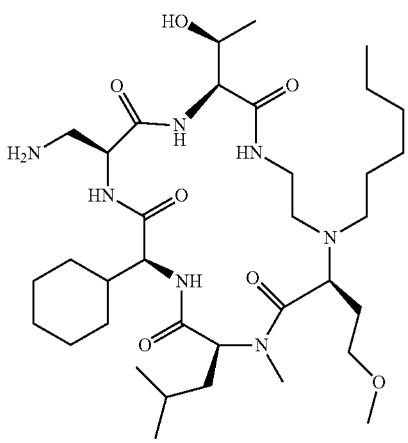 [SMILES: CCCCCCN1CCNC(=O)[C@H]([C@H](C)O)NC(=O)[C@H](CN)NC(=O)[C@H](C2CCCCC2)NC(=O)[C@H](CC(C)C)N(C)C(=O)[C@@H]1CCOC] | (3S,6S,9S,12S,15S)-6-(aminomethyl)-9-cyclohexyl-16-hexyl-3-((S)-1-hydroxyethyl)-12-isobutyl-15-(2-methoxyethyl)-13-methyl-1,4,7,10,13,16-hexaazacyclooctadecane-2,5,8,11,14-pentaone |
| 50 | 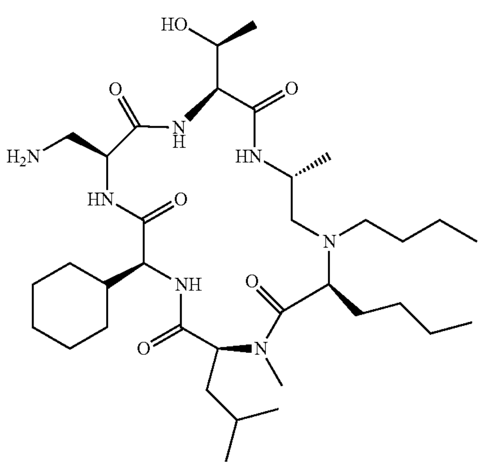 [SMILES: CCCC[C@H]1C(=O)N(C)[C@@H](CC(C)C)C(=O)N[C@@H](C2CCCCC2)C(=O)N[C@@H](CN)C(=O)N[C@@H]([C@H](C)O)C(=O)N[C@H](C)CN1CCCC] | (3S,6S,9S,12S,15S,18R)-6-(aminomethyl)-15,16-dibutyl-9-cyclohexyl-3-((S)-1-hydroxyethyl)-12-isobutyl-13,18-dimethyl-1,4,7,10,13,16-hexaazacyclooctadecane-2,5,8,11,14-pentaone |

TABLE 1-continued

| Ex. | Structure | Name |
|---|---|---|
| 51 | 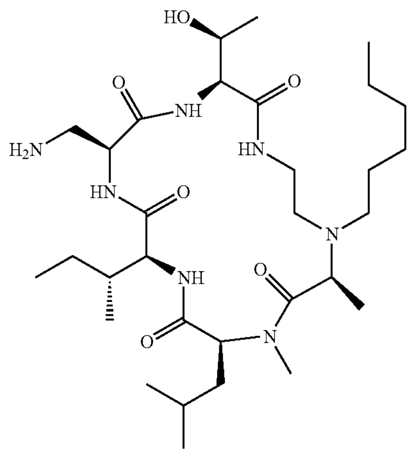 [SMILES: CCCCCCN1CCNC(=O)[C@H]([C@H](C)O)NC(=O)[C@H](CN)NC(=O)[C@H]([C@H](C)CC)NC(=O)[C@H](CC(C)C)N(C)C(=O)[C@@H]1C] | (3S,6S,9S,12S,15S)-6-(aminomethyl)-9-((R)-sec-butyl)-16-hexyl-3-((S)-1-hydroxyethyl)-12-isobutyl-13,15-dimethyl-1,4,7,10,13,16-hexaazacyclooctadecane-2,5,8,11,14-pentaone |
| 52 | 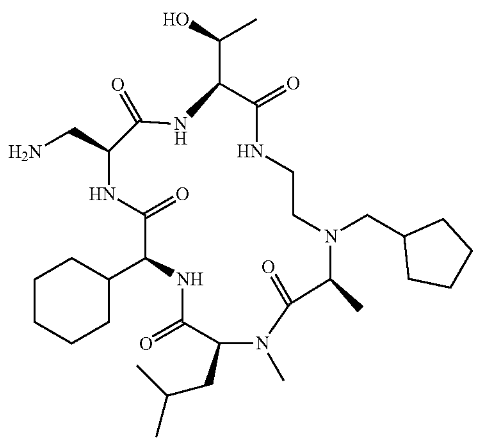 [SMILES: CC(C)C[C@H]1C(=O)N[C@@H](C2CCCCC2)C(=O)N[C@@H](CN)C(=O)N[C@@H]([C@H](C)O)C(=O)NCCN(CC2CCCC2)[C@@H](C)C(=O)N1C] | (3S,6S,9S,12S,15S)-6-(aminomethyl)-9-cyclohexyl-16-(cyclopentylmethyl)-3-((S)-1-hydroxyethyl)-12-isobutyl-13,15-dimethyl-1,4,7,10,13,16-hexaazacyclooctadecane-2,5,8,11,14-pentaone |
| 53 | 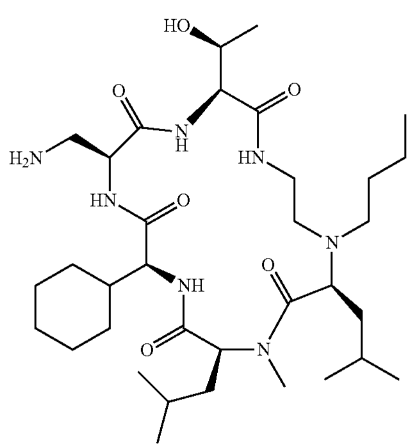 [SMILES: CCCCN1CCNC(=O)[C@H]([C@H](C)O)NC(=O)[C@H](CN)NC(=O)[C@H](C2CCCCC2)NC(=O)[C@H](CC(C)C)N(C)C(=O)[C@@H]1CC(C)C] | (3S,6S,9S,12S,15S)-6-(aminomethyl)-15-butyl-9-cyclohexyl-16-(2-cyclopentylethyl)-3-((S)-1-hydroxyethyl)-12-isobutyl-13-methyl-1,4,7,10,13,16-hexaazacyclooctadecane-2,5,8,11,14-pentaone |

TABLE 1-continued

| Ex. | Structure | Name |
|---|---|---|
| 54 | 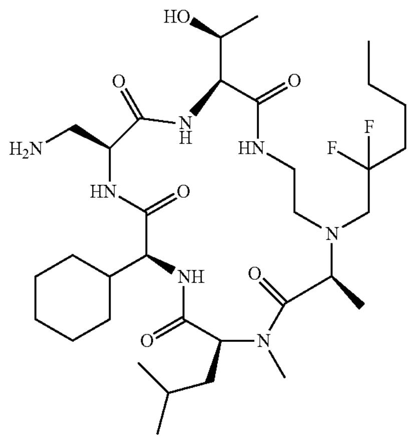 [SMILES: CCCCC(F)(F)CN1CCNC(=O)[C@H]([C@H](C)O)NC(=O)[C@H](CN)NC(=O)[C@H](C2CCCCC2)NC(=O)[C@H](CC(C)C)N(C)C(=O)[C@@H]1C] | (3S,6S,9S,12S,15S)-6-(aminomethyl)-9-cyclohexyl-16-(2,2-difluorohexyl)-3-((S)-1-hydroxyethyl)-12-isobutyl-13,15-dimethyl-1,4,7,10,13,16-hexaazacyclooctadecane-2,5,8,11,14-pentaone |
| 55 | 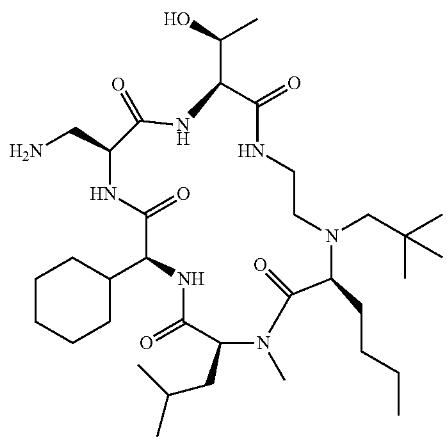 [SMILES: CCCC[C@H]1C(=O)N(C)[C@@H](CC(C)C)C(=O)N[C@@H](C2CCCCC2)C(=O)N[C@@H](CN)C(=O)N[C@@H]([C@H](C)O)C(=O)NCCN1CC(C)(C)C] | (3S,6S,9S,12S,15S)-6-(aminomethyl)-15-butyl-9-cyclohexyl-3-((S)-1-hydroxyethyl)-12-isobutyl-13-methyl-16-neopentyl-1,4,7,10,13,16-hexaazacyclooctadecane-2,5,8,11,14-pentaone |
| 56 | 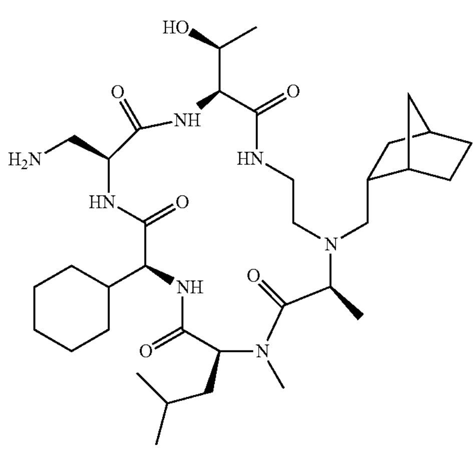 [SMILES: CC(C)C[C@H]1C(=O)N[C@@H](C2CCCCC2)C(=O)N[C@@H](CN)C(=O)N[C@@H]([C@H](C)O)C(=O)NCCN(CC2CC3CCC2C3)[C@@H](C)C(=O)N1C] | (3S,6S,9S,12S,15S)-6-(ammomethyl)-16-((1S,2R,4R)-bicyclo[2.2.1]heptan-2-ylmethyl)-9-cyclohexyl-3-((S)-1-hydroxyethyl)-12-isobutyl-13,15-dimethyl-1,4,7,10,13,16-hexaazacyclooctadecane-2,5,8,11,14-pentaone |

TABLE 1-continued

| Ex. | Structure | Name |
|---|---|---|
| 57 | 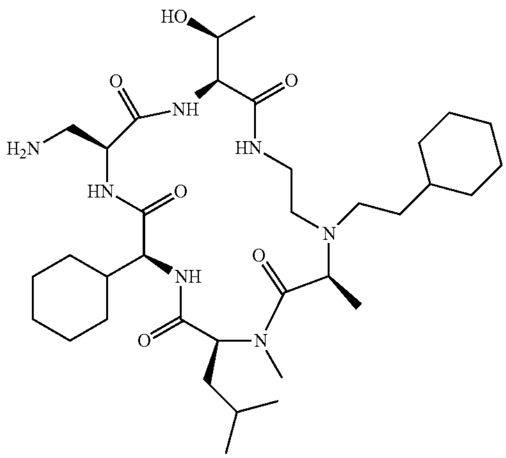 [SMILES: CC(C)C[C@H]1C(=O)N[C@@H](C2CCCCC2)C(=O)N[C@@H](CN)C(=O)N[C@@H]([C@H](C)O)C(=O)NCCN(CCC2CCCCC2)[C@@H](C)C(=O)N1C] | (3S,6S,9S,12S,15S)-6-(aminomethyl)-9-cyclohexyl-16-(2-cyclohexylethyl)-3-((S)-1-hydroxyethyl)-12-isobutyl-13,15-dimethyl-1,4,7,10,13,16-hexaazacyclooctadecane-2,5,8,11,14-pentaone |
| 58 | 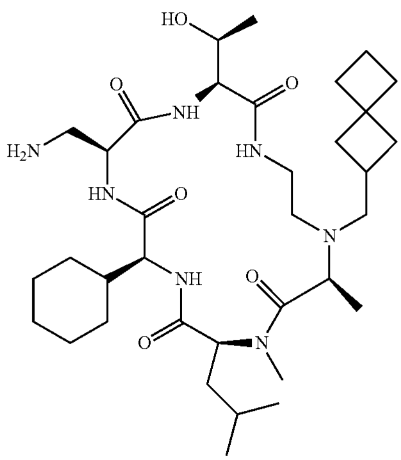 [SMILES: CC(C)C[C@H]1C(=O)N[C@@H](C2CCCCC2)C(=O)N[C@@H](CN)C(=O)N[C@@H]([C@H](C)O)C(=O)NCCN(CC2CC3(CCC3)C2)[C@@H](C)C(=O)N1C] | (3S,6S,9S,12S,15S)-6-(aminomethyl)-9-cyclohexyl-3-((S)-1-hydroxyethyl)-12-isobutyl-13,15-dimethyl-16-(spiro[3.3]heptan-2-ylmethyl)-1,4,7,10,13,16-hexaazacyclooctadecane-2,5,8,11,14-pentaone |
| 59 | 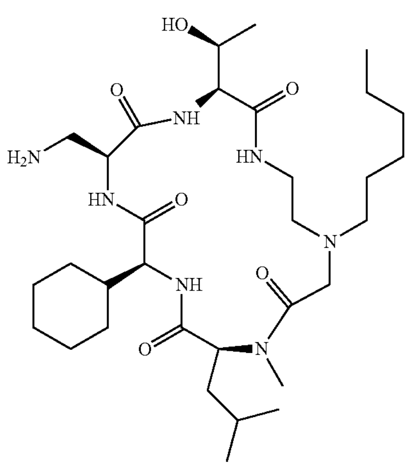 [SMILES: CCCCCCN1CCNC(=O)[C@H]([C@H](C)O)NC(=O)[C@H](CN)NC(=O)[C@H](C2CCCCC2)NC(=O)[C@H](CC(C)C)N(C)C(=O)C1] | (3S,6S,9S,12S)-6-(aminomethyl)-9-cyclohexyl-16-hexyl-3-((S)-1-hydroxyethyl)-12-isobutyl-13-methyl-1,4,7,10,13,16-hexaazacyclooctadecane-2,5,8,11,14-pentaone |

TABLE 1-continued

| Ex. | Structure | Name |
|---|---|---|
| 60 | 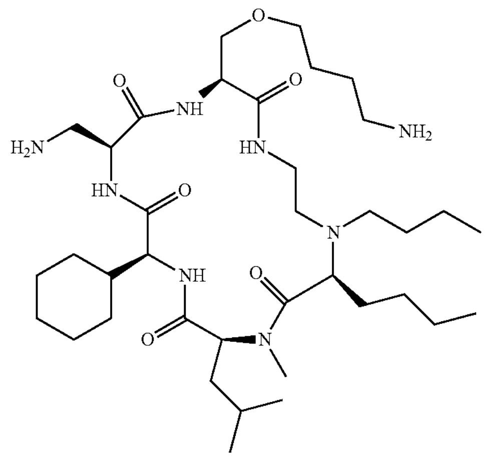 [SMILES: CCCC[C@H]1C(=O)N(C)[C@@H](CC(C)C)C(=O)N[C@@H](C2CCCCC2)C(=O)N[C@@H](CN)C(=O)N[C@@H](COCCCCN)C(=O)NCCN1CCCC] | (3S,6S,9S,12S,15S)-3-((4-aminobutoxy)methyl)-6-(aminomethyl)-15,16-dibutyl-9-cyclohexyl-12-isobutyl-13-methyl-1,4,7,10,13,16-hexaazacyclooctadecane-2,5,8,11,14-pentaone |
| 61 | 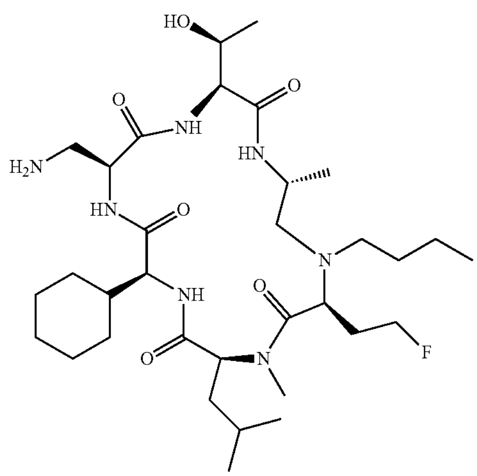 [SMILES: CCCCN1C[C@@H](C)NC(=O)[C@H]([C@H](C)O)NC(=O)[C@H](CN)NC(=O)[C@H](C2CCCCC2)NC(=O)[C@H](CC(C)C)N(C)C(=O)[C@@H]1CCF] | (3S,6S,9S,12S,15S,18R)-6-(aminomethyl)-16-butyl-9-cyclohexyl-15-(2-fluoroethyl)-3-((S)-1-hydroxyethyl)-12-isobutyl-13,18-dimethyl-1,4,7,10,13,16-hexaazacyclooctadecane-2,5,8,11,14-pentaone |
| 62 | 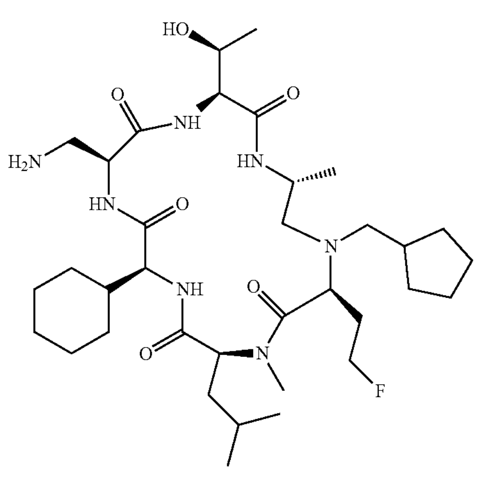 [SMILES: CC(C)C[C@H]1C(=O)N[C@@H](C2CCCCC2)C(=O)N[C@@H](CN)C(=O)N[C@@H]([C@H](C)O)C(=O)N[C@H](C)CN(CC2CCCC2)[C@@H](CCF)C(=O)N1C] | (3S,6S,9S,12S,15S,18R)-6-(aminomethyl)-9-cyclohexyl-16-(cyclopentylmethyl)-15-(2-fluoroethyl)-3-((S)-1-hydroxyethyl)-12-isobutyl-13,18-dimethyl-1,4,7,10,13,16-hexaazacyclooctadecane-2,5,8,11,14-pentaone |

TABLE 1-continued

| Ex. | Structure | Name |
|---|---|---|
| 63 | 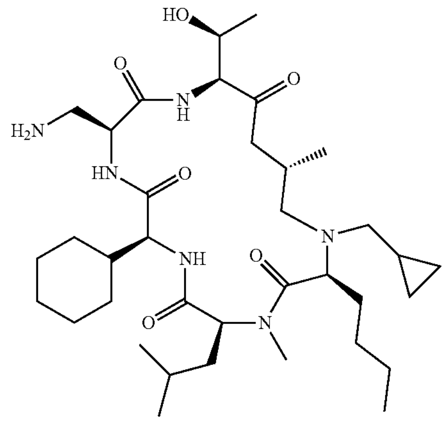 [SMILES: CCCC[C@H]1C(=O)N(C)[C@@H](CC(C)C)C(=O)N[C@@H](C2CCCCC2)C(=O)N[C@@H](CN)C(=O)N[C@@H]([C@H](C)O)C(=O)C[C@H](C)CN1CC1CC1] | (3S,6S,9S,12S,15S)-6-(aminomethyl)-15-butyl-9-cyclohexyl-16-(cyclopropylmethyl)-3-((S)-1-hydroxyethyl)-12-isobutyl-13-methyl-1,4,7,10,13,16-hexaazacyclooctadecane-2,5,8,11,14-pentaone |
| 64 | 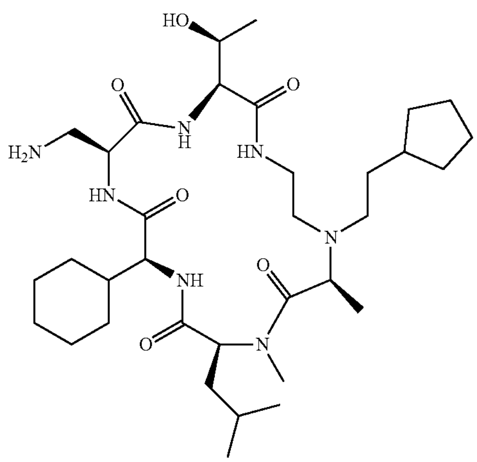 [SMILES: CC(C)C[C@H]1C(=O)N[C@@H](C2CCCCC2)C(=O)N[C@@H](CN)C(=O)N[C@@H]([C@H](C)O)C(=O)NCCN(CCC2CCCC2)[C@@H](C)C(=O)N1C] | (3S,6S,9S,12S,15S)-6-(aminomethyl)-9-cyclohexyl-16-hexyl-3-((S)-1-hydroxyethyl)-12,15-diisobutyl-13-methyl-1,4,7,10,13,16-hexaazacyclooctadecane-2,5,8,11,14-pentaone |
| 65 | 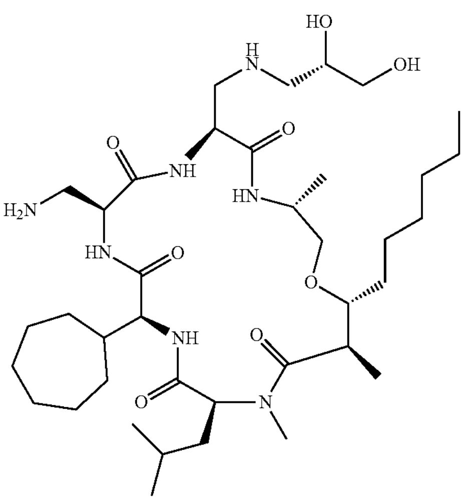 [SMILES: CCCCCC[C@H]1OC[C@@H](C)NC(=O)[C@H](CNC[C@H](O)CO)NC(=O)[C@H](CN)NC(=O)[C@H](C2CCCCCC2)NC(=O)[C@H](CC(C)C)N(C)C(=O)[C@@H]1C] | (3R,6S,9S,12S,15S,18R,19R)-9-(aminomethyl)-12-cycloheptyl-6-((((S)-2,3-dihydroxypropyl)amino)methyl)-19-hexyl-15-isobutyl-3,16,18-trimethyl-1-oxa-4,7,10,13,16-pentaazacyclononadecane-5,8,11,14,17-pentaone |

TABLE 1-continued

| Ex. | Structure | Name |
|---|---|---|
| 66 | 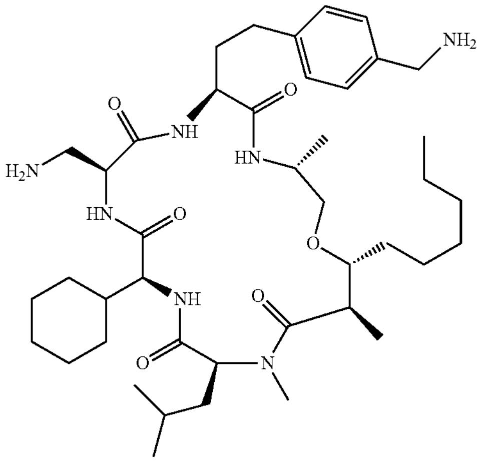 [SMILES: CCCCCC[C@H]1OC[C@@H](C)NC(=O)[C@H](CCc2ccc(CN)cc2)NC(=O)[C@H](CN)NC(=O)[C@H](C2CCCCC2)NC(=O)[C@H](CC(C)C)N(C)C(=O)[C@@H]1C] | (3R,6S,9S,12S,15S,18R,19R)-9-(aminomethyl)-6-(4-(aminomethyl)phenethyl)-12-cyclohexyl-19-hexyl-15-isobutyl-3,16,18-trimethyl-1-oxa-4,7,10,13,16-pentaazacyclononadecane-5,8,11,14,17-pentaone |
| 67 | 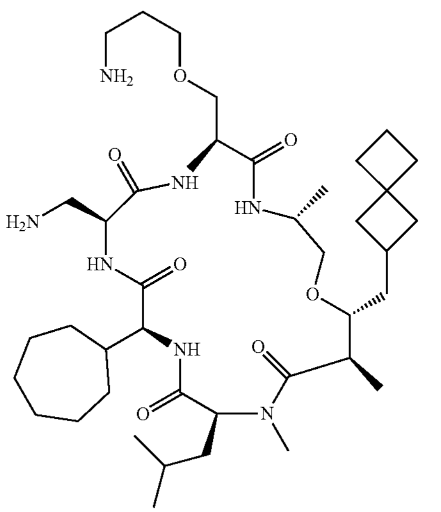 [SMILES: CC(C)C[C@H]1C(=O)N[C@@H](C2CCCCCC2)C(=O)N[C@@H](CN)C(=O)N[C@@H](COCCCN)C(=O)N[C@H](C)CO[C@H](CC2CC3(CCC3)C2)[C@@H](C)C(=O)N1C] | (3R,6S,9S,12S,15S,18R,19R)-9-(aminomethyl)-6-((3-aminopropoxy)methyl)-12-cycloheptyl-15-isobutyl-3,16,18-trimethyl-19-(spiro[3.3]heptan-2-ylmethyl)-1-oxa-4,7,10,13,16-pentaazacyclononadecane-5,8,11,14,17-pentaone |
| 68 | 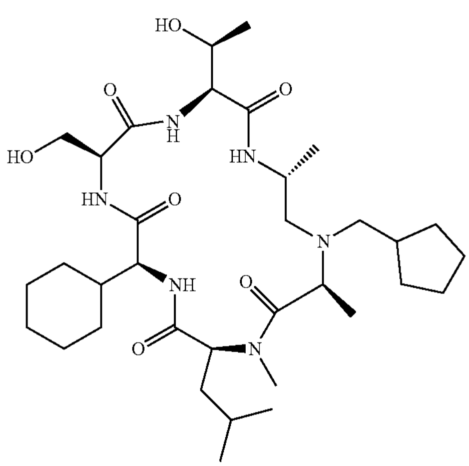 [SMILES: CC(C)C[C@H]1C(=O)N[C@@H](C2CCCCC2)C(=O)N[C@@H](CO)C(=O)N[C@@H]([C@H](C)O)C(=O)N[C@H](C)CN(CC2CCCC2)[C@@H](C)C(=O)N1C] | (3S,6S,9S,12S,15S,18R)-9-cyclohexyl-16-(cyclopentylmethyl)-3-((S)-1-hydroxyethyl)-6-(hydroxymethyl)-12-isobutyl-13,15,18-trimethyl-1,4,7,10,13,16-hexaazacyclooctadecane-2,5,8,11,14-pentaone |

TABLE 1-continued

| Ex. | Structure | Name |
|---|---|---|
| 69 | 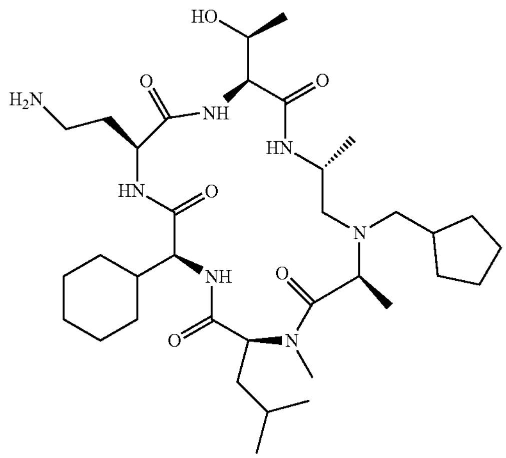 [SMILES: CC(C)C[C@H]1C(=O)N[C@@H](C2CCCCC2)C(=O)N[C@@H](CCN)C(=O)N[C@@H]([C@H](C)O)C(=O)N[C@H](C)CN(CC2CCCC2)[C@@H](C)C(=O)N1C] | (3S,6S,9S,12S,15S,18R)-6-(2-aminoethyl)-9-cyclohexyl-16-(cyclopentylmethyl)-3-((S)-1-hydroxyethyl)-12-isobutyl-13,15,18-trimethyl-1,4,7,10,13,16-hexaazacyclooctadecane-2,5,8,11,14-pentaone |
| 70 | 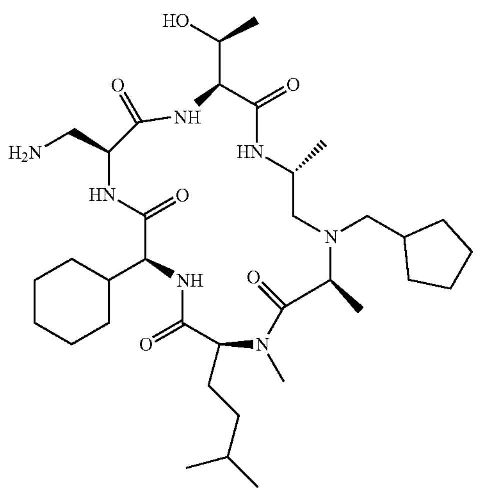 [SMILES: CC(C)CC[C@H]1C(=O)N[C@@H](C2CCCCC2)C(=O)N[C@@H](CN)C(=O)N[C@@H]([C@H](C)O)C(=O)N[C@H](C)CN(CC2CCCC2)[C@@H](C)C(=O)N1C] | (3S,6S,9S,12S,15S,18R)-6-(aminomethyl)-9-cyclohexyl-16-(cyclopentylmethyl)-3-((S)-1-hydroxyethyl)-12-isopentyl-13,15,18-trimethyl-1,4,7,10,13,16-hexaazacyclooctadecane-2,5,8,11,14-pentaone |
| 71 | 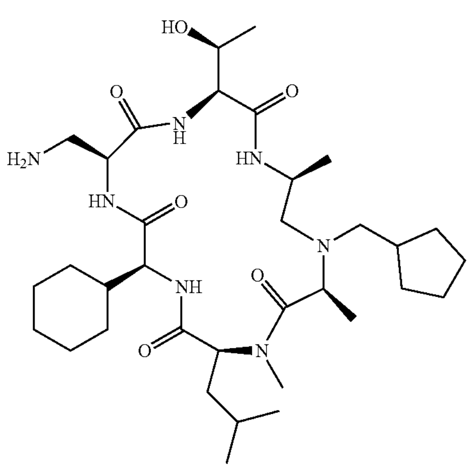 [SMILES: CC(C)C[C@H]1C(=O)N[C@@H](C2CCCCC2)C(=O)N[C@@H](CN)C(=O)N[C@@H]([C@H](C)O)C(=O)N[C@@H](C)CN(CC2CCCC2)[C@@H](C)C(=O)N1C] | (3S,6S,9S,12S,15S,18R)-6-(aminomethyl)-9-cyclohexyl-16-(cyclopentylmethyl)-3-((S)-1-hydroxyethyl)-12-isobutyl-13,15,18-trimethyl-1,4,7,10,13,16-hexaazacyclooctadecane-2,5,8,11,14-pentaone |

TABLE 1-continued

| Ex. | Structure | Name |
|---|---|---|
| 72 | 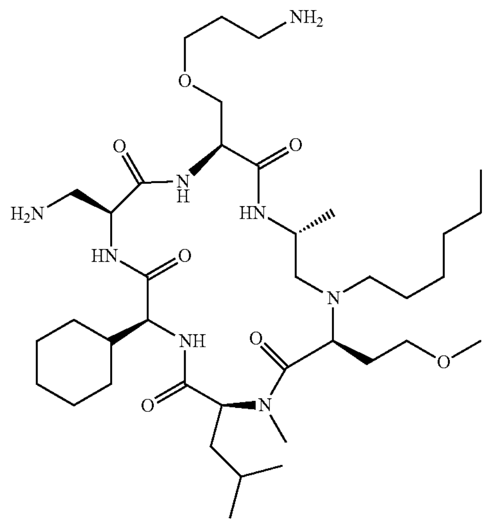 [SMILES: CCCCCCN1C[C@@H](C)NC(=O)[C@H](COCCCN)NC(=O)[C@H](CN)NC(=O)[C@H](C2CCCCC2)NC(=O)[C@H](CC(C)C)N(C)C(=O)[C@@H]1CCOC] | (3S,6S,9S,12S,15S,18R-6-(aminomethyl)-3-((3-aminopropoxy)methyl)-9-cyclohexyl-16-hexyl-12-isobutyl-15-(2-methoxyethyl)-13,18-dimethyl-1,4,7,10,13,16-hexaazacyclooctadecane-2,5,8,11,14-pentaone |
| 73 | 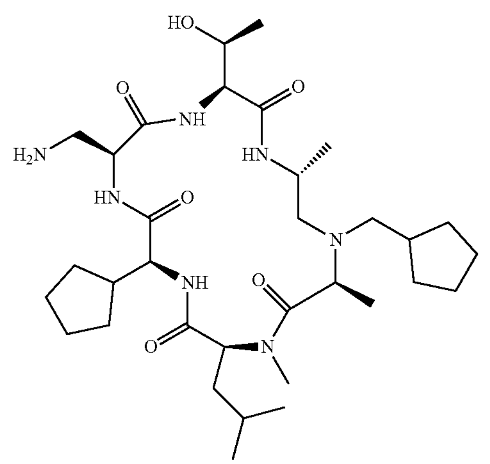 [SMILES: CC(C)C[C@H]1C(=O)N[C@@H](C2CCCC2)C(=O)N[C@@H](CN)C(=O)N[C@@H]([C@H](C)O)C(=O)N[C@H](C)CN(CC2CCCC2)[C@@H](C)C(=O)N1C] | (3S,6S,9S,12S,15S,18R)-6-(aminomethyl)-9-cyclopentyl-16-(cyclopentylmethyl)-3-((S)-1-hydroxyethyl)-12-isobutyl-13,15,18-trimethyl-1,4,7,10,13,16-hexaazacyclooctadecane-2,5,8,11,14-pentaone |
| 74 | 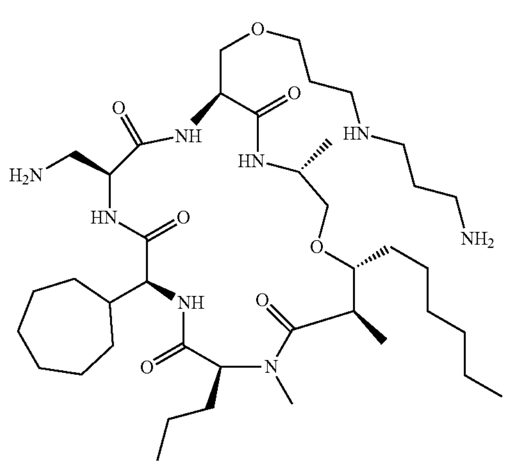 [SMILES: CCCCCC[C@H]1OC[C@@H](C)NC(=O)[C@H](COCCCNCCCN)NC(=O)[C@H](CN)NC(=O)[C@H](C2CCCCCC2)NC(=O)[C@H](CCC)N(C)C(=O)[C@@H]1C] | (3S,6S,9S,12S,15S,18R,19R)-9-(aminomethyl)-6-((3-((3-aminopropyl)amino)propoxy)methyl)-12-cycloheptyl-19-hexyl-3,16,18-trimethyl-15-propyl-1-oxa-4,7,10,13,16-pentaazacyclononadecane-5,8,11,14,17-pentaone |

TABLE 1-continued

| Ex. | Structure | Name |
|---|---|---|
| 75 | 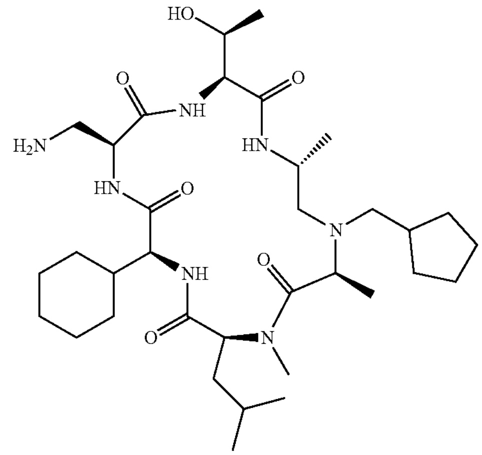 [SMILES: CC(C)C[C@H]1C(=O)N[C@@H](C2CCCCC2)C(=O)N[C@@H](CN)C(=O)N[C@@H]([C@H](C)O)C(=O)N[C@H](C)CN(CC2CCCC2)[C@@H](C)C(=O)N1C] | (3S,6S,9S,12S,15S,18R)-6-(aminomethyl)-9-cyclohexyl-16-(cyclopentylmethyl)-3-((S)-1-hydroxyethyl)-12-isobutyl-13,15,18-trimethyl-1,4,7,10,13,16-hexaazacyclooctadecane-2,5,8,11,14-pentaone |
| 76 | 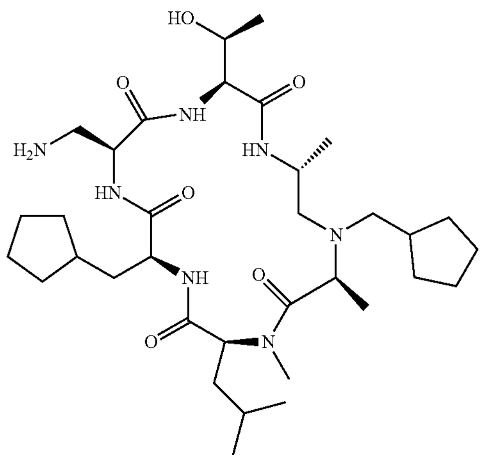 [SMILES: CC(C)C[C@H]1C(=O)N[C@@H](CC2CCCC2)C(=O)N[C@@H](CN)C(=O)N[C@@H]([C@H](C)O)C(=O)N[C@H](C)CN(CC2CCCC2)[C@@H](C)C(=O)N1C] | (3S,6S,9S,12S,15S,18R)-6-(aminomethyl)-9,16-bis(cyclopentylmethyl)-3-((S)-1-hydroxyethyl)-12-isobutyl-13,15,18-trimethyl-1,4,7,10,13,16-hexaazacyclooctadecane-2,5,8,11,14-pentaone |
| 77 | 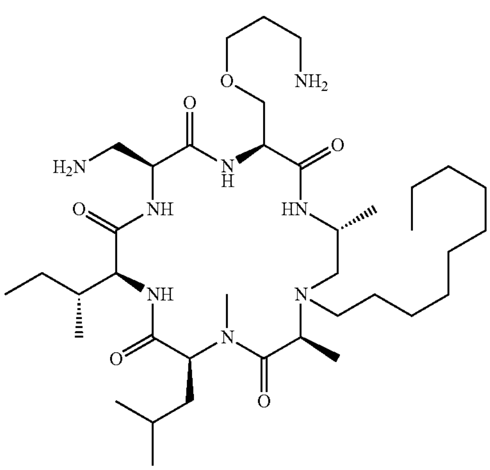 [SMILES: CCCCCCCCCCN1C[C@@H](C)NC(=O)[C@H](COCCCN)NC(=O)[C@H](CN)NC(=O)[C@H]([C@H](C)CC)NC(=O)[C@H](CC(C)C)N(C)C(=O)[C@@H]1C] | ((3S,6S,9S,12S,15S,18R)-6-(aminomethyl)-3-((3-aminopropoxy)methyl)-9-((R)-sec-butyl)-16-decyl-12-isobutyl-13,15,18-trimethyl-1,4,7,10,13,16-hexaazacyclooctadecane-2,5,8,11,14-pentaone |

| Ex. | Structure | Name |
|---|---|---|
| 78 | 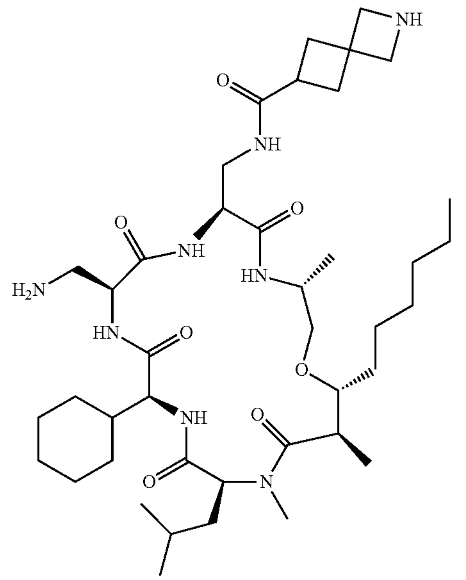 [SMILES: CCCCCC[C@H]1OC[C@@H](C)NC(=O)[C@H](CNC(=O)C2CC3(CNC3)C2)NC(=O)[C@H](CN)NC(=O)[C@H](C2CCCCC2)NC(=O)[C@H](CC(C)C)N(C)C(=O)[C@@H]1C] | N-[[(3R,6S,9S,12S,15S,18R,19R)-9-(aminomethyl)-12-cyclohexyl-19-hexyl-15-isobutyl-3,16,18-trimethyl-5,8,11,14,17-pentaoxo-1-oxa-4,7,10,13,16-pentazacyclononadec-6-yl]methyl]-2-azaspiro[3.3]heptane-6-carboxamide |
| 79 | 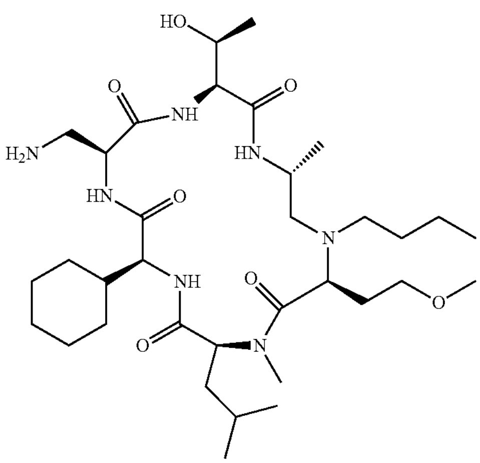 [SMILES: CCCCN1C[C@@H](C)NC(=O)[C@H]([C@H](C)O)NC(=O)[C@H](CN)NC(=O)[C@H](C2CCCCC2)NC(=O)[C@H](CC(C)C)N(C)C(=O)[C@@H]1CCOC] | (3S,6S,9S,12S,15S,18R)-6-(aminomethyl)-16-butyl-9-cyclohexyl-3-((S)-1-hydroxyethyl)-12-isobutyl-15-(2-methoxyethyl)-13,18-dimethyl-1,4,7,10,13,16-hexaazacyclooctadecane-2,5,8,11,14-pentaone |
| 80 | 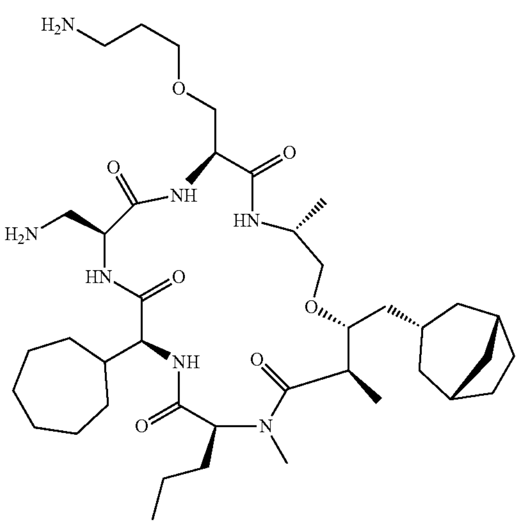 [SMILES: CCC[C@H]1C(=O)N[C@@H](C2CCCCCC2)C(=O)N[C@@H](CN)C(=O)N[C@@H](COCCCN)C(=O)N[C@H](C)CO[C@H](C[C@@H]2C[C@@H]3CC[C@@H](C3)C2)[C@@H](C)C(=O)N1C] | (3S,6S,9S,12S,15S,18R,19R)-9-(aminomethyl)-6-((3-aminopropoxy)methyl)-19-((1R,3s,5S)-bicyclo[3.2.1]octan-3-ylmethyl)-12-cycloheptyl-3,16,18-trimethyl-15-propyl-1-oxa-4,7,10,13,16-pentaazacyclononadecane-5,8,11,14,17-pentaone |

TABLE 1-continued

| Ex. | Structure | Name |
|---|---|---|
| 81 | 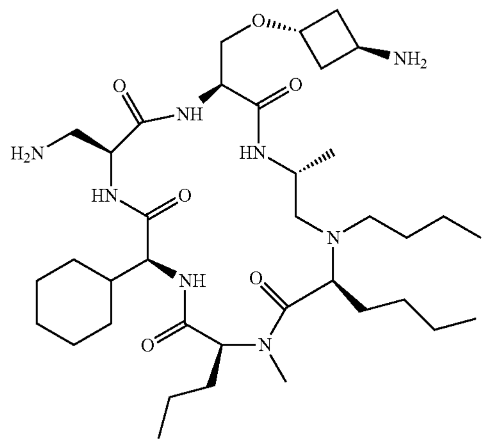 [SMILES: CCCC[C@H]1C(=O)N(C)[C@@H](CCC)C(=O)N[C@@H](C2CCCCC2)C(=O)N[C@@H](CN)C(=O)N[C@@H](CO[C@H]2C[C@H](N)C2)C(=O)N[C@H](C)CN1CCCC] | (3S,6S,9S,12S,15S,18R)-3-(((1r,3S)-3-aminocyclobutoxy)methyl)-6-(aminomethyl)-15,16-dibutyl-9-cyclohexyl-13,18-dimethyl-12-propyl-1,4,7,10,13,16-hexaazacyclooctadecane-2,5,8,11,14-pentaone |
| 82 | 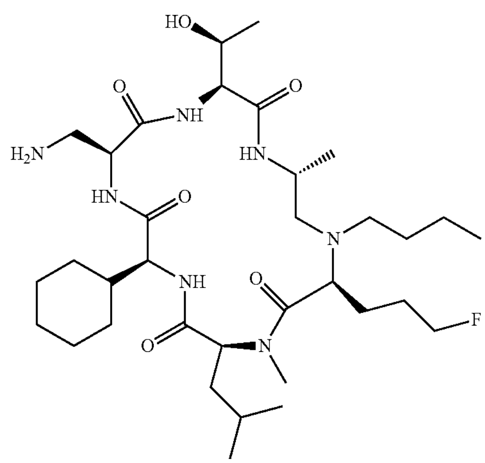 [SMILES: CCCCN1C[C@@H](C)NC(=O)[C@H]([C@H](C)O)NC(=O)[C@H](CN)NC(=O)[C@H](C2CCCCC2)NC(=O)[C@H](CC(C)C)N(C)C(=O)[C@@H]1CCCF] | (3S,6S,9S,12S,15S,18R)-6-(aminomethyl)-16-butyl-9-cyclohexyl-15-(3-fluoropropyl)-3-((S)-1-hydroxyethyl)-12-isobutyl-13,18-dimethyl-1,4,7,10,13,16-hexaazacyclooctadecane-2,5,8,11,14-pentaone |
| 83 | 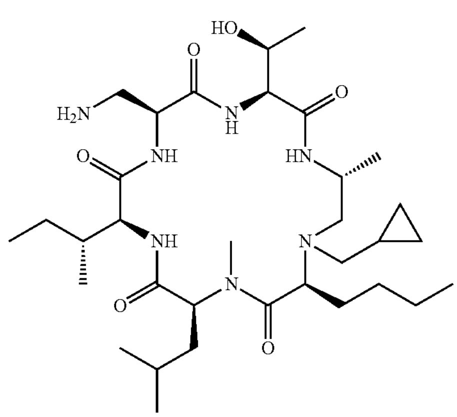 [SMILES: CCCC[C@H]1C(=O)N(C)[C@@H](CC(C)C)C(=O)N[C@@H]([C@H](C)CC)C(=O)N[C@@H](CN)C(=O)N[C@@H]([C@H](C)O)C(=O)N[C@H](C)CN1CC1CC1] | (3S,6S,9S,12S,15S,18R)-6-(aminomethyl)-9-((R)-sec-butyl)-15-butyl-16-(cyclopropylmethyl)-3-((S)-1-hydroxyethyl)-12-isobutyl-13,18-dimethyl-1,4,7,10,13,16-hexaazacyclooctadecane-2,5,8,11,14-pentaone |

TABLE 1-continued

| Ex. | Structure | Name |
|---|---|---|
| 84 | 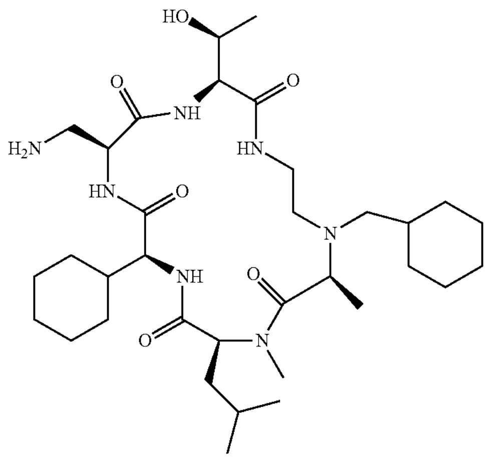 [SMILES: CC(C)C[C@H]1C(=O)N[C@@H](C2CCCCC2)C(=O)N[C@@H](CN)C(=O)N[C@@H]([C@H](C)O)C(=O)NCCN(CC2CCCCC2)[C@@H](C)C(=O)N1C] | (3S,6S,9S,12S,15S)-6-(aminomethyl)-9-cyclohexyl-16-(cyclohexylmethyl)-3-((S)-1-hydroxyethyl)-12-isobutyl-13,15-dimethyl-1,4,7,10,13,16-hexaazacyclooctadecane-2,5,8,11,14-pentaone |
| 85 | 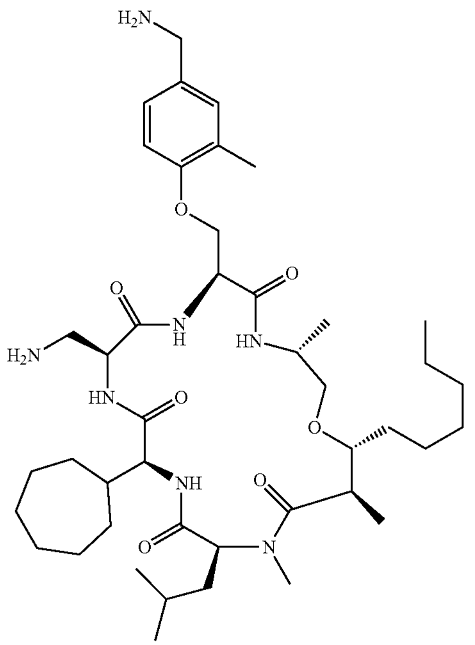 [SMILES: CCCCCC[C@H]1OC[C@@H](C)NC(=O)[C@H](COc2ccc(CN)cc2C)NC(=O)[C@H](CN)NC(=O)[C@H](C2CCCCCC2)NC(=O)[C@H](CC(C)C)N(C)C(=O)[C@@H]1C] | (3S,6S,9S,12S,15S,18R,19R)-9-(aminomethyl)-6-((4-(aminomethyl)-2-methylphenoxy)methyl)-12-cyclohexyl-19-hexyl-15-isobutyl-3,16,18-trimethyl-1-oxa-4,7,10,13,16-pentaazacyclononadecane-5,8,11,14,17-pentaone |
| 86 | 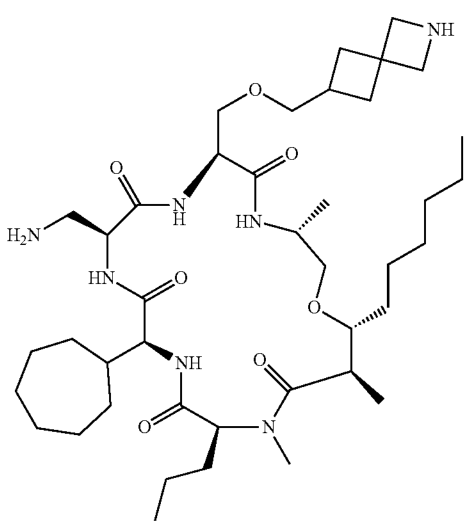 [SMILES: CCCCCC[C@H]1OC[C@@H](C)NC(=O)[C@H](COCC2CC3(CNC3)C2)NC(=O)[C@H](CN)NC(=O)[C@H](C2CCCCCC2)NC(=O)[C@H](CCC)N(C)C(=O)[C@@H]1C] | (3S,6S,9S,12S,15S,18R,19R)-6-((2-azaspiro[3.3]heptan-6-ylmethoxy)methyl)-9-(aminomethyl)-12-cycloheptyl-19-hexyl-3,16,18-trimethyl-15-propyl-1-oxa-4,7,10,13,16-pentaazacyclononadecane-5,8,11,14,17-pentaone |

TABLE 1-continued

| Ex. | Structure | Name |
|---|---|---|
| 87 | 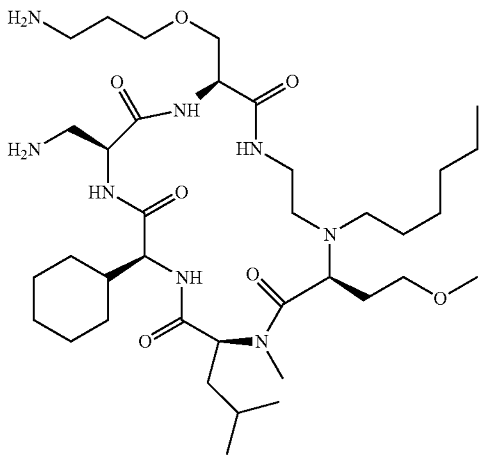 [SMILES: CCCCCCN1CCNC(=O)[C@H](COCCCN)NC(=O)[C@H](CN)NC(=O)[C@H](C2CCCCC2)NC(=O)[C@H](CC(C)C)N(C)C(=O)[C@@H]1CCOC] | (3S,6S,9S,12S,15S)-6-(aminomethyl)-3-((3-aminopropoxy)methyl)-9-cyclohexyl-16-hexyl-12-isobutyl-15-(2-methoxyethyl)-13-methyl-1,4,7,10,13,16-hexaazacyclooctadecane-2,5,8,11,14-pentaone |
| 88 | 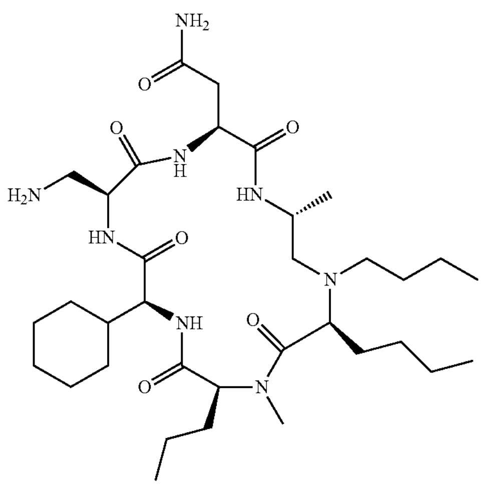 [SMILES: CCCC[C@H]1C(=O)N(C)[C@@H](CCC)C(=O)N[C@@H](C2CCCCC2)C(=O)N[C@@H](CN)C(=O)N[C@@H](CC(N)=O)C(=O)N[C@H](C)CN1CCCC] | 2-((2S,5R,8S,11S,14S,17S)-17-(aminomethyl)-7,8-dibutyl-14-cyclohexyl-5,10-dimethyl-3,9,12,15,18-pentaoxo-11-propyl-1,4,7,10,13,16-hexaazacyclooctadecan-2-yl)acetamide |
| 89 | 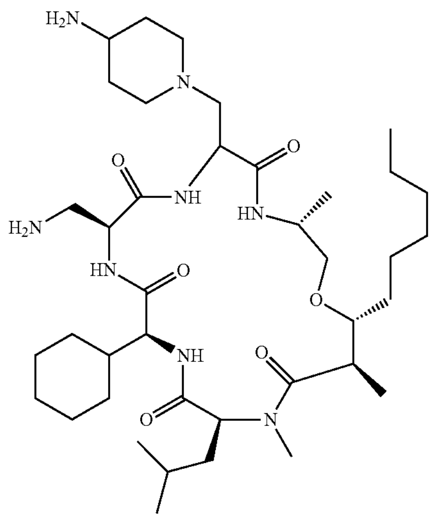 [SMILES: CCCCCC[C@H]1OC[C@@H](C)NC(=O)C(CN2CCC(N)CC2)NC(=O)[C@H](CN)NC(=O)[C@H](C2CCCCC2)NC(=O)[C@H](CC(C)C)N(C)C(=O)[C@@H]1C] | (3R,6S,9S,12S,15S,18R,19R)-9-(aminomethyl)-6-((4-aminopiperidin-1-yl)methyl)-12-cyclohexyl-19-hexyl-15-isobutyl-3,16,18-trimethyl-1-oxa-4,7,10,13,16-pentaazacyclononadecane-5,8,11,14,17-pentaone (mixture of 2 diastereomers) |

| Ex. | Structure | Name |
|-----|-----------|------|
| 90 | 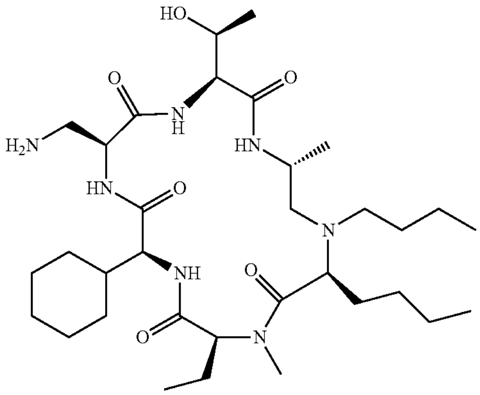 [SMILES: CCCC[C@H]1C(=O)N(C)[C@@H](CC)C(=O)N[C@@H](C2CCCCC2)C(=O)N[C@@H](CN)C(=O)N[C@@H]([C@H](C)O)C(=O)N[C@H](C)CN1CCCC] | (3S,6S,9S,12S,15S,18R-6-(aminomethyl)-15,16-dibutyl-9-cyclohexyl-12-ethyl-3-((S)-1-hydroxyethyl)-13,18-dimethyl-1,4,7,10,13,16-hexaazacyclooctadecane-2,5,8,11,14-pentaone |
| 91 | 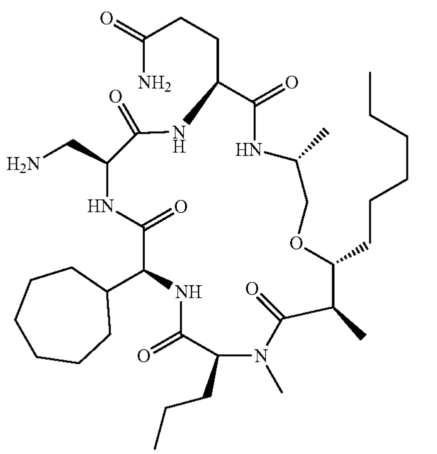 [SMILES: CCCCCC[C@H]1OC[C@@H](C)NC(=O)[C@H](CCC(N)=O)NC(=O)[C@H](CN)NC(=O)[C@H](C2CCCCCC2)NC(=O)[C@H](CCC)N(C)C(=O)[C@@H]1C] | 3-((3S,6S,9S,12S,15S,18R,19R)-9-(aminomethyl)-12-cycloheptyl-19-hexyl-3,16,18-trimethyl-5,8,11,14,17-pentaoxo-15-propyl-1-oxa-4,7,10,13,16-pentaazacyclononadecan-6-yl)propanamide |
| 92 | 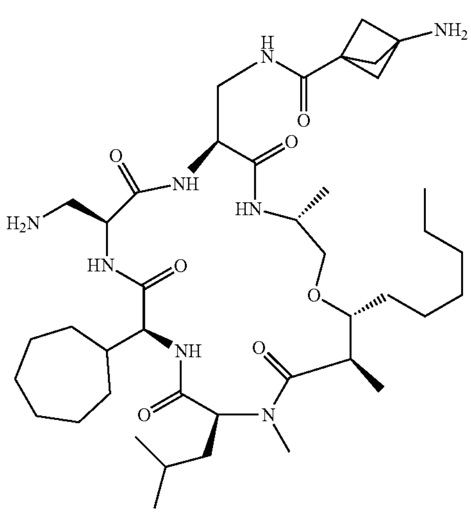 [SMILES: CCCCCC[C@H]1OC[C@@H](C)NC(=O)[C@H](CNC(=O)C23CC(N)(C2)C3)NC(=O)[C@H](CN)NC(=O)[C@H](C2CCCCCC2)NC(=O)[C@H](CC(C)C)N(C)C(=O)[C@@H]1C] | 3-amino-N-(((3R,6S,9S,12S,15S,18R,19R)-9-(aminomethyl)-12-cyclohexyl-19-hexyl-15-isobutyl-3,16,18-trimethyl-5,8,11,14,17-pentaoxo-1-oxa-4,7,10,13,16-pentaazacyclononadecan-6-yl)methyl)bicyclo[1.1.1]pentane-1-carboxamide |

TABLE 1-continued

| Ex. | Structure | Name |
| --- | --- | --- |
| 93 | 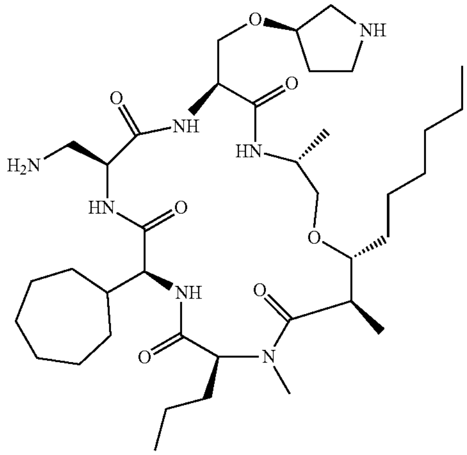 [SMILES: CCCCCC[C@H]1OC[C@@H](C)NC(=O)[C@H](CO[C@@H]2CCNC2)NC(=O)[C@H](CN)NC(=O)[C@H](C2CCCCCC2)NC(=O)[C@H](CCC)N(C)C(=O)[C@@H]1C] | (3S,6S,9S,12S,15S,18R,19R-9-(aminomethyl)-12-cycloheptyl-19-hexyl-3,16,18-trimethyl-15-propyl-6-(((S)-pyrrolidin-3-yloxy)methyl)-1-oxa-4,7,10,13,16-pentaazacyclononadecane-5,8,11,14,17-pentaone |
| 94 | 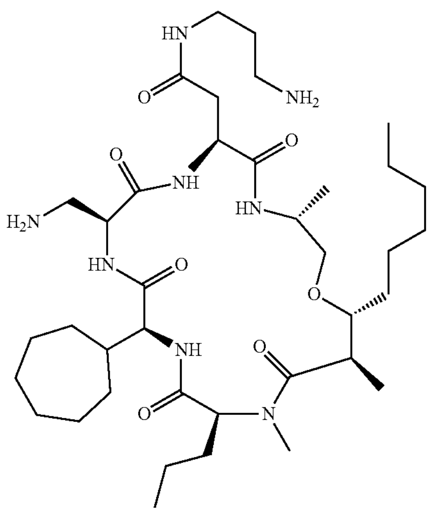 [SMILES: CCCCCC[C@H]1OC[C@@H](C)NC(=O)[C@H](CC(=O)NCCCN)NC(=O)[C@H](CN)NC(=O)[C@H](C2CCCCCC2)NC(=O)[C@H](CCC)N(C)C(=O)[C@@H]1C] | 2-((3S,6S,9S,12S,15S,18R,19R)-9-(aminomethyl)-12-cycloheptyl-19-hexyl-3,16,18-trimethyl-5,8,11,14,17-pentaoxo-15-propyl-1-oxa-4,7,10,13,16-pentaazacyclononadecan-6-yl)-N-(3-aminopropyl)acetamide |
| 95 | 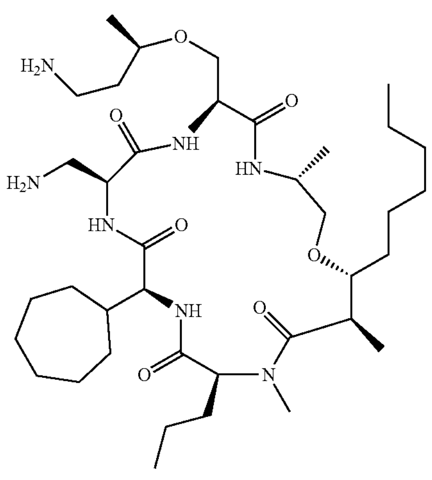 [SMILES: CCCCCC[C@H]1OC[C@@H](C)NC(=O)[C@H](CO[C@H](C)CCN)NC(=O)[C@H](CN)NC(=O)[C@H](C2CCCCCC2)NC(=O)[C@H](CCC)N(C)C(=O)[C@@H]1C] | (3S,6S,9S,12S,15S,18R,19R)-6-(((((R)-4-aminobutan-2-yl)oxy)methyl)-9-(aminomethyl)-12-cycloheptyl-19-hexyl-3,16,18-trimethyl-15-propyl-1-oxa-4,7,10,13,16-pentaazacyclononadecane-5,8,11,14,17-pentaone |

TABLE 1-continued

| Ex. | Structure | Name |
|---|---|---|
| 96 | 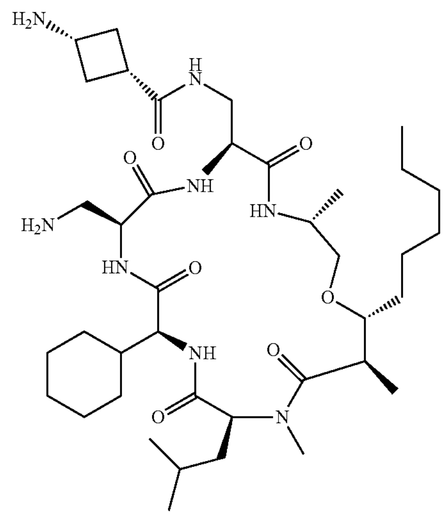 [SMILES: CCCCCC[C@H]1OC[C@@H](C)NC(=O)[C@H](CNC(=O)[C@H]2C[C@@H](N)C2)NC(=O)[C@H](CN)NC(=O)[C@H](C2CCCCC2)NC(=O)[C@H](CC(C)C)N(C)C(=O)[C@@H]1C] | 3-amino-N-[[(3R,6S,9S,12S,15S,18R,19R)-9-(aminomethyl)-12-cyclohexyl-19-hexyl-15-isobutyl-3,16,18-trimethyl-5,8,11,14,17-pentaoxo-1-oxa-4,7,10,13,16-pentazacyclononadec-6-yl]methyl]cyclobutanecarboxamide |
| 97 | 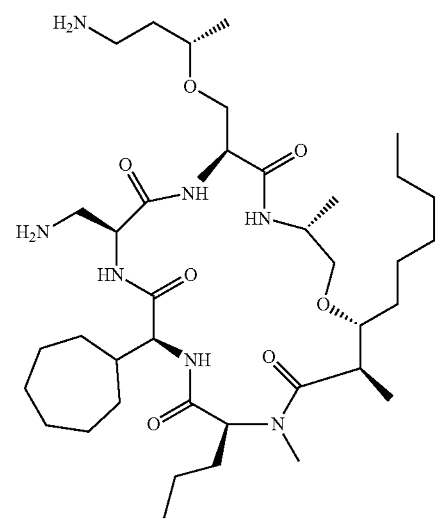 [SMILES: CCCCCC[C@H]1OC[C@@H](C)NC(=O)[C@H](CO[C@@H](C)CCN)NC(=O)[C@H](CN)NC(=O)[C@H](C2CCCCCC2)NC(=O)[C@H](CCC)N(C)C(=O)[C@@H]1C] | (3S,6S,9S,12S,15S,18R,19R)-6-((((S)-4-aminobutan-2-yl)oxy)methyl)-9-(aminomethyl)-12-cycloheptyl-19-hexyl-3,16,18-trimethyl-15-propyl-1-oxa-4,7,10,13,16-pentaazacyclononadecane-5,8,11,14,17-pentaone |
| 98 | 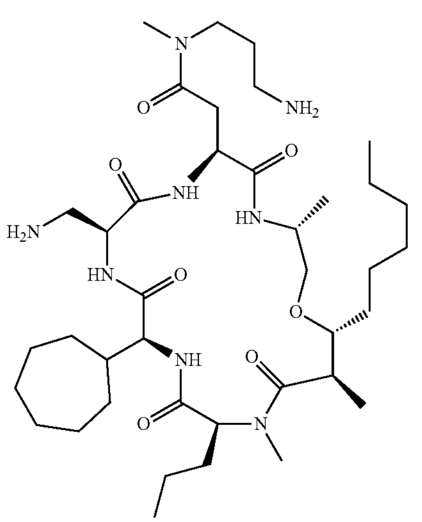 [SMILES: CCCCCC[C@H]1OC[C@@H](C)NC(=O)[C@H](CC(=O)N(C)CCCN)NC(=O)[C@H](CN)NC(=O)[C@H](C2CCCCCC2)NC(=O)[C@H](CCC)N(C)C(=O)[C@@H]1C] | 2-((3S,6S,9S,12S,15S,18R,19R)-9-(aminomethyl)-12-cycloheptyl-19-hexyl-3,16,18-trimethyl-5,8,11,14,17-pentaoxo-15-propyl-1-oxa-4,7,10,13,16-pentaazacyclononadecan-6-yl)-N-(3-aminopropyl)-N-methylacetamide |

TABLE 1-continued

| Ex. | Structure | Name |
|---|---|---|
| 99 | 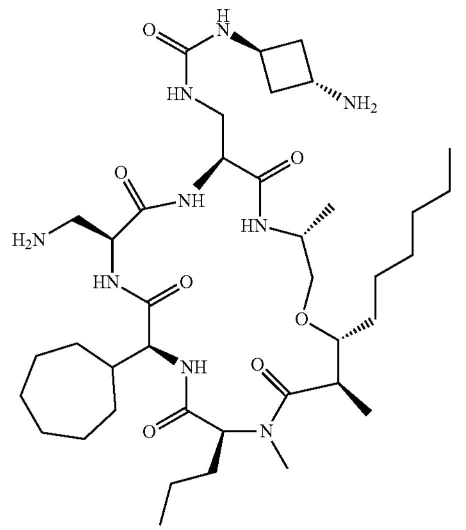 [SMILES: CCCCCC[C@H]1OC[C@@H](C)NC(=O)[C@H](CNC(=O)N[C@H]2C[C@H](N)C2)NC(=O)[C@H](CN)NC(=O)[C@H](C2CCCCCC2)NC(=O)[C@H](CCC)N(C)C(=O)[C@@H]1C] | 1-((1r,3S)-3-aminocyclobutyl)-3-(((3S,6S,9S,12S,15S,18R,19R)-9-(aminomethyl)-12-cycloheptyl-19-hexyl-3,16,18-trimethyl-5,8,11,14,17-pentaoxo-15-propyl-1-oxa-4,7,10,13,16-pentaazacyclononadecan-6-yl)methyl)urea |
| 100 | 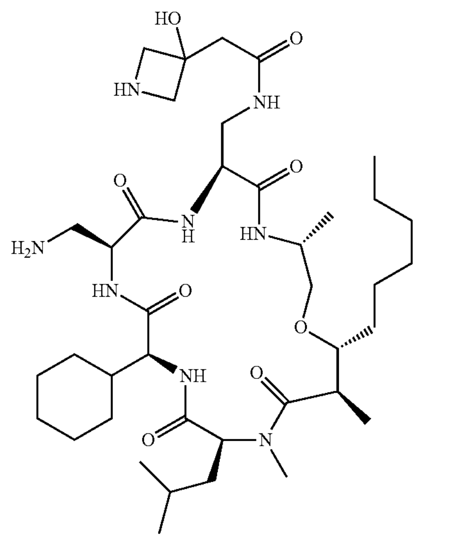 [SMILES: CCCCCC[C@H]1OC[C@@H](C)NC(=O)[C@H](CNC(=O)CC2(O)CNC2)NC(=O)[C@H](CN)NC(=O)[C@H](C2CCCCC2)NC(=O)[C@H](CC(C)C)N(C)C(=O)[C@@H]1C] | N-[[(3R,6S,9S,12S,15S,18R,19R)-9-(aminomethyl)-12-cyclohexyl-19-hexyl-15-isobutyl-3,16,18-trimethyl-5,8,11,14,17-pentaoxo-1-oxa-4,7,10,13,16-pentazacyclononadec-6-yl]methyl]-2-(3-hydroxyazetidin-3-yl)acetamide |
| 101 | 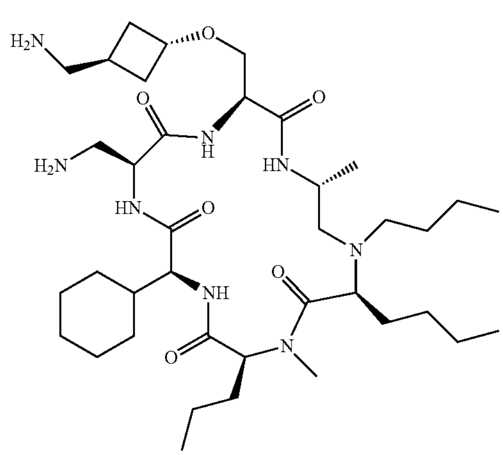 [SMILES: CCCC[C@H]1C(=O)N(C)[C@@H](CCC)C(=O)N[C@@H](C2CCCCC2)C(=O)N[C@@H](CN)C(=O)N[C@@H](CO[C@H]2C[C@H](CN)C2)C(=O)N[C@H](C)CN1CCCC] | (3S,6S,9S,12S,15S,18R)-6-(aminomethyl)-3-(((1r,3S)-3-(aminomethyl)cyclobutoxy)methyl)-15,16-dibutyl-9-cyclohexyl-13,18-dimethyl-12-propyl-1,4,7,10,13,16-hexaazacyclooctadecane-2,5,8,11,14-pentaone |

TABLE 1-continued

| Ex. | Structure | Name |
|---|---|---|
| 102 | 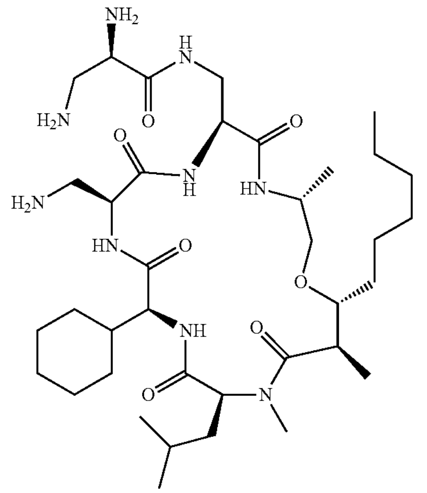 [SMILES: CCCCCC[C@H]1OC[C@@H](C)NC(=O)[C@H](CNC(=O)[C@H](N)CN)NC(=O)[C@H](CN)NC(=O)[C@H](C2CCCCC2)NC(=O)[C@H](CC(C)C)N(C)C(=O)[C@@H]1C] | (2R)-2,3-diamino-N-[[(3R,6S,9S,12S,15S,18R,19R)-9-(aminomethyl)-12-cyclohexyl-19-hexyl-15-isobutyl-3,16,18-trimethyl-5,8,11,14,17-pentaoxo-1-oxa-4,7,10,13,16-pentazacyclononadec-6-yl]methyl]propanamide |
| 103 | 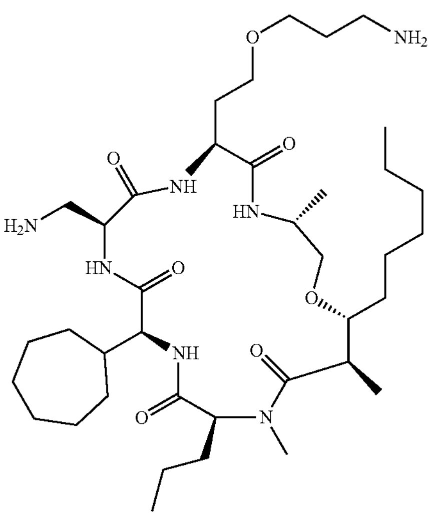 [SMILES: CCCCCC[C@H]1OC[C@@H](C)NC(=O)[C@H](CCOCCCN)NC(=O)[C@H](CN)NC(=O)[C@H](C2CCCCCC2)NC(=O)[C@H](CCC)N(C)C(=O)[C@@H]1C] | (3S,6S,9S,12S,15S,18R,19R)-9-(aminomethyl)-6-(2-(3-aminopropoxy)ethyl)-12-cycloheptyl-19-hexyl-3,16,18-trimethyl-15-propyl-1-oxa-4,7,10,13,16-pentaazacyclononadecane-5,8,11,14,17-pentaone |
| 104 | 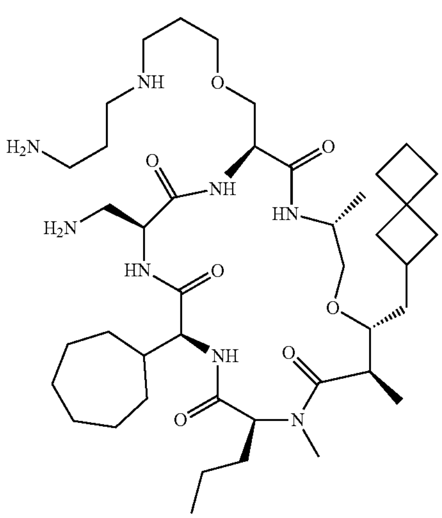 [SMILES: CCC[C@H]1C(=O)N[C@@H](C2CCCCCC2)C(=O)N[C@@H](CN)C(=O)N[C@@H](COCCCNCCCN)C(=O)N[C@H](C)CO[C@H](CC2CC3(CCC3)C2)[C@@H](C)C(=O)N1C] | (3S,6S,9S,12S,15S,18R,19R)-9-(aminomethyl)-6-((3-((3-aminopropyl)amino)propoxy)methyl)-12-cycloheptyl-3,16,18-trimethyl-15-propyl-19-(spiro[3.3]heptan-2-ylmethyl)-1-oxa-4,7,10,13,16-pentaazacyclononadecane-5,8,11,14,17-pentaone |

TABLE 1-continued

| Ex. | Structure | Name |
|---|---|---|
| 105 | 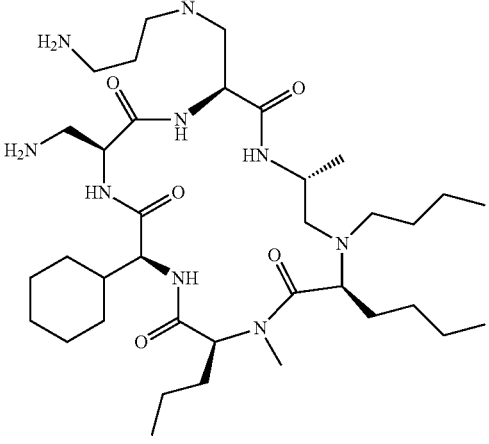 | (3S,6S,9S,12S,15S,18R)-6-(aminomethyl)-3-(((3-aminopropyl)amino)methyl)-15,16-dibutyl-9-cyclohexyl-13,18-dimethyl-12-propyl-1,4,7,10,13,16-hexaazacyclooctadecane-2,5,8,11,14-pentaone |
| 106 | 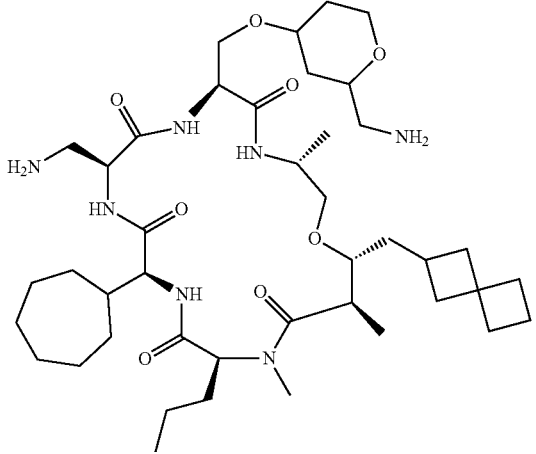 [SMILES: CCC[C@H]1C(=O)N[C@@H](C2CCCCCC2)C(=O)N[C@@H](CN)C(=O)N[C@@H](COC2CCOC(CN)C2)C(=O)N[C@H](C)CO[C@H](CC2CC3(CCC3)C2)[C@@H](C)C(=O)N1C] | (3S,6S,9S,12S,15S,18R,19R)-9-(aminomethyl)-6-(((cis-2-(aminomethyl)tetrahydro-2H-pyran-4-yl)oxy)methyl)-12-cycloheptyl-3,16,18-trimethyl-15-propyl-19-(spiro[3.3]heptan-2-ylmethyl)-1-oxa-4,7,10,13,16-pentaazacyclononadecane-5,8,11,14,17-pentaone (cis single unknown stereoisomer 1) |
| 107 | 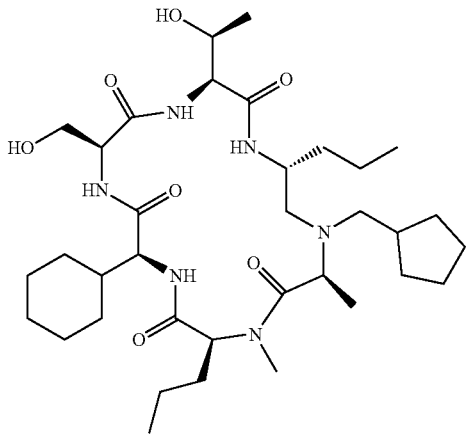 [SMILES: CCC[C@@H]1CN(CC2CCCC2)[C@@H](C)C(=O)N(C)[C@@H](CCC)C(=O)N[C@@H](C2CCCCC2)C(=O)N[C@@H](CO)C(=O)N[C@@H]([C@H](C)O)C(=O)N1] | (3S,6S,9S,12S,15S,18R)-6-(aminomethyl)-9-cyclohexyl-16-(cyclopentylmethyl)-3-((S)-1-hydroxyethyl)-13,15-dimethyl-12,18-dipropyl-1,4,7,10,13,16-hexaazacyclooctadecane-2,5,8,11,14-pentaone |

TABLE 1-continued

| Ex. | Structure | Name |
|---|---|---|
| 108 | 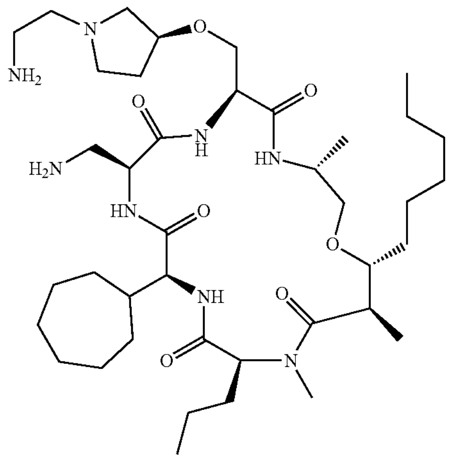 [SMILES: CCCCCC[C@H]1OC[C@@H](C)NC(=O)[C@H](CO[C@H]2CCN(CCN)C2)NC(=O)[C@H](CN)NC(=O)[C@H](C2CCCCCC2)NC(=O)[C@H](CCC)N(C)C(=O)[C@@H]1C] | (3S,6S,9S,12S,15S,18R,19R)-6-((((S)-1-(2-aminoethyl)pyrrolidin-3-yl)oxy)methyl)-9-(aminomethyl)-12-cycloheptyl-19-hexyl-3,16,18-trimethyl-15-propyl-1-oxa-4,7,10,13,16-pentaazacyclononadecane-5,8,11,14,17-pentaone |
| 109 | 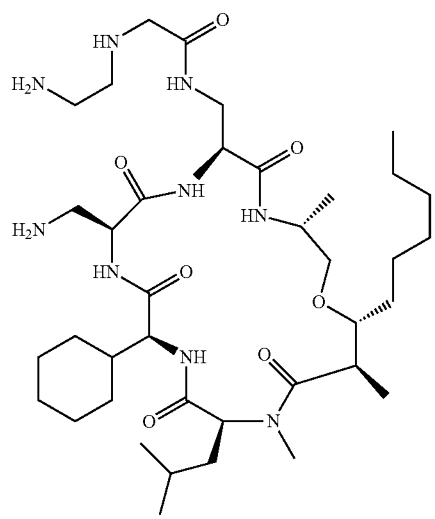 [SMILES: CCCCCC[C@H]1OC[C@@H](C)NC(=O)[C@H](CNC(=O)CNCCN)NC(=O)[C@H](CN)NC(=O)[C@H](C2CCCCC2)NC(=O)[C@H](CC(C)C)N(C)C(=O)[C@@H]1C] | 2-(2-aminoethylamino)-N-[[[(3R,6S,9S,12S,15S,18R,19R)-9-(aminomethyl)-12-cyclohexyl-19-hexyl-15-isobutyl-3,16,18-trimethyl-5,8,11,14,17-pentaoxo-1-oxa-4,7,10,13,16-pentazacyclononadec-6-yl]methyl]acetamide |
| 110 | 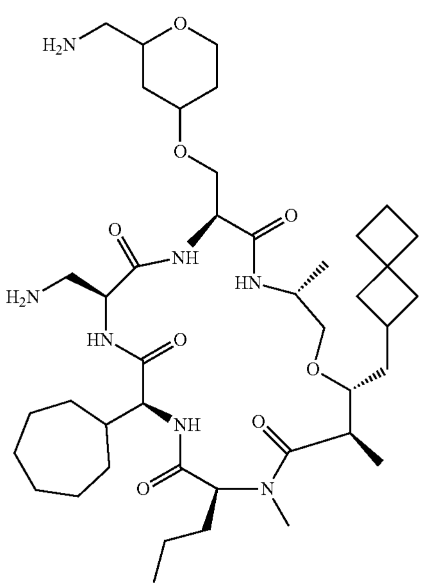 [SMILES: CCC[C@H]1C(=O)N[C@@H](C2CCCCCC2)C(=O)N[C@@H](CN)C(=O)N[C@@H](COC2CCOC(CN)C2)C(=O)N[C@H](C)CO[C@H](CC2CC3(CCC3)C2)[C@@H](C)C(=O)N1C] | (3S,6S,9S,12S,15S,18R,19R)-9-(aminomethyl)-6-(((cis-2-(aminomethyl)tetrahydro-2H-pyran-4-yl)oxy)methyl)-12-cycloheptyl-3,16,18-trimethyl-15-propyl-19-(spiro[3.3]heptan-2-ylmethyl)-1-oxa-4,7,10,13,16-pentaazacyclononadecane-5,8,11,14,17-pentaone (cis single unknown stereoisomer 2) |

TABLE 1-continued

| Ex. | Structure | Name |
|---|---|---|
| 111 | 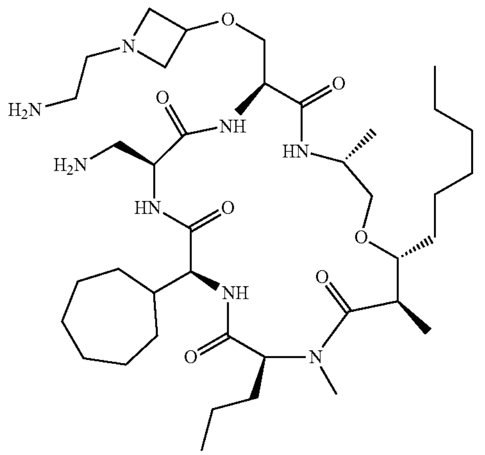 [SMILES: CCCCCC[C@H]1OC[C@@H](C)NC(=O)[C@H](COC2CN(CCN)C2)NC(=O)[C@H](CN)NC(=O)[C@H](C2CCCCCC2)NC(=O)[C@H](CCC)N(C)C(=O)[C@@H]1C] | (3S,6S,9S,12S,15S,18R,19R)-6-(((1-(2-aminoethyl)azetidin-3-yl)oxy)methyl)-9-(aminomethyl)-12-cycloheptyl-19-hexyl-3,16,18-trimethyl-15-propyl-1-oxa-4,7,10,13,16-pentaazacyclononadecane-5,8,11,14,17-pentaone |
| 112 | 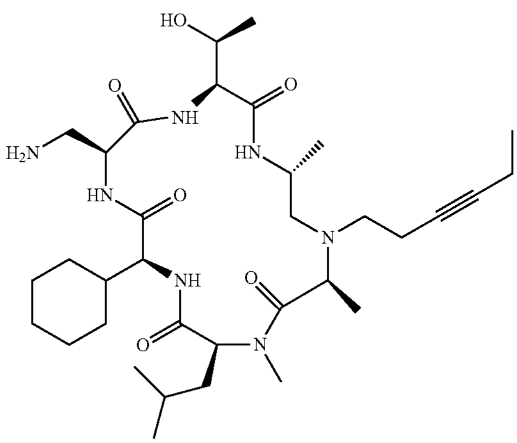 [SMILES: CCC#CCCN1C[C@@H](C)NC(=O)[C@H]([C@H](C)O)NC(=O)[C@H](CN)NC(=O)[C@H](C2CCCCC2)NC(=O)[C@H](CC(C)C)N(C)C(=O)[C@@H]1C] | (3S,6S,9S,12S,15S,18R)-6-(aminomethyl)-9-cyclohexyl-16-(hex-3-yn-1-yl)-3-((S)-1-hydroxyethyl)-12-isobutyl-13,15,18-trimethyl-1,4,7,10,13,16-hexaazacyclooctadecane-2,5,8,11,14-pentaone |
| 113 | 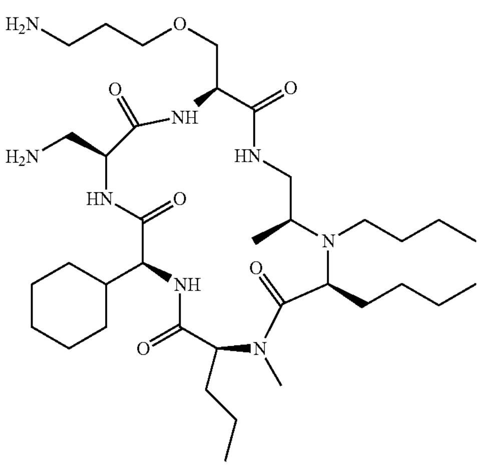 [SMILES: CCCC[C@H]1C(=O)N(C)[C@@H](CCC)C(=O)N[C@@H](C2CCCCC2)C(=O)N[C@@H](CN)C(=O)N[C@@H](COCCCN)C(=O)NC[C@H](C)N1CCCC] | (3S,6S,9S,12S,15S,17S)-6-(aminomethyl)-3-((3-aminopropoxy)methyl)-15,16-dibutyl-9-cyclohexyl-13,17-dimethyl-12-propyl-1,4,7,10,13,16-hexaazacyclooctadecane-2,5,8,11,14-pentaone |

TABLE 1-continued

| Ex. | Structure | Name |
|---|---|---|
| 114 | 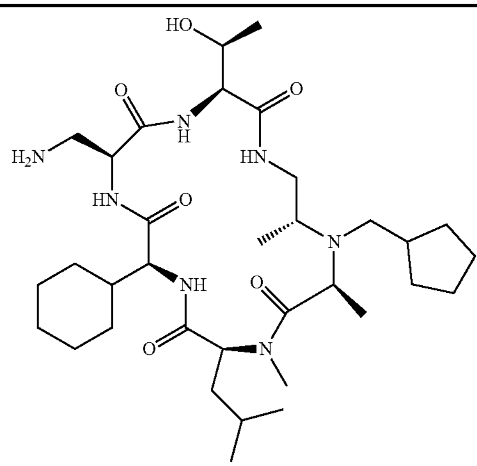 | (3S,6S,9S,12S,15S,17R)-6-(aminomethyl)-9-cyclohexyl-16-(cyclopentylmethyl)-3-((S)-1-hydroxyethyl)-12-isobutyl-13,15,17-trimethyl-1,4,7,10,13,16-hexaazacyclooctadecane-2,5,8,11,14-pentaone |

Further Forms of Compounds Disclosed Herein
Isomers/Stereoisomers

In some embodiments, the compounds described herein exist as geometric isomers. In some embodiments, the compounds described herein possess one or more double bonds. The compounds presented herein include all cis, trans, syn, anti, entgegen (E), and zusammen (Z) isomers as well as the corresponding mixtures thereof. In some situations, the compounds described herein possess one or more chiral centers and each center exists in the R configuration, or S configuration. The compounds described herein include all diastereomeric, enantiomeric, and epimeric forms as well as the corresponding mixtures thereof. In additional embodiments of the compounds and methods provided herein, mixtures of enantiomers and/or diastereoisomers, resulting from a single preparative step, combination, or interconversion are useful for the applications described herein. In some embodiments, the compounds described herein are prepared as their individual stereoisomers by reacting a racemic mixture of the compound with an optically active resolving agent to form a pair of diastereoisomeric compounds, separating the diastereomers and recovering the optically pure enantiomers. In some embodiments, dissociable complexes are preferred. In some embodiments, the diastereomers have distinct physical properties (e.g., melting points, boiling points, solubilities, reactivity, etc.) and are separated by taking advantage of these dissimilarities. In some embodiments, the diastereomers are separated by chiral chromatography, or preferably, by separation/resolution techniques based upon differences in solubility. In some embodiments, the optically pure enantiomer is then recovered, along with the resolving agent.

Labeled Compounds

In some embodiments, the compounds described herein exist in their isotopically-labeled forms. In some embodiments, the methods disclosed herein include methods of treating diseases by administering such isotopically-labeled compounds. In some embodiments, the methods disclosed herein include methods of treating diseases by administering such isotopically-labeled compounds as pharmaceutical compositions. Thus, in some embodiments, the compounds disclosed herein include isotopically-labeled compounds, which are identical to those recited herein, but for the fact that one or more atoms are replaced by an atom having an atomic mass or mass number different from the atomic mass or mass number usually found in nature. Examples of isotopes that can be incorporated into compounds described herein, or a solvate, or stereoisomer thereof, include isotopes of hydrogen, carbon, nitrogen, oxygen, phosphorous, sulfur, fluorine, and chloride, such as $^{2}H$, $^{3}H$, $^{13}C$, $^{14}C$, $^{15}N$, $^{18}O$, $^{17}O$, $^{31}P$, $^{32}P$, $^{35}S$, $^{18}F$, and $^{36}Cl$, respectively. Certain isotopically-labeled compounds, for example those into which radioactive isotopes such as $^{3}H$ and $^{14}C$ are incorporated, are useful in drug and/or substrate tissue distribution assays. Tritiated, i.e., $^{3}H$ and carbon-14, i.e., $^{14}C$, isotopes are particularly preferred for their ease of preparation and detectability. Further, substitution with heavy isotopes such as deuterium, i.e., $^{2}H$, produces certain therapeutic advantages resulting from greater metabolic stability, for example increased in vivo half-life or reduced dosage requirements. In some embodiments, the isotopically labeled compound or a pharmaceutically acceptable salt, solvate, or stereoisomer thereof is prepared by any suitable method.

In some embodiments, the compounds described herein are labeled by other means, including, but not limited to, the use of chromophores or fluorescent moieties, bioluminescent labels, or chemiluminescent labels.

Pharmaceutically Acceptable Salts

In some embodiments, the compounds described herein exist as their pharmaceutically acceptable salts. In some embodiments, the methods disclosed herein include methods of treating diseases by administering such pharmaceutically acceptable salts. In some embodiments, the methods disclosed herein include methods of treating diseases by administering such pharmaceutically acceptable salts as pharmaceutical compositions.

In some embodiments, the compounds described herein possess acidic or basic groups and therefor react with any of a number of inorganic or organic bases, and inorganic and organic acids, to form a pharmaceutically acceptable salt. In some embodiments, these salts are prepared in situ during the final isolation and purification of the compounds disclosed herein, or by separately reacting a purified compound in its free form with a suitable acid or base, and isolating the salt thus formed.

Examples of pharmaceutically acceptable salts include those salts prepared by reaction of the compounds described herein with a mineral, organic acid, or inorganic base, such salts including acetate, acrylate, adipate, alginate, aspartate, benzoate, benzenesulfonate, bisulfate, bisulfite, bromide, butyrate, butyn-1,4-dioate, camphorate, camphorsulfonate, caproate, caprylate, chlorobenzoate, chloride, citrate, cyclopentanepropionate, decanoate, digluconate, dihydrogenphosphate, dinitrobenzoate, dodecylsulfate, ethanesulfonate, formate, fumarate, glucoheptanoate, glycerophosphate, glycolate, hemisulfate, heptanoate, hexanoate, hexyne-1,6-dioate, hydroxybenzoate, γ-hydroxybutyrate, hydrochloride, hydrobromide, hydroiodide, 2-hydroxyethanesulfonate, iodide, isobutyrate, lactate, maleate, malonate, methanesulfonate, mandelate metaphosphate, methanesulfonate, methoxybenzoate, methylbenzoate, monohydrogenphosphate, 1-napthalenesulfonate, 2-napthalenesulfonate, nicotinate, nitrate, palmoate, pectinate, persulfate, 3-phenylpropionate, phosphate, picrate, pivalate, propionate, pyrosulfate, pyrophosphate, propiolate, phthalate, phenylacetate, phenylbutyrate, propanesulfonate, salicylate, succinate, sulfate, sulfite, succinate, suberate, sebacate, sulfonate, tartrate, thiocyanate, tosylateundeconate, and xylenesulfonate.

Further, the compounds described herein can be prepared as pharmaceutically acceptable salts formed by reacting the free base form of the compound with a pharmaceutically acceptable inorganic or organic acid, including, but not limited to, inorganic acids such as hydrochloric acid, hydrobromic acid, sulfuric acid, nitric acid, phosphoric acid metaphosphoric acid, and the like; and organic acids such as acetic acid, propionic acid, hexanoic acid, cyclopentanepropionic acid, glycolic acid, pyruvic acid, lactic acid, malonic acid, succinic acid, malic acid, maleic acid, fumaric acid, p-toluenesulfonic acid, tartaric acid, trifluoroacetic acid, citric acid, benzoic acid, 3-(4-hydroxybenzoyl)benzoic acid, cinnamic acid, mandelic acid, arylsulfonic acid, methane sulfonic acid, ethane sulfonic acid, 1,2-ethanedisulfonic acid, 2-hydroxyethanesulfonic acid, benzenesulfonic acid, 2-naphthalenesulfonic acid, 4-methylbicyclo-[2.2.2]oct-2-ene-1-carboxylic acid, glucoheptonic acid, 4,4'-methylenebis-(3-hydroxy-2-ene-1-carboxylic acid), 3-phenylpropionic acid, trimethylacetic acid, tertiary butylacetic acid, lauryl sulfuric acid, gluconic acid, glutamic acid, hydroxynaphthoic acid, salicylic acid, stearic acid, and muconic acid.

In some embodiments, those compounds described herein which comprise a free acid group react with a suitable base, such as the hydroxide, carbonate, bicarbonate, sulfate, of a pharmaceutically acceptable metal cation, with ammonia, or with a pharmaceutically acceptable organic primary, secondary, tertiary, or quaternary amine. Representative salts include the alkali or alkaline earth salts, like lithium, sodium, potassium, calcium, and magnesium, and aluminum salts and the like. Illustrative examples of bases include sodium hydroxide, potassium hydroxide, choline hydroxide, sodium carbonate, $N^+(C_{1-4}\,alkyl)_4$, and the like.

Representative organic amines useful for the formation of base addition salts include ethylamine, diethylamine, ethylenediamine, ethanolamine, diethanolamine, piperazine, and the like. It should be understood that the compounds described herein also include the quaternization of any basic nitrogen-containing groups they contain. In some embodiments, water or oil-soluble or dispersible products are obtained by such quaternization.

Solvates

In some embodiments, the compounds described herein exist as solvates. The disclosure provides for methods of treating diseases by administering such solvates. The disclosure further provides for methods of treating diseases by administering such solvates as pharmaceutical compositions.

Solvates contain either stoichiometric or non-stoichiometric amounts of a solvent, and, in some embodiments, are formed during the process of crystallization with pharmaceutically acceptable solvents such as water, ethanol, and the like. Hydrates are formed when the solvent is water, or alcoholates are formed when the solvent is alcohol. Solvates of the compounds described herein can be conveniently prepared or formed during the processes described herein. By way of example only, hydrates of the compounds described herein can be conveniently prepared by recrystallization from an aqueous/organic solvent mixture, using organic solvents including, but not limited to, dioxane, tetrahydrofuran, or methanol. In addition, the compounds provided herein can exist in unsolvated as well as solvated forms. In general, the solvated forms are considered equivalent to the unsolvated forms for the purposes of the compounds and methods provided herein.

Tautomers

In some situations, compounds exist as tautomers. The compounds described herein include all possible tautomers within the formulas described herein. Tautomers are compounds that are interconvertible by migration of a hydrogen atom, accompanied by a switch of a single bond and adjacent double bond. In bonding arrangements where tautomerization is possible, a chemical equilibrium of the tautomers will exist. All tautomeric forms of the compounds disclosed herein are contemplated. The exact ratio of the tautomers depends on several factors, including temperature, solvent, and pH.

Method of Treatment

Also disclosed herein are methods of treating a mammal in need of such treatment comprising administering to the mammal an antibacterial effective amount of any of the aforementioned compounds at a frequency and for a duration sufficient to provide a beneficial effect to the mammal. In one embodiment, the mammal has a bacteria-related infection that is resistant to treatment with one or more clinically used antibiotics. In a further embodiment, the causative bacterial species of the bacterial infection is an infection involving *Pseudomonas aeruginosa, Pseudomonas fluorescens, Pseudomonas acidovorans, Pseudomonas alcaligenes, Pseudomonas putida, Stenotrophomonas maltophilia, Burkholderia cepacia, Aeromonas hydrophilia, Escherichia coli, Citrobacter freundii, Salmonella typhimurium, Salmonella typhi, Salmonella paratyphi, Salmonella enteritidis, Shigella dysenteriae, Shigella flexneri, Shigella sonnei, Enterobacter cloacae, Enterobacter aerogenes, Klebsiella pneumoniae, Klebsiella oxytoca, Serratia marcescens, Francisella tularensis, Morganella morganii, Proteus mirabilis, Proteus vulgaris, Providencia alcalifaciens, Providencia rettgeri, Providencia stuartii, Acinetobacter baumannii, Acinetobacter calcoaceticus, Acinetobacter haemolyticus, Yersinia enterocolitica, Yersinia pestis, Yersinia pseudotuberculosis, Yersinia intermedia, Bordetella pertussis, Bordetella parapertussis, Bordetella bronchiseptica, Haemophilus influenzae, Haemophilus parainfluenzae, Haemophilus haemolyticus, Haemophilus parahaemolyticus, Haemophilus ducreyi, Pasteurella multocida, Pasteurella haemolytica, Branhamella catarrhalis, Helicobacter pylori, Campylobacter fetus, Campylobacter jejuni, Campylobacter coli, Borrelia burgdorferi, Vibrio cholerae, Vibrio parahaemolyticus, Legionella pneumophila, Listeria monocytogenes, Neisseria gonorrhoeae, Neisseria meningitidis, Kingella, Moraxella, Gardnerella vaginalis, Bacteroides*

*fragilis, Bacteroides distasonis, Bacteroides* 3452A homology group, *Bacteroides vulgatus, Bacteroides ovalus, Bacteroides thetaiotaomicron, Bacteroides uniformis, Bacteroides eggerthii,* or *Bacteroides splanchnicus*. In this embodiment the bacterial infection is an infection involving a Gram-negative bacteria.

In one embodiment, is a compound described herein which displays antibiotic activity useful in the treatment of bacterial infections, such as by way of example only, various strains of *E. coli, E. cloaceae, K. pneumoniae, A. baumannii* or *P. aeruginosa*.

Combination Therapy

Also disclosed herein are methods of treating a mammal in need of such treatment comprising administering to the mammal a second therapeutic agent to any of the aforementioned methods of treatment. In another embodiment, the second therapeutic agent is a not an LspA inhibitor. In another embodiment, the second therapeutic agent is an aminoglycoside antibiotic, fluoroquinolone antibiotic, β-lactam antibiotic, macrolide antibiotic, glycopeptide antibiotic, rifampicin, chloramphenicol, fluoramphenicol, colistin, mupirocin, bacitracin, daptomycin, or linezolid.

In some embodiments is a method for treating a bacterial infection in a patient, preferably a human, where the treatment includes administering a therapeutically or pharmacologically effective amount of a combination of 1) a (3-lactam antibiotic; and 2) a compound disclosed herein, or a pharmaceutically acceptable salt, solvate, or stereoisomer thereof; and 3) a pharmaceutically acceptable carrier. In some embodiments, the β-lactam antibiotic is a carbapenem, cephalosporin, cephamycin, monobactam, or penicillin. Exemplary carbapenem antibiotics include, but are not limited to, ertapenem, imipenem, biapenem, and meropenem. Exemplary cephalosporin antibiotics include but are not limited to, ceftobiprole, ceftaroline, cefiprome, cefozopran, cefepime, cefotaxime, and ceftriazone. Exemplary penicillin antibiotics include, but are not limited to, ampicillin, amoxacillin, piperacillin, oxacillin, cloxacillin, methicillin, and nafcillin. In some embodiments, the β-lactam is administered with a β-lactamase inhibitor. In some embodiments, the carbapenem is administered with a DHP inhibitor, e.g., cilastatin.

In some embodiments, the β-lactam antibiotic and compound disclosed herein are administered sequentially or concurrently. In some embodiments, the β-lactam antibiotic and compound disclosed herein are administered together. In some embodiments, the β-lactam antibiotic and compound disclosed herein are administered in the same formulation or in separate formulations. In some embodiments, either the β-lactam or compound disclosed herein is administered first. After administration of the first compound, the other compound is administered, for example, within from 1 to 60 minutes, e.g., within 1, 2, 3, 4, 5, 10, 15, 30, or 60 minutes. In one aspect, when a β-lactamase inhibitor is used, it is administered separately, or in a formulation with the compound disclosed herein and/or β-lactam antibiotic. In one aspect, when a DHP inhibitor is used to improve the stability of a carbapenem, it is administered separately, or in a formulation with the compound disclosed herein and/or carbapenem.

Further described herein are pharmaceutical compositions comprising a compound disclosed herein, a pharmaceutically acceptable carrier, and optionally a β-lactam antibiotic. In embodiments where a combination is used, the β-lactam antibiotic and the compound disclosed herein, are present in such amounts that their combination constitutes a therapeutically effective amount. Due to the potentiating effects of the compound disclosed herein, the amount of β-lactam antibiotic present in a combination may be less that of a β-lactam antibiotic used alone. In certain embodiments, the composition further comprises a β-lactamase antibiotic.

In further embodiments where the β-lactam antibiotic is a carbapenem, is provided a pharmaceutical composition comprising a carbapenem antibiotic, a DHP inhibitor, a compound disclosed herein, and a pharmaceutically acceptable carrier. In some embodiments where the β-lactam antibiotic is a carbepenem, the carbapenem antibiotic is preferably selected from the group consisting of ertapenem, imipenem, and meropenem.

In some embodiments is a compound disclosed herein for use in treating a bacterial infection. In some embodiments is a compound disclosed herein, in combination with one or more additional therapeutic agents including a β-lactam antibiotic, for use in treating a bacterial infection. In some embodiments is a compound disclosed herein for use as a medicament for treating a bacterial infection. In some embodiments is a compound disclosed herein, in combination with one or more additional therapeutic agents including a β-lactam antibiotic, for use as a medicament for treating a bacterial infection. In some embodiments is a compound disclosed herein for use in the preparation of a medicament for treating a bacterial infection. In some embodiments is a compound disclosed herein, in combination with one or more additional therapeutic agents including a β-lactam antibiotic, for use in the preparation of a medicament for treating a bacterial infection.

In some embodiments described herein, a compound disclosed herein can enhance the activity of a β-lactam antibacterial agent by inducing susceptibility to the antibacterial agent in a drug-resistant strain such as MRSA. In some embodiments, a compound disclosed herein can enhance the activity of a β-lactam antibacterial agent by reducing the dosage of the antibacterial agent need for a therapeutic effect in a drug-sensitive strain. For example, if a compound disclosed herein reduces the Minimum Inhibitory Concentration (MIC) of an antibacterial agent (where the MIC is the minimum concentration of antibacterial agent which will completely inhibit growth) in a susceptible strain, then such treatment may be advantageous to enable a reduction in the amount of antibacterial agent administered (could reduce side effects of an antibiotic), or to decrease the frequency of administration. In some embodiments, compounds disclosed herein can enhance the activity of an antibacterial agent such as a carbapenem to prevent the emergence of a resistant sub-population in a heterogeneous bacterial population with a resistant sub-population.

In some embodiments, potentiators are used to enhance the activity of antibacterial agents whose clinical efficacy has been limited by the increasing prevalence of resistant strains. In some embodiments described herein, a compound disclosed herein is used as a potentiator wherein a compound disclosed herein can be administered together with a β-lactam antibiotic (either concurrently or sequentially) to allow effective treatment of an infection involving a resistant bacterium, or to reduce the amount of antibacterial agent necessary to treat an infection.

Administration and Pharmaceutical Composition

Pharmaceutical compositions described herein comprise a therapeutically effective amount of a compound described herein (i.e., a compound of any disclosed herein) formulated together with one or more pharmaceutically acceptable carriers. As used herein, the term "pharmaceutically acceptable carrier" means a non-toxic, inert solid, semi-solid or liquid filler, diluent, encapsulating material or formulation auxiliary of any type. Some examples of materials which can serve as pharmaceutically acceptable carriers are sugars such as lactose, glucose and sucrose; starches such as corn starch and potato starch; cellulose and its derivatives such as sodium carboxymethyl cellulose, ethyl cellulose and cellulose acetate; powdered tragacanth; malt; gelatin; talc; excipients such as cocoa butter and suppository waxes; oils such as peanut oil, cottonseed oil; safflower oil; sesame oil; olive oil; corn oil and soybean oil; glycols; such a propylene glycol; esters such as ethyl oleate and ethyl laurate; agar; buffering agents such as magnesium hydroxide and aluminum hydroxide; alginic acid; pyrogen-free water; isotonic saline; Ringer's solution; ethyl alcohol, and phosphate buffer solutions, as well as other non-toxic compatible lubricants such as sodium lauryl sulfate and magnesium stearate, as well as coloring agents, releasing agents, coating agents, sweetening, flavoring and perfuming agents, preservatives and antioxidants can also be present in the composition, according to the judgment of the formulator. The pharmaceutical compositions described herein can be administered to humans and other animals orally, rectally, parenterally, intracisternally, intravaginally, intraperitoneally, topically (as by powders, ointments, or drops), bucally, or as an oral or nasal spray, or a liquid aerosol or dry powder formulation for inhalation.

Liquid dosage forms for oral administration include pharmaceutically acceptable emulsions, microemulsions, solutions, suspensions, syrups and elixirs. In addition to the active compounds, the liquid dosage forms optionally contain inert diluents commonly used in the art such as, for example, water or other solvents, solubilizing agents and emulsifiers such as ethyl alcohol, isopropyl alcohol, ethyl carbonate, ethyl acetate, benzyl alcohol, benzyl benzoate, propylene glycol, 1,3-butylene glycol, dimethylformamide, oils (in particular, cottonseed, groundnut, corn, germ, olive, castor, and sesame oils), glycerol, tetrahydrofurfuryl alcohol, polyethylene glycols and fatty acid esters of sorbitan, and mixtures thereof. Besides inert diluents, the oral compositions can also include adjuvants such as wetting agents, emulsifying and suspending agents, sweetening, flavoring, and perfuming agents.

Injectable preparations, for example, sterile injectable aqueous or oleaginous suspensions are optionally formulated according to the known art using suitable dispersing or wetting agents and suspending agents. The sterile injectable preparation is optionally a sterile injectable solution, suspension or emulsion in a nontoxic parenterally acceptable diluent or solvent, for example, as a solution in 1,3-butanediol. Among the acceptable vehicles and solvents that are optionally employed are water, Ringer's solution, U.S.P. and isotonic sodium chloride solution. In addition, sterile, fixed oils are conventionally employed as a solvent or suspending medium. For this purpose any bland fixed oil can be employed including synthetic mono- or diglycerides. In addition, fatty acids such as oleic acid are used in the preparation of injectables.

The injectable formulations can be sterilized, for example, by filtration through a bacterial-retaining filter, or by incorporating sterilizing agents in the form of sterile solid compositions which can be dissolved or dispersed in sterile water or other sterile injectable medium prior to use.

In order to prolong the effect of a drug, it is often desirable to slow the absorption of the drug from subcutaneous or intramuscular injection. This is optionally accomplished by the use of a liquid suspension of crystalline or amorphous material with poor water solubility. The rate of absorption of the drug then depends upon its rate of dissolution which, in turn, may depend upon crystal size and crystalline form. Alternatively, delayed absorption of a parenterally administered drug form is optionally accomplished by dissolving or suspending the drug in an oil vehicle. Injectable depot forms are made by forming microencapsuled matrices of the drug in biodegradable polymers such as polylactide-polyglycolide. Depending upon the ratio of drug to polymer and the nature of the particular polymer employed, the rate of drug release can be controlled. Examples of other biodegradable polymers include poly(orthoesters) and poly(anhydrides). Depot injectable formulations are optionally prepared by entrapping the drug in liposomes or microemulsions which are compatible with body tissues.

Compositions for rectal or vaginal administration are preferably suppositories which can be prepared by mixing the compound described herein (i.e., a compound disclosed herein) with suitable non-irritating excipients or carriers such as cocoa butter, polyethylene glycol or a suppository wax which are solid at ambient temperature but liquid at body temperature and therefore melt in the rectum or vaginal cavity and release the active compound.

Solid dosage forms for oral administration include capsules, tablets, pills, powders, and granules. In such solid dosage forms, the active compound is mixed with at least one inert, pharmaceutically acceptable excipient or carrier such as sodium citrate or dicalcium phosphate and/or a) fillers or extenders such as starches, lactose, sucrose, glucose, mannitol, and silicic acid, b) binders such as, for example, carboxymethylcellulose, alginates, gelatin, polyvinylpyrrolidinone, sucrose, and acacia, c) humectants such as glycerol, d) disintegrating agents such as agar-agar, calcium carbonate, potato or tapioca starch, alginic acid, certain silicates, and sodium carbonate, e) solution retarding agents such as paraffin, f) absorption accelerators such as quaternary ammonium compounds, g) wetting agents such as, for example, acetyl alcohol and glycerol monostearate, h) absorbents such as kaolin and bentonite clay, and i) lubricants such as talc, calcium stearate, magnesium stearate, solid polyethylene glycols, sodium lauryl sulfate, and mixtures thereof. In the case of capsules, tablets and pills, the dosage form optionally comprise buffering agents.

Solid compositions of a similar type are optionally employed as fillers in soft and hard-filled gelatin capsules using such excipients as lactose or milk sugar as well as high molecular weight polyethylene glycols and the like.

The solid dosage forms of tablets, dragees, capsules, pills, and granules can be prepared with coatings and shells such as enteric coatings and other coatings known in the pharmaceutical formulating art. They optionally contain opacifying agents and can also be of a composition that they release the active ingredient(s) only, or preferentially, in a certain part of the intestinal tract, optionally, in a delayed manner. Examples of embedding compositions which can be used include polymeric substances and waxes.

Solid compositions of a similar type are optionally employed as fillers in soft and hard-filled gelatin capsules using such excipients as lactose or milk sugar as well as high molecular weight polyethylene glycols and the like.

The active compounds can also be in micro-encapsulated form with one or more excipients as noted above. The solid dosage forms of tablets, dragees, capsules, pills, and granules can be prepared with coatings and shells such as enteric coatings, release controlling coatings and other coatings known in the pharmaceutical formulating art. In such solid dosage forms the active compound is optionally admixed with at least one inert diluent such as sucrose, lactose or starch. Such dosage forms optionally comprise, as is normal practice, additional substances other than inert diluents, e.g., tableting lubricants and other tableting aids such a magnesium stearate and microcrystalline cellulose. In the case of capsules, tablets and pills, the dosage forms optionally comprise buffering agents. They optionally contain opacifying agents and can also be of a composition that they release the active ingredient(s) only, or preferentially, in a certain part of the intestinal tract, optionally, in a delayed manner. Examples of embedding compositions which can be used include polymeric substances and waxes.

Dosage forms for topical or transdermal administration of a compound described herein include ointments, pastes, creams, lotions, gels, powders, solutions, sprays, inhalants or patches. The active component is admixed under sterile conditions with a pharmaceutically acceptable carrier and any needed preservatives or buffers as are optionally required. Ophthalmic formulations, ear drops, and the like are also contemplated.

The ointments, pastes, creams and gels may contain, in addition to an active compound described herein, excipients such as animal and vegetable fats, oils, waxes, paraffins, starch, tragacanth, cellulose derivatives, polyethylene glycols, silicones, bentonites, silicic acid, talc and zinc oxide, or mixtures thereof.

Compositions described herein are optionally formulated for delivery as a liquid aerosol or inhalable dry powder. Liquid aerosol formulations are optionally nebulized predominantly into particle sizes that can be delivered to the terminal and respiratory bronchioles where bacteria reside in patients with bronchial infections, such as chronic bronchitis and pneumonia. Pathogenic bacteria are commonly present throughout airways down to bronchi, bronchioli and lung parenchema, particularly in terminal and respiratory bronchioles. During exacerbation of infection, bacteria can also be present in alveoli. Liquid aerosol and inhalable dry powder formulations are preferably delivered throughout the endobronchial tree to the terminal bronchioles and eventually to the parenchymal tissue.

Aerosolized formulations described herein are optionally delivered using an aerosol forming device, such as a jet, vibrating porous plate or ultrasonic nebulizer, preferably selected to allow the formation of an aerosol particles having with a mass medium average diameter predominantly between 1 to 5 μm. Further, the formulation preferably has balanced osmolarity ionic strength and chloride concentration, and the smallest aerosolizable volume able to deliver effective dose of the compounds described herein compound described herein (i.e., a compound disclosed herein) to the site of the infection. Additionally, the aerosolized formulation preferably does not impair negatively the functionality of the airways and does not cause undesirable side effects.

Aerosolization devices suitable for administration of aerosol formulations described herein include, for example, jet, vibrating porous plate, ultrasonic nebulizers and energized dry powder inhalers, that are able to nebulize the formulation into aerosol particle size predominantly in the size range from 1-5μ. Predominantly in this application means that at least 70% but preferably more than 90% of all generated aerosol particles are within 1-5μ range. A jet nebulizer works by air pressure to break a liquid solution into aerosol droplets. Vibrating porous plate nebulizers work by using a sonic vacuum produced by a rapidly vibrating porous plate to extrude a solvent droplet through a porous plate. An ultrasonic nebulizer works by a piezoelectric crystal that shears a liquid into small aerosol droplets. A variety of suitable devices are available, including, for example, AeroNeb™ and AeroDose™ vibrating porous plate nebulizers (AeroGen, Inc., Sunnyvale, California), Sidestream® nebulizers (Medic-Aid Ltd., West Sussex, England), Pari LC® and Pari LC Star® jet nebulizers (Pari Respiratory Equipment, Inc., Richmond, Virginia), and Aerosonic™ (DeVilbiss Medizinische Produkte (Deutschland) GmbH, Heiden, Germany) and UltraAire® (Omron Healthcare, Inc., Vernon Hills, Illinois) ultrasonic nebulizers.

In some embodiments, compounds described herein compound described herein (i.e., a compound disclosed herein) are formulated for use as topical powders and sprays that contain, in addition to the compounds described herein, excipients such as lactose, talc, silicic acid, aluminum hydroxide, calcium silicates and polyamide powder, or mixtures of these substances. Sprays optionally contain customary propellants such as chlorofluorohydrocarbons.

Transdermal patches have the added advantage of providing controlled delivery of a compound to the body. Such dosage forms can be made by dissolving or dispensing the compound in the proper medium. Absorption enhancers can also be used to increase the flux of the compound across the skin. The rate can be controlled by either providing a rate controlling membrane or by dispersing the compound in a polymer matrix or gel.

According to the methods of treatment described herein, bacterial infections are treated or prevented in a patient such as a human or lower mammal by administering to the patient a therapeutically effective amount of a compound described herein, in such amounts and for such time as is necessary to achieve the desired result. By a "therapeutically effective amount" of a compound described herein is meant a sufficient amount of the compound to treat bacterial infections, at a reasonable benefit/risk ratio applicable to any medical treatment. It will be understood, however, that the total daily usage of the compounds and compositions described herein will be decided by the attending physician within the scope of sound medical judgment. The specific therapeutically effective dose level for any particular patient will depend upon a variety of factors including the disorder being treated and the severity of the disorder; the activity of the specific compound employed; the specific composition employed; the age, body weight, general health, sex and diet of the patient; the time of administration, route of administration, and rate of excretion of the specific compound employed; the duration of the treatment; drugs used in combination or coincidental with the specific compound employed; and like factors known in the medical arts.

The total daily dose of the compounds described herein compound described herein (i.e., a compound disclosed herein) administered to a human or other mammal in single or in divided doses can be in amounts, for example, from 0.01 to 50 mg/kg body weight or more usually from 0.1 to 25 mg/kg body weight. Single dose compositions may contain such amounts or submultiples thereof to make up the daily dose. In general, treatment regimens described herein comprise administration to a patient in need of such treatment from about 10 mg to about 2000 mg of the compound(s) described herein per day in single or multiple doses.

EXAMPLES

Compounds disclosed herein are made by the methods depicted in the reaction schemes shown below. Procedures are provided herein that, in combination with the knowledge of the synthetic organic chemist of ordinary skill in the art, are in some embodiments used to prepare the full range of compounds as disclosed and claimed herein.

The starting materials and reagents used in preparing these compounds are either available from commercial suppliers such as Aldrich Chemical Co., (Milwaukee, Wis.), Bachem (Torrance, Calif.), or Sigma (St. Louis, Mo.) or are prepared by methods known to those skilled in the art following procedures set forth in references such as Fieser and Fieser's Reagents for Organic Synthesis, Volumes 1-17 (John Wiley and Sons, 1991); Rodd's Chemistry of Carbon Compounds, Volumes 1-5 and Supplemental (Elsevier Science Publishers, 1989); Organic Reactions, Volumes 1-40 (John Wiley and Sons, 1991), March's Advanced Organic Chemistry, (John Wiley and Sons, 4th Edition) and Larock's Comprehensive Organic Transformations (VCH Publishers Inc., 1989). These schemes are merely illustrative of some methods by which the compounds disclosed herein are in some embodiments synthesized, and various modifications to these schemes can be made and will be suggested to one skilled in the art having referred to this disclosure. The starting materials and the intermediates, and the final products of the reaction may be isolated and purified if desired using conventional techniques, including but not limited to filtration, distillation, crystallization, chromatography and the like. Such materials may be characterized using conventional means, including physical constants and spectral data. Compounds are typically isolated as trifluoroacetic acid salts by reverse phase HPLC using $CH_3CN/H_2O$ with trifluoroacetic acid as an additive. In some instances, purifications are conducted without trifluoroacetic acid, and the compounds are isolated as the free base.

Abbreviations

AcOH acetic acid
DCE 1,2-dichloroethane
DCM dichloromethane
DIPEA N,N-diisopropylethylamine
DMA N,N-dimethylacetamide
DMAP 4-dimethylaminopyridine
DMF N,N-dimethylformamide
DMSO dimethyl sulfoxide
ESI electrospray ionization
EtOAc ethyl acetate
h hour
HATU 1-[bis(dimethylamino)methylene]-1H-1,2,3-triazolo[4,5-h]pyridinium 3-oxid hexafluorophosphate
HBTU O-(benzotriazol-1-yl)-N,N,N',N'-tetramethyluronium hexafluorophosphate
HFIP 1,1,1,3,3,3-hexafluoro-2-propanol
HOBt hydroxybenzotriazole
HPLC high pressure liquid chromatography
IP AC isopropyl acetate
LCMS liquid chromatography mass spectrometry
LDA lithium diisopropyl amide
M molar
min minute
N normal
NMR nuclear magnetic resonance
PE petroleum ether
PyAOP (3-hydroxy-3H-1,2,3-triazolo[4,5-h]pyridinato-O)tri-1-pyrrolidinyl-phosphorus hexafluorophosphate
$R_T$ retention time
SFC super critical fluid chromatography
TEA triethylamine
THF tetrahydrofuran
TFA trifluoroacetic acid
TFE 2,2,2-trifluoroethanol
TfOH trifluoromethanesulfonic acid Compounds disclosed herein were prepared as illustrated in general Schemes 1-6.

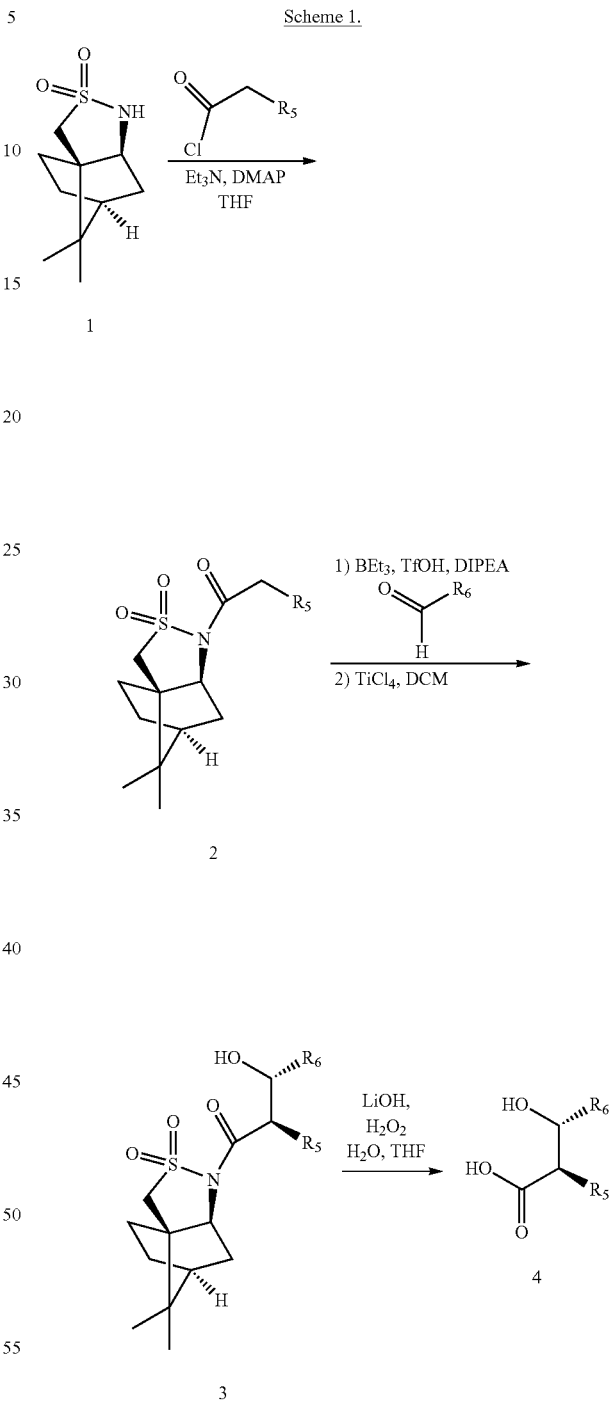

As described in Scheme 1, beta-hydroxy acids 4 may be prepared starting with Oppolzer's sultam 1, which may be acylated with acid chlorides to generate intermediate 2. Intermediate 2 may be subjected to Lewis-acid mediated aldol alkylation to generate the anti-aldol product 3. Compound 3 may be hydrolyzed with aqueous lithium hydroxide and hydrogen peroxide to yield the desired beta-hydroxy acid compounds 4.

Scheme 2.

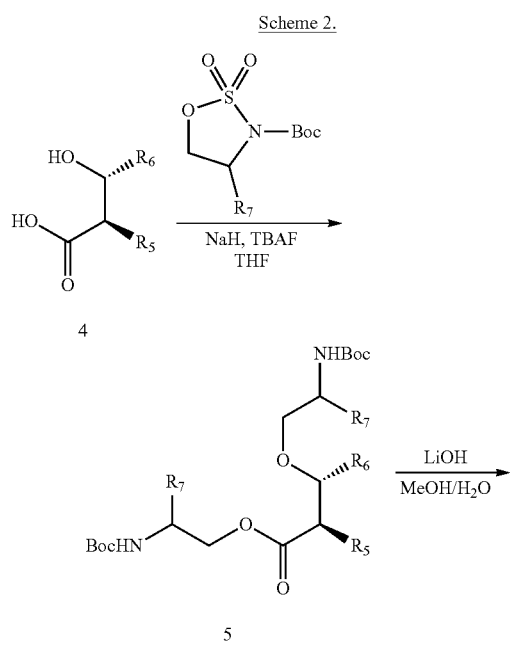

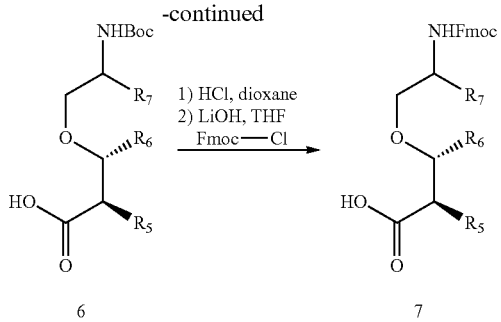

As shown in Scheme 2, beta-hydroxy acid compounds 4 may be alkylated with an appropriately substituted tert-butyl 2,2-dioxo-oxathiazolidine-3-carboxylate to yield esters 5. These esters may be saponified to yield carboxylic acids 6. The amino protecting group may be converted from Boc to Fmoc by acidic deprotection followed by reprotection with 9-fluorenylmethylchloroformate to yield intermediates 7.

Scheme 3.

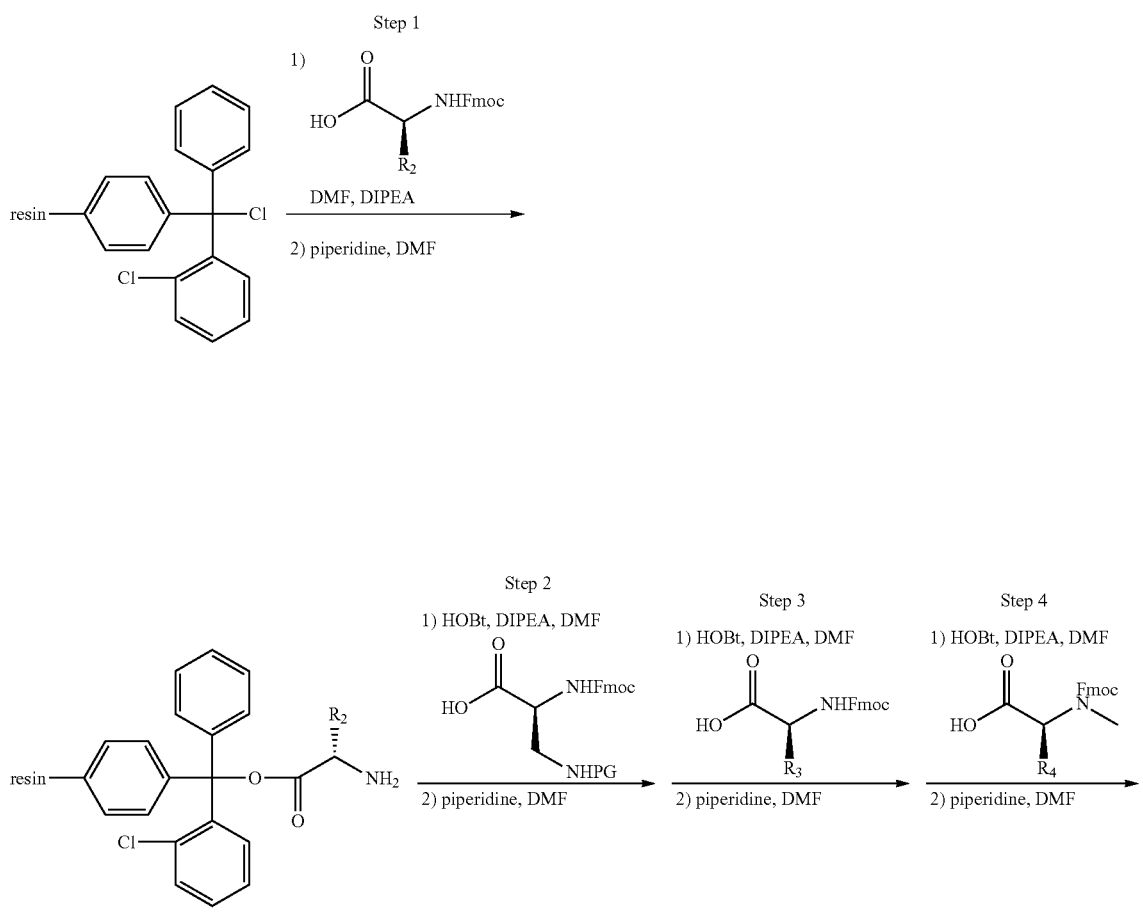

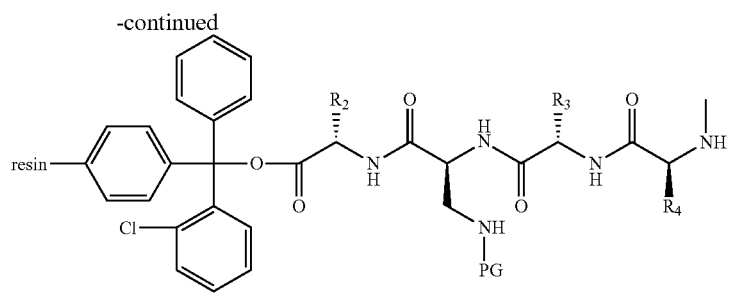

9

As shown in Scheme 3, chloro-(2-chlorotrityl)-resin may be loaded with an Fmoc-protected amino acid, and the Fmoc group removed with piperidine in DMF, to yield intermediate 8. Intermediate 8 may be elaborated through steps 2-4 using standard solid-phase chemistry techniques utilizing HOBt couplings with Fmoc-protected amino acids and standard side-chain protecting groups, to yield elaborated resin-bound peptide 9.

Scheme 4.

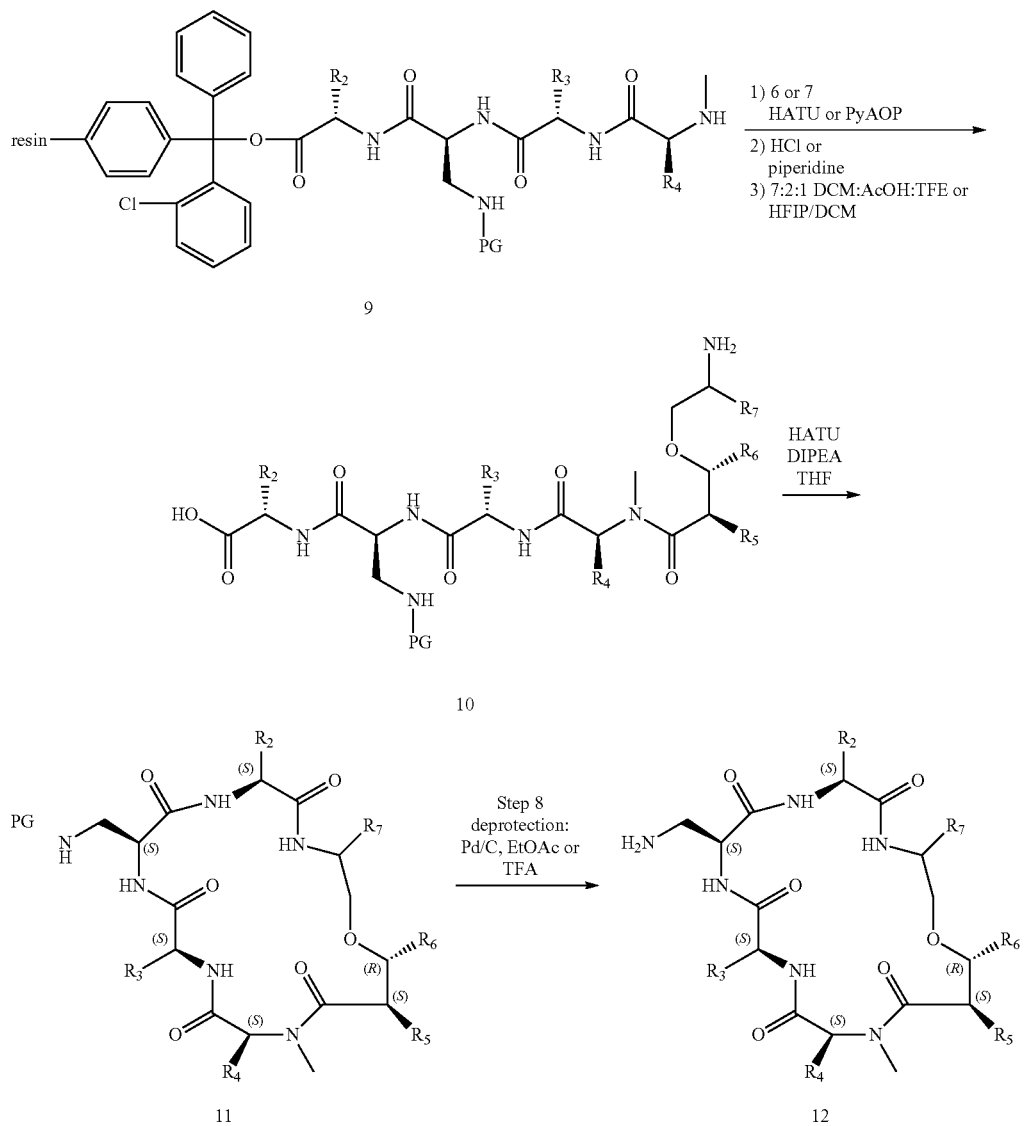

As shown in Scheme 4, resin-bound peptides 9 may be coupled to carboxylic acids 6 or 7 using standard coupling reagents such as HATU or PyAOP, followed by Boc or Fmoc deprotection and resin cleavage to yield protected peptides 10. The linear peptides may be cyclized using macrolactamization conditions such as HATU/DIPEA to yield macrocycles 11. The side chains of macrocyclic depsipeptides 11 may be globally deprotected using palladium/hydrogenation and/or acidic conditions to yield compounds 12.

Scheme 5.

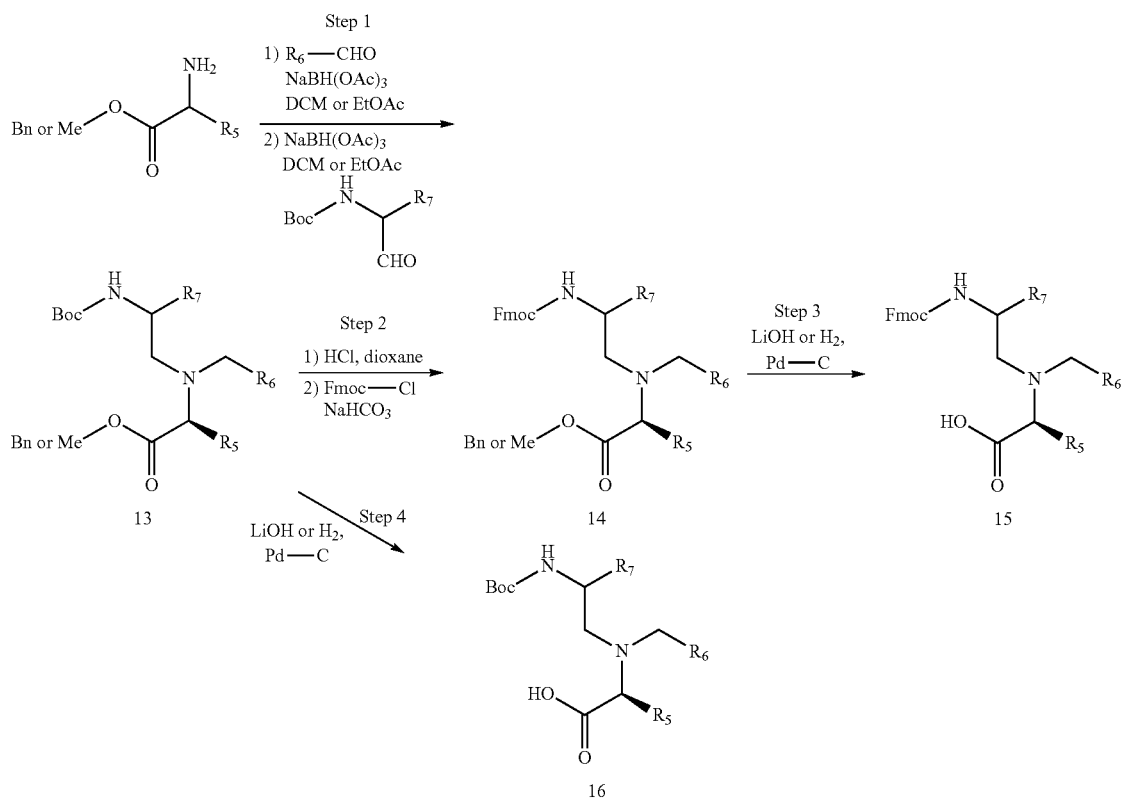

As shown in Scheme 5, benzyl or methyl ester protected amino acids can be subjected to sequential reductive animations to yield protected intermediates 13. Boc deprotection followed by Fmoc protection yields intermediates 14. Deprotection to the carboxylic acid with either saponification or hydrogenation conditions yields Fmoc-protected amino acid intermediates 15. Alternatively, intermediates 13 may be directly converted to the carboxylic acid to yield Boc-protected amino acid intermediates 16.

Scheme 6.

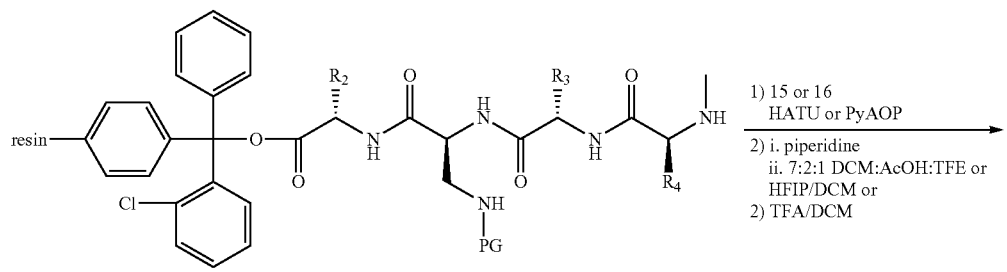

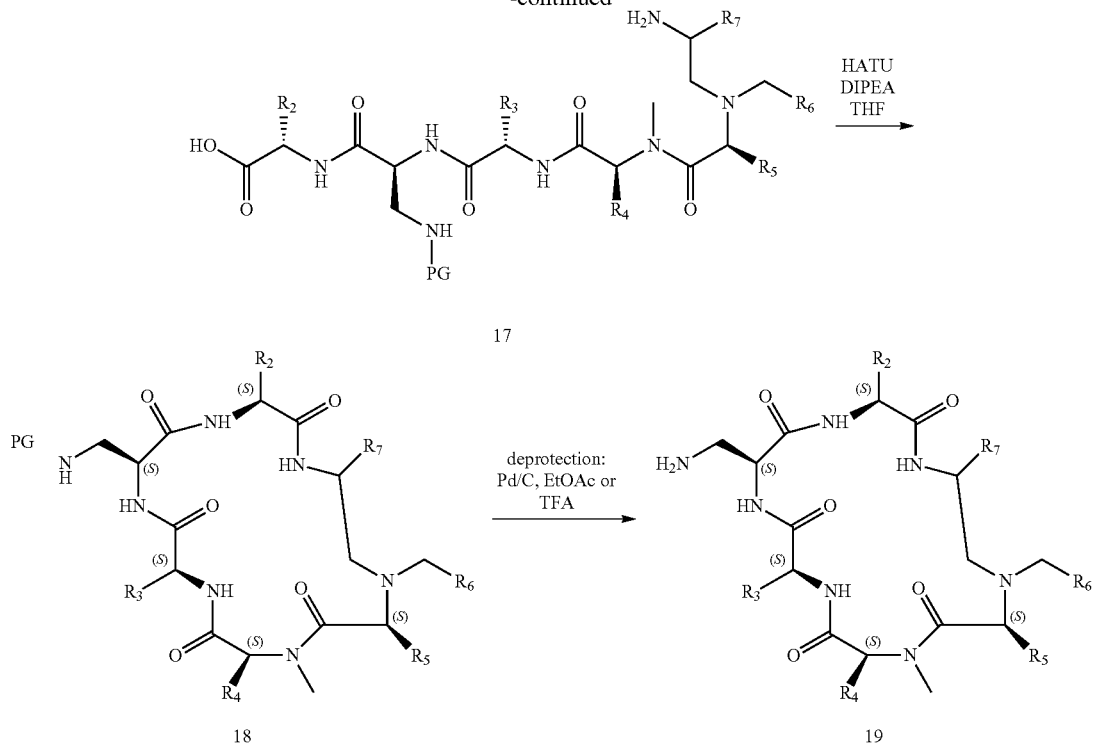

As shown in Scheme 6, resin-bound peptides 9 may be coupled to intermediates 15 or 16 under standard peptide coupling conditions. Deprotection of the Fmoc group with piperidine followed by cleavage from resin, or acidic cleavage from resin to simultaneously remove the Boc protecting group, yields linear peptides 17. The linear peptides may be cyclized using macrolactamization conditions such as HATU/DIPEA to yield macrocycles 18. The side chains of macrocyclic depsipeptides 18 may be globally deprotected using palladium/hydrogenation and/or acidic conditions to yield compounds 19.

General Experimental Conditions $^1$H NMR spectra were recorded at ambient temperature using either a Varian Unity Inova (400 MHz) spectrometer with a triple resonance 5 mm probe, an Avance III (300 MHz) spectrometer or a Bruker Ultrashield (400 MHz or 500 MHz) spectrometer. Chemical shifts are expressed in ppm relative to tetramethylsilane. The following abbreviations have been used: br=broad signal, s=singlet, d=doublet, dd=double doublet, t=triplet, q=quartet, m=multiplet.

Microwave experiments were carried out using a CEM Discover, Smith Synthesiser or a Biotage Initiator 60™, which uses a single-mode resonator and dynamic field tuning, both of which give reproducibility and control. Temperatures from 40-250° C. can be achieved and pressures of up to 30 bar can be reached.

High Pressure Liquid Chromatography-Mass Spectrometry (LCMS) experiments to determine retention times ($R_T$) and associated mass ions were performed using one of the following methods. The spectrometers have an electrospray source operating in positive and negative ion mode. UV absorbance was collected at 220 nm and 254 nm and mass spec full scan was applied to all experiments. Additional detection was achieved using a Sedex 85 evaporative light scattering detector. A Thermo Scientific charged aerosol detector (model: Corona) was used to measure the purity of the UV-insensitive analytes. The CAD parameters are set up as follows:

Gas pressure: 35-40 psi
Flow ratio: 0.51
Ion Trap: 20.3 v
Charger voltage: 2.91 kv
Charger current: 1.01 uA LCMS Method A: Experiments performed on an Agilent 1290 HPLC coupled with Agilent MSD mass spectrometer using ESI as ionization source. The LC separation was using a Phenomenex XB-C18, 1.7 mm, 50×2.1 mm column with a 0.4 mL/minute flow rate. Solvent A is water with 0.1% formic acid and solvent B is acetonitrile with 0.1% formic acid. The gradient consisted with 2-98% solvent B over 7 minutes and hold 97% B for 1.5 minutes following equilibration for 1.5 minutes. LC column temperature is 40° C.

LCMS Method B: Experiments were performed on an Agilent 1290 HPLC coupled with Agilent MSD mass spectrometer using ESI as ionization source. The LC separation was done on an Agilent Zorbax Eclipse XDB-C18, 3.5 mm, 100×3.0 mm column at a flow rate of 0.7 ml/minute. MPA (mobile phase A) was water with 0.1% FA and MPB (mobile phase B) was acetonitrile with 0.1% FA. The gradient started at 2% MPB and ended at 98% MPB over 25.5 min and held at 98% B for 2.5 min following equilibration for 1.5 min. LC column temperature was 40° C. UV absorbance were collected at 220 nm and 254 nm and mass spec full scan was applied to all experiments.

LCMS Method C: Experiments performed on a Waters Micromass ZQ2000 quadrupole mass spectrometer linked to a Waters Acquity UPLC system with a PDA UV detector. The spectrometer has an electrospray source operating in positive and negative ion mode. This system uses an Acquity BEH C18 1.7 um 100×2.1 mm column, maintained at 40° C.

or an Acquity BEH Shield RP18 1.7 µm 100×2.1 mm column, maintained at 40° C. and a 0.4 mL/minute flow rate. The initial solvent system was 95% water containing 0.1% formic acid (solvent A) and 5% acetonitrile containing 0.1% formic acid (solvent B) for the first 0.4 minute followed by a gradient up to 5% solvent A and 95% solvent B over the next 5.6 minutes. This was maintained for 0.8 minutes before returning to 95% solvent A and 5% solvent B over the next 0.2 minutes.

LCMS Method D: Experiments were performed on a Waters Acquity UPLC with Waters LCT Premier XE mass spectrometer using ESI ionization. The LC separation was done on an Acquity UPLC BEH C18, 1.7 mm, 2.1×50 mm column at a flow rate of 0.6 ml/min. MPA (mobile phase A) was water with 0.05% TFA and MPB (mobile phase B) was acetonitrile. The gradient started at 2% MPB and ended at 98% MPB over 18.5 min and held at 98% MPB for 1.0 min following an equilibration for 0.5 min. LC column temperature was 40° C. UV data was collected at 220 nm and 254 nm and mass spec full scan was applied to all experiments.

LCMS Method E: Experiments were performed on a Dionex Ultimate 3000 coupled with Thermo Scientific Q Exactive HRMS using ESI as ionization source. The LC separation was done on an Agilent Zorbax Eclipse XDB-C18, 3.5 µm, 100×3.0 mm column at a flow rate of 0.7 ml/minute. MPA (mobile phase A) was water with 0.1% FA and MPB (mobile phase B) was acetonitrile with 0.1% FA. The gradient started at 2% MPB and ended at 98% MPB over 25.5 min and held at 98% B for 2.5 min following equilibration for 1.5 min. LC column temperature was 40° C. UV absorbance was collected by a DAD detector and mass spec full scan was applied to all experiments.

LCMS Method F: Experiments performed on Shimadzu UFLC coupled with DAD detector, ELSD detector and 2020EV MS. The spectrometer has an electrospray source operating in positive ion mode. This system uses a Shim-Pack XR-ODS C18 2.2 µm 50*3.0 mm column, maintained at 40° C. and a 1.2 mL/minute flow rate. The initial solvent system was 95% water containing 0.05% trifluoroacetic acid (solvent A) and 5% acetonitrile containing 0.05% trifluoroacetic acid (solvent B) for the first 0.01 minute followed by a gradient up to 5% solvent A and 95% solvent B over the next 2.0 minutes. This was maintained for 0.7 minutes before returning to 95% solvent A and 5% solvent B over the next 0.3 minutes.

LCMS Method G: Experiments performed on Shimadzu UFLC coupled with DAD detector, ELSD detector and 2020EV MS. The spectrometer has an electrospray source operating in positive ion mode. This system uses a Shim-Pack XR-ODS C18 2.2 µm 50*3.0 mm column, maintained at 40° C. and a 1.2 mL/minute flow rate. The initial solvent system was 95% water containing 0.05% trifluoroacetic acid (solvent A) and 5% acetonitrile containing 0.05% trifluoroacetic acid (solvent B) for the first 0.01 minute followed by a gradient up to 100% solvent B over the next 2.0 minutes. This was maintained for 0.7 minutes before returning to 95% solvent A and 5% solvent B over the next 0.3 minutes.

LCMS Method H: Experiments performed on Shimadzu UFLC coupled with DAD detector, ELSD detector and 2020EV MS. The spectrometer has an electrospray source operating in positive ion mode. This system uses a Shim-Pack XR-ODS C18 2.2 µm 50*3.0 mm column, maintained at 40° C. and a 1.2 mL/minute flow rate. The initial solvent system was 70% water containing 0.05% trifluoroacetic acid (solvent A) and 30% acetonitrile containing 0.05% trifluoroacetic acid (solvent B) for the first 0.01 minute followed by a gradient up to 30% solvent A and 70% solvent B over the next 3.6 minutes. And then followed by a gradient up 100% solvent B over the next 0.4 minutes. This was maintained for 0.5 minutes before returning to 95% solvent A and 5% solvent B over the next 0.3 minutes.

LCMS Method I: Experiments performed on Shimadzu UFLC coupled with DAD detector, ELSD detector and 2020EV MS. The spectrometer has an electrospray source operating in positive ion mode. This system uses a Shim-Pack XR-ODS C18 2.2 µm 50*3.0 mm column, maintained at 40° C. and a 1.2 mL/minute flow rate. The initial solvent system was 95% water containing 0.05% trifluoroacetic acid (solvent A) and 5% acetonitrile containing 0.05% trifluoroacetic acid (solvent B) for the first 0.01 minute followed by a gradient up to 30% solvent A and 70% solvent B over the next 3.2 minutes. And then followed by a gradient up 100% solvent B over the next 0.5 minutes. This was maintained for 0.8 minutes before returning to 95% solvent A and 5% solvent B over the next 0.3 minutes.

LCMS Method J: Experiments performed on Shimadzu UFLC coupled with DAD detector, ELSD detector and 2020EV MS. The spectrometer has an electrospray source operating in positive ion mode. This system uses a Shim-Pack XR-ODS C18 2.2 µm 50*3.0 mm column, maintained at 40° C. and a 1.2 mL/minute flow rate. The initial solvent system was 95% water containing 0.05% trifluoroacetic acid (solvent A) and 5% acetonitrile containing 0.05% trifluoroacetic acid (solvent B) for the first 0.01 minute followed by a gradient up to 40% solvent A and 60% solvent B over the next 3.2 minutes. And then followed by a gradient up 100% solvent B over the next 0.5 minutes. This was maintained for 0.8 minutes before returning to 95% solvent A and 5% solvent B over the next 0.3 minutes.

LCMS Method K: Experiments performed on Shimadzu UFLC coupled with DAD detector, ELSD detector and 2020EV MS. The spectrometer has an electrospray source operating in positive ion mode. This system uses a Shim-Pack XR-ODS C18 2.2 µm 50*3.0 mm column, maintained at 40° C. and a 1.2 mL/minute flow rate. The initial solvent system was 80% water containing 0.05% trifluoroacetic acid (solvent A) and 20% acetonitrile containing 0.05% trifluoroacetic acid (solvent B) for the first 0.01 minute followed by a gradient up to 40% solvent A and 60% solvent B over the next 3.6 minutes. And then followed by a gradient up 100% solvent B over the next 0.4 minutes. This was maintained for 0.5 minutes before returning to 95% solvent A and 5% solvent B over the next 0.3 minutes.

LCMS Method L: Experiments performed on Shimadzu UFLC coupled with DAD detector, ELSD detector and 2020EV MS. The spectrometer has an electrospray source operating in positive ion mode. This system uses a Shim-Pack XR-ODS C18 2.2 µm 50*3.0 mm column, maintained at 40° C. and a 1.2 mL/minute flow rate. The initial solvent system was 95% water containing 0.05% trifluoroacetic acid (solvent A) and 5% acetonitrile containing 0.05% trifluoroacetic acid (solvent B) for the first 0.01 minute followed by a gradient up to 30% solvent A and 70% solvent B over the next 3.5 minutes. And then followed by a gradient up 100% solvent B over the next 0.2 minutes. This was maintained for 1.0 minutes before returning to 95% solvent A and 5% solvent B over the next 0.3 minutes.

Intermediate 1.
(2R,3R)-3-Hydroxy-2-methylnonanoic acid

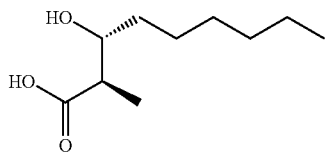

Step 1. 1-((3aR,6S,7aS)-8,8-Dimethyl-2,2-dioxido-tetrahydro-3H-3a,6-methanobenzo[c]isothiazol-1(4H)-yl)propan-1-one

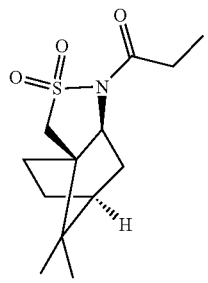 [SMILES: CCC(=O)N1[C@H]2C[C@@H]3CC[C@@]2(CS1(=O)=O)C3(C)C]

Propionyl chloride (844 g, 894 mmol) was added to a solution of (3aR,6S,7aS)-8,8-dimethylhexahydro-3H-3a,6-methanobenzo[c]isothiazole 2,2-dioxide (175 g, 813 mmol), DMAP (10.5 g, 81.3 mmol), and triethylamine (172 mL, 1220 mmol) in THF (1.4 L) at 0° C. After 30 min, the reaction was warmed to room temperature and was allowed to stir for an additional 3 h. The reaction was evaporated under reduced pressure. The resulting residue was diluted with water and isopropyl acetate. The aqueous layer was extracted with isopropyl acetate (×2). The combined organic layers were washed with 1 M NaOH (×2), 1 M HCl (×2), brine, dried with magnesium sulfate, and evaporated in vacuo. The crude solid was recrystallized from DCM and heptane to give the title compound (213.3 g, 97% yield).

Step 2. (2R,3R)-1-((3aR,6S,7aS)-8,8-Dimethyl-2,2-dioxidotetrahydro-3H-3a,6-methanobenzo[c]isothiazol-1(4H)-yl)-3-hydroxy-2-methylnonan-1-one

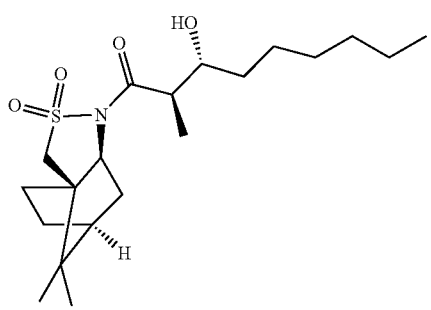 [SMILES: CCCCCC[C@@H](O)[C@@H](C)C(=O)N1[C@H]2C[C@@H]3CC[C@@]2(CS1(=O)=O)C3(C)C]

To a solution of triethylborane (91 mL, 1 mol/L in hexane) in DCM (50 mL) in a 500 mL 3-neck round-bottom flask was added TfOH (13.825 g, 92.122 mmol) dropwise at 0° C. under nitrogen. The mixture was then stirred for 30 min at 0° C., and then cooled to −15° C. To this was added a solution of 1-((3aR,6S,7aS)-8,8-dimethyl-2,2-dioxidotetrahydro-3H-3a,6-methanobenzo[c]isothiazol-1(4H)-yl)propan-1-one (10.00 g, 36.8 mmol) and DIPEA (12.3 g) in DCM (50 mL) dropwise at −15° C. The resulting solution was stirred for 1 h at −10° C. in a water/brine bath (mixture A).

Into a 250 mL 3-necked round-bottom flask, was placed titanium tetrachloride (110 mL, 1 mol/L in DCM, 3.0 equiv) under nitrogen. To this solution was added heptaldehyde (6.3 g, 55.3 mmol, 1.5 equiv) dropwise at −78° C., and the mixture was stirred for 30 min at −50° C. The resulting solution was then transferred to an additional funnel (mixture B).

The mixture B was added to mixture A dropwise at −78° C., and stirred for 4 h at −50° C. The reaction was quenched with 300 mL of saturated aqueous ammonium chloride, and extracted with 2×500 mL of ethyl acetate. The organic layers were combined and washed with 1×300 mL brine, dried over anhydrous sodium sulfate, filtered and evaporated in vacuo. The residue was applied onto a silica gel column eluting with ethyl acetate/petroleum ether (1:4). The appropriate fractions were combined and concentrated under vacuum to afford the title compound (12 g) as a light yellow oil of 85% purity (containing ~15% starting material), and was carried forward to the next step without purification. LCMS (ESI): [M+H]$^+$=386.

Step 3. (2R,3R)-3-Hydroxy-2-methylnonanoic acid

Into a 250 mL round-bottom flask, was placed THF (60 mL), 30% H$_2$O$_2$ (6.3 mL), LiOH (1.96 g, 81.844 mmol), water (30 mL, 1.665 mol), (2R,3R)-1-((3aR,6S,7aS)-8,8-dimethyl-2,2-dioxidotetrahydro-3H-3a,6-methanobenzo[c]isothiazol-1(4H)-yl)-3-hydroxy-2-methylnonan-1-one (6.30 g, 16.340 mmol). The resulting solution was stirred overnight at 25° C. The reaction was then quenched by the addition of 100 mL of saturated aqueous Na$_2$SO$_3$ solution. The pH value of the solution was adjusted to 3 with 1 N HCl solution. The resulting solution was extracted with 3×200 mL of ethyl acetate and the organic layers combined and dried over anhydrous sodium sulfate, filtered and concentrated under vacuum. The residue was applied onto a silica gel column eluting with ethyl acetate/petroleum ether (1:2). The appropriate fractions were combined and concentrated under vacuum. This resulted in 2.2 g (70% yield) of the title compound as a light yellow oil. LCMS (ESI): [M−H]$^-$=187; $^1$H NMR (400 MHz, DMSO-d$_6$) δ 11.95 (s, 1H), 4.60 (d, J=5.2 Hz, 1H), 3.59 (s, 1H), 2.43-2.31 (m, 1H), 1.48-1.15 (m, 10H), 0.98 (d, J=7.0 Hz, 3H), 0.92-0.82 (m, 3H).

Intermediate 2. (2R,3R)-3-((R)-2-((tert-Butoxycarbonyl)amino)propoxy)-2-methylnonanoic acid

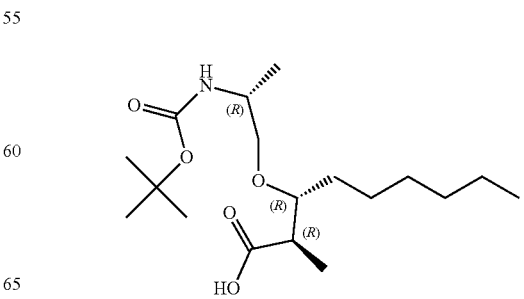

Step 1. (R)-2-((tert-Butoxycarbonyl)amino)propyl (2S,3R)-3-((R)-2-((tert-butoxy carbonyl)amino)propoxy)-2-methylnonanoate

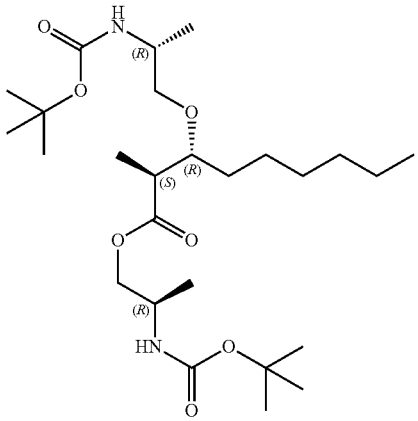

To a solution of (2R,3R)-3-hydroxy-2-methyl-nonanoic acid (10.13 g, 53.81 mmol, Intermediate 1) in anhydrous THF (100 mL) was added tert-butyl (4R)-4-methyl-2,2-dioxo-oxathiazolidine-3-carboxylate (38.31 g, 161.46 mmol) and tetrabutylammonium fluoride (1 mol/L solution in THF, 80 mL, 53.81 mmol) at room temperature. Sodium hydride (60% in mineral oil, 8.61 g, 215.2 mmol) was added portionwise at 0° C. After the completion of sodium hydride addition and hydrogen evolution ceased, the reaction mixture was allowed to warm to room temperature and stirred at room temperature for 16 h. Aqueous HCl solution (1 mol/F) was carefully added with stirring until pH~6-7. The resulting solution was extracted with ethyl acetate (3×100 mL) and the organic layers were combined. The combined organic phases were dried over anhydrous sodium sulfate, filtered and concentrated under reduced pressure. The residue was purified by flash chromatography on silica gel eluting with ethyl acetate/petroleum ether (1/9) to afford the title compound (23.01 g, 85% yield) as a colorless oil. LCMS (ESI): [M+H]$^+$=503.4.

Step 3. (2R,3R)-3-((R)-2-((tert-Butoxycarbonyl)amino)propoxy)-2-methylnonanoic acid To a solution of (R)-2-((tert-butoxycarbonyl)amino)propyl (2S,3R)-3-((R)-2-((tert-butoxy carbonyl)amino)propoxy)-2-methylnonanoate (5.02 g, 9.98 mmol) in methanol (50 mL) was added a solution of lithium hydroxide (2.3 g, 99.87 mmol) in water (23 mL) at 25° C. The resulting solution was stirred at 30° C. for 16 h. The resulting solution was concentrated under reduced pressure to approximately ⅓ of volume (evaporating methanol). Aqueous HCl (1 mol/L) was carefully added until pH~6. The resulting solution was extracted with ethyl acetate (3×100 mL). The combined organic layers were dried over anhydrous sodium sulfate and concentrated under reduced pressure. The residue was purified by flash chromatography on silica gel eluting with ethyl acetate/petroleum ether (1/6) to afford the title compound (3.03 g, 87% yield) as a colorless oil. LCMS (ESI): [M+H]$^+$=346.2; $^1$H NMR (300 MHz, DMSO-d$_6$) δ 12.11 (s, 1H), 6.56 (d, 0.7=8.1 Hz, 1H), 3.53-3.15 (m, 4H), 2.64-2.60 (m, 1H), 1.37 (s, 9H), 1.35-1.25 (m, 10H), 0.99 (d, J=6.9 Hz, 3H), 0.95 (d, J=7.2 Hz, 3H), 0.86 (t, J=6.6 Hz, 3H).

Intermediate 3. (2R,3R)-3-((R)-2-((((9H-Fluoren-9-yl)methoxy)carbonyl)amino)propoxy)-2-methyl-nonanoic acid

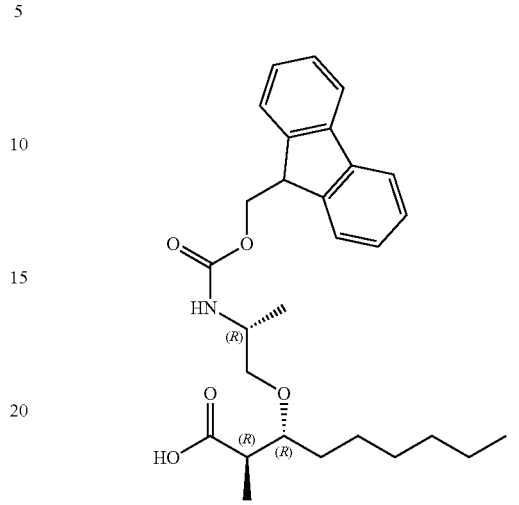

To a solution of (2S,3R)-3-[(2R)-2-(tert-butoxycarbonylamino)propoxy]-2-methyl-nonanoic acid (1.15 g, 3.33 mmol, Intermediate 2) in dioxane (10 mL) was added a solution of HCl/dioxane (40 mL, 4 mol/L). The mixture was stirred at 25° C. for 1 h, and concentrated under reduced pressure. The residue was dissolved with water (10 mL) and THF (30 mL) and a solution of lithium hydroxide (320.0 mg, 13.33 mmol) in water (5 mL) was added at 0° C., followed by a solution of 9-fluorenylmethylchloroformate (1.03 g, 3.99 mmol) in THF (5 mL) at 0° C. The reaction mixture was stirred at 25° C. for 4 h, and concentrated under reduced pressure. The residue was diluted with water (10 mL), and aqueous HCl solution (1 M) was carefully added until pH~6. The resulting solution was concentrated under reduced pressure. The residue was purified by flash chromatography on silica gel eluting with PE/EtOAc (2/1) to afford the title compound (1.12 g, 72% yield) as a colorless oil. LCMS (ESI): [M+H]$^+$=468.2; $^1$H NMR (400 MHz, DMSO-d$_6$) δ 12.16 (S, 1H), 7.88 (d, J=IB Hz, 2H), 7.69 (d, J=IB Hz, 2H), 7.43-7.39 (m, 2H), 7.34-7.30 (m, 2H), 7.14 (d, J=8.4 Hz, 1H), 4.28-4.18 (m, 3H), 3.64-3.47 (m, 2H), 3.36-3.21 (m, 2H), 2.67-2.60 (m, 1H), 1.34-1.18 (m, 10H), 1.04 (d, J=6.4 Hz, 3H), 0.96 (d, 0.7=7.2 Hz, 3H), 0.80 (t, J=6.4 Hz, 3H).

Intermediate 4. (2R,3R)-3-((R)-2-((((9H-fluoren-9-yl)methoxy)carbonyl)amino) propoxy)-2-methyl-4-(spiro[3.3]heptan-2-yl)butanoic acid

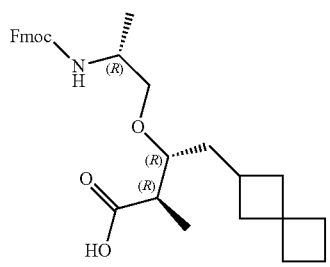

Step 1. 2-(Spiro[3.3]heptan-2-yl)ethan-1-ol

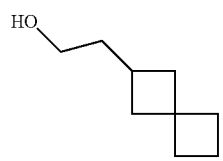

To a solution of triethyl phosphonoacetate (11.47 g, 51.18 mmol) in THF (150 mL) was added NaH (2.23 g, 55.84 mmol, 60% in mineral oil) at 0° C. The reaction mixture was stirred at room temperature for 1 h and cooled to 0° C. Spiro[3.3]heptan-2-one (5.13 g, 46.53 mmol) was added portionwise at 0° C. The reaction mixture was stirred at room temperature for 2 h and then quenched by the addition of HCl (100 mL, 1 mol/L in water). The mixture was extracted with ethyl acetate (100 mL×3) and the combined organic phases were dried over sodium sulfate and evaporated under reduced pressure. The residue was purified by flash chromatography on silica gel eluting with petroleum ether/ethyl acetate (5/1) to afford ethyl 2-spiro[3.3]heptan-2-ylideneacetate (8.02 g, 95% yield) as a yellow oil.

To a solution of ethyl 2-spiro[3.3]heptan-2-ylideneacetate (8.02 g, 44.47 mmol) in ethyl acetate (150 mL) was added palladium (0.8 g, 10% loading on carbon) at 0° C. The mixture was evacuated and recharged with hydrogen and stirred at room temperature under a hydrogen balloon for 5 h. The mixture was filtered and the filtrate was evaporated under reduced pressure. The resulting residue was dissolved in THF (150 mL), then LiAlH$_4$ (2.48 g, 65.19 mmol) was added at 0° C. The reaction mixture was stirred at room temperature for 3 h and quenched by careful addition of water (50 mL). The solid was removed via filtration and the filtrate was extracted with DCM (100 mL×3). The combined organic phases were dried over sodium sulfate and concentrated under reduced pressure. The residue was purified by flash chromatography on silica gel eluting with PE/EtOAc (2/1) to afford the title compound (5.52 g, 90% yield) as a colorless oil. TLC R$_f$=0.4, PE/EtOAc=2/1.

Step 2. 2-(Spiro[3.3]heptan-2-yl)acetaldehyde

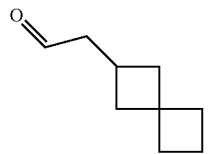

To a solution of 2-spiro[3.3]heptan-2-ylethanol (5.52 g, 39.37 mmol) in DCM (300 mL) was added pyridinium chlorochromate (12.63 g, 58.74 mmol). The reaction mixture was stirred at room temperature for 3 h. The solid was removed via filtration. The filtrate was evaporated under reduced pressure and the crude product was used directly for the next step. TLC R$_f$=0.5, PE/EA=4/1.

Step 3. (2R,3R)-3-Hydroxy-2-methyl-4-(spiro[3.3] heptan-2-yl)butanoic acid

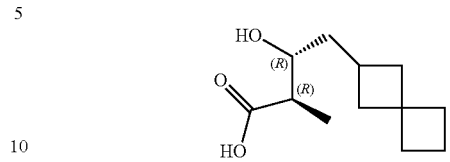

The title compound was prepared using 2-(spiro[3.3] heptan-2-yl)acetaldehyde instead of heptaldehyde and following procedures analogous to those described for Intermediate 1. LCMS (ESI): [M−H]$^-$=211.1.

Step 4. (2R,3R)-3-((R)-2-((((9H-Fluoren-9-yl) methoxy)carbonyl)amino) propoxy)-2-methyl-4-(spiro[3.3]heptan-2-yl)butanoic acid The title compound was prepared following procedures analogous to those described for Intermediate 3, using (2R,3R)-3-hydroxy-2-methyl-4-(spiro[3.3]heptan-2-yl)butanoic acid. LCMS (ESI): [M+H]$^+$=492.3.

Intermediate 5. (2R,3R)-3-((R)-2-((((9H-Fluoren-9-yl)methoxy)carbonyl)amino)propoxy)-4-((1R,3s,5S)-bicyclo[3.2.1]octan-3-yl)-2-methylbutanoic acid

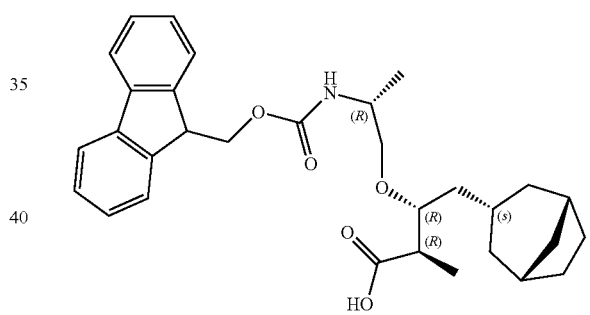

Step 1. 2-((1R,3s,5S)-Bicyclo[3.2.1]octan-3-yl)ethan-1-ol

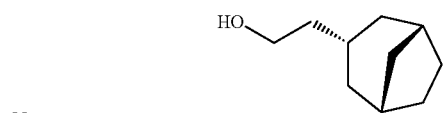

To a suspension of NaH (1.93 g, 48.3 mmol, 60% in mineral oil) in 1,2-dimethoxyethane (30 ml) was added triethyl phosphonoacetate (11.7 g, 52.3 mmol) at 0° C. The resulting mixture was stirred for min at 0° C. Then a solution of bicyclo[3.2.1]octan-3-one (4.06 g, 32.7 mmol) in 1,2-dimethoxyethane (20 mL) was added. The resulting solution was stirred for 15 min at 0° C. and stirred for 3 days at room temperature, poured into an ice cold solution of HCl (1 mol/L in water, 100 ml). The resulting solution was extracted with ethyl acetate (100 ml×4) and the organic layers were combined. The organic layer was dried over anhydrous sodium sulfate and concentrated under vacuum. The residue was purified by flash chromatography on silica gel eluting with EtOAc/PE (1/4) to afford ethyl 2-(3-bicyclo [3.2.1]octanylidene)acetate (2.51 g). This material was dissolved in ethyl acetate (100 mL). A drop of TFA was added, then the flask was evacuated and flushed 3 times with nitrogen. Palladium (1.3 g, 10% loading on carbon) was added. The system was evacuated and charged with hydrogen. The mixture was stirred under a hydrogen balloon overnight at room temperature. The solid was filtered off and the filtrate was concentrated under vacuum to afford crude ethyl 2-(3-bicyclo[3.2.1]octanyl)acetate (6.53 g). This material was dissolved in THF (120 mL) and treated with lithium aluminum hydride (2.31 g, 60.7 mmol) in small portions at 0° C. under nitrogen. The reaction mixture was allowed to warm to room temperature and stirred at this temperature for 2 hours, cooled over ice bath, and quenched by careful addition of 2.3 mL water, 2.3 mL aqueous sodium hydroxide solution (25%) and 2.3 mL water sequentially. The precipitate was removed via filtration and the filtrate was evaporated under vacuum. The residue was purified by flash chromatography on silica gel eluting with ethyl acetate/ petroleum ether (11-15% ethyl acetate) to afford the title compound (2.66 g, 84% yield) as a colorless oil. $^1$H NMR (400 MHz, DMSO-$d_6$) δ 4.24 (t, J=5.2 Hz, 1H), 3.39-3.34 (m, 2H), 2.13-2.12 (m, 2H), 1.75-1.56 (m, 3H), 1.48-1.32 (m, 5H), 1.29-1.24 (m, 3H), 1.01-0.94 (m, 2H). $^1$H NMR suggested a ratio of endo and exo isomers of ~6:1.

Step 2. 2-((1R,3s,5S)-Bicyclo[3.2.1]octan-3-yl)acetaldehyde

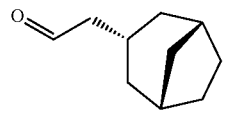 [SMILES: O=CC[C@H]1C[C@H]2CC[C@@H](C1)C2]

To a solution of 2-(3-bicyclo[3.2.1]octanyl)ethanol (4.21 g, 27.29 mmol) in DCM (150 mL) was added pyridinium chlorochromate (8.86 g, 41.21 mmol). The reaction mixture was stirred at room temperature for 3 h. The solid was removed via filtration and the filtrate was evaporated under reduced pressure. The crude product was used directly in the next step without purification. TLC $R_f$=0.5, PE/EA=4/1.

Step 3. (2R,3R)-4-((1R,3s,5S)-Bicyclo[3.2.1]octan-3-yl)-3-hydroxy-2-methylbutanoic acid

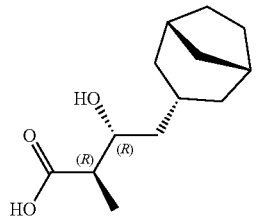

Trifluoromethanesulfonic acid (3.66 g, 24.4 mmol) was added dropwise to triethyl borane (24.9 mL, 24.9 mmol, 1 M in THF) in DCM (30 mL) at −10° C., the reaction mixture was stirred at room temperature for 30 min. Then a solution of 1-((3aR,6S,7aS)-8,8-dimethyl-2,2-dioxidotetrahydro-3H- 3a,6-methanobenzo[c]isothiazol-1(4H)-yl)propan-1-one (5.95 g, 21.92 mmol) and DIPEA (3.63 g, 28.14 mmol) in DCM (30 mL) was added at 0° C. The reaction mixture was stirred at 0° C. for 30 min. Then the reaction mixture was stirred at −78° C. Titanium tetrachloride (28.4 mL, 1 M in DCM) was added. Then a solution of 2-(3-bicyclo[3.2.1] octanyl)acetaldehyde (3.96 g, 26.01 mmol) in DCM (40 mL) was added. The reaction mixture was stirred at −78° C. for 2 h. The reaction mixture was poured into saturated aqueous ammonium chloride (100 mL) and extracted with DCM (150 mL×3). The combined organic phases were dried over Na$_2$SO$_4$ and evaporated under reduced pressure. The residue was purified by flash chromatography on silica gel eluting with petroleum ether/ethyl acetate (5/1) to afford (2R,3R)- 4-((1R,5S)-bicyclo[3.2.1]octan-3-yl)-1-((3aR,6S',7aS)-8,8- dimethyl-2,2-dioxidotetrahydro-3H-3a,6-methanobenzo[c] isothiazol-1(4H)-yl)-3-hydroxy-2-methylbutan-1-one (7.45 g, 17.6 mmol, 80.2% yield) as a yellow oil.

A solution of LiOH (1.67 g, 69.52 mmol) in H$_2$O (40 mL) was added to a solution of (2R,3R)-4-((1R,5S)-bicyclo [3.2.1]octan-3-yl)-1-((3aR,6S,7aS)-8,8-dimethyl-2,2-dioxidotetrahydro-3H-3a,6-methanobenzo[c]isothiazol-1(4H)- yl)-3-hydroxy-2-methylbutan-1-one (7.37 g, 17.39 mmol) in acetonitrile (120 mL) at 0° C. The reaction mixture was stirred at room temperature for 16 h and then acidified by the addition of HCl (1 mol/L in water) to pH~6 and extracted with ethyl acetate (100 mL×3). The combined organic phases were dried over Na$_2$SO$_4$ and evaporated under reduced pressure. The residue was purified by flash chromatography on silica gel eluting with petroleum ether/ethyl acetate (5/1) to afford the title compound (2.96 g, 75% yield, endo/exo=6/1) as a light red solid. The mixture (2.96 g) was dissolved in petroleum ether/ethyl acetate (5/1, 100 ml) at 60° C., and cooled to 0° C. The resulting crystalline solid was collected by filtration to afford the title compound as pure endo isomer (1.05 g). LCMS (ESI): [M−H]$^-$=225.2.

Step 4. [(2R)-2-(tert-Butoxycarbonylamino)propyl] (2R,3R)-4-[(1R,5R)-3-bicyclo[3.2.1]octanyl]-3- [(2R)-2-(tert-butoxycarbonylamino)propoxy]-2- methyl-butanoate

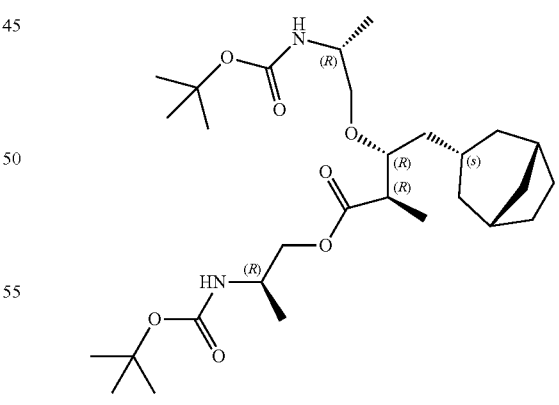

To a solution of the hydroxy acid from Step 3 (3.6 g, 15.9 mmol) in anhydrous THF (36 mL) was added tert-butyl (4R)-4-methyl-2,2-dioxo-oxathiazolidine-3-carboxylate (11.33 g, 47.75 mmol) and TBAF (24 mL, 1M in THF) followed by the addition of NaH (2.55 g, 63.68 mmol, 60% in mineral oil) in small portions at 0° C. under nitrogen. The reaction mixture was stirred overnight at room temperature and quenched with HCl (1M in water) to pH~4-5. Ethyl acetate (200 mL) was added and the phases were separated. The aqueous phase was extracted with ethyl acetate (2×). The organic layers were combined, dried over anhydrous sodium sulfate and concentrated under vacuum. The residue was purified by flash chromatography on silica gel eluting with ethyl acetate and petroleum ether (1:9) to afford the title compound (3.412 g, 39.6% yield) as a colorless oil. LCMS (ESI): [M+H]$^+$=541.4.

Step 5. (2R,3R)-4-[(1S,5R)-3-Bicyclo[3.2.1]octanyl]-3-[(2R)-2-(tert-butoxycarbonylamino)propoxy]-2-methyl-butanoic acid

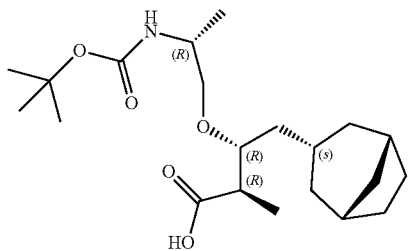

A solution of LiOH (1.45 g, 63.1 mmol) in water (15 mL) was added to a solution of [(2R)-2-(tert-butoxycarbonylamino)propyl](2R,3R)-4-[(1S,5R)-3-bicyclo[3.2.1]octanyl]-3-[(2R)-2-(tert-butoxycarbonylamino)propoxy]-2-methyl-butanoate (3.41 g, 6.31 mmol) in MeOH (35 mL) at room temperature. The resulting solution was stirred overnight at 30° C. MeOH was distilled off under reduced pressure and the residual aqueous solution was acidified with 1 N HCl solution to pH 4-5. Ethyl acetate (200 mL) was added and the phases were separated. The aqueous phase was extracted with ethyl acetate (2×). The organic layers were combined, dried over anhydrous sodium sulfate and concentrated under vacuum. The residue was purified by flash chromatography on silica gel eluting with ethyl acetate and petroleum ether (1:6) to afford the title compound (2.04 g, 84.3% yield) as a colorless oil. LCMS (ESI): [M+H]$^+$=384.3.

Step 6. (2R,3R)-3-((R)-2-((((9H-Fluoren-9-yl)methoxy)carbonyl)amino)propoxy)-4-((1R,3s,5S)-bicyclo[3.2.1]octan-3-yl)-2-methylbutanoic acid A solution of HCl/dioxane (32 mL, 4 M, 160 mmol) was added to a solution of (2R,3R)-4-[(1S,5R)-3-bicyclo[3.2.1]octanyl]-3-[(2R)-2-(tert-butoxycarbonylamino)propoxy]-2-methyl-butanoic acid (1.84 g, 4.81 mmol) in DCM (8 mL). The mixture was stirred at room temperature for 1 h and concentrated under vacuum. Then the residue was dissolved with water (10 mL) and THF (30 mL). LiOH (331.8 mg, 14.43 mmol) (dissolved in 6 mL water) was added at 0° C. Fluorenylmethyloxycarbonyl chloride (1.49 g, 5.77 mmol) (dissolved in 20 mL THF) was added dropwise at 0° C. with stirring. The mixture was stirred at 25° C. for 1 h. THF was distilled off under reduced pressure and the residual aqueous solution was acidified with 1 N HCl to pH 5-6. Ethyl acetate (100 ml) was added and the phases were separated. The aqueous phase was extracted with ethyl acetate (2×). The organic layers were combined, dried over anhydrous sodium sulfate and concentrated under vacuum. The residue was purified by flash chromatography on silica gel eluting with DCM/MeOH (49/1) to afford the title compound (2.24 g, 4.43 mmol 92.2% yield) as a white solid. LCMS (ESI): [M+1]$^+$=506.3; $^1$H NMR (400 MHz, DMDO-d$_6$): δ 12.17 (s, 1H), 7.88 (d, J=7.2 Hz, 2H), 7.70 (d, J=IB Hz, 2H), 7.43-7.39 (m, 2H), 7.34-7.30 (m, 2H), 7.15 (d, J=8.0 Hz, 1H), 4.29-4.18 (m, 3H), 3.64-3.56 (m, 2H), 3.34-3.18 (m, 2H), 2.74-2.70 (m, 1H), 2.20-2.10 (m, 2H), 1.73-1.62 (m, 1H), 1.56-1.41 (m, 3H), 1.39-1.22 (m, 6H), 1.08-0.92 (m, 9H).

Intermediate 6. N-(((9H-Fluoren-9-yl)methoxy)carbonyl)-O-(3-((tert-butoxycarbonyl)amino)propyl)-L-serine

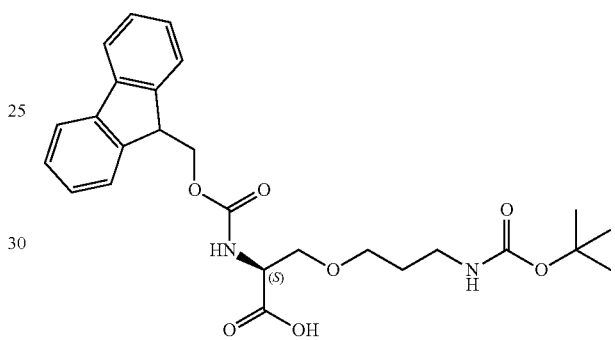

Step 1. Methyl N-((benzyloxy)carbonyl)-O-(3-nitropropyl)-L-serinate

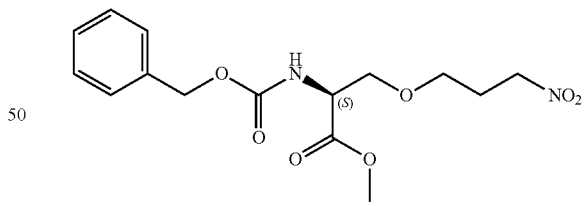

To a solution of 1-benzyl 2-methyl (S)-aziridine-1,2-dicarboxylate (11.32 g, 48.14 mmol) and 3-nitropropan-1-ol (5.06 g, 48.12 mmol) in chloroform (150 mL) at 0° C. was added BF$_3$·Et$_2$O (0.1 mL) under nitrogen. The reaction mixture was allowed to warm to room temperature and stirred at room temperature for 16 h. The solvent was removed under reduced pressure. The residue was purified by flash chromatography on silica gel eluting with petroleum ether/ethyl acetate (5/1) to afford the title compound (11.02 g, 67% yield) as a colorless oil. LCMS (ESI): [M+H]$^+$=341.1.

Step 2. Methyl N-((benzyloxy)carbonyl)-O-(3-((tert-butoxycarbonyl)amino)propyl)-L-serinate

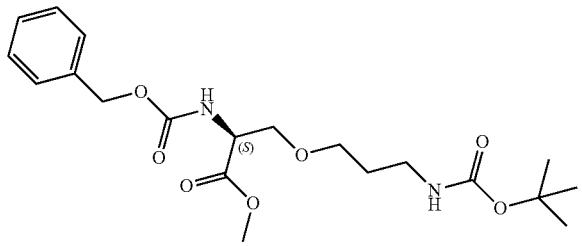

To a solution of methyl N-((benzyloxy)carbonyl)-O-(3-nitropropyl)-L-serinate (11.02 g, 32.4 mmol) in ethanol (80 mL) and water (80 mL) was added NH$_4$Cl (8.75 g, 162 mmol), followed by the addition of iron powder (9.07 g, 162 mmol). The reaction mixture was stirred at reflux for 4 h. The solid was filtered off and washed with ethanol. The filtrate was concentrated under reduced pressure to remove approximately half of the volume. The residue was partitioned between water and ethyl acetate. The aqueous phase was extracted with ethyl acetate (2×). The combined organic phases were dried over sodium sulfate and concentrated under reduced pressure to afford a residue (8.89 g), which was re-dissolved in DCM (100 mL), then di-tert-butyl dicarbonate (9.36 g, 42.95 mmol) was added, followed by triethylamine (8.68 g, 85.89 mmol). The reaction mixture was stirred at ambient temperature for 2 h. The solvent was evaporated under reduced pressure. The residue was purified by flash chromatography on silica gel eluting with ethyl acetate/petroleum ether (0-50%) to afford the title compound (9.22 g, 78% yield) as a yellow oil. LCMS (ESI): [M+H]$^+$=411.2.

Step 3. Methyl O-(3-((tert-butoxycarbonyl)amino)propyl)-L-serinate

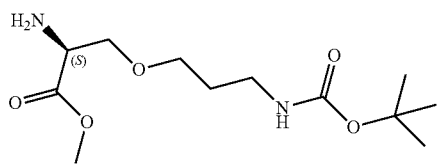

To a solution of methyl N-((benzyloxy)carbonyl)-O-(3-((tert-butoxycarbonyl)amino)propyl)-L-serinate (9.22 g, 22.48 mmol) in ethyl acetate (100 mL) under nitrogen was added palladium (10 wt. % on carbon, 0.93 g) at 0° C. The flask was evacuated and backfilled with hydrogen, and then stirred at 25° C. under a hydrogen balloon for 3 h. The reaction mixture was filtered through celite, and the filtrate was concentrated under reduced pressure to give the title compound. LCMS (ESI) [M+H]$^+$=277.2.

Step 4. N-(((9H-Fluoren-9-yl)methoxy)carbonyl)-O-(3-((tert-butoxycarbonyl)amino)propyl)-L-serine To a solution of methyl O-(3-((tert-butoxycarbonyl) amino)propyl)-L-serinate (5.90 g, 21.35 mmol) in THF (150 mL) and water (150 mL) was added lithium hydroxide (2.05 g, 85.41 mmol) at ambient temperature. The resulting mixture was stirred at 25° C. for 3 h, cooled to 0° C., and then a solution of 9-fluorenylmethylchloroformate (8.71 g, 33.74 mmol) in THF (10 mL) was added dropwise. The reaction mixture was stirred at 0° C. for 2 h. The reaction mixture was acidified by the addition of 1M HCl to pH~6 and extracted with ethyl acetate (3×100 mL). The combined organic phases were dried with Na$_2$SO$_4$, filtered and concentrated under reduced pressure. The residue was purified by flash chromatography on silica gel eluting with petroleum ether/ethyl acetate (5/1) to afford the title compound (6.12 g, 56% yield) as a white solid. LCMS (ESI): [M+H]$^+$=485.1. $^1$H NMR (300 MHz, DMSO-d$_6$) δ 12.78 (s, 1H), 7.90 (d, J=7.5 Hz, 2H), 7.75 (d, J=7.5 Hz, 2H), 7.64 (d, J=8.1 Hz, 1H), 7.45-7.37 (m, 2H), 7.32-7.30 (m, 2H), 6.79 (t, J=5.7 Hz, 1H), 4.30-4.09 (m, 4H), 3.67-3.61 (m, 2H), 3.46-3.39 (m, 2H), 3.00-2.94 (m, 2H), 1.63-1.56 (m, 2H), 1.37 (s, 9H).

Intermediate 7. N-(((9H-Fluoren-9-yl)methoxy)carbonyl)-O-((1r,3S)-3-((tert-butoxy carbonyl)amino) cyclobutyl)-L-serine

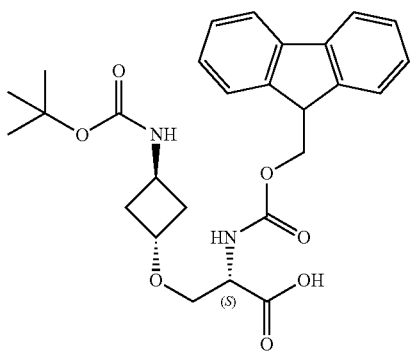

Step 1. Methyl N-((benzyloxy)carbonyl)-O-((1r,3S)-3-((tert-butoxycarbonyl)amino) cyclobutyl)-L-serinate

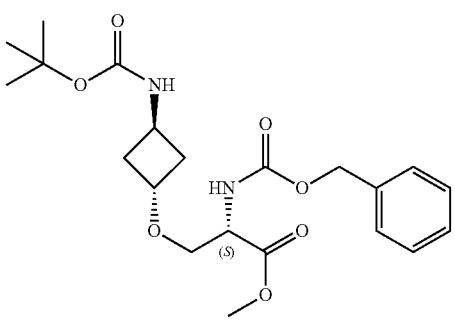

A solution of trans-tert-butyl N-(3-hydroxycyclobutyl) carbamate (7.95 g, 42.46 mmol) and BF$_3$·Et$_2$O (1.23 g, 8.54 mmol) in chloroform (100 mL) was stirred at 0° C. Then a solution of 1-benzyl 2-methyl (S)-aziridine-1,2-dicarboxylate (10.0 g, 42.51 mmol) in chloroform (10 mL) was added dropwise at 0° C. The reaction mixture was then stirred at 25° C. for 20 h and concentrated under reduced pressure. The residue was purified by flash chromatography on silica gel eluting with petroleum ether/ethyl acetate (2/1) to afford the title compound (2.5 g, 13% yield) as a white solid. LCMS (ESI): [M+H]⁺=423.2.

Step 2. N-(((9H-Fluoren-9-yl)methoxy)carbonyl)-O-((1r,3S)-3-((tert-butoxy carbonyl)amino)cyclobutyl)-L-serine To a solution of methyl (2S)-2-(benzyloxycarbonylamino)-3-[3-(tert-butoxycarbonylamino) cyclobutoxy] propanoate (2.5 g, 5.92 mmol) in ethyl acetate (30 mL) was added palladium (10 wt. % on carbon, 1.0 g) under nitrogen. The reaction mixture was evacuated and backfilled with hydrogen and stirred at 25° C. for 1 h under a hydrogen balloon. The catalyst was filtered off and rinsed with ethyl acetate. The filtrate was concentrated under reduced pressure to afford methyl (2S)-2-amino-3-[3-(tert-butoxycarbonylamino)cyclobutoxy]propanoate (1.7 g, crude) as a yellow oil. To 1.5 g of this material was added a solution of lithium hydroxide (250.0 mg, 10.42 mmol) in water (5 mL) and dioxane (15 mL). The resulting solution was stirred for 1 h at 25° C. Then 9-fluorenylmethylchloroformate (1.61 g, 6.24 mmol) was added. The mixture was stirred at 25° C. for 1 h, diluted with water (20 ml) and acidified to pH 6 with 1 N HCl. The resulting solution was extracted with ethyl acetate (3×100 mL). The organic combined layers were dried over anhydrous sodium sulfate, filtered and concentrated under reduced pressure. The residue was purified by flash chromatography on silica gel eluting with petroleum ether/ethyl acetate (4/1) to afford the title compound (1.85 g, 71% yield) as a white solid. LCMS (ESI): [M+H]⁺=497.2; ¹H NMR (400 MHz, DMSO-d₆) δ 12.76 (s, 1H), 7.89 (d, J=7.6 Hz, 2H), 7.76 (d, J=IB Hz, 2H), 7.64 (d, J=8.4 Hz, 1H), 7.44-7.40 (m, 2H), 7.35-7.31 (m, 2H), 7.16 (d, J=7.2 Hz, 1H), 4.29-4.17 (m, 4H), 4.04-3.98 (m, 2H), 3.58-3.49 (m, 2H), 2.17-2.01 (m, 4H), 1.37 (s, 9H),

TABLE 2

Intermediates illustrated below were prepared following methods analogous to those described for Intermediate 7.

| Intermediate Number | Structure | Chemical name | LCMS (ESI) [M + H]⁺ |
|---|---|---|---|
| P2C | 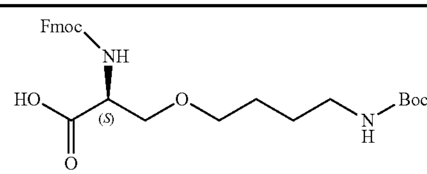 | N-(((9H-fluoren-9-yl)methoxy)carbonyl)-O-(4-((tert-butoxycarbonyl)amino)butyl)-L-serine | 499.4 |
| P2D | 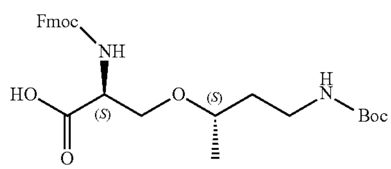 | N-(((9H-fluoren-9-yl)methoxy)carbonyl)-O-((S)-4-((tert-butoxycarbonyl)amino)butan-2-yl)-L-serine | 499.2 |
| P2E | 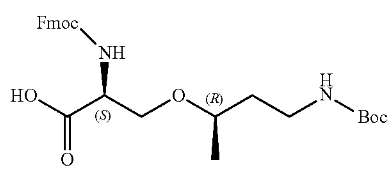 | N-(((9H-fluoren-9-yl)methoxy)carbonyl)-O-((R)-4-((tert-butoxycarbonyl)amino)butan-2-yl)-L-serine | 499.2 |
| P2F | 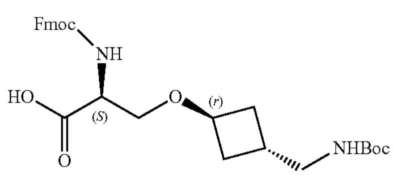 | N-(((9H-fluoren-9-yl)methoxy)carbonyl)-O-((1r,3S)-3-(((tert-butoxycarbonyl)amino)methyl)cyclobutyl)-L-serine | 511.3 |
| P2G | 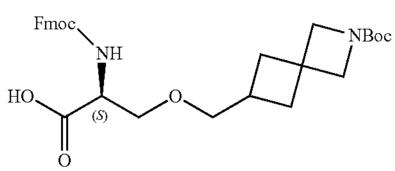 | N-(((9H-fluoren-9-yl)methoxy)carbonyl)-O-((2-(tert-butoxycarbonyl)-2-azaspiro[3.3]heptan-6-yl)methyl)-L-serine | 537.3 |
| P2H | 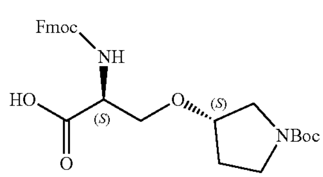 | N-(((9H-fluoren-9-yl)methoxy)carbonyl)-O-((S)-1-(tert-butoxycarbonyl)pyrrolidin-3-yl)-L-serine | 497.2 |

TABLE 2-continued

Intermediates illustrated below were prepared following methods analogous to those described for Intermediate 7.

| Intermediate Number | Structure | Chemical name | LCMS (ESI) [M + H]+ |
|---|---|---|---|
| P2I | (cis-isomer 1) | N-(((9H-fluoren-9-yl)methoxy)carbonyl)-O-(2-(((tert-butoxycarbonyl)amino)methyl)tetrahydro-2H-pyran-4-yl)-L-serine (cis, single unknown stereoisomer 1) | 541.3 |
| P2J | (cis-isomer 2) | N-(((9H-fluoren-9-yl)methoxy)carbonyl)-O-(2-(((tert-butoxycarbonyl)amino)methyl)tetrahydro-2H-pyran-4-yl)-L-serine (cis, single unknown stereoisomer 2) | 541.3 |
| P2K | 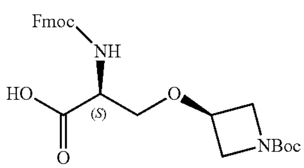 | N-(((9H-fluoren-9-yl)methoxy)carbonyl)-O-(1-(tert-butoxycarbonyl)azetidin-3-yl)-L-serine | 483.2 |

Intermediate 8. N-(((9H-Fluoren-9-yl)methoxy)carbonyl)-O-(2-(tert-butoxycarbonyl)-2-azaspiro[3.3]heptan-6-yl)-L-serine Step 1. tert-Butyl (S)-6-(2-(((benzyloxy)carbonyl)amino)-3-methoxy-3-oxopropoxy)-2-azaspiro[3.3]heptane-2-carboxylate

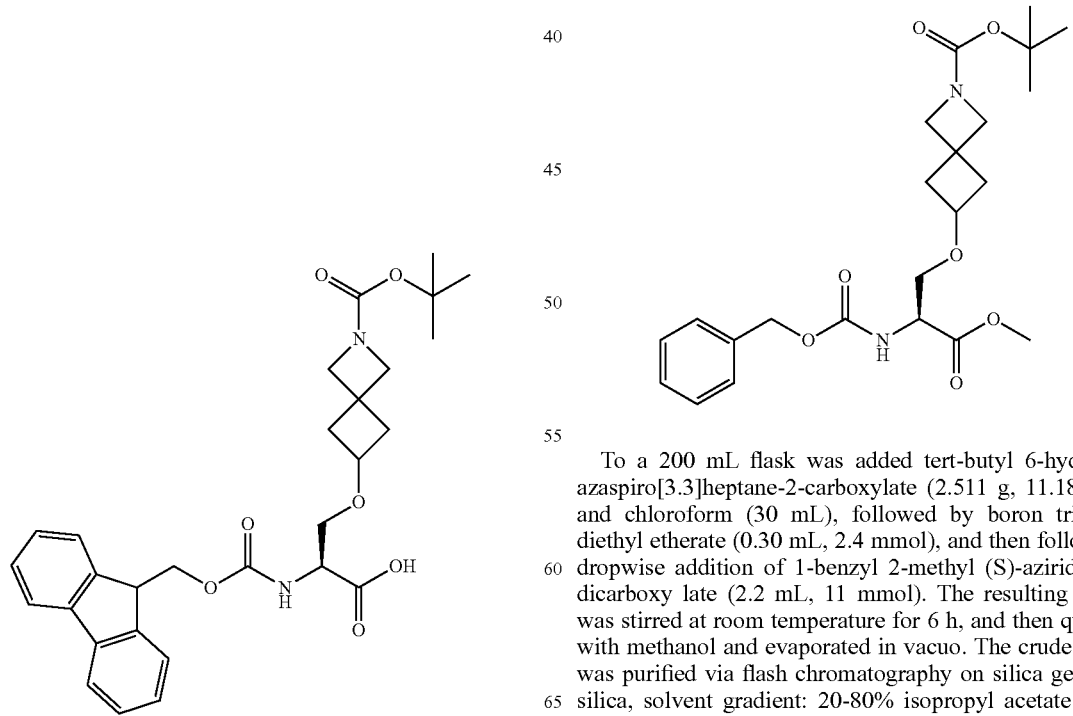

To a 200 mL flask was added tert-butyl 6-hydroxy-2-azaspiro[3.3]heptane-2-carboxylate (2.511 g, 11.18 mmol) and chloroform (30 mL), followed by boron trifluoride diethyl etherate (0.30 mL, 2.4 mmol), and then followed by dropwise addition of 1-benzyl 2-methyl (S)-aziridine-1,2-dicarboxylate (2.2 mL, 11 mmol). The resulting mixture was stirred at room temperature for 6 h, and then quenched with methanol and evaporated in vacuo. The crude product was purified via flash chromatography on silica gel (200 g silica, solvent gradient: 20-80% isopropyl acetate in heptanes) to afford 1.093 g (22%) of the title compound. LCMS (ESI): [M+H-Boc]+=349.15; $^1$H NMR (400 MHz, DMSO-d₆) δ 7.69 (d, J=8.0 Hz, 1H), 7.40-7.27 (m, 5H), 5.04 (s, 2H), 4.25 (m, 1H), 3.85-3.69 (m, 5H), 3.64 (s, 3H), 3.54-3.42 (m, 2H), 2.41-2.29 (m, 2H), 1.99 (s, 2H), 1.35 (s, 9H).

Step 2. N-((Benzyloxy)carbonyl)-O-(2-(tert-butoxycarbonyl)-2-azaspiro[3.3]heptan-6-yl)-L-serine

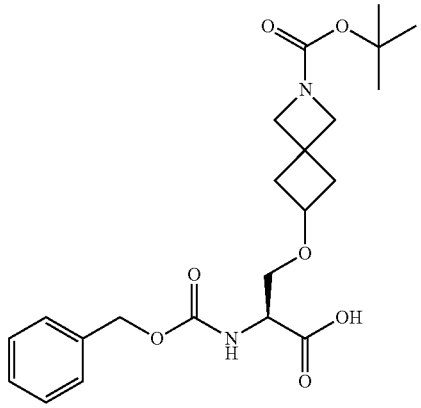 [SMILES: CC(C)(C)OC(=O)N1CC2(CC(OC[C@H](NC(=O)OCc3ccccc3)C(=O)O)C2)C1]

To a solution of tert-butyl (S)-6-(2-(((benzyloxy)carbonyl)amino)-3-methoxy-3-oxopropoxy)-2-azaspiro[3.3]heptane-2-carboxylate (1.093 g, 2.436 mmol) in 1,4-dioxane (12 mL) was added lithium hydroxide (1.0 M in water, 4 mL, 4.0 mmol). The reaction mixture was stirred at room temperature for 90 min. The reaction mixture was poured into 10% aqueous citric acid and extracted with DCM (2×50 mL). The combined DCM extracts were dried over magnesium sulfate, filtered, and evaporated in vacuo to yield 1.0618 g (quant.) of the title compound. LCMS (ESI): [M+H]⁺=435.3.

Step 3. N-(((9H-Fluoren-9-yl)methoxy)carbonyl)-O-(2-(tert-butoxycarbonyl)-2-azaspiro[3.3]heptan-6-yl)-L-serine To a solution of N-((benzyloxy)carbonyl)-O-(2-(tert-butoxycarbonyl)-2-azaspiro[3.3]heptan-6-yl)-L-serine in ethanol (10 mL) was added palladium (10 wt. % on carbon) (250.5 mg, 0.2354 mmol). The reaction mixture was stirred under a hydrogen balloon at room temperature for 4 h. The reaction mixture was filtered through celite, rinsing with 2×100 mL ethanol, and evaporated in vacuo to afford a quantitative yield of 0-(2-(tert-butoxycarbonyl)-2-azaspiro[3.3]heptan-6-yl)-L-serine. LCMS (ESI): [M+H-tBu]⁺=245.2.

The resulting material was dissolved in 1,4-dioxane (10 mL) and water (10 mL), and treated with sodium hydrogen carbonate (626.8 mg, 7.44 mmol) and (9H-fluoren-9-yl)methyl (2,5-dioxopyrrolidin-1-yl) carbonate (1.192 g, 3.534 mmol). The reaction mixture was stirred at room temperature for 15 h. The reaction mixture was poured into 10% aqueous citric acid and extracted with DCM (3×100 mL). The combined organic extracts were dried over magnesium sulfate, filtered, and evaporated in vacuo. The crude product was purified via flash chromatography on silica gel (80 g silica, solvent gradient: 0-100% isopropyl acetate in heptanes) to yield 779.1 mg (61%) of the title compound as a white foam. LCMS (ESI): [M+H]⁺=523.3.

Intermediate 9. (2S)-2-((((9H-Fluoren-9-yl)methoxy)carbonyl)amino)-4-(4-((benzyloxy)carbonyl)piperazin-1-yl)-3-((tert-butyldimethylsilyl)oxy)butanoic acid

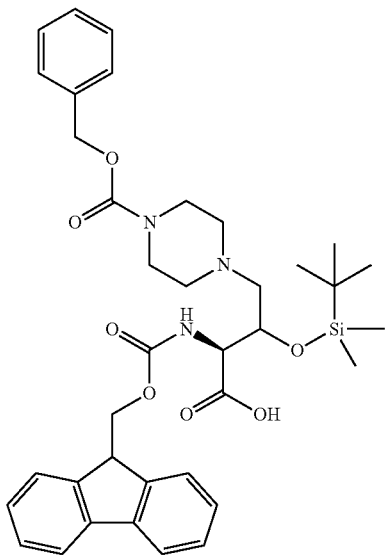 [SMILES: CC(C)(C)[Si](C)(C)OC(CN1CCN(C(=O)OCc2ccccc2)CC1)[C@H](NC(=O)OCC1c2ccccc2-c2ccccc21)C(=O)O]

Step 1. Benzyl (S)-2-((tert-butoxycarbonyl)amino)but-3-enoate

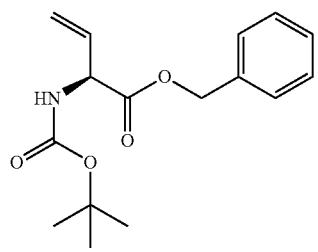 [SMILES: C=C[C@H](NC(=O)OC(C)(C)C)C(=O)OCc1ccccc1]

A mixture of (S)-2-aminobut-3-enoic acid hydrochloride (1.0 g, 7.3 mmol), di tert-buyldicarbonate (1.6 g, 7.3 mmol) and sodium bicarbonate (1.2 g, 14.6 mmol) in THF:water (1:1, 6 mL) was heated at 60° C. for 2 h. The reaction mixture was cooled and concentrated. The residue was dissolved in DMF (3 mL) and benzyl bromide (1.5 g, 8.7 mmol) was added and the mixture stirred overnight at room temperature. The reaction mixture was diluted with water and extracted with 20% heptane/IPAC. The organic layer was washed with brine, dried over sodium sulfate and concentrated. The residue was purified by flash chromatography on silica gel eluting with heptane/IPAC (0-50%) to afford the title compound (0.87 g, 55%). ¹H NMR (400 MHz, Chloroform-d) δ 7.42-7.31 (m, 5H), 5.91 (ddd, J=16.3, 10.2, 5.3 Hz, 1H), 5.34 (ddd, J=17.2, 1.9, 0.7 Hz, 1H), 5.25 (ddd, J=10.3, 1.8, 0.6 Hz, 1H), 5.23-5.15 (m, 3H), 4.92 (s, 1H), 1.44 (s, 9H); LCMS (ESI): [M+H]⁺=292.

Step 2. Benzyl (2S)-2-((tert-butoxycarbonyl)amino)-2-(oxiran-2-yl)acetate

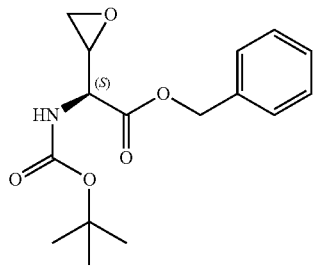

A mixture of (2S)-2-(tert-butoxycarbonylamino)but-3-enoate (1.35 g, 4.6 mmol) and m-CPBA (2.0 g, 70%) in DCM (20 mL) was stirred at room temperature overnight. The reaction mixture was concentrated and triturated with 10% DCM/heptane. The solid was removed by filtration and washed well with 10% DCM/heptane. The filtrate was concentrated and the residue was purified by flash chromatography (silica gel, 0-100% heptane/IPAC) to obtain the title compound (0.9 g, 63%). LCMS (ESI): [M+H]$^+$=308 and [M+Na]$^+$=330.1; $^1$H NMR (400 MHz, DMSO-d$_6$) δ 7.52 (d, J=7.9 Hz, 1H), 7.42-7.22 (m, 5H), 5.89 (ddd, J=17.0, 10.4, 6.4 Hz, 1H), 5.33 (d, J=17.3 Hz, 1H), 5.22 (d, J=10.4 Hz, 1H), 5.14 (q, J=12.7 Hz, 2H), 4.66 (t, J=7.2 Hz, 1H), 1.38 (d, J=2.4 Hz, 9H).

Step 3. Benzyl 4-((3S)-4-(benzyloxy)-3-((tert-butoxycarbonyl)amino)-2-hydroxy-4-oxobutyl)piperazine-1-carboxylate

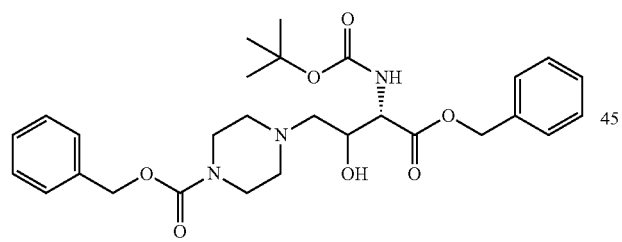

A mixture of benzyl (2S)-2-(tert-butoxycarbonylamino)-2-(oxiran-2-yl)acetate (0.8 g, 2.6 mmol) and benzyl piperazine-1-carboxylate (0.58 g, 2.6 mmol) in THF (5 mL) was heated at 70° C. for 4 h and then cooled and concentrated. The residue was purified by flash chromatography (silica gel; 0-10% methanol/DCM) to obtain the title compound (0.92 g, 67%).). LCMS (ESI): [M+H]$^+$=528.4; $^1$H NMR (400 MHz, DMSO-d$_6$) δ 7.43-7.25 (m, 10H), 6.59 (d, J=9.1 Hz, 1H), 5.23-5.12 (m, 2H), 5.06 (s, 2H), 4.30 (dd, J=9.1, 3.0 Hz, 1H), 4.05 (q, J=6.3, 5.3 Hz, 1H), 3.50-3.34 (m, 4H), 2.44-2.22 (m, 5H), 1.38 (s, 9H).

Step 4. Benzyl 4-[(3S)-4-benzyloxy-3-(tert-butoxycarbonylamino)-2-[tert-butyl(dimethyl)silyl]oxy-4-oxo-butyl]piperazine-1-carboxylate

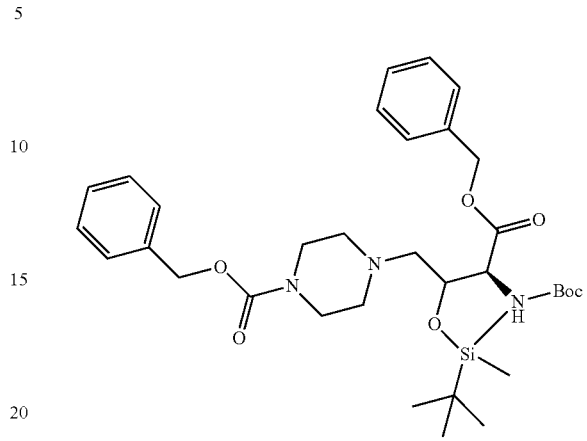

To benzyl 4-((3S)-4-(benzyloxy)-3-((tert-butoxycarbonyl)amino)-2-hydroxy-4-oxobutyl)piperazine-1-carboxylate (0.9 g, 1.7 mmol) in dry THF (10 mL) was added 2,6-lutidine (0.6 mL, 5.0 mmol) followed by tert-butyldimethylsilyl trifluoromethanesulfonate (0.9 g, 3.4 mmol) and the reaction mixture was stirred for 1 h and then diluted with water and extracted with IPAC. The organic layer was washed with brine, dried over sodium sulfate and was concentrated. The residue was purified by flash chromatography (silica gel, 0-5% MeOH/DCM) to obtain the title compound (0.53 g, 50%). LCMS (ESI): [M+H]=642.5; $^1$H NMR (400 MHz, DMSO-d$_6$) δ 7.49-7.27 (m, 10H), 6.49 (d, J=9.3 Hz, 1H), 5.17 (d, J=6.9 Hz, 2H), 5.11 (s, 2H), 4.43 (td, J=9.2, 3.2 Hz, 1H), 4.30-4.14 (m, 1H), 3.48-3.38 (m, 4H), 2.50-2.27 (m, 6H), 1.42 (s, 9H), 0.84 (d, J=1.2 Hz, 9H), 0.13-0.05 (m, 6H).

Step 5. (2S)-2-Amino-4-(4-((benzyloxy)carbonyl)piperazin-1-yl)-3-((tert-butyldimethylsilyl)oxy)butanoic acid

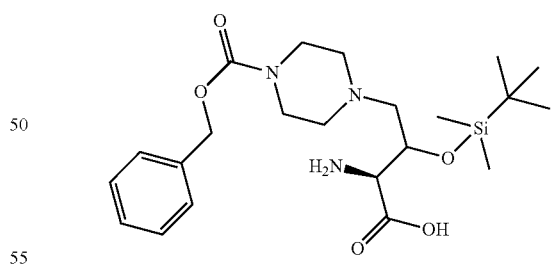

Benzyl 4-[(3S)-4-benzyloxy-3-(tert-butoxycarbonylamino)-2-[tert-butyl(dimethyl)silyl]oxy-4-oxo-butyl]piperazine-1-carboxylate (0.5 g, 0.78 mmol) was dissolved in THF:methanol (4 mL; 3:1) and LiOH (1 N, 2 equiv.) was added and the mixture stirred for 1 h. The reaction mixture was acidified with a minimal amount of aqueous citric acid and extracted with IPAC. The organic layer was dried over sodium sulfate and concentrated. The residue was dissolved in DCM (2 mL) and HCl (4 mL, 4N in dioxane) was added and the reaction mixture stirred for 1 h. The reaction mixture was concentrated and used as is in the next step.

Step 6. (2S)-2-((((9H-fluoren-9-yl)methoxy)carbonyl)amino)-4-(4-((benzyloxy)carbonyl)piperazin-1-yl)-3-((tert-butyldimethylsilyl)oxy)butanoic acid (2S)-2-Amino-4-(4-((benzyloxy)carbonyl)piperazin-1-yl)-3-((tert-butyldimethylsilyl)oxy)butanoic acid (used directly from Step 5) was dissolved in dioxane:water (5 mL, 1:1) and sodium bicarbonate (0.2 g, 2.3 mmol) and Fmoc-OSu (0.32 g, 0.93 mmol) were added. The mixture was stirred overnight, acidified with citric acid and extracted with IPAC. The organic layer washed with brine, dried over sodium sulfate and concentrated. The residue was purified by flash chromatography (0-10% MeOH/DCM) to obtain 0.38 g of the title compound. LCMS (ESI): [M+H]$^+$=674.5.

Intermediate 10. Fmoc-allothreonine(Bzl)-OH

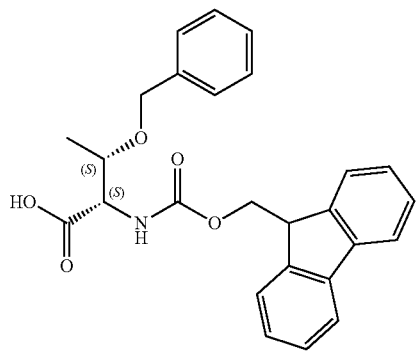

Step 1.
O-Benzyl-N-(tert-butoxycarbonyl)-L-allothreonine

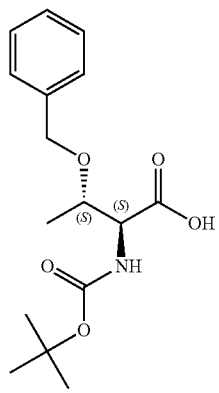

Into a 2000 mL 3-necked round-bottom flask purged and maintained with an inert atmosphere of nitrogen, was placed (2S,3S)-2-amino-3-hydroxybutanoic acid (85 g, 714 mmol), methanol (450 mL), water (450 mL), and sodium bicarbonate (150 g, 1.79 mol). This was followed by the addition of Boc$_2$O (187 g, 856.82 mmol, 1.20 equiv), in portions at 0° C. over 60 min. The resulting solution was stirred for 12 h at 25° C. The resulting mixture was concentrated under reduced pressure. The resulting solution was diluted with 500 mL of water. The resulting solution was extracted with 3×500 mL of ether and the aqueous layers combined. The pH value of the aqueous was adjusted to 3 with hydrogen chloride (1 mol/L). The resulting solution was extracted with 3×500 mL of ethyl acetate and the organic layers combined and dried over anhydrous sodium sulfate and concentrated under reduced pressure. This resulted in 110 g (67%) of (2S,3S)-2-[[(tert-butoxy)carbonyl]amino]-3-hydroxybutanoic acid Into a 2000 mL 3-necked round-bottom flask purged and maintained with an inert atmosphere of nitrogen, was placed (2S,3S)-2-[[(tert-butoxy)carbonyl]amino]-3-hydroxybutanoic acid (110 g, 501.74 mmol) and DMF (1100 mL). This was followed by the addition of sodium hydride (84.4 g, 3.52 mol), in portions at 0° C. over 60 min. The resulting solution was stirred for 2 h at 0° C. To this was added benzyl bromide (85.4 g, 499.33 mmol) dropwise with stirring at 0° C. over 30 min. The resulting solution was stirred for 5 h at 0° C. The reaction was then quenched by the addition of 1000 mL of water/ice. The resulting solution was extracted with 3×2000 mL of ethyl acetate and the aqueous layers combined. The pH value of the solution was adjusted to 3 with aqueous hydrogen chloride (1 mol/L). The resulting solution was extracted with 3×2000 mL of ethyl acetate and the organic layers combined and dried over anhydrous sodium sulfate and concentrated under vacuum. The crude product was re-crystallized from petroleum ether:ethyl acetate in the ratio of 10:1. This resulted in 60 g (37%) of the title compound.

Step 2. Fmoc-allothreonine(Bzl)-OH

Into a 2000 mL 3-necked round-bottom flask, was placed O-benzyl-N-(tert-butoxycarbonyl)-L-allothreonine (60 g, 193.95 mmol), dioxane (600 mL), hydrogen chloride (4N solution in dioxane, 600 mL). The resulting solution was stirred for 12 h at 25° C. The resulting mixture was concentrated under vacuum. This resulted in 50 g (crude) O-benzyl-L-allothreonine hydrochloride as a white solid.

Into a 2000 mL 3-necked round-bottom flask purged and maintained with an inert atmosphere of nitrogen, was placed O-benzyl-L-allothreonine hydrochloride (50 g, 203.50 mmol), dioxane (500 mL), water (500 mL), sodium carbonate (43.3 g, 408.53 mmol), and FmocONSu (69 g, 1.00 equiv). The resulting solution was stirred for 12 h at 25° C. The pH value of the solution was adjusted to 3 with hydrogen chloride (1 mol/L). The resulting solution was extracted with 3×500 mL of ethyl acetate and the organic layers combined and concentrated under vacuum. The residue was purified via silica gel chromatography with ethyl acetate/petroleum ether (1:1). This resulted in 53.4 g (58% yield over two steps) of the title compound as a white solid. LCMS (ESI): [M+H]$^+$=432; $^1$H NMR (300 MHz, CDCl$_3$) δ 12.85 (1H, s), 7.88-7.90 (2H, m), 7.74-7.77 (2H, m), 7.64-7.67 (1H, m), 7.41-7.44 (2H, m), 7.22-7.39 (7H, m), 4.46-4.50 (2H, m), 4.34-4.38 (1H, m), 4.20-4.30 (3H, m), 3.89-3.93 (1H, m), 1.16 (3H, s).

Intermediate 11. N-(((9H-Fluoren-9-yl)methoxy)carbonyl)-O-(4-(((tert-butoxycarbonyl)amino)methyl)-2-methylphenyl)-L-serine

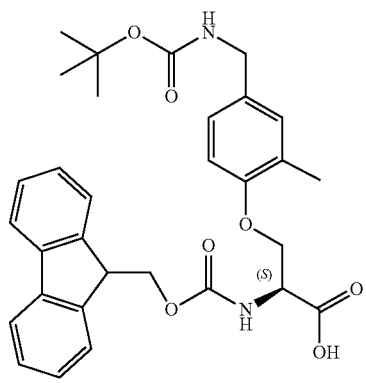

Step 1. tert-Butyl N-[(4-bromo-3-methyl-phenyl)methyl]carbamate

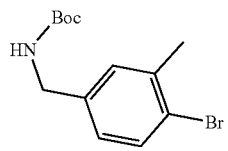

To a solution of (4-bromo-3-methyl-phenyl)methanamine (5.00 g, 25.0 mmol) and DIPEA (6.48 g, 50.14 mmol) in DCM (100 mL) was added dropwise a solution of Boc$_2$O (8.22 g, 37.7 mmol) in 10 mL of DCM. The resulting solution was stirred at room temperature for 4 h and then concentrated under vacuum. The residue was purified by flash chromatography on silica gel eluting with PE/EA (5% of EA) to afford the title compound (6.04 g, 80.5% yield) as a light-yellow solid. $^1$H NMR (400 MHz, DMSO-d$_6$): δ 7.36-7.33 (m, 3H), 7.11 (d, J=8.0 Hz, 1H), 4.05 (d, J=6.0 Hz, 2H), 2.25 (s, 3H), 1.39 (s, 9H).

Step 2. tert-Butyl N-[[4-[(2S)-2-(benzyloxycarbonylamino)-3-[methoxy(methyl)amino]-3-oxo-propoxy]-3-methyl-phenyl]methyl]carbamate

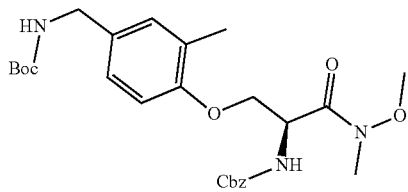 [SMILES: CON(C)C(=O)[C@H](COc1ccc(CNC(=O)OC(C)(C)C)cc1C)NC(=O)OCc1ccccc1]

To a solution of tert-butyl N-[(4-bromo-3-methyl-phenyl)methyl]carbamate (1.00 g, 3.33 mmol) in toluene (15 mL) was added benzyl A-[(1S)-1-(hydroxymethyl)-2-[methoxy(methyl)amino]-2-oxo-ethyl]carbamate (943 mg, 3.34 mmol), [Pd(allyl)Cl]$_2$ (61.0 mg, 0.167 mmol), t-BuBrett-Phos (162 mg, 0.334 mmol), and Cs$_2$CO$_3$ (2.18 g, 6.65 mmol) under nitrogen. The reaction was stirred at 60° C. for 5 hours with microwave irradiation. The reaction was repeated at the same scale in parallel. The two runs were combined and concentrated under vacuum. The residue was purified by flash chromatography on silica gel eluting with PE/EA (35% of EA) to afford the title compound (895 mg, 26.7% yield) as a light-yellow oil. LCMS (ESI): [M+Na]$^+$=524.2.

Step 3. tert-Butyl N-[[4-[(2S)-2-amino-3-[methoxy(methyl)amino]-3-oxo-propoxy]-3-methyl-phenyl]methyl]carbamate

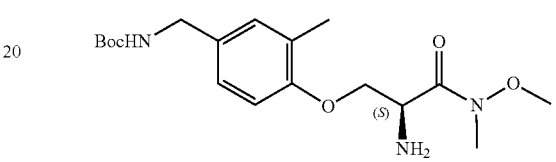

A mixture of tert-butyl N-[[4-[(2S)-2-(benzyloxycarbonylamino)-3-[methoxy(methyl)amino]-3-oxo-propoxy]-3-methyl-phenyl]methyl]carbamate (950 mg, 1.89 mmol) and 10% Pd/C (500 mg) in ethyl acetate (190 mL) was stirred under an atmosphere of hydrogen for 45 min at room temperature. The catalyst was filtered off and the filtrate was concentrated under vacuum to afford the title compound (668 mg, 96% yield) as a yellow oil. LCMS (ESI): [M+H]$^+$=368.2.

Step 4. N-(((9H-Fluoren-9-yl)methoxy)carbonyl)-O-(4-(((tert-butoxycarbonyl)amino)methyl)-2-methylphenyl)-L-serine A solution of LiOH (173 mg, 7.21 mmol) in water (5.0 mL) was added to a solution of tert-butyl N-[[4-[(2S)-2-amino-3-[methoxy(methyl)amino]-3-oxo-propoxy]-3-methyl-phenyl]methyl]carbamate (662.0 mg, 1.8 mmol) in THF (21 mL) and H$_2$O (7.0 mL) at 0° C. The reaction mixture was stirred overnight at room temperature and cooled to 0° C. Then fluorenylmethyloxycarbonyl chloride (930 mg, 3.6 mmol) (dissolved in 5 mL of THF) was added dropwise at 0° C. The reaction mixture was stirred at room temperature for 1 h. The majority of THF was stripped off under vacuum. The residual solution was diluted with water (3.0 mL) and adjusted to pH 6 with 1M HCl. The resulting solution was concentrated under vacuum and the residue was purified by flash chromatography on silica gel eluting with DCM/MeOH (10/1) to afford the title compound (648 mg, 65.8% yield) as a white solid. LCMS (ESI): [M+1]$^+$=547.3. $^1$H NMR (400 MHZ, DMSO-d$_6$): δ 7.92 (d, J=IB Hz, 2H), 7.85 (d, J=8.0 Hz, 2H), 7.85 (d, J=IB Hz, 1H), 7.69-7.64 (m, 2H), 7.45-7.40 (m, 2H), 7.36 (d, J=7.2 Hz, 1H), 7.32 (dd, J=7.2, 3.2 Hz, 1H), 6.75-6.71 (m, 2H), 4.43-4.40 (m, 1H), 4.39-4.21 (m, 4H), 4.43-4.40 (m, 3H), 2.24 (s, 3H), 1.39 (s, 9H).

181

Intermediate 12. (2S)-4-[3-(Benzyloxycarbonylamino)propoxy]-2-(9H-fluoren-9-ylmethoxycarbonylamino)butanoic acid

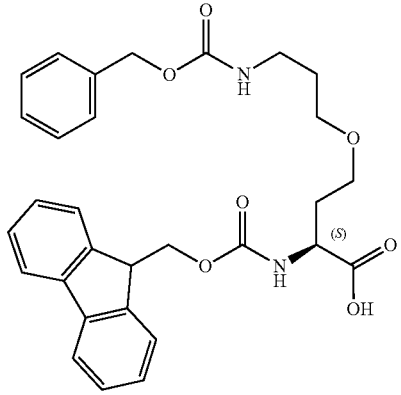

Step 1. (2S)-4-Allyloxy-2-(tert-butoxycarbonylamino)butanoic acid

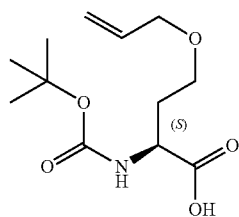

To a suspension of sodium hydride (228 mg, 60% dispersion in mineral oil, 5.70 mmol) in DMF (20 mL) was added dropwise a solution of Boc-L-homoserine (500 mg, 2.28 mmol) in DMF (5 mL) with stirring at 0° C. Upon the completion of adding Boc-L-homoserine, the reaction mixture was stirred for an additional 10 min at 0-10° C. under nitrogen. To this solution was added allyl bromide (304 mg, 2.51 mmol) in 5.0 mL of DMF. The reaction mixture was stirred at room temperature for 2 hours and concentrated under vacuum. Water (10 mL) was added and the mixture was acidified to pH ~5 with HCl (1M) and extracted with ethyl acetate (3×20 mL). The organic layers were combined, dried over anhydrous sodium sulfate and concentrated under vacuum. The residue was purified by flash chromatography on silica gel eluting with 30% ethyl acetate in petroleum ether to afford the title compound (350 mg, 59.2% yield) as a colorless oil. LCMS (ESI): [M+H-Boc]$^+$=533.2; $^1$H NMR (300 MHz, DMSO-d$_6$): δ 12.47 (s, 1H), 7.06 (d, J=8.1 Hz, 1H), 5.94-5.80 (m, 1H), 5.29-5.10 (m, 2H), 4.07-3.90 (m, 3H), 3.40 (dd, J=7.2, 5.1 Hz, 2H), 1.97-1.88 (m, 1H), 1.80-1.69 (m, 1H), 1.41 (s, 9H).

Step 2. Methyl (2S)-4-allyloxy-2-(tert-butoxycarbonylamino)butanoate

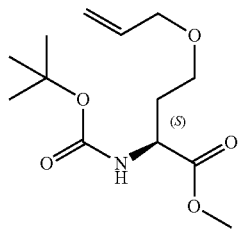

(2S)-4-allyloxy-2-(tert-butoxycarbonylamino)butanoic acid (3.50 g, 13.5 mmol) was treated with trimethylsilyl diazomethane (13.5 mL, 2.0 M in hexane, 27.0 mmol) in DCM (60 mL) and MeOH (30 mL) at 0° C. The reaction mixture was stirred at room temperature for 30 min and then concentrated under reduced pressure. The residue was purified by flash chromatography on silica gel eluting with PE/EA 2/1 to afford the title compound (3.65 g, 13.4 mmol, 99% yield) as a colorless oil. $^1$H NMR (300 MHz, DMSO-d$_6$). δ 7.23 (d, J=7.8 Hz, 1H), 5.91-5.78 (m, 1H), 5.26-5.09 (m, 2H), 4.12-4.06 (m, 1H), 3.91-3.86 (m, 2H), 3.62 (s, 3H), 3.40 (dd, J=6.9, 5.1 Hz, 2H), 1.96-1.85 (m, 1H), 1.83-1.71 (m, 1H), 1.38 (s, 9H).

Step 3. Methyl (2)-2-(tert-butoxycarbonylamino)-4-(3-hydroxypropoxy)butanoate

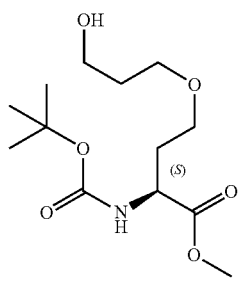

To a solution of methyl (2S)-4-allyloxy-2-(tert-butoxycarbonylamino)butanoate (4.03 g, 14.7 mmol) in THF (10 mL) was added dropwise a solution of 1 M BH$_3$·THF in THF (12.5 mL, 12.5 mmol) at 0° C. under nitrogen. The reaction mixture was stirred at room temperature for 2 h. Water (0.5 mL) was added at 0° C., followed by 3 N NaOH (2.5 mL, 7.5 mmol) and 30% H$_2$O$_2$ (10 mL). The reaction mixture was stirred at room temperature for 2 h. 50 mL of water was added, and a small amount of Na$_2$SO$_3$ added to consume excess H$_2$O$_2$. EtOAc (100 mL) was added and the phases were separated. The aqueous phase was extracted with EtOAc (2×), the organic phases were combined, dried with Na$_2$SO$_4$, filtered and concentrated under reduced pressure. The residue was purified by flash chromatography on silica gel eluting with PE/EA (1/1) to afford the title compound (1.77 g, 6.09 mmol, 41.3% yield) as a colorless oil. $^1$H NMR (400 MHz, DMSO-d$_6$): δ 7.21 (d, J=7.6 Hz, 1H), 4.37 (br, 1H), 4.09-4.00 (m, 1H), 3.62 (s, 3H), 3.44-3.32 (m, 6H), 1.89-1.85 (m, 1H), 1.78-1.71 (m, 1H), 1.65-1.58 (m, 2H), 1.38 (s, 9H).

Step 4. (S)-Methyl 4-(3-(((benzyloxy)carbonyl) amino)propoxy)-2-((tert-butoxycarbonyl)amino) butanoate

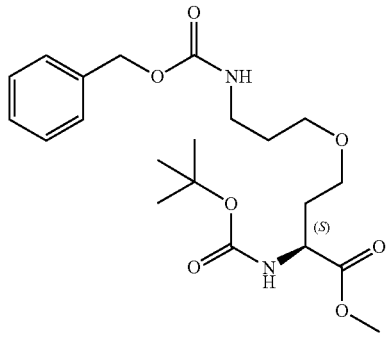

Methanesulfonyl chloride (1.19 g, 10.4 mmol) was added to a solution of methyl (2S)-2-(tert-butoxycarbonylamino)-4-(3-hydroxypropoxy)butanoate (2.01 g, 6.91 mmol) and triethylamine (2.09 g, 20.7 mmol) in DCM (40 mL) at 0° C. The reaction mixture was stirred at room temperature for 2 hours. Water (50 mL) was added and the phases were separated. The aqueous phase was extracted with DCM (2×), the organic phases were combined, dried with $Na_2SO_4$ and concentrated under vacuum.

The resulting residue was dissolved in DMF (40 mL) and treated with sodium azide (2.34 g, 36.0 mmol) at 0° C. The reaction mixture was stirred overnight at room temperature. Water (30 mL) was added and the resulting mixture was extracted with ethyl acetate (3×), the combined extracts were washed with brine, and dried with $Na_2SO_4$, filtered and concentrated under vacuum.

The resulting residue was dissolved in ethyl acetate (40 mL), and to this mixture was added 10% Pd/C (500 mg). The mixture was stirred under an atmosphere of hydrogen at room temperature for 2 h. The catalyst was filtered off and the filtrate was concentrated under reduced pressure.

The resulting residue was combined with triethylamine (2.1 g, 20.8 mmol) in DCM (40 mL), and to this mixture was added Cbz-Cl (1.77 g, 10.4 mmol) at 0° C. The reaction was stirred at room temperature for 2 h and then concentrated under vacuum. The residue was purified by flash chromatography on silica gel eluting with PE/EA (1/1) to afford the title compound (1.02 g, over four steps for 34.7% yield) as a colorless oil. LCMS (ESI): [M+H]$^+$=425.4. $^1$H NMR (300 MHz, DMSO-$d_6$): δ 7.39-7.27 (m, 5H), 7.25-7.21 (m, 2H), 5.00 (s, 2H), 4.11-4.01 (m, 1H), 3.62 (s, 3H), 3.44-3.26 (m, 4H), 3.07-3.00 (m, 2H), 1.94-1.84 (m, 1H), 1.81-1.71 (m, 1H), 1.65-1.58 (m, 2H), 1.38 (s, 9H).

Step 5. (2S)-4-[3-(Benzyloxycarbonylamino) propoxy]-2-(9H-fluoren-9-ylmethoxycarbonylamino)butanoic acid A solution of HCl/dioxane (20 mL, 80 mmol, 4 M) was added to a solution of methyl (2S)-4-[3-(benzyloxycarbonylamino)propoxy]-2-(tert-butoxycarbonylamino)butanoate (950 mg, 2.24 mmol) in DCM (20 mL) at 0° C. The reaction was stirred at room temperature for 2 h and then concentrated under reduced pressure. THF (60 mL) was added, and then a solution of LiOH (163 mg, 6.78 mmol) in water (20 mL) was added at 0° C. The resulting mixture was stirred at room temperature for 1 h, and then fluorenylmethyloxycarbonyl chloride (693 mg, 2.68 mmol) in 10 mL of THF was added at 0° C. The reaction mixture was stirred at room temperature for 1 h and acidified to pH ~5 with 1 N HCl. Ethyl acetate (100 mL) was added and the phases were separated. The aqueous phase was extracted with ethyl acetate (2×). The organic phases were combined, washed with brine, dried over $Na_2SO_4$ and concentrated under reduced pressure. The residue was purified by flash chromatography on silica gel eluting with [DCM]/[MeOH] (10/1) to afford the title compound (660 mg, 55.4% yield) as a white solid. LCMS (ESI): [M+H]$^+$=533.2; $^1$H NMR (300 MHz, DMSO-$d_6$): δ 12.59 (s, 1H), 7.89 (d, J=7.5 Hz, 2H), 7.89 (d, J=7.5 Hz, 2H), 7.62 (d, J=8.4 Hz, 1H), 7.44-7.37 (m, 2H), 7.34-7.21 (m, 8H), 4.99 (s, 2H), 4.30-4.19 (m, 3H), 4.09-4.02 (m, 1H), 3.41-3.31 (m, 4H), 3.07-3.01 (m, 2H), 1.96-1.88 (m, 1H), 1.81-1.73 (m, 1H), 1.66-1.57 (m, 2H).

Intermediate 13. (S)-2-((((9H-Fluoren-9-yl) methoxy)carbonyl)amino)-2-cycloheptylacetic acid

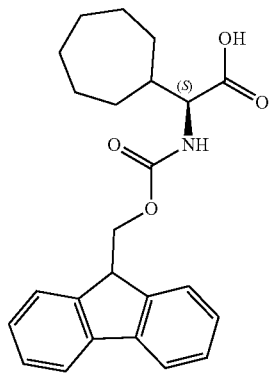

To a solution of (2S)-2-amino-2-cycloheptyl-acetic acid (1.0 g, 5.84 mmol) in DMF (25 mL) and water (25 mL) was added $NaHCO_3$ (982.0 mg, 11.69 mmol). A solution of 9-fluorenylmethylchloroformate (1.8 g, 6.98 mmol) in THF (5 mL) was added dropwise at 0° C. The reaction mixture was allowed to warm to room temperature and stirred at 25° C. for 24 h. Aqueous HCl (1 mol/L) was carefully added until pH ~6. The resulting solution was extracted with ethyl acetate (3×100 mL). The organic layers were combined and washed with water (5×), dried over sodium sulfate and concentrated under reduced pressure. The residue was purified by flash chromatography on silica gel eluting with DCM/MeOH (10/1) to afford the title compound (1.77 g, 77% yield) as a white solid. LCMS (ESI): [M+H]$^+$=394.2. $^1$H NMR (400 MHz, DMSO-$d_6$) 12.58 (s, 1H), 7.89 (d, J=7.6 Hz, 2H), 7.76 (d, J=7.6 Hz, 2H), 7.59 (d, J=8.8 Hz, 1H), 7.44-7.40 (m, 2H), 7.35-7.30 (m, 2H), 4.31-3.93 (m, 4H), 1.95-1.33 (m, 13H).

Intermediate 14. (2R,3R)-3-((R)-2-((((9H-Fluoren-9-yl)methoxy)carbonyl)amino)propoxy)-2-(but-3-en-1-yl)non-8-enoic acid

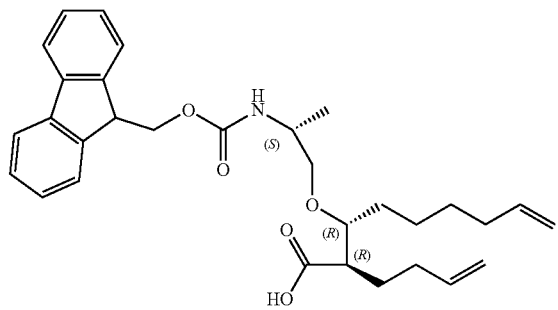

The title compound was prepared following methods analogous to those described for Intermediate 3. LCMS (ESI): [M+1]+=506.3.

Intermediate 15. O-Benzyl-N—((S)-3-(((benzyloxy)carbonyl)amino)-2-((S)-2-cyclohexyl-2-((S)-4-methyl-2-(methylamino)pentanamido)acetamido)propanoyl)-L-allothreonine-(2-chlorotrityl resin)

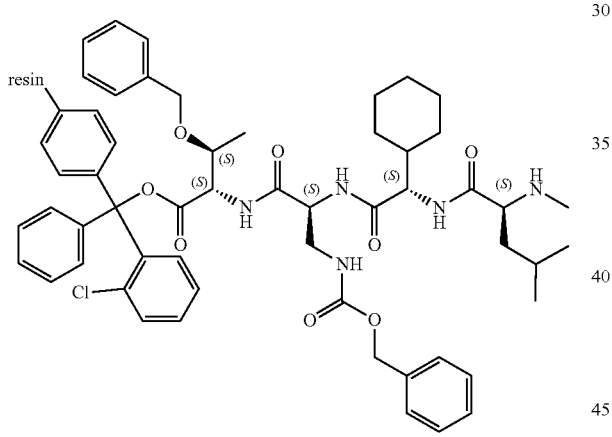

2-Chlorotrityl chloride resin (loading 0.956 mmol/g, 5 g) was swelled with the mixture of DMF:DCM (1:1, 20 mL) for 40 min. The resin was drained and then a solution of (2S,3S)-3-benzyloxy-2-(9H-fluoren-9-ylmethoxycarbonylamino)butanoic acid (Intermediate 10) (2.461 g, 5.70 mmol), DMF (10 mL) and DIPEA (495.6 mg, 3.84 mmol) was added. The resin was agitated with nitrogen bubbling for 4 h, drained, and rinsed sequentially with 10 mL DCM/MeOH/DIPEA (10/10/1=V/V/V). 10 mL DMF, 10 mL DCM, 10 mL DMF.

The resin was treated with 25 mL of 20% piperidine in DMF, and agitated with nitrogen bubbling for 1.5 h. The resin was drained and rinsed sequentially with DMF (3×25 mL) and DCM (3×25 mL). The resin was treated with a solution of (2S)-3-(benzyloxycarbonylamino)-2-(9H-fluoren-9-ylmethoxycarbonylamino)propanoic acid (4.372 g, 9.494 mmol), a pre-prepared stock solution of HOBt/HATU (1:1) in DMF (0.4 mmol/mF, 25 mL) and DIPEA (2.4 g, 19 mmol). The resin was agitated with nitrogen bubbling for 2.5 h, drained and rinsed sequentially with 10 mL DMF, 10 mL DCM, 10 mL DMF. The resin was treated with 25 mL of 20% piperidine in DMF, and agitated with nitrogen bubbling for 1.5 h. The resin was drained and rinsed sequentially with DMF (3×25 mL) and DCM (3×25 mL). The resin was treated with a solution of (S)-2-((((9H-fluoren-9-yl)methoxy)carbonyl)amino)-2-cyclohexylacetic acid (3.61 g, 9.52 mmol), a pre-prepared stock solution of HOBt/HATU (1:1) in DMF (0.4 mmol/mF, 25 mL) and DIPEA (2.4 g, 19 mmol). The resin was agitated with nitrogen bubbling for 2.5 h, drained, and rinsed sequentially with 10 mL DMF, 10 mL DCM, 10 mL DMF. The resin was treated with 25 mL of 20% piperidine in DMF, and agitated with nitrogen bubbling for 1.5 h. The resin was drained and rinsed sequentially with DMF (3×25 mL) and DCM (3×25 mL). The resin was treated with a solution of (2S)-2-{[(9H-fluoren-9-ylmethoxy)carbonyl](methyl)amino}-4-methylpentanoic acid (3.492 g, 9.50 mmol), a pre-prepared stock solution of HOBt/HATU (1:1) in DMF (0.4 mmol/mF, 25 mL) and DIPEA (2.4 g, 19 mmol). The resin was agitated with nitrogen bubbling for 2.5 h, drained and rinsed sequentially with 10 mL DMF, 10 mL DCM, 10 mL DMF. The resin was treated with 25 mL of 20% piperidine in DMF, and agitated with nitrogen bubbling for 1.5 h. The resin was drained and rinsed with DMF (3×25 mL) and DCM (3×25 mL) to afford a resin-bound tetrapeptide with a loading of 0.44 mmol/g.

Intermediate T1 (Method A). (A)-2-((2-((tert-Butoxycarbonyl)amino)ethyl)(butyl)amino)hexanoic acid

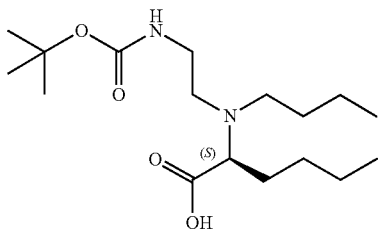

Step 1. Methyl (2S)-2-[2-(tert-butoxycarbonylamino)ethylamino]hexanoate

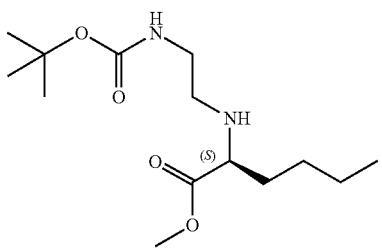

A solution of methyl (2S)-2-aminohexanoate hydrochloride (8.02 g, 44.2 mmol) and tert-butyl N-(2-oxoethyl)carbamate (6.68 g, 42.0 mmol) and AcOH (2.65 g, 44.2 mmol) in ethyl acetate (300 mL) was stirred at room temperature for 2 h. Then sodium triacetoxyborohydride (14.1 g, 66.3 mmol) was added. The resulting reaction mixture was stirred overnight at room temperature, washed with water (2×) and brine. The organic phase was dried over anhydrous sodium sulfate and concentrated under vacuum. The residue was purified by flash chromatography on silica gel eluting with petroleum ether and ethyl acetate (1/1) to afford the title compound (7.82 g, 61.4% yield) as a yellow oil. LCMS (ESI): [M+H]$^+$=289.3.

Step 2. Methyl (2S)-2-[2-(tert-butoxycarbonylamino)ethyl-butyl-amino]hexanoate

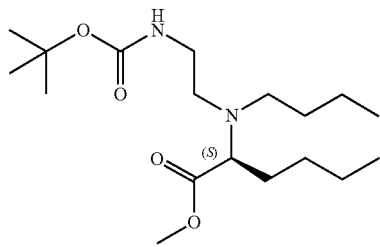

To a solution of methyl (2S)-2-[2-(tert-butoxycarbonylamino)ethylamino]hexanoate (7.81 g, 27.1 mmol) in ethyl acetate (300 mL) was added butyraldehyde (2.93 g, 40.6 mmol) and AcOH (1.63 g, 27.1 mmol). The reaction mixture was stirred at room temperature for 2 hours. Then sodium triacetoxyborohydride (8.62 g, 40.65 mmol) was added. The reaction mixture was stirred overnight at room temperature, washed with water and brine successively. The organic phase was dried and concentrated under vacuum. The residue was purified by flash chromatography on silica gel eluting with petroleum ether and ethyl acetate (5/1) to afford the title compound (2.32 g, 24.9% yield) as a yellow oil. LCMS (ESI): [M+H]$^+$=345.3.

Step 3. (2S)-2-[2-(tert-Butoxycarbonylamino)ethyl-butyl-amino]hexanoic acid

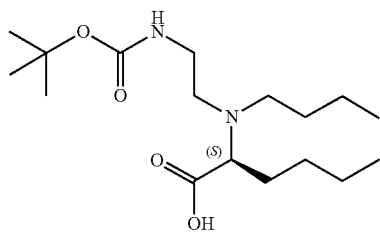

Lithium hydroxide (1.13 g, 47.0 mmol) was added to a solution of methyl (2S)-2-[2-(tert-butoxycarbonylamino)ethyl-butyl-amino]hexanoate (4.04 g, 11.7 mmol) in MeOH (100 mL) and water (30 mL) at room temperature. The reaction mixture was stirred overnight at room temperature and acidified with 1N HCl to pH ~4, and concentrated under reduced pressure. The residue was purified by flash chromatography on silica gel eluting with DCM and MeOH (5/1) to afford the title compound acid (2.56 g, 66.1% yield) as a yellow solid. LCMS (ESI): [M+H]$^+$=331.3; $^1$H NMR (300 MHz, DMSO-d$_6$): δ 12.11 (s, 1H), 6.74 (t, J=5.9 Hz, 1H), 3.40-3.38 (m, 1H), 3.03 (t, J=6.3 Hz, 2H), 2.82-2.80 (m, 1H), 2.69-2.66 (m, 3H), 1.65-1.60 (m, 2H), 1.46-1.30 (m, 17H), 0.90-0.85 (m, 6H).

Intermediate T2 (Method B). 2-((2-((tert-Butoxycarbonyl)amino)ethyl)(methyl)amino)octanoic acid

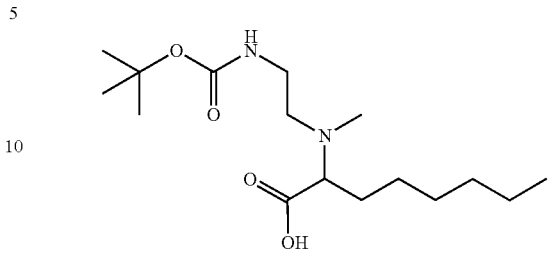

To a solution of tert-butyl (2-(methylamino)ethyl)carbamate (1.75 g, 10.0 mmol) and DIPEA (3.32 mL, 19.1 mmol) in CH$_3$CN (30 mL) was added 2-bromooctanoic acid (2.06 g, 9.22 mmol) at room temperature. The reaction mixture was stirred overnight at 60° C. and then concentrated under vacuum. The residue was purified by flash chromatography on silica gel eluting with MeOH/DCM (1/9) to afford the title compound (2.065 g, 70.8% yield) as a colorless oil. LCMS (ESI): [M+H]$^+$=317.3; $^1$H NMR (300 MHz, DMSO-d$_6$): δ 10.60 (s, 1H), 6.59 (t, J=5.7 Hz, 1H), 3.08-2.92 (m, 3H), 2.64-2.57 (m, 1H), 2.44-2.37 (m, 1H), 2.24 (s, 3H), 1.60-1.56 (m, 2H), 1.47 (s, 9H), 1.45-1.22 (m, 8H), 0.84 (t, J=6.3 Hz, 3H).

Intermediate T12 (Method C). (S)-2-((2-((((9H-Fluoren-9-yl)methoxy)carbonyl)amino)ethyl)(butyl)amino)hexanoic acid

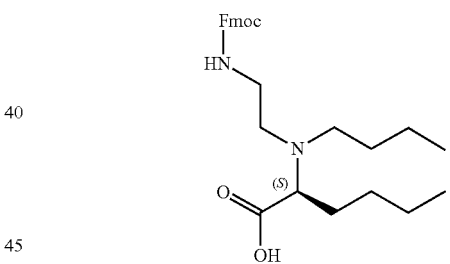

To a solution of (2S)-2-[2-(tert-butoxycarbonylamino)ethyl-butyl-amino]hexanoic acid (2.50 g, 7.57 mmol) in dioxane (10 mL) was added HCl/dioxane (4.0 M, 40 .mL) at room temperature. The reaction mixture was stirred at room temperature for 1 h and then concentrated under vacuum. The resulting residue was dissolved with water (10 mL) and THF (30 mL). Then LiOH (545 mg, 22.71 mmol) (dissolved in water) was added at 0° C. and then fluorenylmethyloxycarbonyl chloride (2.3 g, 8.91 mmol) (dissolved in THF) was added at this temperature. The reaction mixture was stirred at 25° C. for 1 h. THF was evaporated under vacuum. The residual aqueous solution was acidified to pH ~4-5 with 1M aqueous HCl and concentrated under vacuum. The residue was purified by flash chromatography on silica gel eluting with DCM/MeOH (10/1) to afford the title compound (3.15 g, 92% yield) as a white solid. LCMS (ESI): [M+H]$^+$=453.3; $^1$H NMR (400 MHz, DMSO-d$_6$): δ 12.09 (s, 1H), 7.88 (d, J=7.6 Hz, 2H), 7.68 (d, J=7.6 Hz, 2H), 7.43-7.41 (m, 2H), 7.34-7.30 (m, 2H), 7.19 (t, J=5.8 Hz, 1H), 4.34-4.18 (m, 3H), 3.07-3.02 (m, 1H), 3.00-2.95 (m, 2H), 2.79-2.72 (m, 1H), 2.60-2.55 (m, 3H), 1.65-1.60 (m, 1H), 1.59-1.53 (m, 1H), 1.45-1.15 (m, 8H), 0.88-0.82 (m, 6H).

Intermediate T13 (Method D). (S)-2-(((R)-2-((((9H-Fluoren-9-yl)methoxy)carbonyl)amino)propyl)(butyl)amino)hexanoic acid

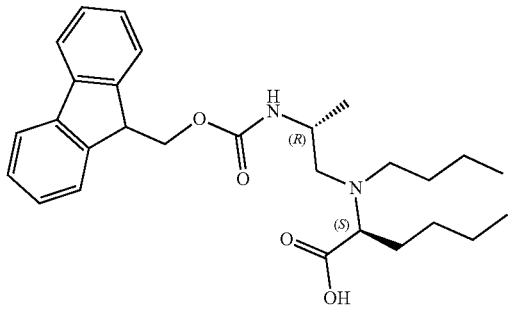

Step 1. Methyl (2S)-2-[[(2R)-2-(tert-butoxycarbonylamino)propyl]amino]hexanoate

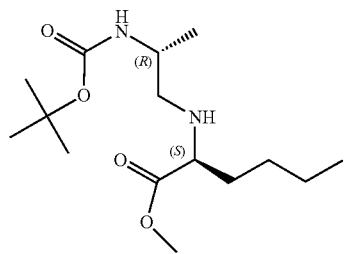

A solution of tert-butyl (4R)-4-methyl-2,2-dioxo-oxathiazolidine-3-carboxylate (16.5 g, 69.3 mmol) and methyl (2S)-2-aminohexanoate (40.3 g, 277 mmol) was stirred in CH$_3$CN (500 mL) at 60° C. for 5 h. The reaction mixture was allowed to cool to room temperature and concentrated under reduced pressure and the residue was purified by flash chromatography on silica gel eluting with petroleum ether and ethyl acetate (2/1) to afford the title compound (17.6 g, 83.7% yield) as a yellow oil. LCMS (ESI): [M+H]$^+$=303.3; $^1$H NMR (300 MHz, DMSO-d$_6$): δ 6.50 (d, J=8.4 Hz, 1H), 3.60 (s, 3H), 3.47-3.42 (m, 1H), 3.13-3.10 (m, 1H), 2.45-2.42 (m, 1H), 2.26-2.20 (m, 1H), 1.50-1.44 (m, 2H), 1.35 (s, 9H), 1.25-1.13 (m, 4H), 0.96 (d, J=6.6 Hz, 3H), 0.87-0.80 (m, 3H).

Step 2. Methyl (2S)-2-[[(2R)-2-(tert-butoxycarbonylamino)propyl]-butyl-amino]hexanoate

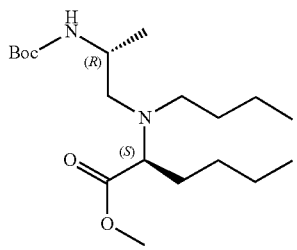

A solution of methyl (2S)-2-[[(2R)-2-(tert-butoxycarbonylamino)propyl]amino]hexanoate (17.6 g, 58.0 mmol) and butyraldehyde (8.36 g, 116 mmol) in DCM (200 mL) was stirred at room temperature for 2 h. Then sodium triacetoxyborohydride (25.0 g, 118 mmol) was added. The reaction mixture was stirred overnight at room temperature. Water (100 mL) was added and the phases were separated. The organic phase was dried over sodium sulfate and concentrated under vacuum. The residue was purified by flash chromatography on silica gel eluting with petroleum ether and ethyl acetate (5/1) to afford the title compound (20.1 g, 96.7% yield) as a yellow oil. LCMS (ESI): [M+H]$^+$=359.3.

Step 3. (2S)-2-[[(2R)-2-(tert-Butoxycarbonylamino)propyl]-butyl-amino]hexanoic acid

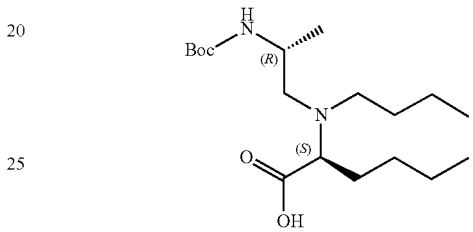

A solution of LiOH (5.44 g, 227 mmol) in water (100 mL) was added to a solution of methyl (2S)-2-[[(2R)-2-(tert-butoxycarbonylamino)propyl]-butyl-amino]hexanoate (20.3 g, 56.7 mmol) in MeOH (300 mL). The reaction mixture was stirred overnight at room temperature and acidified to pH ~5 with 1N HCl, and concentrated under vacuum. The residue was purified by flash chromatography on silica gel eluting with DCM and methanol (5/1) to afford the title compound (15.5 g, 79.2% yield) as a yellow solid. LCMS (ESI): [M+H]$^+$=345.3.

Step 4. (S)-2-(((R)-2-((((9H-Fluoren-9-yl)methoxy)carbonyl)amino)propyl)(butyl)amino)hexanoic acid A solution of 4 N HCl/dioxane (150 mL, 600 mmol) was added to a solution of (2S)-2-[[(2R)-2-(tert-butoxycarbonylamino)propyl]-butyl-amino]hexanoic acid (15.5 g, 44.9 mmol) in DCM (150 mL) at 0° C. The reaction mixture was stirred at room temperature for 2 h and concentrated under vacuum. The residue was dissolved in THF (150 mL) and a solution of LiOH (3.02 g, 125.71 mmol) in water (50 mL) was added at 0° C. Fluorenylmethyloxycarbonyl chloride (13.0 g, 50.3 mmol) dissolved 20 mL of THF was added at 0° C. The reaction mixture was stirred at room temperature for 1 h, then acidified to pH ~5 with 1N HCl. The majority of THF was evaporated under vacuum. The residual solution was extracted with ethyl acetate (2×5 0 mL) and the combined organic phases were dried with anhydrous sodium sulfate and concentrated under vacuum. The residue was purified by flash chromatography on silica gel eluting with DCM and methanol (5/1) to afford the title compound (16.5 g, 84.4% yield) as a yellow solid. LCMS (ESI): [M+H]$^+$=467.3; $^1$H NMR (300 MHz, DMSO-d$_6$): δ 12.08 (s, 1H), 7.88 (d, J=7.5 Hz, 2H), 7.67 (d, J=7.5 Hz, 2H), 7.43-7.40 (m, 2H), 7.33-7.28 (m, 2H), 7.16 (br, 1H), 4.30-4.17 (m, 3H), 3.76-3.71 (m, 2H), 2.88-2.65 (m, 4H), 1.68-1.64 (m, 2H), 1.58-1.50 (m, 2H), 1.28-1.21 (m, 6H), 1.05 (d, J=6.3 Hz, 3H), 0.86-0.80 (m, 6H).

Intermediate T14 (Method E). N—((R)-2-((((9H-fluoren-9-yl)methoxy)carbonyl)amino)propyl)-N-(hex-3-yn-1-yl)-L-alanine

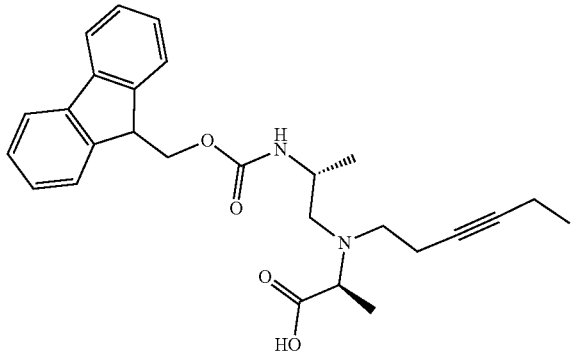 [SMILES: CCC#CCCN(C[C@@H](C)NC(=O)OCC1c2ccccc2-c2ccccc21)[C@@H](C)C(=O)O]

Step 1. Benzyl (2S)-2-[[(2R)-2-(tert-butoxycarbonylamino)propyl]amino]propanoate

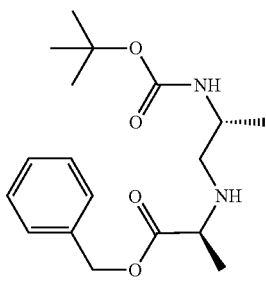 [SMILES: C[C@H](CN[C@@H](C)C(=O)OCc1ccccc1)NC(=O)OC(C)(C)C]

A mixture of benzyl (2S)-2-aminopropanoate (11.4 g, 63.7 mmol) and tert-butyl (4R)-4-methyl-2,2-dioxo-oxathiazolidine-3-carboxylate (5.04 g, 21.2 mmol) and benzyl (2S)-2-aminopropanoate (11.4 g, 63.7 mmol) was stirred in $CH_3CN$ (150 mL) overnight at 60° C. The reaction mixture was concentrated under vacuum and the residue was purified by flash chromatography on silica gel eluting with petroleum ether and ethyl acetate to afford the title compound (5.66 g, 79.2% yield) as a yellow oil. LCMS (ESI): $[M+H]^+$=337.2.

Step 2. Benzyl (2S)-2-[[(2R)-2-(tert-butoxycarbonylamino)propyl]-hex-3-ynyl-amino]propanoate

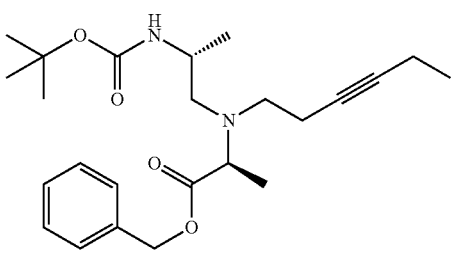 [SMILES: CCC#CCCN(C[C@@H](C)NC(=O)OC(C)(C)C)[C@@H](C)C(=O)OCc1ccccc1]

To a solution of $Tf_2O$ (34.5 g, 122 mmol) in DCM (100 mL) was added a mixture of 3-hexyn-1-ol (10.0 g, 102.1 mmol) and pyridine (12.1 g, 154 mmol) in DCM (60 mL) at 0° C. The reaction was stirred at this temperature for 30 min. Water (100 mL) was added and the phases were separated. The organic phase (containing of hex-3-ynyl trifluoromethanesulfonate) was dried with $Na_2SO_4$, and used directly for the next operation.

To a mixture of benzyl (2S)-2-[[(2R)-2-(tert-butoxycarbonylamino)propyl]amino]propanoate (3.10 g, 9.21 mmol) and pyridine (1.46 g, 18.4 mmol) in DCM (40 mL) was added the solution of hex-3-ynyl trifluoromethanesulfonate from previous operation at 0° C. The reaction was stirred at 0° C. for 4 h, allowed to rise to room temperature and stirred overnight at room temperature. The reaction mixture was concentrated under reduced pressure and the residue was purified by flash chromatography on silica gel eluting with petroleum ether and ethyl acetate (5/1) to afford the title compound (1.21 g, 31.7% yield) as a yellow solid. LCMS (ESI): $[M+H]^+$=417.4; $^1H$ NMR (300 MHz, DMSO-$d_6$): δ 7.38-7.30 (m, 5H), 6.43 (d, J=8.4 Hz, 1H), 5.10 (s, 2H), 3.58 (q, J=6.9 Hz, 1H), 3.48-3.42 (m, 1H), 2.65-2.62 (m, 2H), 2.49-2.38 (m, 2H), 2.18-2.06 (m, 4H), 1.36 (s, 9H), 1.18 (d, J=12 Hz, 3H), 1.04-0.94 (m, 6H).

Step 3. (2S)-2-[[(2R)-2-(tert-Butoxycarbonylamino)propyl]-hex-3-ynyl-amino]propanoic acid

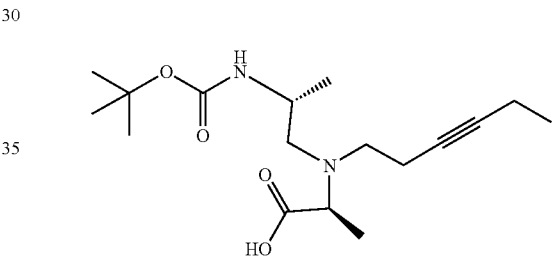

A solution of LiOH (476 mg, 19.8 mmol) in $H_2O$ (20 mL) was added to benzyl (2S)-2-[[(2R)-2-(tert-butoxycarbonylamino)propyl]-hex-3-ynyl-amino]propanoate (2.02 g, 4.85 mmol) in MeOH (60 mL) at 0° C. The reaction mixture was stirred overnight at room temperature and then acidified to pH~5 with 1M HCl at 0° C. The majority of MeOH was evaporated under vacuum. The remaining solution was extracted with ethyl acetate (3×50 mL). The organic layers were combined, dried with $Na_2SO_4$ and concentrated under reduced pressure. The residue was purified by flash chromatography on silica gel eluting with dichloromethane and methanol (5/1) to afford the title compound (681 mg, 43% yield) as a yellow oil. LCMS (ESI): $[M+H]^+$=327.4.

Step 4. N—((R)-2-((((9H-Fluoren-9-yl)methoxy)carbonyl)amino)propyl)-N-(hex-3-yn-1-yl)-L-alanine (2S)-2-[[(2R)-2-(tert-Butoxycarbonylamino)propyl]-(hex-3-ynyl-amino]propanoic acid (980 mg, 3.01 mmol) was treated with TFA (20 mL) in DCM (20 mL) at room temperature for 1 h. Then the reaction mixture was concentrated under reduced pressure. THF (30 mL) was added to the residue, and then a solution of LiOH (216 mg, 9.01 mmol) in $H_2O$ (10 mL) was added at 0° C. A solution of fluorenylmethyloxycarbonyl chloride (930 mg, 3.60 mmol) in THF (10 mL) was added at 0° C. The reaction mixture was stirred at room temperature for 1 h and acidified to pH ~5 with 1 M HCl. Ethyl acetate (50 mL) was added and the phases were separated. The aqueous phase was extracted with ethyl acetate (2×50 mL). The organic layers were combined, dried with $Na_2SO_4$ and concentrated under reduced pressure. The residue was purified by flash chromatography on silica gel eluting with DCM and methanol (5/1) to afford the title compound (1.12 g, 83.4% yield) as a white solid. LCMS (ESI): $[M+H]^+$=449.2; $^1$H NMR (300 MHz, DMSO-$d_6$): δ 7.89 (d, J=7.5 Hz, 2H), 7.68 (d, J=7.5 Hz, 2H), 7.44-7.39 (m, 2H), 7.35-7.30 (m, 2H), 7.14 (br, 1H), 4.29-4.21 (m, 3H), 3.62-3.45 (m, 2H), 2.80-2.63 (m, 3H), 2.32-2.21 (m, 3H), 2.13-2.06 (m, 2H), 1.20 (J=6.9 Hz, 3H), 1.06-0.98 (m, 6H).

TABLE 3

The intermediates described in Table 3 were prepared following procedures analogous to those described by the above synthetic methods A through D.

| Intermediate Number | Structure | Chemical name | LCMS (ESI) $[M + H]^+$ | Synthetic method |
|---|---|---|---|---|
| T3 | 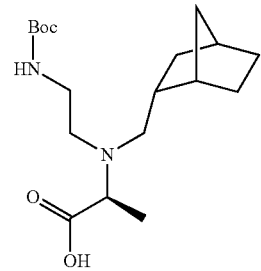 [SMILES: C[C@@H](C(=O)O)N(CCNC(=O)OC(C)(C)C)CC1CC2CCC1C2] | N-(((1S,2R,4R)-bicyclo[2.2.1]heptan-2-yl)methyl)-N-(2-((tert-butoxycarbonyl)amino)ethyl)-L-alanine | 341.3 | Method A |
| T4 | 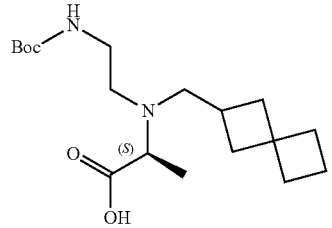 | N-(2-((tert-butoxycarbonyl)amino)ethyl)-N-(spiro[3.3]heptan-2-ylmethyl)-L-alanine | 341.3 | Method A |
| T5 | 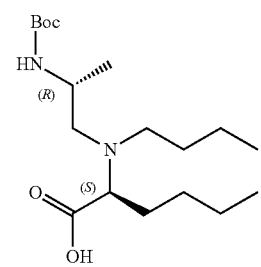 | (S)-2-(((R)-2-((tert-butoxycarbonyl)amino)propyl)(butyl)amino)hexanoic acid | 345.3 | Method A |
| T6 | 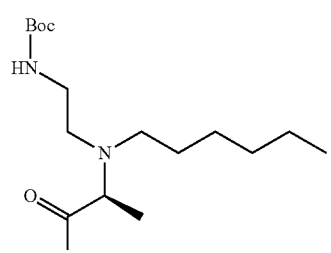 | N-(2-((tert-butoxycarbonyl)amino)ethyl)-N-hexyl-L-alanine | 317.2 | Method A |

TABLE 3-continued

The intermediates described in Table 3 were prepared following procedures analogous to those described by the above synthetic methods A through D.

| Intermediate Number | Structure | Chemical name | LCMS (ESI) [M + H]+ | Synthetic method |
|---|---|---|---|---|
| T7 | 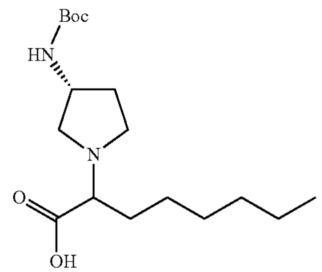 [SMILES: CCCCCCC(C(=O)O)N1CC[C@@H](NC(=O)OC(C)(C)C)C1] | 2-((R)-3-((tert-butoxycarbonyl)amino)pyrrolidin-1-yl)octanoic acid | 329.3 | Method B |
| T8 | 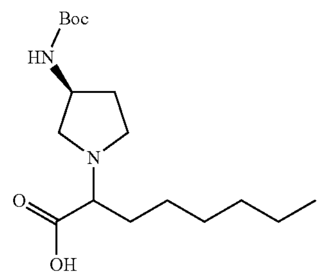 [SMILES: CCCCCCC(C(=O)O)N1CC[C@H](NC(=O)OC(C)(C)C)C1] | 2-((S)-2-((tert-butoxycarbonyl)amino)pyrrolidin-1-yl)octanoic acid | 329.3 | Method B |
| T9 | 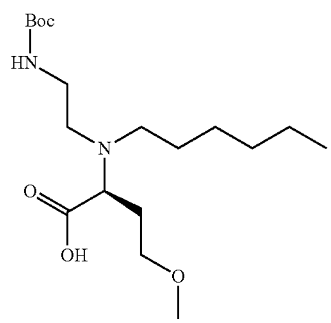 [SMILES: CCCCCCN(CCNC(=O)OC(C)(C)C)[C@@H](CCOC)C(=O)O] | N-(2-((tert-butoxycarbonyl)amino)ethyl)-N-hexyl-O-methyl-L-homoserine | 361.3 | Method A |
| T10 | 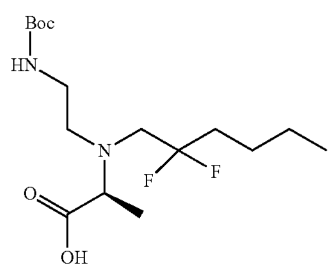 [SMILES: CCCCC(F)(F)CN(CCNC(=O)OC(C)(C)C)[C@@H](C)C(=O)O] | N-(2-((tert-butoxycarbonyl)amino)ethyl)-N-(2,2-difluorohexyl)-L-alanine | 353.2 | Method A |
| T11 | 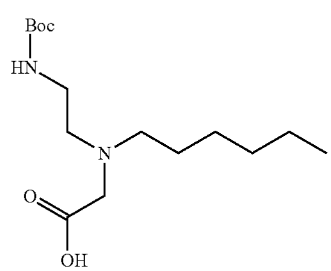 [SMILES: CCCCCCN(CCNC(=O)OC(C)(C)C)CC(=O)O] | N-(2-((tert-butoxycarbonyl)amino)ethyl)-N-hexylglycine | 303.2 | Method A |

TABLE 3-continued

The intermediates described in Table 3 were prepared following procedures analogous to those described by the above synthetic methods A through D.

| Intermediate Number | Structure | Chemical name | LCMS (ESI) [M + H]+ | Synthetic method |
|---|---|---|---|---|
| T15 | 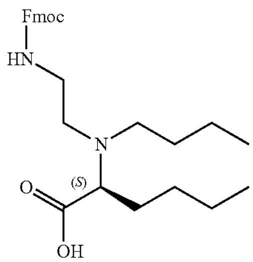 | (S)-2-((2-((((9H-fluoren-9-yl)methoxy)carbonyl)amino)ethyl)(butyl)amino)hexanoic acid | 453.3 | Method A and C |
| T16 | 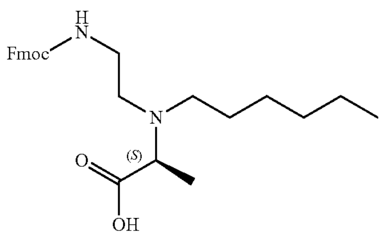 | N-(2-((((9H-fluoren-9-yl)methoxy)carbonyl)amino)ethyl)-N-hexyl-L-alanine | 439.3 | Method A and C |
| T17 | 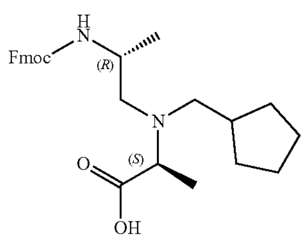 | N-((R)-2-((((9H-fluoren-9-yl)methoxy)carbonyl)amino)propyl)-N-(cyclopentylmethyl)-L-alanine | 451.3 | Method D |
| T18 | 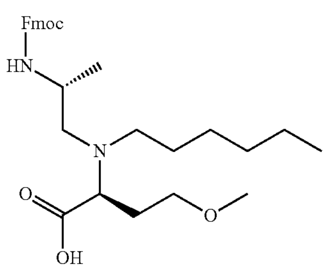 | N-((R)-2-((((9H-fluoren-9-yl)methoxy)carbonyl)amino)propyl)-N-hexyl-(9-methyl-L-homoserine | 497.3 | Method A and C |
| T19 | 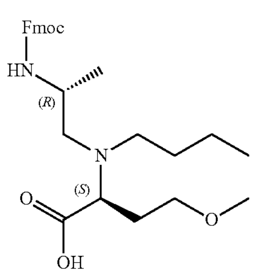 | N-((R)-2-((((9H-fluoren-9-yl)methoxy)carbonyl)amino)propyl)-N-butyl-O-methyl-L-homoserine | 469.2 | Method A and C |

TABLE 3-continued

The intermediates described in Table 3 were prepared following procedures analogous to those described by the above synthetic methods A through D.

| Intermediate Number | Structure | Chemical name | LCMS (ESI) [M + H]+ | Synthetic method |
|---|---|---|---|---|
| T20 | 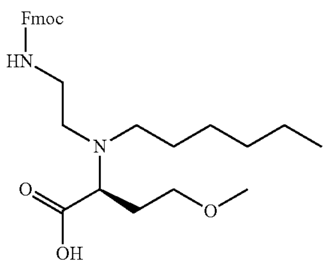 | N-(2-((((9H-fluoren-9-yl)methoxy)carbonyl)amino)ethyl)-N-hexyl-O-methyl-L-homoserine | 483.3 | Method A and C |
| T21 | 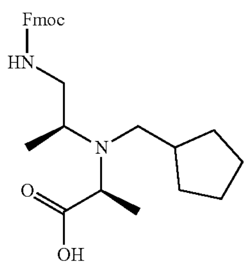 | N-((S)-1-((((9H)-fluoren-9-yl)methoxy)carbonyl)amino)propan-2-yl)-N-(cyclopentylmethyl)-L-alanine | 451.3 | Method D |
| T22 | 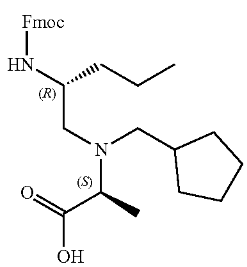 | N-((R)-2-((((9H-fluoren-9-yl)methoxy)carbonyl)amino)pentyl)-N-(cyclopentylmethyl)-L-alanine | 479.2 | Method A and C |
| T23 | 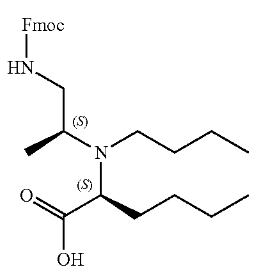 | (S)-2-(((S)-1-((((9H-fluoren-9-yl)methoxy)carbonyl)amino)propan-2-yl)(butyl)amino)hexanoic acid | 467.3 | Method D |
| T24 | 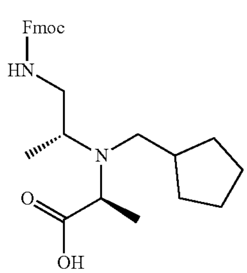 | N-((R)-1-((((9H-fluoren-9-yl)methoxy)carbonyl)amino)propan-2-yl)-N-(cyclopentylmethyl)-L-alanine | 451.3 | Method D |

Example 1. (3S,6S,9S,12S,15S)-6-(Aminomethyl)-15,16-dibutyl-9-cyclohexyl-3-(hydroxymethyl)-12-isobutyl-13-methyl-1,4,7,10,13,16-hexaazacyclooctadecane-2,5,8,11,14-pentaone (trifluoroacetate salt)

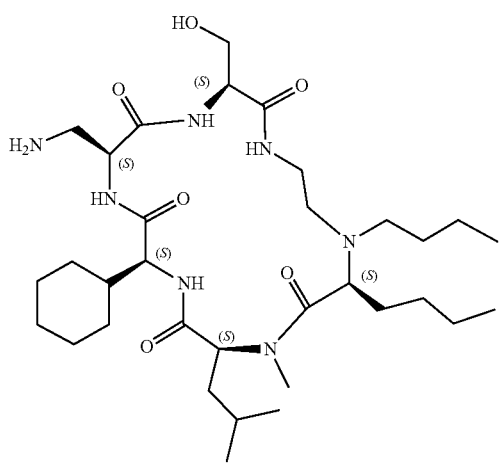

Step 1. Methyl (S)-2-((2-((tert-butoxycarbonyl)amino)ethyl)(butyl)amino)hexanoate

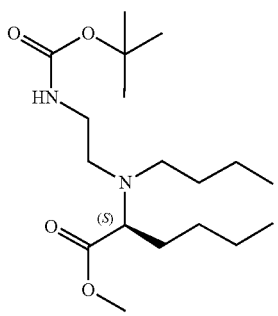

To a mixture of methyl (2S)-2-aminohexanoate hydrochloride (1.55 g, 7.68 mmol) and methanol (20 mL) was added sodium acetate (1.279 g, 15.59 mmol) followed by butyraldehyde (0.70 mL, 7.8 mmol) and sodium cyanoborohydride (1.07 g, 16.2 mmol). The reaction mixture was stirred at room temperature for 2 h. To the reaction mixture was added N-Boc-2-aminoacetaldehyde (1.628 g, 9.72 mmol) and sodium cyanoborohydride (1.03 g, 15.6 mmol), and the reaction mixture continued at room temperature for 2.5 h and then at 50° C. for 18 h. To the reaction mixture was added A-Boc-2-aminoacetaldehyde (1.098 g, 6.556 mmol) and sodium cyanoborohydride (1.13 g, 17.1 mmol) and the reaction mixture continued stirring at room temperature for 20 h. The reaction mixture was quenched with saturated aqueous sodium bicarbonate and extracted with DCM (3×100 mL). The DCM portion was dried over magnesium sulfate, filtered, and evaporated in vacuo. The crude product was purified via flash chromatography on silica gel (80 g silica, solvent gradient: 0-50% ethyl acetate in heptanes) to yield 1.491 g (56%) of the title compound as a clear, colorless oil. LCMS (ESI): [M+H]$^+$=345.2.

Step 2. (S)-2-((2-((tert-Butoxycarbonyl)amino)ethyl)(butyl)amino)hexanoic acid

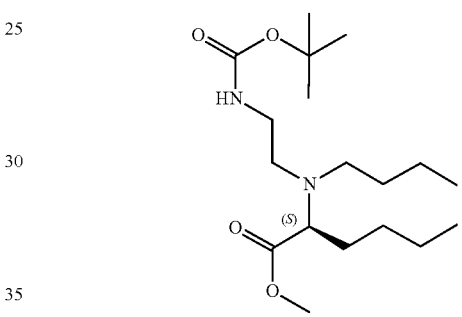

To a solution of methyl (S)-2-((2-((tert-butoxycarbonyl)amino)ethyl)(butyl)amino)hexanoate (1.488 g, 4.319 mmol) in THF (12 mL) was added lithium hydroxide (1.0 M in water, 9 mL, 9 mmol). The resulting mixture was stirred at room temperature for 20 h, and then at 50° C. for 4 h. Additional lithium hydroxide (1.0 M in water, 4 mL, 4 mmol) was added and the reaction mixture stirred at room temperature for 3 days. The reaction mixture was evaporated in vacuo, and the crude product was purified via flash chromatography on silica gel (40 g silica, solvent gradient: 5-10% methanol in dichloromethane+0.5% formic acid) to yield 1.3437 g (94%) of the title compound. LCMS (ESI): [M+H]$^+$=331.15.

Step 3. (3S,6S,9S,12S,15S)-6-(Aminomethyl)-15,16-dibutyl-9-cyclohexyl-3-(hydroxymethyl)-12-isobutyl-13-methyl-1,4,7,10,13,16-hexaazacyclooctadecane-2,5,8,11,14-pentaone The title compound was prepared as the trifluoroacetate salt using (S)-2-((2-((tert-butoxycarbonyl)amino)ethyl)(butyl)amino)hexanoic acid and following procedures analogous to those described for Intermediate 15 (substituting the appropriate Fmoc-protected amino acid) and Example 9, Steps 2-5. LCMS (ESI): R$_T$ (min)=3.503, [M+H]$^+$=652.5, method=A.

Example 2. (3S,6S,9S,12S,15S)-6-(Aminomethyl)-16-(4-butylbenzyl)-9-cyclohexyl-3-(hydroxymethyl)-12-isobutyl-13,15-dimethyl-1,4,7,10,13,16-hexaazacyclooctadecane-2,5,8,11,14-pentaone (trifluoroacetate salt)

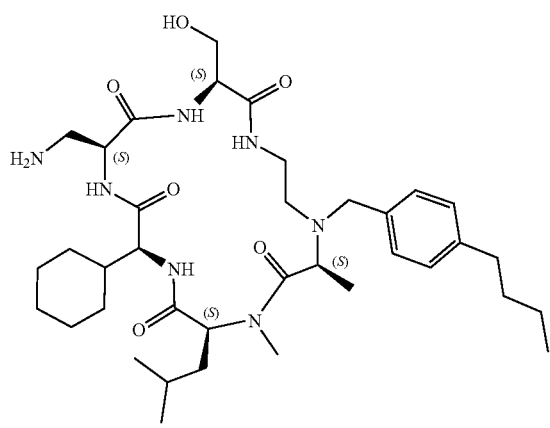

Step 1. Benzyl (((2S,5S,11S,14S,17S)-5-((benzyloxy)methyl)-10-(4-butyl benzyl)-17-cyclohexyl-14-isobutyl-11,13-dimethyl-3,6,12,15,18-pentaoxo-1,4,7,10,13,16-hexaazacyclooctadecane-2-yl)methyl) carbamate

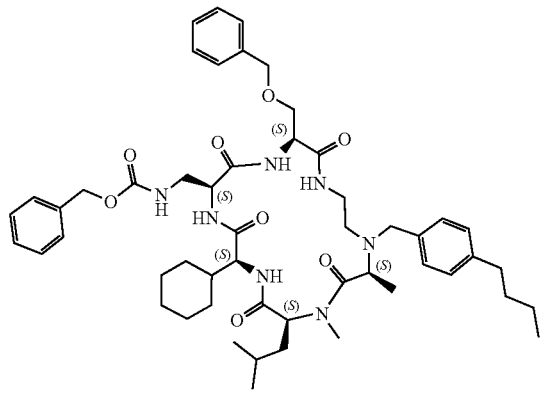

The title compound was prepared following procedures analogous to those described for Example 4. LCMS (ESI): [M+H]$^+$=924.45.

Step 2. (3S,6S,9S,12S,15S)-6-(Aminomethyl)-16-(4-butylbenzyl)-9-cyclohexyl-3-(hydroxymethyl)-12-isobutyl-13,15-dimethyl-1,4,7,10,13,16-hexaazacyclooctadecane-2,5,8,11,14-pentaone To a solution of benzyl (((2S,5S,11S,14S,17S)-5-((benzyloxy)methyl)-10-(4-butylbenzyl)-17-cyclohexyl-14-isobutyl-11,13-dimethyl-3,6,12,15,18-pentaoxo-1,4,7,10,13,16-hexaazacyclooctadecane-2-yl)methyl)carbamate (198 mg, 0.214 mmol) in DCM (2.0 mL, 31 mmol) at 0° C. was added boron tribromide (1 mol/L in DCM) (0.52 mL, 0.52 mmol). The reaction mixture was stirred at 0° C. for 2 h, after which additional boron tribromide (1 mol/L in dichloromethane) (0.30 mL, 0.30 mmol) was added. The reaction mixture was stirred at 0° C. for 1 h and at room temperature for 2 h. The reaction mixture was quenched with methanol, diluted with DCM, and washed with saturated aqueous sodium bicarbonate. The layers were separated and the aqueous layer extracted with an additional portion of DCM. The combined DCM layers were dried over magnesium sulfate, filtered, and evaporated in vacuo. The crude product was purified via reverse-phase HPLC and lyophilized to yield 36.4 mg (24%) of the title compound as its trifluoroacetate salt. LCMS (ESI): R$_T$ (min)=4.586, [M+H]$^+$=700.5, method=A.

Example 3. (3S,6S,9S,12S,15S)-6-(Aminomethyl)-9-cyclohexyl-15-(2-fluoroethyl)-16-hexyl-3-((S)-1-hydroxyethyl)-12-isobutyl-13-methyl-1,4,7,10,13,16-hexaazacyclooctadecane-2,5,8,11,14-pentaone (trifluoroacetate salt)

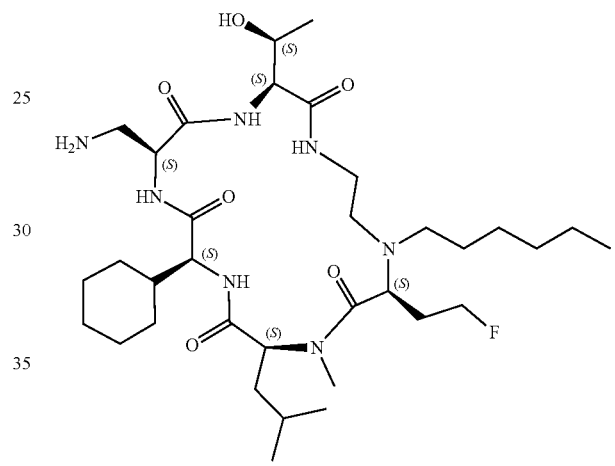

Step 1. Benzyl (tert-butoxycarbonyl)-L-homoserinate

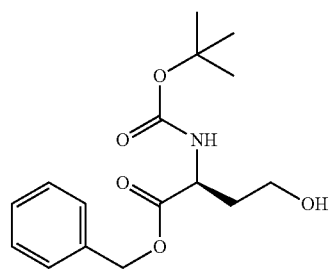 [SMILES: CC(C)(C)OC(=O)N[C@@H](CCO)C(=O)OCc1ccccc1]

To a solution of (3S)-4-benzyloxy-3-(tert-butoxycarbonylamino)-4-oxo-butanoic acid (1.016 g, 3.143 mmol) dissolved in 1,2-dimethoxyethane (3 mL) at 0° C. was added 4-methylmorpholine (0.35 mL, 3.2 mmol) followed by a slow addition of isobutyl chloroformate (0.44 mL, 3.4 mmol). The reaction mixture was stirred at 0° C. for 30 min, and then filtered through celite, rinsing with 1,2-dimethoxyethane (3 mL). The filtrate was cooled to 0° C., and treated with slow addition of a solution of sodium borohydride (158 mg, 4.135 mmol) in water (1.5 mL). After 5 min, water (15 mL) was added. The resulting suspension extracted with ethyl acetate. The organic portion was dried over brine and magnesium sulfate, filtered, and evaporated in vacuo. The crude product was purified via flash chromatography on silica gel (40 g silica, solvent gradient: 0-100% ethyl acetate in DCM) to yield 485.6 mg (50%) of the title compound as a clear, colorless oil. LCMS (ESI): [M+H-tButyl]$^+$=254.1, [M+H-Boc]$^+$=210.1.

Step 2. Benzyl (S)-2-((tert-butoxycarbonyl)amino)-4-fluorobutanoate

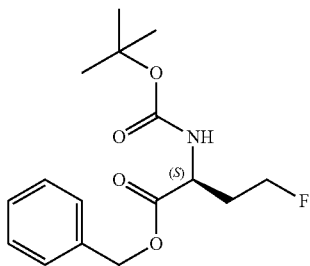

To a solution of benzyl (tert-butoxycarbonyl)-L-homoserinate (550.2 mg, 1.778 mmol) in 1,4-dioxane (3.5 mL) was added pyridine-2-sulfonyl fluoride (324.6 mg, 1.913 mmol) followed by 1,3,4,6,7,8-hexahydro-1-methyl-2H-pyrimido[1,2-a]pyrimidine (0.52 mL, 3.6 mmol). The resulting mixture was stirred at room temperature in a sealed vial under air for 19 h. The reaction mixture was diluted with ethyl acetate, washed with water (2×) and brine, dried over magnesium sulfate, filtered, and evaporated in vacuo. The crude product was purified via flash chromatography on silica gel (24 g silica, solvent gradient: 0-40% ethyl acetate in heptanes) to yield 356.6 mg (64%) of the title compound as a clear, colorless oil, which crystallizes after standing at room temperature overnight. LCMS (ESI): [M+H-Boc]$^+$=212.1; $^1$H NMR (400 MHz, DMSO-d$_6$) δ 7.43-7.30 (m, 6H), 5.23-5.05 (m, 2H), 4.60-4.34 (m, 2H), 4.12 (td, J=8.9, 4.8 Hz, 1H), 2.17-1.87 (m, 2H), 1.37 (s, 9H).

Step 3. Benzyl (S)-2-amino-4-fluorobutanoate hydrochloride

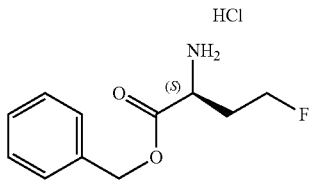

To a solution of benzyl (2S)-2-(tert-butoxycarbonylamino)-4-fluoro-butanoate (355 mg, 1.14 mmol) in DCM (3 mL) was added hydrogen chloride (4.0 mol/L in dioxane, 3.0 mL, 12 mmol). The reaction mixture was stirred at room temperature for 5 h. The reaction mixture was evaporated in vacuo to yield the title compound as the HCl salt, which was carried forward without purification. LCMS (ESI): [M+H]$^+$=LCMS m/z=212.05.

Step 4. (3S,6S,9S,12S,15S)-6-(Aminomethyl)-9-cyclohexyl-15-(2-fluoroethyl)-16-hexyl-3-((S)-1-hydroxyethyl)-12-isobutyl-13-methyl-1,4,7,10,13,16-hexaazacyclooctadecane-2,5,8,11,14-pentaone The title compound was prepared as the trifluoroacetate salt using benzyl (5)-2-amino-4-fluorobutanoate hydrochloride and following procedures analogous to those described for Example 4. LCMS (ESI): R$_T$ (min)=7.733, [M+H]$^+$=684.5, method=B; $^1$H NMR (400 MHz, Methanol-d$_4$) δ 4.66-4.33 (m, 4H), 4.19-3.96 (m, 3H), 3.69-3.36 (m, 7H), 2.83 (s, 2H), 2.11-1.54 (m, 12H), 1.54-1.13 (m, 15H), 1.13-0.90 (m, 12H).

Example 4. (3S,6S,9S,12S,15S)-6-(Aminomethyl)-9-cyclohexyl-16-hexyl-3-((5)-1-hydroxyethyl)-12-isobutyl-13-methyl-15-(2,2,2-trifluoroethyl)-1,4,7,10,13,16-hexaazacyclooctadecane-2,5,8,11,14-pentaone (trifluoroacetate salt)

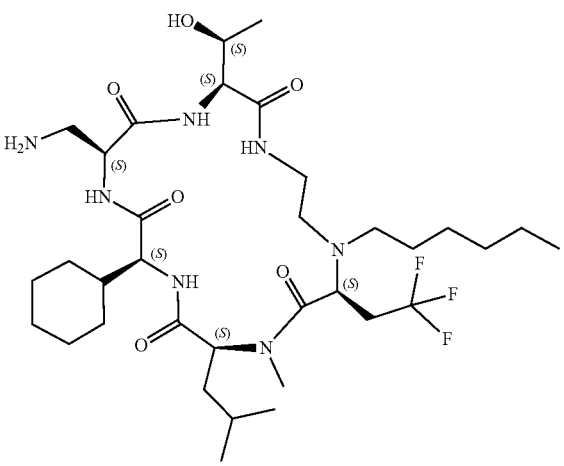

Step 1. Benzyl (5)-2-((2-((tert-butoxycarbonyl)amino)ethyl)(hexyl)amino)-4,4,4-trifluorobutanoate

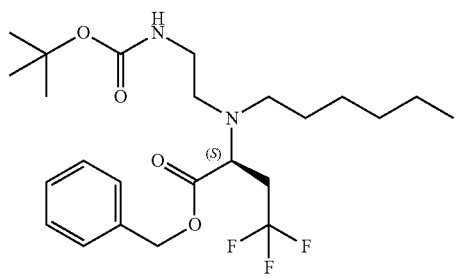

To a mixture of benzyl (2S)-2-amino-4,4,4-trifluoro-butanoate hydrochloride (275.4 mg, 0.9708 mmol) and A-Boc-2-aminoacetaldehyde (175.0 mg, 1.04 mmol) in ethyl acetate (10.0 mL) was added sodium triacetoxyborohydride (421 mg, 1.98 mmol). The reaction mixture was stirred at room temperature for 3 days. To the reaction mixture was added hexanal (0.25 mL, 2.1 mmol) and sodium triacetoxyborohydride (439 mg, 2.0713 mmol). The reaction mixture was heated at 50° C. for 2 h, after which hexanal (0.30 mL, 2.5 mmol) and sodium triacetoxyborohydride (380 mg, 1.79 mmol) were added. After an additional 3.5 h the reaction mixture was diluted with ethyl acetate, washed with aqueous sodium bicarbonate and brine, dried over magnesium sulfate, filtered, and evaporated in vacuo. The crude product was purified via flash chromatography on silica gel (40 g silica, solvent gradient: 0-75% ethyl acetate in heptanes) to yield 350.8 mg (76%) of the title compound as a clear, colorless oil. LCMS (ESI): [M+H]$^+$=475.25.

Step 2. (3S,6S,9S,12S,15S)-6-(Aminomethyl)-9-cyclohexyl-16-hexyl-3-((S)-1-hydroxyethyl)-12-isobutyl-13-methyl-15-(2,2,2-trifluoroethyl)-1,4,7,10,13,16-hexaazacyclooctadecane-2,5,8,11,14-pentaone The title compound was prepared as the trifluoroacetate salt using benzyl (S)-2-((2-((tert-butoxycarbonyl)amino)ethyl)(hexyl)amino)-4,4,4-trifluorobutanoate and following procedures analogous to those described for Example 9, steps 2-5. LCMS (ESI): R$_T$ (min)=3.00, [M+H]$^+$=720.47, method=C; $^1$H NMR (400 MHz, DMSO-d$_6$) δ 9.40 (s, 1H), 8.22 (d, J=8.4 Hz, 1H), 7.89-7.66 (m, 3H), 7.48-7.21 (m, 1H), 4.44 (dd, J=9.8, 4.9 Hz, 1H), 4.30-3.77 (m, 3H), 3.71 (d, J=9.4 Hz, 1H), 3.24-2.77 (m, 7H), 2.71 (s, 2H), 2.68-2.57 (m, 1H), 2.41-2.30 (m, 2H), 1.92-0.81 (m, 36H).

Example 5. (3S,6S,9S,12S,15S)-6-(Aminomethyl)-15-butyl-9-cyclohexyl-16-(3-fluoropropyl)-3-((S)-1-hydroxyethyl)-12-isobutyl-13-methyl-1,4,7,10,13,16-hexaazacyclooctadecane-2,5,8,11,14-pentaone (trifluoroacetate salt)

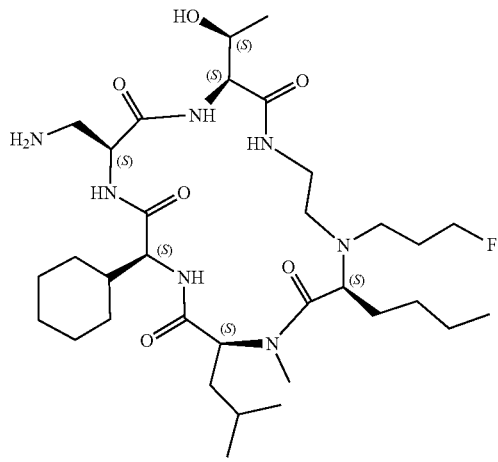

Step 1. Benzyl (S)-2-((tert-butoxycarbonyl)amino)hexanoate

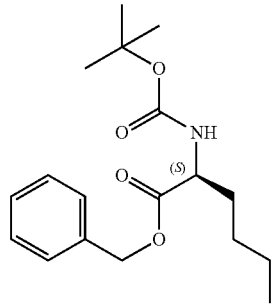

To a solution of (2S)-2-(tert-butoxycarbonylamino)hexanoic acid (5.1549 g, 22.288 mmol) in DMF (50 mL) was added sodium hydrogen carbonate (2.34 g, 27.8 mmol) and benzyl bromide (3.0 mL, 25 mmol). The reaction mixture was stirred at room temperature for 18 h, followed by the addition of sodium hydrogen carbonate (1.607 g, 19.06 mmol) and benzyl bromide (1.5 mL, 12.5 mmol). The reaction mixture was stirred at room temperature for an additional 4 h and then
was diluted with ethyl acetate, washed with water (2×) and brine, dried over magnesium sulfate, filtered, and evaporated in vacuo. The crude product was purified via flash chromatography on silica gel (220 g silica, solvent gradient: 0-100% ethyl acetate in heptanes) to yield 5.2931 g (74%) of the title compound as a clear colorless oil. LCMS (ESI): [M+H-tButyl]$^+$=266.15; $^1$H NMR (400 MHz, DMSO-d$_6$) δ 7.53-7.28 (m, 5H), 7.26 (d, J=7.7 Hz, 1H), 5.15 (d, J=12.7 Hz, 1H), 5.07 (d, J=12.7 Hz, 1H), 4.00-3.91 (m, 1H), 1.78-1.48 (m, 2H), 1.37 (s, 9H), 1.28-1.20 (m, 4H), 0.89-0.77 (m, 3H).

Step 2. Benzyl (S)-2-((2-((tert-butoxycarbonyl)amino)ethyl)amino)hexanoate

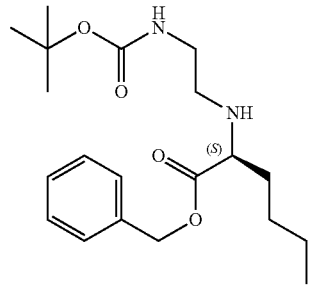

Benzyl (S)-2-(tert-butoxycarbonylamino)hexanoate (5.2931 g, 16.47 mmol) was dissolved in DCM (50 mL) and treated with hydrogen chloride (4M solution in dioxane, 21 mL, 84 mmol). The resulting mixture was stirred at room temperature for 15 h and then evaporated in vacuo. The resulting residue was combined with N-Boc-2-aminoacetaldehyde (2.762 g, 16.5 mmol) in ethyl acetate (50.0 mL) at 40° C., followed by the addition of sodium triacetoxyborohydride (32 mmol, 32 mmol) in 3 portions over 2.5 h. The reaction mixture was stirred at 40° C. for 16 h. The reaction mixture was diluted with ethyl acetate, washed with aqueous sodium bicarbonate and brine, dried over magnesium sulfate, filtered, and evaporated in vacuo. The crude product was purified via flash chromatography on silica gel (220 g silica, solvent gradient: 0-5% methanol in DCM) to yield 2.2081 g (37%) of the title compound as a yellow oil. LCMS (ESI): [M+H]$^+$=365.2; $^1$H NMR (400 MHz, DMSO-d$_6$) δ 7.40-7.29 (m, 5H), 6.75-6.63 (m, 1H), 5.12 (d, J=2.0 Hz, 2H), 3.20 (t, J=6.6 Hz, 1H), 2.95 (h, J=6.6 Hz, 2H), 2.55 (dd, J=11.6, 6.4 Hz, 1H), 2.40 (dt, J=11.5, 6.3 Hz, 1H), 1.59-1.44 (m, 2H), 1.37 (s, 9H), 1.28-1.17 (m, 4H), 0.85-0.77 (m, 3H).

Step 3. Benzyl (S)-2-((2-((tert-butoxycarbonyl)amino)ethyl)(3-((tert-butyldimethylsilyl)oxy)propyl)amino)hexanoate

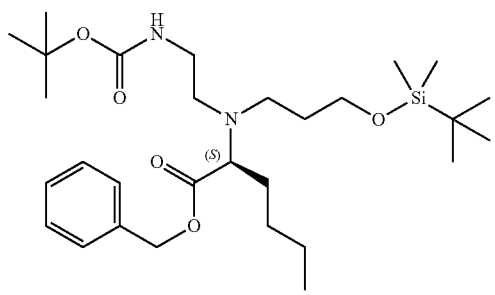

To a mixture of benzyl (S)-2-((2-((tert-butoxycarbonyl)amino)ethyl)amino)hexanoate (0.6066 g, 1.664 mmol) and 3-[(tert-butyldimethylsilyl)]-1-propanal (0.6 mL, 3 mmol) in ethyl acetate (8.0 mL) was added sodium triacetoxyborohydride (855 mg, 4.034 mmol). The reaction mixture was stirred at 50° C. for 2 h. The reaction mixture was diluted with ethyl acetate, washed with aqueous sodium bicarbonate and brine, dried over magnesium sulfate, filtered, and evaporated in vacuo. The crude product was purified via flash chromatography on silica gel (40 g silica, solvent gradient: 0-50% ethyl acetate in heptanes) to yield 618.0 mg (69%) of the title compound as a clear, colorless oil. LCMS (ESI): [M+H]$^+$=537.35.

Step 4. Benzyl (S)-2-((2-((tert-butoxycarbonyl)amino)ethyl)(3-hydroxypropyl)amino)hexanoate

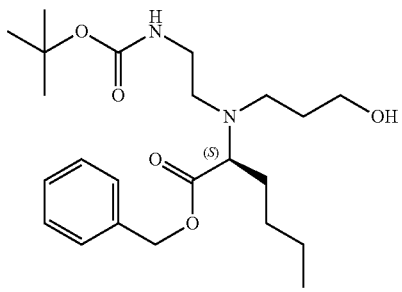

To a solution of benzyl (S)-2-((2-((tert-butoxycarbonyl)amino)ethyl)(3-((tert-butyldimethylsilyl)oxy)propyl)amino)hexanoate (618.0 mg, 1.151 mmol) in THF (5 mL) was added tetrabutylammonium fluoride (1 mol/L in THF, 1.4 mL, 1.4 mmol). The reaction mixture was stirred at room temperature for 2 h. The reaction material was quenched with saturated aqueous ammonium chloride, diluted with ethyl acetate and washed with saturated aqueous sodium bicarbonate (2×50 mL). The organic portion was dried over magnesium sulfate, filtered, and evaporated in vacuo. The crude product was purified via flash chromatography on silica gel (24 g silica, solvent gradient: 0-5% methanol in dichloromethane, monitor at 210 nm) to yield 321.0 mg (66%) of the title compound. LCMS (ESI): [M+H]$^+$=423.25; $^1$H NMR (400 MHz, DMSO-d$_6$) δ 7.41-7.29 (m, 4H), 6.57 (t, T=5.7 Hz, 1H), 5.11 (s, 2H), 4.30 (t, J=5.0 Hz, 1H), 3.46-3.33 (m, 2H), 2.97-2.79 (m, 2H), 2.76-2.57 (m, 2H), 2.47-2.32 (m, 2H), 1.68-1.42 (m, 4H), 1.36 (s, 9H), 1.32-1.19 (m, 3H), 0.85 (t, J=7.0 Hz, 3H).

Step 5. Benzyl (S)-2-((2-((tert-butoxycarbonyl)amino)ethyl)(3-fluoropropyl)amino)hexanoate

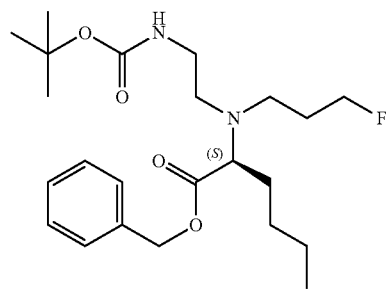

To a solution of benzyl (S)-2-((2-((tert-butoxycarbonyl)amino)ethyl)(3-hydroxypropyl)amino)hexanoate (321.0 mg, 0.7596 mmol) in 1,4-dioxane (1.5 mL) was added pyridine-2-sulfonyl fluoride (150.8 mg, 0.8890 mmol) followed by 1,3,4,6,7,8-hexahydro-1-methyl-2/7-pyrimido[1,2-a]pyrimidine (0.24 mL, 1.7 mmol). The resulting mixture was stirred in a sealed vial (under air) at room temperature for 63 h. The reaction mixture was diluted with ethyl acetate, washed with water (2×) and brine, dried over magnesium sulfate, filtered, and evaporated in vacuo. The crude product was purified via flash chromatography on silica gel (12 g silica, solvent gradient: 0-80% ethyl acetate in heptanes) to yield 233.1 mg (72%) of the title compound as a clear, colorless oil. LCMS (ESI): [M+H]$^+$=425.2.

Step 6. (3S,6S,9S,12S,15S)-6-(Aminomethyl)-15-butyl-9-cyclohexyl-16-(3-fluoropropyl)-3-((S)-1-hydroxyethyl)-12-isobutyl-13-methyl-1,4,7,10,13,16-hexaazacyclooctadecane-2,5,8,11,14-pentaone The title compound was prepared using benzyl (5)-2-((2-((tert-butoxycarbonyl)amino)ethyl)(3-fluoropropyl)amino)hexanoate and following procedures analogous to those described for Example 4. LCMS (ESI): R$_T$ (min)=8.210, [M+H]$^+$=670.5, method=B.

Example 6. (3S,6S,9S,12S,15S)-6-(Aminomethyl)-15-butyl-9-cyclohexyl-16-(2-fluoroethyl)-3-((S)-1-hydroxyethyl)-12-isobutyl-13-methyl-1,4,7,10,13,16-hexaazacyclooctadecane-2,5,8,11,14-pentaone (trifluoroacetate salt)

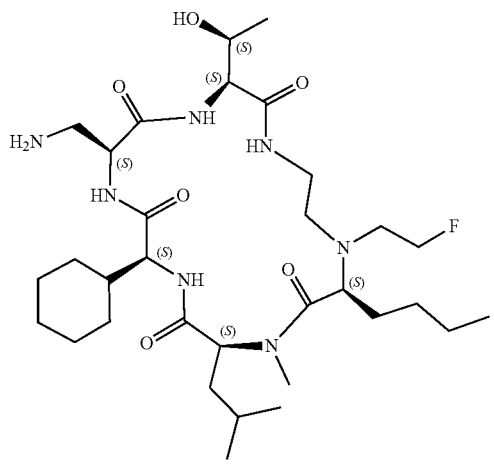

Step 1. Benzyl (S)-2-((2-((tert-butoxycarbonyl)amino)ethyl)(2-fluoroethyl)amino)hexanoate

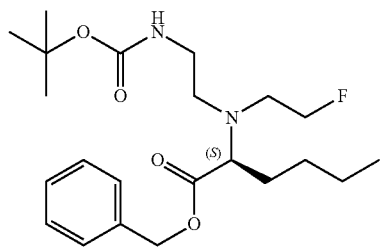

To a solution of benzyl (S)-2-((tert-butoxycarbonyl)amino)hexanoate (Example 5, Step 1) (702 mg, 1.93 mmol) in DMF (4.0 mL) was added triethylamine (3.0 mL, 21 mmol) and 1-fluoro-2-iodoethane (2.0 mL, 25 mmol). The reaction mixture was stirred in a sealed vial at 60° C. for 17 h. To the reaction mixture was added 1-bromo-2-fluoroethane (1.0 mL, 13 mmol) and the mixture was heated at 60° C. for 24 h. To the reaction mixture was added trimethylamine (2.0 mL, 14 mmol) and 1-bromo-2-fluoroethane (1.0 mL, 13 mmol) and the mixture was heated at 60° C. for 24 h. The reaction mixture was diluted with ethyl acetate, washed with water (2×) and brine, dried over magnesium sulfate, filtered, and evaporated in vacuo. The crude product was purified via flash chromatography on silica gel (40 g silica, solvent gradient: 0-100% ethyl acetate in DCM) to yield 391.7 mg (50%) of the title compound as an orange oil. LCMS (ESI): $[M+H]^+$=411.25

Step 2. (3S,6S,9S,12S,15S)-6-(Aminomethyl)-15-butyl-9-cyclohexyl-16-(2-fluoroethyl)-3-((S)-1-hydroxyethyl)-12-isobutyl-13-methyl-1,4,7,10,13,16-hexaazacyclooctadecane-2,5,8,11,14-pentaone The title compound was prepared using benzyl (S)-2-((2-((tert-butoxycarbonyl)amino)ethyl)(2-fluoroethyl)amino) hexanoate and following procedures analogous to those described for Example 4. LCMS (ESI): $R_T$ (min)=6.69, $[M+H]^+$=656.56, method=D.

Example 7. (3S,6S,9S,12S,15S,18R)-6-(Aminomethyl)-15,16-dibutyl-9-cyclohexyl-3-((S)-1-hydroxyethyl)-13,18-dimethyl-12-propyl-1,4,7,10,13,16-hexaazacyclooctadecane-2,5,8,11,14-pentaone (trifluoroacetate salt)

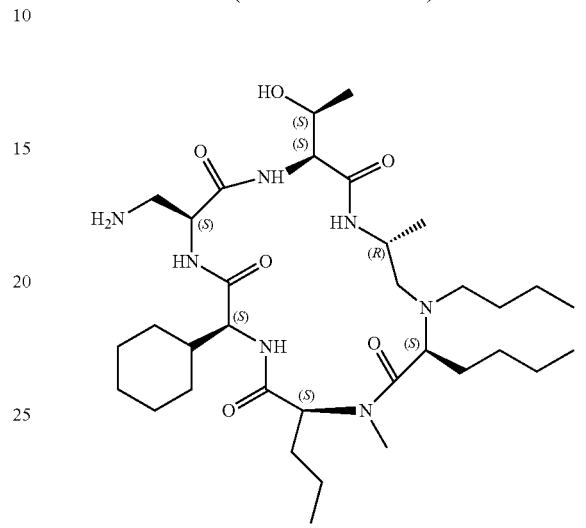

Step 1. N-Me-norvaline-cyclohexylglycine-Dap(Cbz)-allothreonine(Bzl)-(2-chlorotrityl resin)

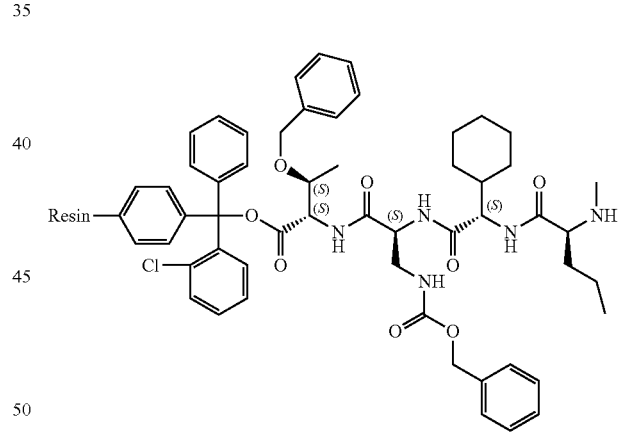

Commercially available 2-chlorotrityl resin (resin loading 0.95 mmol/g, 5.0 g) was swelled with 40 mL DMF/DCM (1:1) for 40 min. The resin was drained, and treated with a solution of Fmoc-allothreonine(Bzl)-OH (2.46 g, 5.7 mmol) and DIPEA (2.5 g, 19.4 mmol) in DMF (15 mL). The resin was agitated with nitrogen bubbling for 1.5 h, and then drained and rinsed sequentially with DCM/MeOH/DIPEA (10:10:1, 15 mL), DCM (3×15 mL) and DMF (3×15 mL).

The resin was treated with 25 mL of 20% piperidine in DMF, and agitated with nitrogen bubbling for 1 h. The resin was drained and rinsed with DMF (3×10 mL) and DCM (3×10 mL). The resin was treated with a solution (premixed at room temperature for 15 min) of (S)-2-(Fmoc-amino)-3-(((benzyloxy)carbonyl)amino)propanoic acid (4.37 g, 9.49 mmol), HATU (3.61 g, 9.50 mmol), HOBt (1.29 g, 9.53 mmol) and DIPEA (3.31 mL, 19.03 mmol) in DMF (50 mL). The resin was shaken on a rotator overnight, drained and rinsed with DMF (2×15 mL) and DCM (3×15 mL).

The resin was treated with 10 mL of 20% piperidine in DMF, and agitated with nitrogen bubbling for 60 min. The resin was drained and rinsed with DMF (3×15 mL) and DCM (3×15 mL). The resin was treated with a solution (premixed at room temperature for 15 min) of Fmoc-S-cyclohexylglycine-OH (3.61 g, 9.50 mmol), a stock solution of HATU/HOBt (1/1) (0.4 M in DMF, 24 mL, 9.6 mmol) and DIPEA (2.45 g, 19 mmol). The resin was agitated with nitrogen bubbling for 2 h, and then drained and rinsed with DMF (3×15 mL) and DCM (3×15 mL).

The resin was treated with 25 mL of 20% piperidine in DMF, and agitated with nitrogen bubbling for 60 min. The resin was drained and rinsed with DMF (3×15 mL) and DCM (3×15 mL). The resin was treated with a pre-mixed solution of (S)-Fmoc-A-Me-norvaline-OH (3.37 g, 9.52, HATU/HOBt (1/1) (0.4 M in DMF, 24 mL, 9.6 mmol) and DIPEA (2.53 g, 19.6 mmol). The resin was agitated for 3 h, drained and rinsed with DMF (3×15 mL) and DCM (3×15 mL).

The resin was treated with 25 mL of 20% piperidine in DMF, and the vial was placed on a rotator at room temperature for 3 h, and then filtered and rinsed with DMA (3×15 mL) and DCM (3×15 mL) and dried under vacuum to afford the resin-bound peptide (7.58 g, resin loading estimated 0.5 mmol/g).

Step 2. (6R,9S,12S,15S,18S,21S)-18-((((Benzyloxy)carbonyl)amino)methyl)-21-((S)-1-(benzyloxy)ethyl)-8,9-dibutyl-15-cyclohexyl-2,2,6,11-tetramethyl-4,10,13,16,19-pentaoxo-12-propyl-3-oxa-5,8,11,14,17,20-hexaazadocosan-22-oic acid

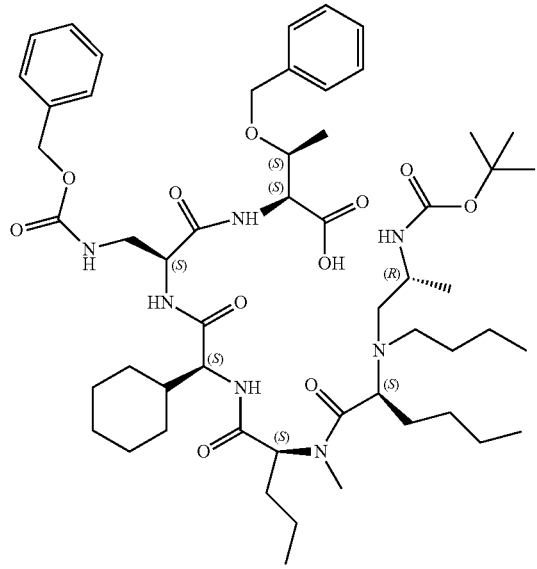

The resin bound peptide from previous step (1.00 g, resin loading ~0.5 mmol/g) was treated with a premixed solution of (2S)-2-[[(2R)-2-tert-butoxycarbonylamino)propyl]-butyl-amino]hexanoic acid (447 mg, 1.29 mmol, Intermediate T5), PyAOP (782 mg, 1.51 mmol) and DIPEA (387 mg, 3 mmol) in DMF (10 mL). The resin was shaken for 24 h on a rotator. The resin was drained and rinsed with DMF (3×10 mL) and DCM (3×10 mL). The resin was treated with a HFIP/DCM=1/4 solution (enough to cover the resin 1.5 times) and shaken at room temperature for 1 h, then filtered. The liquid phase was collected. The process was repeated with HFIP/DCM=1/4 and the liquid phase collected. The resin was washed with DCM (3×10 mL). The filtrates were combined and concentrated under vacuum. The residue was purified by reverse phase flash chromatography on C18 column to afford the title compound (364 mg, 0.361 mmol). LCMS (ESI): [M+H]$^+$=1008.6.

Step 3. (2S,5S,8S,11S,14S)-15-((R)-2-Aminopropyl)-5-((((benzyloxy)carbonyl)amino)methyl)-2-((S)-1-(benzyloxy)ethyl)-14-butyl-8-cyclohexyl-12-methyl-4,7,10,13-tetraoxo-11-propyl-3,6,9,12,15-pentaazanonadecane-1-oic acid

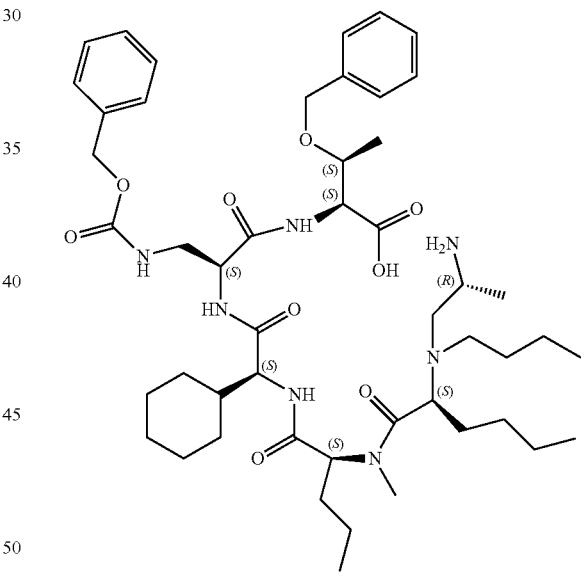

(6R,9S,12S,15S,18S,21S)-18-((((benzyloxy)carbonyl)amino)methyl)-21-((S)-1-(benzyloxy)ethyl)-8,9-dibutyl-15-cyclohexyl-2,2,6,11-tetramethyl-4,10,13,16,19-pentaoxo-12-propyl-3-oxa-5,8,11,14,17,20-hexaazadocosan-22-oic acid (204 mg, 0.202 mmol) was dissolved in TFA (20 mL) at 0° C. The resulting mixture was stirred at 0° C. for 1 h and then diluted with toluene (40 mL). The resulting mixture was concentrated under vacuum. Another 40 mL of toluene was added and the resulting mixture was concentrated under vacuum to afford the title compound as TFA salt (180 mg). LCMS (ESI): [M+H]$^+$=908.5.

Step 4. Benzyl (((2S,5S,8R,11S,14S,17S)-5-((S)-1-(benzyloxy)ethyl)-10,11-dibutyl-17-cyclohexyl-8,13-dimethyl-3,6,12,15,18-pentaoxo-14-propyl-1,4,7,10,13,16-hexaazacyclooctadecane-2-yl)methyl)carbamate stirred at 25° C. for 24 h under hydrogen gas (1 atm). The catalyst was removed via filtration and the filtrate was concentrated under vacuum. The residue was purified via Prep-LCMS to afford the title compound as TFA salt (13.0 mg) as a white solid. LCMS (ESI): [M+H]$^+$=666.5, R$_t$=2.38 min, method J. $^1$H NMR (400 MHz, DMSO-d$_6$): δ 8.74-8.64 (m, 2H), 8.05 (br, 3H), 7.92-7.04 (m, 2H), 6.09 (br, 1H), 5.22-5.14 (m, 1H), 4.81-4.73 (m, 2H), 4.47-4.41 (m, 1H), 4.33-4.28 (m, 1H), 4.03-3.87 (m, 3H), 3.78-3.73 (m, 1H), 3.21 (s, 2H), 3.19-3.10 (m, 3H), 2.99-2.92 (m, 1H), 2.05-1.95 (m, 2H), 1.88-1.76 (m, 3H), 1.72-1.62 (m, 6H), 1.44-1.06 (m, 16H), 0.97-0.84 (m, 15H).

Example 8. (1R,4S,7S,10S,13S,16R,19R)-10-(Aminomethyl)-7-cyclohexyl-13-[(1S)-1-hydroxyethyl]-4-isobutyl-3,16-dimethyl-18-oxa-3,6,9,12,15-pentaazabicyclo[17.8.0]heptacosane-2,5,8,11,14-pentone (trifluoroacetate salt)

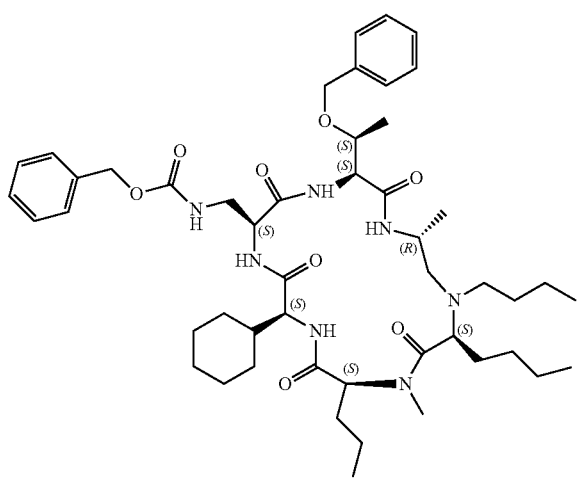

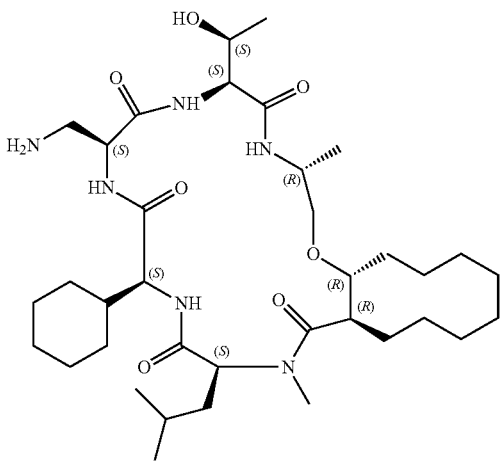

(2S,5S,8S,11S,14S)-15-((R)-2-aminopropyl)-5-((((benzyloxy)carbonyl)amino)methyl)-2-((S)-1-(benzyloxy)ethyl)-14-butyl-8-cyclohexyl-12-methyl-4,7,10,13-tetraoxo-11-propyl-3,6,9,12,15-pentaazanonadecane-1-oic acid (184 mg, 0.202 mmol) was dissolved in THF (160 mL) and DIPEA (78 mg, 0.60 mmol) was added. The resulting solution was cooled to 0° C. A solution of HATU (76.9 mg, 0.200 mmol) and HOBt (27.0 mg, 0.200 mmol) in DMF (2.0 mL) was diluted with THF (20 mL), and then the resulting THF/DMF solution was added dropwise to the cold peptide solution. After the reaction was completed, the reaction mixture was concentrated under vacuum to strip off THF. The residue was diluted with 3 mL of DMF and added dropwise to water (60 mL) with vigorous stirring. The mixture was stirred for an additional 15 min. The solid was collected by filtration, washed with water and dried under vacuum to afford the crude cyclic peptide (170 mg), which was used directly without further purification. LCMS (ESI): [M+H]$^+$=890.5.

Step 4. (3S,6S,9S,12S,15S,18R)-6-(aminomethyl)-15,16-dibutyl-9-cyclohexyl-3-[(EV)-1-hydroxyethyl]-13,18-dimethyl-12-propyl-1,4,7,10,13,16-hexaazacyclooctadecane-2,5,8,11,14-pentone A mixture of the crude cyclic peptide from Step 3 (132 mg) and 10% Pd/C (232 mg) in ethyl acetate (20 mL) was Step 1. N-Me-leucine-cyclohexylglycine-Dap(Boc)-allothreonine(t-Bu)-(2-chlorotrityl resin)

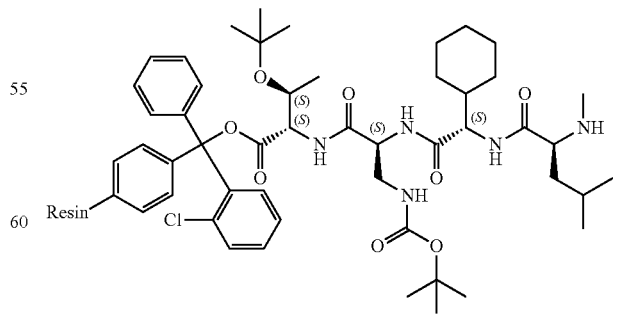

The resin bound tetrapeptide was prepared following methods analogous to those described for Example 7.

Step 2. (2S,5S,8S,11S,14R,15R,18R)-18-Amino-14-(but-3-en-1-yl)-2-((S)-1-(tert-butoxy)ethyl)-5-(((tert-butoxycarbonyl)amino)methyl)-8-cyclohexyl-15-(hex-5-en-1-yl)-11-isobutyl-12-methyl-4,7,10,13-tetraoxo-16-oxa-3,6,9,12-tetraazanonadecan-1-oic acid

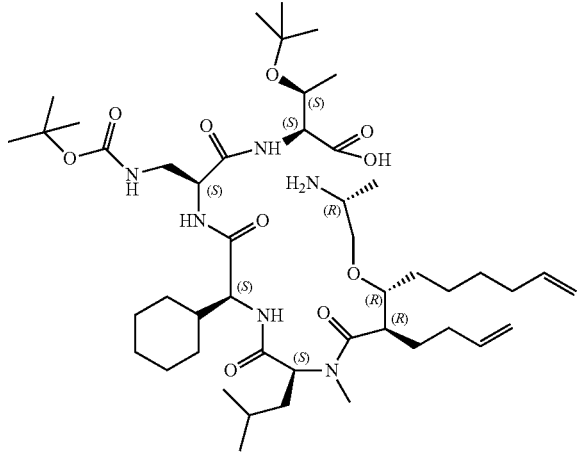

The resin-bound tetrapeptide from Step 1 (1.0 g, ~0.45 mmol/g loading) was treated with THF (5 mL) and DIPEA (308 mg, 2.39 mmol), and allowed to swell for 30 min. Separately a solution of (2R,3R)-2-but-3-enyl-3-[(2R)-2-(9H-fluoren-9-ylmethoxycarbonylamino)propoxy]non-8-enoic acid (364 mg, 0.720 mmol, Intermediate 14) in THF (2.0 mL) was added to a solution of triphosgene (71.5 mg, 0.240 mmol) in THF (2.0 mL). 2,4,6-Trimethylpyridine (1.25 g, 10.4 mmol) was added dropwise, upon which the mixture evolves heat and a colorless precipitate formed. This suspension was gently shaken for about 1 minute, after which it was added to the pretreated resin. The mixture was placed on a rotator at room temperature for 3 h, drained and then rinsed with DMF (10 mL) and DCM (2×10 mL). The resin was treated with 10 mL of 20% piperidine in DMF, agitated with nitrogen bubbling for 1 h, drained and rinsed with DMF (2×10 mL) and DCM (2×10 mL). The resin was then treated with a HFIP/DCM=1/4 solution (20 mL) and shaken on a rotator at room temperature for 1 h then filtered. The liquid phase was collected. The process was repeated with HFIP/DCM=1/4 and the liquid phase collected. The resin was washed with DCM (3×10 mL). The filtrates were combined and concentrated under vacuum. The residue was purified by reverse phase flash chromatography on C18 column to afford the title compound as a yellow solid (300 mg, 62%). LCMS (ESI): [M+H]$^+$=893.6.

Step 3. tert-Butyl N-[[(3R,6S,9S,12S,15S,18R,19R)-18-but-3-enyl-6-[(1S)-1-tert-butoxyethyl]-12-cyclohexyl-19-hex-5-enyl-15-isobutyl-3,16-dimethyl-5,8,11,14,17-pentaoxo-1-oxa-4,7,10,13,16-pentazacyclononadec-9-yl]methyl]carbamate To a mixture of the peptide from Step 2 (300 mg, 0.340 mmol) in THF (200 mL) with DIPEA (175 mg, 1.35 mmol) at 0° C. was added dropwise a solution of HATU (129 mg, 0.340 mmol) and HOBt (129 mg, 0.34 mmol) in DMF (2.0 mL). The reaction mixture was stirred for 2 h at 0° C. and then concentrated under vacuum to strip off THF. The residue was diluted with DMF (3 mL) and added dropwise to 60 mL of water with vigorous stirring. The resulting solid was collected by filtration and washed with water (3×10 mL) and dried to afford the crude product (271 mg) as a yellow solid. LCMS (ESI): [M+H]$^+$=875.5.

Step 4. tert-Butyl N-[[(1R,4S,7S,10S,13S,16R,19R,24Z)-13-[(1S)-1-tert-butoxyethyl]-7-cyclohexyl-4-isobutyl-3,16-dimethyl-2,5,8,11,14-pentaoxo-18-oxa-3,6,9,12,15-pentazabicyclo[17.8.0]heptacos-24-en-10-yl]methyl]carbamate To a solution of the cyclic peptide from Step 3 (110 mg, 0.130 mmol) in DCE (70 mL) was added dropwise a solution of dichloro-[(2-isopropoxyphenyl)methylene]-(tricyclohexyl-λ^{5}-phosphanyl)ruthenium (43 mg, CAS 203714-71-0) in DCE (1.0 mL) at 0° C. under nitrogen. The reaction was stirred at 80° C. overnight and then more catalyst (43 mg, CAS 203714-71-0) was added. The reaction was stirred for another 8 h at 80° C. and another portion of catalyst (43 mg, CAS 203714-71-0) was added. This process repeated 2 more times. The total catalyst added was 5×43 mg and the total reaction time was 3 days. The reaction mixture was concentrated under reduced pressure. The residue was dissolved in 2.0 mL of DCE and the DCE solution was added dropwise to 40 mL of n-hexane. The mixture was stirred overnight at room temperature. The solid was collected by filtration and washed with n-hexane (3×10 mL) and dried to afford the crude product (100 mg) as a brown solid, which was carried forward to the next step without further purification.

Step 5. tert-Butyl N-[[(1R,4S,7S,10S,13S,16R, 19R)-13-[(1S)-1-tert-butoxyethyl]-7-cyclohexyl-4-isobutyl-3,16-dimethyl-2,5,8,11,14-pentaoxo-18-oxa-3,6,9,12,15-pentazabicyclo[17.8.0]heptacosan-10-yl]methyl]carbamate

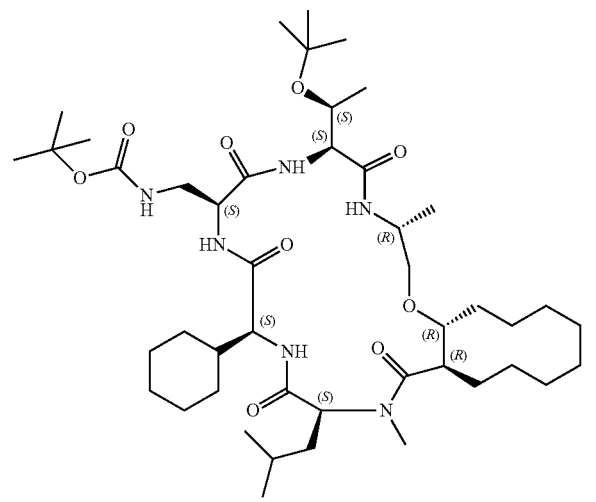

A mixture of the crude bicyclic olefin from Step 4 and 10% Pd/C (433 mg) in ethyl acetate (50 mL) was stirred under an atmosphere of hydrogen gas for 15 h at 25° C. The catalyst was removed via filtration and the filtrate was concentrated under reduced pressure. The residue was purified by reverse phase chromatography on C18 column to afford the title compound (23.2 mg) as a yellow oil. LCMS (ESI): [M+H]$^+$=849.5.

Step 6. (1R,4S,7S,10S,13S,16R,19R)-10-(Aminomethyl)-7-cyclohexyl-13-[(1S)-1-hydroxyethyl]-4-isobutyl-3,16-dimethyl-18-oxa-3,6,9,12,15-pentazabicyclo[17.8.0]heptacosane-2,5,8,11,14-pentone

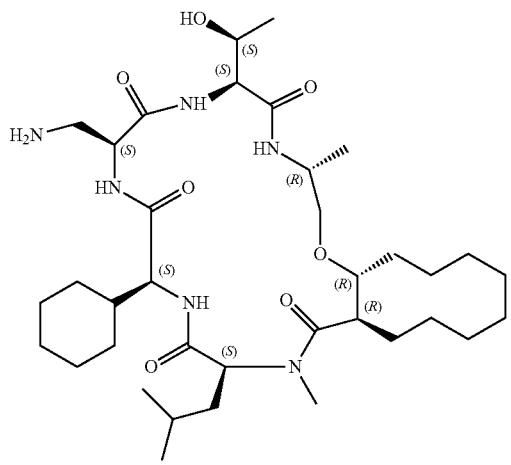

The product from Step 5 (23.2 mg) was treated with TFA (5.0 mL) at 0° C. for 1 h and then concentrated under reduced pressure. The residue was purified by Prep-LCMS (Column: XBridge Prep C18 OBD Column, 5 um, 19*150 mm; Mobile Phase A: Water (0.05% TFA), Mobile Phase B: ACN; Flow rate: 25 mL/min; Gradient: 20% B to 50% B in 20 min; 220 nm; Rt: 18.74 min) to afford the trifluoroacetate salt of the title compound (5.3 mg) as a yellow solid. LCMS (ESI): [M+H]$^+$=693.5, R$_t$=2.5 min, method H. $^1$H NMR (400 MHz, DMSO-d$_6$): δ 8.72-8.67 (m, 1H), 8.40-8.25 (m, 1H), 7.94-7.88 (m, 3H), 7.64-7.45 (m, 1H), 7.24-6.95 (m, 1H), 4.63-4.54 (m, 2H), 4.18-4.07 (m, 2H), 3.95-3.86 (m, 2H), 3.67-3.60 (m, 2H), 3.50-3.43 (m, 1H), 3.21-3.03 (m, 4H), 2.78 (s, 2H), 2.14-2.07 (m, 1H), 1.83-1.43 (m, 24H), 1.24-1.09 (m, 6H), 1.01-0.88 (m, 12H).

Example 9. (3S,6S,9S,12S,15S,18R)-6-(Aminoethyl)-9-cyclohexyl-16-(cyclopentylmethyl)-18-ethyl-3-((S)-1-hydroxyethyl)-12-isobutyl-13,15-dimethyl-1,4,7,10,13,16-hexaazacyclooctadecane-2, 5,8,11,14-pentaone (trifluoroacetate salt)

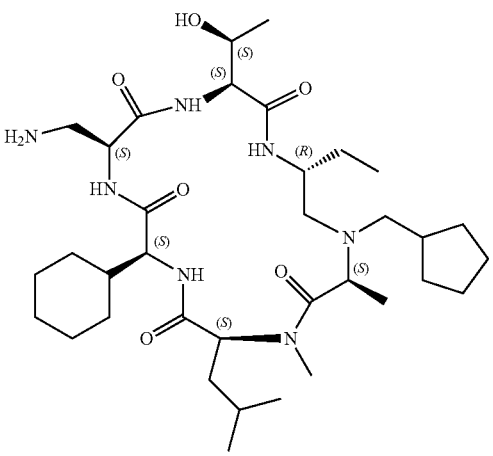

Step 1. Benzyl N—((R)-2-((tert-butoxycarbonyl)amino)butyl)-N-(cyclopentylmethyl)-L-alaninate

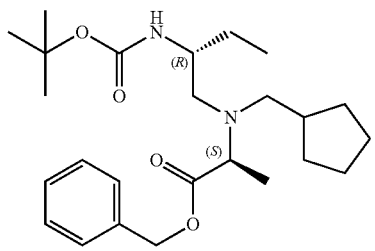

To a solution of tert-butyl N-[(1R)-1-(hydroxymethyl)propyl]carbamate (1.037 g, 5.480 mmol) in DCM (16 mL, 249.6 mmol) was added Dess-Martin periodinane (1.2 equiv.). The reaction mixture was stirred at room temperature for 4 h. To the reaction mixture was added benzyl (2S)-2-aminopropanoate hydrochloride (911 mg, 4.22 mmol), sodium triacetoxyborohydride (1.816 g, 8.568 mmol) and ethyl acetate (10 mL). The reaction mixture was stirred at room temperature for 2 h. To this mixture was then added cyclopentane carbaldehyde (0.80 mL, 7.6 mmol) and sodium triacetoxyborohydride (1.65 g, 7.79 mmol), and the reaction continued at room temperature for 18 h. The reaction mixture was diluted with ethyl acetate, washed with aqueous sodium bicarbonate and brine, dried over magnesium sulfate, filtered, and evaporated in vacuo. The crude product was purified via flash chromatography on silica gel (80 g silica, solvent gradient: 0-70% isopropyl acetate in heptanes) to yield 1.025 g (56%) of the title compound. LCMS (ESI): $[M+H]^+=433.3$

Step 2. N—((R)-2-((tert-Butoxycarbonyhamino)butyl)-N-(cyclopentylmethyl)-L-alanine

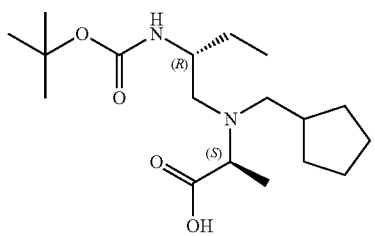

To a solution of benzyl N—((R)-2-((tert-butoxycarbony)amino)butyl)-N-(cyclopentylmethyl)-L-alaninate (1.1878 g, 2.746 mmol) in ethanol (10 mL) under nitrogen was added palladium (10 wt. % on carbon) (154 mg, 0.1447 mmol). The reaction vessel was purged with nitrogen and then hydrogen, and stirred under a balloon of hydrogen at room temperature for 4 h. The reaction mixture was filtered through celite, rinsing with methanol, and evaporated in vacuo to afford the title compound which was carried forward without purification. LCMS (ESI): $[M+H]+=343.25$.

Step 3. N—((S)-2-((S)-2-((S)-2-((S)-2-(((R)-2-Aminobutyl)(cyclopentylmethyl)amino)-N-methylpropanamido)-4-methylpentanamido)-2-cyclohexylacetamido)-3-(((benzyloxy)carbonyl)amino)propanoyl)-O-benzyl-L-allothreonine

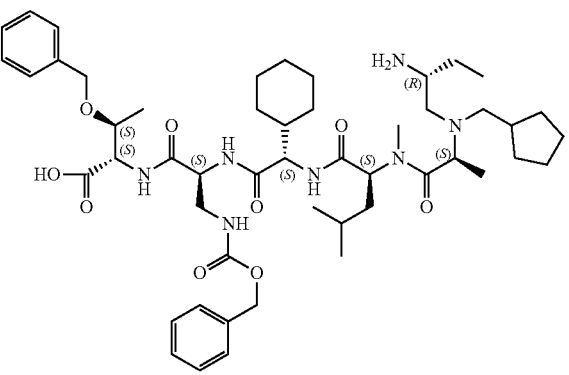

To a filter tube was added Intermediate 15 (0.770 g, estimated 0.47 mmol/g) and 8 mL DMA. The resin was allowed to swell at room temperature for 90 min and then drained. To the resin was added a solution of N—((R)-2-((tert-butoxycarbonyl)amino)butyl)-N-(cyclopentylmethyl)-L-alanine (231 mg, 0.674 mmol) and PyAOP (789 mg, 1.453 mmol) in DMF (4 mL), followed by DIPEA (0.40 mL, 2.3 mmol). The resulting mixture was placed on a rotator at room temperature for 16 h. The resin was drained and rinsed with DMA (5×) and DCM (5×). To the resin was added 6 mL of 7:2:1 DCM:AcOH:trifluoroethanol. This mixture was placed on a rotator at room temperature for 2 h, and then filtered, rinsing with DCM. The filtrate was evaporated in vacuo, azeotroping with toluene (3×2 mL). The resulting residue was dissolved in DCM (5 mL) and treated with hydrogen chloride (4.0 mol/L in dioxane, 1.0 mL, 4.0 mmol). This mixture was stirred at room temperature for 90 min, and then evaporated in vacuo to yield the crude peptide (177.7 mg, 51% crude yield) which was carried forward to the next step without purification. LCMS (ESI): $[M+H]^+=920.7$.

Step 4. Benzyl (((2S,5S,8R,11S,14S,17S)-5-((S)-1-(benzyloxy)ethyl)-17-cyclohexyl-10-(cyclopentylmethyl)-8-ethyl-14-isobutyl-11,13-dimethyl-3,6,12,15,18-pentaoxo-1,4,7,10,13,16-hexaazacyclooctadecan-2-yl)methyl)carbamate

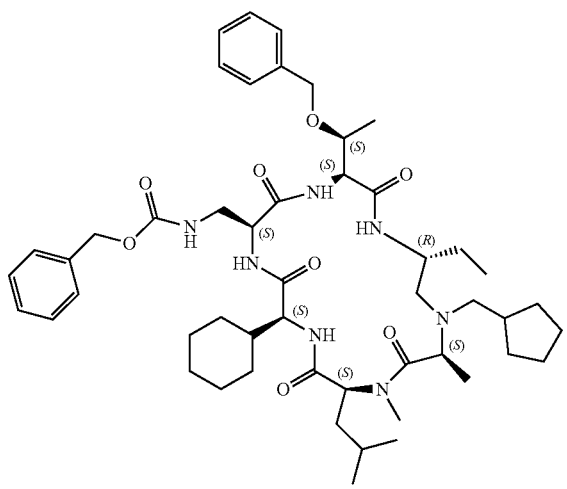

To a room temperature, stirring solution of DIPEA (0.2 mL, 1 mmol) and HATU (167 mg, 0.430 mmol) in THF (100 mL) was added a solution of N—((S)-2-((5)-2-((S)-2-((5)-2-(((R)-2-aminobutyl)(cyclopentylmethyl)amino)-N-methylpropanamido)-4-methylpentanamido)-2-cyclohexylacetamido)-3-(((benzyloxy)carbonyl)amino)propanoyl)-O-benzyl-L-allothreonine (177.7 mg, 0.1858 mmol) in THF (50 mL), dropwise over 1 h. After an additional 90 min the reaction mixture was evaporated in vacuo. The resulting residue was diluted with ethyl acetate, washed with water (2×) and brine, dried over magnesium sulfate, filtered, and evaporated in vacuo. The crude product was purified via flash chromatography on silica gel (12 g silica, solvent gradient: 0-10% methanol in DCM) to yield 76.6 mg of the title compound. LCMS (ESI): [M+H]⁺=902.7.

Step 5. (3S,6S,9S,12S,15S,18R)-6-(Aminomethyl)-9-cyclohexyl-16-(cyclopentylmethyl)-18-ethyl-3-((S)-1-hydroxyethyl)-12-isobutyl-13,15-dimethyl-1,4,7,10,13,16-hexaazacyclooctadecane-2,5,8,11,14-pentaone A flask was charged with benzyl (((2S,5S,8R,11S,14S,17S)-5-((S)-1-(benzyloxy)ethyl)-17-cyclohexyl-10-(cyclopentylmethyl)-8-ethyl-14-isobutyl-11,13-dimethyl-3,6,12,15,18-pentaoxo-1,4,7,10,13,16-hexaazacyclooctadecan-2-yl)methyl)carbamate (76.6 mg, 0.085 mmol) and ethyl acetate (5 mL), and the flask purged with nitrogen. After the addition of trifluoroacetic acid (25 µL, 0.323 mmol) and palladium (10 wt. % on carbon) (104 mg, 0.0977 mmol) the reaction mixture was evacuated and backfilled with hydrogen, and then stirred at room temperature under a hydrogen balloon for 18 h. The reaction mixture was filtered through celite, rinsing with 100 mL of 5% AcOH in ethanol, and the filtrate was evaporated in vacuo, azeotroping with toluene (3×1 mL). The crude product was purified via reverse-phase HPLC and lyophilized to yield 27.6 mg (48%) of the title compound as its trifluoroacetate salt. LCMS (ESI): R$_T$ (min)=7.920, [M+H]⁺=762.5, method=B; ¹H NMR (400 MHz, Methanol-d₄) δ 4.93 (d, J=15.6 Hz, 1H), 4.64-4.17 (m, 4H), 4.15-3.94 (m, 2H), 3.79-3.44 (m, 4H), 3.38 (s, 1H), 3.26 (d, J=11.8 Hz, 2H), 3.13-2.92 (m, 1H), 2.08 (dd, J=42.7, 18.2 Hz, 4H), 1.99-1.11 (m, 27H), 1.11-0.90 (m, 11H).

Example 10. (3R,6S,9S,12S,15S,18R,19R)-9-(Aminomethyl)-6-0(1r,3S)-3-(aminomethybcyclobutoxy)methyl)-12-cycloheptyl-3,16,18-trimethyl-15-propyl-19-(spiro[3.3]heptan-2-ylmethyl)-1-oxa-4,7,10,13,16-pentaazacyclononadecane-5,8,11,14,17-pentaone (trifluoroacetate salt)

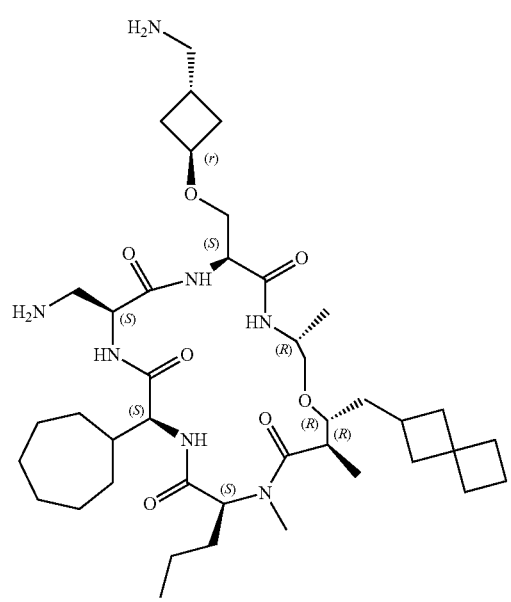

Step 1. N-Me-Norvaline-cycloheptylglycine-Dap(Boc)-trans-tert-butoxycarbonyl)amino)methyl)cyclobutyl)-serine-(2-chlorotrityl resin)

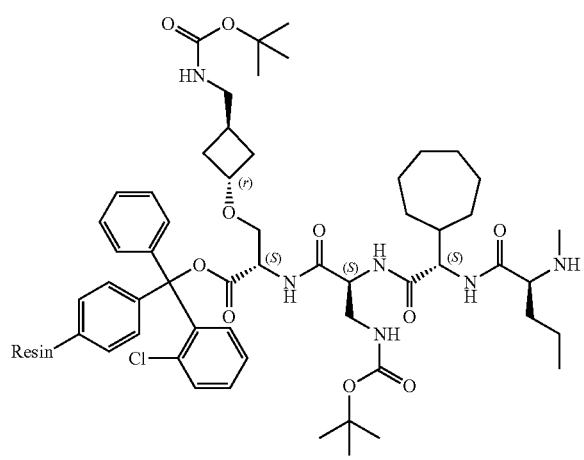

The resin bound tetrapeptide was prepared following methods analogous to those described in Example 7.

Step 2. (3R,6S,9S,12S,15S,18R,19R)-9-(Aminomethyl)-6-[[3-(aminomethyl)cyclobutoxy]methyl]-12-cycloheptyl-3,16,18-trimethyl-15-propyl-19-(spiro[3.3]heptan-2-ylmethyl)-1-oxa-4,7,10,13,16-pentazacyclononadecane-5,8,11,14,17-pentone Using the intermediate from Step 1 and (2R,3R)-3-((R)-2-((((9H-fluoren-9-yl)methoxy)carbonyl)amino)propoxy)-2-methyl-4-(spiro[3.3]heptan-2-yl)butanoic acid (Intermediate 4), the title compound was prepared as the TFA salt following methods analogous to those described in Example 13, steps 2-4. LCMS (ESI): [M+H]$^+$=774.6, R$_t$=2.21 min, method H. $^1$H NMR (400 MHz, DMSO-d$_6$): δ 8.52-8.12 (m, 2H), 8.08-8.02 (m, 3H), 7.76 (br, 3H), 7.46-7.38 (m, 1H), 4.68-4.56 (m, 7H), 4.36-4.28 (m, 2H), 4.11-4.02 (m, 2H), 3.96-3.82 (m, 2H), 3.76-3.68 (m, 1H), 3.48-3.40 (m, 1H), 3.38-3.12 (m, 4H), 3.07 (s, 1H), 2.90-2.87 (m, 3H), 2.73 (s, 2H), 2.39-2.28 (m, 2H), 2.07-1.94 (m, 8H), 1.83-1.70 (m, 5H), 1.67-1.27 (m, 15H), 1.02-0.87 (m, 8H).

Example 11. (3R,6S,9S,12S,15S,18R,19R)-6-(((2-Azaspiro[3.3]heptan-6-yl)oxy)methyl)-9-(aminomethyl)-12-cycloheptyl-19-hexyl-3,16,18-trimethyl-15-propyl-1-oxa-4,7,10,13,16-pentaazacyclononadecane-5,8,11,14,17-pentaone (trifluoroacetate salt)

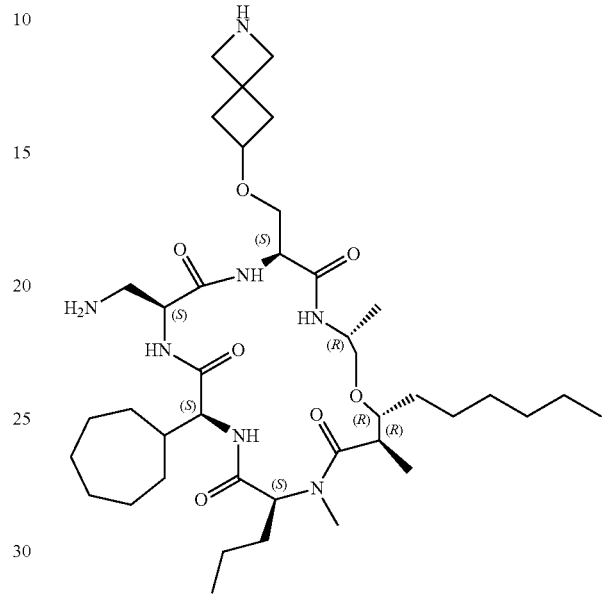

Step 1. N—((S)-2-((S)-2-((S)-2-((2R,3R)-3-((R)-2-Aminopropoxy)-N,2-dimethylnonanamido)pentanamido)-2-cycloheptylacetamido)-3-(((benzyloxy)carbonyl)amino)propanoyl)-O-(2-(tert-butoxycarbonyl)-2-azaspiro[3.3]heptan-6-yl)-L-serine

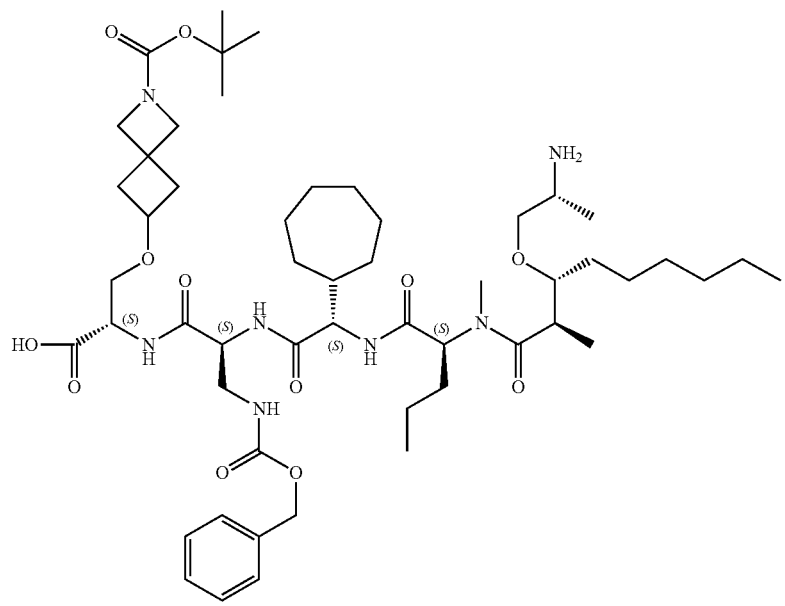

Commercially available 2-chlorotrityl chloride resin (resin loading 1.5 mmol/g, 1.255 g) was swelled with 10 mL DMA for 4.5 h. The resin was drained, and treated with a solution of N-(((9H-fluoren-9-yl)methoxy)carbonyl)-O-(2-(tert-butoxycarbonyl)-2-azaspiro[3.3]heptan-6-yl)-L-serine (Intermediate 8) (0.775 g, 1.48 mmol) and DIPEA (0.60 mL, 3.4 mmol) in DMA (5 mL). The resin was placed on a rotator at room temperature overnight. The resin was drained and rinsed with DMA (2×8 mL), and then unreacted resin was capped by treatment with 6 mL of 2:1 DCM:methanol for 15 min. The resin was drained and rinsed with DMA (3×8 mL).

(premixed at room temperature for 15 min) of Fmoc-allothreonine(Bzl)-OH (3.267 g, 7.571 mmol), HBTU (2.904 g, 7.657 mmol), DIPEA (1.9 mL, 11 mmol) and DMA (25 mL). The resin was agitated with nitrogen bubbling for 2.5 hr, and then drained and rinsed with DMA. Unreacted starting material was capped by treating the resin with 25 mL DMA, 1 mL DIPEA and 1 mL acetic anhydride. The resin was agitated with nitrogen bubbling for 5 min, and then drained and rinsed with DMA (2×25 mL) and DCM (3×25 mL). The resin was treated with 8 mL of 20% piperidine in DMF for 2.5 h. The resin was drained and rinsed sequentially with DMA (3×8 mL), DCM (3×8 mL), and DMA (2×8 mL).

The resin was treated with a solution (premixed at room temperature for 20 min) of Fmoc-Dap(Cbz)-OH (1.384 g, 3.005 mmol), HBTU (1.14 g, 3.01 mmol), and DIPEA (0.8 mL, 5 mmol) in DMA (5 mL). The resin was placed on a rotator at room temperature for 1.75 h, and then drained and rinsed sequentially with 3×50 mL DMA and 3×50 mL DCM. The resin was treated with 8 mL of 20% piperidine in DMF for 90 min. The resin was drained and rinsed sequentially with DMA (4×8 mL), DCM (4×8 mL).

The resin was treated with a solution (premixed at room temperature for 15 min) of (2S)-2-cycloheptyl-2-(9H-fluoren-9-ylmethoxycarbonylamino)acetic acid (Intermediate 11, 824 mg, 2.09 mmol), HBTU (1.14 g, 3.01 mmol), and DIPEA (0.8 mL, 5 mmol) in DMA (5 mL). The resin was placed on a rotator at room temperature for 2 h, and then drained and rinsed with DMA (3×8 mL). The resin was treated with 8 mL of 20% piperidine in DMF for 1 h. The resin was drained and rinsed sequentially with DMA (3×8 mL), DCM (3×8 mL), and DMA (2×8 mL).

The resin was treated with a solution (premixed at room temperature for 15 min) of Fmoc-N-Me-norvaline (1.06 g, 3.00 mmol), HBTU (1.12 g, 2.95 mmol) and DIPEA (0.8 mL, 5 mmol) in DMA (5 mL). The resin was placed on a rotator at room temperature for 2 h, and then drained and rinsed with DMA (3×8 mL), and DCM (3×8 mL). The resin was treated with 8 mL of 20% piperidine in DMF for 2 h. The resin was drained and rinsed sequentially with DMA (4×8 mL), DCM (4×8 mL).

The resin was swelled in DMA, and then drained and treated with a mixture of (2R,3R)-3-((R)-2-((((9H-fluoren-9-yl)methoxy)carbonyl)amino)propoxy)-2-methylnonanoic acid (Intermediate 3) (644.0 mg, 1.377 mmol), PyAOP (980.4 mg, 1.805 mmol) and DIPEA (0.45 mL, 2.6 mmol) in DMF (5 mL, 64.4 mmol). The resulting mixture was placed on a rotator at room temperature for 18 h. The resin was filtered and rinsed with DMA (3×8 mL) and DCM (3×8 mL).

To the resin was added 8 mL of 20% piperidine in DMF. The reaction vessel was placed on rotator at room temperature for 2.5 hr, and then drained and rinsed sequentially with DMA (4×8 mL) and DCM (4×8 mL).

To the resin was added DCM (6 mL, 93.61 mmol) and HFIP (2 mL, 19.07 mmol). The reaction vessel was placed on a rotator at room temperature for 2.5 h. The resin was filtered, rinsing with DCM, and the filtrate was evaporated in vacuo to yield the crude peptide. LCMS (ESI): [M+H]$^+$=1014.8.

Step 2. tert-Butyl 6-(((3R,6S,9S,12S,15S,18R,19R)-9-((((benzyloxy)carbonyl)amino)methyl)-12-cyclo-heptyl-19-hexyl-3,16,18-trimethyl-5,8,11,14,17-pentaoxo-15-propyl-1-oxa-4,7,10,13,16-pentaazacyclononadecan-6-yl)methoxy)-2-azaspiro[3.3]heptane-2-carboxylate

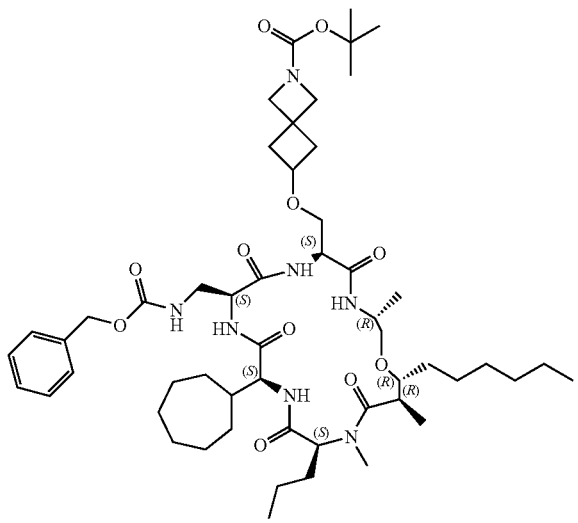

To a room temperature, stirring solution of DIPEA (0.20 mL, 1.1 mmol) and HATU (314 mg, 0.809 mmol) in THF (200 mL) was added a solution N—((S)-2-((S)-2-((S)-2-((2R,3R)-3-((R)-2-aminopropoxy)-N,2-dimethylnonanamido)pentanamido)-2-cycloheptylacetamido)-3-(((benzyloxy)carbonyl)amino)propanoyl)-O-(2-(tert-butoxycarbonyl)-2-azaspiro[3.3]heptan-6-yl)-L-serine (412.0 mg, 0.4062 mmol) in THF (100 mL), dropwise over 90 min. After an additional 1 h, the reaction mixture was evaporated in vacuo. The resulting residue was diluted with ethyl acetate, washed with water (2×) and brine, dried over magnesium sulfate, filtered, and evaporated in vacuo. The crude product was purified via flash chromatography on silica gel (24 g silica, solvent gradient: 0-10% methanol in DCM), to yield 157.4 mg (39%) of the title compound. LCMS (ESI): [2M+H]$^+$=1992.15.

Step 3. (3R,6S,9S,12S,15S,18R,19R)-6-(((2-Azaspiro[3.3]heptan-6-yl)oxy)methyl)-9-(aminomethyl)-12-cycloheptyl-19-hexyl-3,16,18-trimethyl-15-propyl-1-oxa-4,7,10,13,16-pentaazacyclononadecane-5,8,11,14,17-pentaone A flask was charged with tert-butyl 6-(((3R,6S,9S,12S,15S,18R,19R)-9-((((benzyloxy)carbonyl)amino)methyl)-12-cycloheptyl-19-hexyl-3,16,18-trimethyl-5,8,11,14,17-pentaoxo-15-propyl-1-oxa-4,7,10,13,16-pentaazacyclononadecan-6-yl)methoxy)-2-azaspiro[3.3]heptane-2-carboxylate (157.4 mg, 0.1580 mmol) and ethyl acetate (5 mL), and the flask purged with nitrogen. After the addition of trifluoroacetic acid (25 μL, 0.323 mmol) and palladium (10 wt. % on carbon) (187 mg, 0.176 mmol) the reaction mixture was evacuated and backfilled with hydrogen, and then stirred at room temperature under a hydrogen balloon for 16 h. The reaction mixture was filtered through celite, rinsing with 100 mL of 5% acetic acid in ethanol, and the filtrate was evaporated in vacuo, azeotroping with toluene (3×1 mL). To the resulting residue at 0° C. was added DCM (2.0 mL) and trifluoroacetic acid (0.2 mL, 3 mmol). This mixture was stirred at 0° C. for 5 h and then evaporated in vacuo, azeotroping with toluene (2×2 mL), and the resulting residue was purified via reverse-phase HPLC and lyophilized to yield 30.1 mg (21%) of the title compound as its trifluoroacetate salt. LCMS (ESI): $R_T$ (min)=10.073, $[M+H]^+$=762.5, method=B; $^1$H NMR (400 MHz, DMSO-$d_6$) δ 8.66-8.27 (m, 3H), 8.18-7.69 (m, 5H), 7.37 (d, J=8.4 Hz, 1H), 4.56 (dd, J=10.6, 4.7 Hz, 1H), 4.47-4.13 (m, 2H), 4.04 (d, J=14.5 Hz, 1H), 3.99-3.72 (m, 8H), 3.64 (d, J=13.2 Hz, 2H), 3.29-2.70 (m, 9H), 2.11 (d, J=70.9 Hz, 4H), 1.87-1.11 (m, 25H), 1.11-0.79 (m, 12H).

Example 12. (3S,6S,9S,12S,15S,18R)-6-(Aminomethyl)-3-((3-aminopropoxy)methyl)-15,16-dibutyl-9-cyclohexyl-12-isobutyl-13,18-dimethyl-1,4,7,10,13,16-hexaazacyclooctadecane-2,5,8,11,14-pentaone (trifluoroacetate salt)

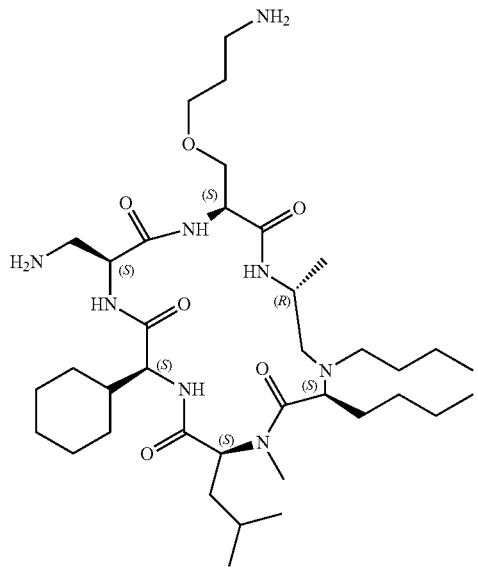

Step 1. N-Me-Leucine-cyclohexylglycine-Dap (Boc)-3-(((tert-butoxycarbonyl)amino)propyl)-serine-(2-chlorotrityl resin)

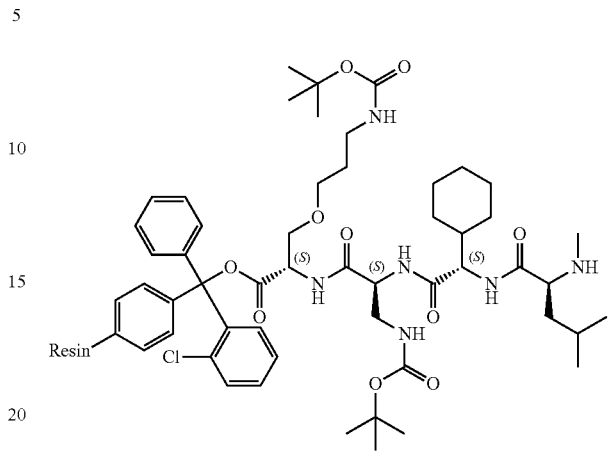

The resin bound tetrapeptide was prepared following methods analogous to those described for Example 7, Step 1.

Step 2. (2S,5S,8S,11S,14S)-15-((R)-2-Aminopropyl)-5-(((tert-butoxycarbonyl)amino)methyl)-2-((3-((tert-butoxycarbonyl)amino)propoxy)methyl)-14-butyl-8-cyclohexyl-11-isobutyl-12-methyl-4,7,10,13-tetraoxo-3,6,9,12,15-pentaazanonadecan-1-oic acid

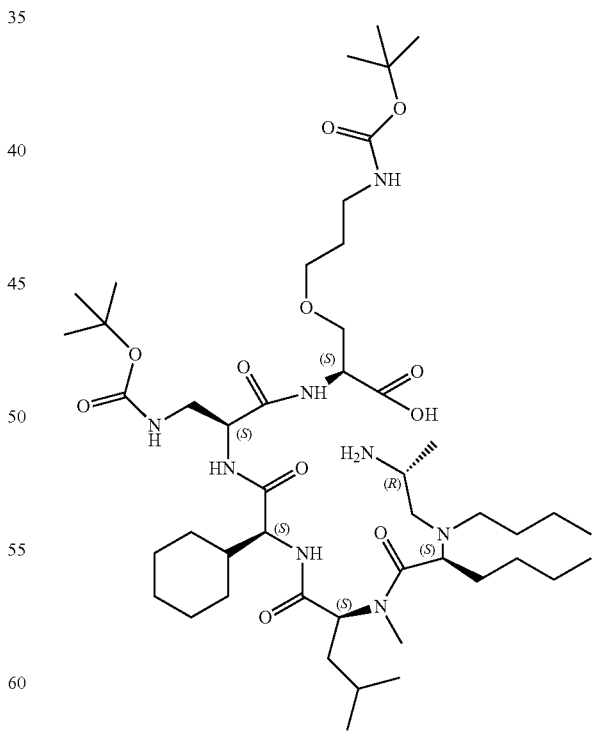

The resin bound tetrapeptide from Step 1 (1.50 g, resin loading ~0.6 mmol/g) was treated with a mixture (pre-mixed for 10 min at room temperature) of (2S)-2-[butyl-[(2R)-2-(9H-fluoren-9-ylmethoxycarbonylamino)propyl]amino]

hexanoic acid (672 mg, 1.44 mmol, Intermediate T13), PyAOP (1.88 g, 3.60 mmol) and DIPEA (0.94 mL, 5.4 mmol) in 10 mL of DMF. The resin was shaken for 16 h on a rotator, drained, and rinsed with DMF (4×10 mL) and DCM (2×10 mL). The resin was then treated with 15 mL of 20% piperidine in DMF, shaken for 1 h on a rotator, then drained and rinsed with DMF (4×10 mL) and DCM (2×10 mL). The resin was treated with 10 mL of HFIP/DCM (1/4) mixture, and agitated with nitrogen bubbling for 1 h. The liquid phase was collected and the resin was treated with 10 mL of HFIP/DCM (1/4) two more times for 1 h each. The liquid phases were combined and the resin was washed with DCM (2×10 mL). The filtrates were combined and concentrated under vacuum. The residue was purified by flash chromatography on C18 eluting with $CH_3CN/H_2O$ to afford the title compound (330 mg, 39% yield) as a yellow solid. LCMS (ESI): $[M+H]^+$=941.7.

Step 3. N-[3-[[(2S,5R,8S,11S,14S,17S)-17-[(tert-Butoxycarbonylamino)methyl]-7,8-dibutyl-14-cyclohexyl-11-isobutyl-5,10-dimethyl-3,9,12,15,18-pentaoxo-1,4,7,10,13,16-hexazacyclooctadec-2-yl]methoxy]propyl]carbamate

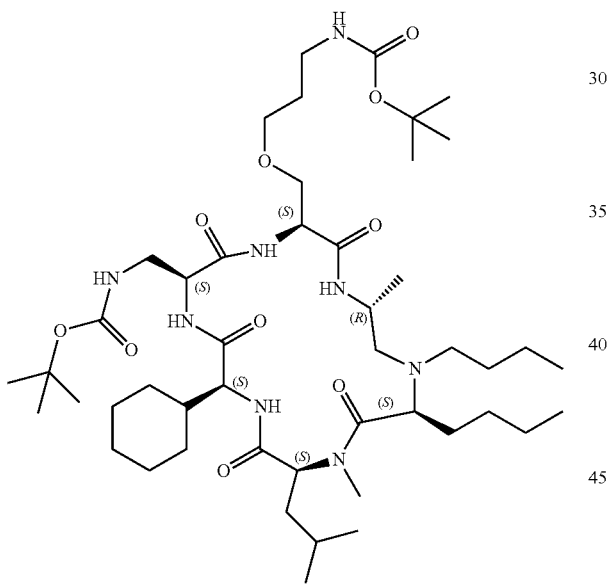

The title compound was prepared using the material from Step 2 following methods analogous to those described in Example 7, Step 3. LCMS (ESI): $[M+H]^+$=923.7.

Step 4. (3S,6S,9S,12S,15S,18R)-6-(Aminomethyl)-3-(3-aminopropoxymethyl)-15,16-dibutyl-9-cyclohexyl-12-isobutyl-13,18-dimethyl-1,4,7,10,13,16-hexazacyclooctadecane-2,5,8,11,14-pentone The title compound was prepared as the trifluoroacetate salt using the material from Step 3 and following methods analogous to those described for Example 7, Step 4. LCMS (ESI): $[M+H]^+$=723.6, $R_t$=2.19 min, method=J. $^1$H NMR (400 MHz, DMSO-$d_6$): δ 9.01-8.64 (m, 2H), 8.21-8.05 (m, 3H), 7.85-7.72 (m, 3H), 7.60-7.22 (m, 2H), 4.82-4.72 (m, 1H), 4.44-4.31 (m, 2H), 4.09-3.92 (m, 2H), 3.49-3.32 (m, 10H), 3.23-3.12 (m, 4H), 2.92-2.80 (m, 3H), 2.21-2.11 (m, 1H), 2.06-1.93 (m, 2H), 1.81-1.73 (m, 3H), 1.70-1.55 (m, 8H), 1.42-1.26 (m, 6H), 1.19-1.10 (m, 5H), 1.07-0.83 (m, 15H).

Example 13. (3R,6S,9S,12S,15S,18R,19R)-6-(((1r,3S)-3-Aminocyclobutoxy)methyl)-9-(aminomethyl)-19-01R,3s,5S)-bicyclo[3.2.1]octan-3-ylmethyl)-12-cycloheptyl-3,16,18-trimethyl-15-propyl-1-oxa-4,7,10,13,16-pentaazacyclononadecane-5,8,11,14,17-pentaone (trifluoroacetate salt)

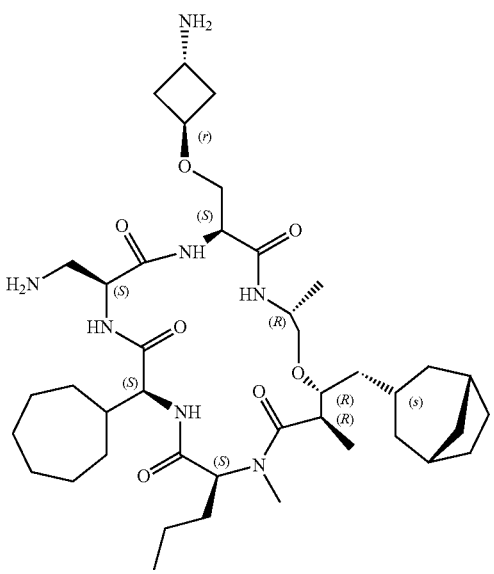

Step 1. N-Me-Norvaline-cycloheptylglycine-Dap(Boc)-trans-tert-butoxycarbonyl)amino-cyclobutyl)-serine-(2-chlorotrityl resin)

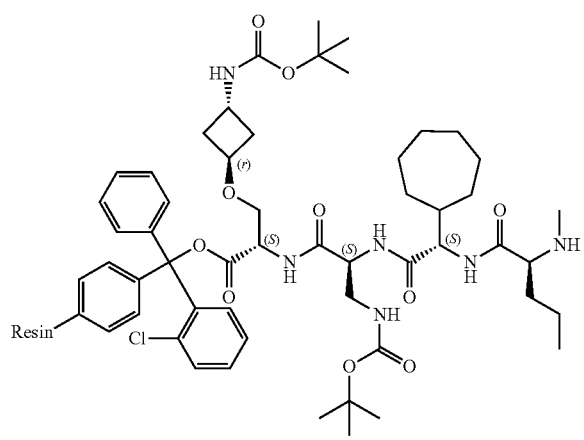

The resin bound tetrapeptide was prepared following methods analogous to those described in Example 7, Step 1.

233

Step 2. (2S,5S,8S,11S,14R,15R,18R)-18-Amino-15-01R,3s,5S)-bicyclo[3.2.1]octan-3-ylmethyl)-2-(((1r,3S)-3-((tert-butoxycarbonyl)amino)cyclobutoxy)methyl)-5-(((tert-butoxycarbonyl)amino)methyl)-8-cycloheptyl-12,14-dimethyl-4,7,10,13-tetraoxo-11-propyl-16-oxa-3,6,9,12-tetraazanonadecan-1-oic acid

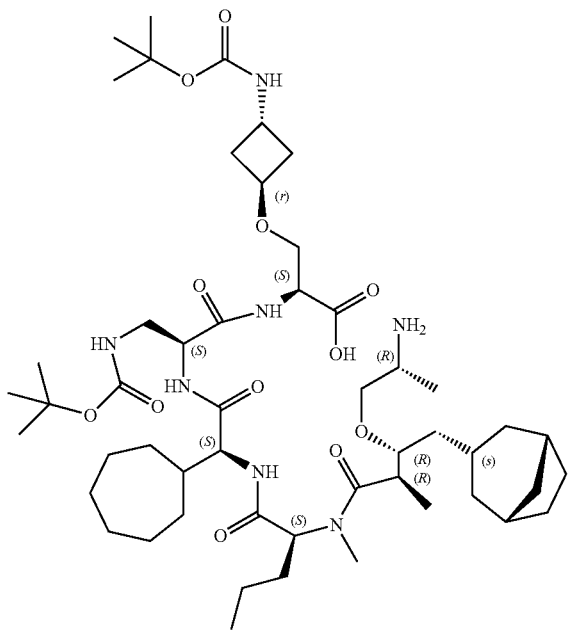

The resin-bound tetrapeptide from Step 1 (600 mg, 0.5 mmol/g) was treated with THF (3 mL) and DIPEA (0.31 mL, 1.8 mmol), and allowed to swell for 30 min. Separately a solution of (2R,3R)-4-[(1S,5R)-3-bicyclo[3.2.1]octanyl]-3-[(2R)-2-(9H-fluoren-9-ylmethoxycarbonylamino)propoxy]-2-methyl-butanoic acid (243 mg, 0.478 mmol, Intermediate 5) in THF (6.0 mL) was added to a solution of triphosgene (55.2 mg, 0.19 mmol) in THF (3.0 mL). 2,4,6-Trimethylpyridine (0.87 mL, 6.6 mmol) was added dropwise, upon which the mixture evolves heat and a colorless precipitate formed. This suspension was gently shaken for about 1 min, after which it was added to the pretreated resin. The mixture was placed on a rotator at room temperature for 3 h, drained and then rinsed with DMF (10 mL) and DCM (2×10 mL).

The resin was treated with 10 mL of 20% piperidine in DMF, agitated with nitrogen bubbling for 1 h, then drained and rinsed with DMF (2×10 mL) and DCM (2×10 mL). The resin was then treated with a HFIP/DCM=1/4 solution (20 mL) and shaken on a rotator at room temperature for 1 h, then filtered. The liquid phase was collected. The process was repeated with HFIP/DCM=1/4 and the liquid phase collected. The resin was washed with DCM (3×10 mL). The liquid phases and filtrates were combined and concentrated under vacuum. The residue was purified by reverse phase flash chromatography on C18 column to afford the title compound (262 mg) as a yellow solid. LCMS (ESI): [M+H]$^+$=992.7.

234

Step 3. tert-Butyl N-[[(3R,6S,9S,12S,15S,18R,19R)-19-[[(1S,5R)-3-bicyclo[3.2.1]octanyl]methyl]-6-[[3-(tert-butoxycarbonylamino)cyclobutoxy]methyl]-12-cycloheptyl-3,16,18-trimethyl-5,8,11,14,17-pentaoxo-15-propyl-1-oxa-4,7,10,13,16-pentazacyclononadec-9-yl]methyl]carbamate

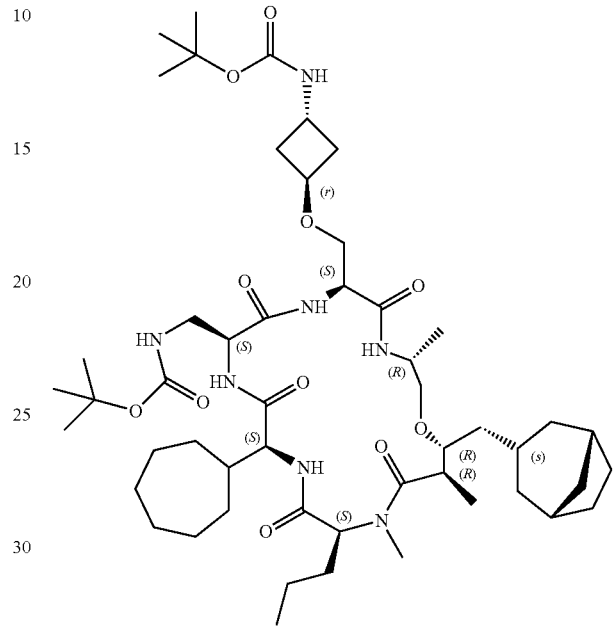

The product from Step 2 (240 mg, 0.242 mmol) was dissolved in THF (240 mL) containing DIPEA (0.17 mL, 0.97 mmol). The solution was cooled to 0° C. To this solution was added dropwise a premixed solution of HATU (138 mg, 0.36 mmol) and HOBt (49.1 mg, 0.36 mmol) in DMF (2 mL) and THF (8 mL) at 0° C. The mixture was stirred at 0° C. for 1 h. The mixture was concentrated under vacuum to remove THF. The residue was diluted with DMF (3 mL) and added dropwise to water (300 mL) with vigorous stirring. The resulting solid was collected by filtration, washed with water (2×10 mL) and dried to afford the title compound (185 mg, crude) as a colorless solid. LCMS (ESI): [M+H]$^+$=974.6.

Step 4. (3R,6S,9S,12S,15S,18R,19R)-6-(((1r,3S)-3-Aminocyclobutoxy)methyl)-9-(aminomethyl)-19-((1R,3s,5S)-bicyclo[3.2.1]octan-3-ylmethyl)-12-cycloheptyl-3,16,18-trimethyl-15-propyl-1-oxa-4,7,10,13,16-pentaazacyclononadecane-5,8,11,14,17-pentaone The product from Step 3 (175 mg, crude) was treated with trifluoroacetic acid (3.0 mL) and stirred at 0° C. for 2 h. The reaction mixture was concentrated under vacuum. The residue was purified by Prep-HPLC with the following conditions: Column: XSelect CSH Prep C18 OBD Column, 19*250 mm, 5 um; Mobile Phase A: Water (0.05% TFA), Mobile Phase B: ACN; Flow rate: 25 mL/min; Gradient: 20% B to 40% B in 20 min; 210 nm; R$_t$: 19.57 min to afford the title compound as the TFA salt (46.1 mg) as a white solid. LCMS (ESI): [M+H]$^+$=774.6, R$_t$=1.97 min, method H. $^1$H NMR (400 MHz, DMSO-d$_6$): δ 8.52-8.12 (m, 2H), 8.03-7.93 (m, 6H), 7.65-7.33 (m, 1H), 4.56-4.15 (m, 4H), 3.84-

3.60 (m, 4H), 3.28-2.82 (m, 9H), 2.74 (s, 2H), 2.24-2.02 (m, 8H), 1.79-1.58 (m, 10H), 1.52-1.39 (m, 10H), 1.37-1.26 (m, 5H), 1.03-0.93 (m, 11H).

Example 14. (3R,6S,9S,12S,15S,18R,19R)-9-(Aminomethyl)-6-1(3-aminopropylamino)methyl]-12-cycloheptyl-19-hexyl-3,16,18-trimethyl-15-propyl-1-oxa-4,7,10,13,16-pentazacyclononadecane-5,8,11,14,17-pentone (trifluoroacetate salt)

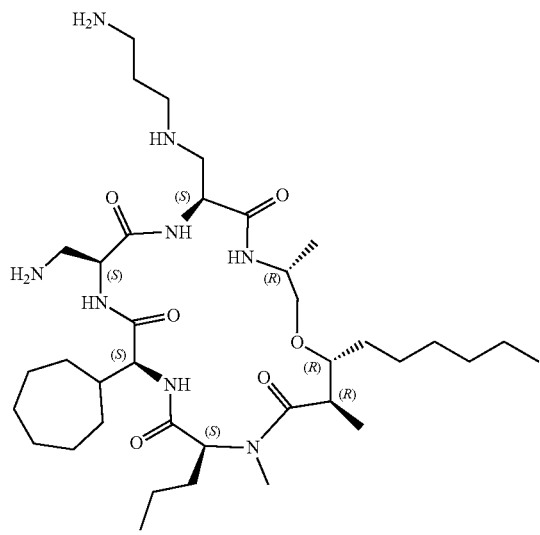

Step 1. Benzyl tert-butyl (((3R,6S,9S,12S,15S,18R,19R)-12-cycloheptyl-19-hexyl-3,16,18-trimethyl-5,8,11,14,17-pentaoxo-15-propyl-1-oxa-4,7,10,13,16-pentaazacyclononadecane-6,9-diyl)bis(methylene)) dicarbamate

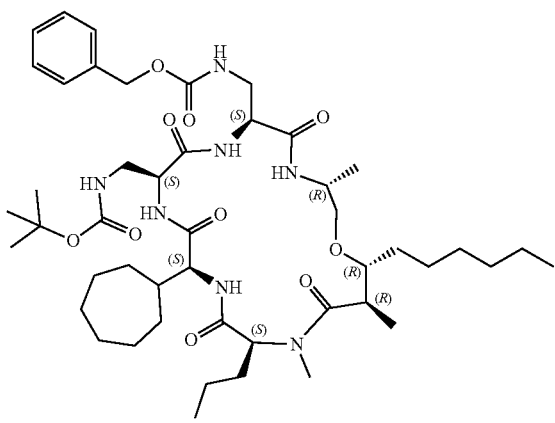

The title compound was prepared following methods analogous to those described in Example 13, Steps 1-3.

Step 2. tert-Butyl N-[1(3R,6S,9S,12S,15S,18R,19R)-6-(aminomethyl)-12-cycloheptyl-19-hexyl-3,16,18-trimethyl-5,8,11,14,17-pentaoxo-15-propyl-1-oxa-4,7,10,13,16-pentazacyclononadec-9-yl]methyl] carbamate

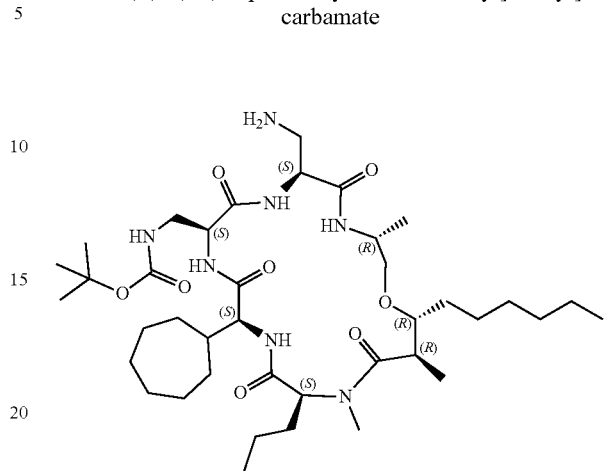

The product of Step 1 (905 mg, 1.01 mmol) and 10% Pd/C (450 mg) in isopropanol (100 mL) was stirred for 16 h at room temperature under hydrogen gas (1 atm). The catalyst was removed via filtration and the filtrate was concentrated under reduced pressure. The residue was purified by reverse phase chromatography on C18 column (0-46% acetonitrile/ 0.05% TFA in water) to afford the title compound (350 mg) as a white solid. LCMS (ESI): $[M+H]^+$=766.6.

Step 3. tert-Butyl N-[3-[[(3R,6S,9S,12S,15S,18R,19R)-9-[(tert-butoxycarbonylamino)methyl]-12-cycloheptyl-19-hexyl-3,16,18-trimethyl-5,8,11,14,17-pentaoxo-15-propyl-1-oxa-4,7,10,13,16-pentazacyclononadec-6-yl]methylamino]propyl] carbamate

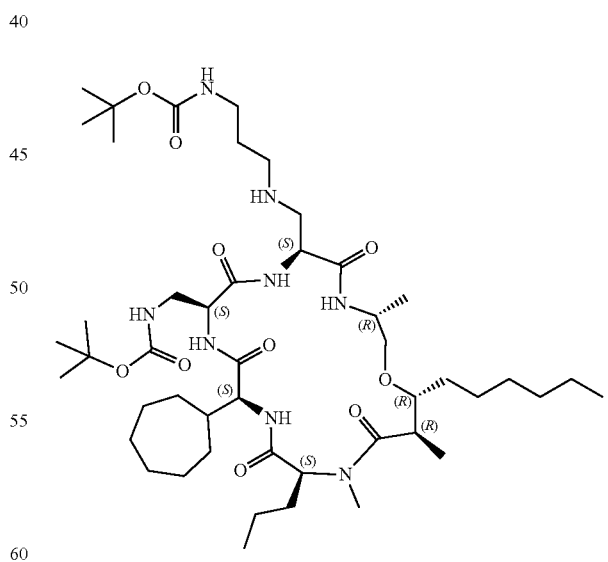

To a solution of the product from Step 2 (420 mg, 0.548 mmol) in DCM (400 mL) was added tert-butyl N-(3-oxopropyl)carbamate (95.7 mg, 0.55 mmol). The solution was stirred for 2 h at room temperature, followed by the addition sodium triacetoxyborohydride (233.6 mg, 1.1 mmol). The resulting mixture was stirred for 2 h at room temperature, and then washed with water and brine. The organic phase was dried over anhydrous sodium sulfate and concentrated under vacuum. The residue was purified by reverse phase flash chromatography on C18 column eluting with CH₃CN/H₂O (45/55) to afford the title compound (235 mg, 46.3% yield) as a white solid. LCMS (ESI): [M+H]⁺=923.6.

Step 4. (3R,6S,9S,12S,15S,18R,19R)-9-(Aminomethyl)-6-1(3-aminopropylamino)methyl]-12-cycloheptyl-19-hexyl-3,16,18-trimethyl-15-propyl-1-oxa-4,7,10,13,16-pentazacyclononadecane-5,8,11,14,17-pentone The product from Step 3 (100.4 mg, 0.11 mmol) was treated with TFA (5.0 mL) at 0° C. for 30 min and then concentrated under vacuum. The residue was purified by prep-LCMS to afford the title compound as its TFA salt (45.5 mg) as a white solid. LCMS (ESI): [M+H]⁺=723.6, $R_f$=2.2 min, method=K. ¹H NMR (400 MHz, DMSO-d₆): δ 8.93-8.56 (m, 3H), 8.38-7.90 (m, 7H), 7.52-7.44 (m, 1H), 4.62-4.55 (m, 2H), 4.28-4.09 (m, 2H), 3.91-3.74 (m, 3H), 3.65-3.48 (m, 4H), 3.23-3.03 (m, 5H), 2.98-2.79 (m, 6H), 2.72 (s, 1H), 2.13-1.90 (m, 5H), 1.80-1.62 (m, 6H), 1.57-1.26 (m, 16H), 1.05-0.84 (m, 11H).

Step 1. (2S,5S,8S,11S,14S,16S)-17-Amino-2-((S)-1-(tert-butoxy)ethyl)-5-(((tert-butoxycarbonyl)amino)methyl)-8-cyclohexyl-15-(cyclopentylmethyl)-11-isobutyl-12,14,16-trimethyl-4,7,10,13-tetraoxo-3,6,9,12,15-pentaazaheptadecan-1-oic acid

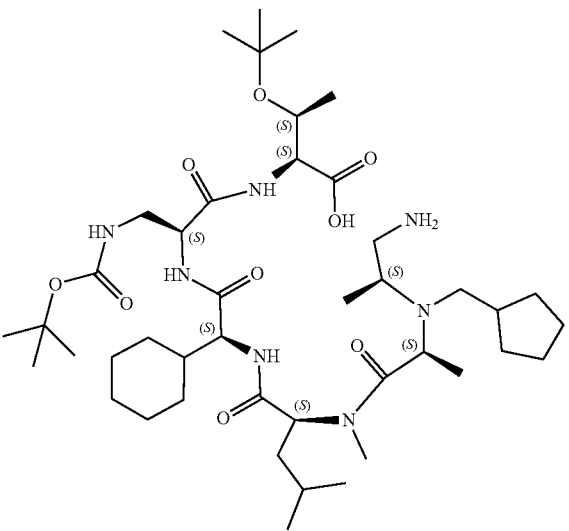

The title compound was prepared from N-Me-leucine-cyclohexylglycine-Dap(Boc)-allothreonine(t-Bu)-(2-chlorotrityl resin) (Example 8, Step 1) and (2S)-2-[cyclopentylmethyl-[(1S)-2-(9H-fluoren-9-ylmethoxycarbonylamino)-1-methyl-ethyl]amino]propanoic acid (Intermediate T21) following methods analogous to those described in Example 12, Step 2. LCMS (ESI): [M+1-1]⁺=838.6.

Step 2. tert-Butyl (((2S,5S,9S,11S,14S,17S)-5-((S)-1-(tert-butoxy)ethyl)-17-cyclohexyl-10-(cyclopentylmethyl)-14-isobutyl-9,11,13-trimethyl-3,6,12,15,18-pentaoxo-1,4,7,10,13,16-hexaazacyclooctadecan-2-yl)methyl)carbamate Example 15. (3S,6S,9S,12S,15S,17S)-6-(Aminomethyl)-9-cyclohexyl-16-(cyclopentylmethyl)-3-((S)-1-hydroxyethyl)-12-isobutyl-13,15,17-trimethyl-1,4,7,10,13,16-hexaazacyclooctadecane-2,5,8,11,14-pentaone (trifluoroacetate salt)

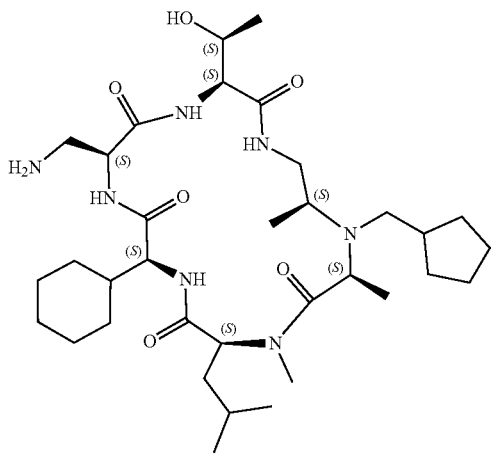

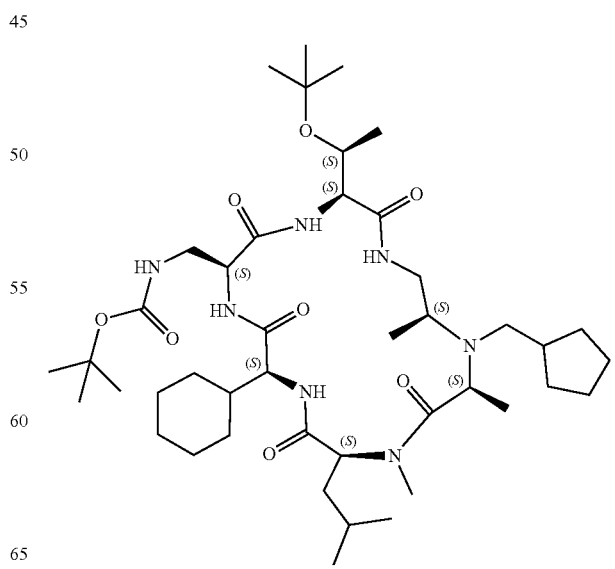

The title compound was prepared using the product of Step 1 and following methods analogous to those described in Example 12, Step 3. LCMS (ESI): [M+H]⁺=820.6.

Step 3. (3S,6S,9S,12S,15S,17S)-6-(Aminomethyl)-9-cyclohexyl-16-(cyclopentylmethyl)-3-((S)-1-hydroxyethyl)-12-isobutyl-13,15,17-trimethyl-1,4,7,10,13,16-hexaazacyclooctadecane-2,5,8,11,14-pentaone The product from Step 2 (192 mg, 0.234 mmol) was treated with TFA (10 mL) for 1 h at 0° C. The mixture was evaporated under reduced pressure and the residue was purified by Preparatory-LCMS: Column: XBridge Prep C18 OBD Column, 5 um, 19*150 mm; Mobile Phase A: Water (0.05% TFA), Mobile Phase B: ACN; Flow rate: 25 mL/min; Gradient: 10% B to 35% B in 20 min; 210 nm; Rt: 14.86 min to afford the title compound as its TFA salt (14.6 mg) as a white solid. LCMS (ESI): [M+H]⁺=664.5, $R_f$=2.18 min, method=J. ¹H NMR (300 MHz, DMSO-$d_6$): δ 9.00-8.59 (m, 1H), 8.09-7.95 (m, 3H), 7.84-7.24 (m, 2H), 4.98-4.86 (m, 1H), 4.65-4.57 (m, 1H), 4.06-3.99 (m, 3H), 3.91-3.65 (m, 1H), 3.21-2.69 (m, 11H), 2.35-2.12 (m, 4H), 1.81-1.47 (m, 14H), 1.36-0.88 (m, 20H).

Example 16. N-[1(2S,5R,8S,11S,14S,17S)-17-(Aminomethyl)-7,8-dibutyl-14-cyclohexyl-5,10-dimethyl-3,9,12,15,18-pentaoxo-11-propyl-1,4,7,10,13,16-hexazacyclooctadec-2-yl]methyl]-2-azaspiro[3.3]heptane-6-carboxamide (trifluoroacetate salt)

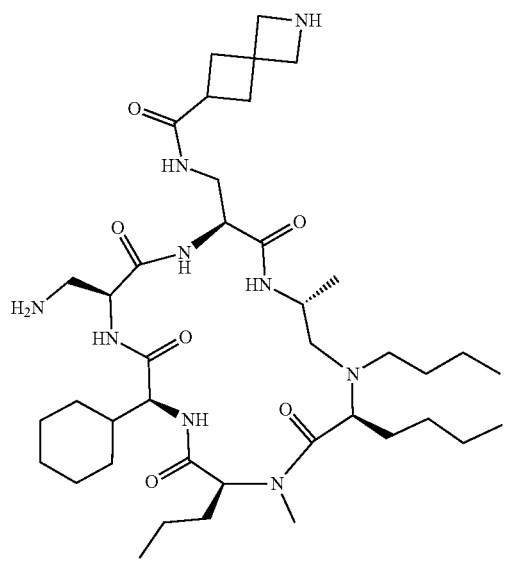 [SMILES: CCCC[C@H]1C(=O)N(C)[C@@H](CCC)C(=O)N[C@@H](C2CCCCC2)C(=O)N[C@@H](CN)C(=O)N[C@@H](CNC(=O)C2CC3(CNC3)C2)C(=O)N[C@H](C)CN1CCCC]

Step 1. tert-Butyl N-[1(2S,5R,8S,11S,14S,17S)-5-(benzyloxycarbonylaminomethyl)-10,11-dibutyl-17-cyclohexyl-8,13-dimethyl-3,6,12,15,18-pentaoxo-14-propyl-1,4,7,10,13,16-hexazacyclooctadec-2-yl]methyl]carbamate

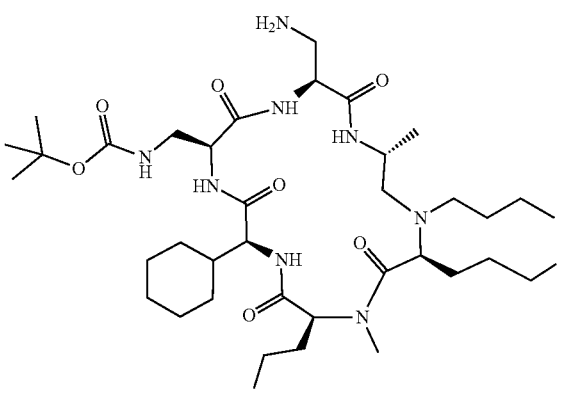 [SMILES: CCCC[C@H]1C(=O)N(C)[C@@H](CCC)C(=O)N[C@@H](C2CCCCC2)C(=O)N[C@@H](CNC(=O)OC(C)(C)C)C(=O)N[C@@H](CN)C(=O)N[C@H](C)CN1CCCC]

The title compound was prepared following methods analogous to those described in Example 7, Steps 1-4. LCMS (ESI): [M+H]⁺=885.5.

Step 2. tert-Butyl (((2S,5R,8S,11S,14S,17S)-5-(aminomethyl)-10,11-dibutyl-17-cyclohexyl-8,13-dimethyl-3,6,12,15,18-pentaoxo-14-propyl-1,4,7,10,13,16-hexazacyclooctadecan-2-yl)methyl)carbamate A mixture of the product from Step 1 (181 mg, 0.205 mmol) and Pd/C (200 mg, 10% Pd loading on carbon) in ethyl acetate (17 mL) was stirred under an atmosphere of hydrogen for 6 h at 40° C. The catalyst was removed via filtration and the filtrate was concentrated under reduced pressure. The crude product was used directly in the next step. LCMS (ESI): [M+H]⁺=751.5.

Step 3. tert-Butyl 6-[[(2S,5R,8S,11S,14S,17S)-17-[(tert-butoxycarbonylamino)methyl]-7,8-dibutyl-14-cyclohexyl-5,10-dimethyl-3,9,12,15,18-pentaoxo-11-propyl-1,4,7,10,13,16-hexazacyclooctadec-2-yl]methylcarbamoyl]-2-azaspiro[3.3]heptane-2-carboxylate

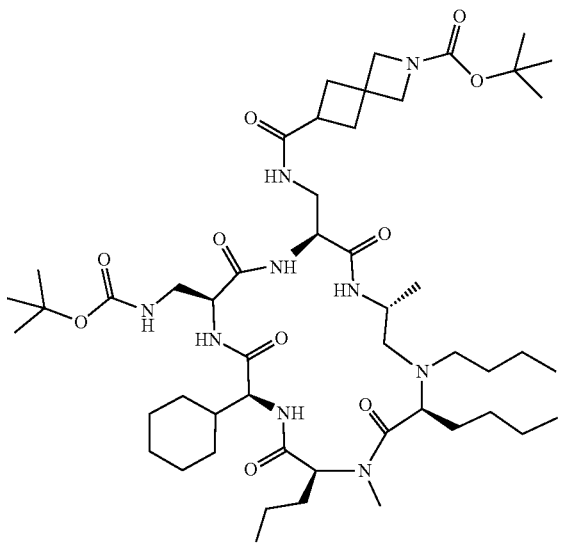 [SMILES: CCCC[C@H]1C(=O)N(C)[C@@H](CCC)C(=O)N[C@@H](C2CCCCC2)C(=O)N[C@@H](CNC(=O)OC(C)(C)C)C(=O)N[C@@H](CNC(=O)C2CC3(C2)CN(C(=O)OC(C)(C)C)C3)C(=O)N[C@H](C)CN1CCCC]

To a solution of tert-butyl (((2S,5R,8S,11S,14S,17S)-5-(aminomethyl)-10,11-dibutyl-17-cyclohexyl-8,13-dimethyl-3,6,12,15,18-pentaoxo-14-propyl-1,4,7,10,13,16-hexaazacyclooctadecan-2-yl)methyl)carbamate (100 mg, 0.130 mmol) and 2-tert-butoxycarbonyl-2-azaspiro[3.3]heptane-6-carboxylic acid (52.7 mg, 0.220 mmol) and DIPEA (65.8 mg, 0.510 mmol) in THF (10 mL) was added dropwise a solution of HATU (77.5 mg, 0.204 mmol) and HOBt (21.4 mg, 0.159 mmol) in DMF (1.0 mL) at 0° C. The mixture was stirred for 1 h at 0° C. Water (30 mL) was added with stirring. The resulting solids were collected and washed with water (3×) to afford the crude title compound (120.5 mg) as a yellow solid. LCMS (ESI): [M+H]$^+$=974.6.

Step 4. N-[[(2S,5R,8S,11S,14S,17S)-17-(Aminomethyl)-7,8-dibutyl-14-cyclohexyl-5,10-dimethyl-3,9,12,15,18-pentaoxo-11-propyl-1,4,7,10,13,16-hexazacyclooctadec-2-yl]methyl]-2-azaspiro[3.3]heptane-6-carboxamide The product of Step 3 (110 mg, 0.113 mmol) was treated with TFA (6.0 mL) at 0° C. for 1 h and then concentrated under vacuum. The residue was purified by Preparatory-HPLC to afford the title compound (15.9 mg) as its TFA salt as a white solid. LCMS (ESI): [M+H]$^+$=774.6, R$_t$=2.05 min, method=J. $^1$H NMR (400 MHz, DMSO-d$_6$): δ 8.91-8.49 (m, 3H), 8.16-8.03 (m, 4H), 7.96-7.86 (m, 1H), 7.62-6.96 (m, 2H), 4.79-4.70 (m, 1H), 4.58-4.42 (m, 2H), 4.31-4.15 (m, 2H), 4.02-3.87 (m, 8H), 3.22-3.01 (m, 8H), 2.91-2.82 (m, 2H), 2.35-2.21 (m, 5H), 2.04-1.84 (m, 3H), 1.67-1.54 (m, 7H), 1.47-1.23 (m, 9H), 1.15-1.06 (m, 4H), 1.02-0.93 (m, 8H), 0.90-0.83 (m, 4H).

Examples 17 and 18. (3R,6S,9S,12S,15S,18R,19R)-9-(aminomethyl)-12-cyclohexyl-19-hexyl-15-isobutyl-3,16,18-trimethyl-6-(piperazin-1-ylmethyl)-1-oxa-4,7,10,13,16-pentaazacyclononadecane-5,8,11,14,17-pentaone (trifluoroacetate salt) and (3R,6S,9S,12S,15S,18R,19R)-9-(aminomethyl)-12-cyclohexyl-19-hexyl-15-isobutyl-3,16,18-trimethyl-6-(piperazin-1-ylmethyl)-1-oxa-4,7,10,13,16-pentaazacyclononadecane-5,8,11,14,17-pentaone (trifluoroacetate salt), single unknown stereoisomers

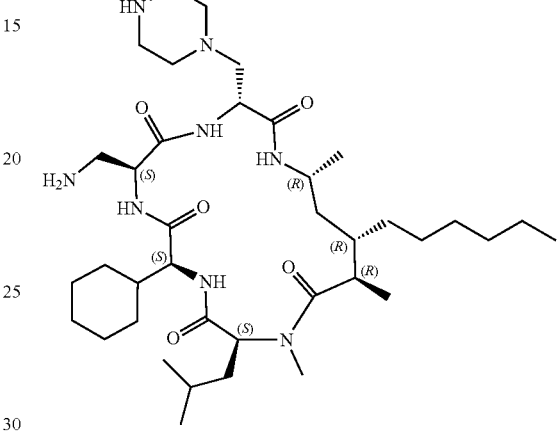

and

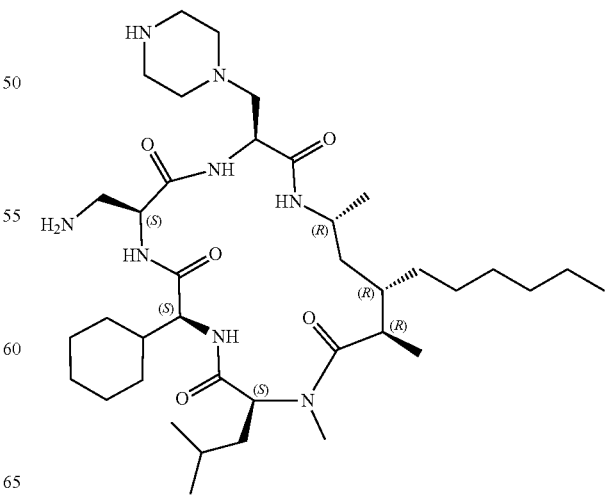

243

Step 1. Benzyl 4-(((3R,9S,12S,15S,18R,19R)-9-((((benzyloxy)carbonyl)amino)methyl)-12-cyclohexyl-19-hexyl-15-isobutyl-3,16,18-trimethyl-5,8,11,14,17-pentaoxo-1-oxa-4,7,10,13,16-pentaazacyclononadecan-6-yl)methyl)piperazine-1-carboxylate

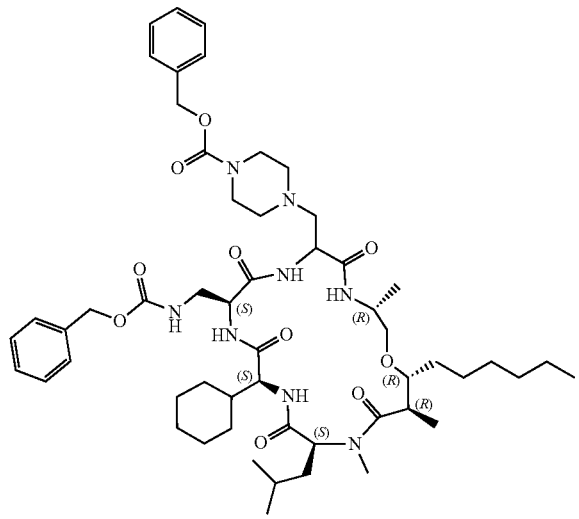

The title compound was prepared following procedures analogous to those described for Examples 25 and 11. The two diastereomers were separated via flash chromatography on silica gel (12 g silica, solvent gradient: 0-10% methanol in DCM) to yield the two single unknown stereoisomers.

Stereoisomer 1: yield=46.5 mg; LCMS (ESI): $[M+H]^+$=1003.7

Stereoisomer 2: yield=41.2 mg; LCMS (ESI): $[M+H]^+$=1003.8

Step 2. (3R,6S,9S,12S,15S,18R,19R)-9-(aminomethyl)-12-cyclohexyl-19-hexyl-15-isobutyl-3,16,18-trimethyl-6-(piperazin-1-ylmethyl)-1-oxa-4,7,10,13,16-pentaazacyclononadecane-5,8,11,14,17-pentaone (trifluoroacetate salt) and (3R,6S,9S,12S,15S,18R,19R)-9-(aminomethyl)-12-cyclohexyl-19-hexyl-15-isobutyl-3,16,18-trimethyl-6-(piperazin-1-ylmethyl)-1-oxa-4,7,10,13,16-pentaazacyclononadecane-5,8,11,14,17-pentaone (trifluoroacetate salt)

The title compounds were prepared each as a single unknown steroisomer, using the isomers isolated in Step 1 and following procedures analogous to those described for Example 11. Example 17: LCMS (ESI): $R_T$ (min)=9.98, $[M+H]^+$=735.6, method=B; $^1$H NMR (400 MHz, DMSO-$d_6$) δ 8.53 (s, 2H), 8.15 (d, J=4.7 Hz, 1H), 7.98-7.81 (m, 4H), 7.68 (d, J=8.2 Hz, 1H), 4.75-4.60 (m, 1H), 4.28-4.14 (m, 1H), 3.98-3.76 (m, 3H), 3.15 (s, 4H), 3.10-2.57 (m, 13H), 1.90-0.74 (m, 41H). Example 18: LCMS (ESI): $R_T$ (min)=10.12, $[M+H]^+$=735.6, method=B; $^1$H NMR (400 MHz, DMSO-$d_6$) δ 8.63 (d, J=93.7 Hz, 3H), 8.34-8.09 (m, 1H), 8.02-7.59 (m, 5H), 4.75-3.64 (m, 8H), 3.23-2.55 (m, 17H), 2.21-0.71 (m, 39H).

244

Example 19. (3R,6S,9S,12S,15S,18R,19R)-9-(Aminomethyl)-6-((3-(((3-aminopropyl)amino)methyl)phenoxy)methyl)-12-cycloheptyl-19-hexyl-3,16,18-trimethyl-15-propyl-1-oxa-4,7,10,13,16-pentaazacyclononadecane-5,8,11,14,17-pentaone (trifluoroacetate salt)

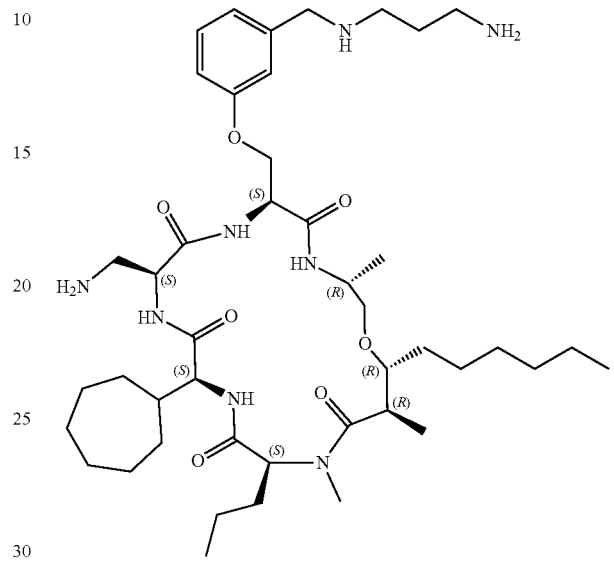

Step 1. tert-Butyl N-[3-((3-1(2S)-2-(benzyloxycarbonylamino)-3-[methoxy(methyl)amino]-3-oxopropoxy]phenyl]methylamino]propyl]carbamate

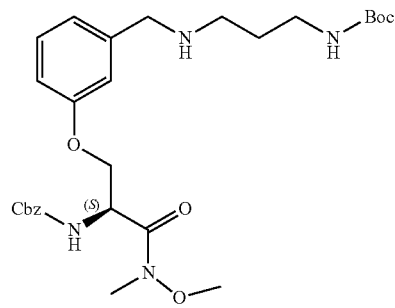

To a solution of (2S)-2-(benzyloxycarbonylamino)-3-hydroxy-propanoic acid (10.0 g, 41.9 mmol) in DMF (120 mL) was added HATU (23.9 g, 63.0 mmol), N,O-dimethylhydroxylamine hydrochloride (6.15 g, 63.0 mmol), and DIPEA (10.8 g, 83.9 mmol) at 0° C. The reaction mixture was stirred for 2 h at room temperature. The system was diluted with ethyl acetate (500 mL) and washed sequentially with 0.5M aqueous NaOH (3×250 mL) and brine (250 mL). The organic layer was dried over anhydrous sodium sulfate and concentrated under vacuum, and the residue was purified by chromatography on silica gel eluting with (EtOAc/PE=8/2) to give benzylN-[(1S)-1-(hydroxymethyl)-2-[methoxy(methyl)amino]-2-oxo-ethyl]carbamate (11.0 g, 93.1% yield) as a light yellow oil. LCMS (ESI): $[M+H]^+$=283.1.

To a solution of benzyl N-[(1S)-1-(hydroxymethyl)-2-[methoxy(methyl)amino]-2-oxo-ethyl]carbamate (860 mg, 3.05 mmol) in toluene (10 mL) was added 3-bromobenzaldehyde (673 mg, 3.64 mmol), Cs₂CO₃ (1.99 g, 6.11 mmol), t-BuBrettphos (148 mg, 0.305 mmol) and [Pd(allyl)Cl]₂ (55.5 mg, 0.152 mmol) under nitrogen. The reaction mixture was stirred overnight at 60° C. and concentrated under vacuum. The residue was purified by flash chromatography on silica gel column eluting with (EtOAc/PE=4/6) to afford benzyl N-[(1S)-1-[(3-formylphenoxy)methyl]-2-[methoxy(methyl)amino]-2-oxo-ethyl]carbamate (140 mg, 11.9% yield) as a yellow oil. LCMS (ESI): [M+Na]⁺=409.1.

To a solution of tert-butyl (3-aminopropyl) carbamate (336 mg, 1.93 mmol) in DCM (12 mL) was added a solution of benzyl N-[(1S)-1-[(3-formylphenoxy)methyl]-2-[methoxy(methyl)amino]-2-oxo-ethyl]carbamate (670 mg, 1.73 mmol) in DCM (3.0 ml) at 0° C. The mixture was stirred for 2 h at room temperature. Sodium triacetoxyborohydride (818 mg, 3.86 mmol) was added portionwise at 0° C. The mixture was stirred for 1 h at room temperature and then concentrated under vacuum. The residue was loaded onto a silica gel column eluting with (DCM/MeOH=91/9) to give the title compound (810 mg, 77.2% yield) as a yellow oil. LCMS (ESI): [M+H]⁺=545.4.

Step 2. tert-Butyl N-[[3-[(2S)-2-(benzyloxycarbonylamino)-3-[methoxy(methyl)amino]-3-oxo-propoxy]phenyl]methyl]-N-[3-(tert-butoxycarbonylamino)propyl]carbamate

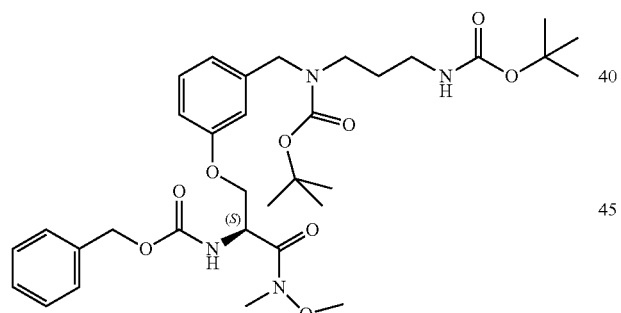

To a solution of tert-butyl N-[3-[[3-[(2S)-2-(benzyloxycarbonylamino)-3-[methoxy(methyl)amino]-3-oxo-propoxy]phenyl]methylamino]propyl]carbamate (710 mg, 1.3 mmol) and DIPEA (336.7 mg, 2.61 mmol) in DCM (20 mL) was added a solution of (Boc)₂O (569.7 mg, 2.61 mmol) in DCM (5 mL) at 0° C. The reaction mixture was stirred at 25° C. for 1.5 h and then concentrated under vacuum. The residue was purified by flash chromatography on silica gel eluting with PE/EtOAc (2/1) to afford the title compound (692 mg, 82.3% yield) as a yellow oil. LCMS (ESI): [M+H]⁺=645.3.

Step 3. tert-Butyl N-[[3-[(2S)-2-amino-3-[methoxy(methyl)amino]-3-oxo-propoxy]phenyl]methyl]-N-[3-(tert-butoxycarbonylamino)propyl]carbamate

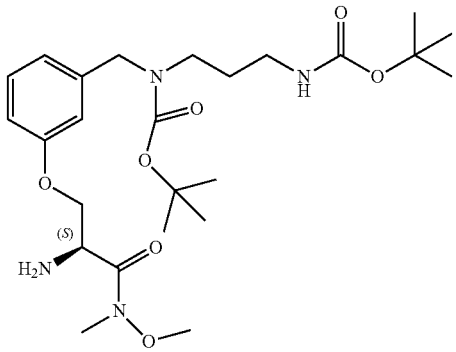

A mixture of tert-butyl N-[[3-[(2S)-2-(benzyloxycarbonylamino)-3-[methoxy(methyl)amino]-3-oxo-propoxy]phenyl]methyl]-N-[3-(tert-butoxycarbonylamino)propyl]carbamate (588 mg, 0.909 mmol) and Pd (10 wt % on carbon, 600 mg) in EtOAc (120 mL) was stirred under an atmosphere of hydrogen for 45 min at 25° C. The catalyst was removed via filtration and the filtrate was concentrated under vacuum to afford the title compound (460 mg) as a yellow oil. LCMS (ESI): [M+H]⁺=511.3.

Step 4. (2S)-3-[3-[[tert-butoxycarbonyl-[3-(tert-butoxycarbonylamino)propyl]amino]methyl]phenoxy]-2-(9H-fluoren-9-ylmethoxycarbonylamino) propanoic acid

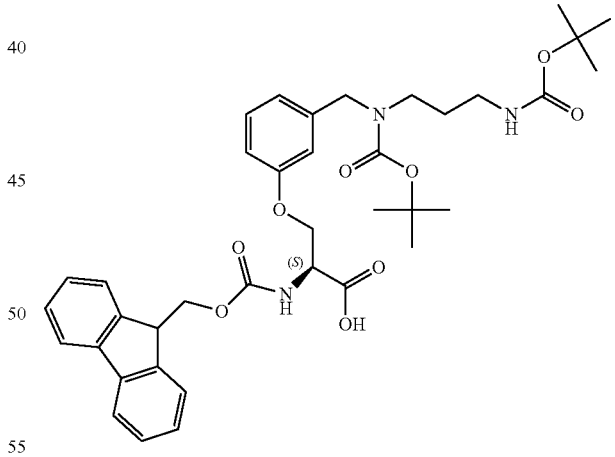

A solution of LiOH (108 mg, 4.5 mmol) in water (2 mL) was added to a solution of tert-butyl N-[ [3-[(2S)-2-amino-3-[methoxy(methyl)amino]-3-oxo-prop oxy]phenyl] methyl]-N-[3-(tert-butoxycarbonylamino)propyl]carbamate (460 mg, 0.90 mmol) in THF (24 mL) and water (8 mL) at room temperature. The reaction mixture was stirred at 25° C. for 3 days and then cooled to 0° C. 9-Fluorenylmethyl chloroformate (465.4 mg, 1.8 mmol) dissolved in 5 mL THF was added dropwise at 0° C. The reaction mixture was stirred at 25° C. for 0.5 h. THF was evaporated under vacuum. The residue was diluted with water (2 mL) and adjusted to pH ~6 with 1 M aqueous HCl. The resulting solution was concentrated under vacuum and the residue was purified by flash chromatography on silica gel eluting with DCM/MeOH (10/1) to afford the title compound (241.5 mg, 38.9% yield) as a white solid. LCMS (ESI): [M+H]$^+$=690.2. $^1$H NMR (300 MHz, DMSO-d$_6$): δ 13.16 (s, 1H), 7.88 (d, J=8.1 Hz, 2H), 7.73-7.62 (m, 3H), 7.44-7.41 (m, 2H), 7.33-7.20 (m, 3H), 6.84-6.77 (m, 4H), 4.38-4.21 (m, 8H), 3.10-3.07 (m, 2H), 2.88-2.85 (m, 2H), 1.60-1.57 (m, 2H), 1.35 (s, 18H).

Step 5. O-(3-(((tert-Butoxycarbonyl)(3-((tert-butoxycarbonyl)amino)propyl)amino)methyl)phenyl)-N—((S)-3-((tert-butoxycarbonyl)amino)-2-((S)-2-cycloheptyl-2-((S)-2-(methylamino)pentanamido)acetamido)propanoyl)-L-serine-(2-chlorotrityl resin)

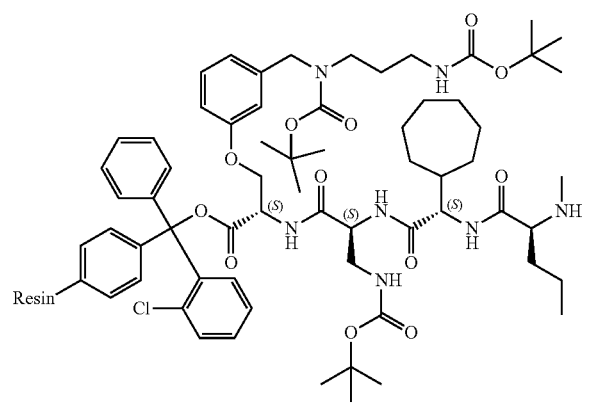

The resin bound tetrapeptide was prepared following procedures analogous to those described in Example 7, Step 1.

Step 6. (3R,6S,9S,12S,15S,18R,19R)-9-(Aminomethyl)-6-((3-(((3-aminopropyl)amino)methyl)phenoxy)methyl)-12-cycloheptyl-19-hexyl-3,16,18-trimethyl-15-propyl-1-oxa-4,7,10,13,16-pentaazacyclononadecane-5,8,11,14,17-pentaone The title compound was prepared using the resin-bound tetrapeptide from Step 5 and following procedures analogous to those described in Example 13, Steps 2-4. LCMS (ESI): [M+H]$^+$=829.6, R$_t$=2.78 min, method=J. $^1$H NMR (400 MHz, DMSO-d$_6$): δ 9.05-8.34 (m, 4H), 8.10-7.90 (m, 7H), 7.53-6.96 (m, 5H), 4.62-4.58 (m, 1H), 4.39-4.37 (m, 1H), 4.28-4.23 (m, 1H), 4.14-4.05 (m, 2H), 3.88-3.82 (m, 2H), 3.29-3.15 (m, 4H), 3.11 (s, 1H), 3.01-2.91 (m, 4H), 2.87-2.78 (m, 4H), 2.70 (s, 2H), 2.07-1.91 (m, 4H), 1.79-1.23 (m, 25H), 1.04-0.83 (m, 12H).

Example 20. (3S,6S,9S,12S,15S,18R)-6-(Aminomethyl)-9-cyclohexyl-18-(2-fluoroethyl)-16-hexyl-3-((S)-1-hydroxyethyl)-12-isobutyl-13,15-dimethyl-1,4,7,10,13,16-hexaazacyclooctadecane-2,5,8,11,14-pentaone

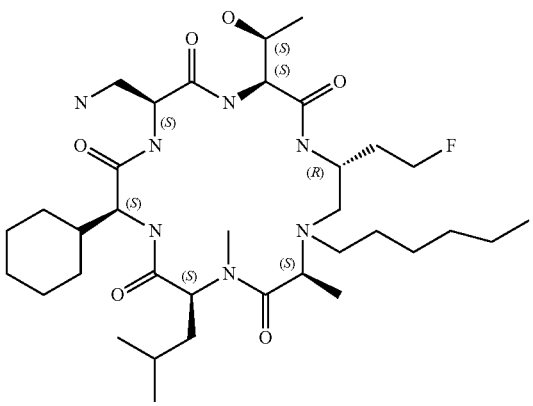

Step 1. Benzyl (tert-butoxycarbonyl)-D-homoserinate

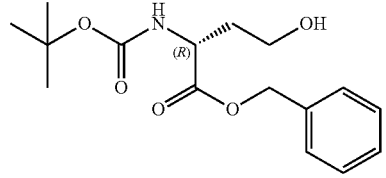

A mixture of Boc (D)-homoserine (1.0 g, 4.3 mmol), benzyl bromide (1.1 g, 6.5 mmol) and potassium carbonate (0.8 g, 8.7 mmol) in DMF (5 mL) was stirred overnight. The reaction mixture was diluted with water and extracted with IPAC/heptane mixture. The organic layer was washed with brine, dried over sodium sulfate and concentrated. The residue was purified by flash chromatography (silica gel, 0-100% IPAC/heptane) to obtain 1.2 g (91%) of the title compound.

Step 2. Benzyl (R)-2-((tert-butoxycarbonyl)amino)-4-fluorobutanoate

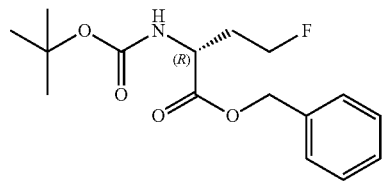

To a solution of benzyl (tert-butoxycarbonyl)-D-homoserinate (1.2 g, 3.9 mmol) in dry 1,4-dioxane (5 mL) were added pyridine-2-sulfonyl fluoride (0.7 g, 3.9 mmol) and 1,3,4,6,7,8-hexahydro-1-methyl-2H-pyrimido[1,2-a]pyrimidine (1.2 g, 7.8 mmol) and the mixture was stirred overnight at room temperature. The reaction mixture was diluted with water and extracted with IPAC/heptane mixture. The organic layer was washed with brine, dried over sodium sulfate and concentrated. The residue was purified by flash chromatography (silica gel, 0-50% IPAC/heptane) to obtain 0.87 g (72%) of the title compound. $^1$H NMR (400 MHz, DMSO-d$_6$) δ 7.47-7.32 (m, 5H), 5.29-4.94 (m, 2H), 4.50 (dt, J=46.9, 5.3 Hz, 2H), 4.24-4.01 (m, 1H), 2.25-1.83 (m, 2H), 1.38 (s, 9H).

Step 3. tert-Butyl (R)-(4-fluoro-1-hydroxybutan-2-yl)carbamate

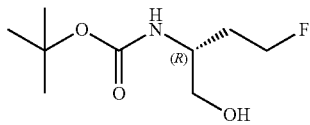

To an ice-cold solution of benzyl (R)-2-((tert-butoxycarbonyl)amino)-4-fluorobutanoate (2.2 g, 7.1 mmol) was added lithium aluminium hydride (3.5 mL, 2M in THF) and the mixture was stirred for 1 h. The reaction mixture was quenched with saturated aqueous ammonium chloride and the solid was removed by filtration and washed well with IPAC. The filtrate was dried over sodium sulfate and concentrated. The residue was purified by flash chromatography (silica gel, 0-5% MeOH/DCM) to obtain 1.0 g (68%) of the title compound. 1H NMR (400 MHz, Chloroform-d) δ 5.12-4.89 (m, 1H), 4.56 (dt, J=47.2, 5.8 Hz, 2H), 3.87-3.59 (m, 3H), 2.77 (s, 1H), 2.09-1.77 (m, 2H), 1.45 (d, J=4.2 Hz, 9H).

Step 4. tert-Butyl (R)-(4-fluoro-1-oxobutan-2-yl)carbamate

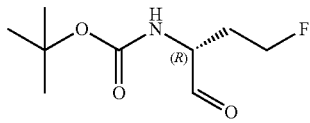

A mixture of tert-butyl (R)-(4-fluoro-1-hydroxybutan-2-yl)carbamate (0.5 g, 2.4 mmol), TEMPO (75 mg, 0.42 mmol), and iodobenzene diacetate (1.2 g, 3.6 mmol) in DCM (20 mL) was stirred at room temperature for 4 h. The reaction mixture was concentrated and triturated with 20% DCM/heptane. The solid was removed by filtration and washed well with 20% DCM/heptane. The filtrate was concentrated and the residue was purified by flash chromatography (silica gel, 0-5% MeOH/DCM) to obtain 0.35 g (70%) of the title compound. $^1$H NMR (400 MHz, Chloroform-d) δ $^1$H NMR (400 MHz, Chloroform-d) δ 9.61 (d, J=2.1 Hz, 1H), 5.34 (s, 1H), 4.59 (dt, J=47.0, 6.0 Hz, 2H), 4.31 (s, 1H), 2.49-2.08 (m, 2H), 1.46 (s, 9H).

Step 5. Benzyl N—((R)-2-((tert-butoxycarbonyl)amino)-4-fluorobutyl)-N-hexyl-L-alaninate

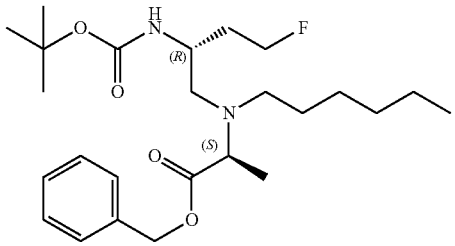

A mixture of tert-butyl (R)-(4-fluoro-1-oxobutan-2-yl) carbamate (0.25 g, 1.2 mmol) and benzyl (2S)-2-aminopropanoate; hydrochloride (0.25 g, 1.2 mmol) in 3 mL of ethyl acetate was stirred for 1 h and then triacetoxyborohydride (0.38 g, 1.8 mmol) was added and the mixture was stirred overnight at room temperature. To this mixture was added hexanal (0.24 g, 2.4 mmol) and triacetoxyborohydride (0.5 g, 2.4 mmol) and the mixture heated at 50° C. overnight. The reaction mixture was cooled, diluted with IPAC and stirred over aqueous sodium bicarbonate. The organic layer was separated, washed with brine, dried over sodium sulfate and concentrated. The residue was purified by flash chromatography (silica gel, 0-50% IPAC/heptane) to obtain 0.2 g (30%) of the title compound. LCMS (ESI): [M+H]$^+$=453.5.

Step 6. Benzyl N—((R)-2-((((9H-fluoren-9-yl)methoxy)carbonyl)amino)-4-fluorobutyl)-N-hexyl-L-alaninate

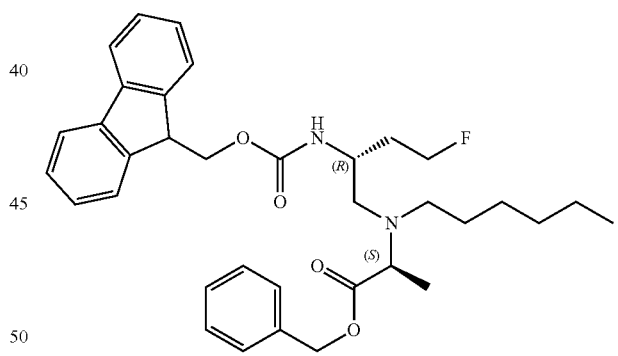

((R)-2-((tert-Butoxycarbonyl)amino)-4-fluorobutyl)-L-alaninate (0.4 g, 0.9 mmol) was dissolved in 2 mL of DCM. HCl (1 mL, 4N in dioxane) was added and the reaction mixture was stirred for 1 h and was then concentrated. The residue was dissolved in dioxane:water (1:1 6 mL) and Fmoc-OSu (0.3 g, 0.9 mmol) and sodium bicarbonate (0.22 g, 2.7 mmol) were added and the mixture was stirred for 1 h. The reaction mixture was diluted with IPAC, washed with water, brine and dried over sodium sulfate and was concentrated. The residue was purified by chromatography on silica gel (solvent gradient 0-50% IPAC/heptane) to obtain 0.46 g (90%) of the title compound. $^1$H NMR (400 MHz, DMSO-d$_6$) δ 7.89 (d, J=7.6 Hz, 2H), 7.68 (d, J=7.5 Hz, 2H), 7.48-7.26 (m, 9H), 7.04 (dd, J=32.9, 8.8 Hz, 1H), 5.16-5.00 (m, 2H), 4.52-4.14 (m, 5H), 3.55 (d, J=9.5 Hz, 2H), 2.60-

2.27 (m, 2H), 2.05-1.44 (m, 2H), 1.37-1.04 (m, 13H), 0.80 (m, 3H). LCMS (ESI): [M+H]⁺=575.2.

Step 7. N—((R)-2-((((9H-Fluoren-9-yl)methoxy)carbonyl)amino)-4-fluorobutyl)-N-hexyl-L-alanine

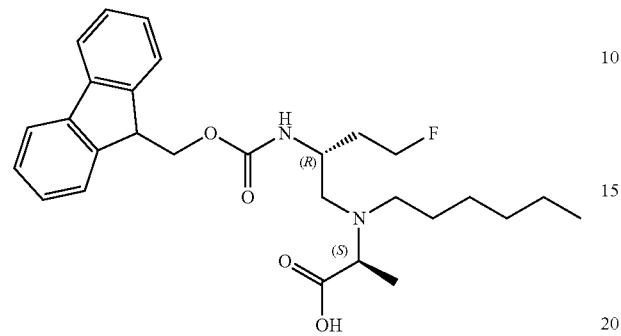

Benzyl (2S)-2-[[(2R)-2-(9H-fluoren-9-ylmethoxycarbonylamino)-4-fluoro-butyl]-hexyl-amino]propanoate (0.46 g, 0.8 mmol) was dissolved in ethanol (5 mL) and Pd (0.05 g, 10% on carbon) was added. The reaction mixture was purged with hydrogen and evacuated three times and then stirred under a hydrogen balloon for 30 min. The catalyst was removed by filtration and the filtrate was concentrated to give the title compound (0.40 g): NMR (400 MHz, DMSO-$d_6$ $D_2O$) δ 7.88 (t, J=6.7 Hz, 2H), 7.69 (dd, J=7.5, 2.3 Hz, 2H), 7.42 (t, J=7.5 Hz, 2H), 7.37-7.29 (m, 2H), 7.04 (d, J=8.9 Hz, 1H), 4.54-4.46 (m, 1H), 4.42-4.18 (m, 3H), 3.61 (s, 2H), 2.68-2.41 (m, 2H), 1.42-1.33 (m, 2H), 1.28-1.09 (m, 13H), 0.91-0.76 (m, 3H). LCMS (ESI): [M+H]⁺=485.4.

Step 8. N—((S)-2-((S)-2-((S)-2-((S)-2-(((R)-2-Amino-4-fluorobutyl)(hexyl)amino)-N-methylpropanamido)-4-methylpentanamido)-2-cyclohexylacetamido)-3-(((benzyloxy)carbonyl)amino)propanoyl)-O-benzyl-L-allothreonine

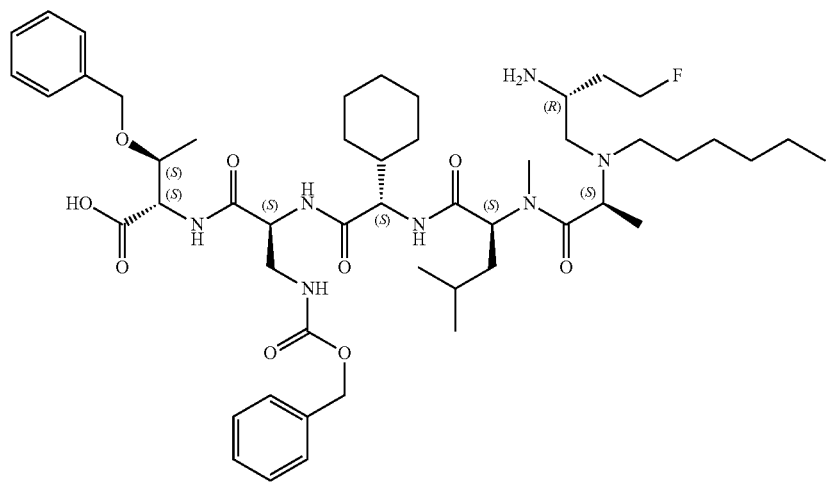

To a filter tube was added Intermediate 15 (0.75 g, estimated 0.45 mmol/g) and 8 mL DMF. The resin was allowed to swell at room temperature for 90 min and then drained. To the resin was added a solution of N—((R)-2-((((9H-fluoren-9-yl)methoxy)carbonyl)amino)-4-fluorobutyl)-N-hexyl-L-alanine (0.33 g, 0.68 mmol) and PyAOP (0.36 mg, 0.68 mmol) in DMF (4 mL), followed by DIPEA (0.35 mL, 2.0 mmol). The resulting mixture was placed on a rotator at room temperature for 16 h. The resin was drained and rinsed with DMA (5×) and DCM (5×). To the resin was added 6 mL of 20% piperidine/DMF solution and agitated for 1 h and then drained and rinsed with DCM (5×). The resin was then suspended in 6 mL 1:3 mixture HFIP:DCM and agitated for 1 h. This mixture was then filtered, rinsing with DCM. The filtrate was evaporated in vacuo, azeotroping with toluene (3×2 mL) to obtain the crude peptide 140 mg (43% crude yield) which was carried forward to the next step without purification. LCMS (ESI): [M+H]⁺=940.9.

Step 9. Benzyl (((2S,5S,8R,11S,14S,17S)-5-((S)-1-(benzyloxy)ethyl)-17-cyclohexyl-8-(2-fluoroethyl)-10-hexyl-14-isobutyl-11,13-dimethyl-3,6,12,15,18-pentaoxo-1,4,7,10,13,16-hexaazacyclooctadecan-2-yl)methyl)carbamate

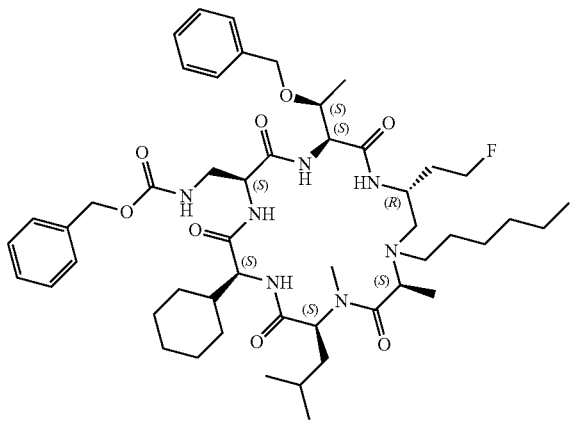

To a room temperature, stirring solution of DIPEA (0.2 mL, 1 mmol) and HATU (0.0.26 mg, 0.43 mmol) in THF (10 mL) was added a solution of N—((S)-2-((S)-2-((S)-2-(((R)-2-amino-4-fluorobutyl)(hexyl)amino)-N-methylpropanamido)-4-methylpentanamido)-2-cyclohexylacetamido)-3-(((benzyloxy)carbonyl)amino)propanoyl)-O-benzyl-L-allothreonine (0.14 g, 0.15 mmol) in THF (100 mL), dropwise over 4 h and was allowed stir overnight. The reaction mixture was evaporated in vacuo. The resulting residue was diluted with ethyl acetate, washed with water (2×) and brine, dried over sodium sulfate, filtered, and evaporated in vacuo. The crude product was purified via flash chromatography on silica gel (12 g silica, solvent gradient: 0-10% methanol in DCM) to yield 60 mg of the title compound. LCMS (ESI): [M+H]+=922.9.

Step 10. (3S,6S,9S,12S,15S,18R)-6-(Aminomethyl)-9-cyclohexyl-18-(2-fluoroethyl)-16-hexyl-3-((S)-1-hydroxyethyl)-12-isobutyl-13,15-dimethyl-1,4,7,10,13,16-hexaazacyclooctadecane-2,5,8,11,14-pentaone A flask was charged with the above residue (60 mg, 0.065 mmol) and ethyl acetate (5 mL), and the flask purged with nitrogen. After the addition of trifluoroacetic acid (25 μL, 0.323 mmol) and palladium (10 wt. % on carbon) (50 mg) the reaction mixture was evacuated and backfilled with hydrogen, and then stirred at room temperature under a hydrogen balloon for 18 h. The reaction mixture was filtered through celite, rinsing with 100 mL of 5% AcOH in methanol, and the filtrate was evaporated in vacuo, azeotroping with toluene (3×1 mL). The crude product was purified via reverse-phase HPLC and lyophilized to yield 19.6 mg (37%, purity 87%) of the title compound as its trifluoroacetate salt. LCMS (ESI): R$_T$ (min)=8.33, [M+H]⁺=698.5, method=B; ¹H NMR (400 MHz, DMSO-d₆) δ 8.69-8.55 (m, 1H), 8.41-8.01 (m, 1H), 8.01-7.74 (m, 3H), 7.66-7.41 (m, 1H), 5.38-4.69 (m, 1H), 4.69-4.18 (m, 4H), 4.18-3.44 (m, 7H), 3.25-3.03 (m, 4H), 3.05-2.85 (m, 1H), 2.16-1.89 (m, 2H), 1.89-1.36 (m, 11H), 1.36-0.77 (m, 25H).

Example 21. 4-(2-Aminoethyl)-N-[[(3R,6S,9S,12S,15S,18R,19R)-9-(aminomethyl)-12-cycloheptyl-19-hexyl-3,16,18-trimethyl-5,8,11,14,17-pentaoxo-15-propyl-1-oxa-4,7,10,13,16-pentazacyclononadec-6-yl]methyl]benzamide (trifluoroacetate salt)

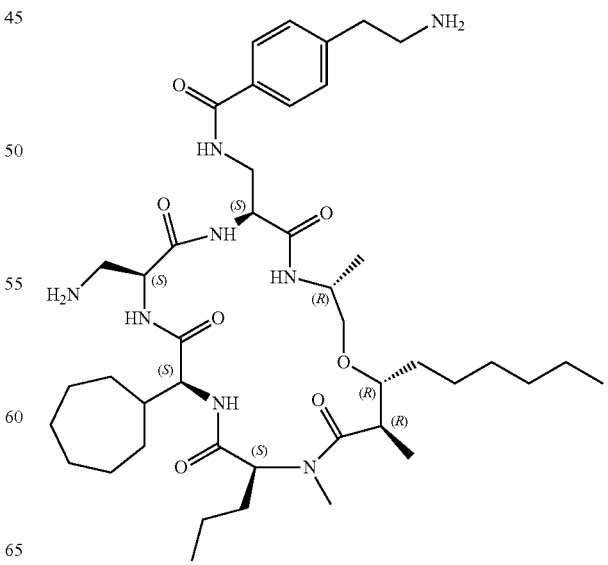

Step 1. tert-Butyl N-[1(3R,6S,9S,12S,15S,18R,19R)-6-[[[4-[2-(tert-butoxycarbonylamino)ethyl]benzoyl]amino]methyl]-12-cycloheptyl-19-hexyl-3,16,18-trimethyl-5,8,11,14,17-pentaoxo-15-propyl-1-oxa-4,7,10,13,16-pentazacyclononadec-9-yl]methyl]carbamate

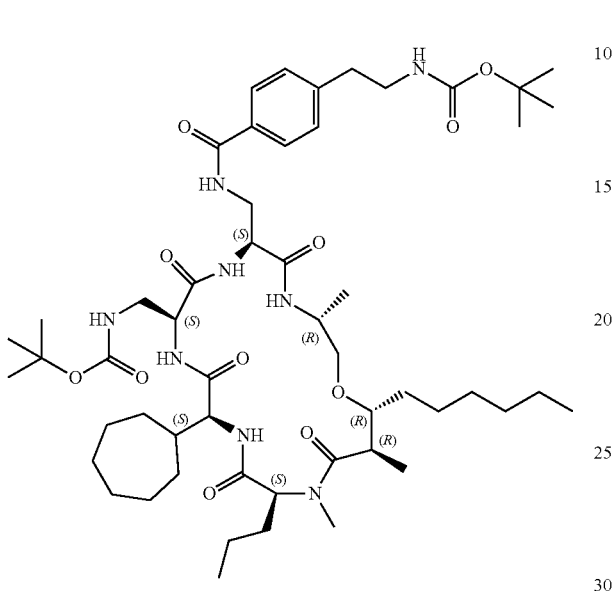

To a solution of 4-(2-((tert-butoxycarbonyl)amino)ethyl)benzoic acid (82.4 mg, 0.31 mmol), HATU (117.8 mg, 0.31 mmol), HOBt (41.8 mg, 0.31 mmol) and DIPEA (0.11 mL, 0.63 mmol) in THF (120 mL) was added a solution of N-[[(3R,6S,9S,12S,15S,18R,19R)-6-(aminomethyl)-12-cycloheptyl-19-hexyl-3,16,18-trimethyl-5,8,11,14,17-pentaoxo-15-propyl-1-oxa-4,7,10,13,16-pentazacyclononadec-9-yl]methyl]carbamate (121 mg, 0.158 mmol, Example 14 Step 2) in 2 mL DMF at 0° C. The mixture was stirred for 1 h and then concentrated under vacuum. The residue was purified by reverse phase chromatography (acetonitrile 0-80/0.05% TFA in water) to afford the title compound (95.4 mg, 59.8% yield) as a white solid. LCMS (ESI): [M+H]⁺=1013.7.

Step 2. 4-(2-Aminoethyl)-N-[[(3R,6S,9S,12S,15S,18R,19R)-9-(aminomethyl)-12-cycloheptyl-19-hexyl-3,16,18-trimethyl-5,8,11,14,17-pentaoxo-15-propyl-1-oxa-4,7,10,13,16-pentazacyclononadec-6-yl]methyl]benzamide The product of Step 1 (95.2 mg, 0.090 mmol) was treated with TFA (5.0 mL) at 0° C. for 30 min and then concentrated under vacuum. The residue was purified by preparatory-LCMS to afford the title compound as its TFA salt (25.5 mg) as a white solid. LCMS (ESI): [M+H]⁺=813.6, $R_t$=2.89 min, method=K; ¹H NMR (400 MHz, DMSO-$d_6$): δ 8.85-8.12 (m, 2H), 7.99-7.90 (m, 3H), 7.88-7.72 (m, 5H), 7.56-7.04 (m, 4H), 4.62-4.43 (m, 1H), 4.22-4.03 (m, 1H), 3.98-3.82 (m, 2H), 3.32-3.15 (m, 4H), 3.12-3.05 (m, 5H), 3.02-2.89 (m, 5H), 2.80 (s, 2H), 2.21-1.94 (m, 3H), 1.79-1.52 (m, 8H), 1.48-1.25 (m, 17H), 1.03-0.90 (m, 7H), 0.88-0.82 (m, 4H).

Example 22. (3S,6S,9S,12S,15S,18R)-6-(Aminomethyl)-3-((3-aminopropoxy)methyl)-15-butyl-9-cyclohexyl-16-(cyclopropylmethyl)-12-isobutyl-13,18-dimethyl-1,4,7,10,13,16-(trifluoroacetate salt)

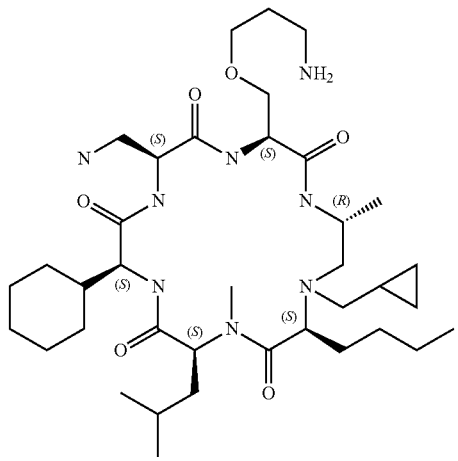

Step 1. Benzyl (2S)-2-[[(2R)-2-(tert-butoxycarbonylamino)propyl]-(cyclopropylmethyl)amino]hexanoate

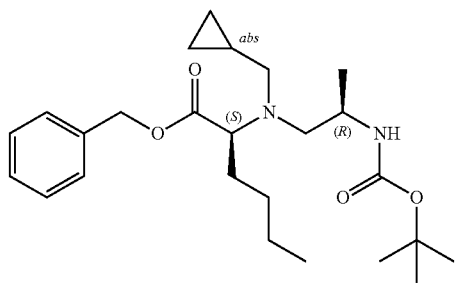

A mixture of benzyl (2S)-2-aminohexanoate:hydrochloride (1.0 g, 3.88 mmol) and tert-butyl (R)-(1-oxopropan-2-yl)carbamate (0.63 g, 3.5 mmol) in ethyl acetate (10 mL) was stirred for 2 h and then sodium triacetoxyborohydride (1.23 g, 5.8 mmol) was added and the mixture stirred at room temperature overnight. To this mixture was then added cyclopropylcarboxaldehyde (0.81 g, 5.82 mmol) and sodium triacetoxyborohydride (1.0 g, 3.5 mmol) and the mixture was stirred at room temperature for 24 h. The reaction mixture was diluted with IPAC and stirred over sodium bicarbonate solution. The organic layer was separated, washed with brine, dried over sodium sulfate and concentrated. The residue was purified by column chromatography (silica gel, 0-50% IPAC/heptane) to afford 1.1 g (65%) of the title compound. LCMS (ESI): [M+H]⁺=433.3. ¹H NMR (400 MHz, DMSO-$d_6$) δ 7.46-7.26 (m, 5H), 6.32 (d, 1H), 5.18-4.99 (m, 2H), 3.52 (t, J=7.4 Hz, 2H), 2.60 (dd, J=13.4, 8.5 Hz, 1H), 2.45 (dd, J=12.4, 5.9 Hz, 1H), 2.38-2.17 (m, 2H), 1.65-1.53 (m, 2H), 1.36 (s, 10H), 1.34-1.18 (m, 3H), 0.98 (d, 3H), 0.90-0.83 (m, 3H), 0.82-0.73 (m, 1H), 0.48-0.39 (m, 1H), 0.38-0.29 (m, 1H), 0.12-0.02 (m, 2H).

Step 2. (S)-2-(((R)-2-((((9H-fluoren-9-yl)methoxy)carbonyl)amino)propyl)(cyclopropylmethyl)amino)hexanoic acid

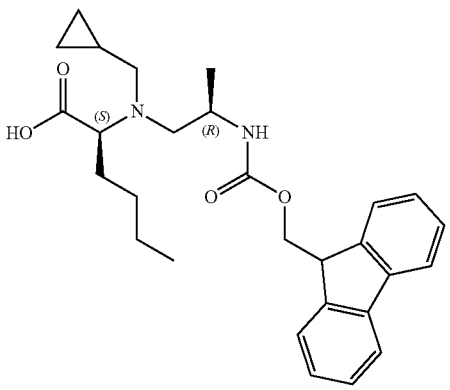

To a solution of benzyl (2S)-2-[[(2R)-2-(tert-butoxycarbonylamino)propyl]-(cyclopropylmethyl)amino]hexanoate (1.1 g, 2.5 mmol) in 4 mL of DCM was added HCl (4 mL, 4 M in dioxane) and the resulting mixture stirred for 2 h and then concentrated. The residue was dissolved in 1:1 mixture of dioxane:water and Fmoc-OSu (1.7 g, 4.65 mmol) and sodium carbonate (0.65 g, 5.00 mmol) were added and the mixture stirred at room temperature overnight. The reaction mixture was diluted with IPAC and the organic layer separated, washed with brine, dried over sodium sulfate and concentrated. The residue was purified by chromatography (silica gel, 0-50% IPAC/heptane) to obtain the benzyl ester (1.4 g). LCMS (ESI) [M+H]$^+$=556.8.

The above residue was dissolved in ethanol (30 mL) with palladium (0.12 g, 10 wt % on carbon) and hydrogenated under a H$_2$ balloon for 30 min. The catalyst was removed by filtration through celite and the filtrate was concentrated. The residue was dried in a vacuum oven at 40° C. overnight to obtain the title compound (1.1 g). LCMS (ESI) [M+H]$^+$=465.1; $^1$H NMR (400 MHz, DMSO-d$_6$) δ 7.96-7.85 (m, 2H), 7.74-7.66 (m, 2H), 7.41 (m, 2H), 7.32 (m, 2H), 6.92 (d, J=8.3 Hz, 1H), 4.35-4.12 (m, 3H), 3.61 (d, J=14.4 Hz, 1H), 3.36 (q, J=8.8, 7.4 Hz, 1H), 2.75-2.58 (m, 1H), 2.48-2.26 (m, 3H), 1.66-1.00 (m, 10H), 0.90-0.76 (m, 4H), 0.54-0.28 (m, 2H), 0.17-0.01 (m, 2H).

Step 3. (11S,14R,17S,20S,23S,26S)-11-amino-26-(((((benzyloxy)carbonyl)amino)methyl)-17-butyl-23-cyclohexyl-16-(cyclopropylmethyl)-20-isobutyl-2,2,14,19-tetramethyl-4,12,18,21,24-pentaoxo-3,9-dioxa-5,13,16,19,22,25-hexaazaheptacosan-27-oic acid

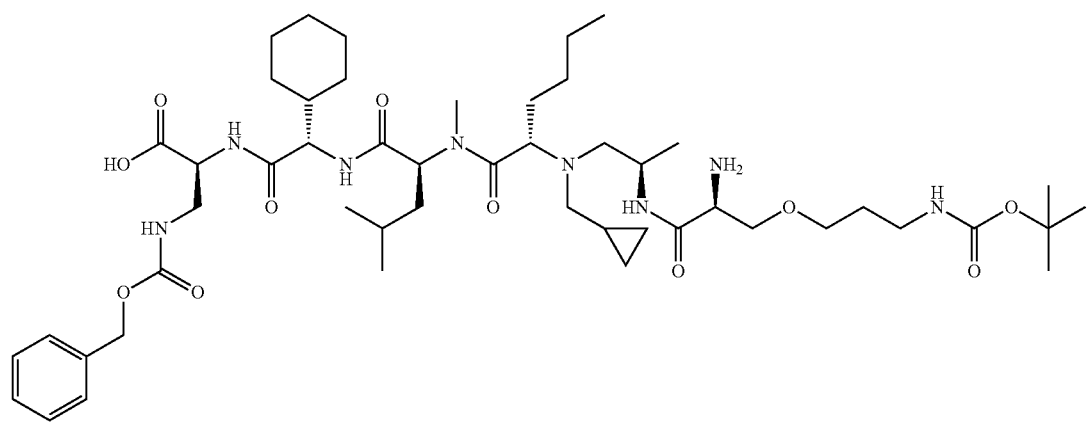 [SMILES: CCCC[C@@H](C(=O)N(C)[C@@H](CC(C)C)C(=O)N[C@H](C(=O)N[C@@H](CNC(=O)OCc1ccccc1)C(=O)O)C1CCCCC1)N(CC1CC1)C[C@@H](C)NC(=O)[C@@H](N)COCCCNC(=O)OC(C)(C)C]

(S)-3-(((benzyloxy)carbonyl)amino)-2-((S)-2-cyclohexyl-2-((S)-4-methyl-2-(methylamino)pentanamido)acetamido)propanoic acid-(2-chlorophenyltrityl-resin) (0.6 g, 0.47 mmol/g, prepared using methods analogous to those described in the synthesis of Intermediate 15) was swelled in DMF (3 mL) for 30 min and then treated with a premixed solution of (S)-2-(((R)-2-((((9H-fluoren-9-yl)methoxy)carbonyl)amino)propyl)(cyclopropylmethyl)amino)hexanoic acid (0.26 g, 0.56 mmol), PyAOP (0.3 g, 0.56 mmol) and DIPEA (0.15 mL, 0.85 mmol) in DMF (4 mL). The resin and solution was agitated for 20 h and then drained and washed well DMF and DCM. The resin was suspended in 20% piperidine/DMF mixture (8 mL) and agitated for 1 h. The resin was then drained and washed well with DMF and DCM. The resin was treated with a premixed solution of Intermediate 6 (0.26 g, 0.6 mmol), PyAOP (0.31 g, 0.6 mmol) and DIPEA (0.1 mL, 0.8 mmol) in DMF (4 mL) and agitated for 3 h, and then drained and washed well with DCM. The resin was treated with 20% piperidine/DMF (8 mL) and agitated for 1 h. The liquid filtered off and the resin washed well with DCM and suspended in 1:3 mixture HFIP and DCM (8 mL) and agitated for 1 h. The liquid was collected by filtration while washing the resin with DCM. The combined filtrate was concentrated while azeotroping with toluene (3 times) to obtain the crude peptide (0.2 g). LCMS (ESI): $[M+H]^+=974.8$.

Step 4. tert-Butyl (3-(((2S,5R,8S,11S,14S,17S)-17-(((((benzyloxy)carbonyl)amino)methyl)-8-butyl-14-cyclohexyl-7-(cyclopropylmethyl)-11-isobutyl-5,10-dimethyl-3,9,12,15,18-pentaoxo-1,4,7,10,13,16-hexaazacyclooctadecan-2-yl)methoxy)propyl)carbamate

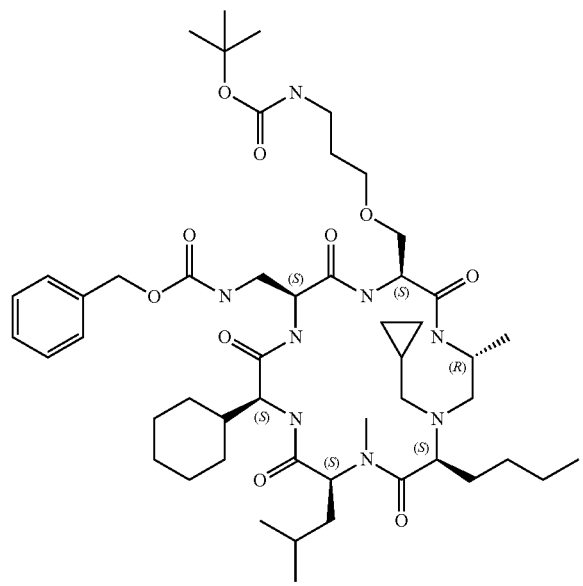

The crude peptide from Step 3 (0.2 g, 0.2 mmol) in dry THF (175 mL) was added to a mixture of HATU (0.16 g, 0.4 mmol) and DIPEA (0.11 mL, 0.62 mmol) dropwise over 3 h and then stirred overnight. The reaction mixture was concentrated and dissolved in IPAC, washed with water, brine, dried over sodium sulfate and concentrated. The residue was purified by column chromatography (silica gel, 0-10% MeOH/DCM) to obtain the cyclic peptide (60 mg, 30%). LCMS (ESI): $[M+H]^+=955.8$.

Step 5. (3S,6S,9S,12S,15S,18R)-6-(Aminomethyl)-3-((3-aminopropoxy)methyl)-15-butyl-9-cyclohexyl-16-(cyclopropylmethyl)-12-isobutyl-13,18-dimethyl-1,4,7,10,13,16-hexaazacyclooctadecane-2,5,8,11,14-pentaone The product of Step 4 was dissolved in ethyl acetate (3 mL) and Pd (10 wt % on carbon, 60 mg) and trifluoroacetic acid (0.2 µL) were added and the flask was evacuated and purged with hydrogen and then stirred for 3 h under a hydrogen balloon. The catalyst was removed by filtration and was washed with 5% AcOH/methanol. The filtrate was concentrated and the resulting residue was treated with 1 mL HCl (4N in dioxane) for 1 h and then concentrated, azeotroping with toluene (3 times). The resulting residue was purified via reverse-phase HPLC and lyophilized to yield 10.3 mg (6%, purity 87%) of the title compound as its trifluoroacetate salt. LCMS (ESI): $R_T$ (min)=6.00, $[M+H]^+=721.5$, method=B; NMR (400 MHz, DMSO-$d_6$) δ 9.01-8.61 (m, 2H), 8.00 (t, J=32.4 Hz, 5H), 7.69 (d, J=23.8 Hz, 3H), 7.33 (d, J=144.9 Hz, 2H), 4.89-4.57 (m, 2H), 4.57-3.87 (m, 7H), 3.59 (d, J=18.1 Hz, 6H), 3.28-3.01 (m, 3H), 2.83 (s, 2H), 2.05 (d, J=50.5 Hz, 2H), 1.91-1.41 (m, 11H), 1.41-0.60 (m, 25H), 0.43 (d, J=41.0 Hz, 2H).

Example 23. 2-03R,6S,9S,12S,15S,18R,19R)-9-(Aminomethyl)-12-cycloheptyl-19-hexyl-3,16,18-trimethyl-5,8,11,14,17-pentaoxo-15-propyl-1-oxa-4,7,10,13,16-pentaazacyclononadecan-6-yl)acetamide (trifluoroacetate salt)

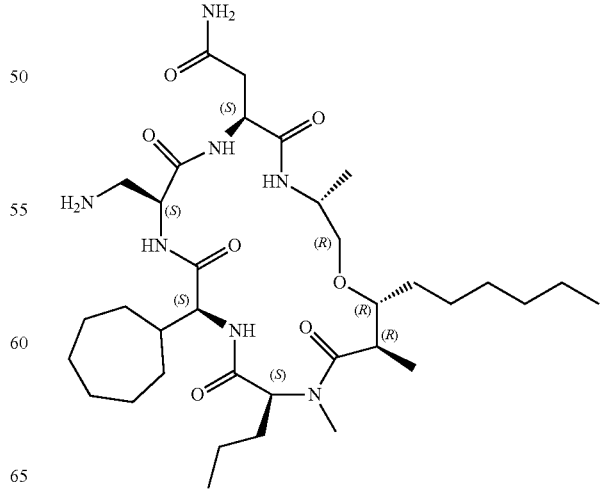

261

Step 1. tert-Butyl-2-[(3R,6S,9S,12S,15S,18R,19R)-9-(benzyloxycarbonylaminomethyl)-12-cycloheptyl-19-hexyl-3,16,18-trimethyl-5,8,11,14,17-pentaoxo-15-propyl-1-oxa-4,7,10,13,16-pentazacyclononadec-6-yl]acetate

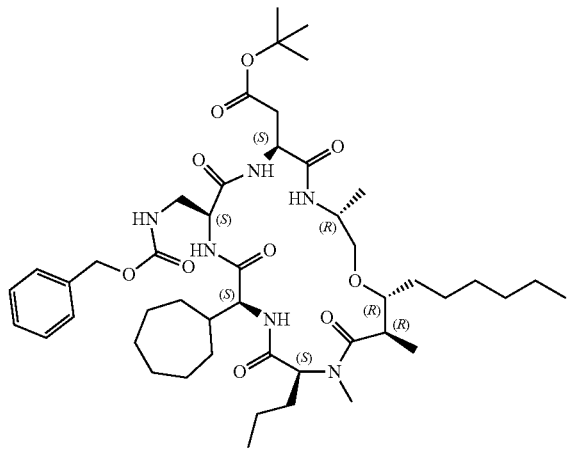

The title compound was prepared following methods analogous to those described for Example 8, Steps 1-3. LCMS (ESI): [M+H]$^+$=885.6.

Step 2. 2-03R,6S,9S,12S,15S,18R,19R)-9-((((Benzyloxy)carbonyl)amino)methyl)-12-cycloheptyl-19-hexyl-3,16,18-trimethyl-5,8,11,14,17-pentaoxo-15-propyl-1-oxa-4,7,10,13,16-pentaazacyclononadecan-6-yl)acetic acid

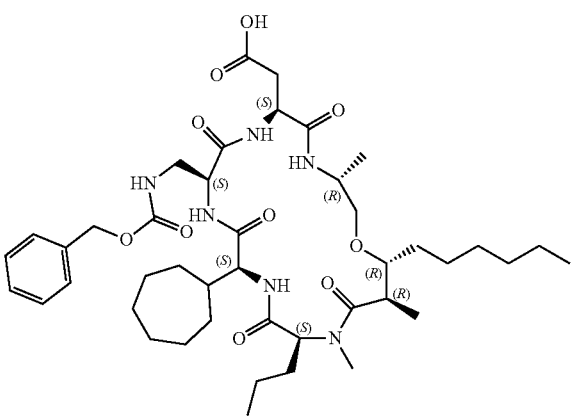

The product from Step 1 (1.04 g, 1.17 mmol) was treated with TFA (15 mL) at 0° C. for 1 h and then concentrated under vacuum. The residue was purified by reverse phase chromatography (solvent gradient: 0-70% acetonitrile/0.05% TFA in water) to afford the title compound (403 mg, 41.4% yield). LCMS (ESI): [M+H]$^+$=829.5.

262

Step 3. Benzyl-N-[[(3R,6S,9S,12S,15S,18R,19R)-6-(2-amino-2-oxo-ethyl)-12-cycloheptyl-19-hexyl-3,16,18-trimethyl-5,8,11,14,17-pentaoxo-15-propyl-1-oxa-4,7,10,13,16-pentazacyclononadec-9-yl]methyl] carbamate

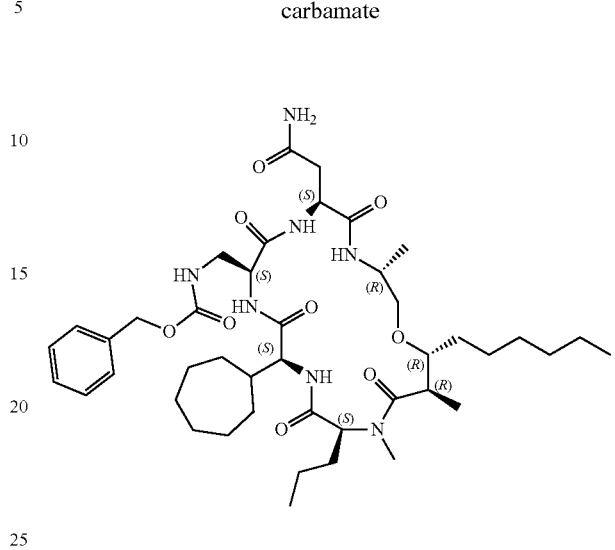

To a solution 24(3R,6S,9S,12S,15S,18R,19R)-9-((((benzyloxy)carbonyl)amino)methyl)-12-cycloheptyl-19-hexyl-3,16,18-trimethyl-5,8,11,14,17-pentaoxo-15-propyl-1-oxa-4,7,10,13,16-pentaazacyclononadecan-6-yl)acetic acid (101 mg, 0.120 mmol) in DMF (2.0 mL) was added HATU (92.0 mg, 0.240 mmol) and DIPEA (62.0 mg, 0.48 mmol). The reaction mixture was stirred for 5 min. To the mixture was added ammonia (1.0 mL, 0.5 M in THF) and ammonium chloride (13.0 mg, 0.24 mmol). The reaction mixture was stirred for 1 h and then concentrated under vacuum. The residue was purified by reverse phase chromatography (solvent gradient: 0-68% acetonitrile/0.05% TFA in water) to afford the title compound (67.0 mg, 66.4% yield). LCMS (ESI): [M+H]$^+$=828.6.

Step 4. 2-[(3R,6S,9S,12S,15S,18R,19R)-9-(Aminomethyl)-12-cycloheptyl-19-hexyl-3,16,18-trimethyl-5,8,11,14,17-pentaoxo-15-propyl-1-oxa-4,7,10,13,16-pentazacyclononadec-6-yl]acetamide A mixture of benzyl-N-[[(3R,6S,9S,12S,15S,18R,19R)-6-(2-amino-2-oxo-ethyl)-12-cycloheptyl-19-hexyl-3,16,18-trimethyl-5,8,11,14,17-pentaoxo-15-propyl-1-oxa-4,7,10, 13,16-pentazacyclononadec-9-yl]methyl]carbamate (67.0 mg, 0.080 mmol) and Pd/C (100 mg, 10% Pd loading on carbon) in 2-propanol (10 mL) was stirred at room temperature for 2.5 h under an atmosphere of hydrogen. The catalyst was removed via filtration and the filtrate was evaporated under vacuum. The residue was purified by preparatory HPLC and lyophilized to afford the title compound as its TFA salt (12.3 mg) as a white solid. LCMS (ESI): [M+H]$^+$=694.5, R$_t$=2.43 min, method=H. $^1$H NMR (400 MHz, DMSO-d$_6$): δ 8.62-8.18 (m, 2H), 8.02-7.92 (m, 4H), 7.48-7.21 (m, 2H), 6.93-6.86 (m, 1H), 4.62-4.41 (m, 1H), 4.32-4.22 (m, 1H), 4.18-4.10 (m, 1H), 3.86-3.78 (m, 1H), 3.30-3.22 (m, 3H), 3.10 (s, 2H), 3.02-2.91 (m, 2H), 2.71 (s, 1H), 2.21-2.02 (m, 2H), 1.76-1.52 (m, 8H), 1.48-1.22 (m, 20H), 1.05-0.85 (m, 13H).

Example 24. (3R,6S,9S,12S,15S,18R,19R)-9-(Aminomethyl)-6-((3-((3-aminopropyl)amino)propoxy)methyl)-19-01R,3s,5S)-bicyclo[3.2.1]octan-3-ylmethyl)-12-cycloheptyl-3,16,18-trimethyl-15-propyl-1-oxa-4,7,10,13,16-pentaazacyclononadecane-5,8,11,14,17-pentaone (trifluoroacetate salt)

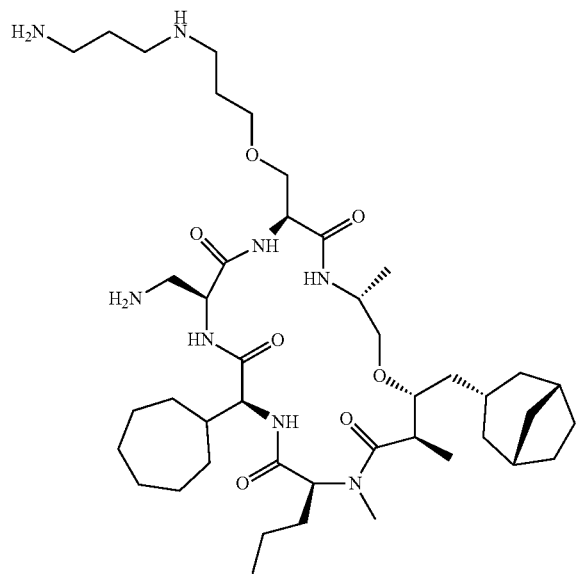 [SMILES: CCC[C@H]1C(=O)N[C@@H](C2CCCCCC2)C(=O)N[C@@H](CN)C(=O)N[C@@H](COCCCNCCCN)C(=O)N[C@H](C)CO[C@H](C[C@@H]2C[C@@H]3CC[C@@H](C3)C2)[C@@H](C)C(=O)N1C]

Step 1. N-Me-norvaline-cycloheptylglycine-Dap(Cbz)-3-((tert-butoxycarbonyl)amino)propyl)-serine-(2-chlorotrityl resin)

Step 2. tert-Butyl N-[3-[[(3R,6S,9S,12S,15S,18R,19R)-9-(benzyloxycarbonylaminomethyl)-19-[[(1S,5R)-3-bicyclo[3.2.1]octanyl]methyl]-12-cycloheptyl-3,16,18-trimethyl-5,8,11,14,17-pentaoxo-15-propyl-1-oxa-4,7,10,13,16-pentazacyclononadec-6-yl]methoxy]propyl]carbamate

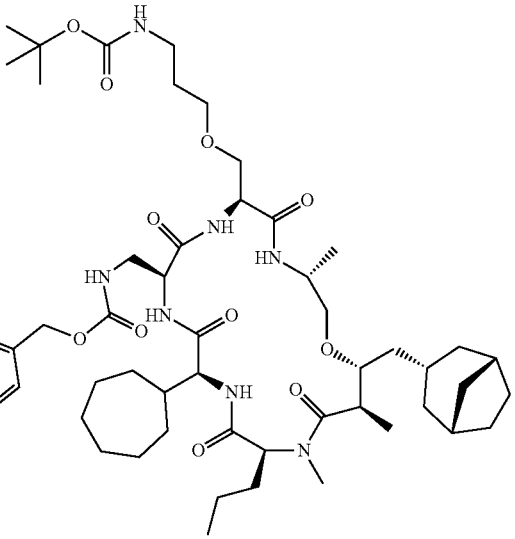

The title compound was prepared using the resin-bound tetrapeptide from Step 1 and and (2R,3R)-4-[(1S,5R)-3-bicyclo[3.2.1]octanyl]-3-[(2R)-2-(9H-fluoren-9-ylmethoxycarbonylamino)propoxy]-2-methyl-butanoic acid (Intermediate 5) and following methods analogous to those described in Example 13. LCMS (ESI): [M+H]$^+$=996.6.

Step 3. Benzyl N-[[(3R,6S,9S,12S,15S,18R,19R)-6-(3-aminopropoxymethyl)-19-[[(1S,5R)-3-bicyclo[3.2.1]octanyl]methyl]-12-cycloheptyl-3,16,18-trimethyl-5,8,11,14,17-pentaoxo-15-propyl-1-oxa-4,7,10,13,16-pentazacyclononadec-9-yl]methyl]carbamate

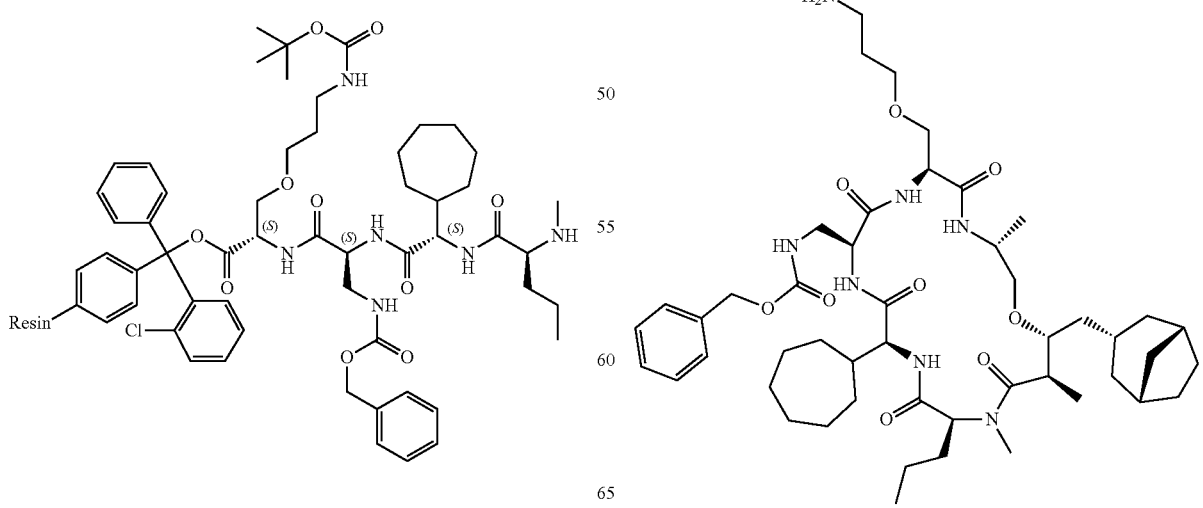

The resin bound tetrapeptide was prepared following methods analogous to those described in Example 7, Step 1.

The product of Step 2 (430 mg, 0.43 mmol) was treated with TFA (12 mL) at 0° C. for 1 h. Toluene (10 mL) was added and the resulting solution was concentrated under vacuum. The residue was partitioned between 100 mL of DCM and 5% Na$_2$CO$_3$ solution (20 mL). The organic phase was washed with brine (20 mL), dried over anhydrous sodium sulfate and concentrated under vacuum to afford the title compound (385 mg) as a light-yellow solid. LCMS (ESI): [M+H]$^+$=896.6.

Step 4. tert-Butyl N-[3-[3-[[(3R,6S,9S,12S,15S, 18R,19R)-9-(benzyloxycarbonylaminomethyl)-19- [[(1S,5R)-3-bicyclo[3.2.1]octanyl]methyl]-12-cycloheptyl-3,16,18-trimethyl-5,8,11,14,17-pentaoxo-15-propyl-1-oxa-4,7,10,13,16-pentazacyclononadec-6-yl]methoxy]propylamino]propyl]carbamate

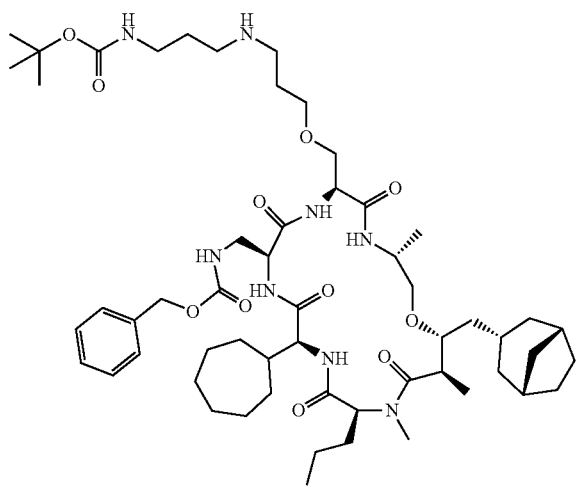 [SMILES: CCC[C@H]1C(=O)N[C@@H](C2CCCCCC2)C(=O)N[C@@H](CNC(=O)OCc2ccccc2)C(=O)N[C@@H](COCCCNCCCNC(=O)OC(C)(C)C)C(=O)N[C@H](C)CO[C@H](C[C@@H]2C[C@@H]3CC[C@@H](C3)C2)[C@@H](C)C(=O)N1C]

The product of Step 3 (385 mg, 0.430 mmol) and tert-butyl N-(3-oxopropyl)carbamate (66.9 mg, 0.39 mmol) in DCM (30 mL) was stirred at room temperature for 2 h. The mixture was cooled to 0° C. and sodium triacetoxyborohydride (137 mg, 0.646 mmol) was added at this temperature. The reaction mixture was allowed to warm to room temperature and stirred at room temperature for 3 h. The reaction was quenched with 5% aqueous NH$_4$Cl (30 mL) and the phases were separated. The aqueous phase was extracted with DCM (100 mL). The combined organic layers were washed with brine (30 mL), dried over anhydrous sodium sulfate and concentrated under vacuum. The residue was purified by reverse phase flash chromatography on C18 column to afford the title compound (194 mg, 42.9% yield) as a white solid. LCMS (ESI): [M+1-1]$^+$=1053.7.

Step 5. tert-Butyl N-[3-[3-[[(3R,6S,9S,12S,15S, 18R,19R)-9-(aminomethyl)-19-11(1S,5R)-3-bicyclo [3.2.1]octanyl]methyl]-12-cycloheptyl-3,16,18-trimethyl-5,8,11,14,17-pentaoxo-15-propyl-1-oxa-4,7,10, 13,16-pentazacyclononadec-6-yl]methoxy] propylamino]propyl]carbamate

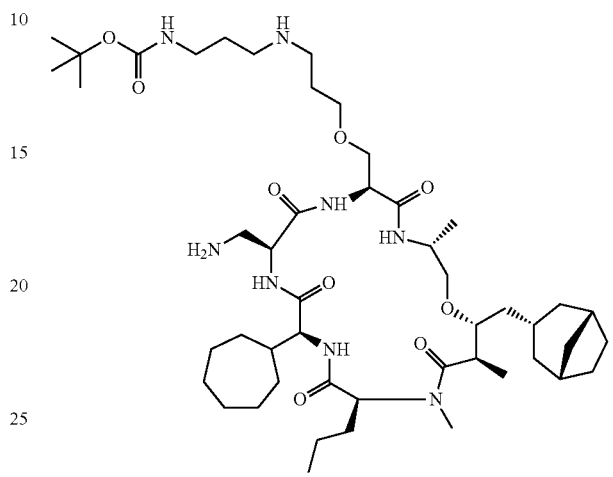

To a solution N-[3-[3-[[(3R,6S,9S,12S,15S,18R,19R)-9- (benzyloxycarbonylaminomethyl)-19-[[(1S,5R)-3-bicyclo [3.2.1]octanyl]methyl]-12-cycloheptyl-3,16,18-trimethyl-5, 8,11,14,17-pentaoxo-15-propyl-1-oxa-4,7,10,13,16-pentazacyclononadec-6-yl]methoxy]propylamino]propyl] carbamate (194 mg, 0.184 mmol) in isopropanol (30 mL) was added palladium (10 wt % on carbon, 194 mg). The mixture was stirred at room temperature for 2.5 h under an atmosphere of hydrogen. The catalyst was removed via filtration and the filtrate was concentrated under vacuum to afford the title compound (159 mg, 93.9% yield) as a white solid, which was used in the next step without further purification. LCMS (ESI): [M+H]$^+$=919.7.

Step 6. (3R,6S,9S,12S,15S,18R,19R)-9-(Aminomethyl)-6-((3-((3-aminopropyl)amino)propoxy) methyl)-19-((1R,3s,5S)-bicyclo[3.2.1]octan-3-ylmethyl)-12-cycloheptyl-3,16,18-trimethyl-15-propyl-1-oxa-4,7,10,13,16-pentaazacyclononadecane-5,8, 11,14,17-pentaone The product of Step 5 (159 mg, 0.173 mmol) was treated with TFA (10 mL) at 0° C. for 1 h. Toluene (10 mL) was added and the mixture was concentrated under vacuum. The residue was purified by Preparatory-HPLC. Column: XSelect CSH Prep C18 OBD Column, 5 um, 19*150 mm; Mobile Phase A: Water (0.05% TFA), Mobile Phase B: MeOH Preparative; Flow rate: 25 mL/min; Gradient: 37% B to 67% B in 20 min; 254/220 nm; Rt: 17.09 min to afford the title compound as its TFA salt (65 mg) as a white solid. LCMS (ESI): [M+H]$^+$=819.6, R$_t$=2.64 min, method=I. $^1$H NMR (400 MHz, DMSO-d$_6$): δ 8.72-8.42 (m, 3H), 8.20-8.02 (m, 5H), 8.00-7.82 (m, 3H), 7.56-7.44 (m, 1H), 4.58-4.45 (m, 1H), 4.38-4.11 (m, 2H), 3.89-3.65 (m, 4H), 3.38-3.12 (m, 4H), 3.09-2.72 (m, 11H), 2.22-1.99 (m, 4H), 1.89-1.52 (m, 15H), 1.49-1.21 (m, 16H), 1.09-0.87 (12H).

Example 25. (3R,9S,12S,15S,18R,19R)-9-(Aminomethyl)-6-((3-(aminomethyl)azetidin-1-yl)methyl)-12-cyclohexyl-19-hexyl-15-isobutyl-3,16,18-trimethyl-1-oxa-4,7,10,13,16-pentaazacyclononadecane-5,8,11,14,17-pentaone (trifluoroacetate salt)

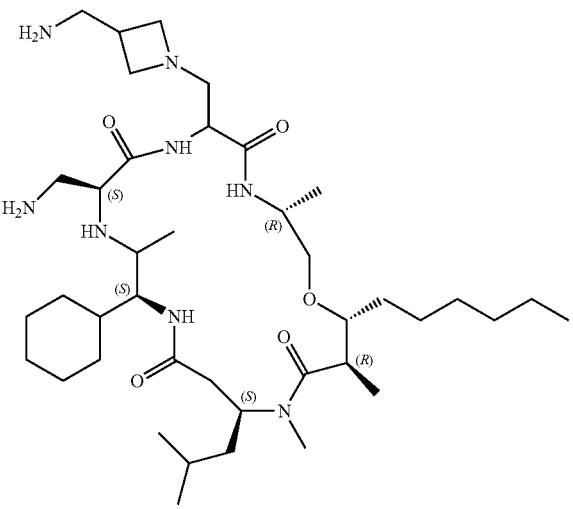

Step 1. Methyl 2-(((benzyloxy)carbonyl)amino)-3-(3-(((tert-butoxycarbonyl)amino)methyl)azetidin-1-yl)propanoate

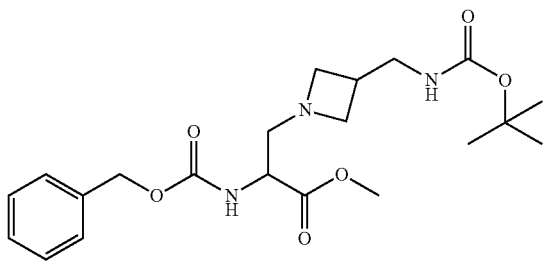 [SMILES: COC(=O)C(CN1CC(CNC(=O)OC(C)(C)C)C1)NC(=O)OCc1ccccc1]

To a mixture of methyl (2S)-2-(benzyloxycarbonylamino)-3-hydroxy-propanoate (2.5191 g, 9.9471 mmol) and triethylamine (3.0 mL, 21 mmol) in DCM (20 mL) at 0° C. was added methanesulfonyl chloride (0.90 mL, 12 mmol). This mixture was stirred at room temperature for 2 h, followed by the addition of tert-butyl (azetidin-3-ylmethyl)carbamate hydrochloride (2.5107 g, 10.935 mmol) and triethylamine (4.0 mL, 28 mmol). The reaction mixture was stirred at room temperature for 16 h. The reaction mixture was washed with saturated aqueous NaHCO$_3$, the aqueous layer was extracted with an additional 100 mL DCM, and the combined organic extracts were dried over MgSO$_4$, filtered, and evaporated in vacuo. The crude product was purified via flash chromatography on silica gel (120 g silica, solvent gradient: 0-10% MeOH in DCM). The resulting thick gum was dried under vacuum overnight to yield 3.4092 g (81%) of the title compound. LCMS (ESI): [M+H]$^+$=422.25; NMR (400 MHz, DMSO-d$_6$) δ 7.53 (d, J=7.8 Hz, 1H), 7.40-7.25 (m, 5H), 6.84 (d, J=6.3 Hz, 1H), 5.03 (s, 2H), 4.02-3.93 (m, 1H), 3.62 (s, 3H), 3.17 (q, J=7.7 Hz, 2H), 3.03 (t, J=6.3 Hz, 2H), 2.80 (q, J=6.7 Hz, 2H), 2.70-2.55 (m, 2H), 2.42-2.33 (m, 1H), 1.37 (s, 9H).

Step 2. 2-((((9H-Fluoren-9-yl)methoxy)carbonyl)amino)-3-(3-(((tert-butoxycarbonyl)amino)methyl)azetidin-1-yl)propanoic acid

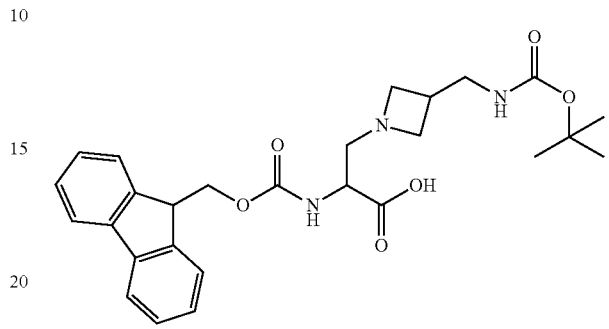

To a solution of methyl 2-(((benzyloxy)carbonyl)amino)-3-(3-(((tert-butoxycarbonyl)amino)methyl)azetidin-1-yl)propanoate (3.4092 g, 8.088 mmol) in 1,4-dioxane (20 mL) was added lithium hydroxide (1.0 M in water, 10.0 mL, 10 mmol). The reaction mixture was stirred at room temperature for 6 h. The reaction mixture was poured into 100 mL DCM and washed with 10% aqueous citric acid. The aqueous portion was extracted with an additional 3×100 mL DCM, and the combined organic extracts were dried over magnesium sulfate, filtered, and evaporated in vacuo, drying under vacuum overnight. The resulting material was dissolved in ethanol (20 mL). Under an atmosphere of nitrogen, palladium (10 wt. % on carbon) (271.7 mg, 0.2554 mmol) was added. The reaction mixture was then stirred under a hydrogen balloon at room temperature for 4 h, and then filtered through celite, rinsing with 200 mL ethanol, and evaporated in vacuo. The resulting material was dissolved in water (15 mL) and 1,4-dioxane (15 mL) with sodium hydrogen carbonate (2.066 g, 24.5 mmol) and Fmoc-OSu (3.274 g, 9.706 mmol). The reaction mixture was stirred at room temperature for 2 h, and then diluted with 100 mL DCM and washed with 10% aqueous citric acid. The aqueous portion was extracted with additional 100 mL DCM, and the combined organic extracts were dried over magnesium sulfate, filtered, and evaporated in vacuo. The crude product was purified via flash chromatography on silica gel (120 g silica, solvent gradient: 0-15% methanol in DCM) to yield 2.3477 g (59%) of the title compound. LCMS (ESI): [M+H]$^+$=496.25.

Step 3. (3R,9S,12S,15S,18R,19R)-9-(Aminomethyl)-6-((3-(aminomethyl)azetidin-1-yl)methyl)-12-cyclohexyl-19-hexyl-15-isobutyl-3,16,18-trimethyl-1-oxa-4,7,10,13,16-pentaazacyclononadecane-5,8,11,14,17-pentaone The title compound (mixture of 2 diastereomers) was prepared using 2-((((9H-fluoren-9-yl)methoxy)carbonyl)amino)-3-(3-(((tert-butoxycarbonyl)amino)methyl)azetidin-1-yl)propanoic acid and following procedures analogous to those described for Example 11. LCMS (ESI): R$_T$ (min)=8.55 and 8.70, [M+H]$^+$=735.6, method=B; $^1$H NMR (400 MHz, DMSO-d$_6$) δ 8.80-8.51 (m, 1H), 8.38-8.17 (m, 1H), 8.17-7.91 (m, 3H), 7.91-7.56 (m, 4H), 4.73-3.64 (m, 8H), 3.02 (d, J=104.9 Hz, 10H), 2.73 (s, 1H), 2.09-1.45 (m, 10H), 1.45-0.73 (m, 33H).

Example 26. (2S)-2,3-Diamino-N-[[(3R,6S,9S,12S,15S,18R,19R)-9-(aminomethyl)-12-cyclohexyl-19-hexyl-15-isobutyl-3,16,18-trimethyl-5,8,11,14,17-pentaoxo-1-oxa-4,7,10,13,16-pentazacyclononadec-6-yl]methyl]propanamide (trifluoroacetate salt)

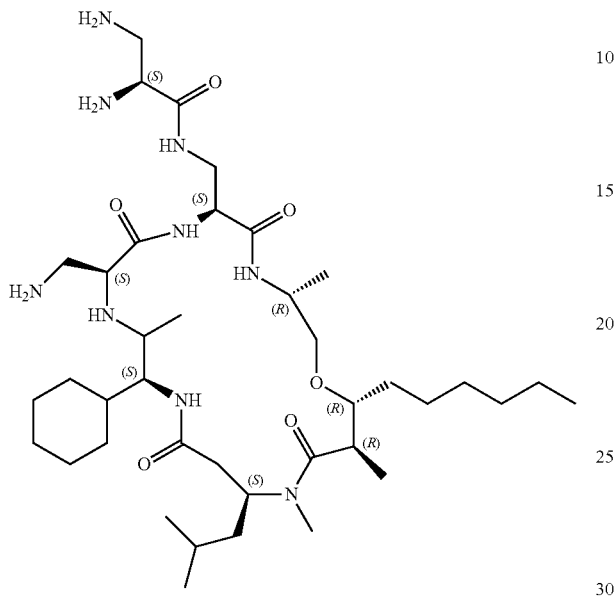

Step 1. (2S)-2-[[(2S)-2-[[(2S)-2-[[(2S)-2-[1(2R,3R)-3-[(2R)-2-Aminopropoxy]-2-methyl-nonanoyl]-methyl-amino]-4-methyl-pentanoyl]amino]-2-cyclohexyl-acetyl]amino]-3-(benzyloxycarbonylamino)propanoyl]amino]-3-(tert-butoxycarbonylamino)propanoic acid

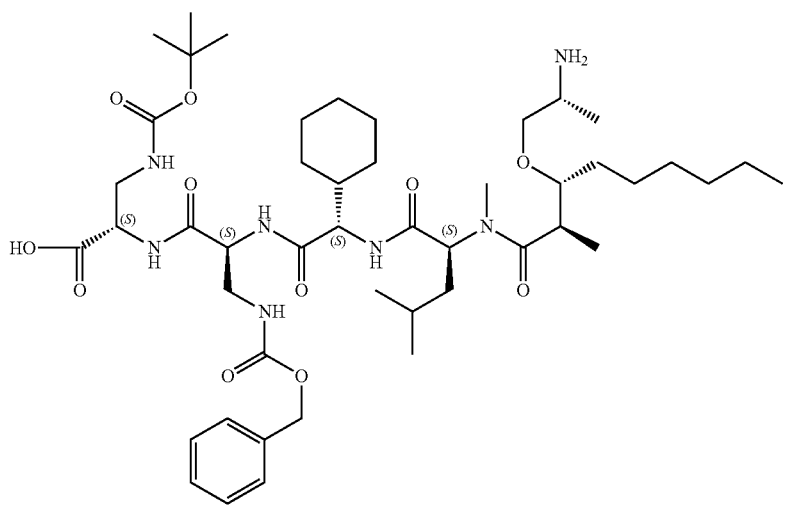

The title compound was prepared following procedures analogous to those described for Example 11, Step 1, using the appropriately protected amino acids. LCMS (ESI): [M+H]$^+$=918.5.

Step 2. tert-Butyl N-[[(3R,6S,9S,12S,15S,18R, 19R)-9-(benzyloxycarbonylaminomethyl)-12-cyclohexyl-19-hexyl-15-isobutyl-3,16,18-trimethyl-5,8,11,14,17-pentaoxo-1-oxa-4,7,10,13,16-pentazacyclononadec-6-yl]methyl]carbamate

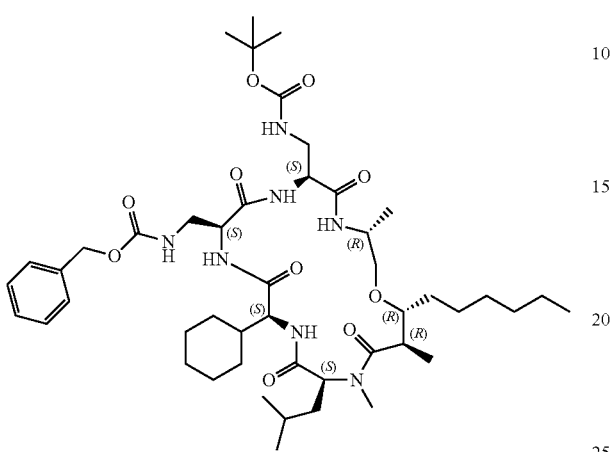

(2S)-2-[[(2S)-2-[[(2S)-2-[[(2S)-2-[[(2R,3R)-3-[(2R)-2-Aminopropoxy]-2-methyl-nonanoyl]-methyl-amino]-4-methyl-pentanoyl]amino]-2-cyclohexyl-acetyl]amino]-3-(benzyloxycarbonylamino)propanoyl]amino]-3-(tert-butoxycarbonylamino)propanoic acid (1.2 g, 1.3 mmol), was dissolved in 1.2 L of THF and charged with DIPEA (0.69 mL, 4 mmol). HATU (1.1 g, 2.6 mmol) was dissolved in 6 mL of DMF and added to the aforementioned mixture. The mixture was then stirred overnight at room temperature and evaporated in vacuo. The residue was then diluted with ethyl acetate and water, shaken vigorously, and partitioned. The organic portion was then concentrated in vacuo and the residue was purified by silica-gel flash chromatography (125 g silica, 0-10% MeOH in DCM) to afford the title compound (650 mg, 0.72 mmol, 55% yield). LCMS (ESI): [M+H]$^+$=900.5.

Step 3. Benzyl N-[[(3R,6S,9 S,12S,15S,18R,19R)-6-(aminomethyl)-12-cyclohexyl-19-hexyl-15-isobutyl-3,16,18-trimethyl-5,8,11,14,17-pentaoxo-1-oxa-4,7,10,13,16-pentazacyclononadec-9-yl]methyl]carbamate

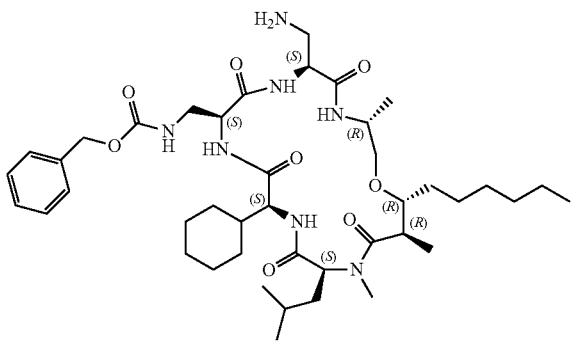

tert-Butyl N-[[(3R,6S,9S,12S,15S,18R,19R)-9-(benzyloxycarbonylaminomethyl)-12-cyclohexyl-19-hexyl-15-isobutyl-3,16,18-trimethyl-5,8,11,14,17-pentaoxo-1-oxa-4,7,10,13,16-pentazacyclononadec-6-yl]methyl]carbamate (600 mg, 0.66 mmol), was dissolved in 4 mL of DCM and charged with 1.6 mL of triisopropylsilane and 0.8 mL of TFA. The mixture was then stirred at room temperature for 1 h, diluted with toluene, and concentrated in vacuo. The residue was then diluted with EtOAc, charged with 0.10 mL of TEA, and diluted with water. The mixture was then shaken vigorously and partitioned. The organic was then concentrated in vacuo to afford the title compound (540 mg, 0.66 mmol, 100% yield). LCMS (ESI): [M+H]$^+$=800.5.

Step 4. tert-Butyl N-[(1S)-2-[[(3R,6S,9S,12S,15S,18R,19R)-9-(benzyloxycarbonylaminomethyl)-12-cyclohexyl-19-hexyl-15-isobutyl-3,16,18-trimethyl-5,8,11,14,17-pentaoxo-1-oxa-4,7,10,13,16-pentazacyclononadec-6-yl]methylamino]-1-[(tert-butoxycarbonylamino)methyl]-2-oxo-ethyl]carbamate

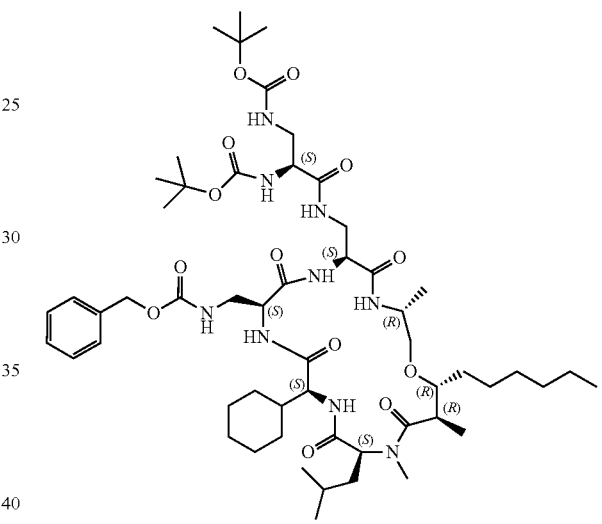

(2S)-2,3-bis(tert-butoxycarbonylamino)propanoic acid (190 mg, 0.63 mmol) was dissolved in 2 mL of DMF and charged with HATU (243 mg, 0.63 mmol) and TEA (174 uL, 1.25 mmol). The mixture was then stirred at room temperature for 5 min and added to benzyl N-[[(3R,6S,9S,12S,15S,18R,19R)-6-(aminomethyl)-12-cyclohexyl-19-hexyl-15-isobutyl-3,16,18-trimethyl-5,8,11,14,17-pentaoxo-1-oxa-4,7,10,13,16-pentazacyclononadec-9-yl]methyl]carbamate (290 mg, 0.36 mmol) dissolved in 0.30 mL of DMF. The mixture was then stirred at room temperature for 30 min. The mixture was then charged with 1 mL of saturated aqueous NaHCO$_3$ and stirred at room temperature for 5 min. The mixture was then diluted with EtOAc and water, shaken vigorously, and partitioned. The organic portion was then washed with water twice and concentrated in vacuo to afford the title compound (400 mg, 0.36 mmol, 100% yield). LCMS (ESI): [M+H]$^+$=1086.7.

Step 5. (2S)-2,3-Diamino-N-[[(3R,6S,9S,12S,15S,18R,19R)-9-(aminomethyl)-12-cyclohexyl-19-hexyl-15-isobutyl-3,16,18-trimethyl-5,8,11,14,17-pentaoxo-1-oxa-4,7,10,13,16-pentazacyclononadec-6-yl]methyl]propanamide (trifluoroacetate salt)

tert-Butyl N-[(1S)-2-[[(3R,6S,9S,12S,15S,18R,19R)-9-(benzyloxycarbonylaminomethyl)-12-cyclohexyl-19-hexyl- 15-isobutyl-3,16,18-trimethyl-5,8,11,14,17-pentaoxo-1-oxa-4,7,10,13,16-pentazacyclononadec-6-yl]methylamino]-1-[(tert-butoxycarbonylamino)methyl]-2-oxo-ethyl] carbamate (400 mg, 0.36 mmol) was dissolved in 40 mL of 1:1 isopropanol:EtOAc and subjected to hydrogenation via an HCube apparatus (10% Pd/C, 50° C., 75 psi). The mixture was then concentrated in vacuo.

The residue was then dissolved in 4 mL of DCM and charged with 1 mL of triisopropylsilane and 0.80 mL of TFA. The mixture was then stirred at room temperature for 1 h, concentrated in vacuo, and azeotroped twice with dioxane. The residue was then purified by reverse-phase HPLC to afford the title compound (88 mg, 0.11 mmol, 36% yield). LCMS (ESI): $R_T$ (min)=9.11, $[M+H]^+$=753.8, method=B; $^1$H NMR (400 MHz, DMSO-$d_6$) δ 8.67 (s, 1H), 8.44 (s, 1H), 8.35 (s, 1H), 8.22 (d, J=5.7 Hz, 1H), 8.11 (s, 1H), 8.02 (s, 1H), 7.96 (d, J=4.9 Hz, 1H), 7.69 (d, J=8.3 Hz, 1H), 7.54 (d, J=8.1 Hz, 1H), 4.66 (t, J=7.7 Hz, 1H), 4.25 (s, 1H), 4.05 (s, 1H), 3.85 (s, 2H), 3.72 (s, 1H), 3.20 (s, 1H), 3.11 (d, J=6.2 Hz, 1H), 2.98-2.70 (m, 5H), 1.87 (s, 2H), 1.65-1.58 (m, 14H), 1.27 (s, 13H), 1.11 (s, 1H), 1.06-0.81 (m, 17H).

Example 27. 3-(Aminomethyl)-N-[[(3R,6S,9S,12S,15S,18R,19R)-9-(aminomethyl)-12-cycloheptyl-19-hexyl-3,16,18-trimethyl-5,8,11,14,17-pentaoxo-15-propyl-1-oxa-4,7,10,13,16-pentazacyclononadec-6-yl]methyl]azetidine-1-carboxamide (trifluoroacetate salt)

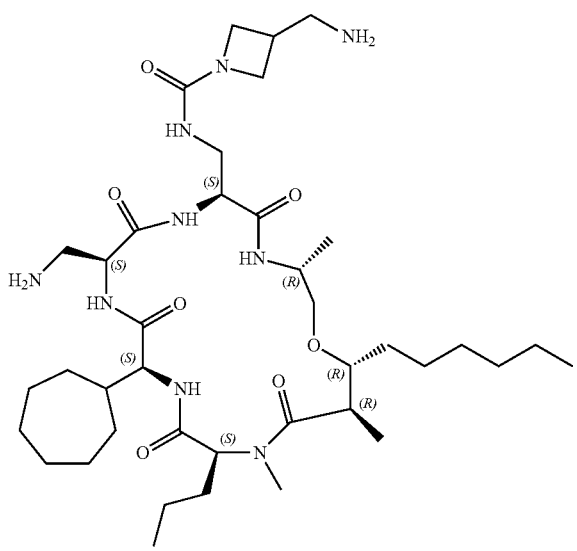

Step 1. tert-Butyl N-[[(3R,6S,9S,12S,15S,18R,19R)-6-[[[3-[(tert-butoxycarbonylamino)methyl] azetidine-1-carbonyl]amino]methyl]-12-cycloheptyl-19-hexyl-3,16,18-trimethyl-5,8,11,14,17-pentaoxo-15-propyl-1-oxa-4,7,10,13,16-pentazacyclononadec-9-yl]methyl]carbamate

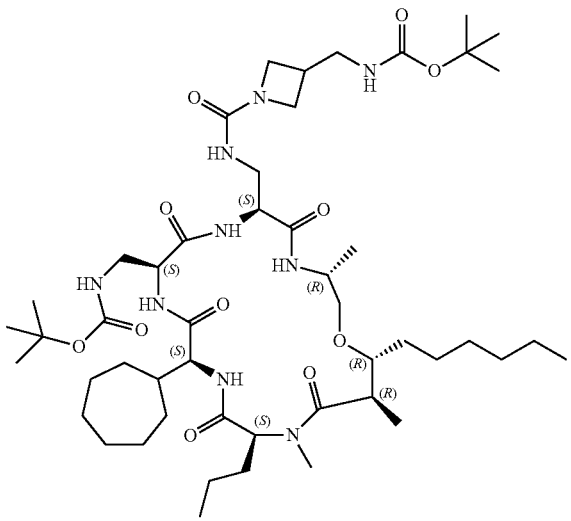

A solution of N-[[(3R,6S,9S,12S,15S,18R,19R)-6-(aminomethyl)-12-cycloheptyl-19-hexyl-3,16,18-trimethyl-5,8,11,14,17-pentaoxo-15-propyl-1-oxa-4,7,10,13,16-pentazacyclononadec-9-yl]methyl]carbamate (70.1 mg, 0.0.090 mmol, Example 14 Step 2) and 1,1'-carbonyldiimidazole (29.7 mg, 0.18 mmol) in THF (5 mL) was stirred at room temperature for 2 h. Then tert-butyl (azetidin-3-ylmethyl) carbamate (34.4 mg, 0.18 mmol) was added. The resulting mixture was stirred at room temperature for 2 h and then concentrated under vacuum. The residue was purified by reverse phase flash chromatography on C18 column eluting with 0-53% acetonitrile/0.1% TFA in water to afford the title compound (65.4 mg, 73.1% yield) as a white solid. LCMS (ESI): $[M+H]^+$=978.8.

Step 2. 3-(Aminomethyl)-N-[[(3R,6S,9S,12S,15S,18R,19R)-9-(aminomethyl)-12-cycloheptyl-19-hexyl-3,16,18-trimethyl-5,8,11,14,17-pentaoxo-15-propyl-1-oxa-4,7,10,13,16-pentazacyclononadec-6-yl]methyl]azetidine-1-carboxamide The product of Step 1 (93.2 mg, 0.10 mmol) was treated with TFA (3 mL) at 0° C. for 30 min with stirring. The mixture was concentrated under vacuum. The residue was purified by preparatory-LCMS to afford the title compound as its TFA salt (28.4 mg) as a white solid. LCMS (ESI): $[M+H]^+$=778.6, $R_t$=2.7 min, method=I. $^1$H NMR (400 MHz, DMSO-$d_6$): δ 8.75-8.55 (m, 1H), 8.21-7.75 (m, 8H), 7.45-7.26 (m, 1H), 4.65-4.17 (m, 3H), 3.93-3.85 (m, 5H), 3.61-3.44 (m, 4H), 3.39-3.35 (m, 3H), 3.15-3.03 (m, 4H), 2.93-2.82 (m, 3H), 2.19-1.98 (m, 2H), 1.86-1.65 (m, 8H), 1.55-1.25 (m, 18H), 1.00-0.88 (m, 12H).

Example 28. (3S,6S,9S,12S,15S)-6-(Aminomethyl)-9-cyclohexyl-16-hexyl-3-(1-hydroxy-2-(piperazin-1-yl)ethyl)-12-isobutyl-13,15-dimethyl-1,4,7,10,13,16-hexaazacyclooctadecane-2,5,8,11,14-pentaone (trifluoroacetate salt)

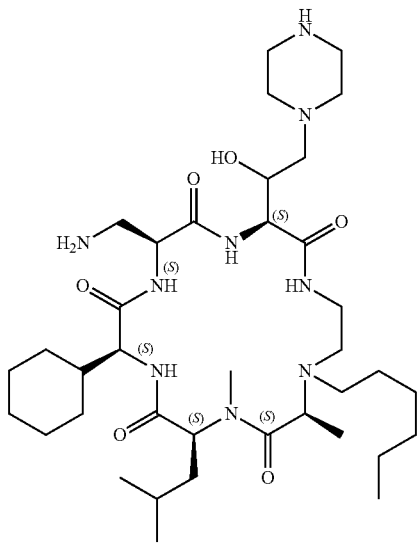

Step 1. Benzyl 4-(2-((2S,8S,11S,14S,17S)-17-((((benzyloxy)carbonyl)amino)methyl)-14-cyclohexyl-7-hexyl-11-isobutyl-8,10-dimethyl-3,9,12,15,18-pentaoxo-1,4,7,10,13,16-hexaazacyclooctadecan-2-yl)-2-((tert-butyldimethylsilyl)oxy)ethyl)piperazine-1-carboxylate

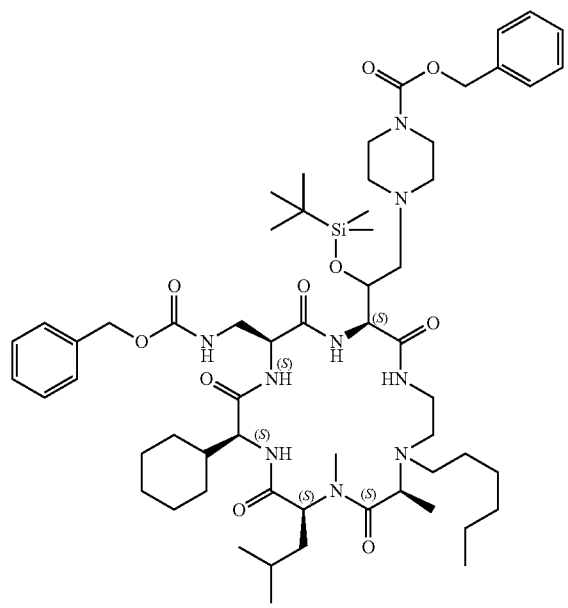

The title compound was obtained using Intermediate 9 and Intermediate T6 and following procedures analogous to those described for Example 22.

Step 2. (3S,6S,9S,12S,15S)-6-(Aminomethyl)-9-cyclohexyl-16-hexyl-3-(1-hydroxy-2-(piperazin-1-yl)ethyl)-12-isobutyl-13,15-dimethyl-1,4,7,10,13,16-hexaazacyclooctadecane-2,5,8,11,14-pentaone (trifluoroacetate salt)

To the material from Step 1 (50 mg) dissolved in THF (1 mL) was added tetrabutylammonium fluoride (1 mL, 1 N in THF) and the mixture stirred overnight. The reaction mixture was diluted with IPAC, washed with water and brine, dried over sodium sulfate and concentrated to obtain crude benzyl 4-(2-((2S,8S,11S,14S,17S)-17-((((benzyloxy)carbonyl)amino)methyl)-14-cyclohexyl-7-hexyl-11-isobutyl-8,10-dimethyl-3,9,12,15,18-pentaoxo-1,4,7,10,13,16-hexaazacyclooctadecan-2-yl)-2-hydroxyethyl)piperazine-1-carboxylate. This material was converted to the title compound using procedures analogous to those described in Example 22 (Step 6) and then purified by reverse phase HPLC to obtain the title compound as the trifluoroacetate salt. LCMS (ESI): $R_T$ (min)=5.95; $[M+H]^+$=736.5, method=B Example 29. (3S,6S,9S,12S,15S,17S)-6-(Aminomethyl)-3-((3-aminopropoxy)methyl)-9-cyclohexyl-16-(cyclopentylmethyl)-13,15,17-trimethyl-12-propyl-1,4,7,10,13,16-hexaazacyclooctadecane-2,5,8,11,14-pentaone (trifluoroacetate salt)

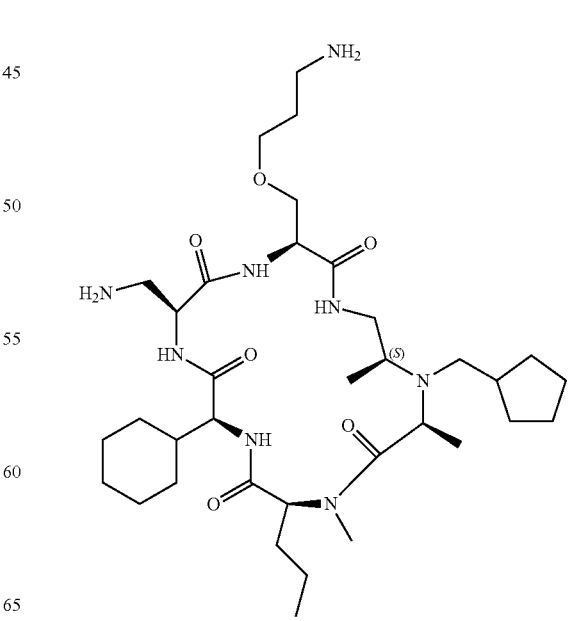

Step 1. N-Me-Norvaline-cyclohexylglycine-Dap(Boc)-3-((tert-butoxycarbonyl)amino)propyl)-serine-(2-chlorotrityl resin)

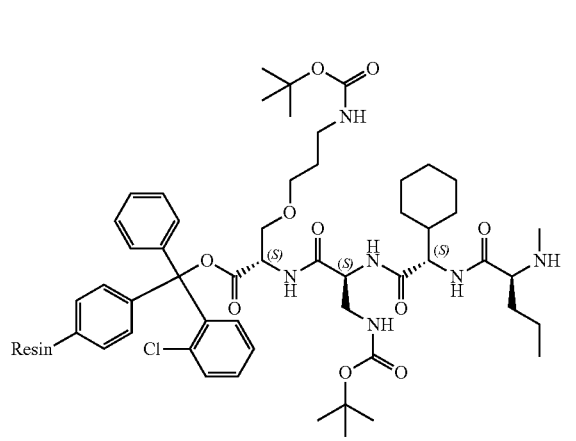

The resin bound tetrapeptide was prepared following methods analogous to those described in Example 7, Step 1.

Step 2. (3S,6S,9S,12S,15S,17S)-6-(Aminomethyl)-3-((3-aminopropoxy)methyl)-9-cyclohexyl-16-(cyclopentylmethyl)-13,15,17-trimethyl-12-propyl-1,4,7,10,13,16-hexaazacyclooctadecane-2,5,8,11,14-pentaone The title compound was prepared as its TFA salt using the resin bound tetrapeptide from Step 1 and (2S)-2-[cyclopentylmethyl-[(1S)-2-(9H-fluoren-9-ylmethoxycarbonylamino)-1-methyl-ethyl]amino]propanoic acid (Intermediate T21), and following methods analogous to those described in Example 12, Steps 2-4. LCMS (ESI): [M+H]$^+$=693.5, R$_t$=1.9 min, method=J. $^1$H NMR (400 MHz, DMSO-d$_6$): δ 8.92-8.75 (m, 1H), 8.18-7.92 (m, 4H), 7.81-7.70 (m, 4H), 4.85-4.72 (m, 1H), 4.58-4.50 (m, 1H), 4.24-4.07 (m, 3H), 3.95-3.77 (m, 2H), 3.28-3.09 (m, 8H), 2.91-2.82 (m, 4H), 2.14-1.92 (m, 5H), 1.80-1.71 (m, 5H), 1.67-1.58 (m, 6H), 1.57-1.50 (m, 5H), 1.44-1.40 (m, 2H), 1.29-1.02 (m, 10H), 0.99-0.88 (m, 4H).

Example 30. (3R,6S,9S,12S,15S,18R,19R)-9-(Aminomethyl)-6-[[3-aminopropyl(methyl)amino]methyl]-12-cycloheptyl-19-hexyl-3,16,18-trimethyl-15-propyl-1-oxa-4,7,10,13,16-pentazacyclononadecane-5,8,11,14,17-pentone (trifluoroacetate salt)

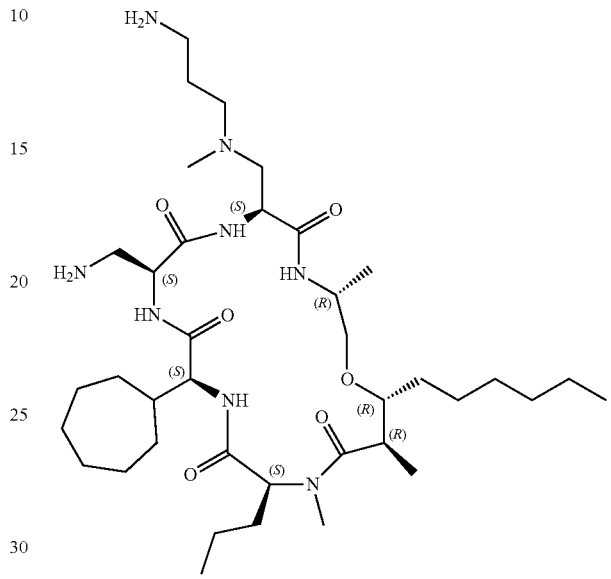

Step 1. tert-Butyl N-[3-[[(3R,6S,9S,12S,15S,18R,19R)-9-[(tert-butoxycarbonylamino)methyl]-12-cycloheptyl-19-hexyl-3,16,18-trimethyl-5,8,11,14,17-pentaoxo-15-propyl-1-oxa-4,7,10,13,16-pentazacyclononadec-6-yl]methyl-methyl-amino]propyl]carbamate

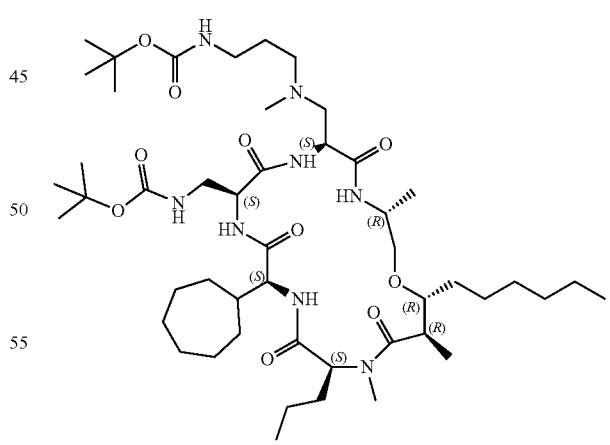

To a solution of tert-butyl N-[3-[[(3R,6S,9S,12S,15S,18R,19R)-9-[(tert-butoxycarbonylamino)methyl]-12-cycloheptyl-19-hexyl-3,16,18-trimethyl-5,8,11,14,17-pentaoxo-15-propyl-1-oxa-4,7,10,13,16-pentazacyclononadec-6-yl]methylamino]propyl]carbamate (Example 14, Step 3) (201 mg, 0.218 mmol) in ethanol (5 mL) was added paraformaldehyde (71.7 mg, 2.39 mmol) and acetic acid (26.1 mg, 0.435 mmol). The reaction mixture was stirred at room temperature for 2 h, followed by the addition of sodium cyanoborohydride (54.7 mg, 0.87 mmol). The reaction mixture was stirred at room temperature for 3 days and then concentrated under vacuum. The residue was purified by reverse phase chromatography on C18 column (0-50% acetonitrile/0.1% TFA in water) to afford the title compound (119 mg) as a white solid. LCMS (ESI): [M+H]$^+$=937.8.

Step 2. (3R,6S,9S,12S,15S,18R,19R)-9-(Aminomethyl)-6-[[(3-aminopropyl)methyl)amino]methyl]-12-cycloheptyl-19-hexyl-3,16,18-trimethyl-15-propyl-1-oxa-4,7,10,13,16-pentazacyclononadecane-5,8,11,14,17-pentone The product of Step 1 (119 mg, 0.126 mmol) was treated with TFA (5.0 mL) at 0° C. for 30 min and then concentrated under vacuum. The residue was purified by preparatory-LCMS to afford the title compound (9.90 mg) as its TFA salt as a white solid. LCMS (ESI): [M+H]$^+$=737.6, R$_t$=2.5 min, method=I. $^1$H NMR (400 MHz, DMSO-d$_6$): δ 9.62-9.45 (m, 1H), 8.62-8.35 (m, 1H), 8.18-8.12 (m, 1H), 8.02-7.92 (m, 2H), 7.88-7.74 (m, 3H), 7.52-7.41 (m, 1H), 7.29-6.95 (m, 1H), 4.62-4.55 (m, 1H), 4.30-4.22 (m, 1H), 4.09-4.02 (m, 1H), 3.92-3.80 (m, 2H), 3.30-3.08 (m, 10H), 2.97-2.74 (m, 8H), 2.15-2.07 (m, 2H), 1.98-1.88 (m, 4H), 1.75-1.59 (m, 7H), 1.45-1.24 (m, 17H), 1.05-0.85 (m, 11H).

Example 31. 1-((1S,3r)-3-(((3R,6S,9S,12S,15S,18R,19R)-9-(Aminomethyl)-12-cycloheptyl-3,16,18-trimethyl-5,8,11,14,17-pentaoxo-15-propyl-19-(spiro[3.3]heptan-2-ylmethyl)-1-oxa-4,7,10,13,16-pentaazacyclononadecan-6-yl)methoxy)cyclobutyl)guanidine (trifluoroacetate salt)

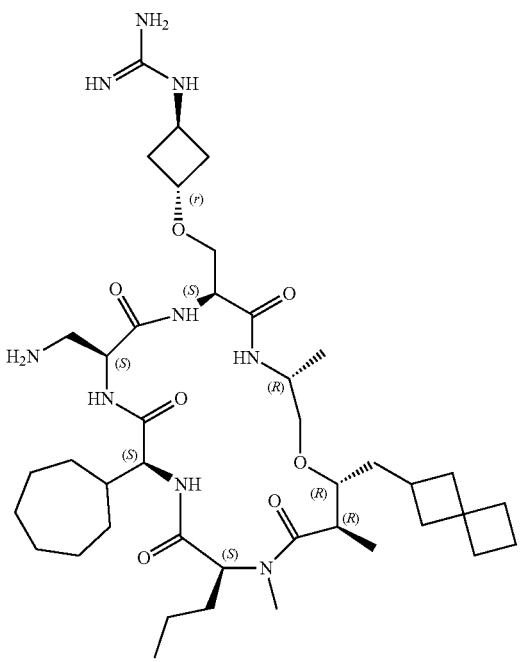

Step 1. tert-Butyl N-[3-[[(3R,6S,9S,12S,15S,18R,19R)-9-(benzyloxycarbonylaminomethyl)-12-cycloheptyl-3,16,18-trimethyl-5,8,11,14,17-pentaoxo-15-propyl-19-(spiro[3.3]heptan-2-ylmethyl)-1-oxa-4,7,10,13,16-pentazacyclononadec-6-yl]methoxy]cyclobutyl]carbamate

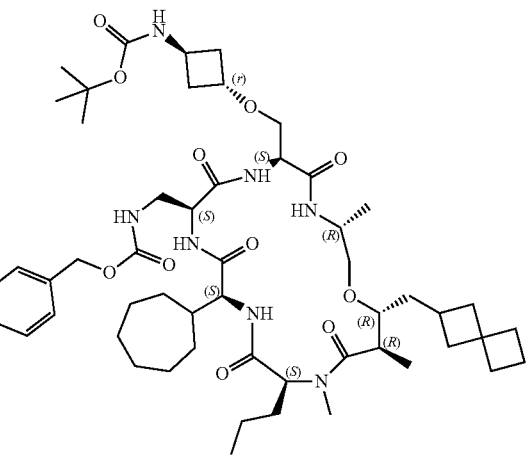

The title compound was prepared following methods analogous to those described in Example 8, Steps 1-3. LCMS (ESI): [M+1-1]$^+$=994.6.

Step 2. Benzyl (((3R,6S,9S,12S,15S,18R,19R)-6-O(1r,3S)-3-aminocyclobutoxy)methyl)-12-cycloheptyl-3,16,18-trimethyl-5,8,11,14,17-pentaoxo-15-propyl-19-(spiro[3.3]heptan-2-ylmethyl)-1-oxa-4,7,10,13,16-pentaazacyclononadecan-9-yl)methyl)carbamate

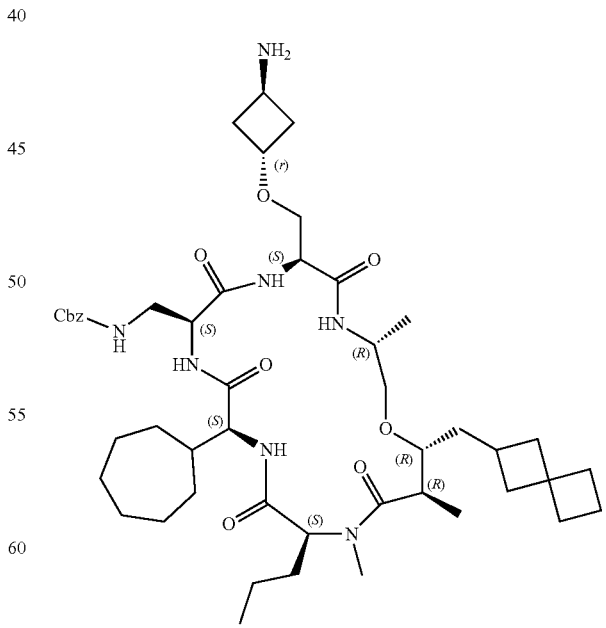

The product of Step 1 (577 mg, 0.580 mmol) was treated with TFA (10 mL) at 0° C. for 1 h and then concentrated under vacuum. The residue was co-evaporated with toluene (2×10 mL) to remove residual TFA. The crude product was used directly in the next step as the TFA salt without purification. LCMS (ESI): [M+1-1]⁺=894.6.

Step 3. tert-Butyl (NZ)—N-[[[3-[[(3R,6S,9S,12S, 15S,18R,19R)-9-(benzyloxycarbonylaminomethyl)-12-cycloheptyl-3,16,18-trimethyl-5,8,11,14,17-pentaoxo-15-propyl-19-(spiro[3.3]heptan-2-ylmethyl)-1-oxa-4,7,10,13,16-pentazacyclononadec-6-yl]methoxy]cyclobutyl]amino]-(tert-butoxycarbonylamino)methylene]carbamate

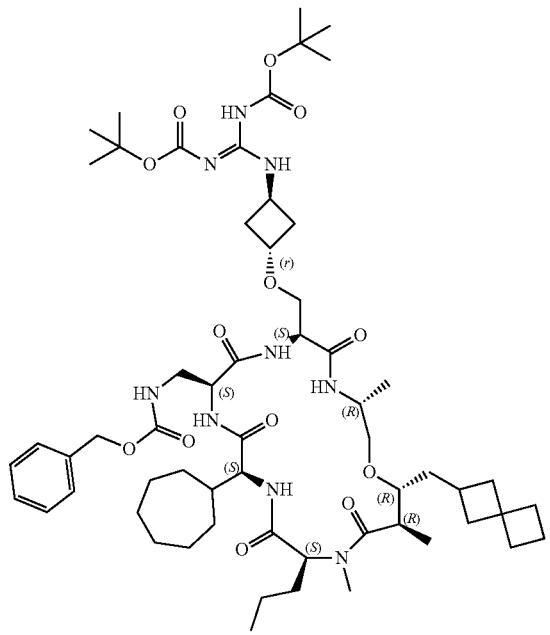

To a solution of the crude product from Step 2 (519 mg) in ethanol (60 mL) was added (Z)-tert-butyl (((tert-butoxycarbonyl)amino)(1H-pyrazol-1-yl)methylene)carbamate (360 mg, 1.16 mmol) and DIPEA (0.40 mL, 2.3 mmol) at room temperature. The reaction mixture was stirred for 4 h at room temperature and then concentrated under vacuum. The residue was dissolved in DCM (150 mL) and washed with 10% ammonium chloride in water (2×150 mL). The organic layer was dried over anhydrous sodium sulfate and concentrated under vacuum. The residue was purified by reverse phase chromatography on C18 column (0-100% acetonitrile/0.05% TFA in water) to afford the title compound (281 mg) as a colorless solid. LCMS (ESI): [M+1-1]⁺=1136.7.

Step 4. tert-Butyl (NZ)—N-[[[3-[[(3R,6S,9S,12S, 15S,18R,19R)-9-(aminomethyl)-12-cycloheptyl-3, 16,18-trimethyl-5,8,11,14,17-pentaoxo-15-propyl-19-(spiro[3.3]heptan-2-ylmethyl)-1-oxa-4,7,10,13, 16-pentazacyclononadec-6-yl]methoxy]cyclobutyl] amino]-(tert-butoxycarbonylamino)methylene] carbamate

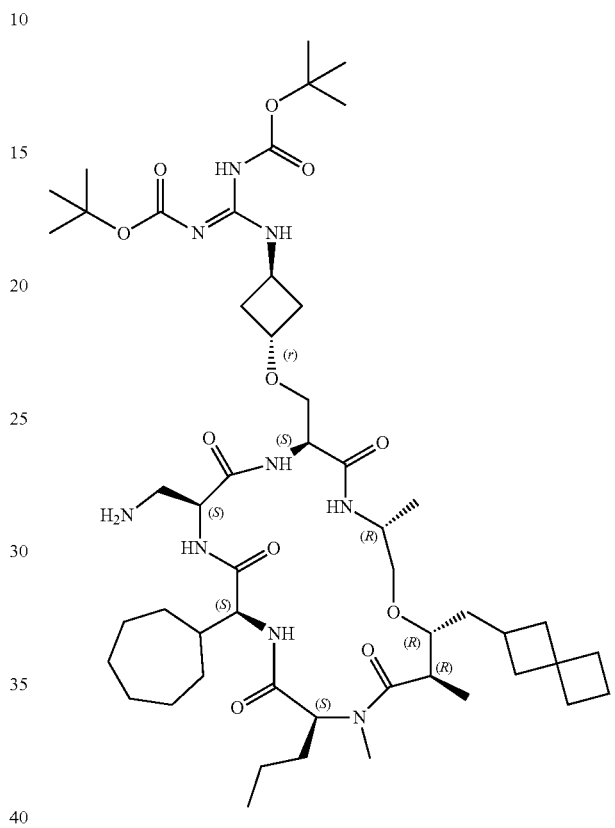

The product from Step 3 (281 mg, 0.247 mmol) was combined with Pd/C (280 mg, 10% Pd loading on carbon) in 2-propanol (35 mL) and stirred at room temperature for 6 h under an atmosphere of hydrogen. The catalyst was removed via filtration and the filtrate was concentrated under reduced pressure to afford the title compound (220 mg, 88.8% yield) as a colorless solid. LCMS (ESI): [M+H]⁺=1002.8. Step 5. 1-01S,3r)-3-(((3R,6S,9S,12S,15S, 18R,19R)-9-(Aminomethyl)-12-cycloheptyl-3,16,18-trimethyl-5,8,11,14,17-pentaoxo-15-propyl-19-(spiro[3.3]heptan-2-ylmethyl)-1-oxa-4,7,10,13,16-pentaazacyclononadecan-6-yl)methoxy)cyclobutyl) guanidine The product from Step 4 (220 mg, 0.220 mmol) was treated with TFA (4.0 mL) at 0° C. for 4 h and then concentrated under vacuum. The residue was co-evaporated with toluene (2×10 mL). The crude product was purified by Preparatory-HPLC to afford the title compound (45.3 mg) as its TFA salt as a white solid. LCMS (ESI): [M+H]⁺=802.6, R$_t$=2.72 min, method=I. ¹H NMR (400 MHz, DMSO-d6): δ 8.56-8.31 (m, 1H), 8.18-8.12 (m, 2H), 8.08-7.99 (m, 4H), 7.92-7.85 (m, 1H), 7.34-7.06 (m, 4H), 4.52-4.35 (m, 2H), 4.20-4.08 (m, 2H), 4.02-3.92 (m, 2H), 3.88-3.80 (m, 1H), 3.68-3.60 (m, 1H), 3.52-3.42 (m, 1H), 3.41-3.34 (m, 1H), 3.32-3.12 (m, 6H), 3.15 (s, 1H), 2.73 (s, 2H), 2.31-2.23 (m, 3H), 2.16-1.98 (m, 8H), 1.88-1.81 (m, 2H), 1.78-1.72 (m, 3H), 1.69-1.55 (m, 8H), 1.53-1.45 (m, 6H), 1.32-1.21 (m, 3H), 0.99-0.89 (m, 6H), 0.88-0.83 (m, 3H).

Example 32. (3S,6S,9S,12S,15S,18S)-6-(Aminomethyl)-16-butyl-9-cyclohexyl-3-((S)-1-hydroxyethyl)-18-(hydroxymethyl)-12-isobutyl-13,15-dimethyl-1,4,7,10,13,16-hexaazacyclooctadecane-2,5,8,11,14-pentaone

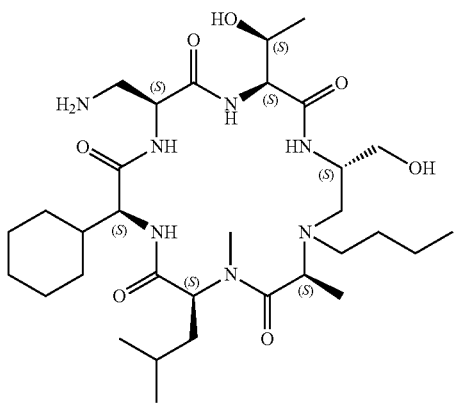

Step 1: Methyl N-(tert-butoxycarbonyl)-O-(tert-butyldiphenylsilyl)-D-serinate

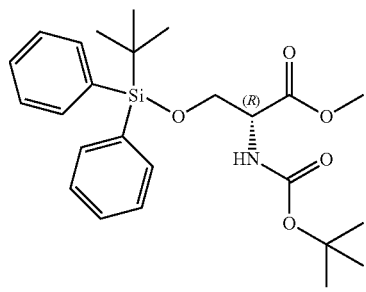

To a suspension of methyl (2R)-2-amino-3-hydroxy-propanoate hydrochloride (2.8 g, 18 mmol) in THF/water mixture was added di-tert-butyl carbonate (3.8 g, 22 mmol) and sodium bicarbonate (1.5 g, 18 mmol) and the mixture was stirred overnight. The reaction mixture was diluted with IPAC, washed with brine, dried over sodium sulfate and concentrated. The residue was dissolved in DCM (30 mL) and tert-butylchlorodiphenylsilane (5.9 g, 22 mmol) and imidazole (2.5 g, 36 mmol) were added and the mixture stirred overnight. The reaction mixture was diluted with IPAC, washed with water and brine, dried over sodium sulfate and concentrated. The residue was purified by chromatography (silica gel 0-50% IPAC/heptane) to obtain the title compound (8.1 g, 98%). $^1$H NMR (400 MHz, Chloroform-d) δ 7.61-7.53 (m, 3H), 7.48-7.34 (m, 7H), 5.41 (d, J=8.8 Hz, 1H), 4.50-4.30 (m, 1H), 4.06 (dd, J=10.1, 3.0 Hz, 1H), 3.89 (dd, J=10.1, 3.1 Hz, 1H), 3.74 (s, 3H), 1.46 (s, 9H), 1.03 (s, 9H).

Step 2: Benzyl N—((S)-2-((tert-butoxycarbonyl)amino)-3-((tert-butyldiphenylsilyl)oxy)propyl)-N-hexyl-L-alaninate

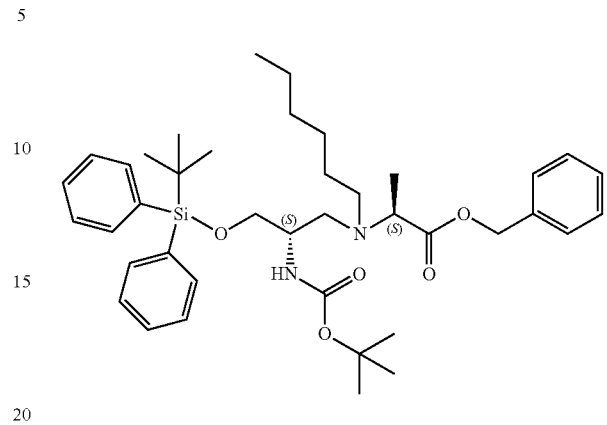

The residue from Step 1 was dissolved in dry THF (30 mL) and cooled in an ice-bath. Lithium aluminum hydride (8.85 mL, 2M in THF) was added and the reaction mixture was allowed to warm to room temperature over 2 h. The reaction mixture was quenched with saturated aqueous ammonium chloride and the solid was removed by filtration through celite. The filtrate was dried over sodium sulfate and concentrated to afford crude tert-butyl (S)-(1-((tert-butyldiphenylsilyl)oxy)-3-hydroxypropan-2-yl)carbamate.

This material was converted to the aldehyde as described in Step 4 of Example 20 to obtain tert-butyl N-[(1R)-1-[[tert-butyl(diphenyl)silyl]oxymethyl]-2-oxo-ethyl]carbamate (3.5 g, 54%). $^1$H NMR (400 MHz, Chloroform-d) δ 9.66 (s, 1H), 7.69-7.56 (m, 4H), 7.51-7.35 (m, 6H), 5.40 (d, J=7.6 Hz, 1H), 4.42-3.88 (m, 3H), 1.45 (d, J=9.5 Hz, 9H), 1.03 (s, 9H).

This material was converted to the title compound (1.75 g, 55%) following procedures as described in Step 5 of Example 20. $^1$H NMR (400 MHz, Chloroform-d) δ 7.70-7.52 (m, 4H), 7.48-7.30 (m, 11H), 5.10 (s, 2H), 4.73 (s, 1H), 3.79-3.50 (m, 4H), 2.88-2.67 (m, 2H), 2.63-2.40 (m, 2H), 1.43 (s, 9H), 1.38-1.18 (m, 11H), 1.05 (s, 9H), 0.94-0.81 (m, 3H).

Step 3. N—((S)-2-(0(9H-fluoren-9-yl)methoxy)carbonyl)amino)-3-((tert-butyldiphenylsilyl)oxy)propyl)-N-hexyl-L-alanine

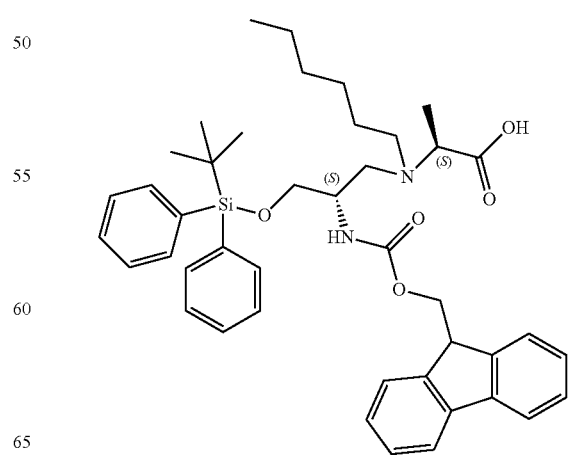

Benzyl N—((S)-2-((tert-butoxycarbonyl)amino)-3-((tert-butyldiphenylsilyl)oxy)propyl)-N-hexyl-L-alaninate (1.75 g) was converted to the title compound (1.0 g, 54%) as described in Steps 6 and 7 of Example 20. $^1$H NMR (400 MHz, Chloroform-d) δ 7.74 (d, J=7.6 Hz, 2H), 7.60 (dd, J=18.3, 7.4 Hz, 6H), 7.46-7.34 (m, 8H), 7.32-7.19 (m, 2H), 5.98 (d, J=7.4 Hz, 1H), 4.33 (d, J=8.5 Hz, 2H), 4.18 (t, J=7.2 Hz, 1H), 3.97-3.59 (m, 4H), 3.07-2.93 (m, 2H), 2.73 (d, J=56.2 Hz, 2H), 1.51 (s, 2H), 1.42-1.35 (m, 3H), 1.22 (d, J=11.7 Hz, 6H), 1.08 (s, 9H), 0.88-0.78 (m, 3H).

Step 4. Benzyl (((2S,5S,8S,11S,14S,17S)-5-((S)-1-(benzyloxy)ethyl)-17-cyclohexyl-8-((((2,2-dimethyl-1,1-diphenylpropyl)dimethylsilyl)oxy)methyl)-10-hexyl-14-isobutyl-11,13-dimethyl-3,6,12,15,18-pentaoxo-1,4,7,10,13,16-hexaazacyclooctadecan-2-yl)methyl)carbamate

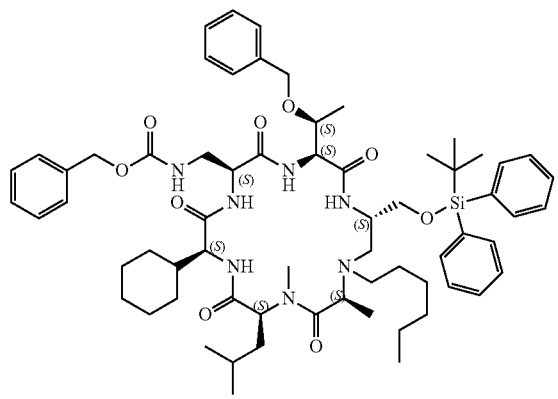

The title compound (0.30 g) was prepared using the intermediate from step 2 and following procedures analogous to those described in steps 8 and 9 of Example 20. LCMS (ESI): [M+H]$^+$=1145.8.

Step 5. (3S,6S,9S,12S,15S,18S)-6-(Aminomethyl)-16-butyl-9-cyclohexyl-3-((S)-1-hydroxyethyl)-18-(hydroxymethyl)-12-isobutyl-13,15-dimethyl-1,4,7,10,13,16-hexaazacyclooctadecane-2,5,8,11,14-pentaone The title compound was prepared as its TFA salt using the intermediate from Step 4 and following procedures analogous to those described in Example 28, Step 2. LCMS (ESI): R$_T$ (min)=7.807, [M+H]$^+$=682.5, method B (purity: 82%).

Example 33. N-[[(3R,6S,9S,12S,15S,18R,19R)-9-(Aminomethyl)-12-cyclohexyl-19-hexyl-15-isobutyl-3,16,18-trimethyl-5,8,11,14,17-pentaoxo-1-oxa-4,7,10,13,16-pentazacyclononadec-6-yl]methyl]methanesulfonamide (trifluoroacetate salt)

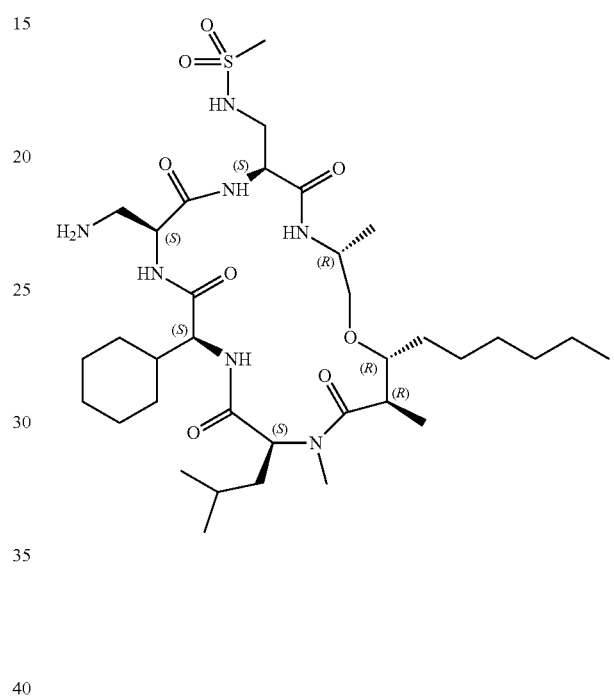

Benzyl N-[[(3R,6S,9S,12S,15S,18R,19R)-6-(aminomethyl)-12-cyclohexyl-19-hexyl-15-isobutyl-3,16,18-trimethyl-5,8,11,14,17-pentaoxo-1-oxa-4,7,10,13,16-pentazacyclononadec-9-yl]methyl]carbamate (Example 26, Step 3) (60 mg, 0.68 mmol) was dissolved in 0.20 mL of DCM and charged with DIPEA (26 uL, 0.15 mmol) and methane sulfonyl chloride (6 uL, 0.075 mmol). The mixture was then stirred at room temperature for one hour. The mixture was then diluted with EtOAc and water, shaken vigorously, and partitioned. The organic portion was then washed once with water and concentrated in vacuo.

The residue was then dissolved in 5 mL of 1:1 isopropanol:EtOAc and charged with 0.1 mL of TFA. The mixture was then hydrogenated using an HCube apparatus (10% Pd/C, 50° C., 75 psi). The mixture was then concentrated in vacuo and purified by reverse-phase HPLC to afford the title compound (21 mg, 0.028 mmol, 41% yield). LCMS (ESI): R$_T$ (min)=12.17, [M+H]$^+$=744.5, method=B; $^1$H NMR (400 MHz, DMSO-d$_6$) δ 8.33-8.07 (m, 2H), 7.86 (d, J=7.1 Hz, 3H), 7.46 (t, J=8.8 Hz, 1H), 7.14-7.00 (m, 1H), 6.51 (s, 1H), 4.61 (dd, J=10.3, 5.1 Hz, 1H), 4.19 (d, J=8.1 Hz, 1H), 3.99 (s, 1H), 3.93 (s, 1H), 3.83 (s, 1H), 3.73 (s, 1H), 3.10 (s, 1H), 2.90 (dd, J=10.0, 8.1 Hz, 4H), 2.81 (d, J=6.9 Hz, 1H), 2.07 (s, 1H), 1.75 (d, J=12.9 Hz, 1H), 1.65 (s, 8H), 1.53 (s, 1H), 1.26 (s, 15H), 1.10 (d, J=12.2 Hz, 1H), 1.09-0.93 (m, 4H), 0.97-0.81 (m, 13H).

Example 34. (3R,6S,9S,12S,15S,18R,19R)-9-(Aminomethyl)-12-cycloheptyl-6-(((1,5-diaminopentan-3-yloxy)methyl)-19-hexyl-3,16,18-trimethyl-15-propyl-1-oxa-4,7,10,13,16-pentaazacyclononadecane-5,8,11,14,17-pentaone (trifluoroacetate salt)

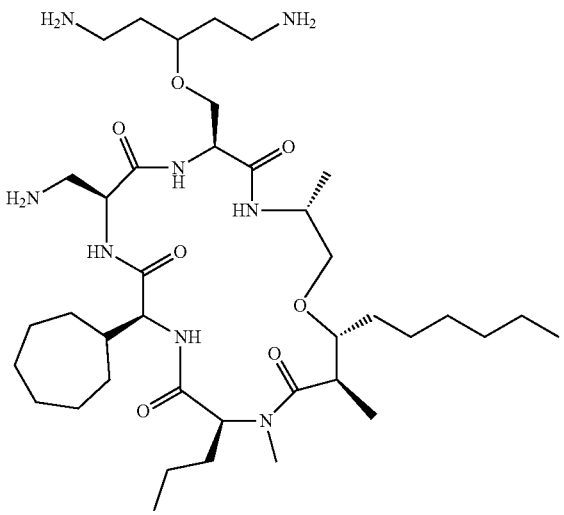 [SMILES: CCCCCC[C@H]1OC[C@@H](C)NC(=O)[C@H](COC(CCN)CCN)NC(=O)[C@H](CN)NC(=O)[C@H](C2CCCCCC2)NC(=O)[C@H](CCC)N(C)C(=O)[C@@H]1C]

Step 1. Dimethyl 3-(benzyloxy)pentanedioate

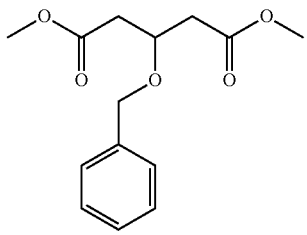

To a round bottom flask was added dimethyl 3-hydroxypentanedioate (10 mL, 67.7 mmol), chlorotrimethylsilane (12.9 mL, 135 mmol), and DCM (135 mL). The reaction flask was cooled to 0° C. in an ice/water bath. Once cooled, imidazole (9.2 g, 135 mmol) was added in two portions. After 10 min the cooling bath was removed and the reaction was left to stir overnight at room temperature. The reaction was filtered to remove excess imidazole, rinsed with DCM, and concentrated to ~20% volume. Diethyl ether was added and the organic layer was washed with water twice. The organic layer were dried over magnesium sulfate, filtered, and concentrated. The crude residue was taken up in acetonitrile (150 mL), and treated with triethylsilane (7.2 mL, 45.0 mmol) and ferric chloride (1.2 g, 7.5 mmol). The reaction was left to stir for 25 min at room temperature, then benzaldehyde (4.6 mL, 45.0 mmol) was added and left overnight to stir. The next day the reaction was concentrated, treated with water, extracted with DCM (three times). The combined organic layers were washed with brine, dried over magnesium sulfate, filtered, and concentrated. The residue was purified by flash chromatography on silica gel (0-100% ethyl acetate/heptane) to give the title compound (6.71 g, 67% yield) as a clear colorless, oil. $^1$H NMR (400 MHz, DMSO-$d_6$) δ 7.33 (m, 2H), 7.26 (m, 3H), 4.5 (s, 2H), 4.18 (m, 1H), 3.60 (s, 6H), 2.65 (d, J=6.3 Hz, 4H).

Step 2. 3-(Benzyloxy)pentane-1,5-diol

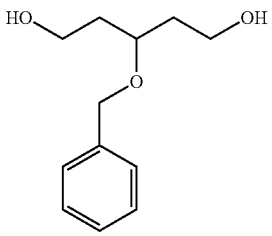 [SMILES: OCCC(CCO)OCc1ccccc1]

To a round bottom flask was added dimethyl 3-benzyloxypentanedioate (1.05 g, 19.7 mmol) and THF (8 mL). The solution was cooled to 0° C. and then lithium aluminum hydride (2 M solution in diethyl ether) (9.8 mL, 19.7 mmol) was added gradually to the reaction over 10 min. After stirring for 20 min at 0° C., the reaction was allowed to warm to room temperature and stir for 3 h. The reaction was cooled to 0° C. and quenched with 0.75 mL water, then 0.75 mL NaOH (15% w/w solution in water), and finally 2.24 mL water. After 10 min, the flask was warmed to room temperature, diluted with ethyl acetate, and left for an additional 45 min to stir. The resulting suspension was removed by filtration and the filtrate was diluted with water and extracted with ethyl acetate three times. The combined organic layers were dried over magnesium sulfate, filtered, and concentrated. The residue was purified by flash chromatography on silica gel (0-15% methanol/DCM) to afford the title compound (0.702 g 85% yield) as a clear, colorless oil. $^1$H NMR (400 MHz, DMSO-$d_6$) δ 7.38-7.22 (m, 5H), 4.46 (s, 2H), 4.37 (t, J=5.1 Hz, 2H), 3.64 (tt, J=6.9, 5.3 Hz, 1H), 3.49 (td, J=6.7, 5.1 Hz, 4H), 1.74-1.56 (m, 4H).

Step 3. (((1,5-Diazidopentan-3-yl)oxy)methyl)benzene

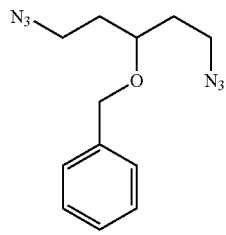 [SMILES: [N-]=[N+]=NCCC(CCN=[N+]=[N-])OCc1ccccc1]

To a round bottom flask was added 3-benzyloxypentane-1,5-diol (0.49 g, 2.33 mmol) and DCM (11.6 mL). The solution was cooled to 0° C. and then treated with triethylamine (0.97 mL, 6.99 mmol) and methansulfonic anhydride (1.05 g, 5.82 mmol). After stirring at 0° C. for 5 min the reaction flask was allowed to warm to room temperature. After 4 h the reaction was evaporated in vacuo. The crude residue was taken up in DMF (10.5 mL) and treated with sodium azide (0.76 g, 11.6 mmol), then heated to 50° C. overnight. The next day the reaction was quenched with water and extracted with DCM three times. The combined organic layers were dried over magnesium sulfate and concentrated under reduced pressure to give 0.588 g of crude material which was carried on to the next step as is. $^1$H NMR (400 MHz, DMSO-d6) δ 7.40-7.24 (m, 5H), 4.48 (s, 2H), 3.59 (quin, J=5.9 Hz, 1H), 3.48-3.33 (m, 4H), 1.78 (td, J=7.0, 6.0 Hz, 4H).

Step 4. Di-tert-butyl (3-hydroxypentane-1,5-diyl)dicarbamate

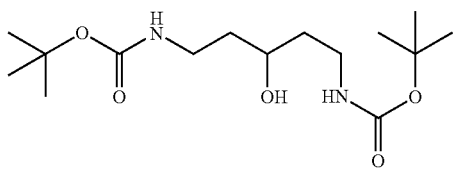 [SMILES: CC(C)(C)OC(=O)NCCC(O)CCNC(=O)OC(C)(C)C]

The crude residue from step 3 was combined with ethanol (111 mL) and di-tert-butyl dicarbonate (1.5 g, 6.68 mmol) and purged with bubbling nitrogen gas for 5 min. Palladium (10 wt % on carbon) (0.950 g, 0.891 mmol) was added and the reaction flask was purged of air, backfilled with hydrogen gas (repeat three times), and then stirred under a balloon of hydrogen gas overnight. The reaction was filtered through a pad of celite, washing with ethanol. The filtrate was collected and concentrated. The residue was purified by flash chromatography on silica gel (0-15% methanol/DCM) to give the title compound (0.502 g, 70% yield) as a white solid. LCMS (ESI): [M+H]$^+$=319; $^1$H NMR (400 MHz, DMSO-d$_6$) δ 6.67 (t, J=5.7 Hz, 2H), 4.42 (d, J=5.4 Hz, 1H), 3.49-3.39 (m, 1H), 3.06-2.88 (m, 4H), 1.59-1.27 (m, 22H).

Step 5. Methyl N-((benzyloxy)carbonyl)-O-(2,2,14, 14-tetramethyl-4,12-dioxo-3,13-dioxa-5,11-diazapentadecan-8-yl)serinate

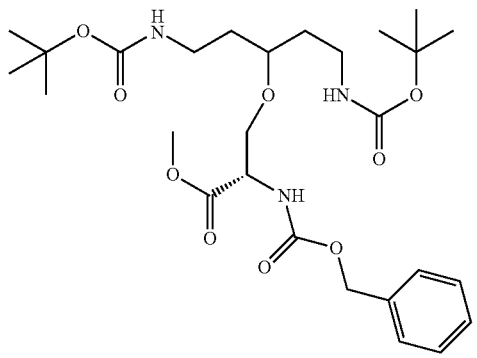 [SMILES: COC(=O)[C@H](COC(CCNC(=O)OC(C)(C)C)CCNC(=O)OC(C)(C)C)NC(=O)OCc1ccccc1]

To an oven-dried round bottom flask was added di-tert-butyl (3-hydroxypentane-1,5-diyl)dicarbamate (0.55 g, 1.73 mmol), 1-benzyl 2-methyl aziridine-1,2-dicarboxylate (0.37 g, 1.57 mmol), chloroform (4 mL), and then cooled to 0° C. Borontrifluoride etherate (0.019 mL, 0.157 mmol) was added gradually producing a yellow colored solution. After stirring for 30 min at 0° C., the reaction was allowed to warm to room temperature and stir overnight. Methanol (~5 mL) was added and the reaction was concentrated. The residue was purified by flash chromatography on silica gel (0-100% ethyl acetate/heptane) to give the title compound (0.30 g, 35% yield). LCMS (ESI): [M+H]$^+$=554.2; $^1$H NMR (400 MHz, DMSO-d$_6$) δ 7.42-7.28 (m, 5H), 6.67 (t, J=5.7 Hz, 2H), 5.11-5.00 (m, 2H), 4.43 (d, J=5.4 Hz, 1H), 3.68-3.57 (m, 4H), 2.97 (tt, J=13.8, 6.0 Hz, 5H), 1.53-1.42 (m, 4H), 1.37 (s, 20H).

Step 6. N-(((9H-Fluoren-9-yl)methoxy)carbonyl)-O-(2,2,14,14-tetramethyl-4,12-dioxo-3,13-dioxa-5,11-diazapentadecan-8-yl)serine

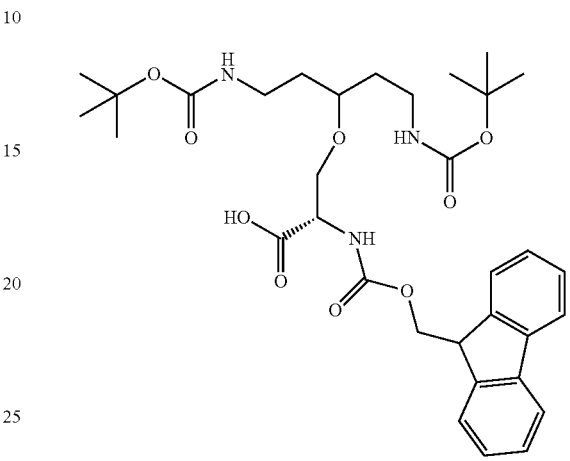

To a vial was added methyl 2-(benzyloxycarbonylamino)-3-[3-(tert-butoxycarbonylamino)-1-[2-(tert-butoxycarbonylamino)ethyl]propoxy]propanoate (0.50 g, 0.90 mmol), THF (1.8 mL), and lithium hydroxide (1 M in water) (1.3 mL, 1.3 mmol). The vial was flushed with nitrogen, capped, and placed on the shaker for 1 h. The reaction was then concentrated, diluted with DCM. The organic layer was washed with 1 M aqueous HCl. The organic layer was dried over magnesium sulfate, filtered, and concentrated. The crude residue was taken up in 1,4-dioxane (2.1 mL) and water (0.1 mL), and treated with sodium bicarbonate (0.184 g, 2.19 mmol). The mixture was cooled to 0° C. and then 9-fluorenylmethyl N-succinimidyl carbonate (0.40 g, 1.20 mmol) was added. The reaction was warmed to room temperature and left to stir overnight, after which the reaction was filtered and concentrated. The residue was purified by flash chromatography on silica gel (0-100% ethyl acetate/heptane) to give the title compound (0.268 g, 39% yield) as a white solid. LCMS (ESI): [M+H]$^+$=628.3; $^1$H NMR (400 MHz, DMSO-d$_6$) δ 12.75 (s, 1H), 7.89 (d, J=7.5 Hz, 2H), 7.73 (d, J=7.3 Hz, 2H), 7.41 (t, J=7.5 Hz, 2H), 7.32 (t, J=7.4 Hz, 2H), 6.74 (s, 2H), 4.38-4.05 (m, 4H), 3.78-3.52 (m, 1H), 3.07-2.84 (m, 5H), 2.62-2.57 (m, 2H), 1.56-1.51 (m, 4H), 1.40-1.32 (m, 18H).

Step 7. (3R,6S,9S,12S,15S,18R,19R)-9-(Aminomethyl)-12-cycloheptyl-6-(((1,5-diaminopentan-3-yl)oxy)methyl)-19-hexyl-3,16,18-trimethyl-15-propyl-1-oxa-4,7,10,13,16-pentaazacyclononadecane-5,8,11,14,17-pentaone (trifluoroacetate salt)

The title compound was prepared as the trifluoroacetate salt using benzyl N-(((9H-fluoren-9-yl)methoxy)carbonyl)-O-(2,2,14,14-tetramethyl-4,12-dioxo-3,13-dioxa-5,11-diazapentadecan-8-yl)serine and following procedures analogous to those described for Example 11. LCMS (ESI): R$_T$ (min)=8.53, [M+H]$^+$=768.6, method=B.

Example 35. (3R,6S,9S,12S,15S,18R,19R)-9-(Aminomethyl)-12-cycloheptyl-6-(((1,3-diaminopropan-2-yl)oxy)methyl)-19-hexyl-3,16,18-trimethyl-15-propyl-1-oxa-4,7,10,13,16-pentaazacyclononadecane-5,8,11,14,17-pentaone (trifluoroacetate salt)

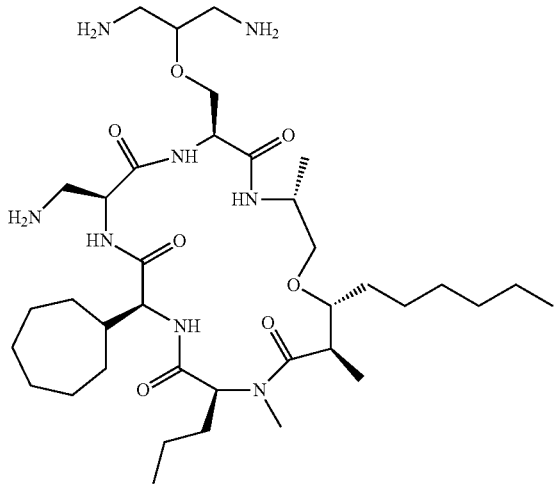 [SMILES: CCCCCC[C@H]1OC[C@@H](C)NC(=O)[C@H](COC(CN)CN)NC(=O)[C@H](CN)NC(=O)[C@H](C2CCCCCC2)NC(=O)[C@H](CCC)N(C)C(=O)[C@@H]1C]

Step 1. N-(((9H-Fluoren-9-yl)methoxy)carbonyl)-O-(2,2,12,12-tetramethyl-4,10-dioxo-3,11-dioxa-5,9-diazatridecan-7-yl)serine

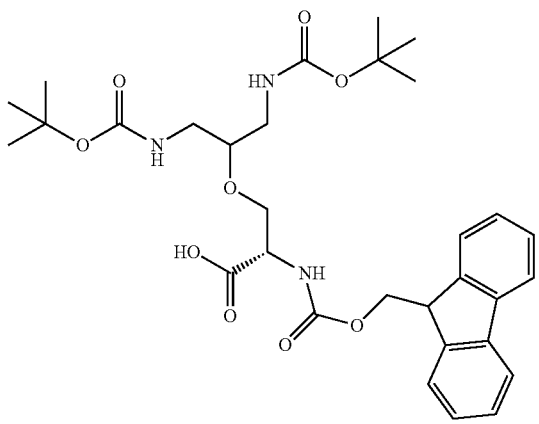 [SMILES: CC(C)(C)OC(=O)NCC(CNC(=O)OC(C)(C)C)OC[C@H](NC(=O)OCC1c2ccccc2-c2ccccc21)C(=O)O]

The title compound was prepared using di-tert-butyl (2-hydroxypropane-1,3-diyl)dicarbamate and following procedures analogous to those described for Steps 5-6, Example 34. LCMS (ESI): [M+H]$^+$=600.2; $^1$H NMR (400 MHz, DMSO-d$_6$) δ 12.76 (s, 1H), 7.89 (d, J=7.6 Hz, 2H), 7.73 (d, J=7.5 Hz, 2H), 7.42 (t, J=7.5 Hz, 2H), 7.33 (t, J=7.5 Hz, 2H), 6.80 (s, 1H), 6.66 (s, 1H), 6.59 (s, 1H), 4.28 (dt, J=16.6, 7.4 Hz, 3H), 4.16 (s, 1H), 3.78 (t, J=7.9 Hz, 1H), 3.72-3.60 (m, 1H), 2.94 (dd, J=19.4, 6.7 Hz, 4H), 1.37 (s, 18H).

Step 2: (3R,6S,9S,12S,15S,18R,19R)-9-(Aminomethyl)-12-cycloheptyl-6-(((1,3-diaminopropan-2-yl)oxy)methyl)-19-hexyl-3,16,18-trimethyl-15-propyl-1-oxa-4,7,10,13,16-pentaazacyclononadecane-5,8,11,14,17-pentaone (trifluoroacetate salt)

The title compound was prepared as the trifluoroacetate salt using N-(((9H-fluoren-9-yl)methoxy)carbonyl)-O-(2,2,12,12-tetramethyl-4,10-dioxo-3,11-dioxa-5,9-diazatridecan-7-yl)serine and following procedures analogous to those described for Example 11. LCMS (ESI): R$_T$ (min)=8.53, [M+H]$^+$=739.6, method=B; $^1$H NMR (400 MHz, DMSO-d$_6$) δ 8.77-8.07 (m, 2H), 7.96 (dd, J=30.6, 17.0 Hz, 9H), 7.67 (dd, J=14.1, 8.2 Hz, 1H), 4.68-4.37 (m, 2H), 4.31-4.06 (m, 1H), 3.92 (s, 1H), 3.83 (d, J=10.6 Hz, 3H), 3.34 (t, J=11.1 Hz, 3H), 3.16 (d, J=16.2 Hz, 7H), 2.96 (d, J=6.5 Hz, 2H), 2.74 (s, 1H), 2.17-1.95 (m, 2H), 1.91-1.24 (m, 24H), 1.12-0.69 (m, 12H).

Example 36. (3R,6S,9S,12S,15S,18R,19R)-9-(Aminomethyl)-6-[[[6-(aminomethyl)pyrimidin-4-yl]amino]methyl]-12-cycloheptyl-19-hexyl-3,16,18-trimethyl-15-propyl-1-oxa-4,7,10,13,16-pentazacyclononadecane-5,8,11,14,17-pentone (trifluoroacetate salt)

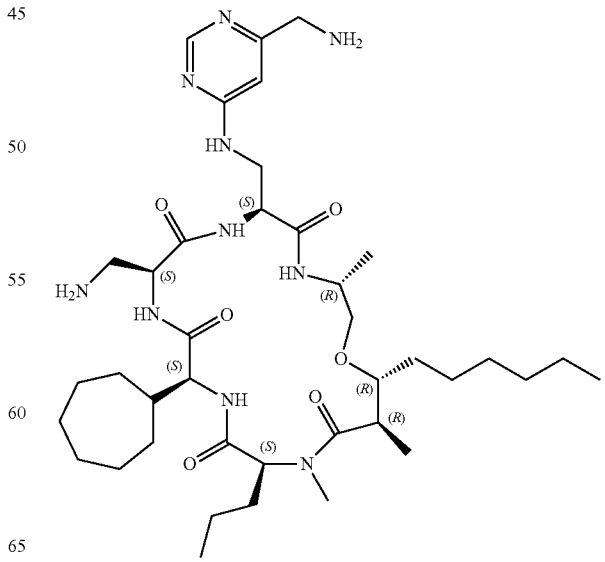

Step 1. tert-Butyl N-[[6-[[(3R,6S,9S,12S,15S,18R, 19R)-9-[(tert-butoxycarbonylamino)methyl]-12-cycloheptyl-19-hexyl-3,16,18-trimethyl-5,8,11,14, 17-pentaoxo-15-propyl-1-oxa-4,7,10,13,16-pentazacyclononadec-6-yl]methylamino]pyrimidin-4-yl]methyl]carbamate

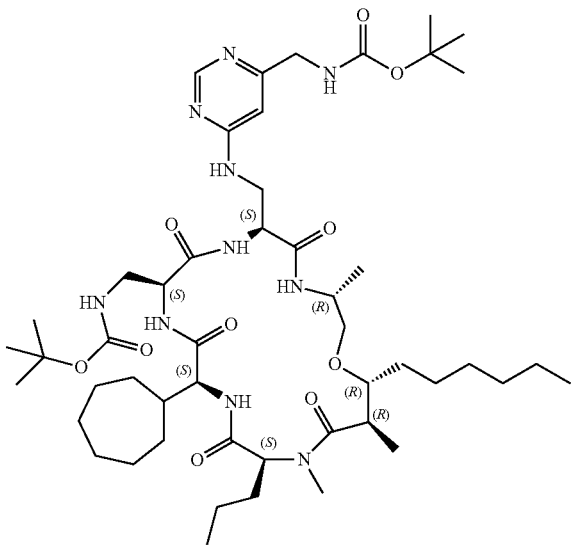

To a solution of N-[[(3R,6S,9S,12S,15S,18R,19R)-6-(aminomethyl)-12-cycloheptyl-19-hexyl-3,16,18-trimethyl-5,8,11,14,17-pentaoxo-15-propyl-1-oxa-4,7,10,13,16-pentazacyclononadec-9-yl]methyl]carbamate (200 mg, 0.26 mmol, Example 14 Step 2) in DMF (2.5 mL) was added tert-butyl N-[(6-chloropyrimidin-4-yl)methyl]carbamate (95.6 mg, 0.39 mmol) and DIPEA (0.09 mL, 0.52 mmol). The mixture was stirred at 100° C. overnight under nitrogen and then allowed to cool to room temperature. The reaction mixture was loaded directly onto a C18 column and purified by reverse phase chromatography (0-100% acetonitrile/ 0.01% TFA in water) to afford the title compound (211 mg, 83% yield) as a solid. LCMS (ESI): [M+H]$^+$=973.7.

Step 2. (3R,6S,9S,12S,15S,18R,19R)-9-(Aminomethyl)-6-[[[6-(aminomethyl)pyrimidin-4-yl]amino] methyl]-12-cycloheptyl-19-hexyl-3,16,18-trimethyl-15-propyl-1-oxa-4,7,10,13,16-pentazacyclononadecane-5,8,11,14,17-pentone The product from Step 1 (210 mg, 0.22 mmol) was treated with TFA (3.0 mL) at 0° C. for 1 h with stirring. Toluene (10 mL) was added and the mixture was concentrated under vacuum. The residue was purified by Prep-HPLC to afford the title compound as its TFA salt (56.5 mg) as a yellow solid. LCMS (ESI): [M+H]$^+$=773.7, R$_t$=2.57 min, method=I. $^1$H NMR (400 MHz, DMSO-d$_6$): δ 8.94-8.56 (m, 3H), 8.52-8.31 (m, 3H), 8.30-8.02 (m, 5H), 7.52-7.36 (m, 1H), 6.58-6.48 (m, 1H), 4.62-4.58 (m, 2H), 4.43-4.12 (m, 2H), 4.05-3.99 (m, 2H), 3.86-3.81 (m, 3H), 3.50-3.25 (m, 4H), 3.15-2.84 (m, 6H), 2.15-2.05 (m, 2H), 1.89-1.80 (m, 1H), 1.74-1.66 (m, 6H), 1.62-1.25 (m, 17H), 1.01-0.83 (m, 12H).

The Examples listed in Table 4 were each prepared as the trifluoroacetate salt following procedures analogous to those described in the above Examples, utilizing the indicated synthesis method, substituting the appropriate Fmoc-protected amino acids, and selecting from commercially available materials and/or Intermediates 1-15, Intermediates P2C-P2K, and Intermediates T1-T24 (structures are shown in table 1).

TABLE 4

| Example | LCMS [M + H]$^+$, LCMS R$^T$ (min), method | Synthesis method |
|---|---|---|
| 37 | 652.5, 1.37, F | Example 7 |
| 38 | 638.5, 3.386, A | Example 1 |
| 39 | 652.2, 1.35, G | Example 7 |
| 40 | 664.5, 1.39, G | Example 7 |
| 41 | 664.5, 1.36, G | Example 7 |
| 42 | 652.5, 1.37, G | Example 7 |
| 43 | 700.5, 4.621, A | Example 2 |
| 44 | 666.5, 1.43, G | Example 7 |
| 45 | 707.5, 1.21, G | Example 12 |
| 46 | 666.5, 8.268, A | Example 1 |
| 47 | 652.5, 7.51, B | Example 4 |
| 48 | 694.6, 10.42, B | Example 4 |
| 49 | 696.5, 2.35, I | Example 12 |
| 50 | 680.5, 2.27, I | Example 7 |
| 51 | 626.4, 3.29, A | Example 1 |
| 52 | 650.5, 7.65, B | Example 4 |
| 53 | 666.5, 8.52, B | Example 4 |
| 54 | 688.5, 2.1, H | Example 7 |
| 55 | 680.5, 11.24, B | Example 4 |
| 56 | 676.4, 2.28, L | Example 7 |
| 57 | 678.5, 9.58, E | Example 4 |
| 58 | 676.5, 1.37, G | Example 7 |
| 59 | 638.4, 2.16, I | Example 7 |
| 60 | 723.5, 2.27, J | Example 12 |
| 61 | 670.5, 7.689, B | Example 3 |
| 62 | 696.5, 9.213, B | Example 3 |
| 63 | 664.5, 8.02, B | Example 9 |
| 64 | 664.5, 8.00, B | Example 4 |
| 65 | 754.6, 2.78, I | Example 14 |
| 66 | 770.6, 2.2, H | Example 13 |
| 67 | 748.5, 2.81, I | Example 13 |
| 68 | 665.5, 2.38, I | Example 12 |
| 69 | 678.5, 2.38, J | Example 12 |
| 70 | 678.5, 2.62, J | Example 12 |
| 71 | 664.5, 8.304, C | Example 4 |
| 72 | 753.6, 2.24, I | Example 12 |
| 73 | 650.5, 2.1, I | Example 12 |
| 74 | 781.6, 2.55,1 | Example 24 |
| 75 | 664.5, 2.25, I | Example 12 |
| 76 | 664.5, 2.34, J | Example 12 |
| 77 | 739.6, 8.18, B | Examples 9 and 12 |
| 78 | 789.8, 10.08, B | Example 26 |
| 79 | 682.5, 2.27, J | Example 12 |
| 80 | 762.6, 2.04, H | Example 13 |
| 81 | 721.5, 2.08, J | Example 12 |
| 82 | 684.5, 7.400, C | Example 3 |
| 83 | 652.5, 6.97, B | Example 9 |
| 84 | 664.5, 8.21, B | Example 4 |
| 85 | 786.6, 2.07, H | Example 13 |
| 86 | 776.6, 2.67, I | Example 13 |
| 87 | 739.5, 2.29, J | Example 12 |
| 88 | 679.5, 2.19, J | Example 12 |
| 89 | 749.3, 8.56 and 8.84, B | Example 25 |
| 90 | 652.5, 2.23, J | Example 12 |
| 91 | 708.5, 2.43, H | Example 13 |
| 92 | 775.8, 10.07, B | Example 26 |
| 93 | 736.6, 2.68, I | Example 13 |
| 94 | 751.6, 2.64, I | Example 23 |
| 95 | 738.6, 2.79, I | Example 13 |
| 96 | 763.8, 10.08, B | Example 26 |
| 97 | 738.6, 1.96, H | Example 13 |
| 98 | 765.6, 1.87, H | Example 23 |
| 99 | 778.6, 2.7, I | Example 27 |
| 100 | 779.5, 10.06, B | Example 26 |
| 101 | 735.6, 2.2, J | Example 12 |
| 102 | 752.6, 9.11, B | Example 26 |
| 103 | 738.6, 1.94, H | Example 13 |
| 104 | 805.6, 2.47, I | Example 24 |
| 105 | 708.5, 1.85, J | Examples 16 and 14 |
| 106 | 804.6, 1.96, H | Example 13 |

TABLE 4-continued

| Example | LCMS [M + H]+, LCMS $R^T$ (min), method | Synthesis method |
|---|---|---|
| 107 | 678.5, 2.24, I | Example 12 |
| 108 | 779.6, 2.39, I | Example 24 |
| 109 | 766.8, 8.77, B | Example 26 |
| 110 | 804.6, 1.95, H | Example 13 |
| 111 | 765.6, 1.69, H | Example 24 |
| 112 | 662.5, 2.28, J | Example 12 |
| 113 | 709.5, 2.11, J | Example 12 |
| 114 | 664.5, 2.29, J | Example 12 |

Biological Assays

Example B1: Determination of Minimum Inhibitory Concentration

In vitro antimicrobial activity of each compound was determined by measuring minimal inhibitor concentrations (MICs) using the broth micro-dilution technique as approved by the Clinical and Laboratory Standards Institute (CLSI) (Methods for Dilution Antimicrobial Susceptibility Tests for Bacteria that Grow Aerobically; Approved Standard—Eighth Edition. CLSI document M07-A8. Wayne, PA: Clinical and Laboratory Standards; 2009). Antibacterial activity was measure against *Escherichia coli* (*E. coli*) strain CFT073 ATCC 700928, which is a clinically relevant Gram-negative strain. Cells were inoculated onto plates of Mueller Hinton Agar and grown at 37° C. for 16-18 hours. Inocula suspensions were prepared by scraping cells into 1 mL of testing media (Mueller Hinton II cation adjusted Broth supplemented with 0.002% v/v Tween-80) and diluting to a final $OD_{600\ nm}$ of 0.01.

Test compounds were prepared in DMSO at a concentration of 100 uM The compounds were tested under several different dilution formats and the data are reported in Tables 6, 7 and 8. In protocol 1, the compound stocks were diluted into testing media at a concentration of 64 µg/ml and serial 2-fold dilutions were made in the same media, in 96-well U bottom microtiter dishes, for a total of 10 compound concentrations. In protocol 2, the compound stocks were diluted into testing media at a concentration of 4 µg/mL and serial 2-fold dilutions were made in the same media, in 96-well U bottom microtiter dishes, for a total of 10 compound concentrations. In protocol 3, compound stocks were diluted into testing media at a concentration of 0.5 µg/mL, with serial 2-fold dilutions conducted as described above. In protocol 4, compound stocks were diluted into testing media at a concentration of 0.13 µg/mL, with serial 2-fold dilutions conducted as described above. Inocula suspensions were added to the 2-fold serial dilutions of test compounds to a final density of OD $OD_{600\ nm}$ of 0.0005 and incubated at 35° C. for 22 hours. After incubation the plates were examined visually and the lowest concentration of test compound that completely prevented bacterial growth were recorded as the MICs. The results are listed in Table 5.

TABLE 5

| Ex. | MIC (µM) |
|---|---|
| 1 | 25 |
| 2 | 25 |
| 3 | 8.8 |
| 4 | 4.4 |
| 5 | 25 |
| 6 | 50 |
| 7 | 1.6 |
| 8 | 6.3 |
| 9 | 3.1 |
| 10 | 1.6 |
| 11 | 8.8 |
| 12 | 3.7 |
| 13 | 0.78 |
| 14 | 3.1 |
| 15 | 1.6 |
| 16 | 12 |
| 17 | 25 |
| 18 | 12 |
| 19 | 0.28 |
| 20 | 35 |
| 21 | 6.3 |
| 22 | 4.4 |
| 23 | 25 |
| 24 | 0.78 |
| 25 | 8.5 |
| 26 | 25 |
| 27 | 25 |
| 28 | 50 |
| 29 | 4.4 |
| 30 | 8.8 |
| 31 | 1.1 |
| 32 | 25 |
| 33 | 50 |
| 34 | 12 |
| 35 | 3.1 |
| 36 | 12 |
| 37 | 18 |
| 38 | 50 |
| 39 | 25 |
| 40 | 50 |
| 41 | 25 |
| 42 | 12 |
| 43 | 25 |
| 44 | 25 |
| 45 | 6.3 |
| 46 | 6.3 |
| 47 | 50 |
| 48 | 4.4 |
| 49 | 18 |
| 50 | 1.6 |
| 51 | 35 |
| 52 | 6.3 |
| 53 | 6.3 |
| 54 | 25 |
| 55 | 6.3 |
| 56 | 12 |
| 57 | 8.8 |
| 58 | 11 |
| 59 | 50 |
| 60 | 18 |
| 61 | 25 |
| 62 | 25 |
| 63 | 6.3 |
| 64 | 18 |
| 65 | 12 |
| 66 | 4.4 |
| 67 | 6.3 |
| 68 | 50 |
| 69 | 35 |
| 70 | 4.4 |
| 71 | 25 |
| 72 | 25 |
| 73 | 25 |
| 74 | 1.6 |
| 75 | 4.4 |
| 76 | 50 |
| 77 | 3.1 |
| 78 | 18 |
| 79 | 6.3 |
| 80 | 2.2 |
| 81 | 6.3 |
| 82 | 12 |
| 83 | 4.4 |
| 84 | 12 |
| 85 | 2.2 |

TABLE 5-continued

| Ex. | MIC (μM) |
|---|---|
| 86 | 3.1 |
| 87 | 12 |
| 88 | 25 |
| 89 | 12 |
| 90 | 3.1 |
| 91 | 18 |
| 92 | 71 |
| 93 | 12 |
| 94 | 18 |
| 95 | 6.3 |
| 96 | 18 |
| 97 | 12 |
| 98 | 12 |
| 99 | 12 |
| 100 | 50 |
| 101 | 4.4 |
| 102 | 25 |
| 103 | 8.8 |
| 104 | 1.6 |
| 105 | 3.1 |
| 106 | 3.1 |
| 107 | 6.3 |
| 108 | 6.3 |
| 109 | 50 |
| 110 | 6.3 |
| 111 | 12 |
| 112 | 12 |
| 113 | 3.1 |
| 114 | 35 |

Pharmaceutical Compositions

Example C1: Parenteral Composition

To prepare a parenteral pharmaceutical composition suitable for administration by injection, 100 mg of a compound disclosed herein is dissolved in DMSO and then mixed with 10 mL of 0.9% sterile saline. The mixture is incorporated into a dosage unit form suitable for administration by injection.

In another embodiment, the following ingredients are mixed to form an injectable formulation:

| Ingredient | Amount |
|---|---|
| Compound disclosed herein | 1.2 g |
| sodium acetate buffer solution (0.4M) | 2.0 mL |
| HCl (1N) or NaOH (1M) | q.s. to suitable pH |
| water (distilled, sterile) | q.s. to 20 mL |

All of the above ingredients, except water, are combined and stirred and if necessary, with slight heating if necessary. A sufficient quantity of water is then added.

Example C2: Oral Composition

To prepare a pharmaceutical composition for oral delivery, 100 mg of a compound disclosed herein is mixed with 750 mg of starch. The mixture is incorporated into an oral dosage unit, such as a hard gelatin capsule, which is suitable for oral administration.

In another embodiment, the following ingredients are mixed intimately and pressed into single scored tablets.

| Ingredient | Quantity per tablet, mg |
|---|---|
| compound disclosed herein | 200 |
| Cornstarch | 50 |
| croscarmellose sodium | 25 |
| Lactose | 120 |
| magnesium stearate | 5 |

In yet another embodiment, the following ingredients are mixed intimately and loaded into a hard-shell gelatin capsule.

| Ingredient | Quantity per tablet, mg |
|---|---|
| compound disclosed herein | 200 |
| lactose, spray-dried | 148 |
| magnesium stearate | 2 |

In yet another embodiment, the following ingredients are mixed to form a solution/suspension for oral administration:

| Ingredient | Amount |
|---|---|
| Compound disclosed herein | 1 g |
| Anhydrous Sodium Carbonate | 0.1 g |
| Ethanol (200 proof), USP | 10 mL |
| Purified Water, USP | 90 mL |
| Aspartame | 0.003 g |

Example C3: Topical Gel Composition

To prepare a pharmaceutical topical gel composition, 100 mg of a compound of disclosed herein is mixed with 1.75 g of hydroxypropyl cellulose, 10 mL of propylene glycol, 10 mL of isopropyl myristate and 100 mL of purified alcohol USP. The resulting gel mixture is then incorporated into containers, such as tubes, which are suitable for topical administration.

While preferred embodiments of the present disclosure have been shown and described herein, it will be obvious to those skilled in the art that such embodiments are provided by way of example only. Numerous variations, changes, and substitutions will now occur to those skilled in the art without departing from the disclosure. It should be understood that various alternatives to the embodiments described herein may be employed in practicing the invention. It is intended that the following claims define the scope of the disclosure and that methods and structures within the scope of these claims and their equivalents be covered thereby.

What is claimed is:

1. A compound of Formula (I), or a pharmaceutically acceptable salt, solvate, or stereoisomer thereof:

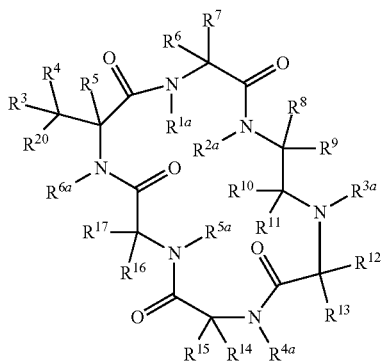

Formula (I)

wherein:

$R^{1a}$, $R^{2a}$, $R^{4a}$, $R^{5a}$, and $R^{6a}$ are each independently hydrogen or optionally substituted $C_1$-$C_6$ alkyl;

$R^{3a}$ is hydrogen, optionally substituted $C_1$-$C_{20}$ alkyl, optionally substituted $C_2$-$C_{20}$ alkenyl, optionally substituted $C_2$-$C_{20}$ alkynyl, optionally substituted cycloalkyl, optionally substituted ($C_1$-$C_6$ alkyl)cycloalkyl, optionally substituted heterocycloalkyl, optionally substituted ($C_1$-$C_6$ alkyl)heterocycloalkyl, optionally substituted aryl, optionally substituted ($C_1$-$C_6$ alkyl)aryl, optionally substituted heteroaryl, or optionally substituted ($C_1$-$C_6$ alkyl)heteroaryl;

$R^{20}$ is hydroxyl or —$NR^1R^2$;

$R^1$ and $R^2$ are each independently hydrogen, optionally substituted $C_1$-$C_6$ alkyl, optionally substituted $C_2$-$C_6$ alkenyl, optionally substituted $C_2$-$C_6$ alkynyl, optionally substituted cycloalkyl, optionally substituted ($C_1$-$C_6$ alkyl)cycloalkyl, optionally substituted heterocycloalkyl, optionally substituted ($C_1$-$C_6$ alkyl)heterocycloalkyl, optionally substituted aryl, optionally substituted ($C_1$-$C_6$ alkyl)aryl, optionally substituted heteroaryl, optionally substituted ($C_1$-$C_6$ alkyl)heteroaryl, —S(=O)$_2R^a$, —S(=O)$_2NR^bR^c$, —C(=O)$R^a$, —C(=O)O$R^b$, —C(=O)N$R^bR^c$, or —(C=N$R^b$)N$R^bR^c$;

or $R^1$ and $R^2$ are taken together with the nitrogen atom to which they are attached to form an optionally substituted heterocycloalkyl;

$R^3$ and $R^4$ are each independently hydrogen, optionally substituted $C_1$-$C_6$ alkyl, optionally substituted $C_2$-$C_6$ alkenyl, optionally substituted $C_2$-$C_6$ alkynyl, optionally substituted cycloalkyl, optionally substituted heterocycloalkyl, optionally substituted aryl, or optionally substituted heteroaryl;

or $R^3$ and $R^4$ are taken together with the carbon atom to which they are attached to form an oxo;

$R^5$ is hydrogen, halogen, optionally substituted $C_1$-$C_6$ alkyl, optionally substituted $C_2$-$C_6$ alkenyl, or optionally substituted $C_2$-$C_6$ alkynyl;

$R^6$ and $R^7$ are each independently hydrogen, halogen, optionally substituted $C_1$-$C_6$ alkyl, optionally substituted $C_2$-$C_6$ alkenyl, optionally substituted $C_2$-$C_6$ alkynyl, optionally substituted cycloalkyl, optionally substituted ($C_1$-$C_6$ alkyl)cycloalkyl, optionally substituted heterocycloalkyl, optionally substituted ($C_1$-$C_6$ alkyl)heterocycloalkyl, optionally substituted aryl, optionally substituted ($C_1$-$C_6$ alkyl)aryl, optionally substituted heteroaryl, or optionally substituted ($C_1$-$C_6$ alkyl)heteroaryl;

$R^8$ and $R^9$ are each independently hydrogen, halogen, optionally substituted $C_1$-$C_6$ alkyl, optionally substituted $C_2$-$C_6$ alkenyl, optionally substituted $C_2$-$C_6$ alkynyl, optionally substituted cycloalkyl, optionally substituted ($C_1$-$C_6$ alkyl)cycloalkyl, optionally substituted heterocycloalkyl, optionally substituted ($C_1$-$C_6$ alkyl)heterocycloalkyl, optionally substituted aryl, optionally substituted ($C_1$-$C_6$ alkyl)aryl, optionally substituted heteroaryl, or optionally substituted ($C_1$-$C_6$ alkyl)heteroaryl;

or, $R^{3a}$ and $R^8$ are taken together with the atoms to which they are attached to form an optionally substituted heterocycloalkyl;

$R^{10}$ and $R^{11}$ are each independently hydrogen, halogen, optionally substituted $C_1$-$C_6$ alkyl, optionally substituted $C_2$-$C_{20}$ alkenyl, optionally substituted $C_2$-$C_6$ alkynyl, optionally substituted cycloalkyl, optionally substituted ($C_1$-$C_6$ alkyl)cycloalkyl, optionally substituted heterocycloalkyl, optionally substituted ($C_1$-$C_6$ alkyl)heterocycloalkyl, optionally substituted aryl, optionally substituted ($C_1$-$C_6$ alkyl)aryl, optionally substituted heteroaryl, or optionally substituted ($C_1$-$C_6$ alkyl)heteroaryl;

$R^{12}$ and $R^{13}$ are each independently hydrogen, halogen, optionally substituted $C_1$-$C_{20}$ alkyl, optionally substituted $C_2$-$C_6$ alkenyl, optionally substituted $C_2$-$C_6$ alkynyl, optionally substituted cycloalkyl, optionally substituted ($C_1$-$C_6$ alkyl)cycloalkyl, optionally substituted heterocycloalkyl, optionally substituted ($C_1$-$C_6$ alkyl)heterocycloalkyl, optionally substituted aryl, optionally substituted ($C_1$-$C_6$ alkyl)aryl, optionally substituted heteroaryl, or optionally substituted ($C_1$-$C_6$ alkyl)heteroaryl;

$R^{14}$ and $R^{15}$ are each independently hydrogen, halogen, optionally substituted $C_1$-$C_6$ alkyl, optionally substituted $C_2$-$C_6$ alkenyl, optionally substituted $C_2$-$C_6$ alkynyl, optionally substituted cycloalkyl, optionally substituted ($C_1$-$C_6$ alkyl)cycloalkyl, optionally substituted heterocycloalkyl, optionally substituted ($C_1$-$C_6$ alkyl)heterocycloalkyl, optionally substituted aryl, optionally substituted ($C_1$-$C_6$ alkyl)aryl, optionally substituted heteroaryl, or optionally substituted ($C_1$-$C_6$ alkyl)heteroaryl;

$R^{16}$ and $R^{17}$ are each independently hydrogen, halogen, optionally substituted $C_1$-$C_6$ alkyl, optionally substituted $C_2$-$C_6$ alkenyl, optionally substituted $C_2$-$C_6$ alkynyl, optionally substituted cycloalkyl, optionally substituted ($C_1$-$C_6$ alkyl)cycloalkyl, optionally substituted heterocycloalkyl, optionally substituted ($C_1$-$C_6$ alkyl)heterocycloalkyl, optionally substituted aryl, optionally substituted ($C_1$-$C_6$ alkyl)aryl, optionally substituted heteroaryl, or optionally substituted ($C_1$-$C_6$ alkyl)heteroaryl;

each $R^a$ is independently optionally substituted $C_1$-$C_6$ alkyl, optionally substituted $C_2$-$C_6$ alkenyl, optionally substituted $C_2$-$C_6$ alkynyl, optionally substituted cycloalkyl, optionally substituted heterocycloalkyl, optionally substituted aryl, or optionally substituted heteroaryl;

each $R^b$ and $R^c$ is independently hydrogen, optionally substituted $C_1$-$C_6$ alkyl, optionally substituted $C_2$-$C_6$ alkenyl, optionally substituted $C_2$-$C_6$ alkynyl, optionally substituted cycloalkyl, optionally substituted heterocycloalkyl, optionally substituted aryl, or optionally substituted heteroaryl;

or $R^b$ and $R^c$ are taken together with the nitrogen atom to which they are attached to form an optionally substituted heterocycloalkyl.

2. The compound of claim 1, wherein $R^{20}$ is hydroxyl.

3. The compound of claim 1, wherein $R^{20}$ is —$NR^1R^2$.

4. The compound of claim 1, having the structure of Formula (Ia):

Formula (Ia)

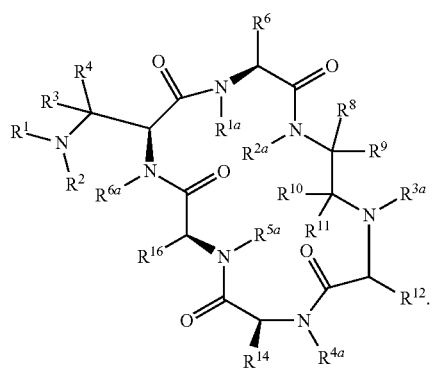

5. The compound of claim 1, having the structure of Formula (Ib):

Formula (Ib)

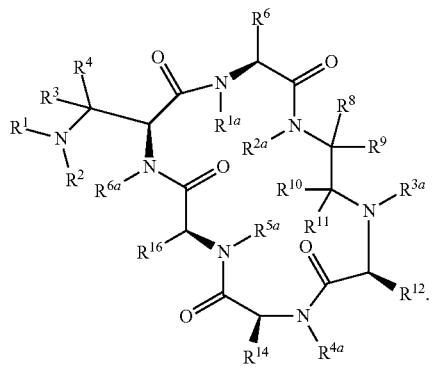

6. The compound of claim 1, wherein $R^1$, $R^2$, $R^3$, $R^4$, $R^{1a}$, $R^{2a}$, $R^{4a}$, $R^{5a}$, $R^{6a}$, $R^9$, $R^{10}$ and $R^{11}$ are hydrogen.

7. The compound of claim 1, wherein $R^8$ is hydrogen or $C_1$-$C_6$ alkyl optionally substituted with one, two, or three halogen.

8. The compound of claim 1, wherein $R^{3a}$ and $R^8$ are taken together with the atoms to which they are attached to form an azetidinyl, a pyrrolidinyl, or a piperidinyl.

9. The compound of claim 1, wherein $R^6$ is:

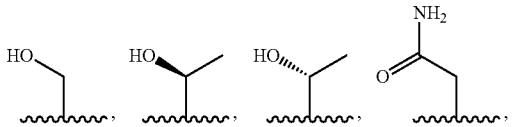

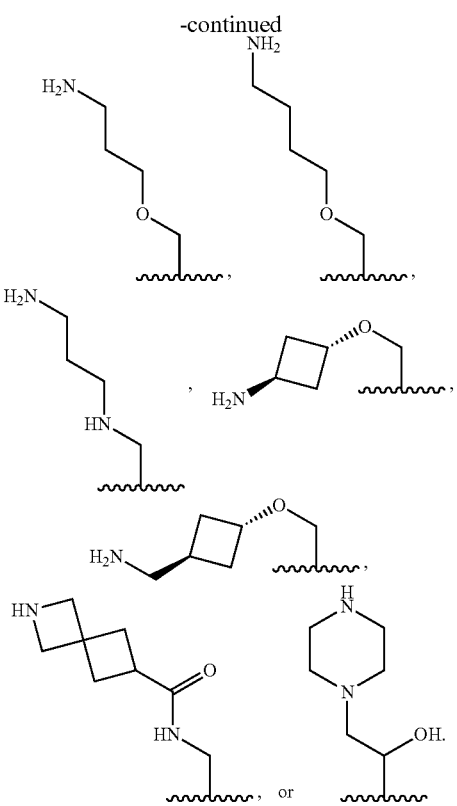

10. The compound of claim 1, wherein $R^6$ is:

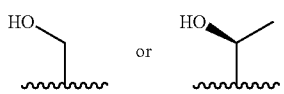

11. The compound of any one of claim 1, wherein $R^{12}$ is $C_1$-$C_6$ alkyl optionally substituted with one, two, or three halogen or —$OCH_3$.

12. The compound of claim 1, wherein $R^{12}$ is

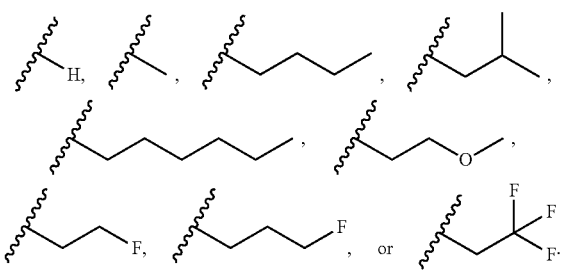

13. The compound of claim 1, wherein $R^{14}$ is $C_1$-$C_6$ alkyl.

14. The compound of any claim 1, wherein $R^{16}$ is:

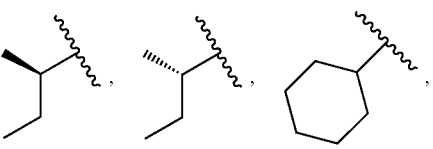

303
-continued
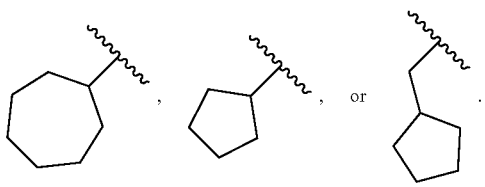
15. The compound of claim 1, wherein $R^{3a}$ is
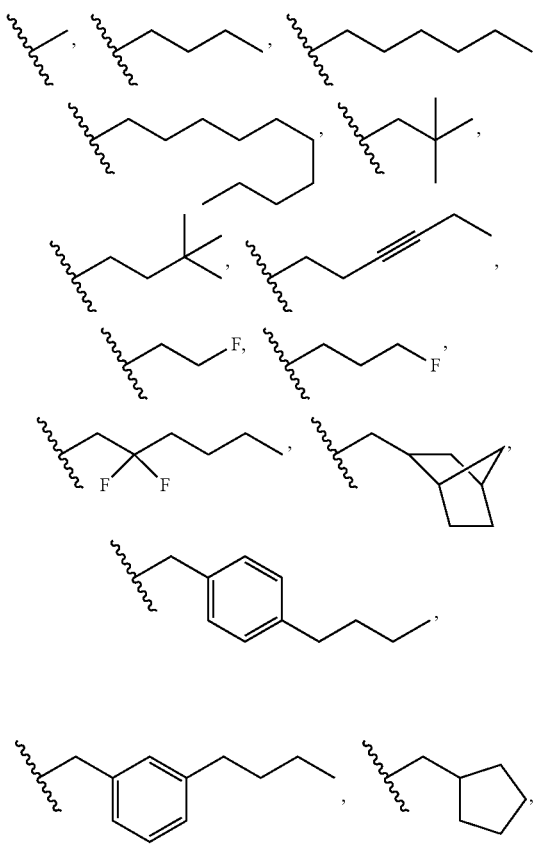
16. The compound of claim 1, wherein each $R^a$ is independently $C_1$-$C_6$ alkyl.
17. The compound of claim 1, wherein each $R^b$ and $R^c$ is hydrogen.
18. The compound of claim 1 selected from the group consisting of:
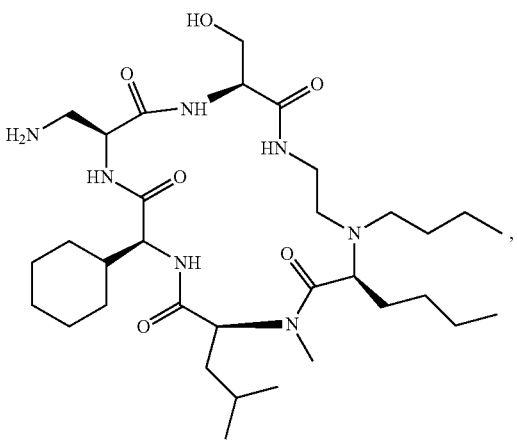
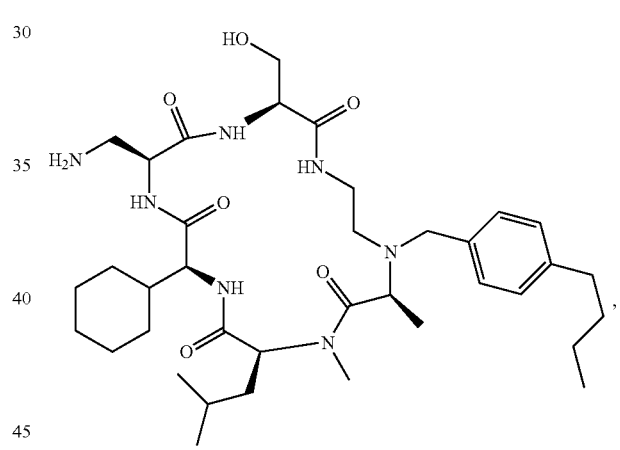
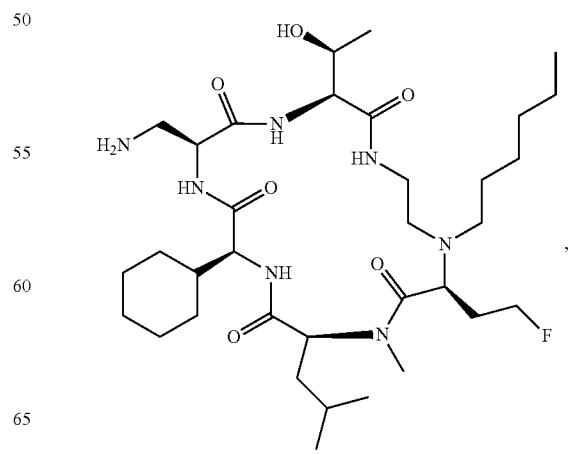

305
-continued
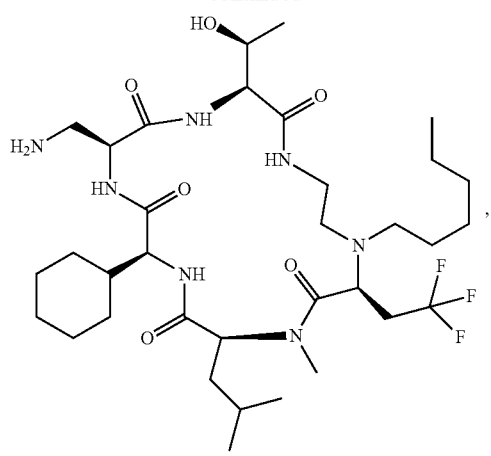
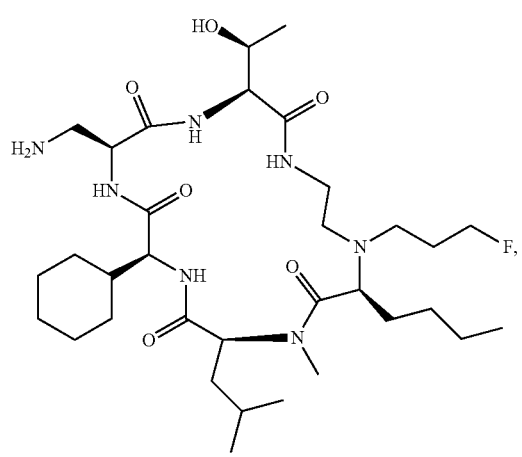
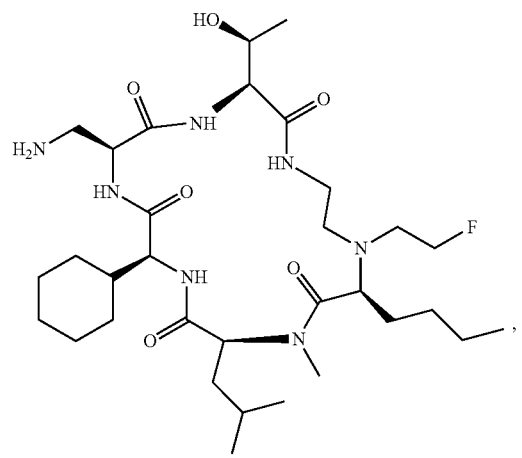
306
-continued
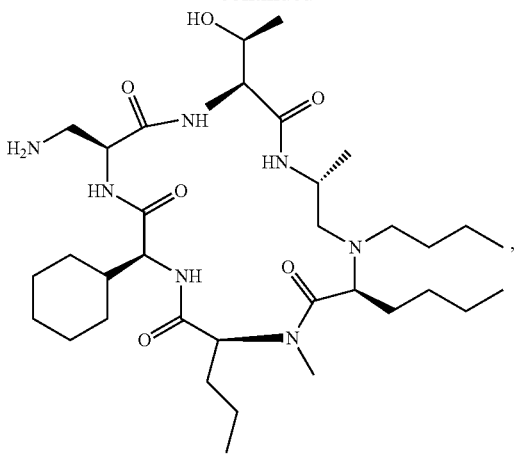
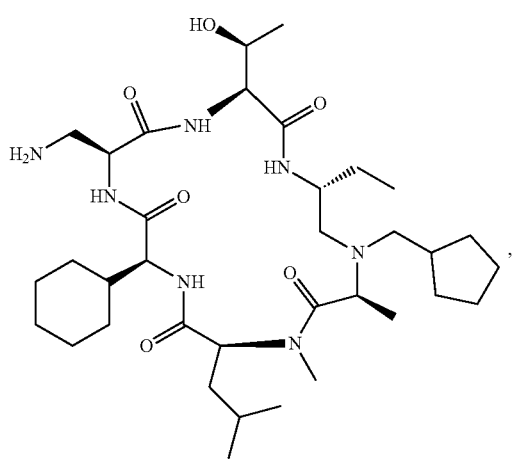
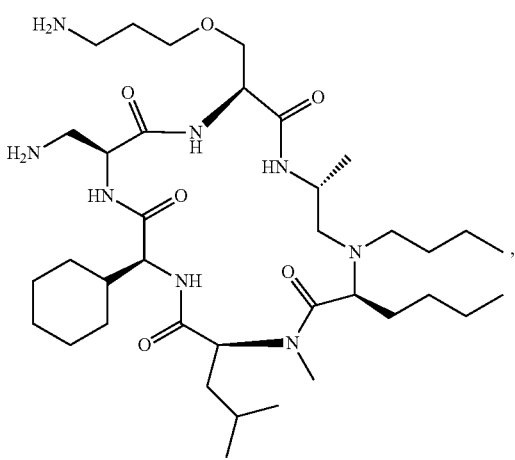

307
-continued
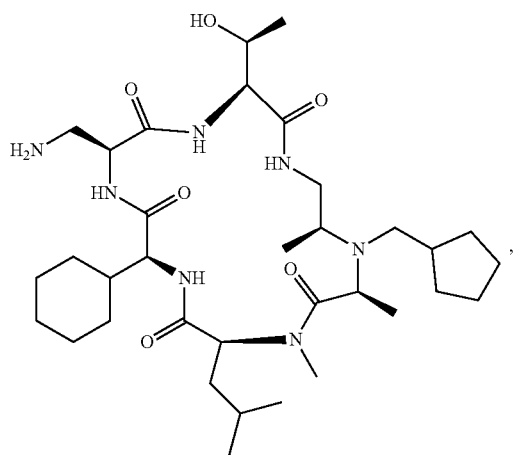
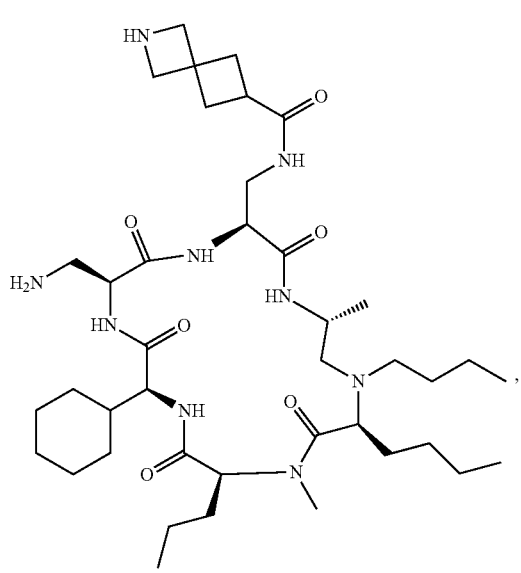
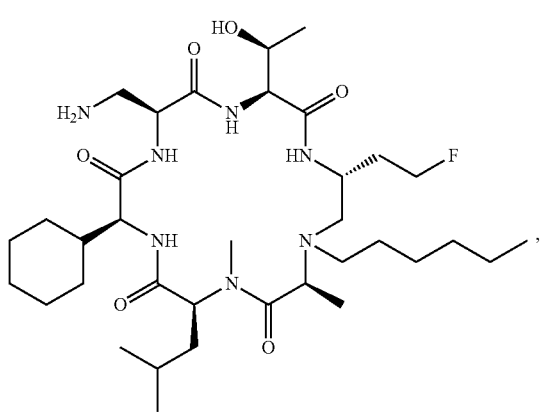
308
-continued
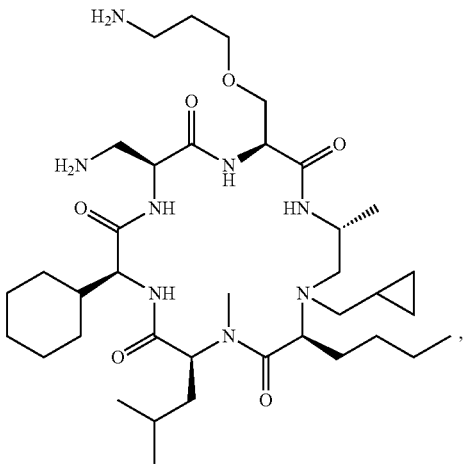
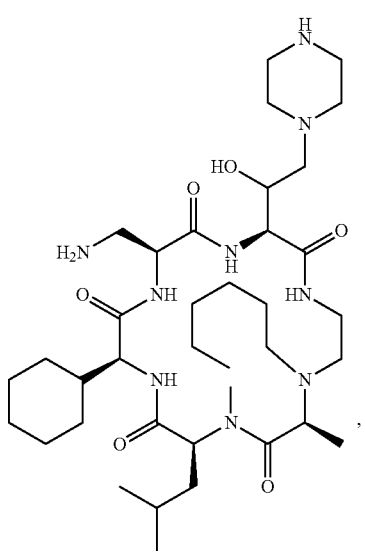
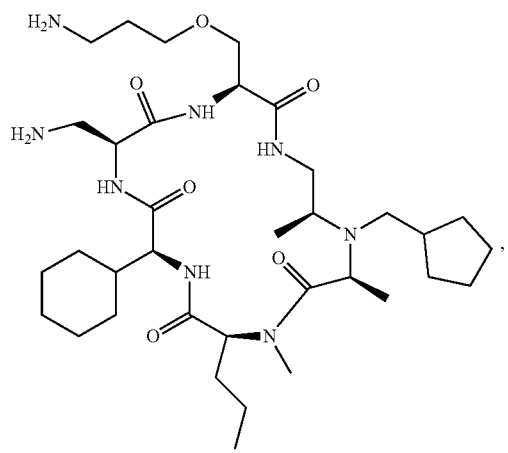

309
-continued
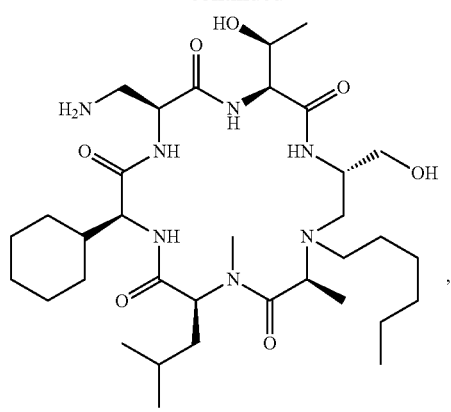
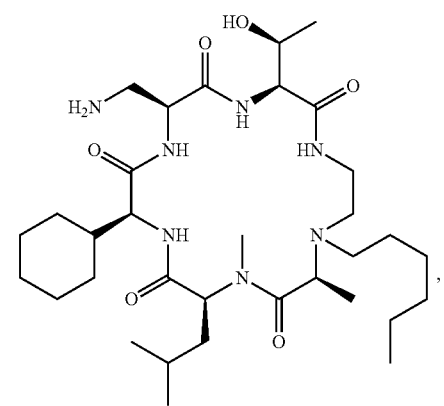
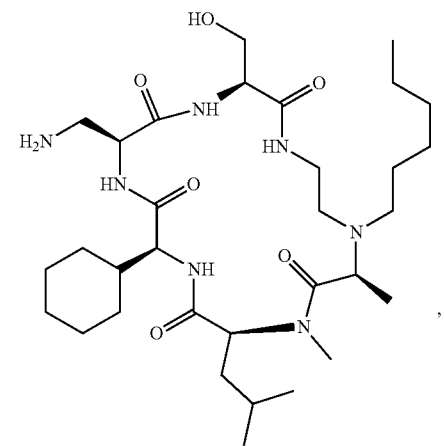
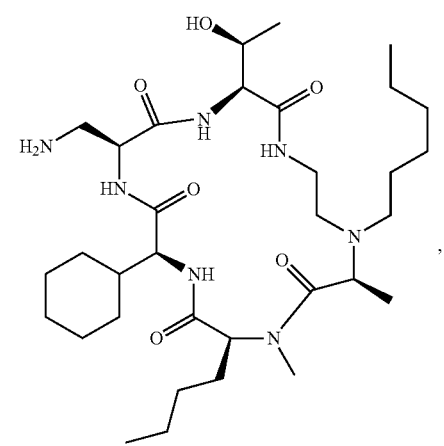
310
-continued
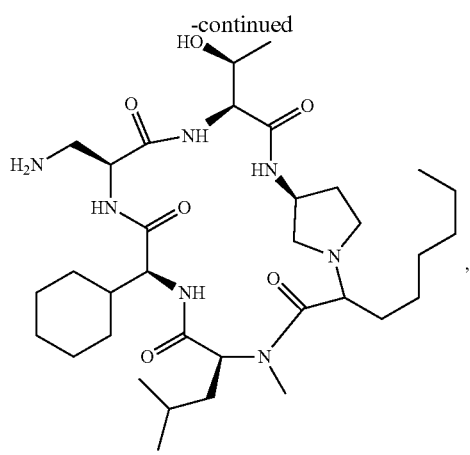
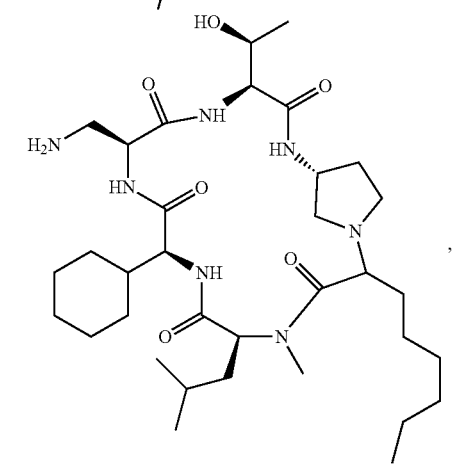
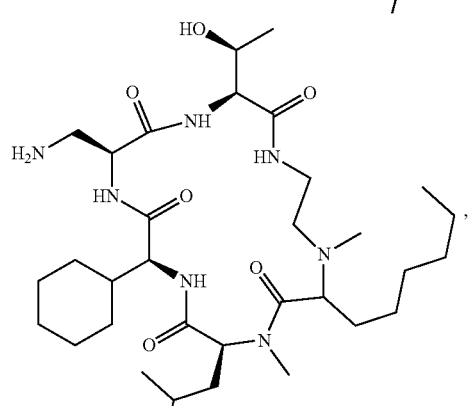
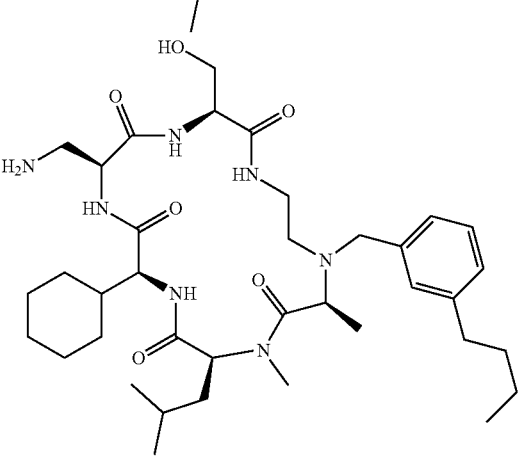

-continued
311
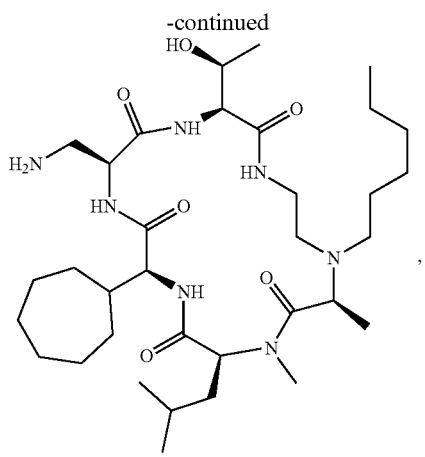
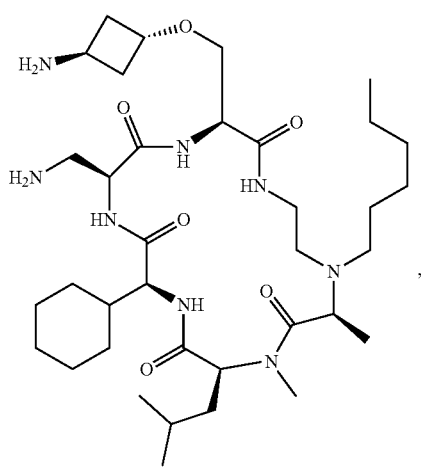
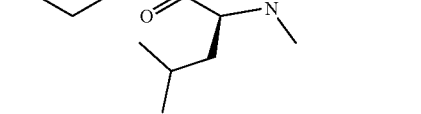
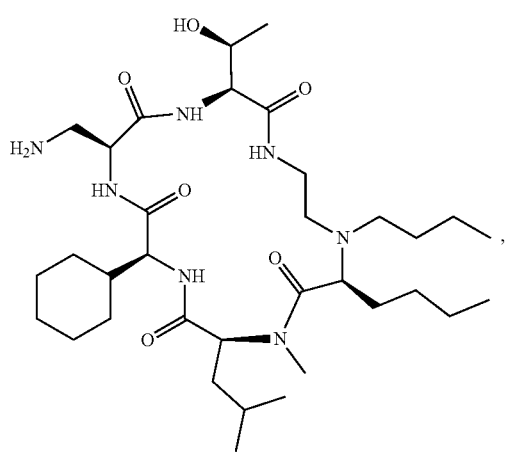
312
-continued
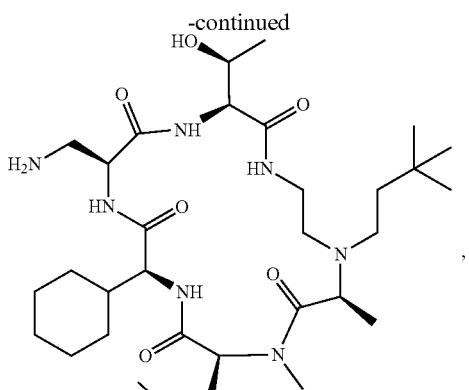
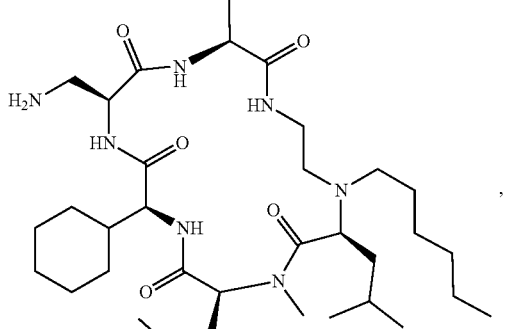
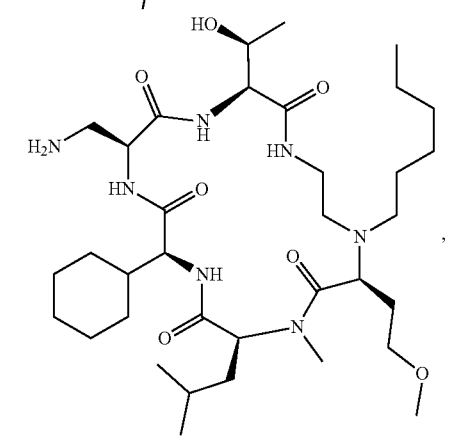
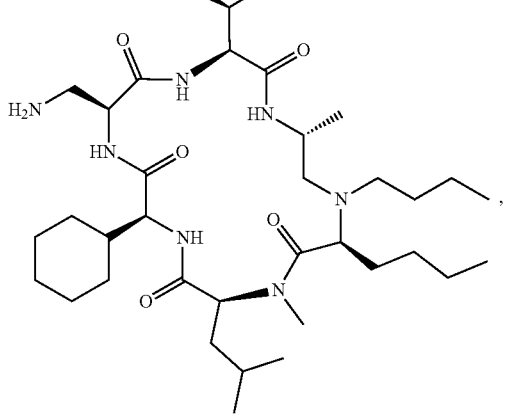

313
-continued
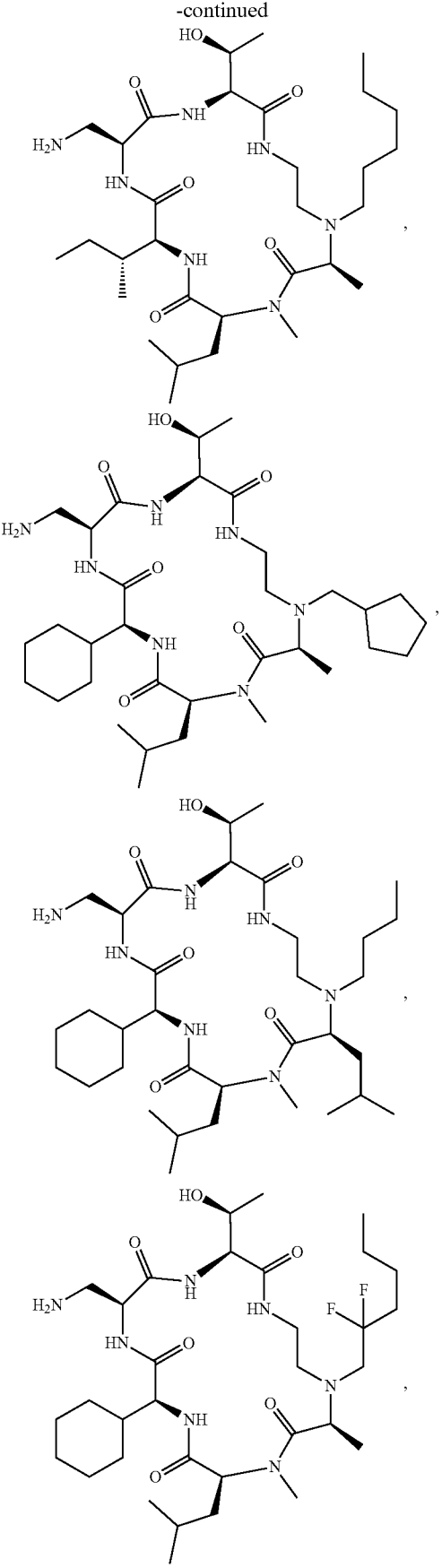
314
-continued
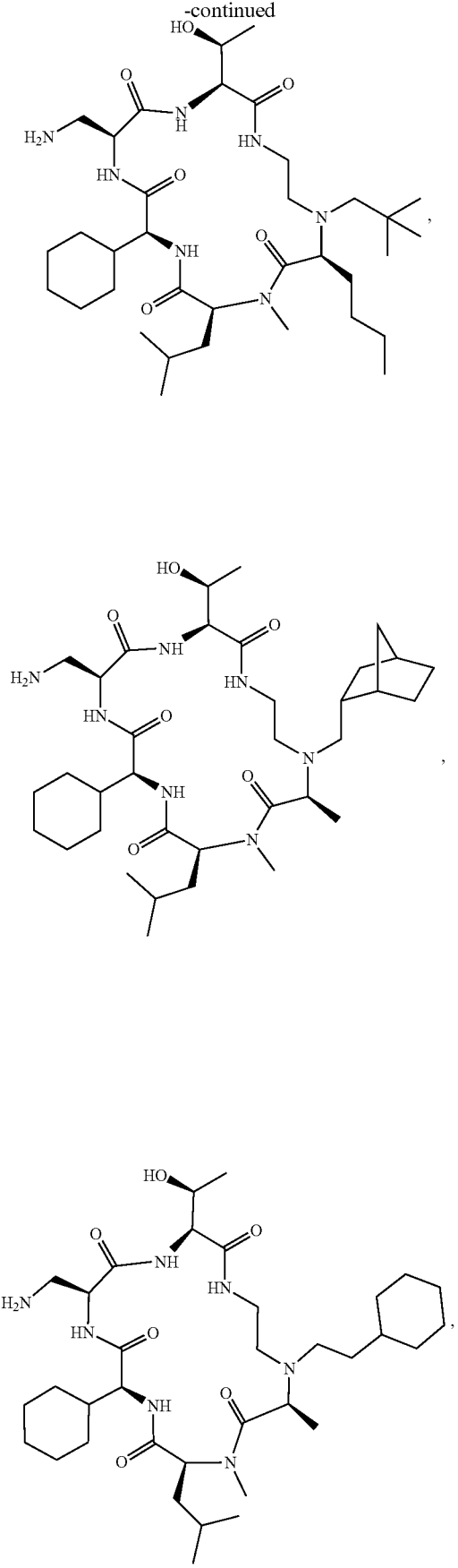

315
-continued
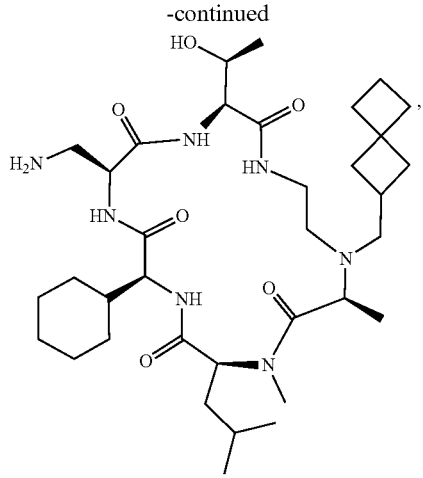
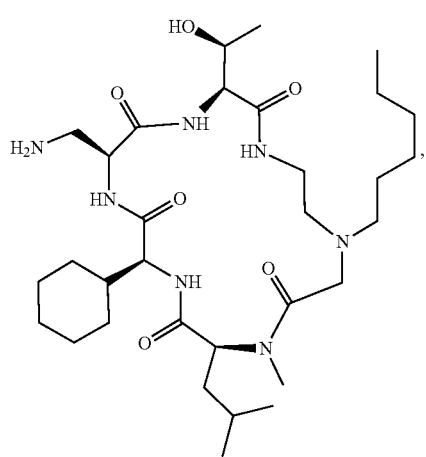
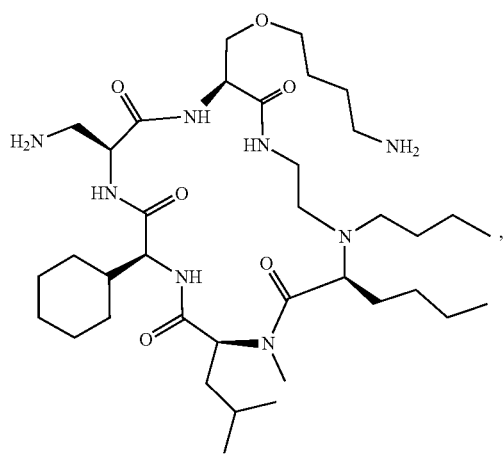
316
-continued
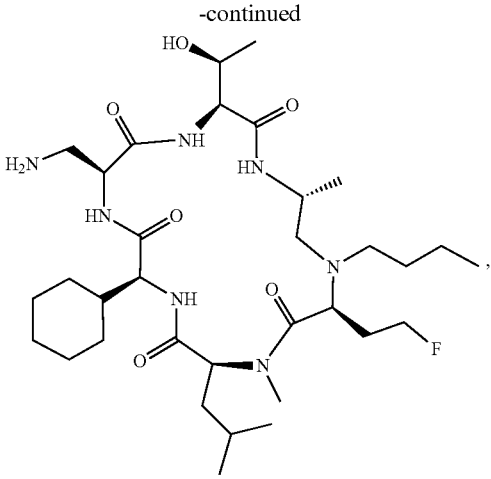
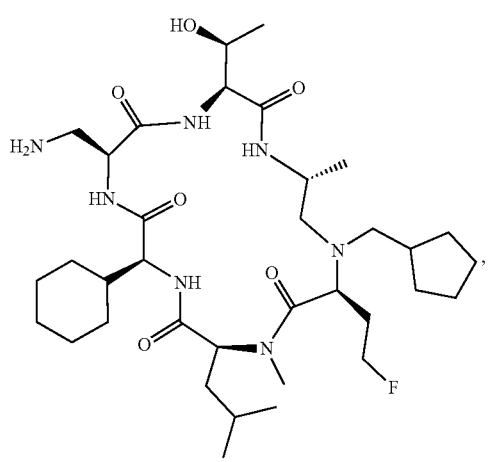
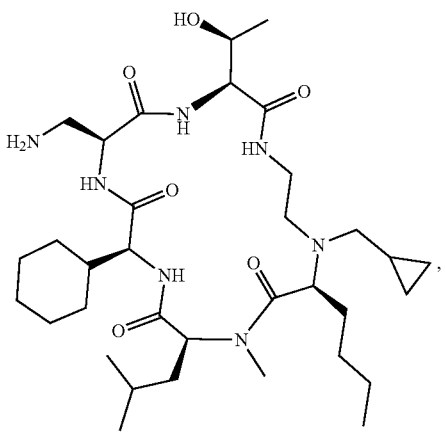

317
-continued
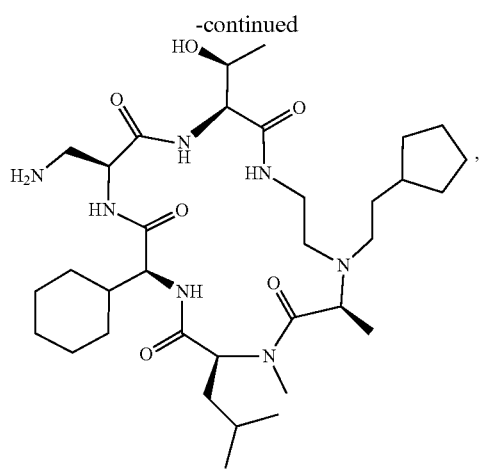
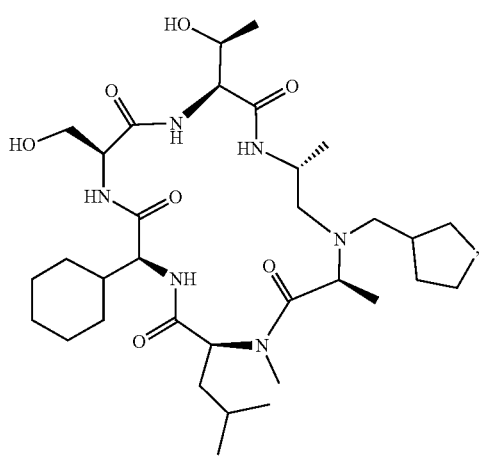
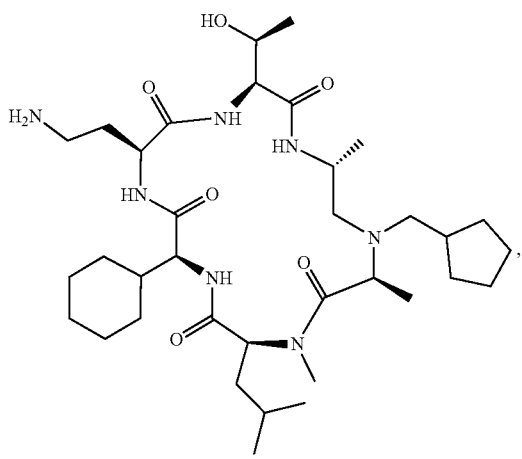
318
-continued
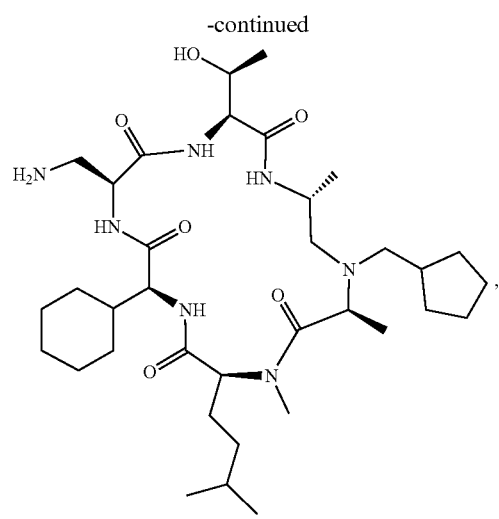
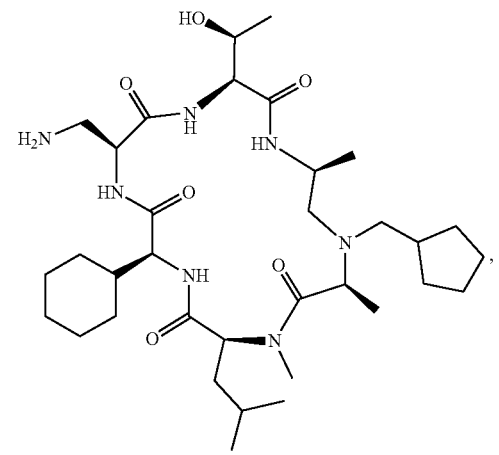
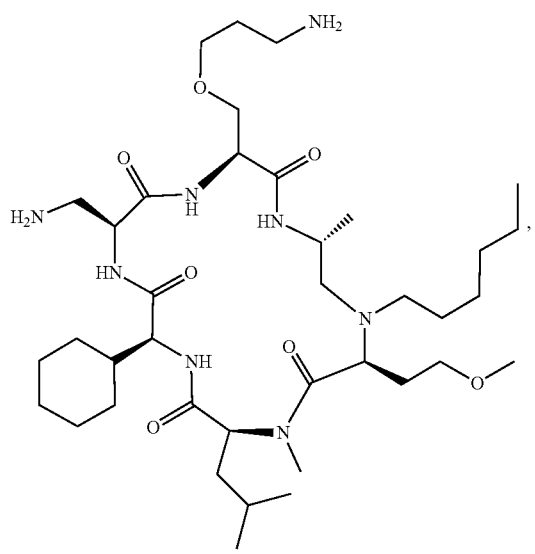

319
-continued
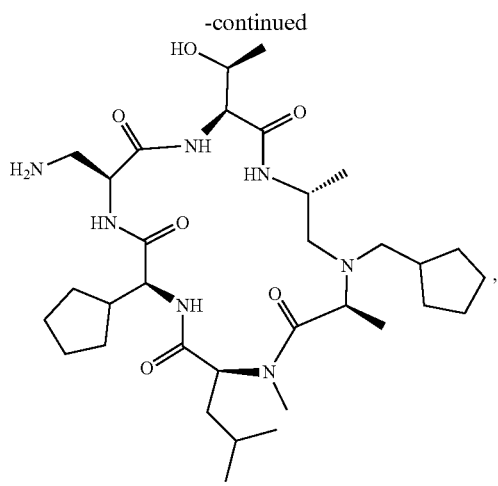
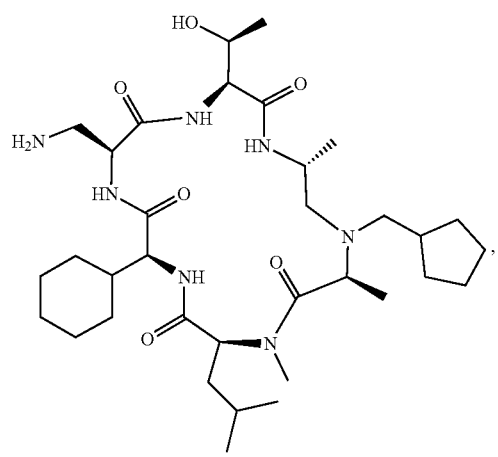
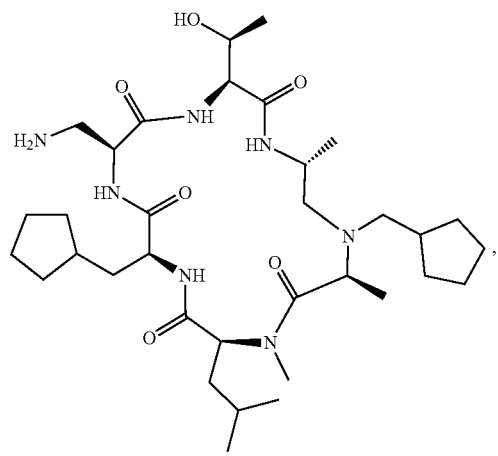
320
-continued
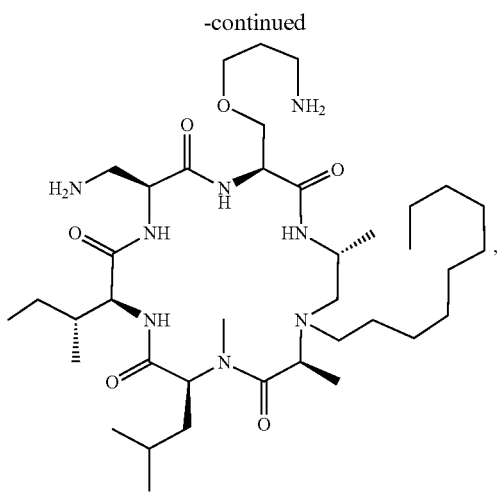
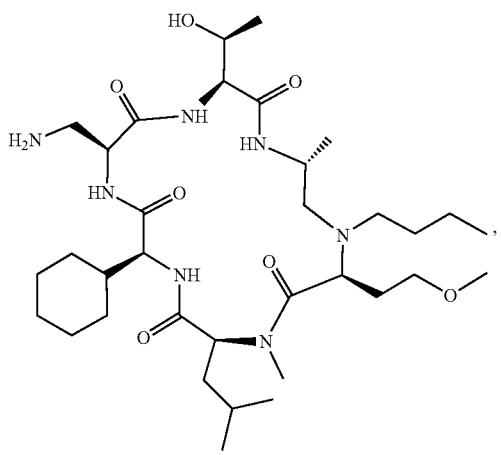
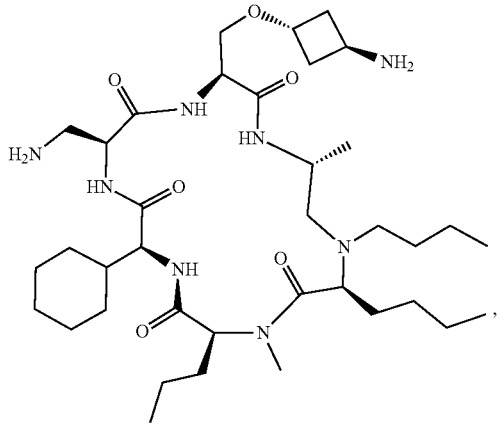

321
-continued
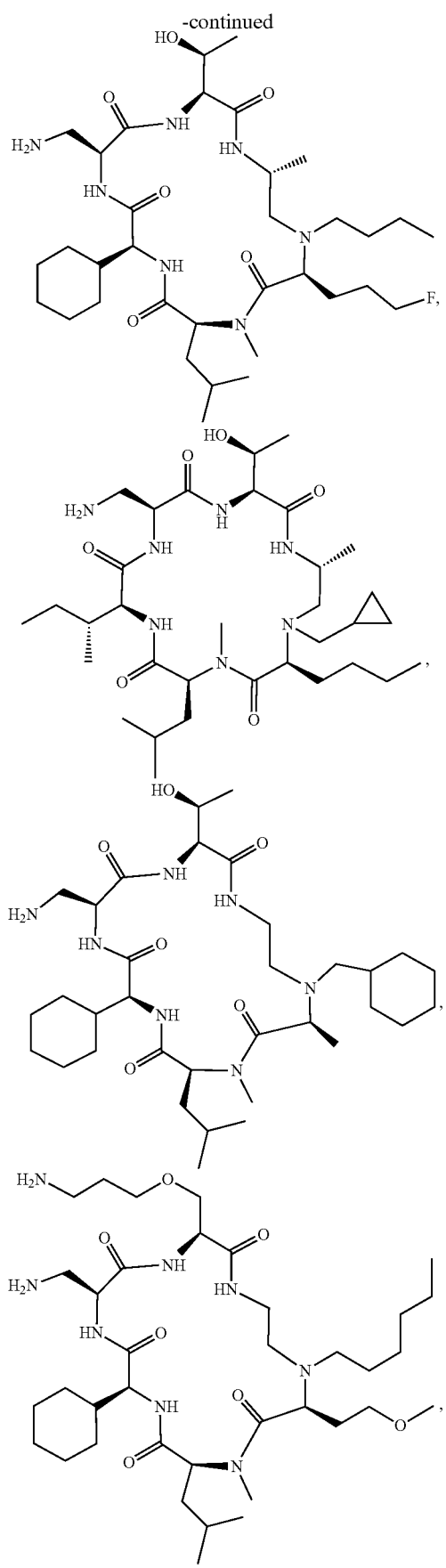
322
-continued
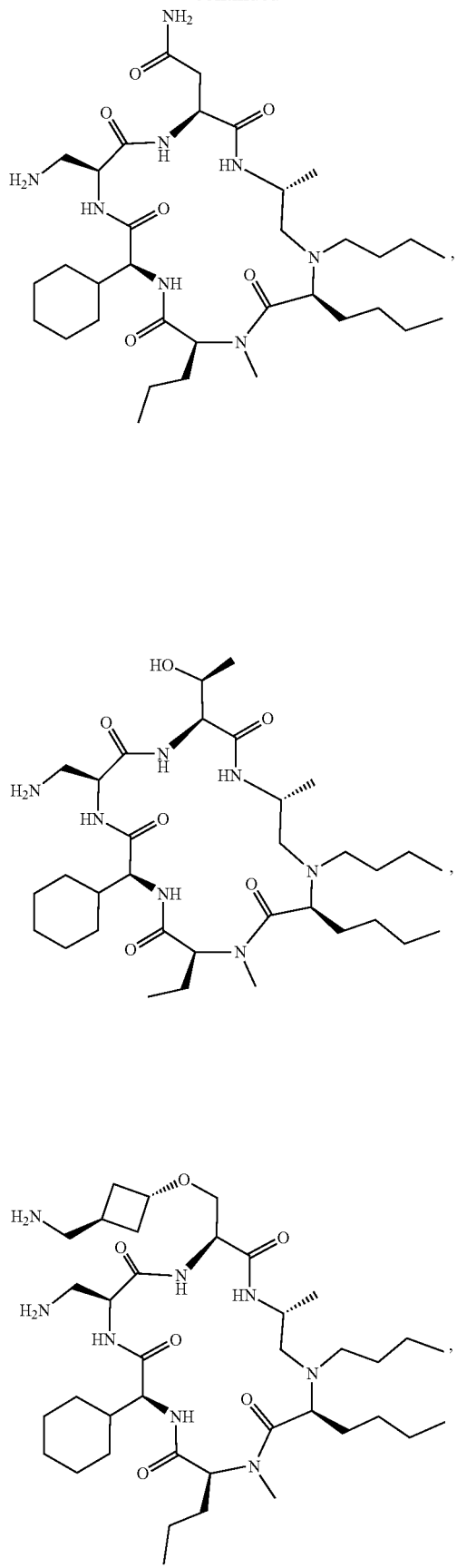

323
-continued

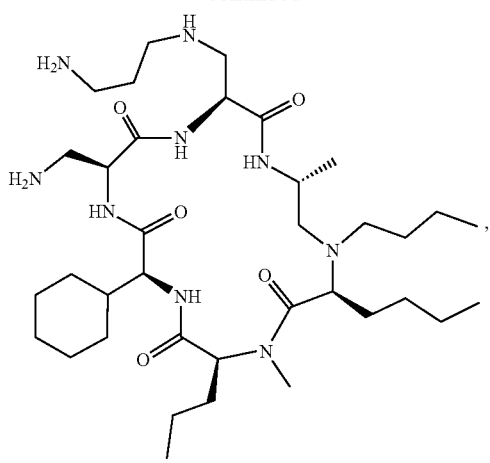

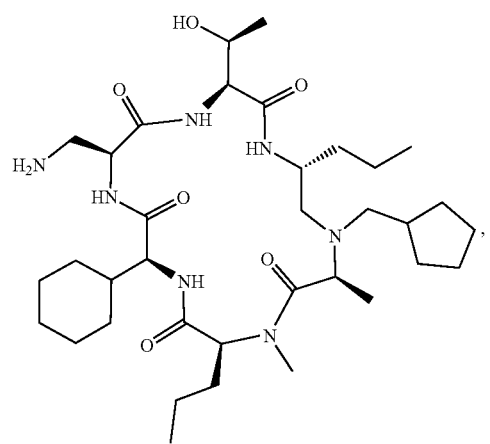

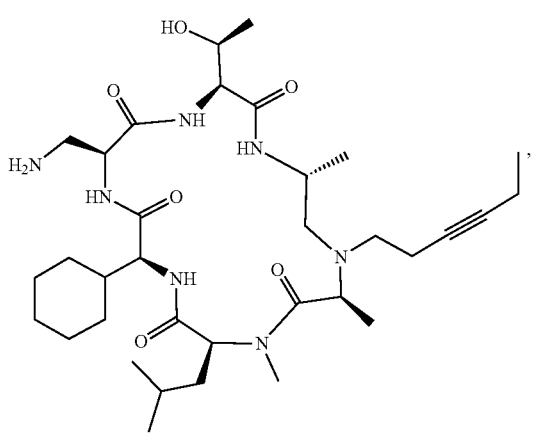

324
-continued

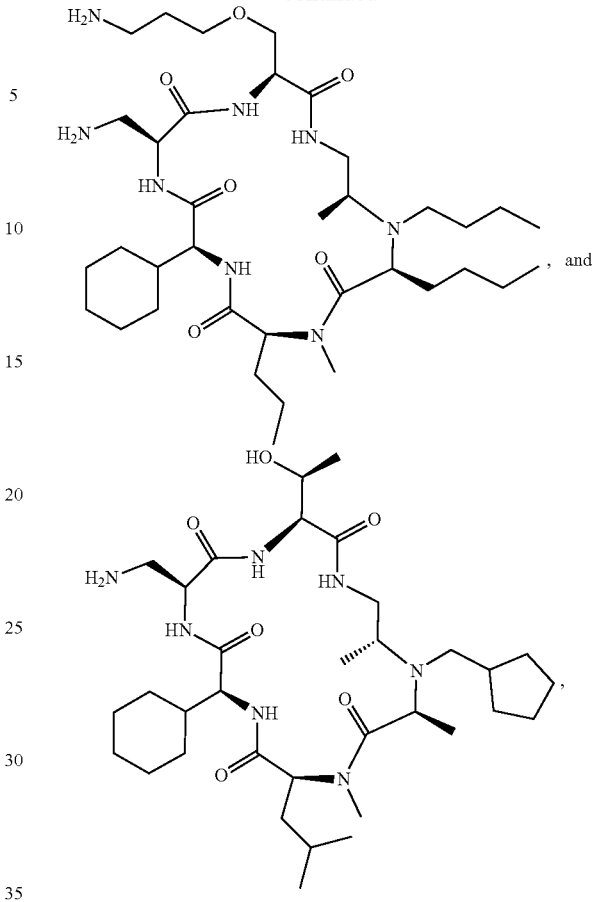

or a pharmaceutically acceptable salt, solvate, or stereoisomer thereof.

19. A compound of Formula (II), or a pharmaceutically acceptable salt, solvate, or stereoisomer thereof:

Formula (II)

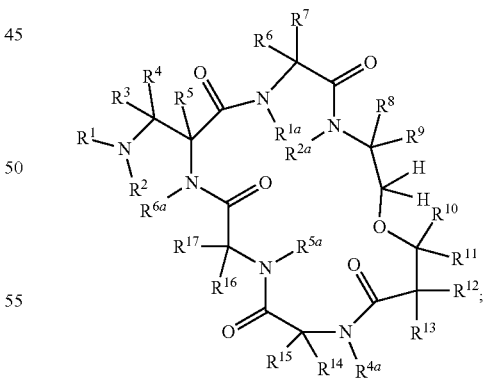

wherein:
$R^{1a}$, $R^{2a}$, $R^{3a}$, $R^{4a}$, $R^{5a}$, and $R^{6a}$ are each independently hydrogen or optionally substituted $C_1$-$C_6$ alkyl;
$R^1$ and $R^2$ are each independently hydrogen, optionally substituted $C_1$-$C_6$ alkyl, optionally substituted $C_2$-$C_6$ alkenyl, optionally substituted $C_2$-$C_6$ alkynyl, optionally substituted cycloalkyl, optionally substituted ($C_1$-$C_6$ alkyl)cycloalkyl, optionally substituted heterocycloalkyl, optionally substituted ($C_1$-$C_6$ alkyl)heterocycloalkyl, optionally substituted aryl, optionally substituted ($C_1$-$C_6$ alkyl)aryl, optionally substituted heteroaryl, optionally substituted ($C_1$-$C_6$ alkyl)heteroaryl, —S(=O)$_2$R$^a$, —S(=O)$_2$NR$^b$R$^c$, —C(=O)R$^a$, —C(=O)OR$^b$, —C(=O)NR$^b$R$^c$, or —(C=NR$^b$)NR$^b$R$^c$;

or R$^1$ and R$^2$ are taken together with the nitrogen atom to which they are attached to form an optionally substituted heterocycloalkyl;

R$^3$ and R$^4$ are each independently hydrogen, optionally substituted $C_1$-$C_6$ alkyl, optionally substituted $C_2$-$C_6$ alkenyl, optionally substituted $C_2$-$C_6$ alkynyl, optionally substituted cycloalkyl, optionally substituted heterocycloalkyl, optionally substituted aryl, or optionally substituted heteroaryl;

or R$^3$ and R$^4$ are taken together with the carbon atom to which they are attached to form an oxo;

R$^5$ is hydrogen, halogen, optionally substituted $C_1$-$C_6$ alkyl, optionally substituted $C_2$-$C_6$ alkenyl, or optionally substituted $C_2$-$C_6$ alkynyl;

R$^6$ and R$^7$ are each independently hydrogen, halogen, optionally substituted $C_1$-$C_6$ alkyl, optionally substituted $C_2$-$C_6$ alkenyl, optionally substituted $C_2$-$C_6$ alkynyl, optionally substituted cycloalkyl, optionally substituted ($C_1$-$C_6$ alkyl)cycloalkyl, optionally substituted heterocycloalkyl, optionally substituted ($C_1$-$C_6$ alkyl)heterocycloalkyl, optionally substituted aryl, optionally substituted ($C_1$-$C_6$ alkyl)aryl, optionally substituted heteroaryl, or optionally substituted ($C_1$-$C_6$ alkyl)heteroaryl;

R$^8$ and R$^9$ are each independently hydrogen, halogen, optionally substituted $C_1$-$C_6$ alkyl, optionally substituted $C_2$-$C_6$ alkenyl, optionally substituted $C_2$-$C_6$ alkynyl, optionally substituted cycloalkyl, optionally substituted ($C_1$-$C_6$ alkyl)cycloalkyl, optionally substituted heterocycloalkyl, optionally substituted ($C_1$-$C_6$ alkyl)heterocycloalkyl, optionally substituted aryl, optionally substituted ($C_1$-$C_6$ alkyl)aryl, optionally substituted heteroaryl, or optionally substituted ($C_1$-$C_6$ alkyl)heteroaryl;

R$^{10}$ and R$^{11}$ are each independently hydrogen, halogen, optionally substituted $C_1$-$C_{20}$ alkyl, optionally substituted $C_2$-$C_{20}$ alkenyl, optionally substituted $C_2$-$C_{20}$ alkynyl, optionally substituted cycloalkyl, optionally substituted ($C_1$-$C_6$ alkyl)cycloalkyl, optionally substituted heterocycloalkyl, optionally substituted ($C_1$-$C_6$ alkyl)heterocycloalkyl, optionally substituted aryl, optionally substituted ($C_1$-$C_6$ alkyl)aryl, optionally substituted heteroaryl, or optionally substituted ($C_1$-$C_6$ alkyl)heteroaryl;

R$^{12}$ and R$^{13}$ are each independently hydrogen, halogen, optionally substituted $C_1$-$C_6$ alkyl, optionally substituted $C_2$-$C_6$ alkenyl, optionally substituted $C_2$-$C_6$ alkynyl, optionally substituted cycloalkyl, optionally substituted ($C_1$-$C_6$ alkyl)cycloalkyl, optionally substituted heterocycloalkyl, optionally substituted ($C_1$-$C_6$ alkyl)heterocycloalkyl, optionally substituted aryl, optionally substituted ($C_1$-$C_6$ alkyl)aryl, optionally substituted heteroaryl, or optionally substituted ($C_1$-$C_6$ alkyl)heteroaryl;

or R$^{10}$ and R$^{12}$ are taken together to form an optionally substituted cycloalkyl or an optionally substituted cycloalkenyl;

R$^{14}$ and R$^{15}$ are each independently hydrogen, halogen, optionally substituted $C_1$-$C_6$ alkyl, optionally substituted $C_2$-$C_6$ alkenyl, optionally substituted $C_2$-$C_6$ alkynyl, optionally substituted cycloalkyl, optionally substituted ($C_1$-$C_6$ alkyl)cycloalkyl, optionally substituted heterocycloalkyl, optionally substituted ($C_1$-$C_6$ alkyl)heterocycloalkyl, optionally substituted aryl, optionally substituted ($C_1$-$C_6$ alkyl)aryl, optionally substituted heteroaryl, or optionally substituted ($C_1$-$C_6$ alkyl)heteroaryl;

or R$^{14}$ and R$^{4a}$ are taken together with the atoms to which they are attached to form an optionally substituted heterocycloalkyl;

R$^{16}$ and R$^{17}$ are each independently hydrogen, halogen, optionally substituted $C_1$-$C_6$ alkyl, optionally substituted $C_2$-$C_6$ alkenyl, optionally substituted $C_2$-$C_6$ alkynyl, optionally substituted cycloalkyl, optionally substituted ($C_1$-$C_6$ alkyl)cycloalkyl, optionally substituted heterocycloalkyl, optionally substituted ($C_1$-$C_6$ alkyl)heterocycloalkyl, optionally substituted aryl, optionally substituted ($C_1$-$C_6$ alkyl)aryl, optionally substituted heteroaryl, or optionally substituted ($C_1$-$C_6$ alkyl)heteroaryl;

R$^{18}$ and R$^{19}$ are each independently hydrogen, halogen, optionally substituted $C_1$-$C_6$ alkyl, optionally substituted $C_2$-$C_6$ alkenyl, optionally substituted $C_2$-$C_6$ alkynyl, optionally substituted cycloalkyl, optionally substituted ($C_1$-$C_6$ alkyl)cycloalkyl, optionally substituted heterocycloalkyl, optionally substituted ($C_1$-$C_6$ alkyl)heterocycloalkyl, optionally substituted aryl, optionally substituted ($C_1$-$C_6$ alkyl)aryl, optionally substituted heteroaryl, or optionally substituted ($C_1$-$C_6$ alkyl)heteroaryl;

or R$^{18}$ and R$^{19}$ are taken together with the carbon atom to which they are attached to form an oxo;

each R$^a$ is independently optionally substituted $C_1$-$C_6$ alkyl, optionally substituted $C_2$-$C_6$ alkenyl, optionally substituted $C_2$-$C_6$ alkynyl, optionally substituted cycloalkyl, optionally substituted heterocycloalkyl, optionally substituted aryl, or optionally substituted heteroaryl;

each R$^b$ and R$^c$ is independently hydrogen, optionally substituted $C_1$-$C_6$ alkyl, optionally substituted $C_2$-$C_6$ alkenyl, optionally substituted $C_2$-$C_6$ alkynyl, optionally substituted cycloalkyl, optionally substituted heterocycloalkyl, optionally substituted aryl, or optionally substituted heteroaryl;

or R$^b$ and R$^c$ are taken together with the nitrogen atom to which they are attached to form an optionally substituted heterocycloalkyl;

or a pharmaceutically acceptable salt, solvate, or stereoisomer thereof;

327
wherein the compound is selected from the group consisting of:
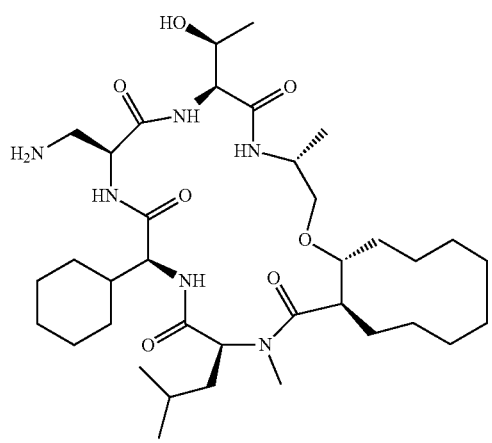
,
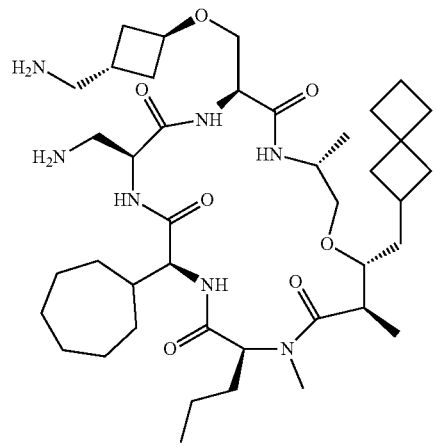
,
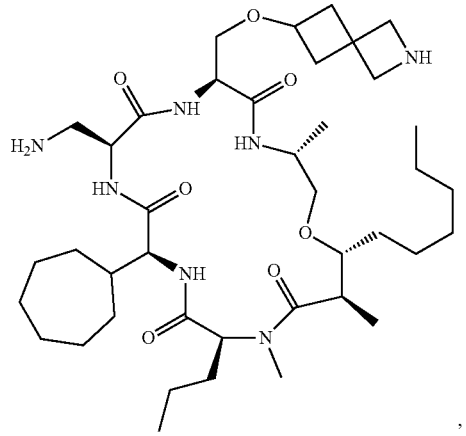
,
328
-continued
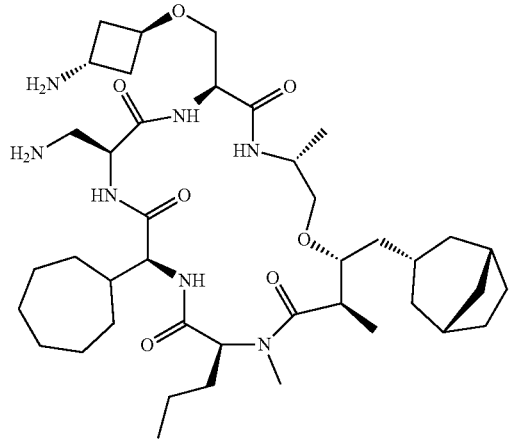
,
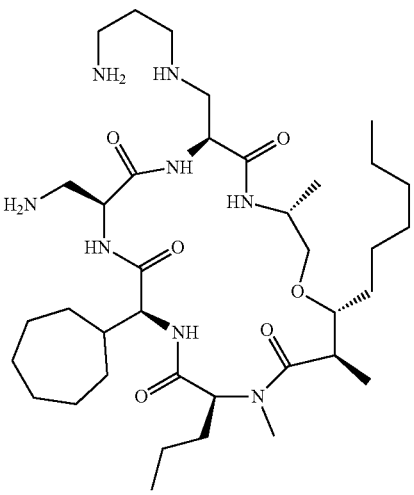
,
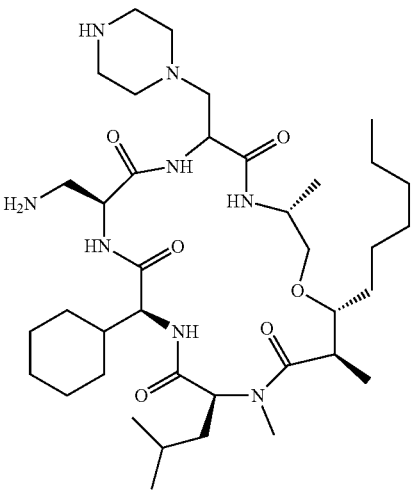
,

329
-continued
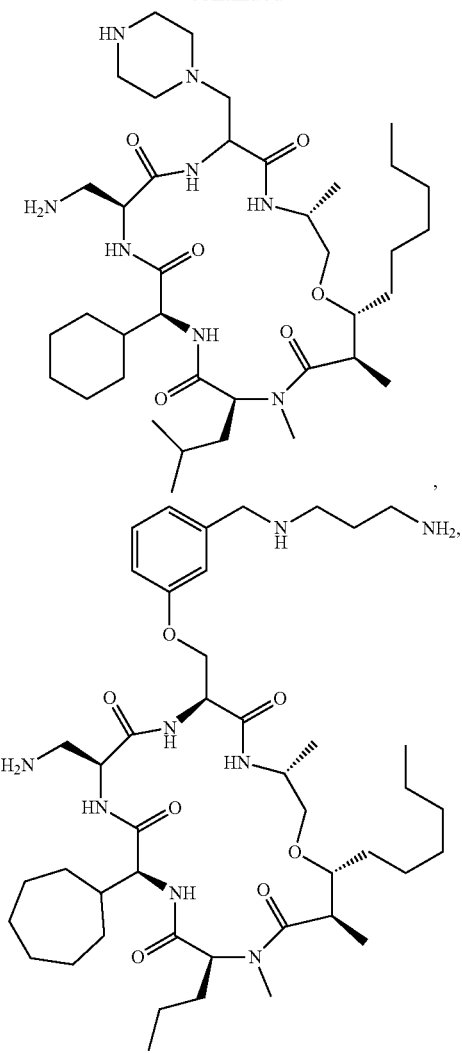
330
-continued
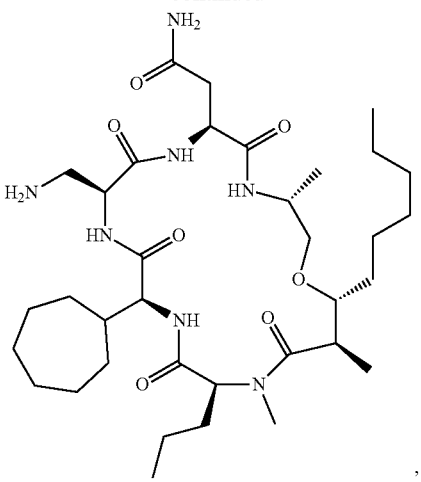
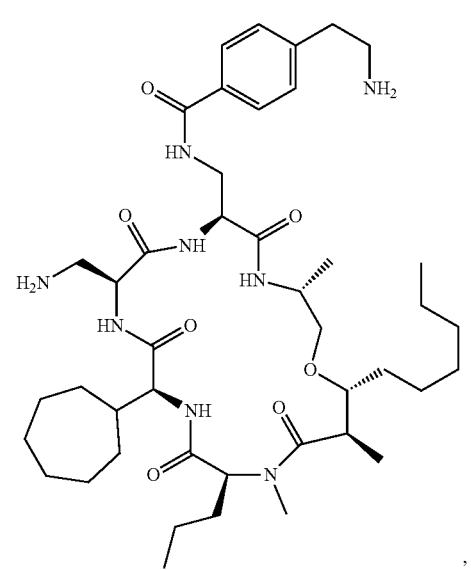
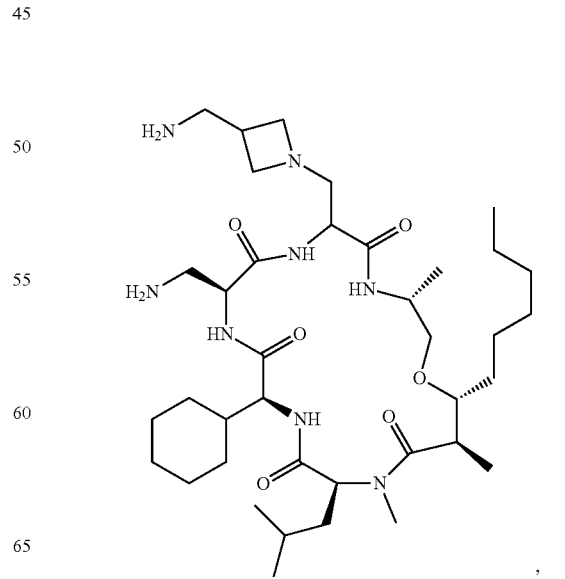

331
-continued
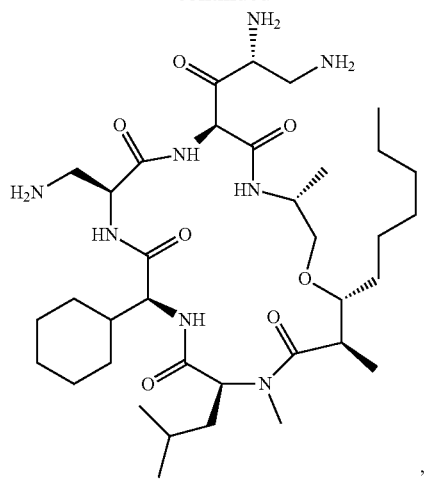
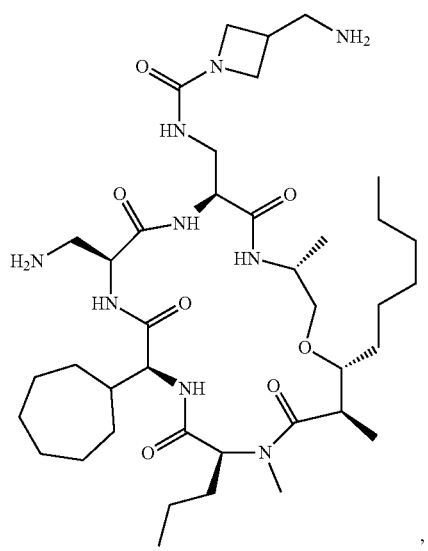
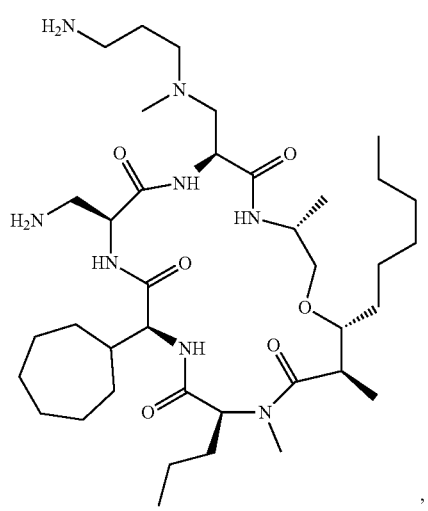
,
332
-continued
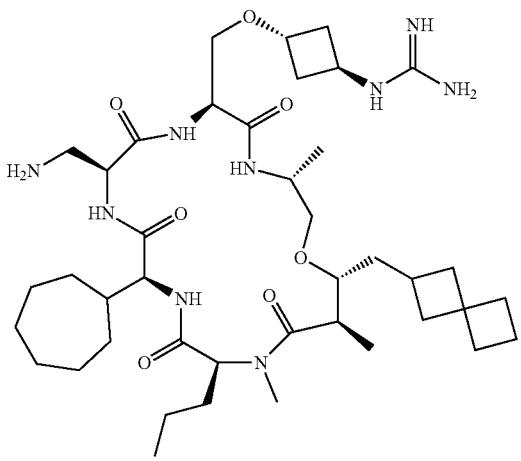
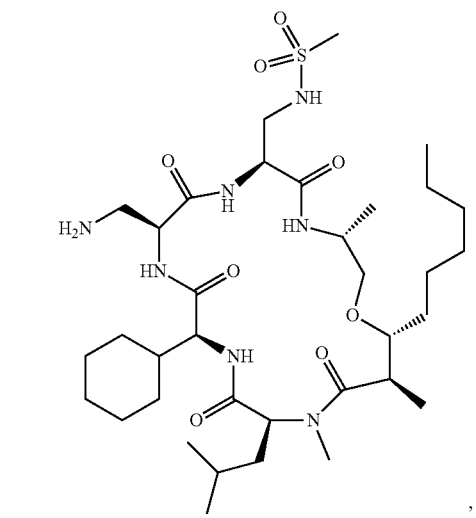
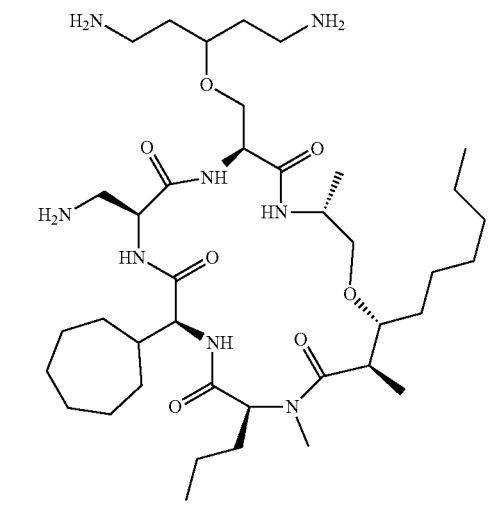
, 333
-continued
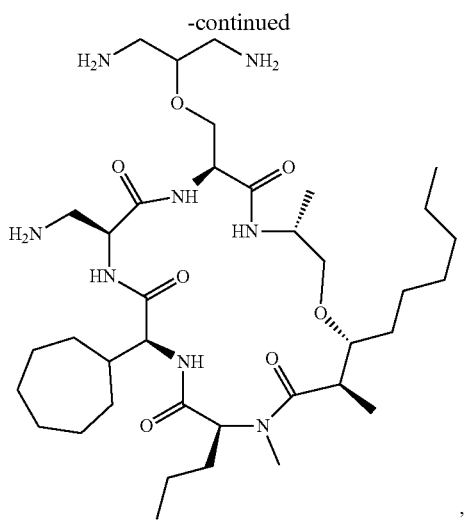
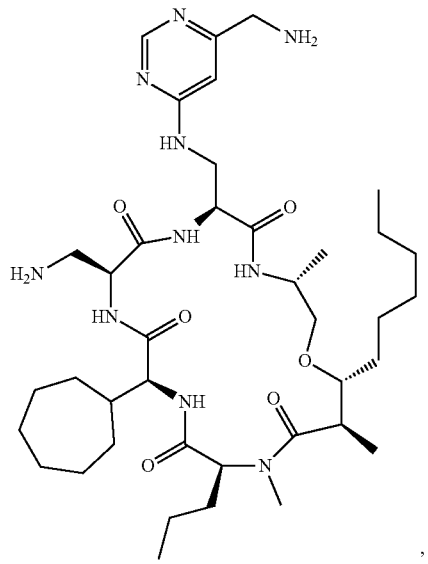
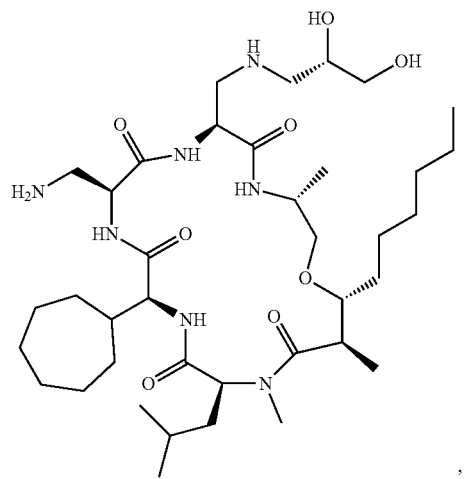
334
-continued
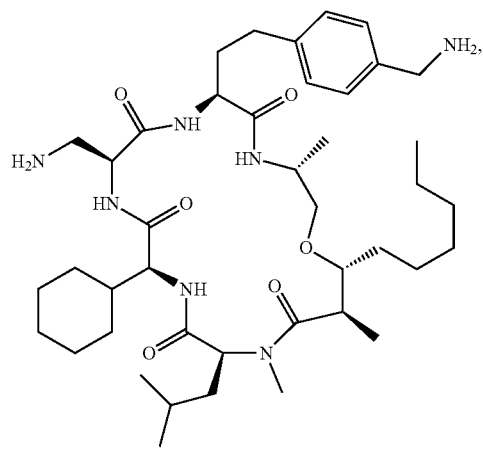
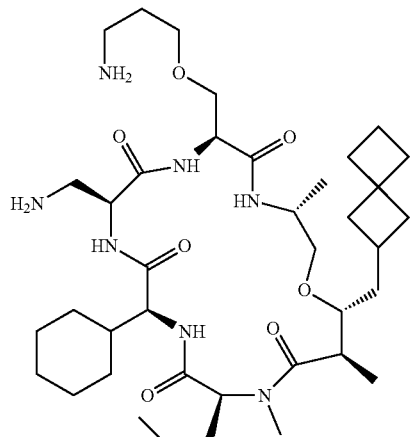
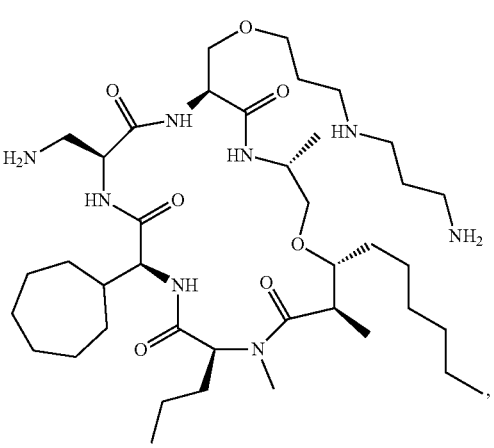

335
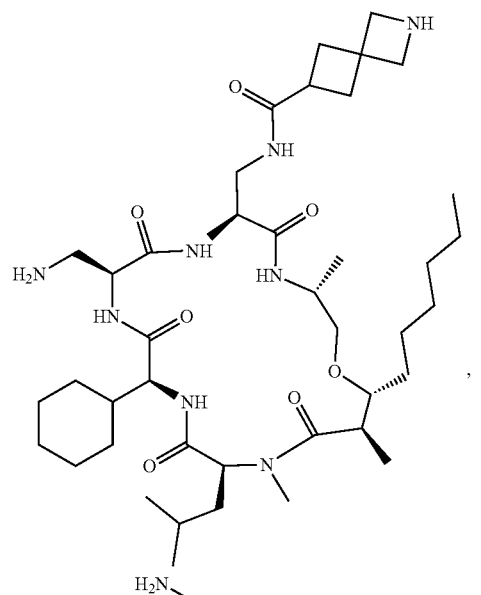
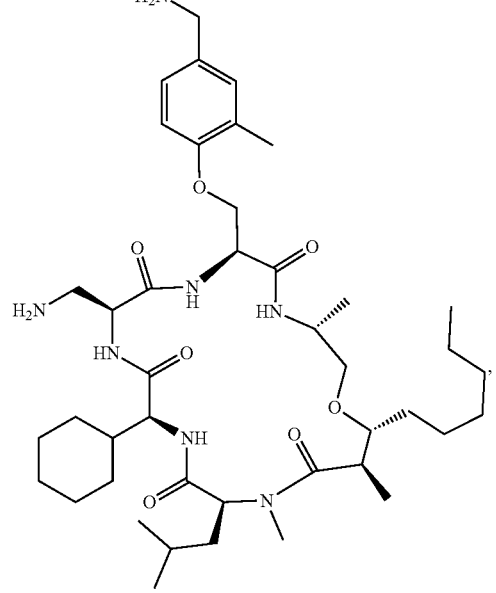
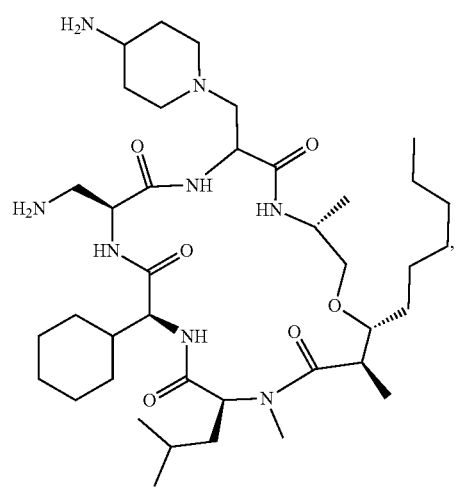
336
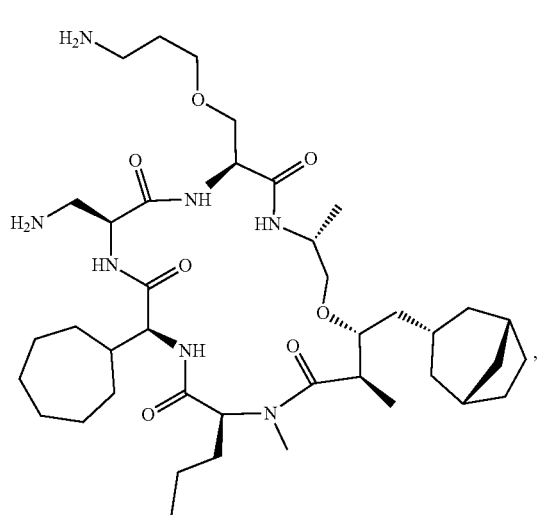
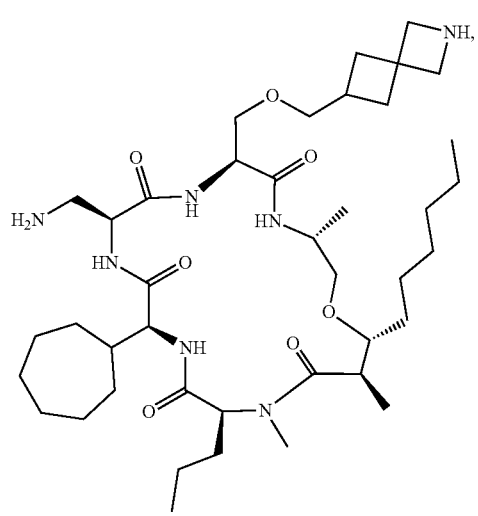
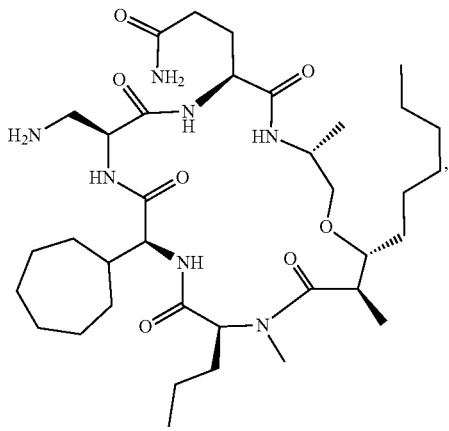

337
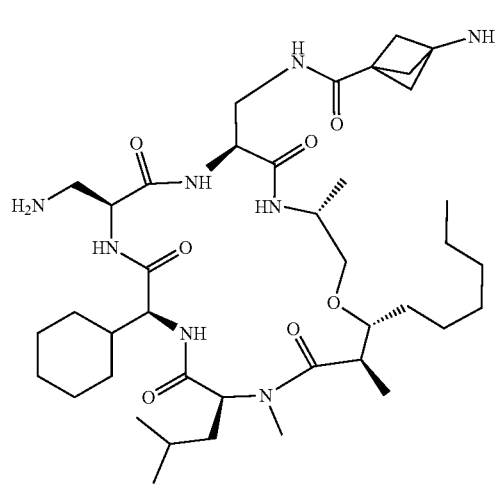
338
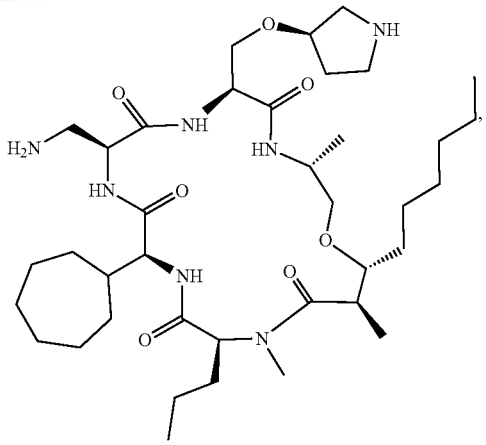
-continued
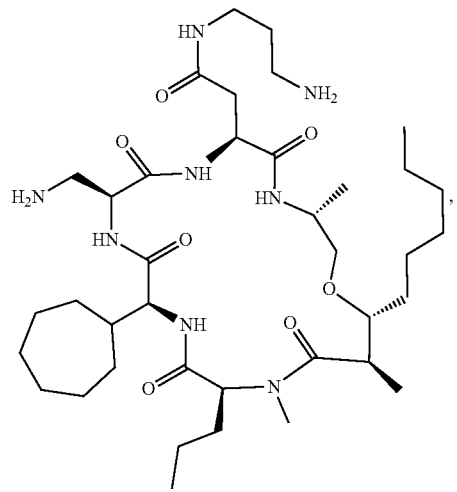
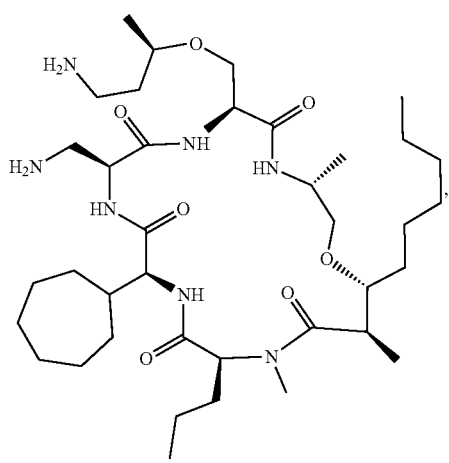
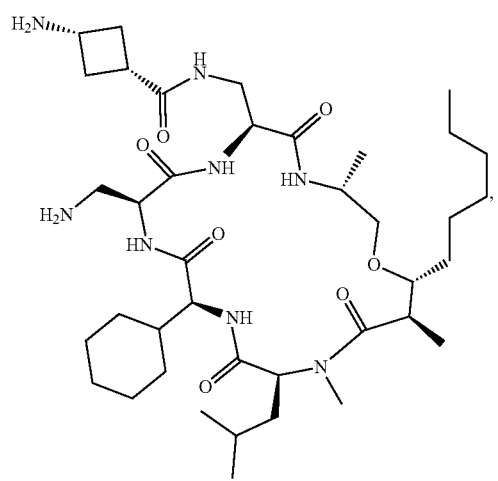
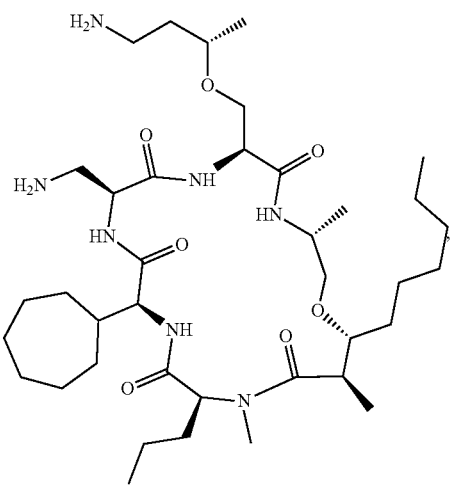

-continued
339
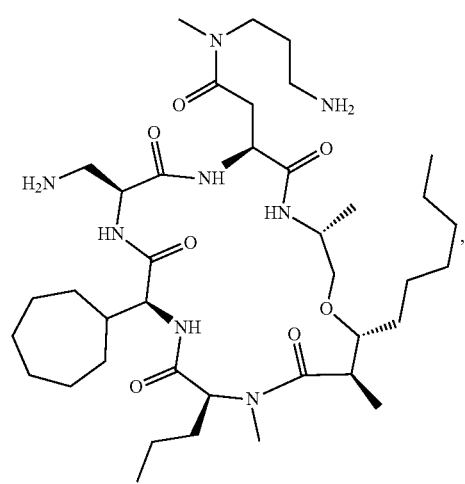,
340
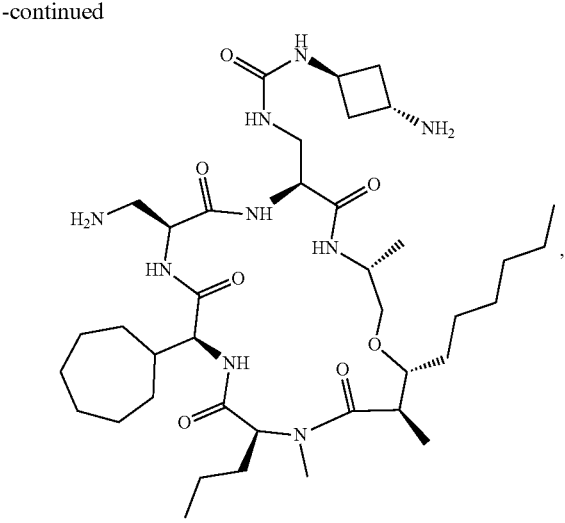,
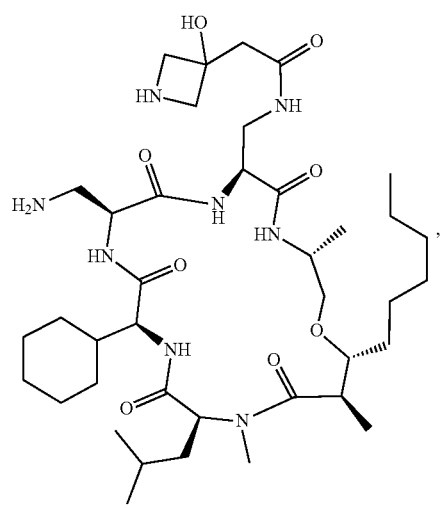,
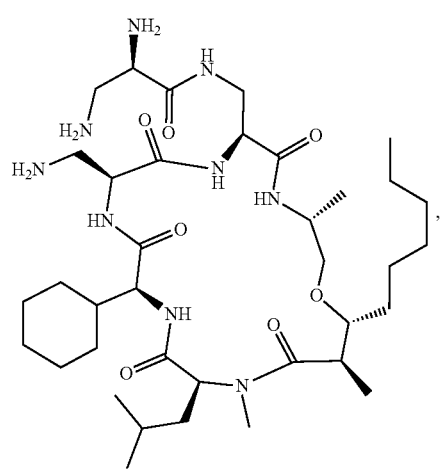,
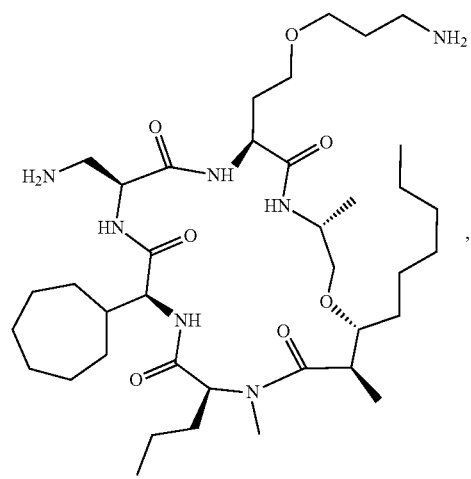,
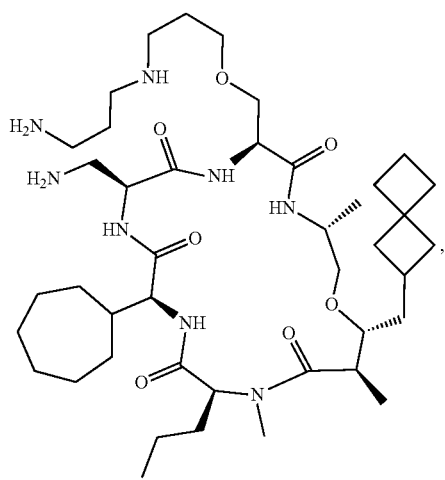,

341

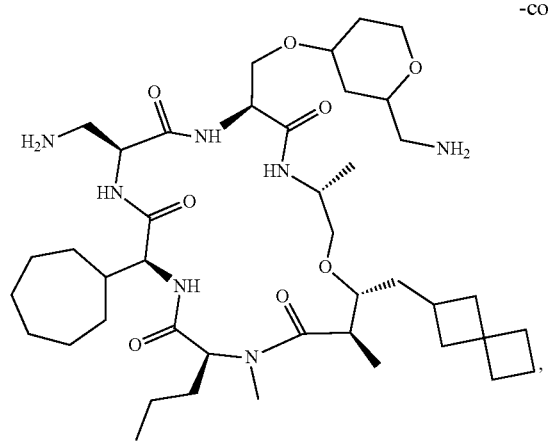

342

-continued

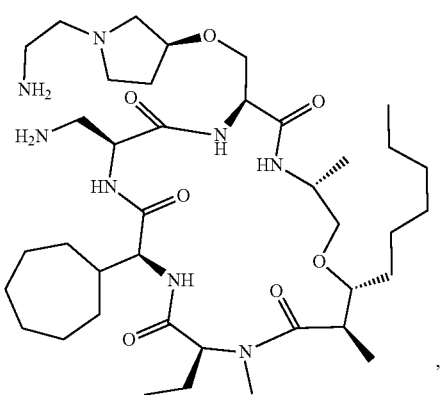

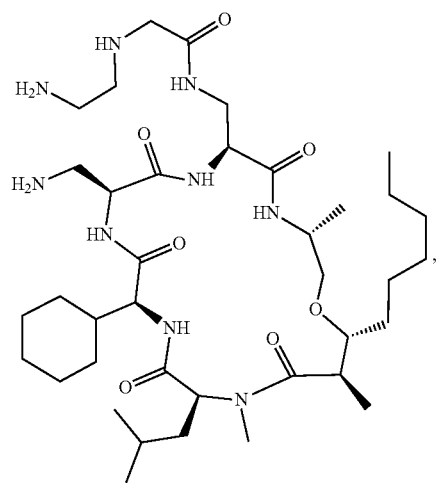

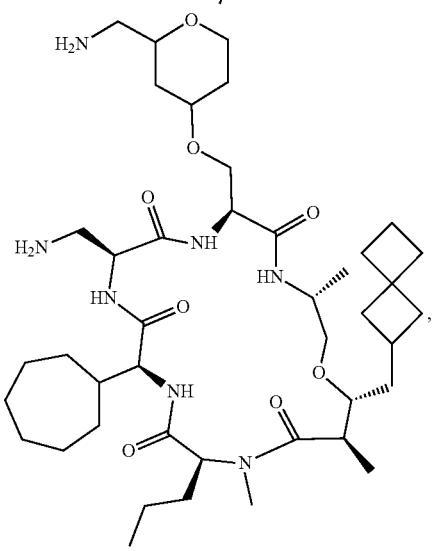

and

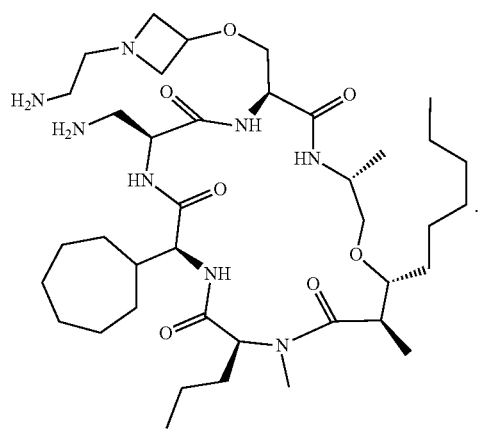

20. A pharmaceutical composition comprising the compound claim 1, or a pharmaceutically acceptable salt, solvate, or stereoisomer thereof, and a pharmaceutically acceptable excipient.

21. A method of treatment of a bacterial infection in a mammal, comprising administering to the mammal an effective amount of a compound of claim 1, or a pharmaceutically acceptable salt, solvate, or stereoisomer thereof, to the mammal at a frequency and for a duration sufficient to provide a beneficial effect to the mammal.

22. The method of claim 21, wherein the bacterial infection is an infection involving *Pseudomonas aeruginosa, Pseudomonas fluorescens, Pseudomonas acidovorans, Pseudomonas alcaligenes, Pseudomonas putida, Stenotrophomonas maltophilia, Burkholderia cepacia, Aeromonas hydrophilia, Escherichia coli, Citrobacter freundii, Salmonella typhimurium, Salmonella typhi, Salmonella paratyphi, Salmonella enteritidis, Shigella dysenteriae, Shigella flexneri, Shigella sonnei, Enterobacter cloacae, Enterobacter aerogenes, Klebsiella pneumoniae, Klebsiella oxytoca, Serratia marcescens, Francisella tularensis, Morgan-* ella morganii, Proteus mirabilis, Proteus vulgaris, Providencia alcalifaciens, Providencia rettgeri, Providencia stuartii, Acinetobacter baumannii, Acinetobacter calcoaceticus, Acinetobacter haemolyticus, Yersinia enterocolitica, Yersinia pestis, Yersinia pseudotuberculosis, Yersinia intermedia, Bordetella pertussis, Bordetella parapertussis, Bordetella bronchiseptica, Haemophilus influenzae, Haemophilus parainfluenzae, Haemophilus haemolyticus, Haemophilus parahaemolyticus, Haemophilus ducreyi, Pasteurella multocida, Pasteurella haemolytica, Branhamella catarrhalis, Helicobacter pylori, Campylobacter fetus, Campylobacter jejuni, Campylobacter coli, Borrelia burgdorferi, Vibrio cholerae, Vibrio parahaemolyticus, Legionella pneumophila, Listeria monocytogenes, Neisseria gonorrhoeae, Neisseria meningitidis, Kingella, Moraxella, Gardnerella vaginalis, Bacteroides fragilis, Bacteroides distasonis, Bacteroides 3452A homology group, Bacteroides vulgatus, Bacteroides ovalus, Bacteroides thetaiotaomicron, Bacteroides uniformis, Bacteroides eggerthii, or Bacteroides splanchnicus.

\* \* \* \* \*